US012610738B2

(12) United States Patent
Park et al.

(10) Patent No.: US 12,610,738 B2

(45) Date of Patent: Apr. 21, 2026

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hyo-Soon Park, Gyeonggi-do (KR); Jeong-Hwan Jeon, Gyeonggi-do (KR); Sang-Hee Cho, Gyeonggi-do (KR); Eun-Joung Choi, Gyeonggi-do (KR); Dong-Gil Kim, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 662 days.

(21) Appl. No.: 17/203,153

(22) Filed: Mar. 16, 2021

(65) Prior Publication Data

US 2022/0109110 A1 Apr. 7, 2022

(30) Foreign Application Priority Data

Mar. 17, 2020 (KR) ........................ 10-2020-0032756
Jan. 18, 2021 (KR) ........................ 10-2021-0006981

(51) Int. Cl.

| | |
|---|---|
| ***H10K 85/60*** | (2023.01) |
| ***C07D 307/91*** | (2006.01) |
| ***C07D 403/04*** | (2006.01) |
| ***C07D 403/10*** | (2006.01) |
| ***C07D 405/04*** | (2006.01) |
| ***C07D 409/10*** | (2006.01) |
| ***C07D 409/12*** | (2006.01) |
| ***C07D 409/14*** | (2006.01) |
| ***C09K 11/06*** | (2006.01) |
| ***H10K 50/11*** | (2023.01) |
| ***H10K 50/15*** | (2023.01) |
| ***H10K 101/10*** | (2023.01) |

(52) U.S. Cl.

CPC ....... *H10K 85/6572* (2023.02); *C07D 307/91* (2013.01); *C07D 403/04* (2013.01); *C07D 403/10* (2013.01); *C07D 405/04* (2013.01); *C07D 409/10* (2013.01); *C07D 409/12* (2013.01); *C07D 409/14* (2013.01); *C09K 11/06* (2013.01); *H10K 85/636* (2023.02); *H10K 85/654* (2023.02); *H10K 85/6574* (2023.02); *H10K 85/6576* (2023.02); *C09K 2211/1018* (2013.01); *H10K 50/11* (2023.02); *H10K 50/15* (2023.02); *H10K 2101/10* (2023.02)

(58) Field of Classification Search

CPC .................................................. H10K 85/6572

See application file for complete search history.

(56) References Cited

U.S. PATENT DOCUMENTS

| | | | | |
|---|---|---|---|---|
| 9,722,182 B2 | 8/2017 | Lee et al. | | |
| 2014/0117326 A1* | 5/2014 | Lee | ...................... | C07D 209/80 546/276.7 |
| 2014/0117331 A1 | 5/2014 | Kim et al. | | |
| 2014/0209880 A1 | 7/2014 | Choi et al. | | |
| 2015/0255726 A1 | 9/2015 | Kawamura et al. | | |
| 2018/0370981 A1 | 12/2018 | Nishimae et al. | | |
| 2020/0028089 A1 | 1/2020 | Cho et al. | | |
| 2020/0227652 A1* | 7/2020 | Nishimae | ........... | C07D 491/052 |
| 2021/0151693 A1 | 5/2021 | Lee et al. | | |

FOREIGN PATENT DOCUMENTS

| | | | |
|---|---|---|---|
| CN | 104387222 A | * | 3/2015 |
| EP | 3498700 A1 | | 6/2019 |
| KR | 20120116884 A | | 10/2012 |
| KR | 20150110891 A | | 10/2015 |
| KR | 2018134231 A | | 12/2018 |

OTHER PUBLICATIONS

Pieters et al. "Regio-Defined Amino[5]Oxa- and Thiahelicenes: A Dramatic Impact of the Nature of the Heteroatom of the Helical Shape and Racemization Barriers" J. Org. Chem. 2010, 75, 2096-2098. (Year: 2010).*

Borkent et al. "Conformational Studies on Helicenes-IX, A Hexahelicene Containing an Aromatic, Carbocyclic, Five-Membered Ring" Tetrahedron, 1982, 38, 12, 1809-1811. (Year: 1982).*

Liu et al. English machine translation of CN 104387222 A. (Year: 2015).*

Chang et al. "Selectivity Enhancement for Petroleum Hydrocarbons Using a Smectic Liquid Crystalline Stationary Phase in Supercritical Fluid Chromatography" Journal of Chromatographic Science, 1988, 26, 280-289. (Year: 1988).*

Search Report from China National Intellectual Property Administration for China Patent application No. 202110195791.8; Application Date: Feb. 20, 2021.

Cited Reference from Japan Patent Office for Japan Patent Application No. 2021-027879, Application Date: Feb. 24, 2021.

Pieters, G. et al., Regio-Defined Amino[5]Oxa- and Thiahelicenes: A Dramatic Impact of the Nature of the Heteroatom on the Helical Shape and Racemization Barriers, J. Org. Chem., USA, ACS Publications, Feb. 12, 2010, 75, 2096-2098.

Borkent, J. H. et al., Conformational studies on helicenes-IX1: A hexahelicene containing an aromatic, carbocyclic, five-membered ring, Tetrahedron, 38(12), England, Elsevier, Dec. 31, 1982, 1809-1811.

* cited by examiner

*Primary Examiner* — Peter F Godenschwager

(74) *Attorney, Agent, or Firm* — G. Creston Campbell

(57) ABSTRACT

The present disclosure relates to an organic electroluminescent compound represented by formula 1, and an organic electroluminescent device comprising the same. By comprising the organic electroluminescent compound of the present disclosure, it is possible to provide an organic electroluminescent device having improved driving voltage, luminous efficiency, lifetime properties, and/or power efficiency.

15 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting display device which has advantages in that it provides a wider viewing angle, a greater contrast ratio, and a faster response time. The first organic EL device was developed by Eastman Kodak in 1987, by using small aromatic diamine molecules and aluminum complexes as materials for forming a light-emitting layer [Appl. Phys. Lett. 51, 913, 1987].

The most important factor determining luminous efficiency in an organic electroluminescent device (OLED) is light-emitting materials. Until now, fluorescent materials have been widely used as light-emitting materials. However, in view of electroluminescent mechanisms, since phosphorescent light-emitting materials theoretically enhance luminous efficiency by four (4) times compared to fluorescent light-emitting materials, phosphorescent light-emitting materials have been widely researched. Until now, Iridium (III) complexes have been widely known as phosphorescent light-emitting materials, including bis(2-(2'-benzothienyl)-pyridinato-N,C-3')iridium(acetylacetonate) [(acac)Ir(btp)$_2$], tris(2-phenylpyridine)iridium[Ir(ppy)$_3$] and bis(4,6-difluorophenylpyridinato-N,C2)picolinato iridium (Firpic) as red-, green-, and blue-emitting materials, respectively.

In the prior art, 4,4'-N,N'-dicarbazol-biphenyl (CBP) is the most widely known phosphorescent host material. Recently, Pioneer (Japan) et al., developed a high performance OLED using bathocuproine (BCP) and aluminum (III)bis(2-methyl-8-quinolinate)(4-phenylphenolate) (BAlq), etc., as host materials, which were known as hole blocking materials.

However, although the conventional materials provide good luminous characteristics, they have the following disadvantages: (1) Due to their low glass transition temperature and poor thermal stability, their degradation may occur during a high-temperature deposition process in a vacuum, and the lifespan of the device may be shortened. (2) The power efficiency of the OLED is given by [(π/voltage)× current efficiency], and the power efficiency is inversely proportional to the voltage. Although the OLED comprising phosphorescent host materials provides higher current efficiency (cd/A) than one comprising fluorescent materials, a significantly high driving voltage is necessary. Thus, there is no merit in terms of power efficiency (lm/W). (3) Also, the operational lifespan of the OLED is short, and it is still necessary to improve luminous efficiency.

In order to enhance luminous efficiency, driving voltage, and/or lifetime properties, various materials or concepts for an organic layer of an organic electroluminescent device have been proposed. However, they were not satisfactory in practical use.

Korean Laid-open Patent Application Nos. 2014-0055137 and 2015-0126340 discloses a fused carbazole derivative. However, there is a continuous need for developing an organic electroluminescent material for improving OLED performance.

DISCLOSURE OF INVENTION

Technical Problem

The objective of the present disclosure is to provide an organic electroluminescent compound which is efficient in producing an organic electroluminescent device having improved driving voltage, luminous efficiency, lifetime properties, and/or power efficiency. Another objective of the present disclosure is to provide an organic electroluminescent device comprising the organic electroluminescent compound.

Solution to Problem

A compound having an aryl moiety can show high stability when used in electrical devices. The present inventors found that phenanthrene-based compounds have higher HOMO, LUMO, and triplet energy gap ($E_T$) than anthracene-based compounds, and accordingly, a phenanthrene-based compound was introduced into an organic electroluminescent device. As a result, it was confirmed that the stability was higher than the case of introducing an anthracene-based compound. This can also be explained by Clar's rule. That is, this higher stability seems to be due to the effect of the phenanthrene structure having lower bridge conjugation and steric hindrance compared to the anthracene structure. More specifically, the present inventors have found that the above objective can be achieved by an organic electroluminescent compound represented by the following formula 1:

(1)

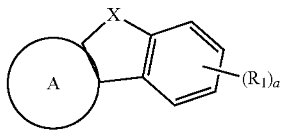

wherein ring A is selected from the following formulas;

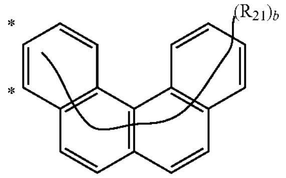

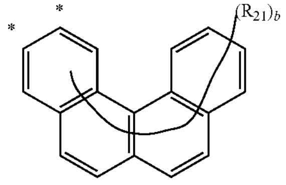

-continued

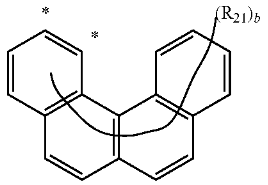

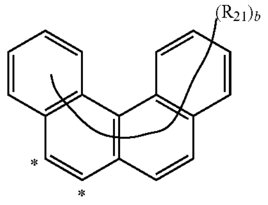

X represents $NR_{11}$, $CR_{12}R_{13}$, O, or S;

$R_1$ each independently represents hydrogen, deuterium, a halogen, or a cyano;

$R_{11}$ represents hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted (C6-C30)aryl, a substituted or unsubstituted (3- to 30-membered)heteroaryl, a substituted or unsubstituted silyl, or a substituted or unsubstituted amino;

$R_{12}$ and $R_{13}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted (C6-C30)aryl, a substituted or unsubstituted (3- to 30-membered)heteroaryl, a substituted or unsubstituted silyl, or a substituted or unsubstituted amino; or are linked to each other to form a ring;

$R_{21}$ represents $-L_1-Ar_1$, where if $R_{21}$ is plural, each of $R_{21}$ may be the same or different;

$L_1$ each independently represents a single bond, a substituted or unsubstituted (C6-C30)arylene, or a substituted or unsubstituted (3- to 30-membered)heteroarylene;

$Ar_1$ each independently represents hydrogen, deuterium, a halogen, a cyano, a substituted or unsubstituted (C1-C30)alkyl, a substituted or unsubstituted (C3-C30) cycloalkyl, a substituted or unsubstituted (3- to 7-membered)heterocycloalkyl, a substituted or unsubstituted (C6-C30)aryl, a substituted or unsubstituted (3- to 30-membered)heteroaryl, a substituted or unsubstituted silyl, or a substituted or unsubstituted amino;

a represents an integer of 1 to 4, b represents an integer of 1 to 10, where if a and b are an integer of 2 or more, each of $R_1$ and each of $R_{21}$ may be the same or different;

* represents a site fused with the 5-membered ring comprising X;

with the proviso that if X is $NR_{11}$, ring A is not

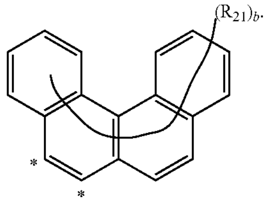

Advantageous Effects of Invention

By using the organic electroluminescent compound of the present disclosure, it is possible to produce an organic electroluminescent device having low driving voltage, high luminous efficiency, excellent lifetime property, and/or high power efficiency.

MODE FOR THE INVENTION

Hereinafter, the present disclosure will be described in detail. However, the following description is intended to explain the disclosure, and is not meant in any way to restrict the scope of the disclosure.

The term "organic electroluminescent compound" in the present disclosure means a compound that may be used in an organic electroluminescent device. If necessary, the organic electroluminescent compound may be comprised in any layer constituting an organic electroluminescent device.

The term "organic electroluminescent material" in the present disclosure means a material that may be used in an organic electroluminescent device, and may comprise at least one compound. If necessary, the organic electroluminescent material may be comprised in any layer constituting an organic electroluminescent device. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron injection material, etc.

The organic electroluminescent material of the present disclosure may comprise at least one compound represented by formula 1. The compound represented by formula 1 may be comprised in a hole injection layer, a hole transport layer, a hole auxiliary layer, a light-emitting auxiliary layer, an electron blocking layer, a light-emitting layer, an electron buffer layer, a hole blocking layer, an electron transport layer, and/or an electron injection layer, etc., but is not limited thereto. The compound represented by formula 1 may be comprised in at least one of the layer constituting a hole transport zone, but is not limited thereto. When comprised in a hole transport layer, a hole auxiliary layer, or a light-emitting auxiliary layer of the hole transport zone, the compound represented by formula 1 may be comprised as a hole transport material, a hole auxiliary material, or a light-emitting auxiliary material. In addition, when comprised in a light-emitting layer, the compound represented by formula 1 may be comprised as a host material, but is not limited thereto. Herein, the host material may be a host material of a blue, green, or red organic electroluminescent device.

Hereinafter, the compound represented by formula 1 will be described in more detail.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, isopropyl, n-butyl, iso-butyl, tert-butyl, sec-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, cyclopentylmethyl, cyclohexylmethyl, etc. The term "(3- to 7-membered)heterocycloalkyl" is meant to be a cycloalkyl having 3 to 7, preferably 5 to 7, ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 25, and more preferably 6 to 18. The above aryl(ene) may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, tetramethyldihydrophenanthrenyl, etc. More specifically, the above aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenylyl, 4"-t-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, 9,9,10,10-tetramethyl-9,10-dihydro-1-phenanthrenyl, 9,9,10,10-tetramethyl-9,10-dihydro-2-phenanthrenyl, 9,9,10,10-tetramethyl-9,10-dihydro-3-phenanthrenyl, 9,9,10,10-tetramethyl-9,10-dihydro-4-phenanthrenyl, etc.

The term "(3- to 30-membered)heteroaryl(ene)" is meant to be an aryl having 3 to 30 ring backbone atoms, and including at least one, preferably 1 to 4 heteroatoms selected from the group consisting of B, N, O, S, Si, and P. The above heteroaryl may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, dibenzoselenophenyl, naphthobenzofuranyl, naphthobenzothiophenyl, benzofuroquinolinyl, benzofuroquinazolinyl, benzofuronaphthyridinyl, benzofuropyrimidinyl, naphthofuropyrimidinyl, benzothienoquinolinyl, benzothienoquinazolinyl, benzothienonaphthyridinyl, benzothienopyrimidinyl, naphthothienopyrimidinyl, pyrimidoindolyl, benzopyrimidoindolyl, benzofuropyrazinyl, naphthofuropyrazinyl, benzothienopyrazinyl, naphthothienopyrazinyl, pyrazinoindolyl, benzopyrazinoindolyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, dihydroacridinyl, benzotriazolephenazinyl, imidazopyridinyl, chromenoquinazolinyl, thiochromenoquinazolinyl, dimethylbenzopyrimidinyl, indolocarbazolyl, indenocarbazolyl, etc. More specifically, the above heteroaryl may include 1-pyrrolyl, 2-pyrrolyl, 3-pyrrolyl, pyrazinyl, 2-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridinyl, 3-imidazopyridinyl, 5-imidazopyridinyl, 6-imidazopyridinyl, 7-imidazopyridinyl, 8-imidazopyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl)pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 2-benzofuro[3,2-d]pyrimidinyl, 6-benzofuro[3,2-d]pyrimidinyl, 7-benzofuro[3,2-d]pyrimidinyl, 8-benzofuro[3,2-d]pyrimidinyl, 9-benzofuro[3,2-d]pyrimidinyl, 2-benzothio[3,2-d]pyrimidinyl, 6-benzothio[3,2-d]pyrimidinyl, 7-benzothio[3,2-d]pyrimidinyl, 8-benzothio[3,2-d]pyrimidinyl, 9-benzothio[3,2-d]pyrimidinyl, 2-benzofuro[3,2-d]pyrazinyl, 6-benzofuro[3,2-d]pyrazinyl, 7-benzofuro[3,2-d]pyrazinyl, 8-benzofuro[3,2-d]pyrazinyl, 9-benzofuro[3,2-d]pyrazinyl, 2-benzothio[3,2-d]pyrazinyl, 6-benzothio[3,2-d]pyrazinyl, 7-benzothio[3,2-d]pyrazinyl, 8-benzothio[3,2-d]pyrazinyl, 9-benzothio[3,2-d]pyrazinyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, 1-dibenzoselenophenyl, 2-dibenzoselenophenyl, 3-dibenzoselenophenyl, 4-dibenzoselenophenyl, etc. Furthermore, "halogen" includes F, Cl, Br, and I.

In addition, "ortho (o-)." "meta (m-)," and "para (p-)" are prefixes, which represent the relative positions of substituents respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent, and substituted with a group in which two or more substituents are connected among the substituents. For example, "a substituent in which two or more substituents are connected" may be pyridine-triazine. That is, pyridine-triazine may be heteroaryl or may be interpreted as a substituent in which two heteroaryls are connected.

The substituents of the substituted alkyl, the substituted cycloalkyl, the substituted heterocycloalkyl, the substituted aryl, the substituted arylene, the substituted heteroaryl, the substituted heteroarylene, the substituted silyl, and the substituted amino in the formulas of the present disclosure each independently are at least one selected from the group consisting of deuterium; a halogen; a cyano; a carboxyl; a nitro; a hydroxyl; a phosphine oxide; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with at least one of a (C1-C30)alkyl(s) and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C2-C30)alkenylamino; a mono- or di-(C6-C30)arylamino; a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a (C6-C30)arylphosphine; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl. According to one embodiment of the present disclosure, the substituents each independently are at least one selected from the group consisting of a (C1-C6)alkyl, a (C6-C20)aryl, a (5- to 15-membered) heteroaryl unsubstituted or substituted with a (C6-C15)aryl(s), a di(C6-C12)arylamino, and a (C1-C6)alkyl(C6-C15)aryl. Specifically, the substituents each independently may be at least one selected from the group consisting of methyl, phenyl, naphthyl, biphenyl, phenanthrenyl, benzophenanthrenyl, dimethylfluorenyl, dibenzofuranyl, dibenzothiophenyl, diphenyltriazinyl, phenylnaphthyltriazinyl, phenylcarbazolyl, and diphenylamino.

In formula 1, ring A is selected from the following formulas.

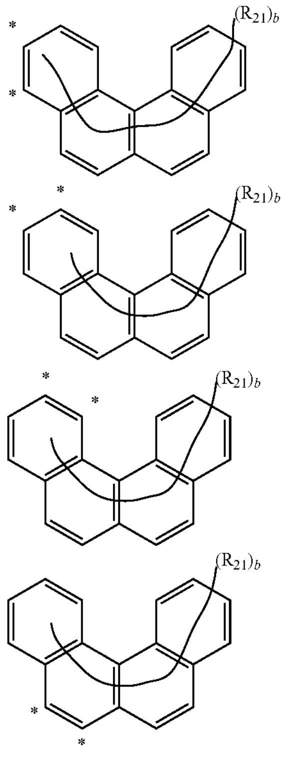

According to another embodiment of the present disclosure, ring A is selected from the following formulas.

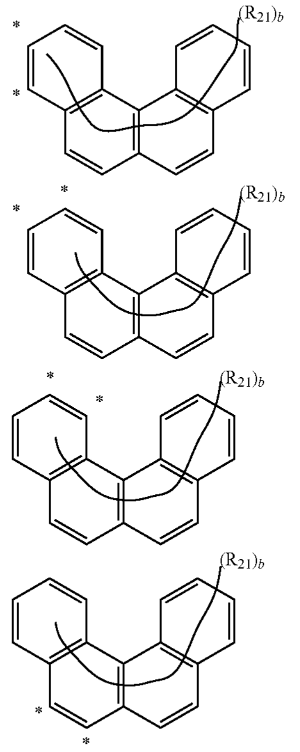

According to still another embodiment of the present disclosure, ring A is selected from the following formulas.

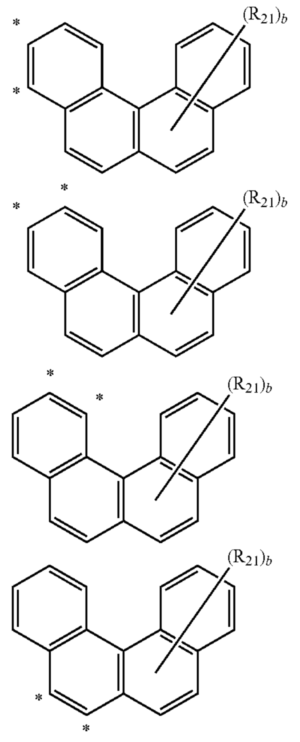

According to yet another embodiment of the present disclosure, ring A is selected from the following formulas.

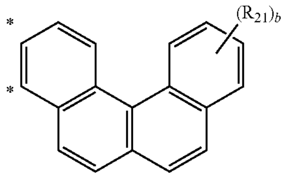

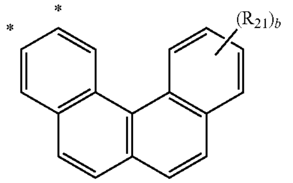

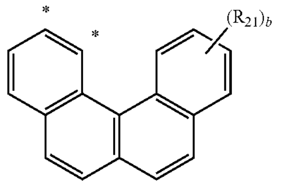

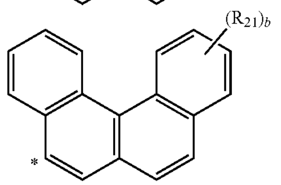

In formula 1, X represents $NR_{11}$, $CR_{12}R_{13}$, O, or S.

Herein, $R_{11}$ represents hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted (C6-C30)aryl, a substituted or unsubstituted (3- to 30-membered)heteroaryl, a substituted or unsubstituted silyl, or a substituted or unsubstituted amino. According to one embodiment of the present disclosure, $R_{11}$ represents a substituted or unsubstituted (C6-C15) aryl, or a substituted or unsubstituted (5- to 15-membered) heteroaryl containing a nitrogen atom(s). According to another embodiment of the present disclosure. $R_{11}$ represents a (C6-C15)aryl substituted with at least one of a (5- to 15-membered)heteroaryl(s) containing a nitrogen atom(s) and a di(C6-C15)arylamino(s); or a (5- to 15-membered) heteroaryl containing a nitrogen atom(s) substituted with at least one of a (C6-C20)aryl(s) and a (5- to 15-membered) heteroaryl(s). According to another embodiment of the present disclosure, the substituted or unsubstituted (3- to 30-membered)heteroaryl of $R_{11}$ to $R_{13}$ each independently represents a substituted or unsubstituted pyridyl, a substituted or unsubstituted pyrimidinyl, a substituted or unsubstituted triazinyl, a substituted or unsubstituted pyrazinyl, a substituted or unsubstituted quinolyl, a substituted or unsubstituted quinazolinyl, a substituted or unsubstituted quinoxalinyl, a substituted or unsubstituted benzoquinolyl, a substituted or unsubstituted benzoquinazolinyl, a substituted or unsubstituted benzoquinoxalinyl, a substituted or unsubstituted dibenzoquinolyl, a substituted or unsubstituted dibenzoquinazolinyl, a substituted or unsubstituted dibenzoquinoxalinyl, a substituted or unsubstituted indenopyridyl, a substituted or unsubstituted indenopyrimidinyl, a substituted or unsubstituted indenopyrazinyl, a substituted or unsubstituted benzofuropyridyl, a substituted or unsubstituted benzofuropyrimidinyl, a substituted or unsubstituted benzofuropyrazinyl, a substituted or unsubstituted benzothiopyridyl, a substituted or unsubstituted benzothiopyrimidinyl, a substituted or unsubstituted benzothiopyranyl, a substituted or unsubstituted carbazolyl, a substituted or unsubstituted dibenzofuranyl, or a substituted or unsubstituted dibenzothiophenyl. Specifically, $R_{11}$ may represent a phenyl substituted with a diphenyltriazinyl or a diphenylamino; a naphthyl substituted with a diphenyltriazinyl or a phenylnaphthyltriazinyl; a triazinyl, quinazolinyl, quinoxalinyl, or benzoquinoxalinyl, which is substituted with at least one of a phenyl(s), a naphthyl(s), a biphenyl(s), a phenanthrenyl(s), a benzophenanthrenyl(s), a dibenzofuranyl(s), a dibenzothiophenyl(s), and a phenylcarbazolyl(s); etc.

In addition, $R_{12}$ and $R_{13}$ each independently represent hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered)heterocycloalkyl, a substituted or unsubstituted (C6-C30)aryl, a substituted or unsubstituted (3- to 30-membered)heteroaryl, a substituted or unsubstituted silyl, or a substituted or unsubstituted amino; or are linked to each other to form a ring. According to one embodiment of the present disclosure, $R_{12}$ and $R_{13}$ each independently represent a methyl, an ethyl, or a propyl.

In formula 1, $R_{21}$ represents $-L_1-Ar_1$. If $R_{21}$ is plural, each of $R_{21}$ may be the same or different.

Herein, $L_1$ each independently represents a single bond, a substituted or unsubstituted (C6-C30)arylene, or a substituted or unsubstituted (3- to 30-membered)heteroarylene. According to one embodiment of the present disclosure, $L_1$ each independently represents a single bond, a substituted or unsubstituted (C6-C15)arylene, or a substituted or unsubstituted (5- to 15-membered)heteroarylene. According to another embodiment of the present disclosure, $L_1$ each independently represents a single bond, a (C6-C15)arylene unsubstituted or substituted with a (C6-C15)aryl(s), or an unsubstituted (5- to 15-membered)heteroarylene. According to still another embodiment of the present disclosure, $L_1$ each independently represents a single bond, a substituted or unsubstituted phenylene, a substituted or unsubstituted biphenylene, a substituted or unsubstituted terphenylene, a substituted or unsubstituted naphthylene, a substituted or unsubstituted phenanthrenylene, a substituted or unsubstituted triphenylenylene, a substituted or unsubstituted fluorenylene, or a substituted or unsubstituted pyridylene. Specifically, $L_1$ may each independently represent a single bond, a phenylene, a naphthylene, a biphenylene, a phenylene substituted with a phenyl, a pyridylene, etc.

In addition, $Ar_1$ each independently represents hydrogen, deuterium, a halogen, a cyano, a substituted or unsubstituted (C1-C30)alkyl, a substituted or unsubstituted (C3-C30)cycloalkyl, a substituted or unsubstituted (3- to 7-membered) heterocycloalkyl, a substituted or unsubstituted (C6-C30) aryl, a substituted or unsubstituted (3- to 30-membered) heteroaryl, a substituted or unsubstituted silyl, or a substituted or unsubstituted amino. According to one embodiment of the present disclosure, $Ar_1$ each independently represents hydrogen, a substituted or unsubstituted (5- to 15-membered)heteroaryl containing a nitrogen atom(s), or a substituted or unsubstituted amino. According to another embodiment of the present disclosure, $Ar_1$ each independently represents hydrogen; a (5- to 15-membered) heteroaryl substituted with at least one of a (C6-C15)aryl(s), a (5- to 15-membered)heteroaryl(s), and a (C1-C6)alkyl(C6-C15)aryl(s); or an amino substituted with at least one of a (C6-C15)aryl(s), a (5- to 15-membered)heteroaryl(s), and a (C1-C6)alkyl(C6-C15)aryl(s). According to still another embodiment of the present disclosure, the substituted or unsubstituted (3- to 30-membered)heteroaryl of $Ar_1$ each independently represents a substituted or unsubstituted pyridyl, a substituted or unsubstituted pyrimidinyl, a substituted or unsubstituted triazinyl, a substituted or unsubstituted pyrazinyl, a substituted or unsubstituted quinolyl, a substituted or unsubstituted quinazolinyl, a substituted or unsubstituted quinoxalinyl, a substituted or unsubstituted benzoquinolyl, a substituted or unsubstituted benzoquinazolinyl, a substituted or unsubstituted benzoquinoxalinyl, a substituted or unsubstituted dibenzoquinolyl, a substituted or unsubstituted dibenzoquinazolinyl, a substituted or unsubstituted dibenzoquinoxalinyl, a substituted or unsubstituted indenopyridyl, a substituted or unsubstituted indenopyrimidinyl, a substituted or unsubstituted indenopyrazinyl, a substituted or unsubstituted benzofuropyridyl, a substituted or unsubstituted benzofuropyrimidinyl, a substituted or unsubstituted benzofuropyrazinyl, a substituted or unsubstituted benzothiopyridyl, a substituted or unsubstituted benzothiopyrimidinyl, a substituted or unsubstituted benzothiopyranyl, a substituted or unsubstituted carbazolyl, a substituted or unsubstituted dibenzofuranyl, or a substituted or unsubstituted dibenzothiophenyl. Specifically, $Ar_1$ may each independently represent hydrogen; a triazinyl, quinazolinyl, quinoxalinyl, or benzoquinoxalinyl, which is substituted with at least one of a phenyl(s), a naphthyl(s), a biphenyl(s), a phenanthrenyl(s), a dimethylfluorenyl(s), a dibenzofuranyl(s), and a dibenzothiophenyl(s); an amino which is substituted with at least one of a phenyl(s), a naphthyl(s), a biphenyl(s), a dimethylfluorenyl(s), a dibenzofuranyl(s), a dibenzothiophenyl(s), and a phenylcarbazolyl(s), etc.

In formula 1, a represents an integer of 1 to 4, b represents an integer of 1 to 10, where if a and b are an integer of 2 or more, each of $R_1$ and each of $R_{21}$ may be the same or different.

According to one embodiment of the present disclosure, $R_{18}$ represents a substituted or unsubstituted (C6-C15)aryl, or a substituted or unsubstituted (5- to 15-membered)heteroaryl containing a nitrogen atom(s); $L_1$ each independently represents a single bond, a substituted or unsubstituted (C6-C15)arylene, or a substituted or unsubstituted (5- to 15-membered)heteroarylene; and $Ar_1$ each independently represents hydrogen, a substituted or unsubstituted (5- to 15-membered)heteroaryl containing a nitrogen atom(s), or a substituted or unsubstituted amino.

According to another embodiment of the present disclosure, $R_{11}$ represents a (C6-C15)aryl unsubstituted or substituted with at least one of a (5- to 15-membered)heteroaryl(s) containing a nitrogen atom(s) and a di(C6-C15)arylamino(s); or a (5- to 15-membered)heteroaryl containing a nitrogen atom(s) substituted with at least one of a (C6-C20)aryl(s) and a (5- to 15-membered)heteroaryl(s); $L_1$ each independently represents a single bond, a (C6-C15)arylene unsubstituted or substituted with a (C6-C15)aryl(s), or an unsubstituted (5- to 15-membered)heteroarylene; $Ar_1$ each independently represents hydrogen; a (5- to 15-membered) heteroaryl substituted with at least one of a (C6-C15)aryl(s), a (5- to 15-membered)heteroaryl(s), and a (C1-C6)alkyl(C6-C15)aryl(s); or an amino substituted with at least one of a (C6-C15)aryl(s), a (5- to 15-membered)heteroaryl(s), and a (C1-C6)alkyl(C6-C15)aryl(s).

In the formulas of the present disclosure, if a substituent is linked to an adjacent substituent or two adjacent substituents are linked to each other to form a ring, the ring may be a substituted or unsubstituted, mono- or polycyclic, (3- to 30-membered) aliphatic or aromatic ring, or the combination thereof. In addition, the formed ring may contain at least one heteroatom selected from B, N, O, S, Si, and P, preferably at least one heteroatom selected from N, O, and S. According to one embodiment of the present disclosure, the number of the ring backbone atoms is 5 to 20. According to another embodiment of the present disclosure, the number of the ring backbone atoms is 5 to 15. For example, the fused ring may be a substituted or unsubstituted dibenzothiophene ring, a substituted or unsubstituted dibenzofuran ring, a substituted or unsubstituted naphthalene ring, a substituted or unsubstituted phenanthrene ring, a substituted or unsubstituted fluorene ring, a substituted or unsubstituted benzothiophene ring, a substituted or unsubstituted benzofuran ring, a substituted or unsubstituted indole ring, a substituted or unsubstituted indene ring, a substituted or unsubstituted benzene ring, or a substituted or unsubstituted carbazole ring.

In the formulas of the present disclosure, heterocycloalkyl and heteroaryl(ene) may each independently contain at least one heteroatom selected from B, N, O, S, Si, and P. In addition, the heteroatom may be bonded to at least one substituent selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

The compound represented by formula 1 may be one selected from the following compounds, but is not limited thereto.

C-1

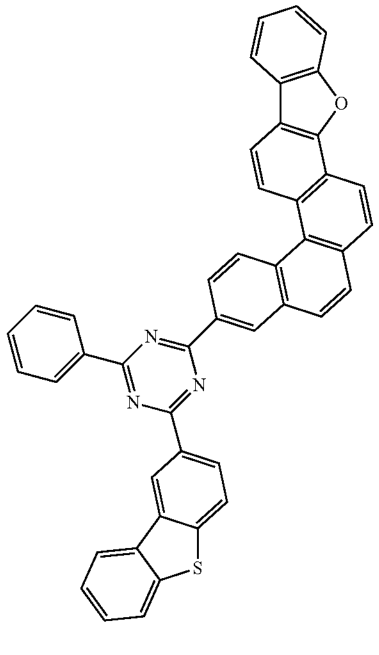

-continued
C-2
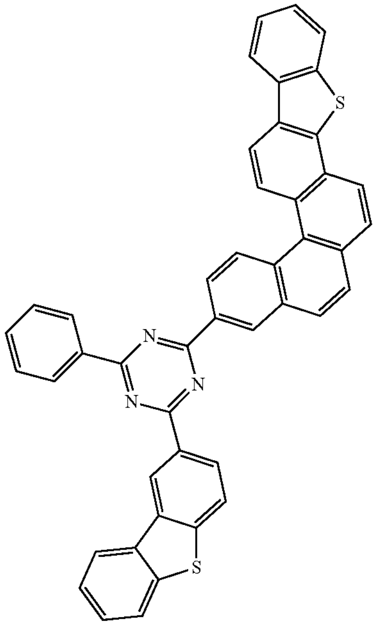
C-3
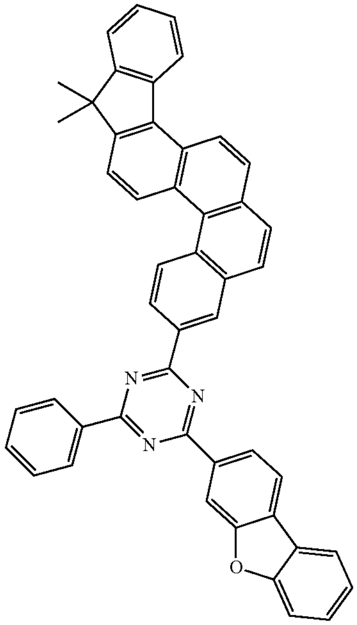
-continued
C-4
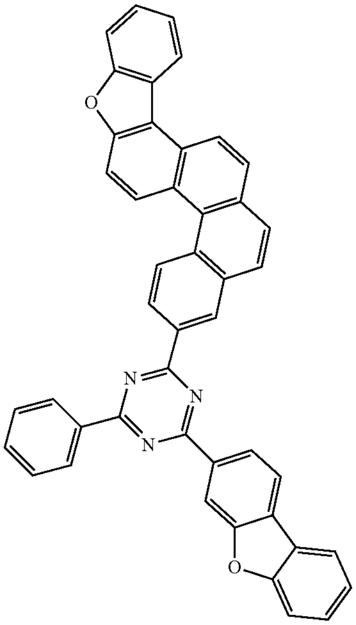
C-5
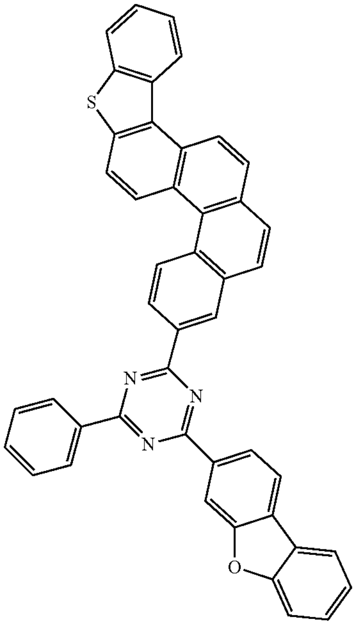

-continued
C-6
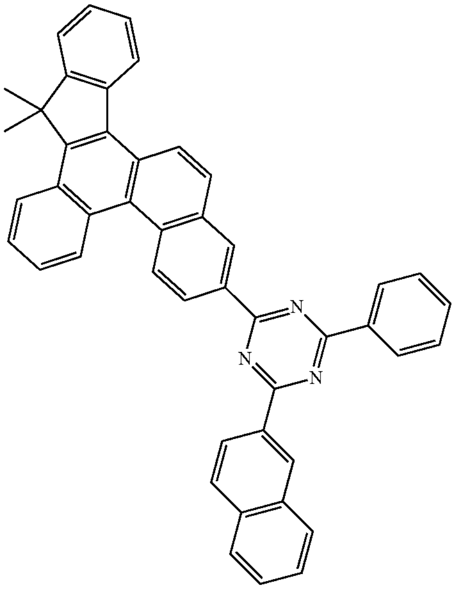
-continued
C-8
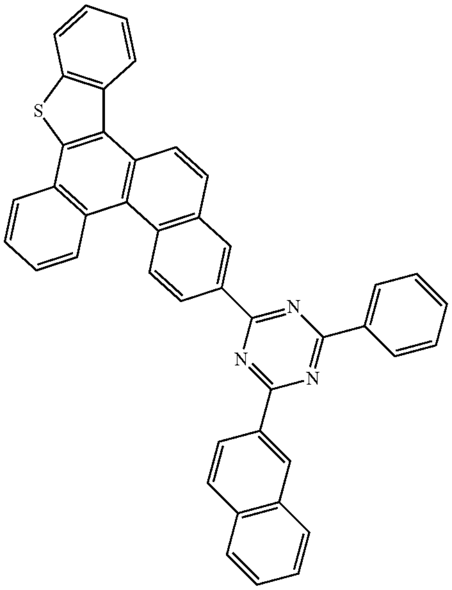
C-7
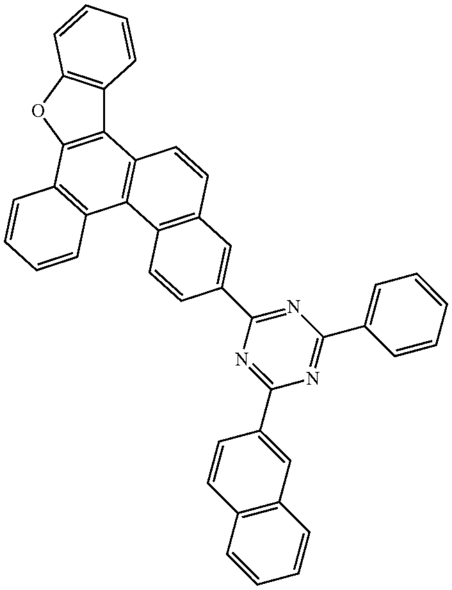
C-9
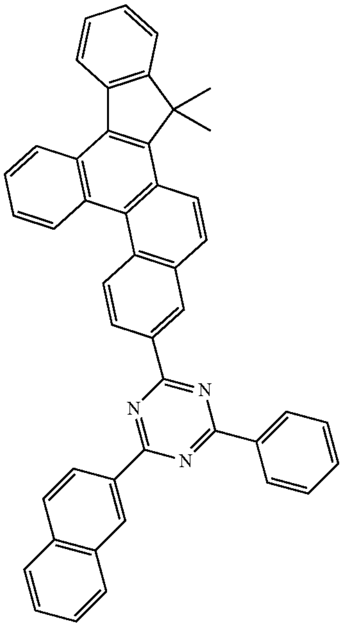

-continued
C-10
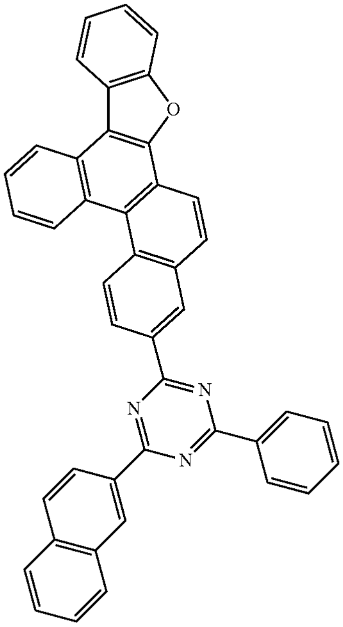
C-11
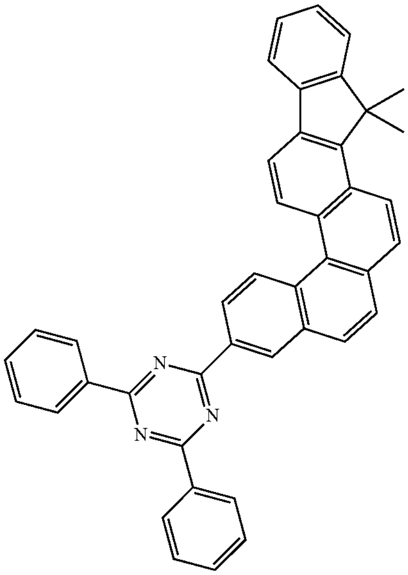
-continued
C-12
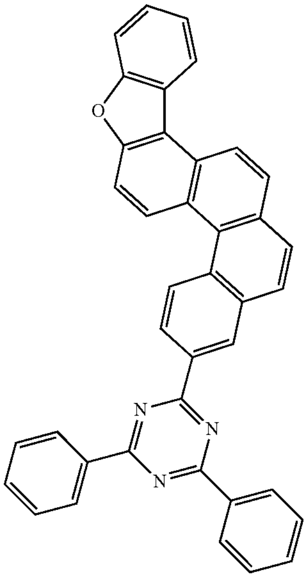
C-13
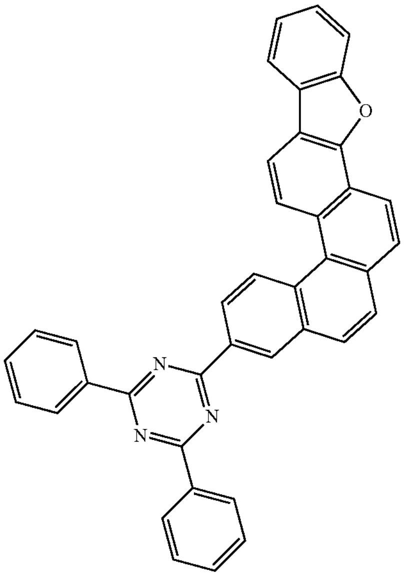

-continued
C-14
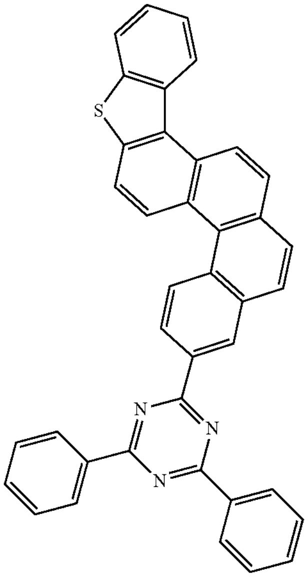
C-15
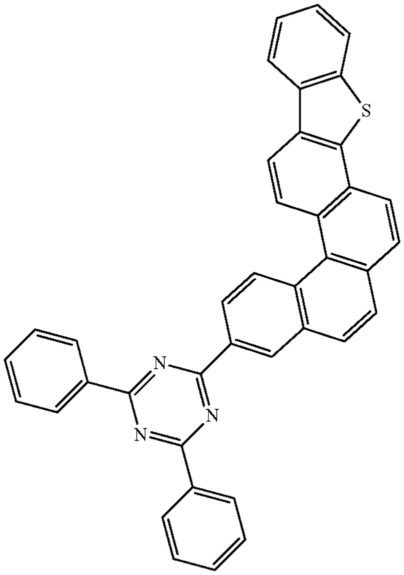
-continued
C-16
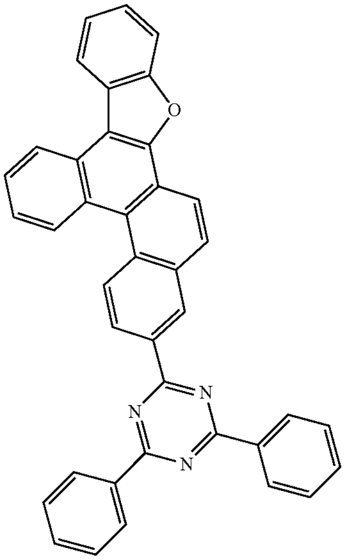
C-17
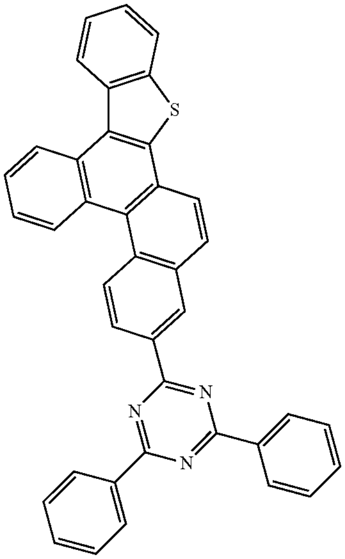

-continued
C-18
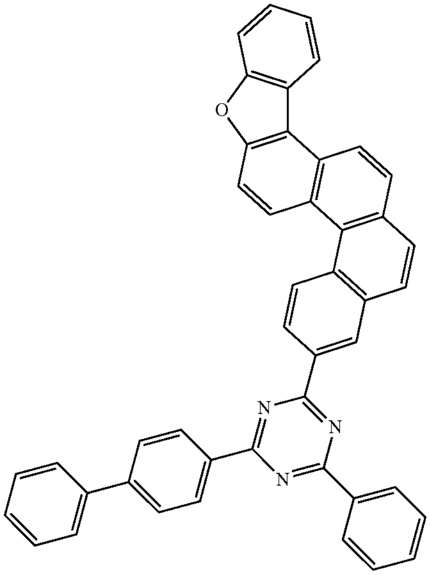
C-19
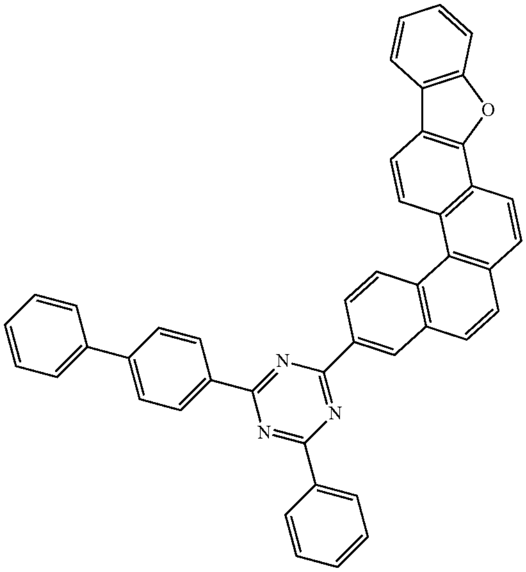
-continued
C-20
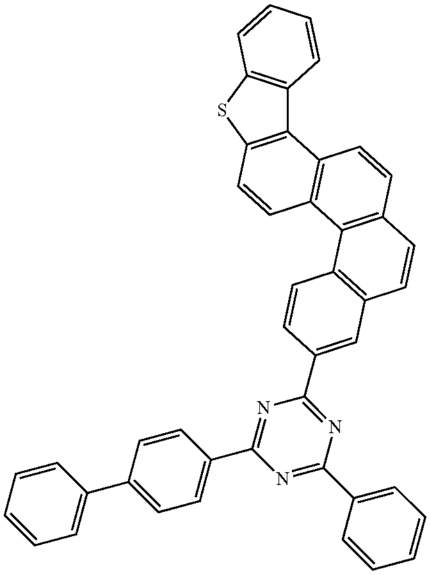
C-21
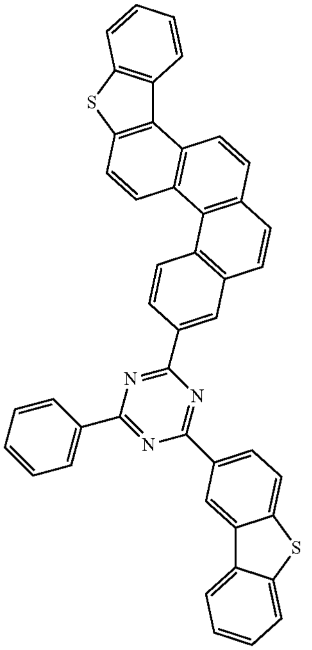

-continued
C-22
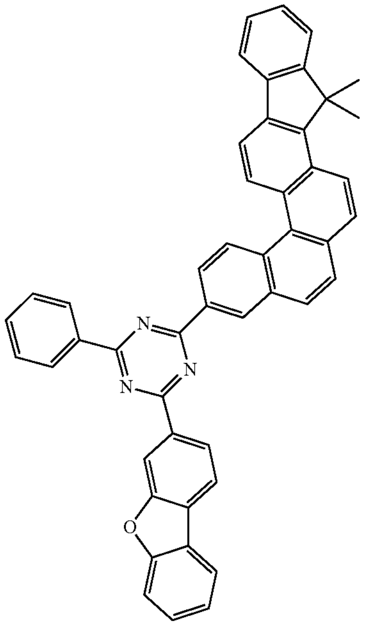
C-23
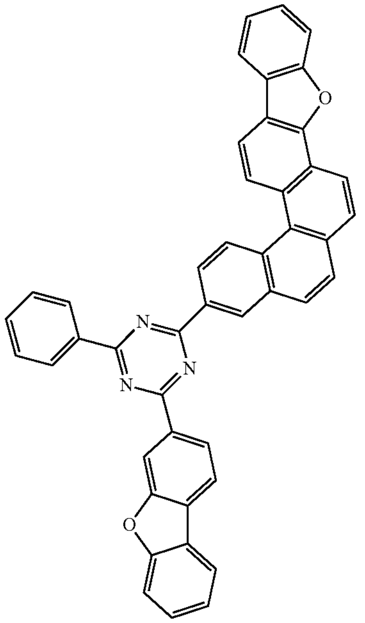
-continued
C-24
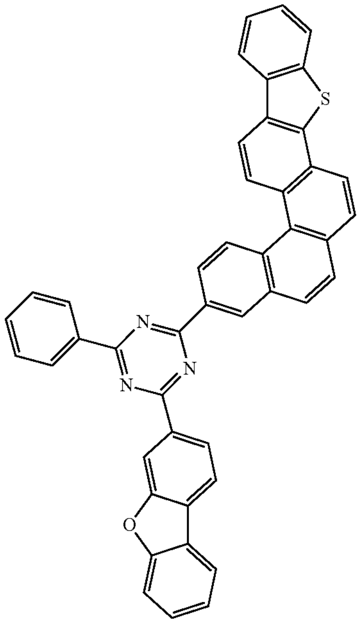
C-25
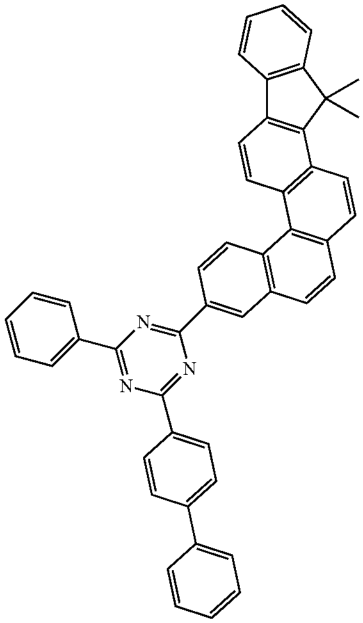

C-26
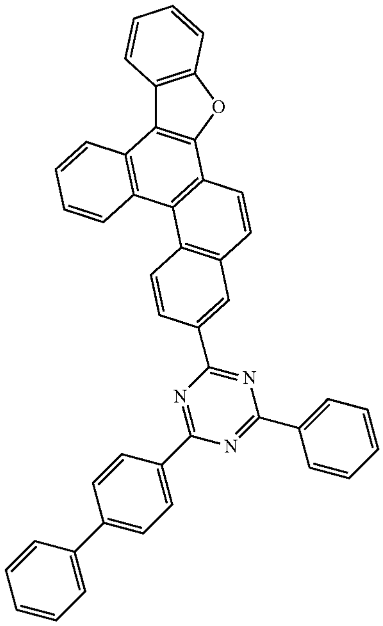
C-27
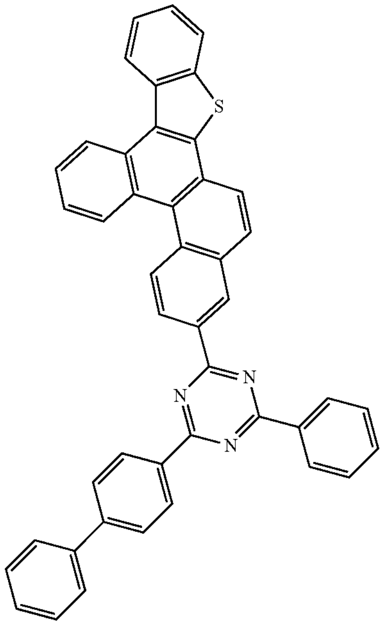
C-28
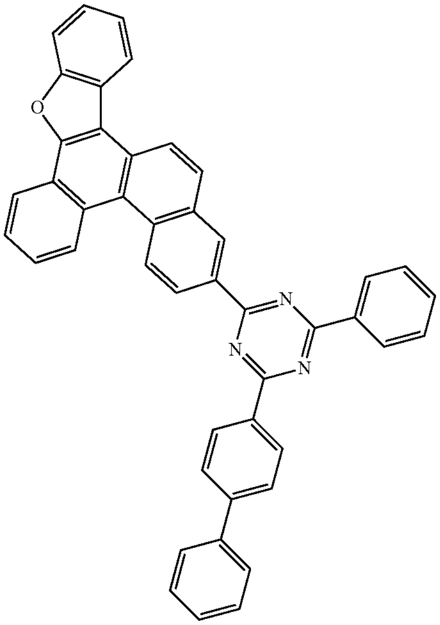
C-29
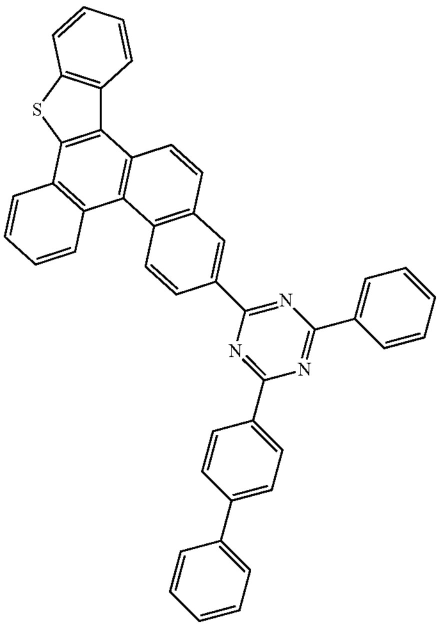

-continued
C-30
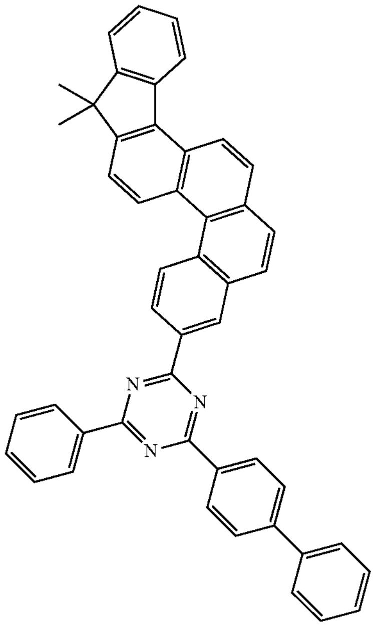
C-31
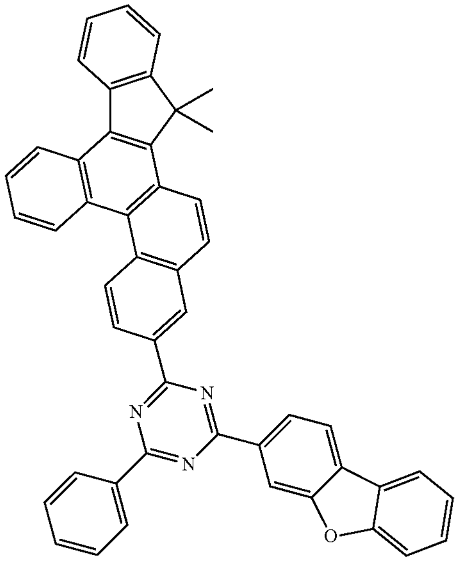
-continued
C-32
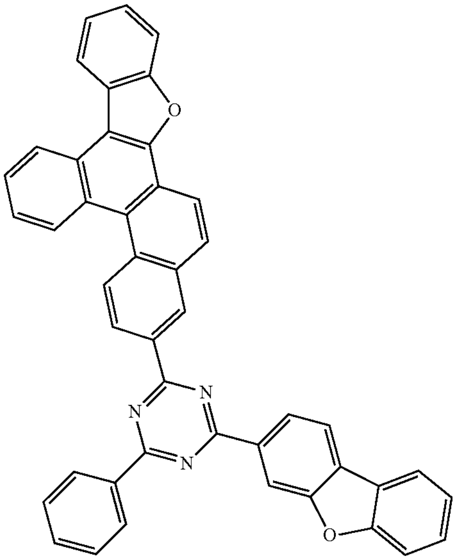
C-33
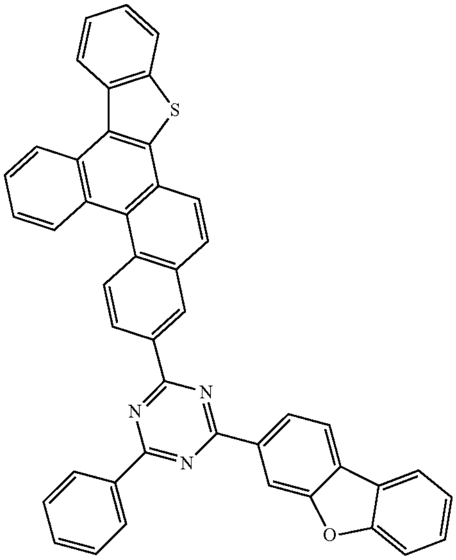

-continued
C-34
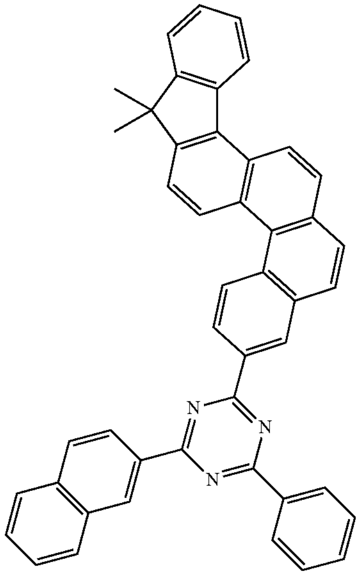
C-35
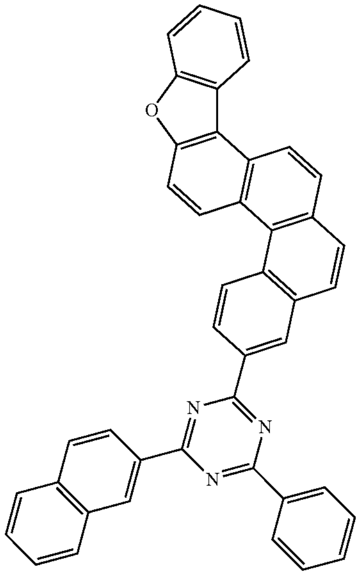
-continued
C-36
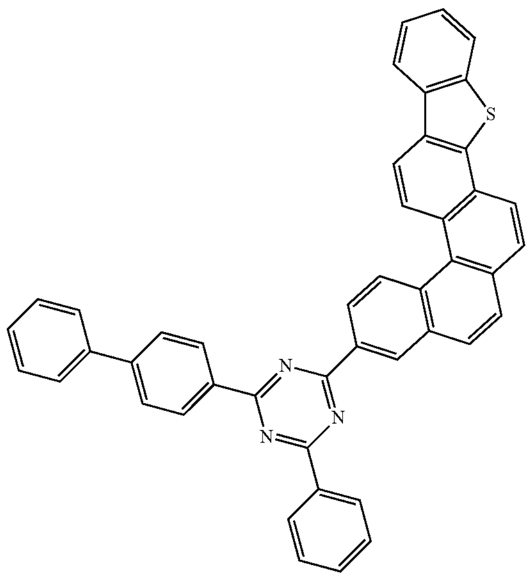
C-37
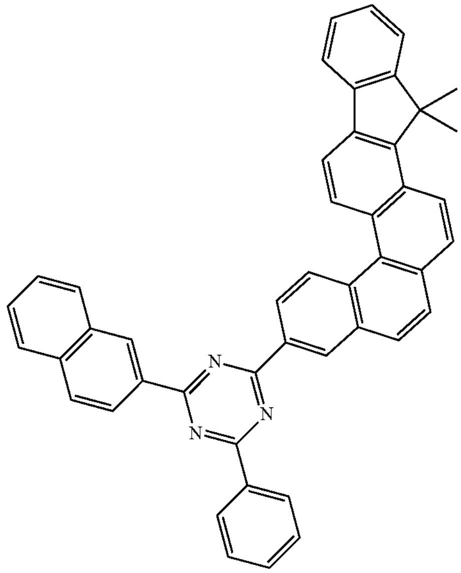

C-38
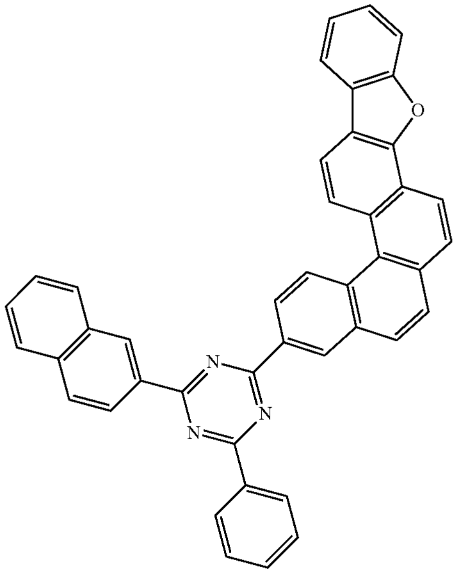
C-39
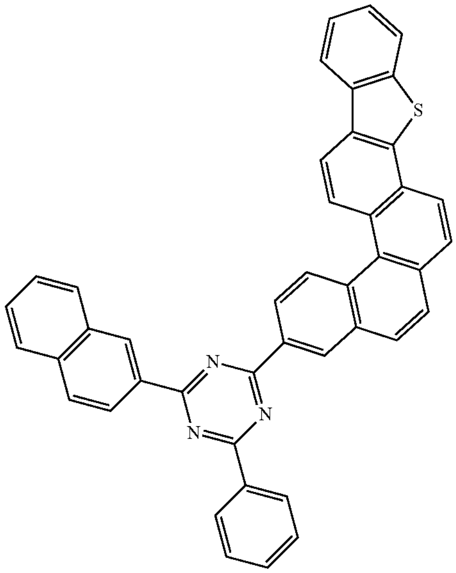
C-40
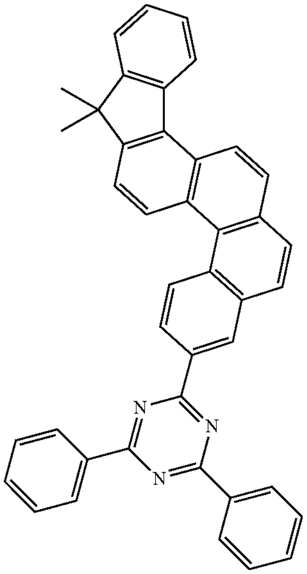
C-41
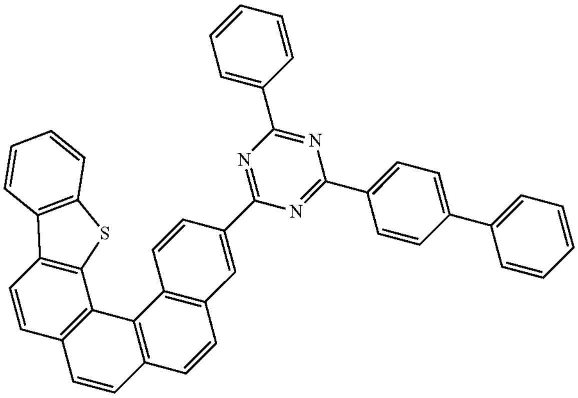
C-42
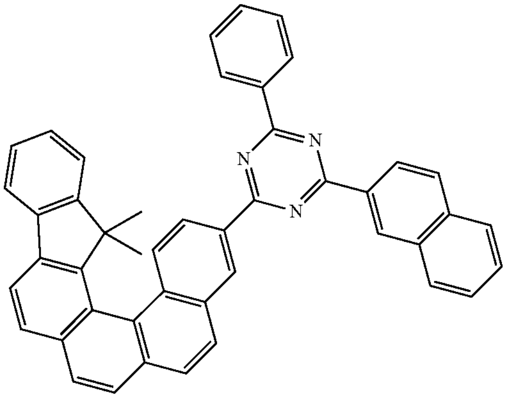

-continued
C-43
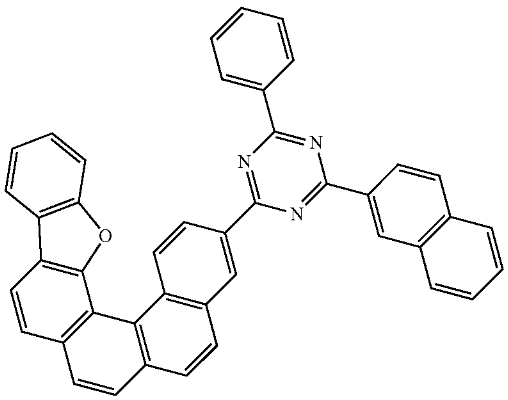
C-44
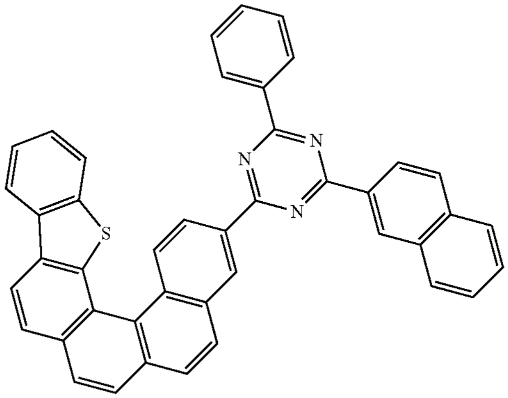
C-45
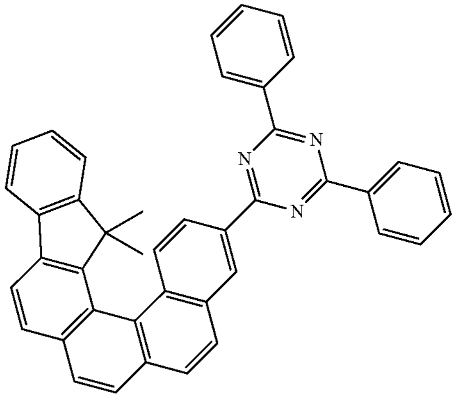
C-46
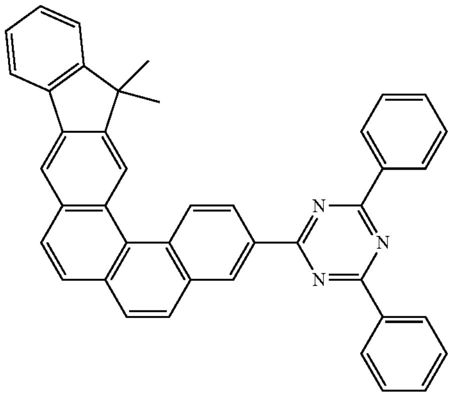
-continued
C-47
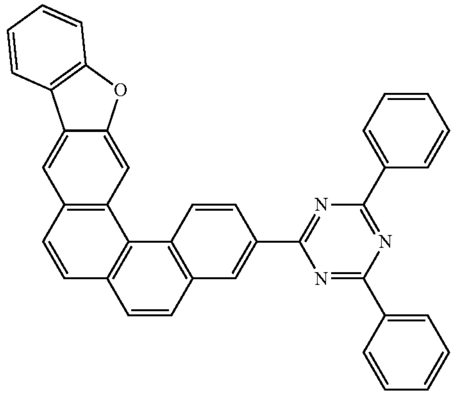
C-48
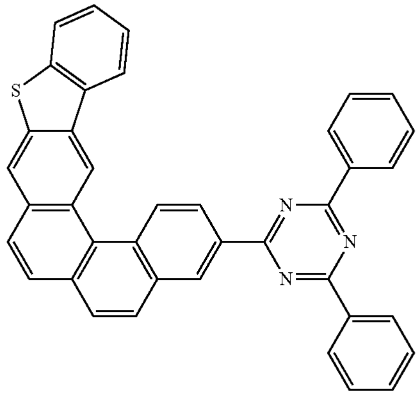
C-49
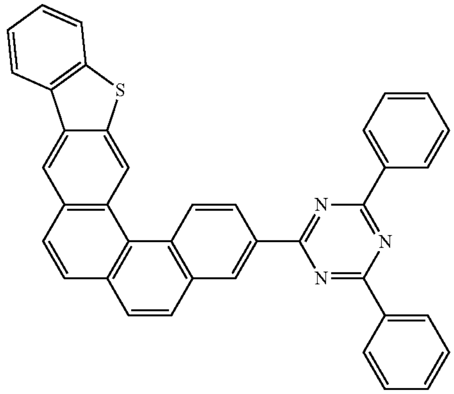
C-50
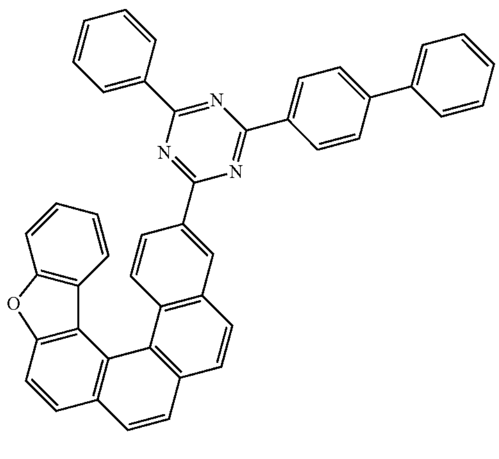

-continued
C-51
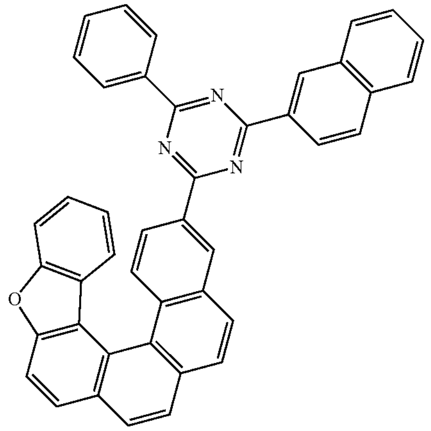
C-52
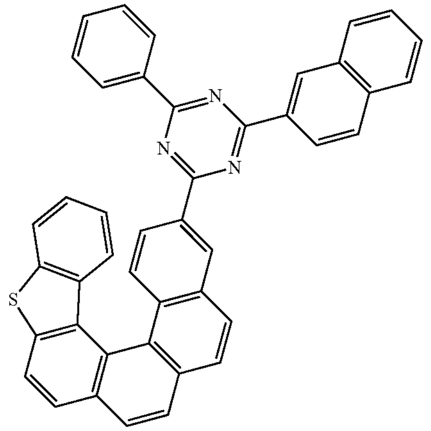
C-53
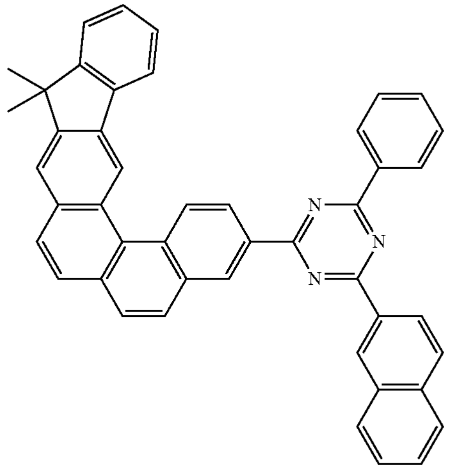
-continued
C-54
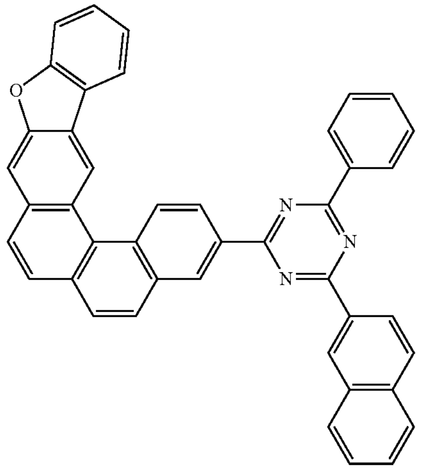
C-55
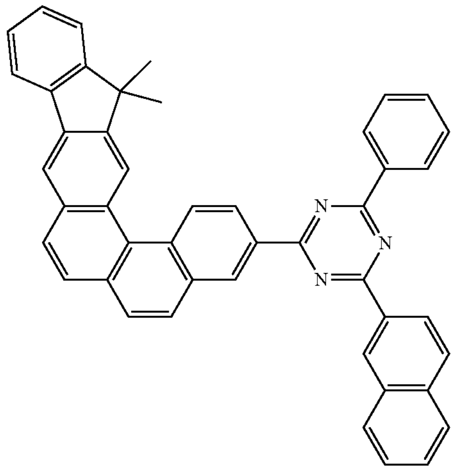
C-56
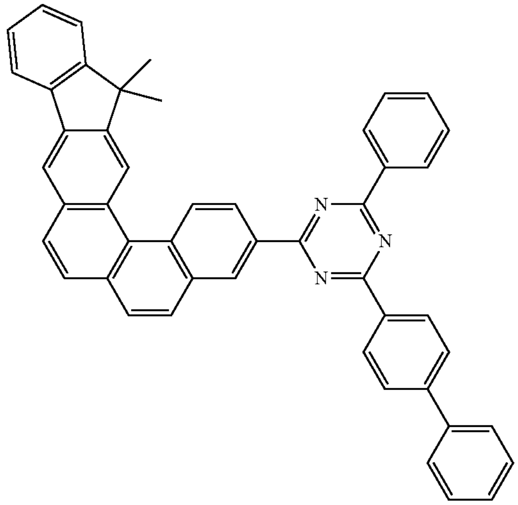

-continued
C-57
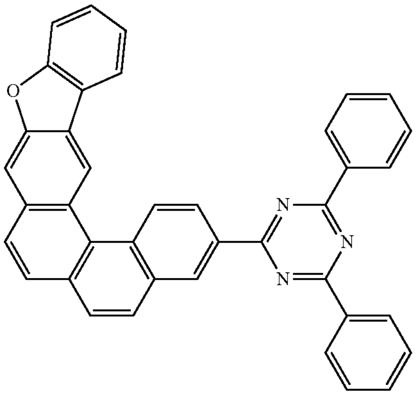
C-58
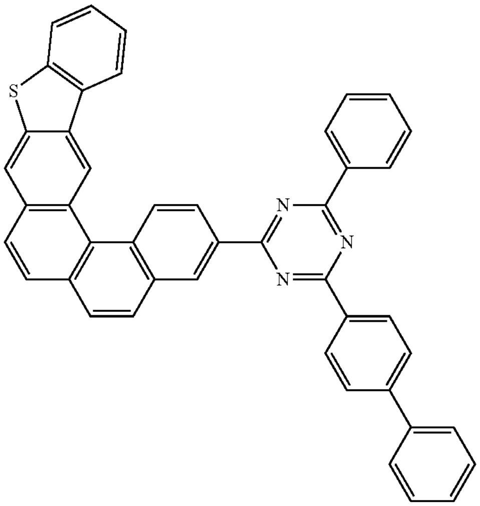
C-59
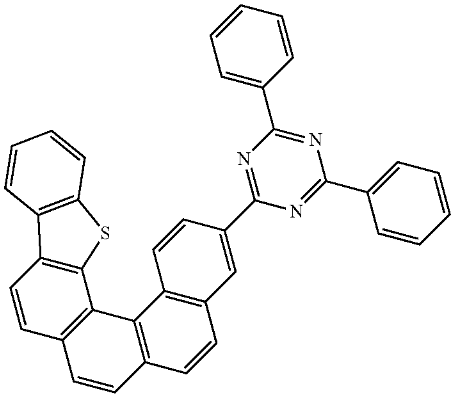
-continued
C-60
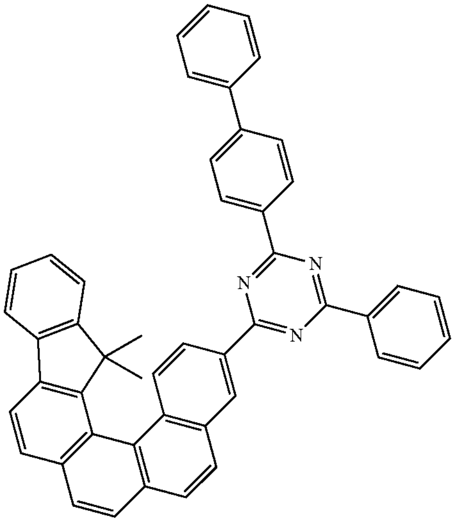
C-61
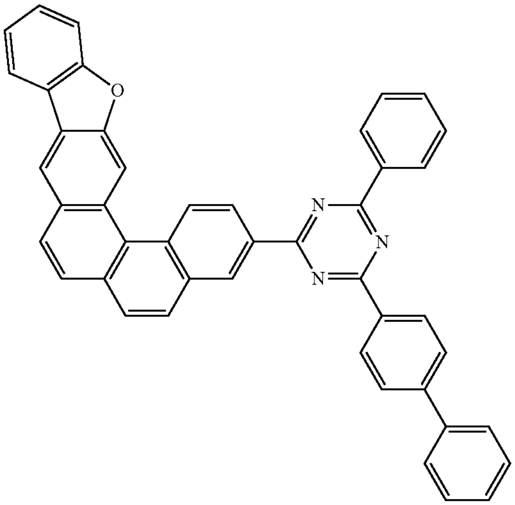
C-62
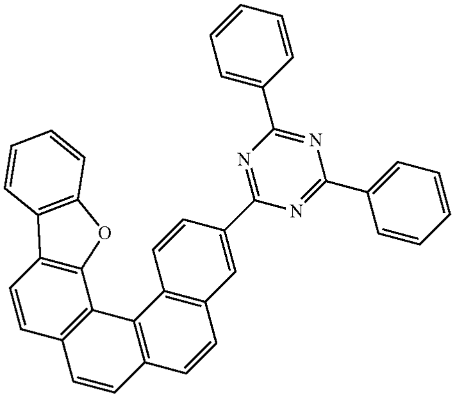

-continued
C-63
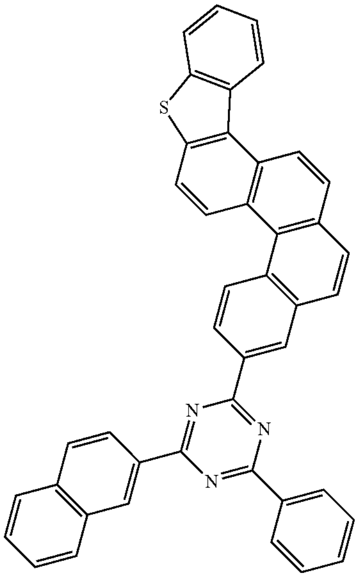
C-64
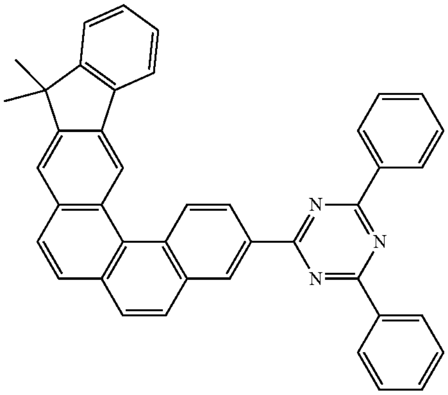
C-65
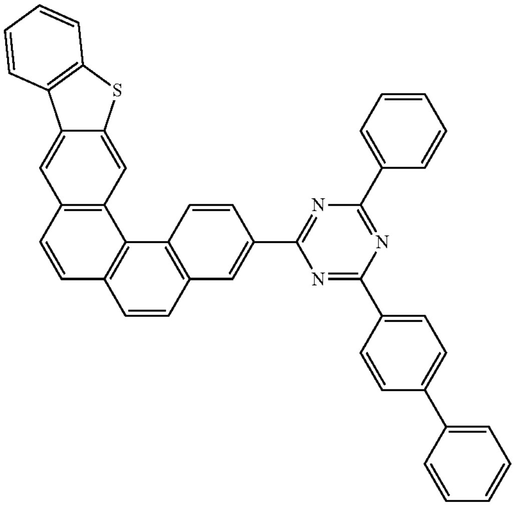
-continued
C-66
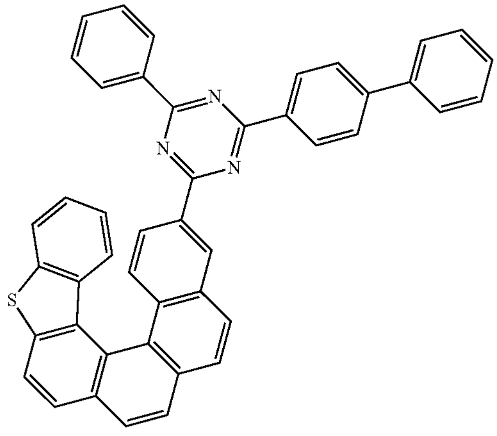
C-67
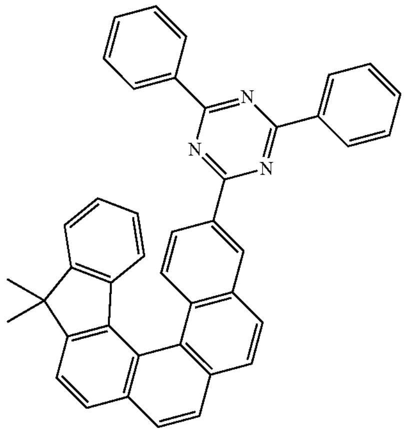
C-68
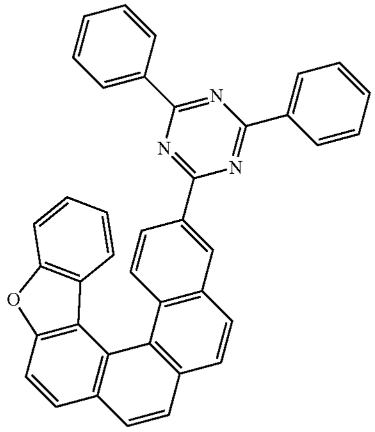

-continued
C-69
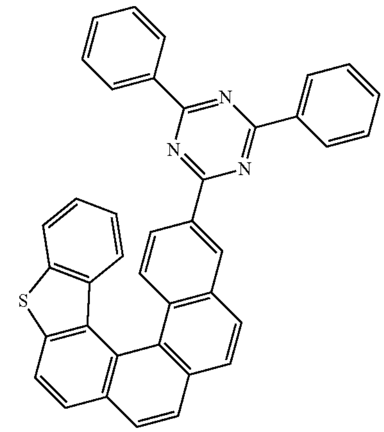
C-70
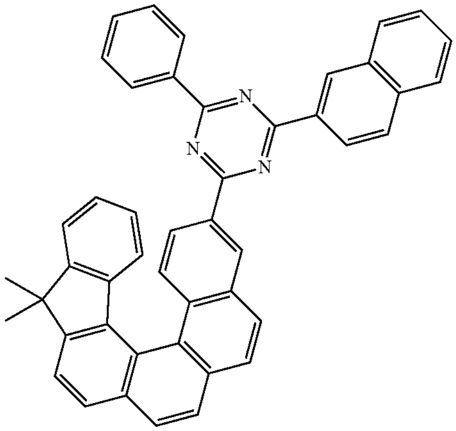
C-71
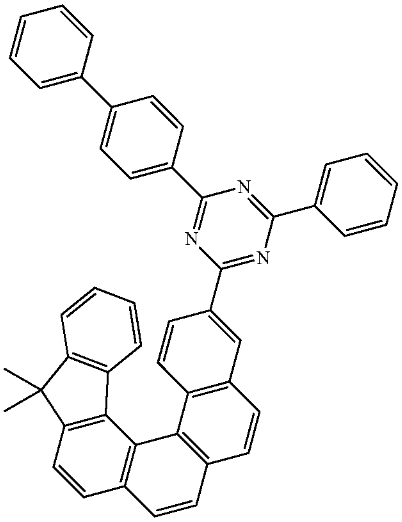
-continued
C-72
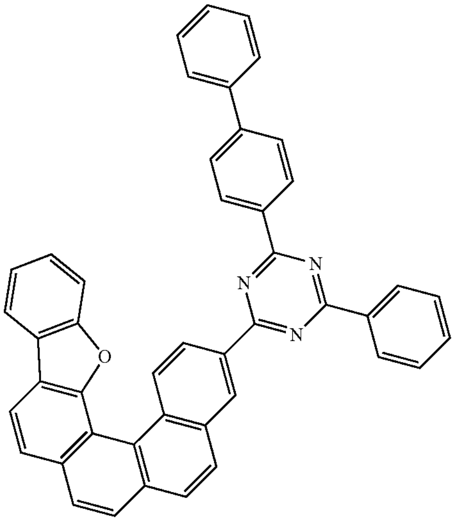
C-73
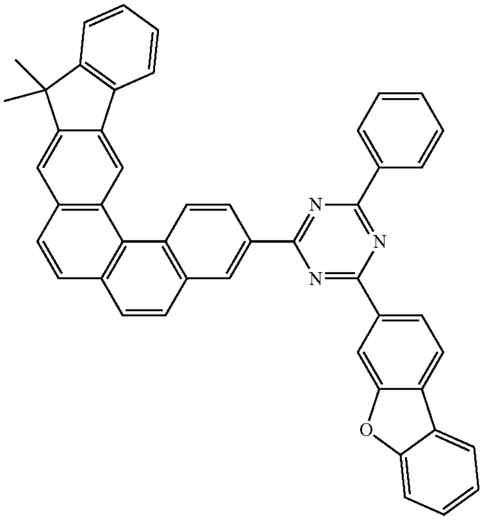
C-74
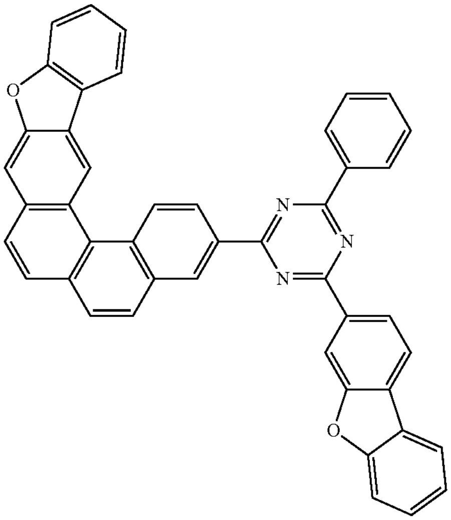

-continued
C-75
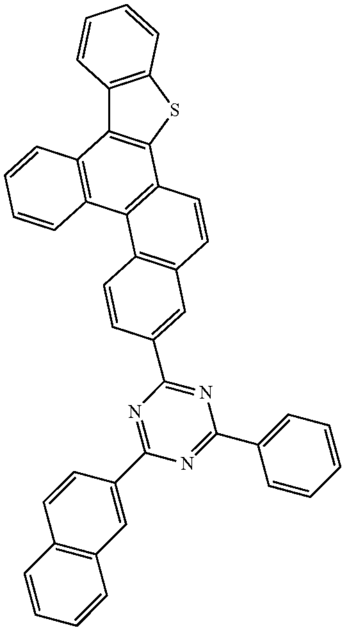
C-76
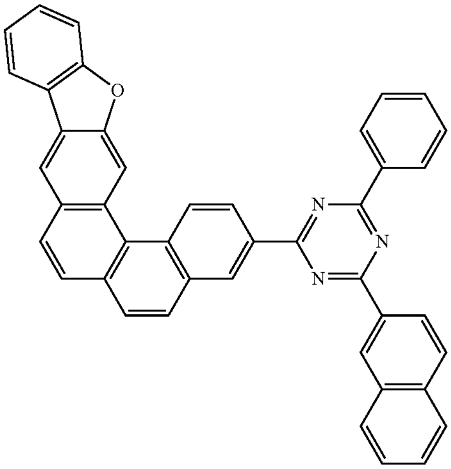
C-77
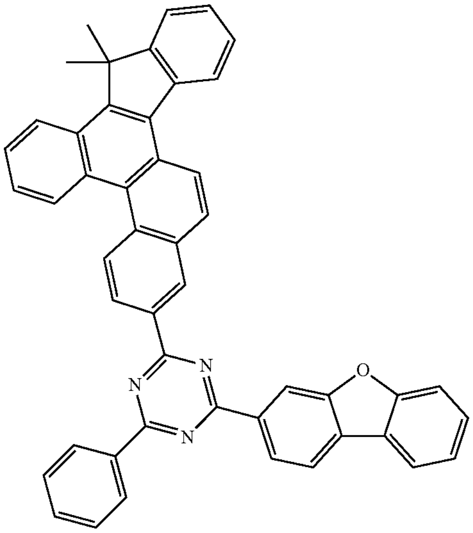
-continued
C-78
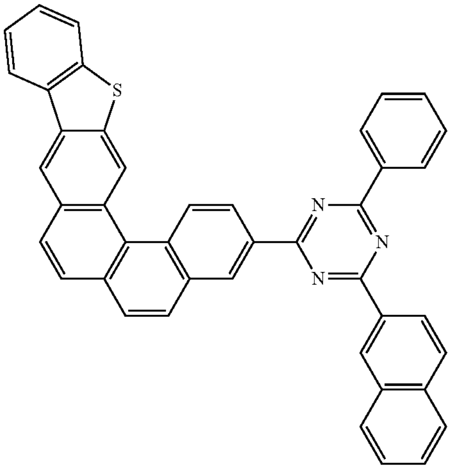
C-79
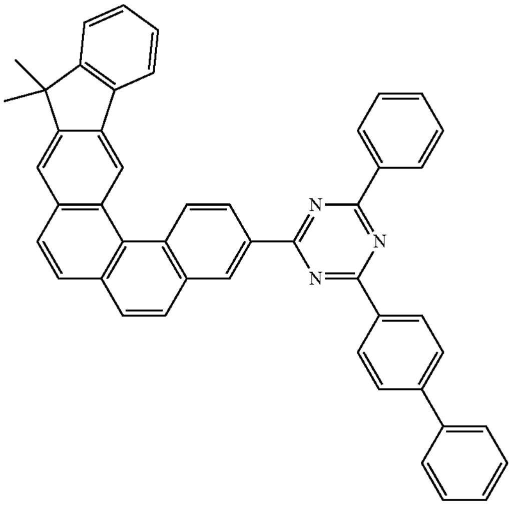
C-80
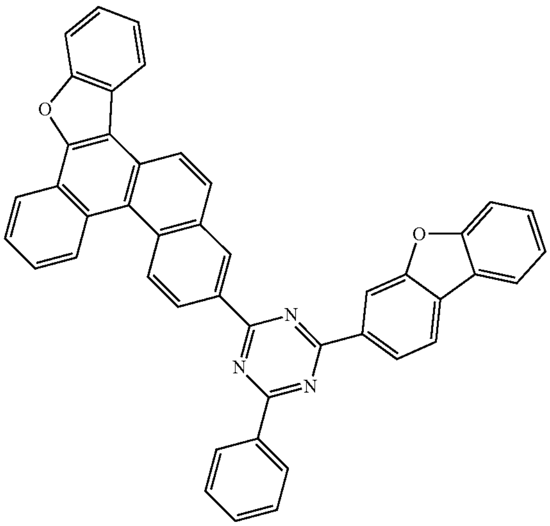

-continued
C-81
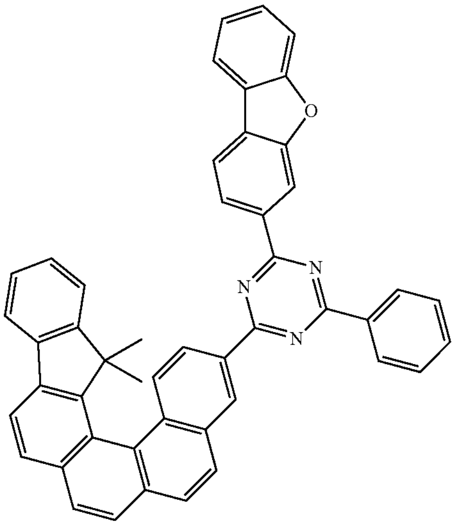
C-82
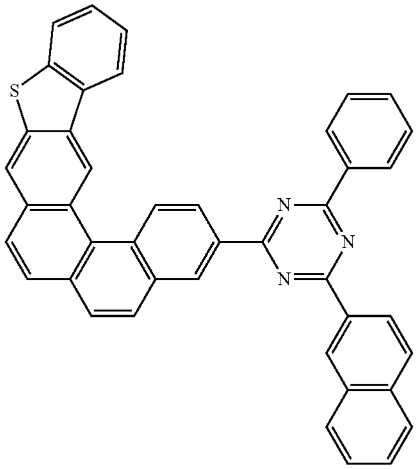
C-83
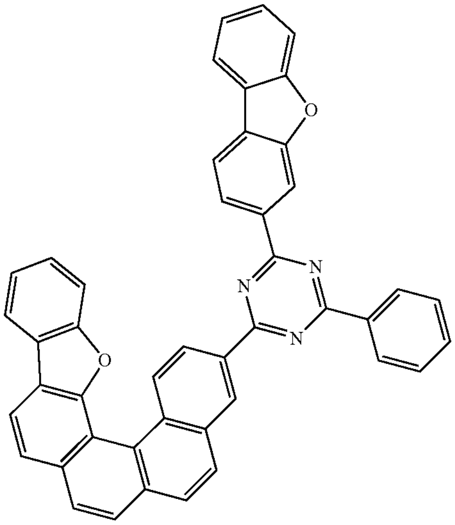
-continued
C-84
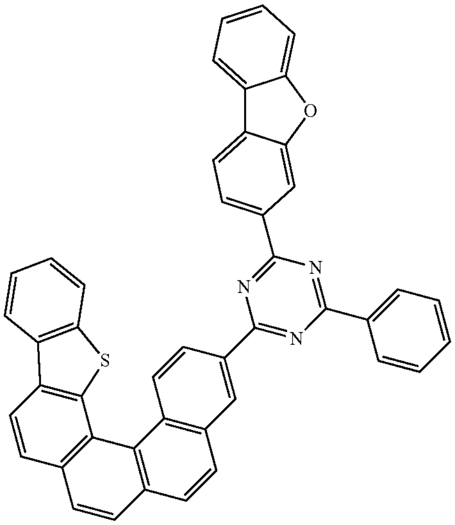
C-85
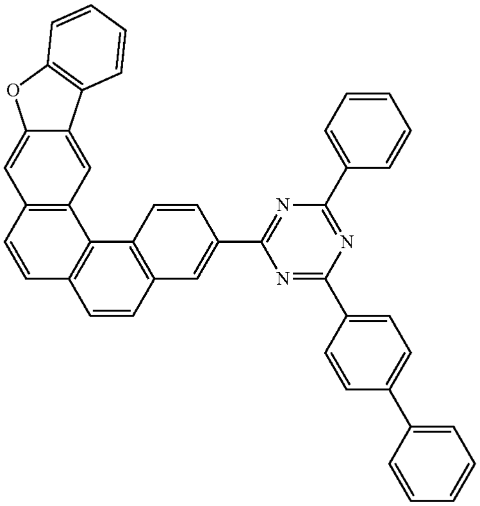
C-86
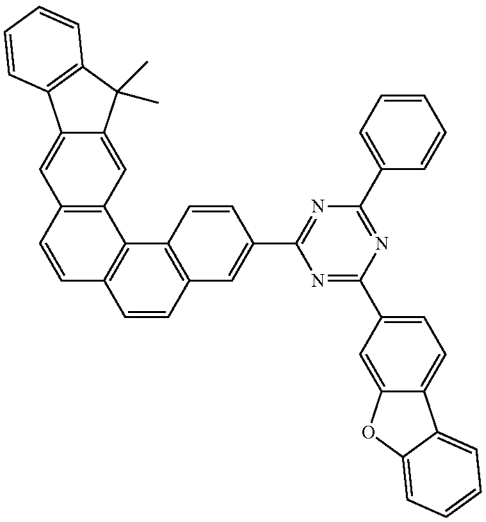

-continued
C-87
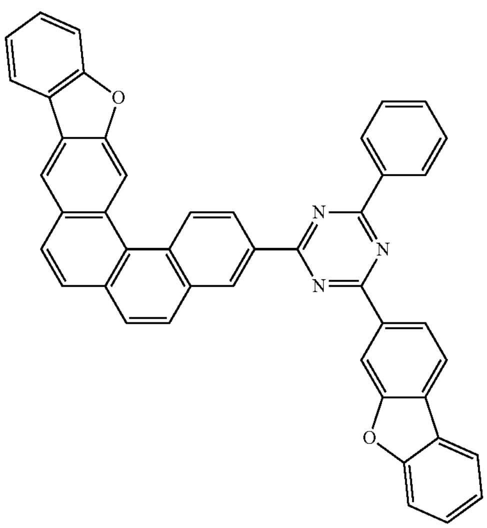
-continued
C-89
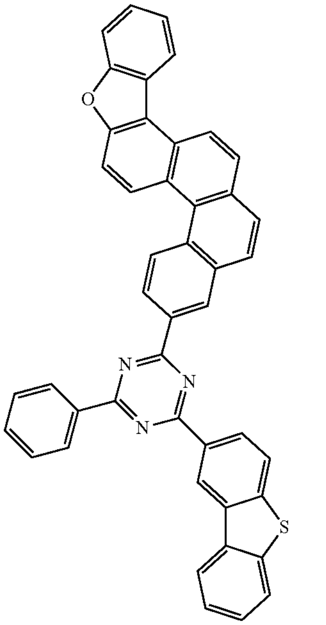
C-88
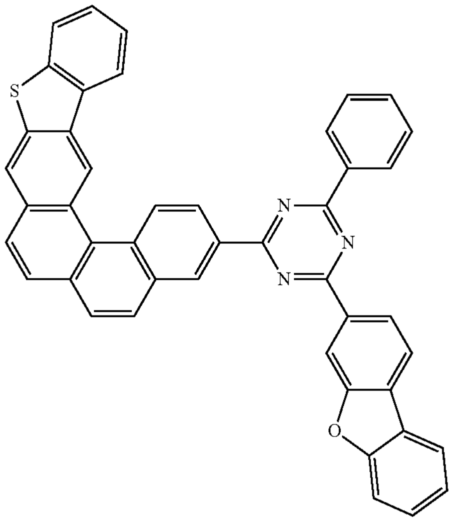
C-90
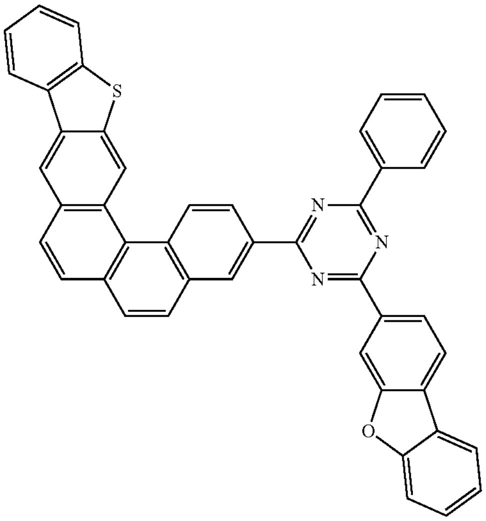

-continued
C-91
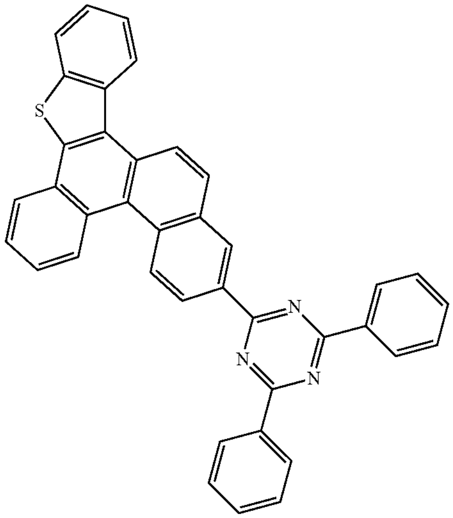
C-92
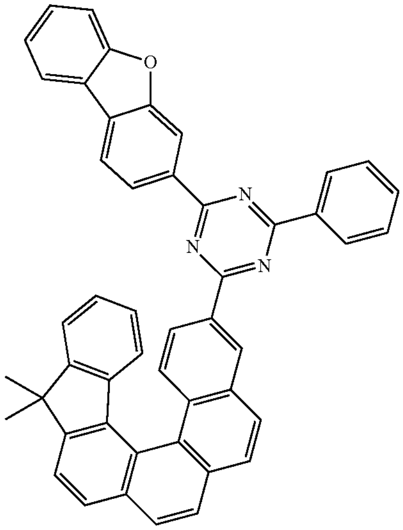
C-93
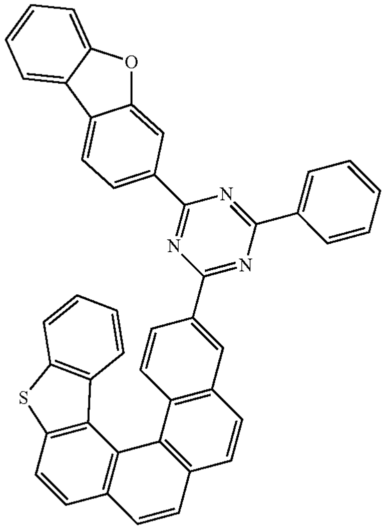
-continued
C-94
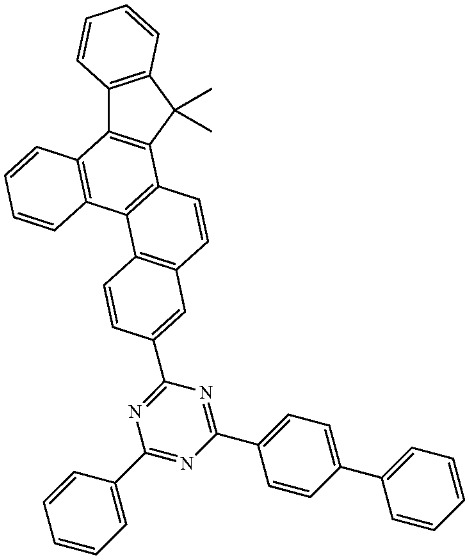
C-95
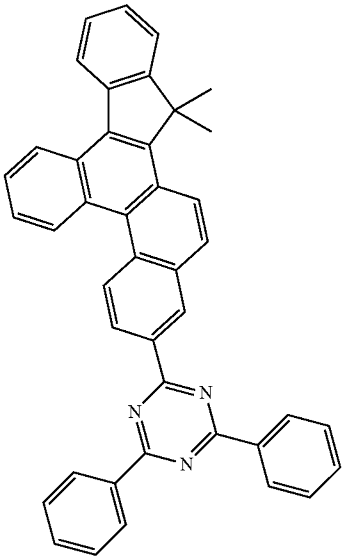
C-96
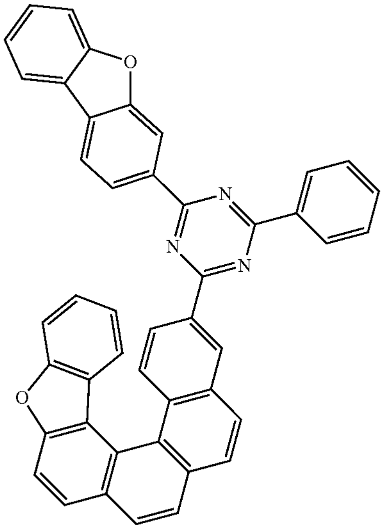

-continued
C-97
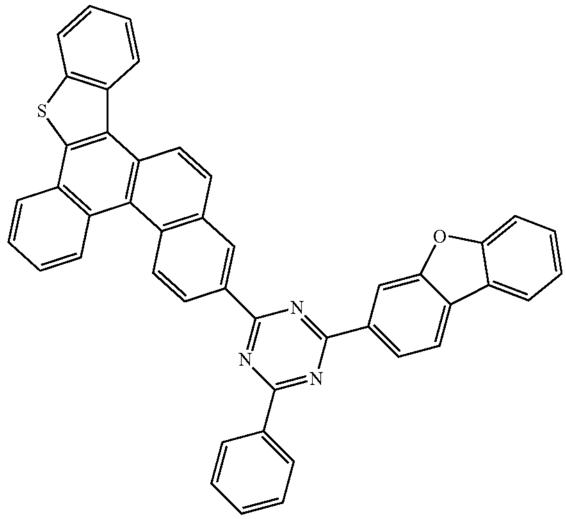
C-98
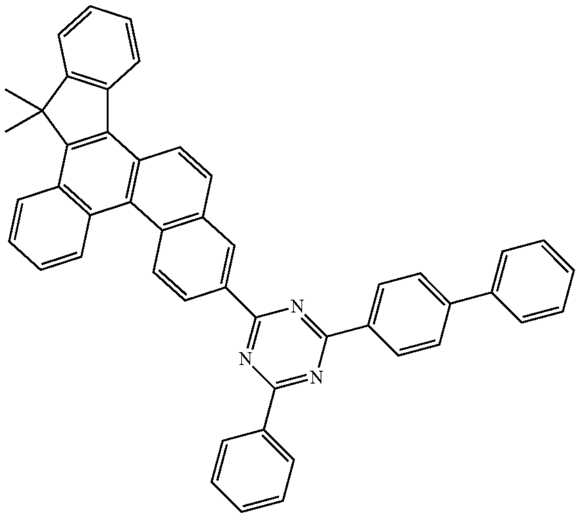
C-99
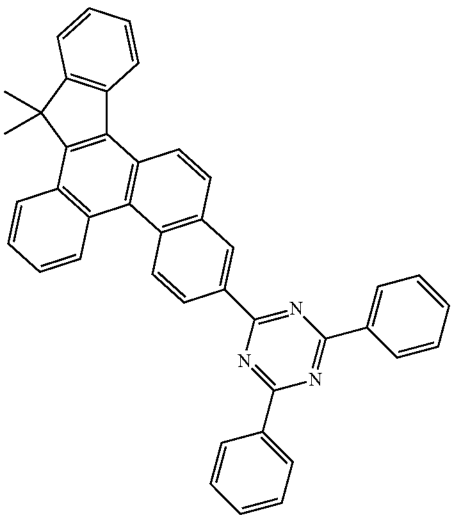
-continued
C-100
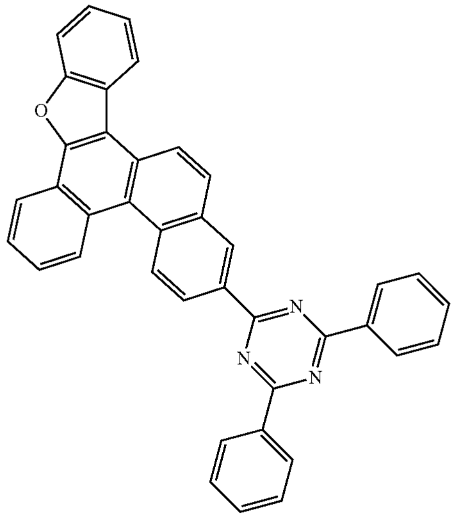
C-101
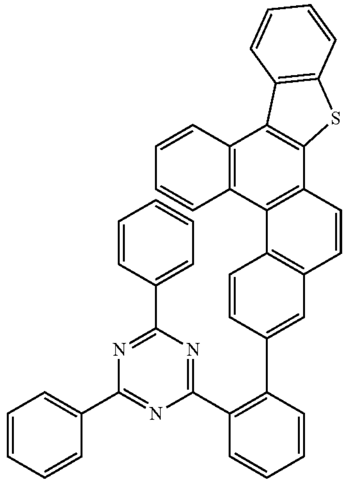
C-102
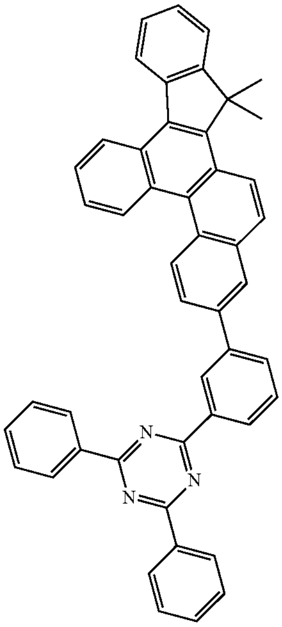

-continued
C-103
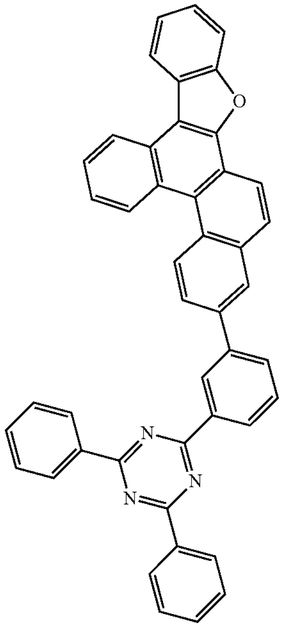
C-104
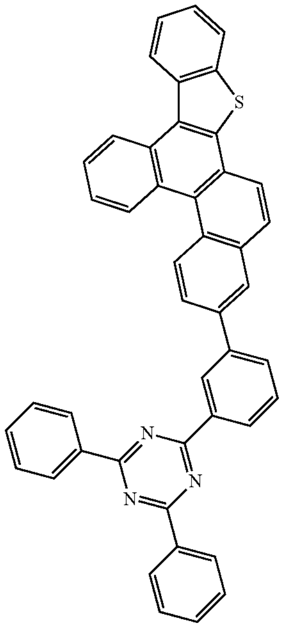
-continued
C-105
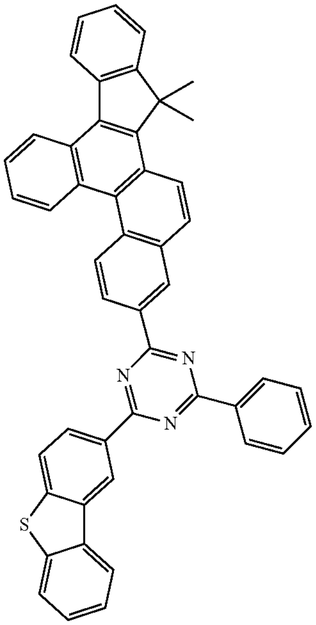
C-106
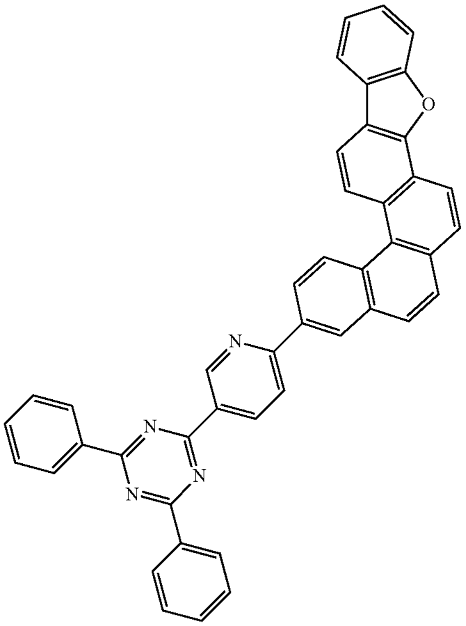

-continued
C-107
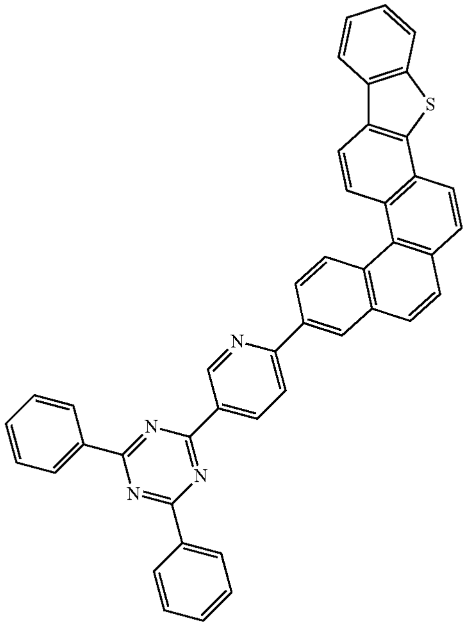
C-108
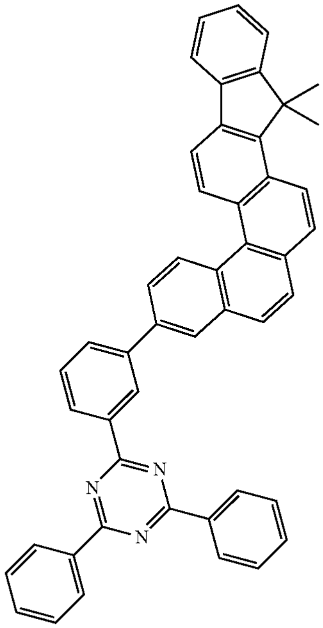
-continued
C-109
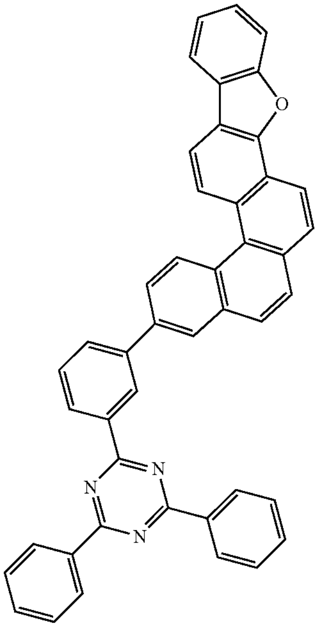
C-110
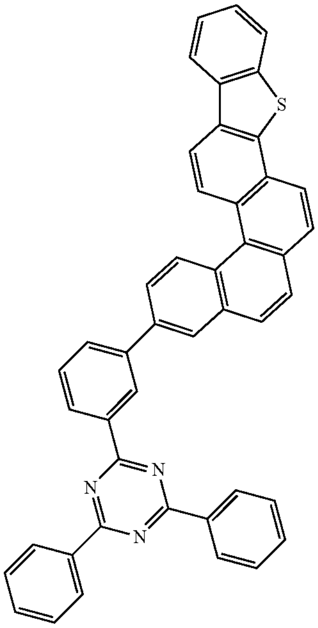

-continued
C-111
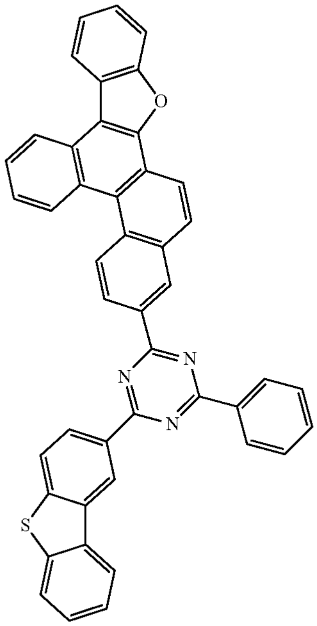
C-112
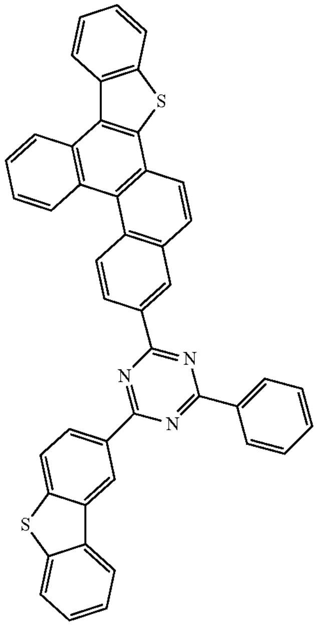
-continued
C-113
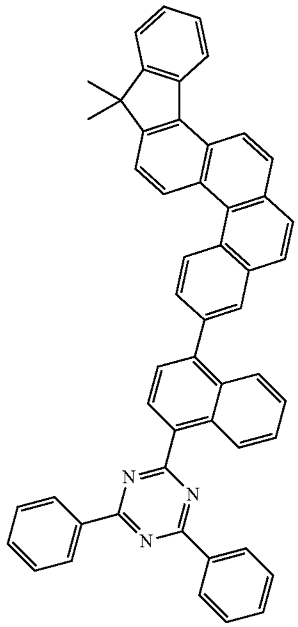
C-114
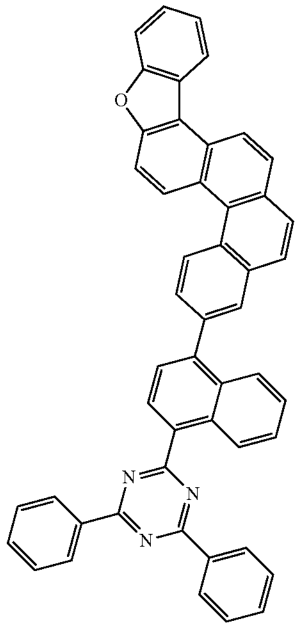

C-115
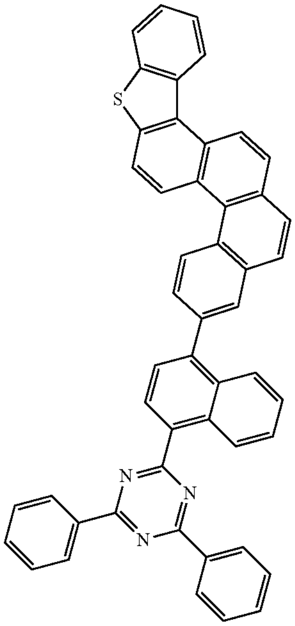
C-116
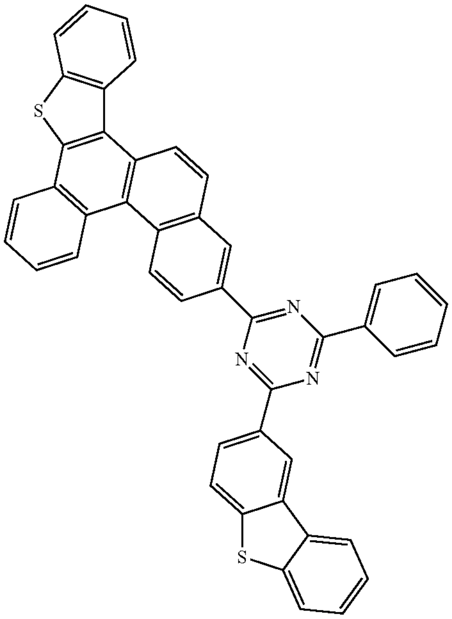
C-117
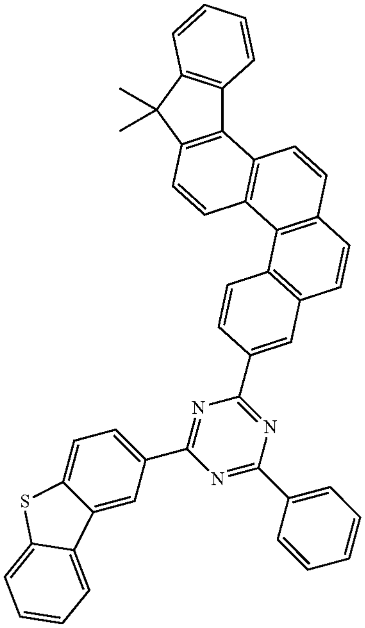
C-118
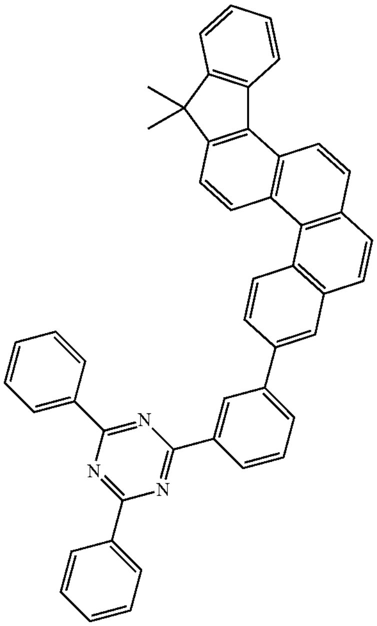

-continued
C-119
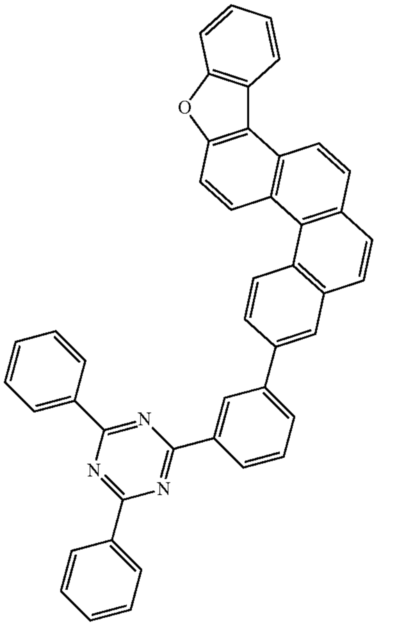
C-120
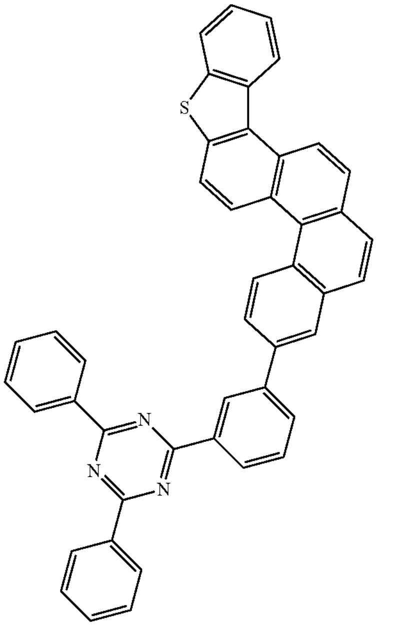
-continued
C-121
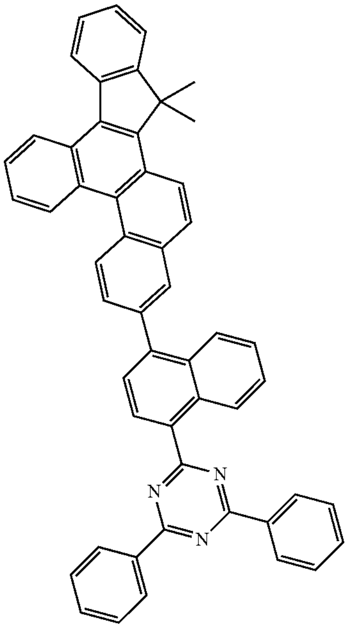
C-122
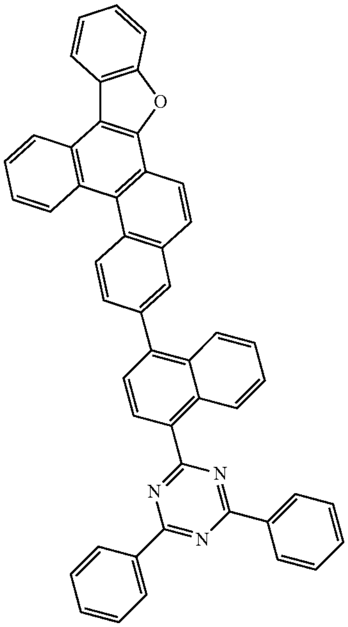

-continued
C-123
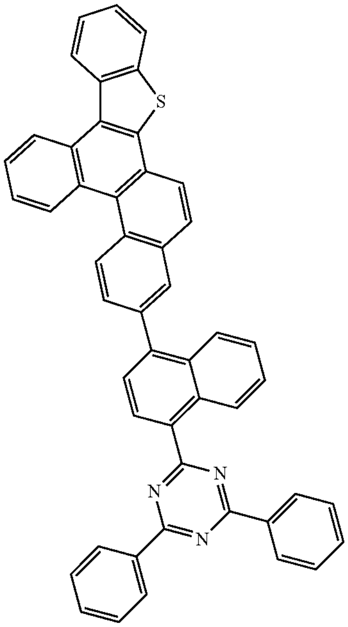
C-124
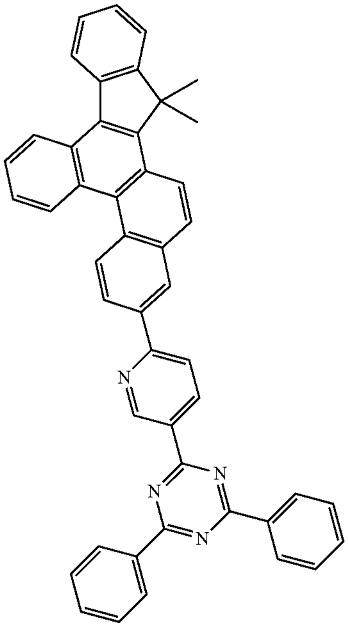
-continued
C-125
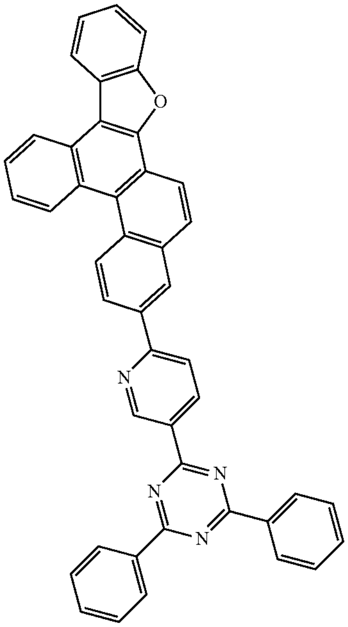
C-126
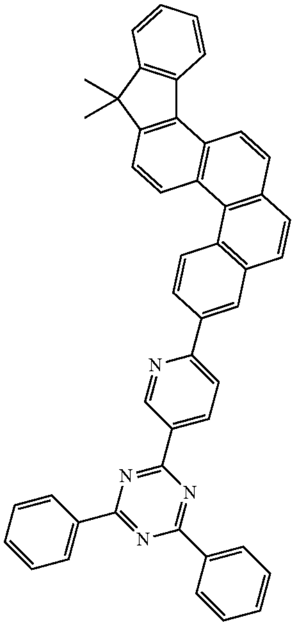

-continued
C-127
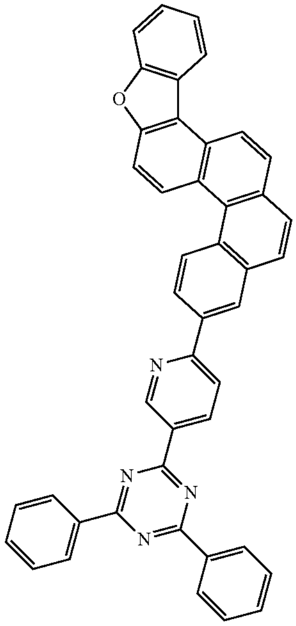
C-128
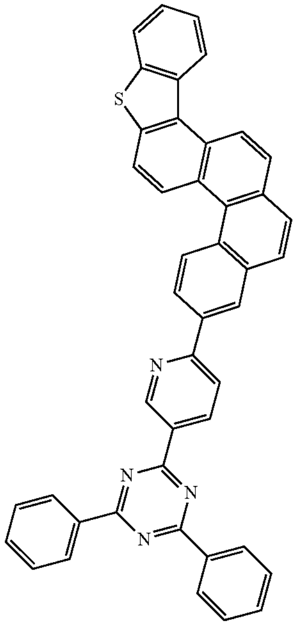
-continued
C-129
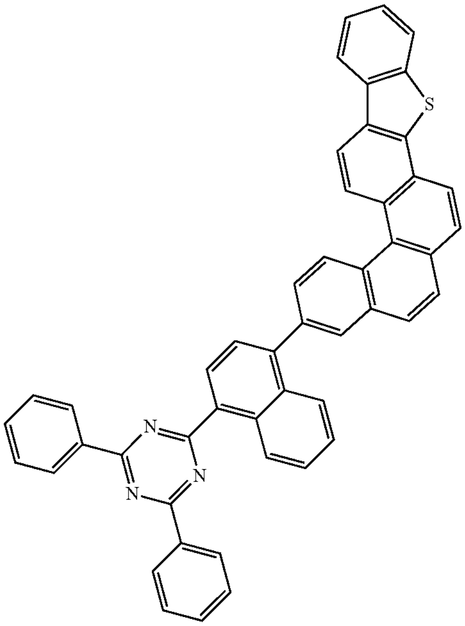
C-130
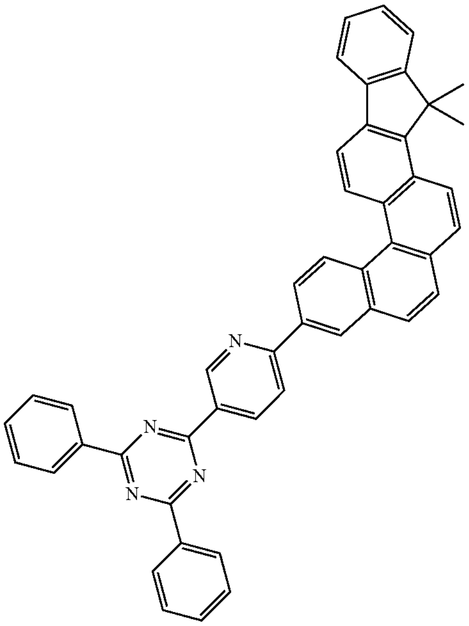

-continued
C-131
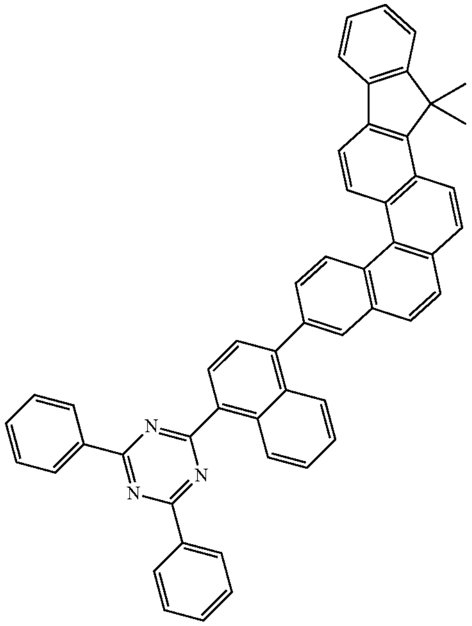
C-132
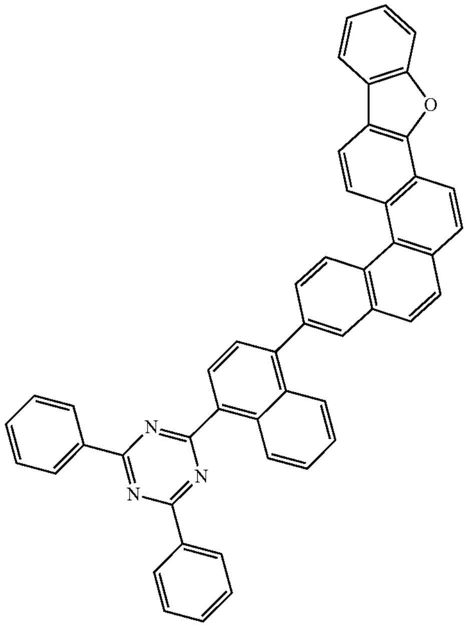
-continued
C-133
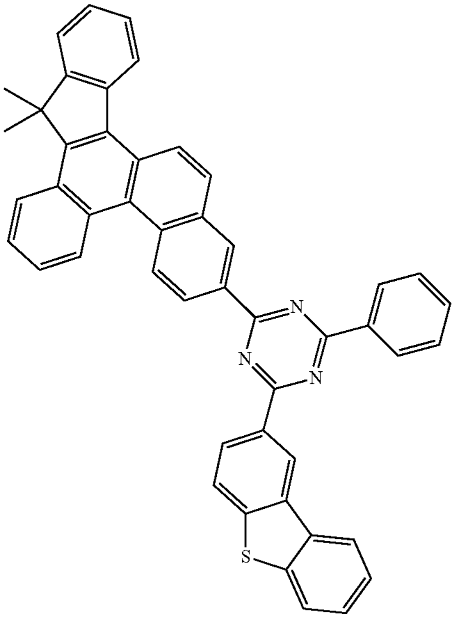
C-134
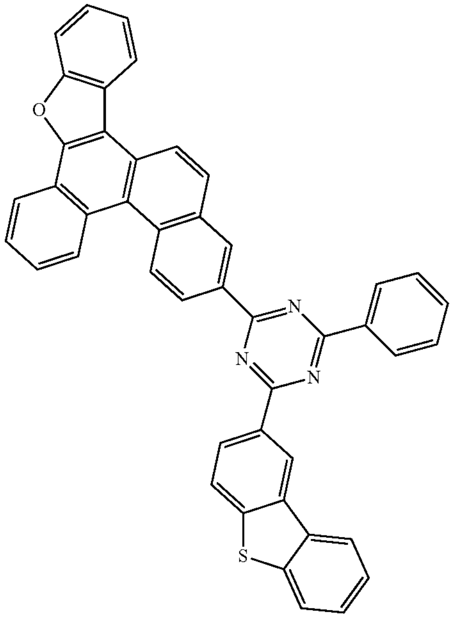

-continued
C-135
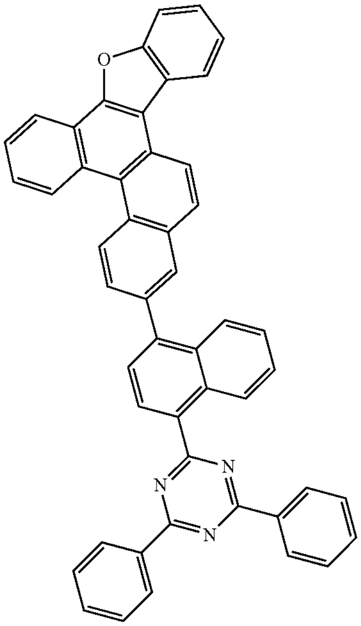
C-136
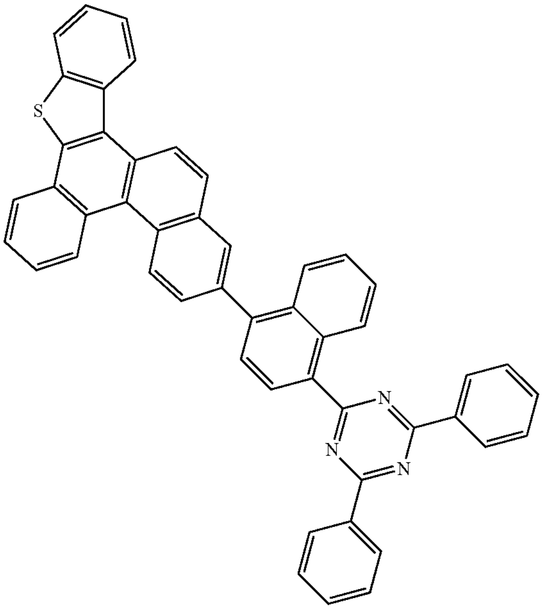
-continued
C-137
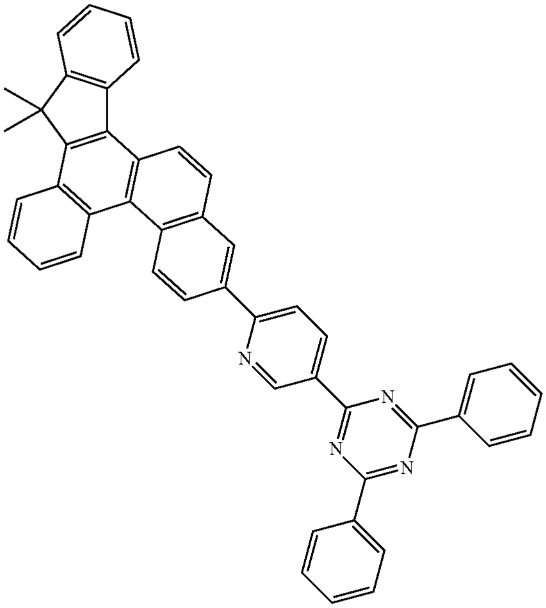
C-138
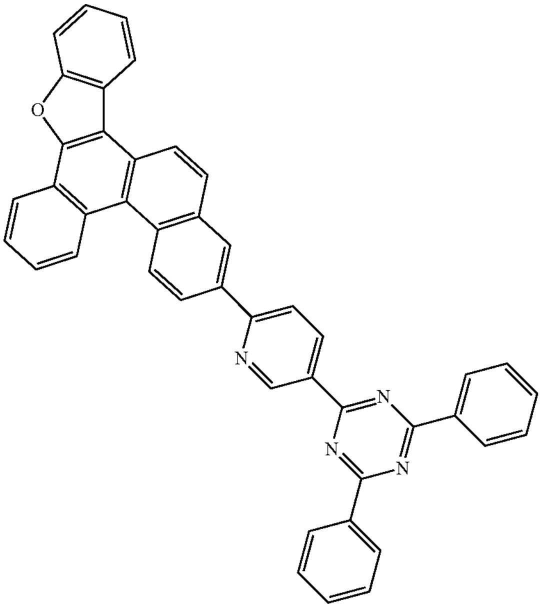

-continued
C-139
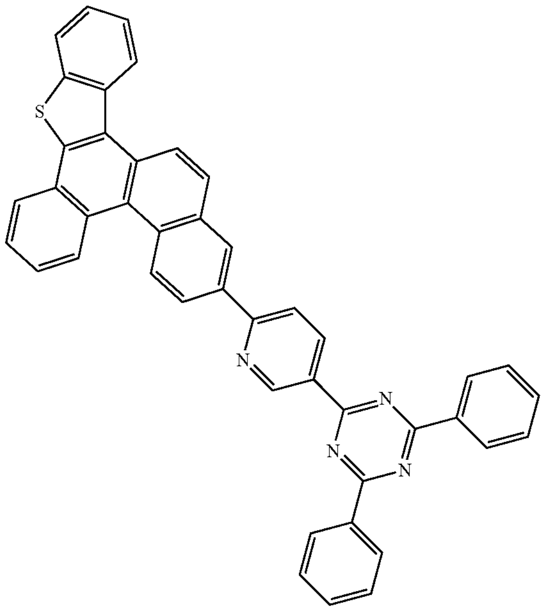
C-140
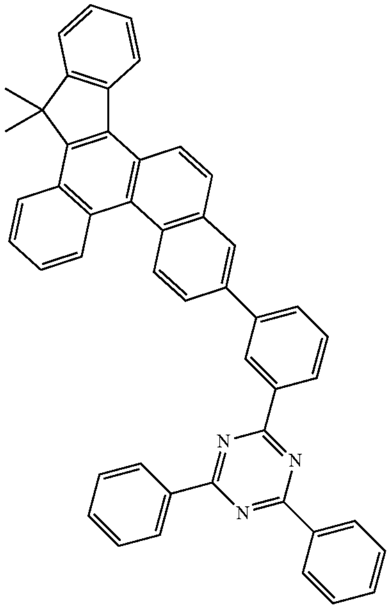
-continued
C-141
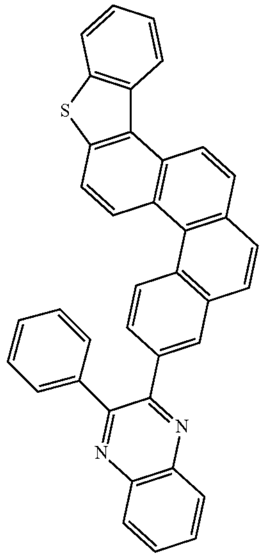
C-142
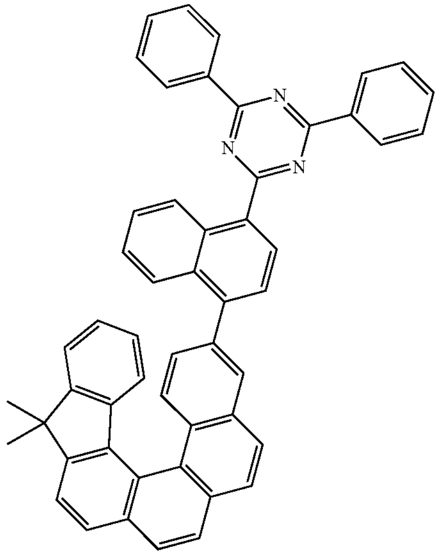
C-143
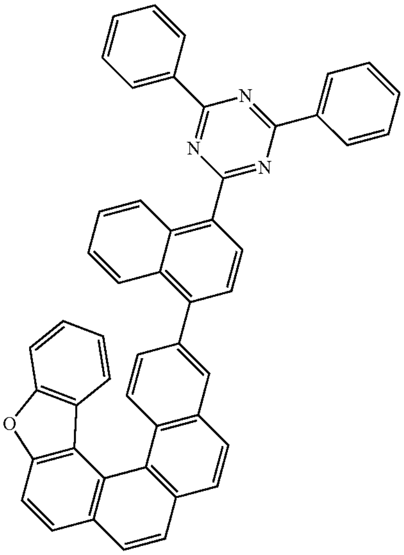

-continued
C-144
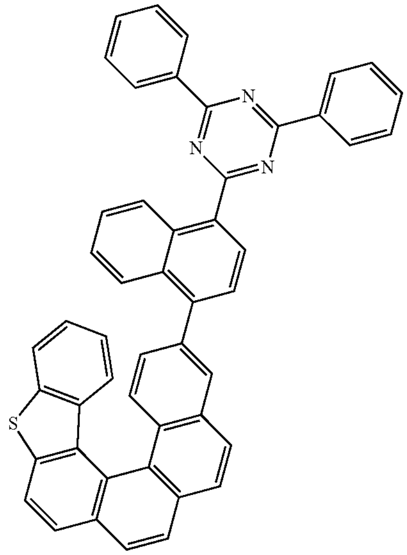
C-145
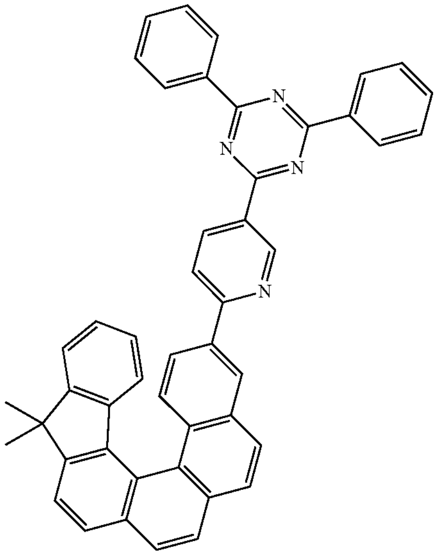
C-146
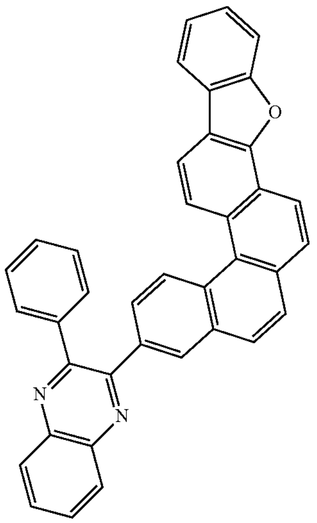
-continued
C-147
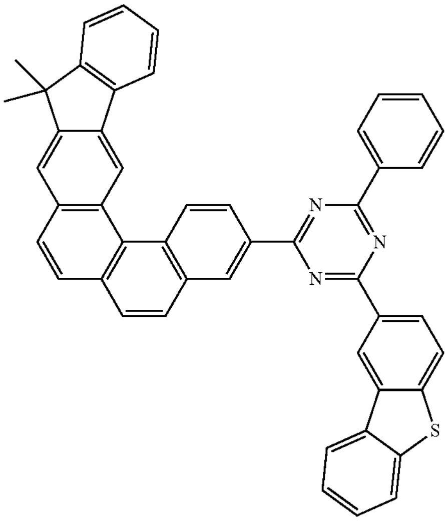
C-148
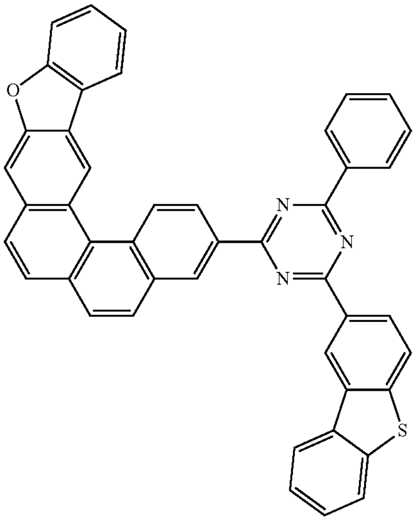
C-149
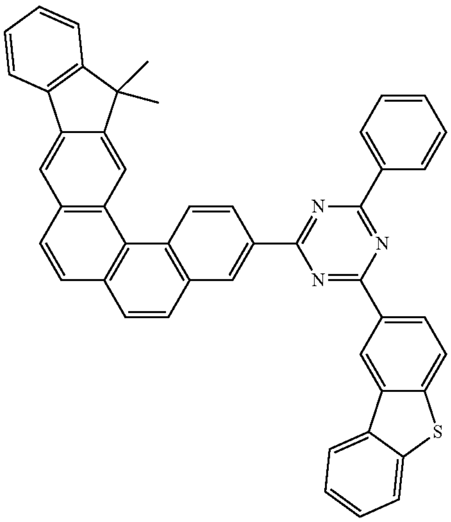

-continued
C-150
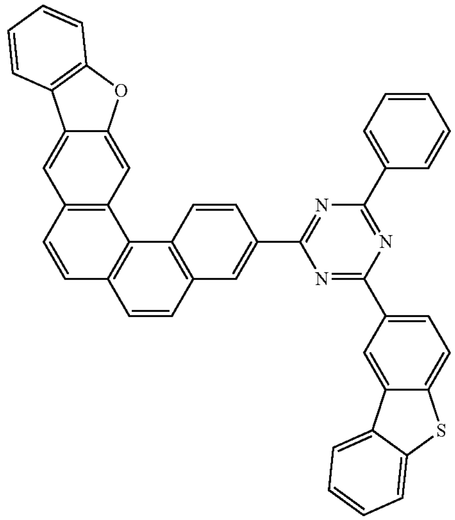
C-151
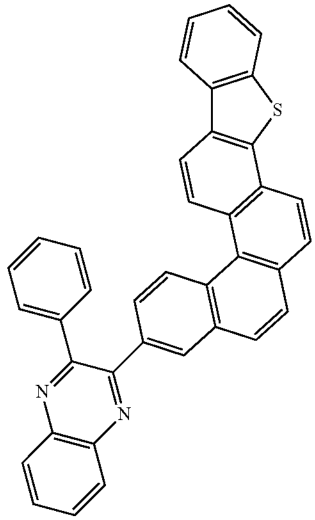
C-152
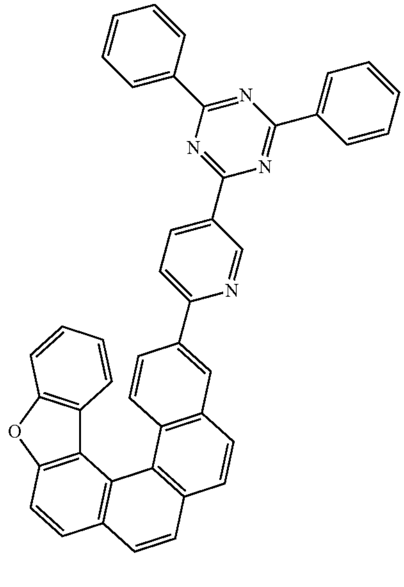
-continued
C-153
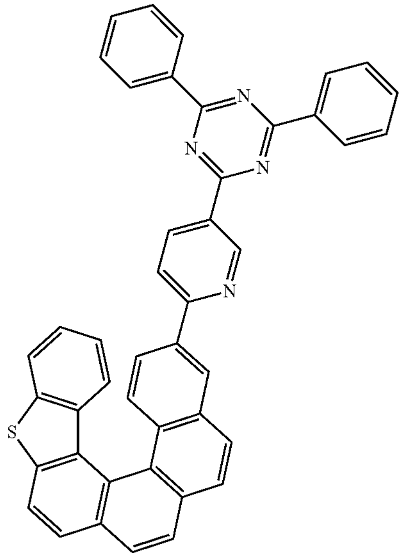
C-154
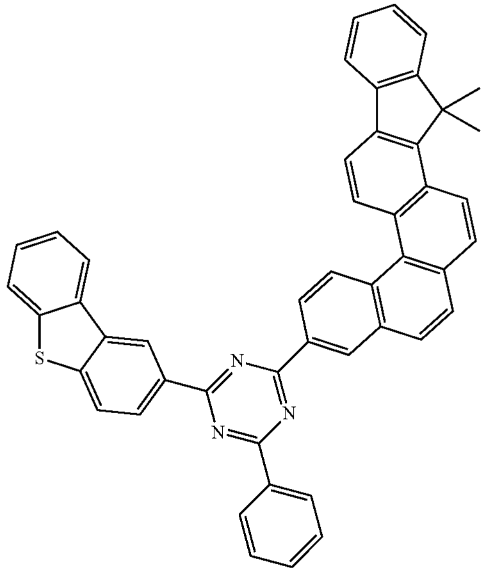

-continued
C-155
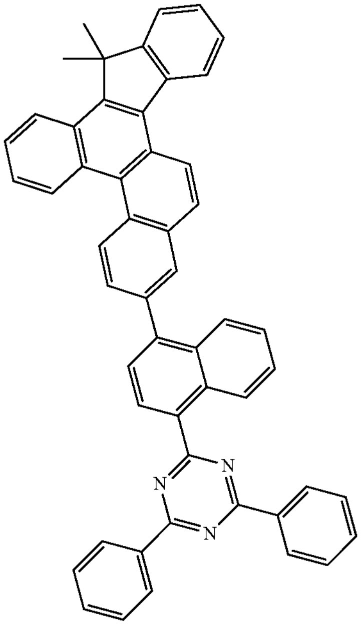
C-156
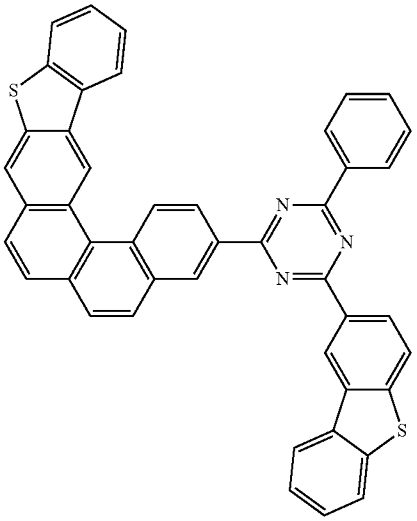
C-157
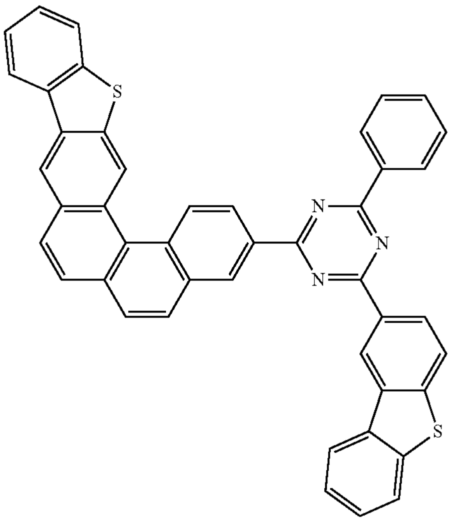
-continued
C-158
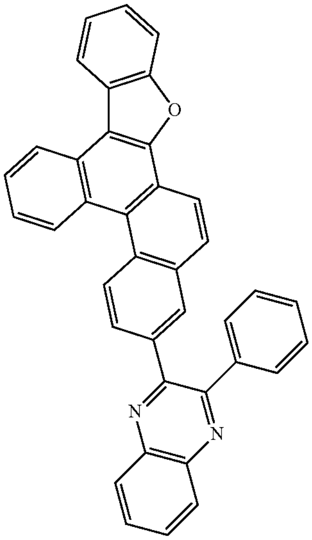
C-159
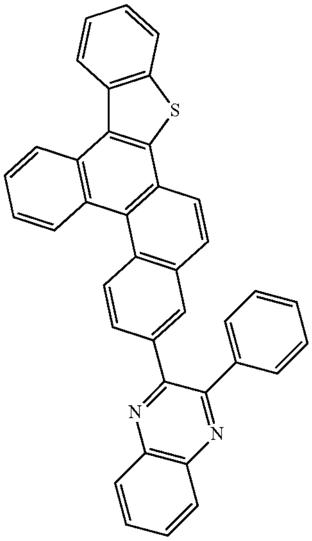
C-160
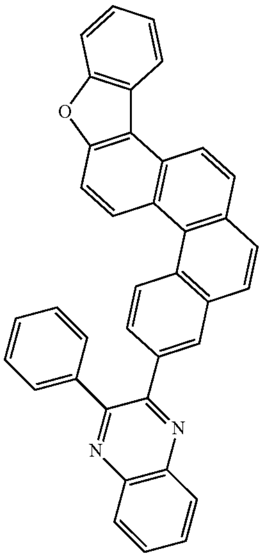

-continued
C-161
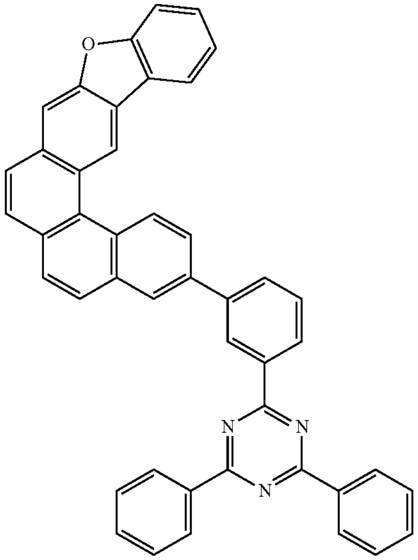
C-162
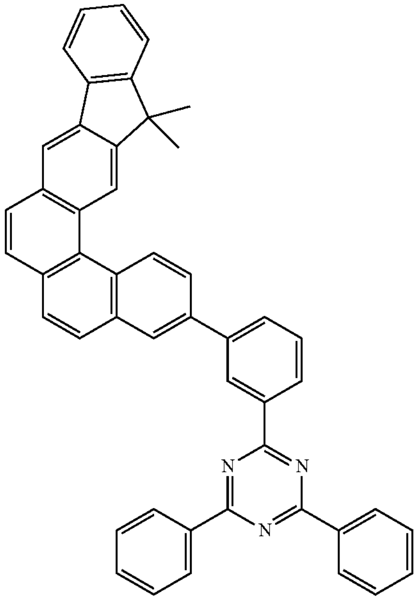
-continued
C-163
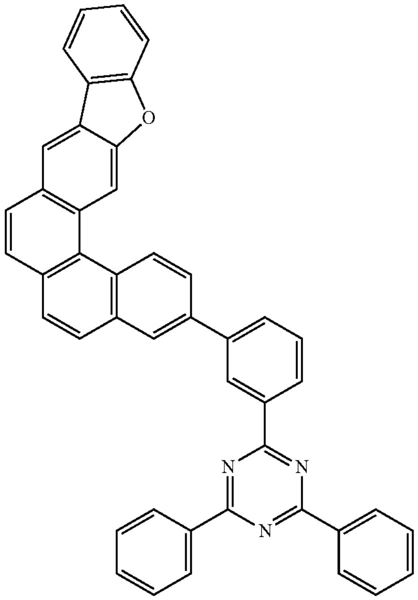
C-164
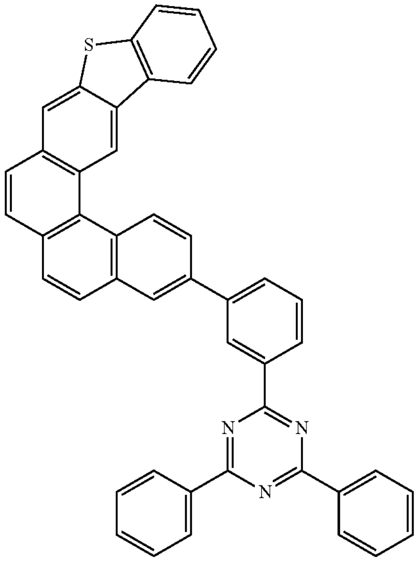

-continued
C-165
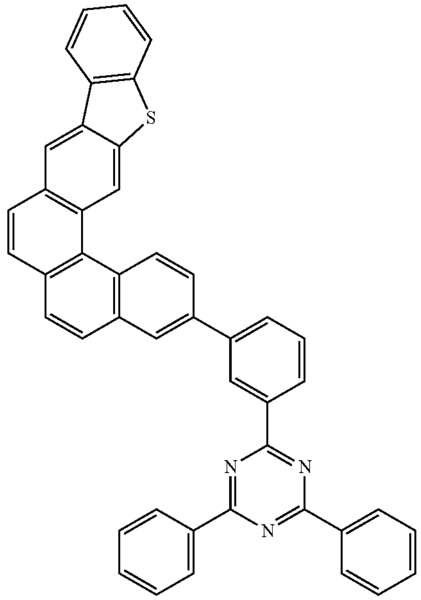
C-166
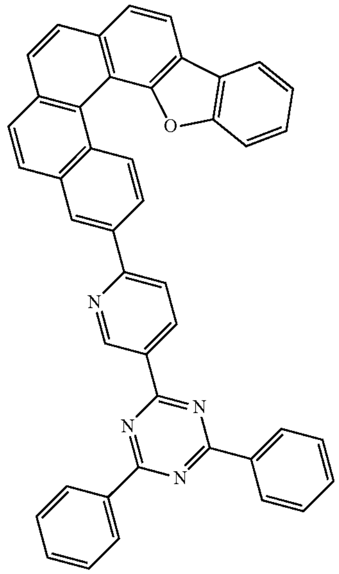
-continued
C-167
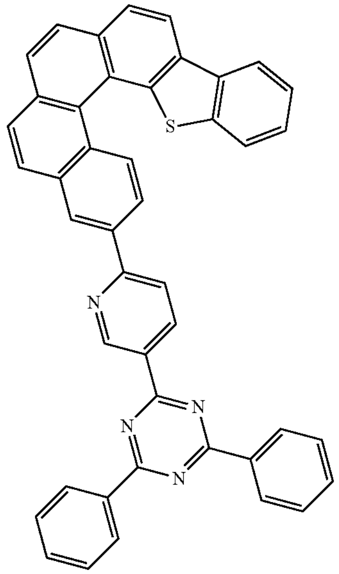
C-168
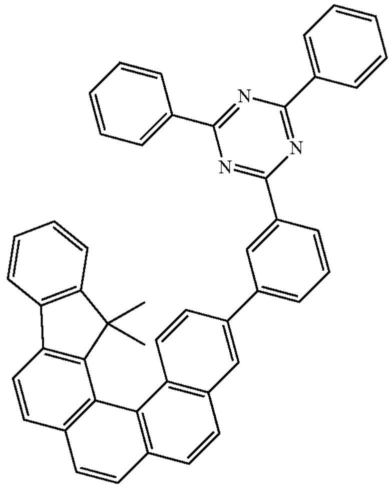
C-169
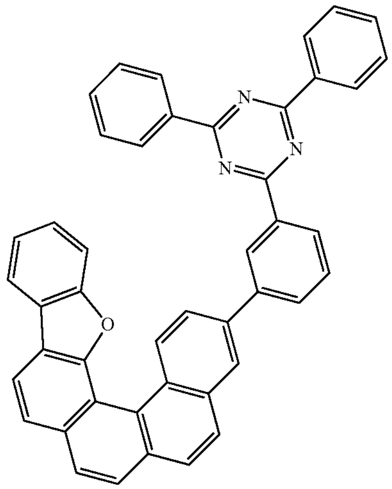

C-170
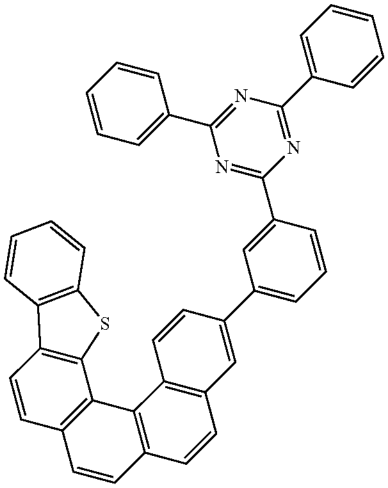
C-171
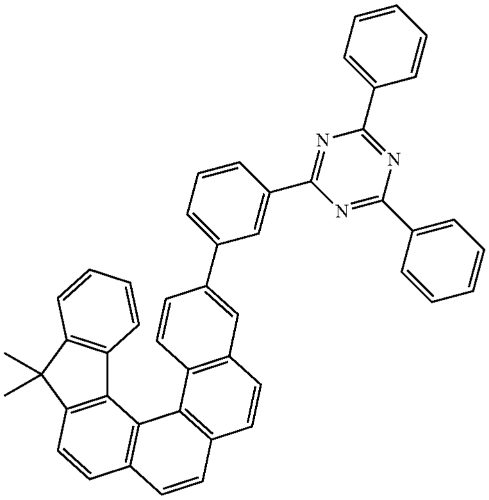
C-172
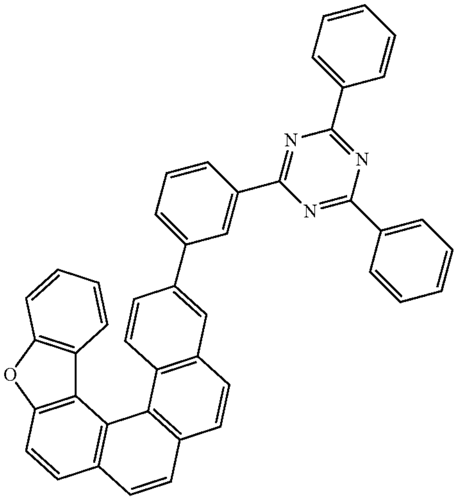
C-173
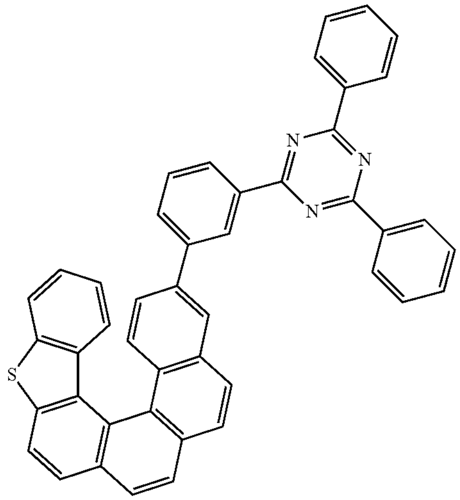
C-174
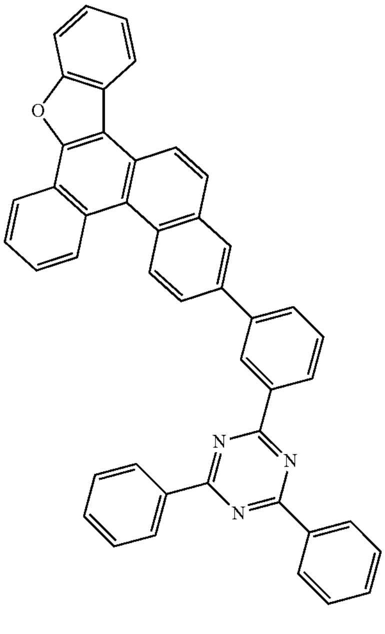

-continued
C-175
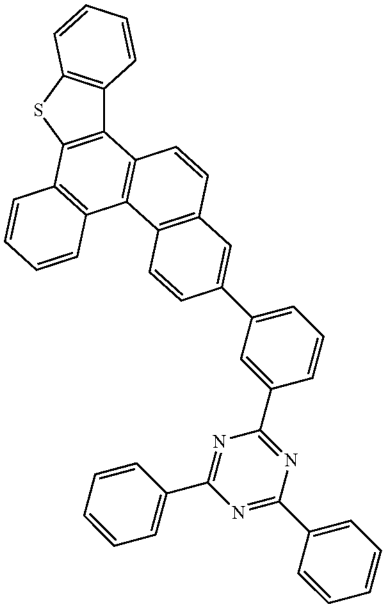
C-176
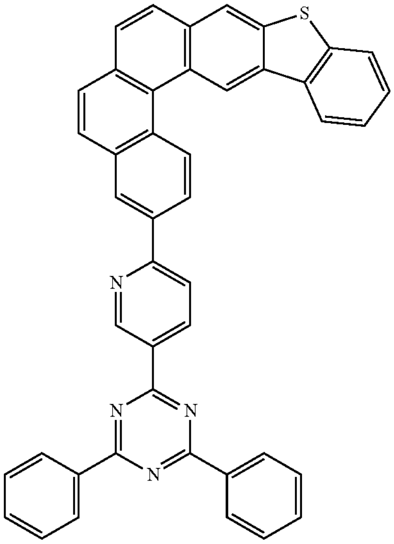
-continued
C-177
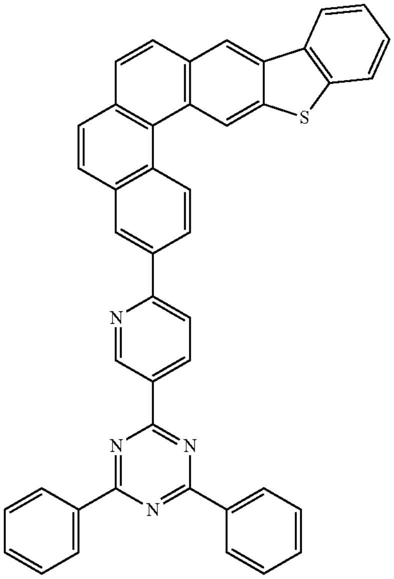
C-178
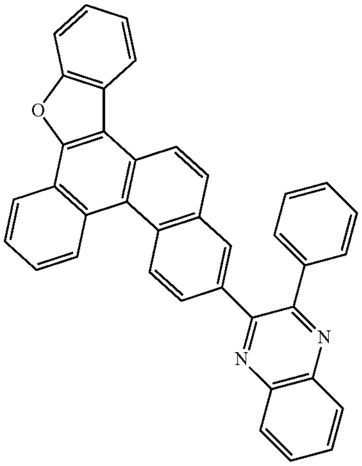
C-179
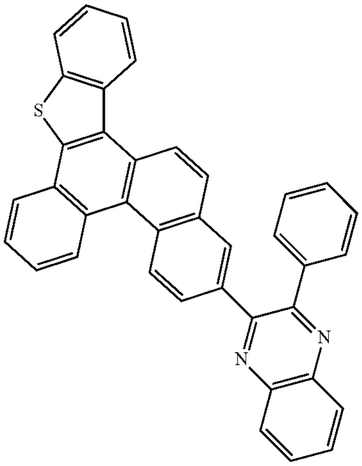

-continued
C-180
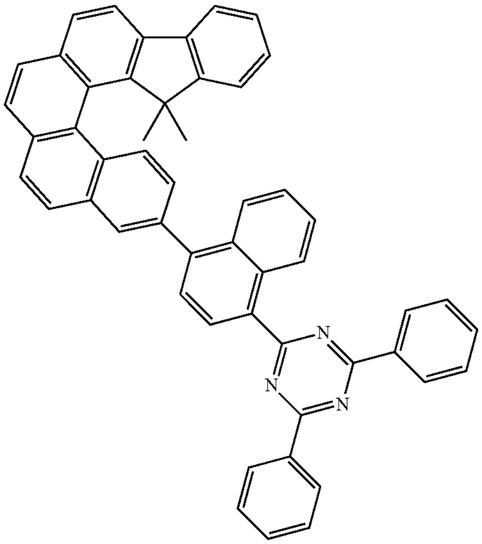
C-181
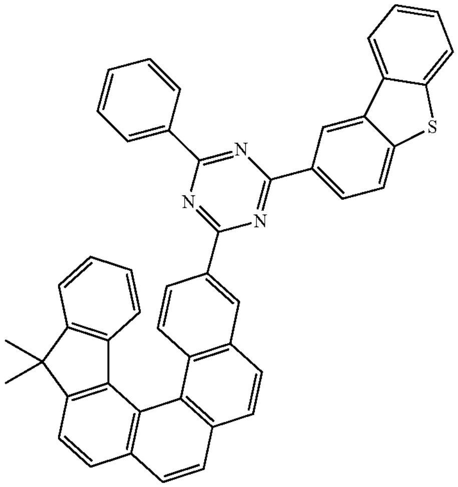
C-182
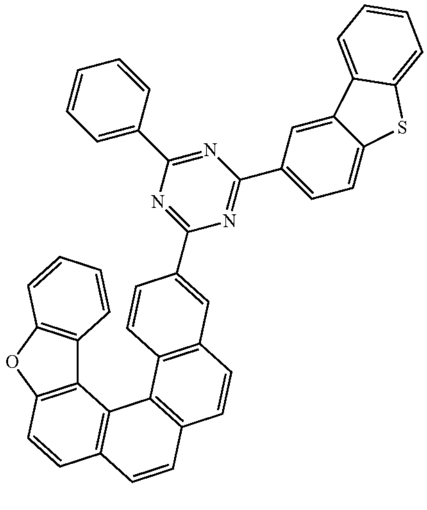
-continued
C-183
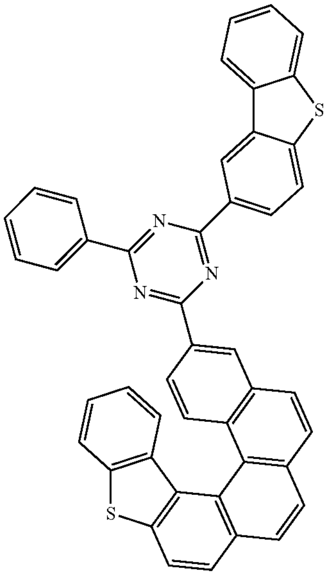
C-184
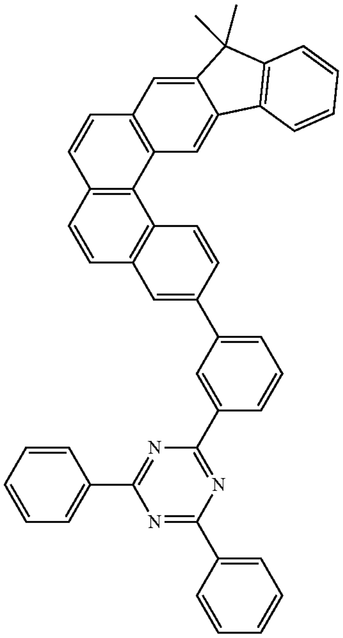

-continued
C-185
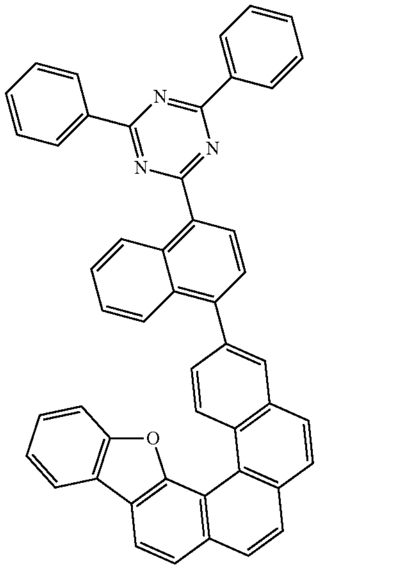
C-186
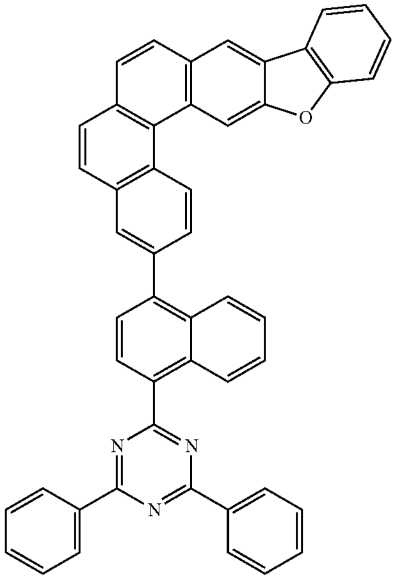
-continued
C-187
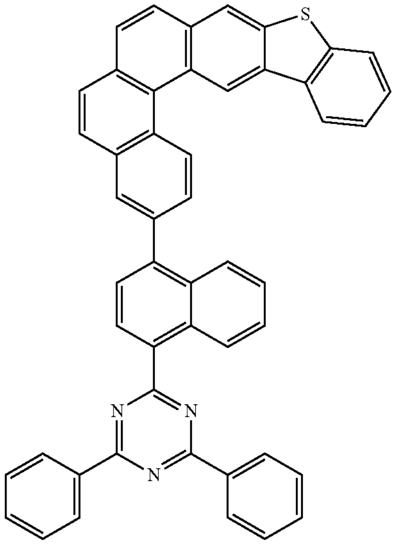
C-188
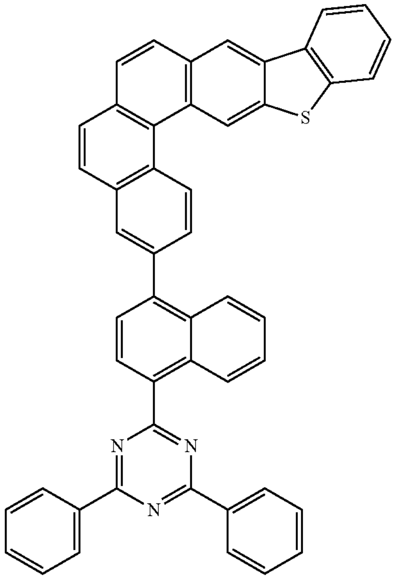

-continued
C-189
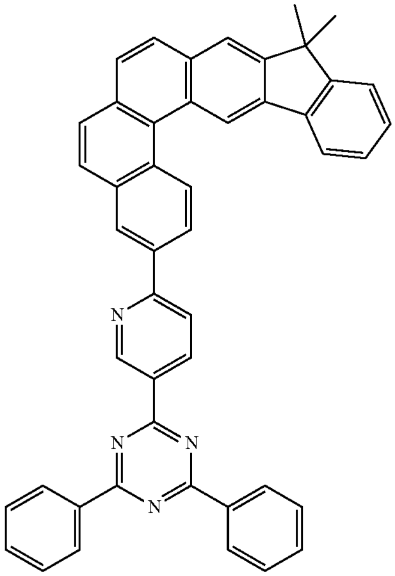
C-190
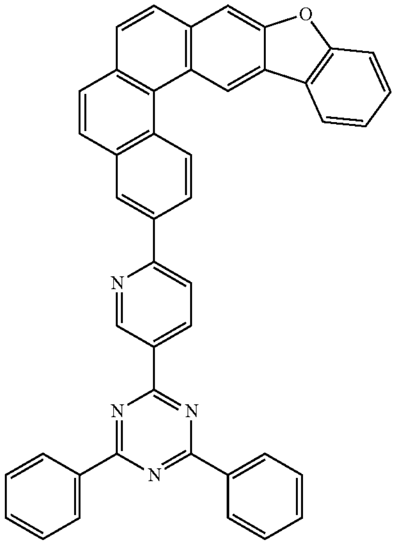
-continued
C-191
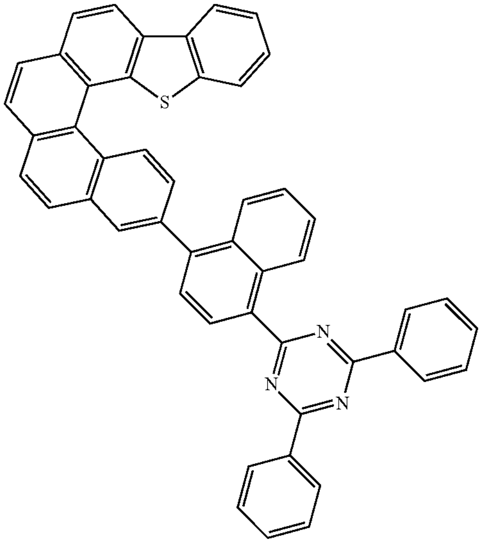
C-192
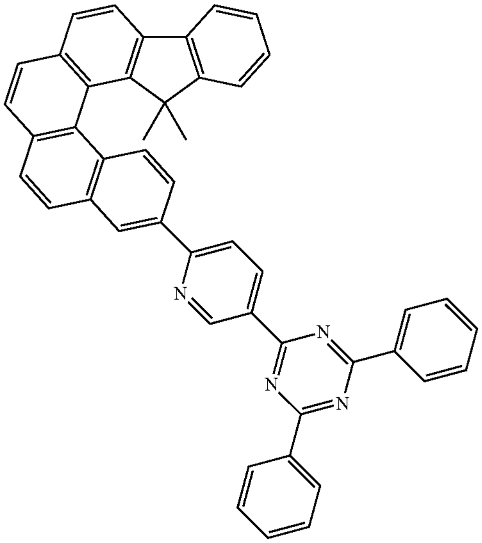

-continued
C-193
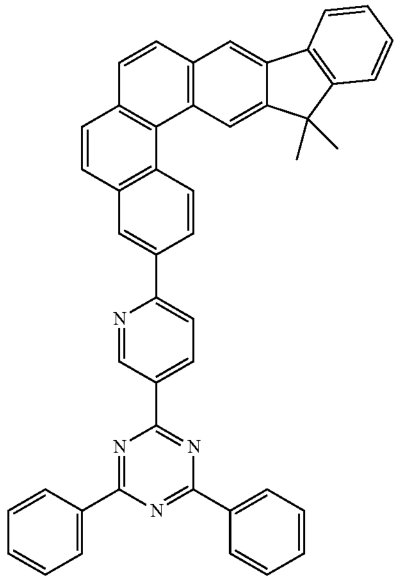
C-194
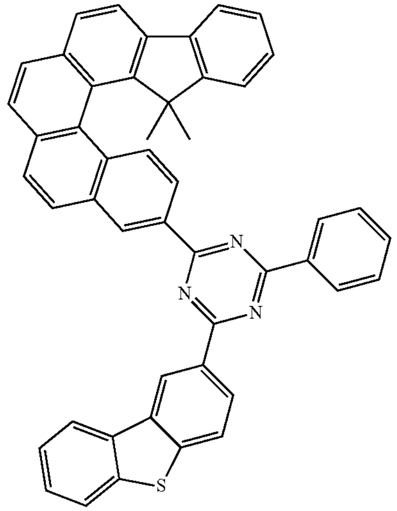
-continued
C-195
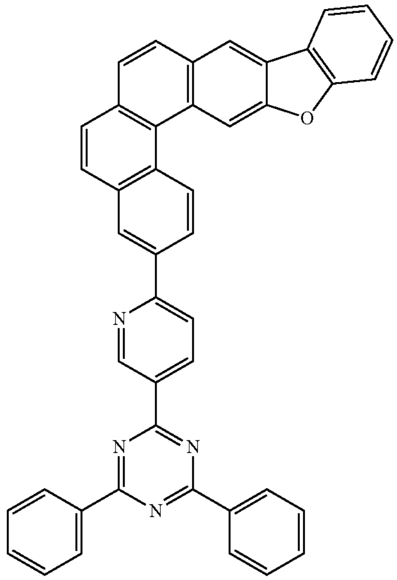
C-196
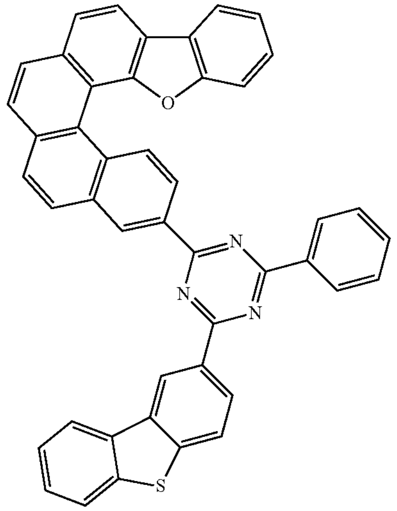
C-197
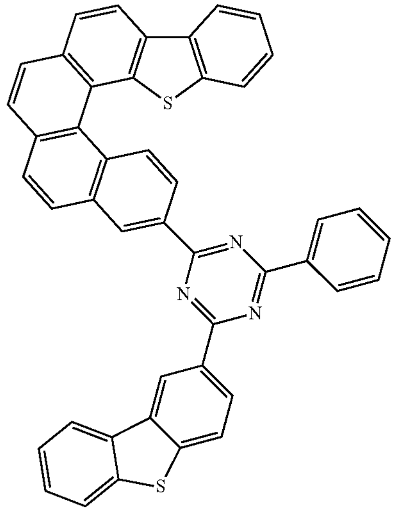

-continued
C-198
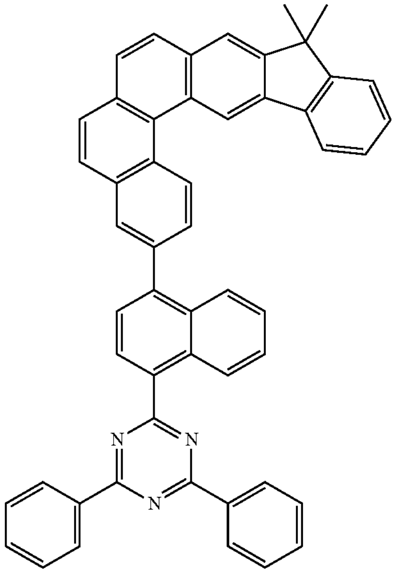
C-199
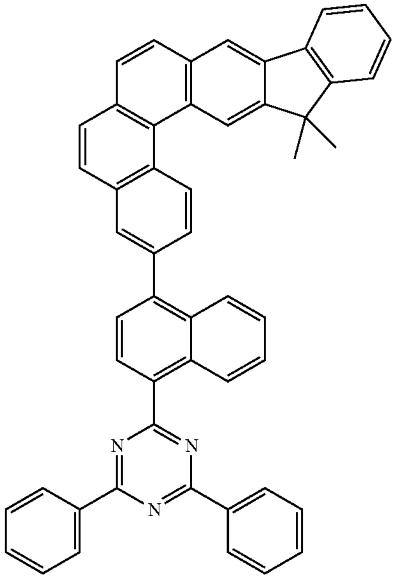
-continued
C-200
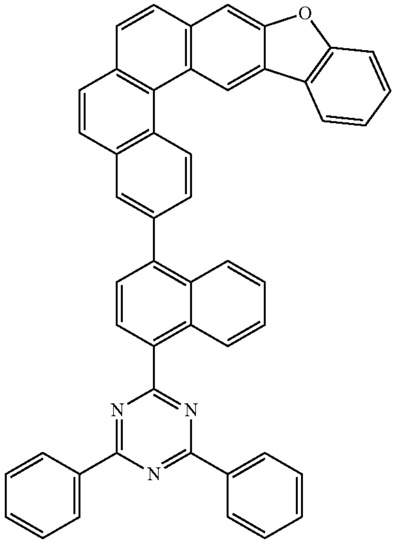
C-201
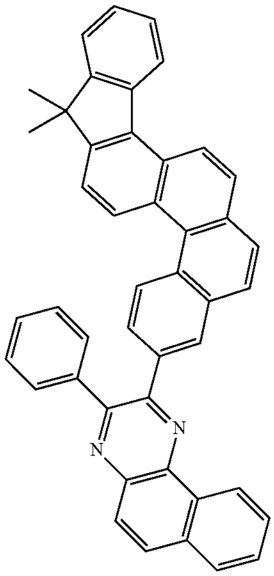

-continued
C-202
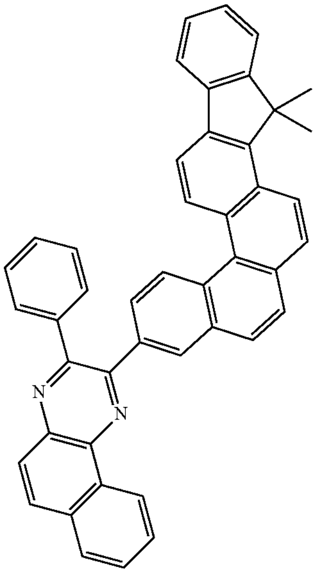
C-203
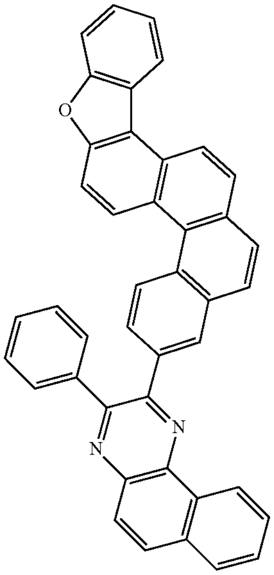
-continued
C-204
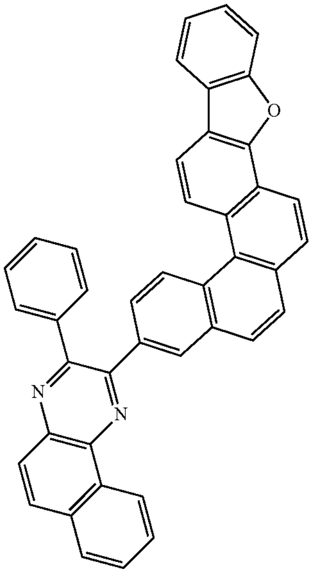
C-205
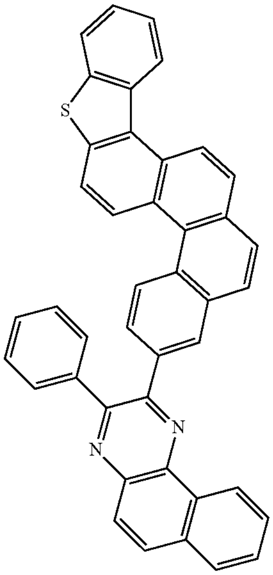

-continued
C-206
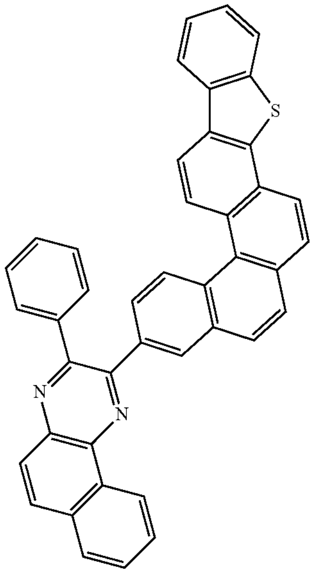
C-207
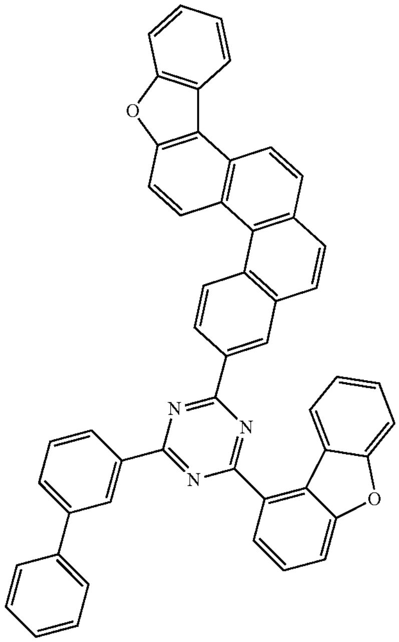
-continued
C-208
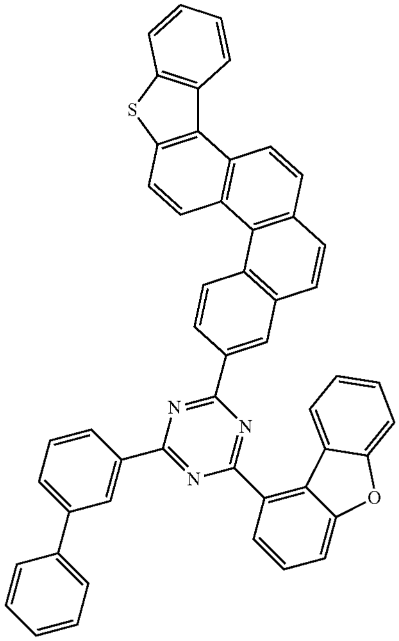
C-209
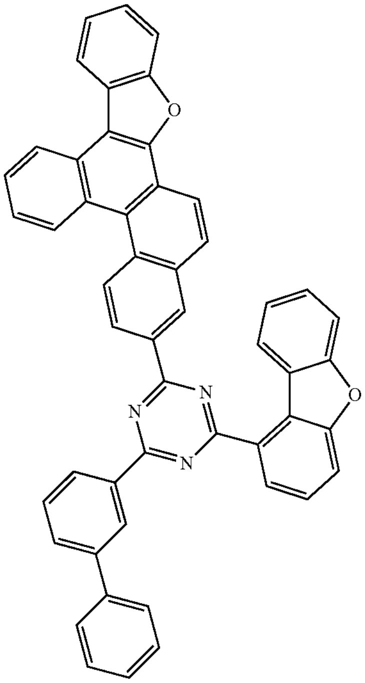

-continued
C-210
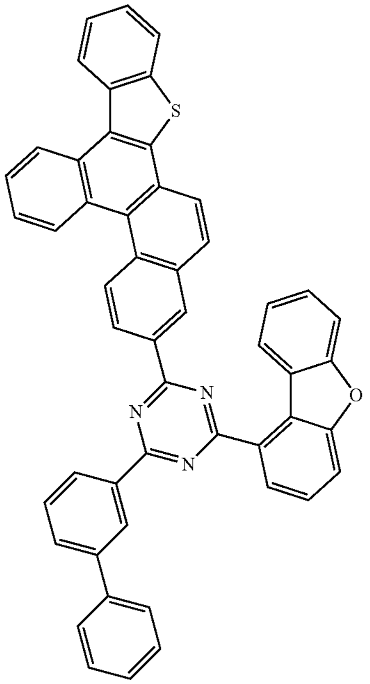
C-211
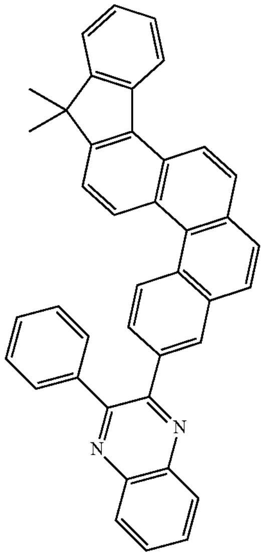
-continued
C-212
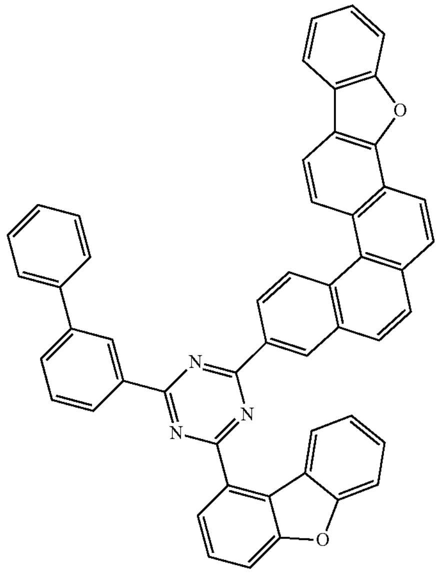
C-213
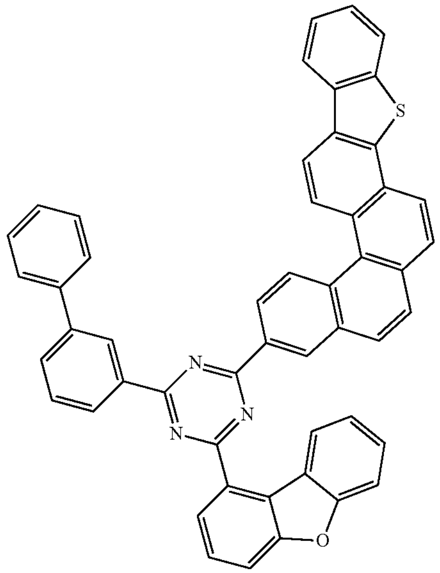

-continued
C-214
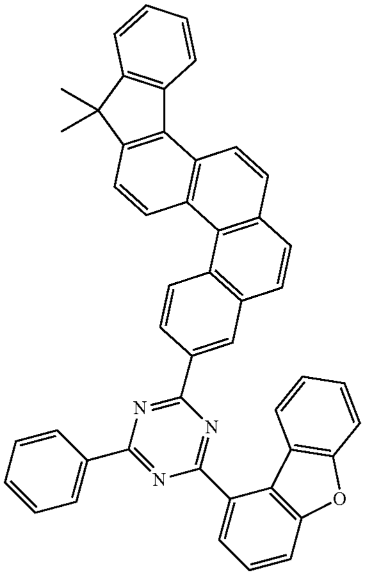
C-216
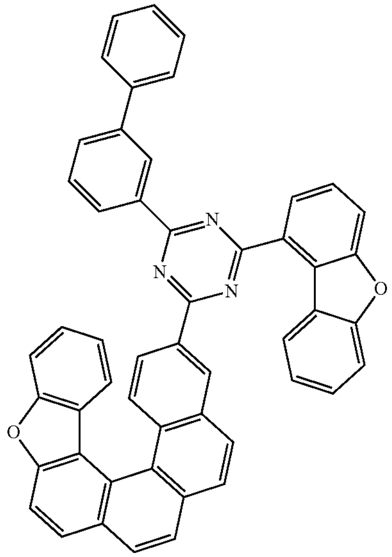
C-215
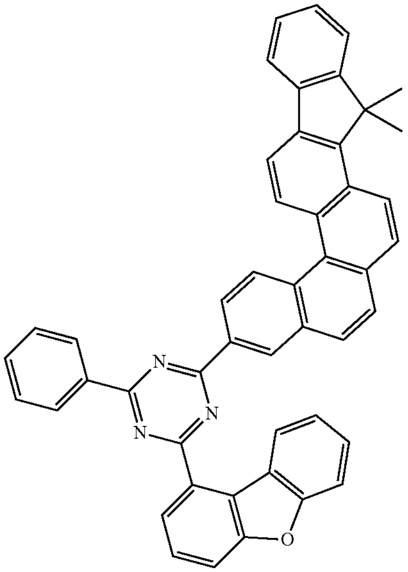
C-217
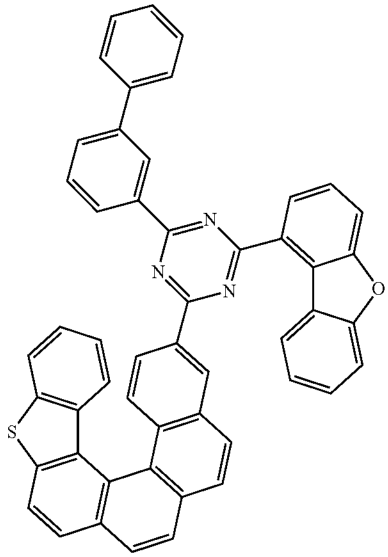

-continued
C-218
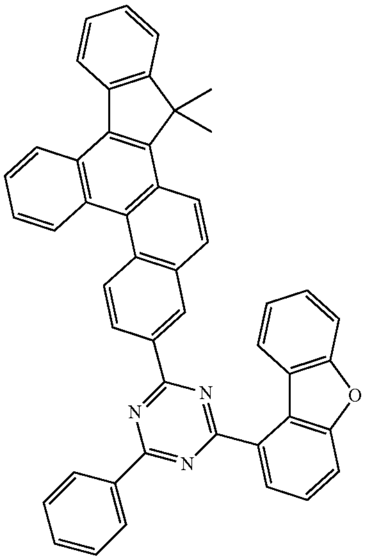
C-219
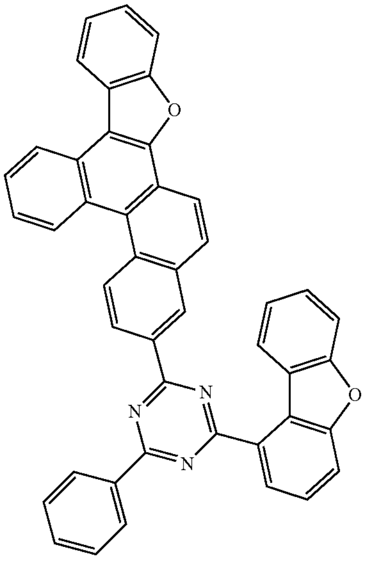
-continued
C-220
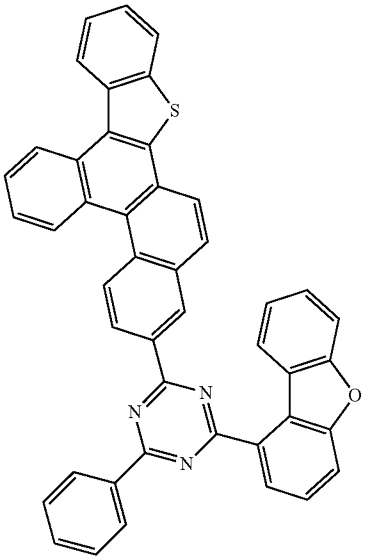
C-221
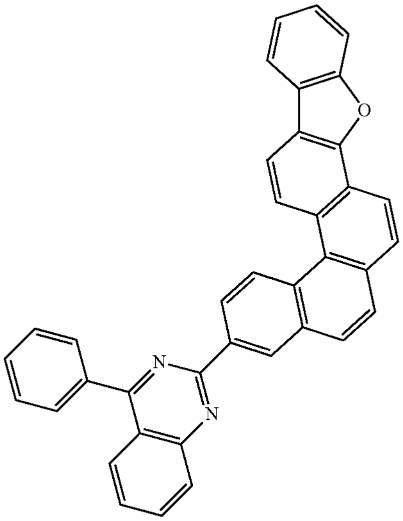
C-222
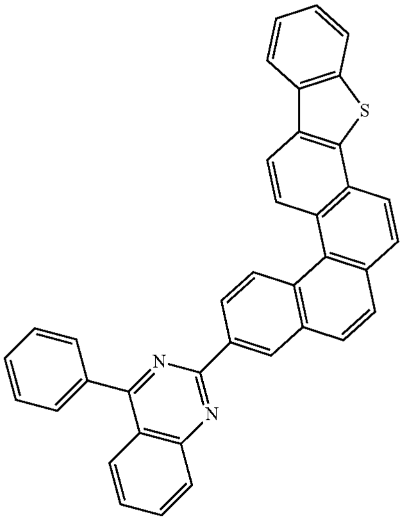

-continued
C-223
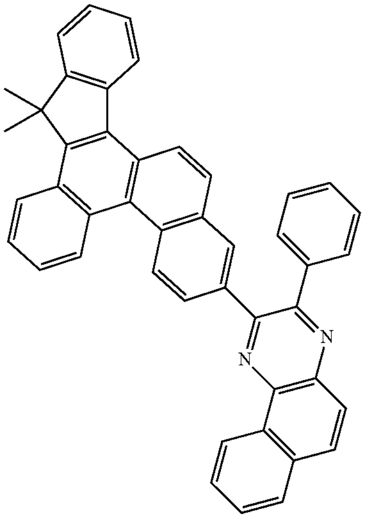
C-224
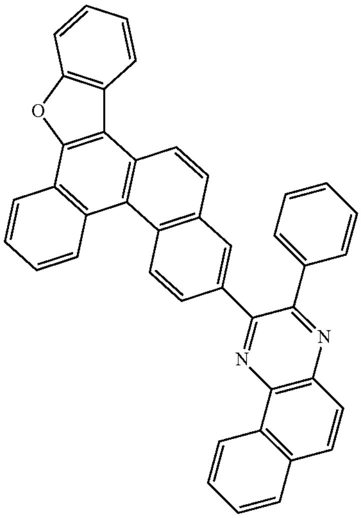
C-225
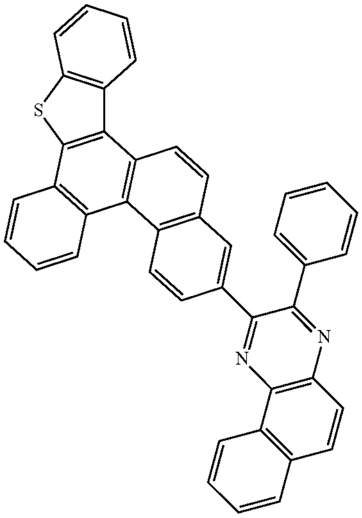
-continued
C-226
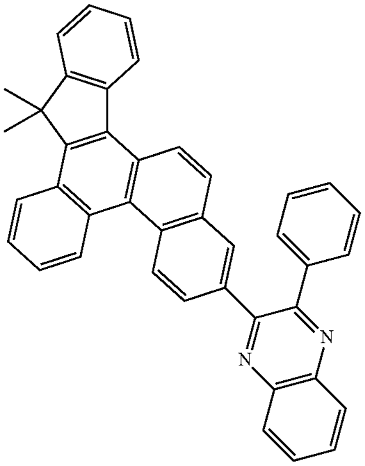
C-227
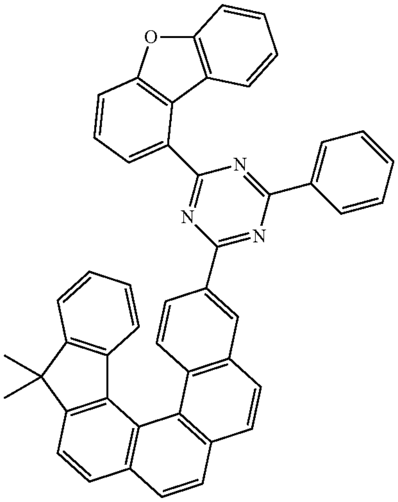
C-228
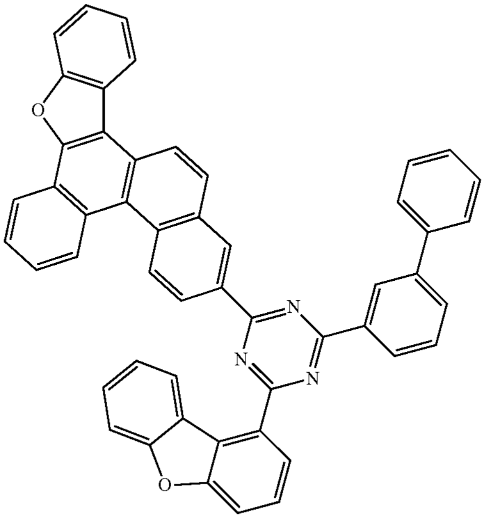

-continued
C-229
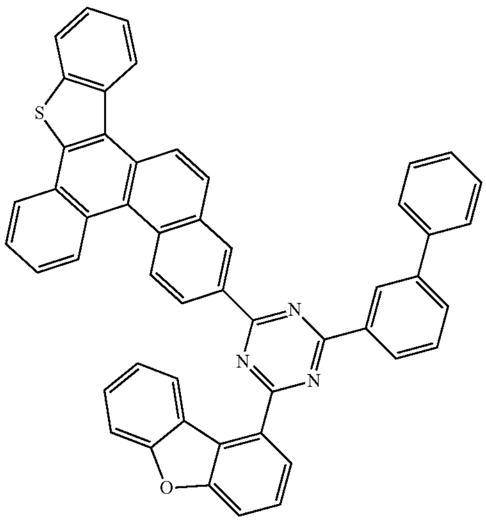
C-230
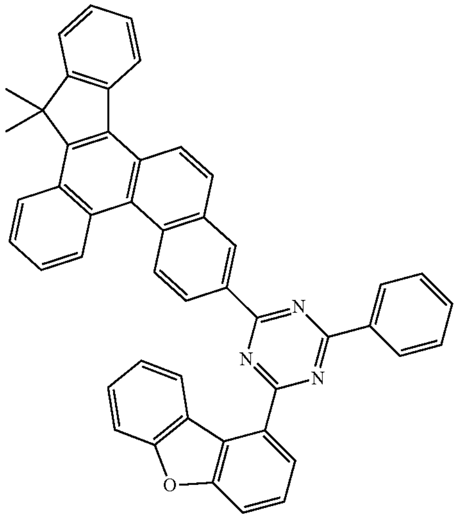
C-231
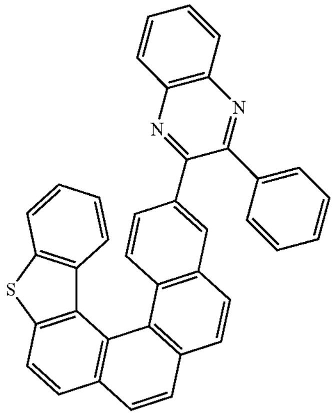
-continued
C-232
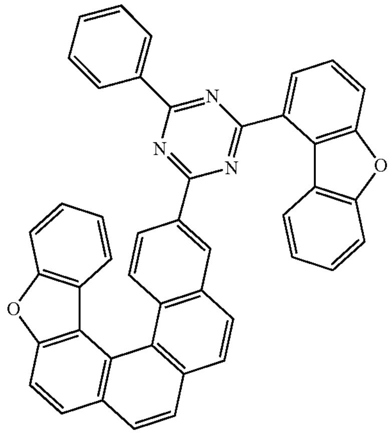
C-233
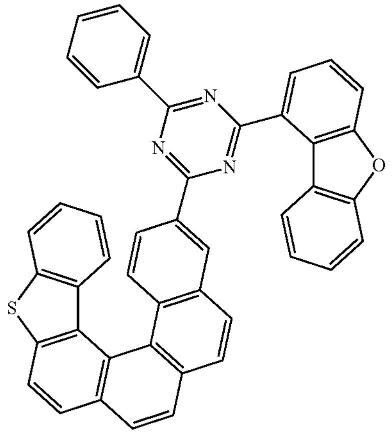
C-234
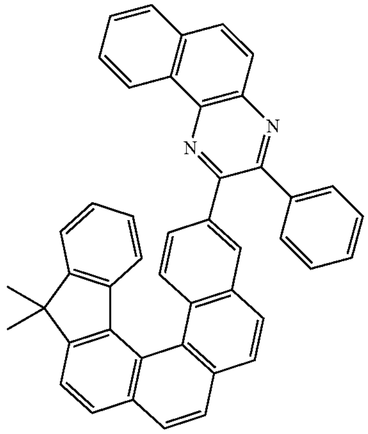

-continued
C-235
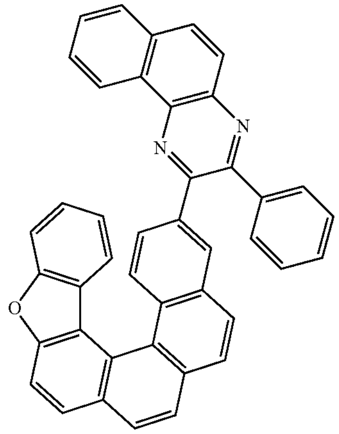
C-236
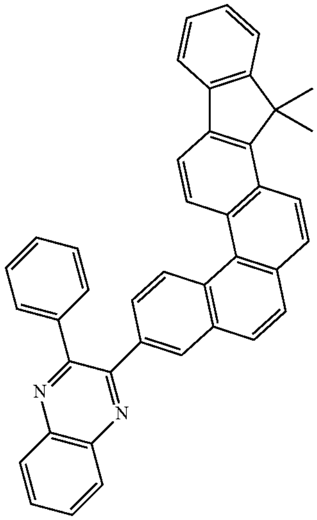
C-237
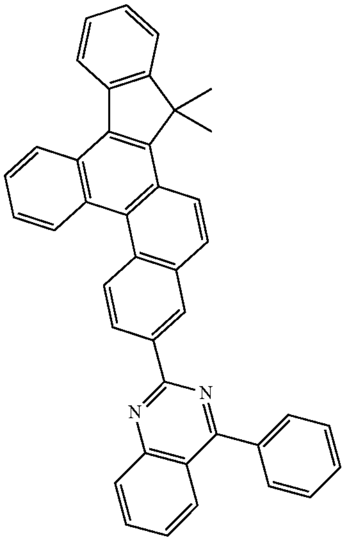
-continued
C-238
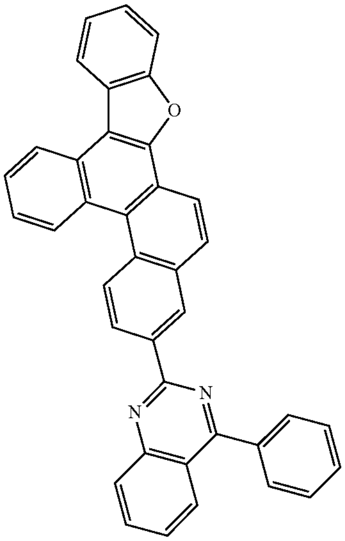
C-239
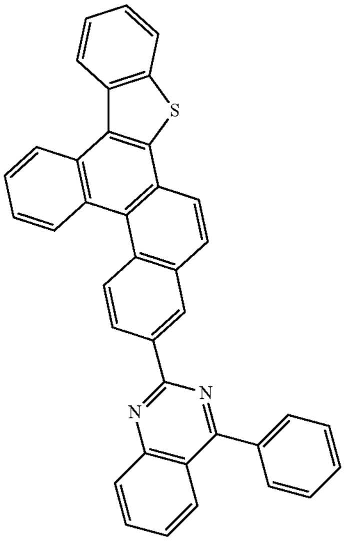
C-240
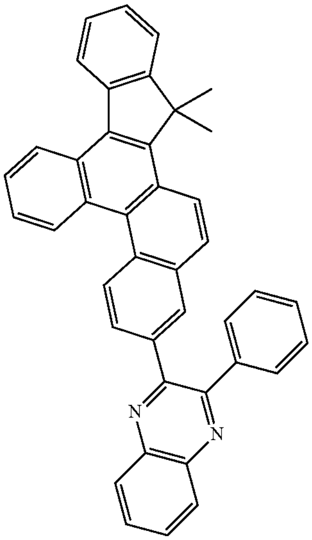

-continued
C-241
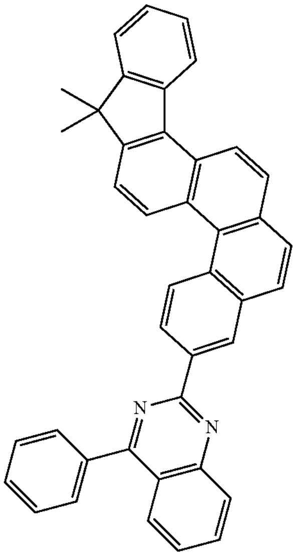
C-242
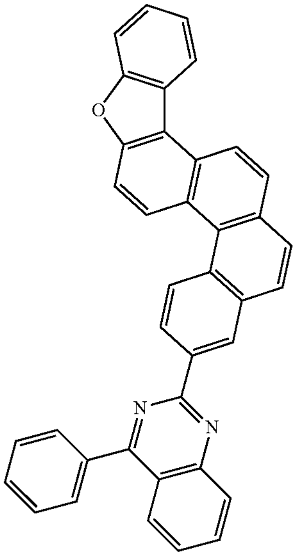
C-243
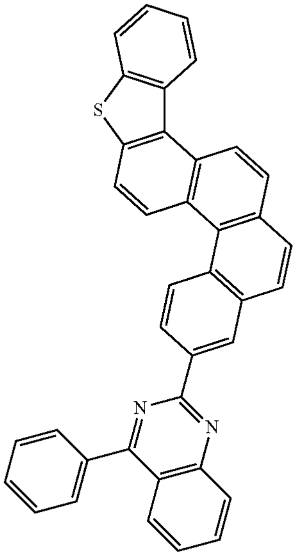
-continued
C-244
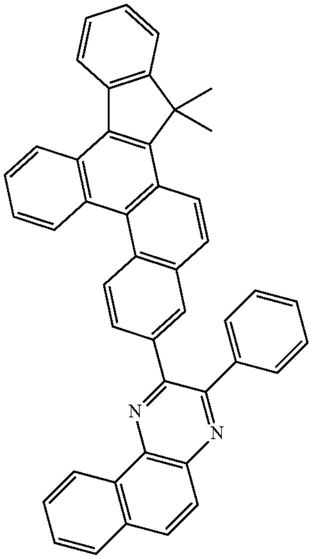
C-245
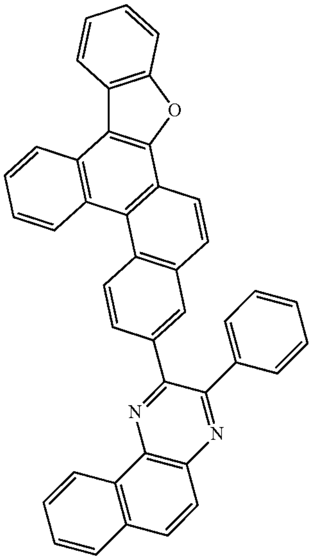

-continued
C-246
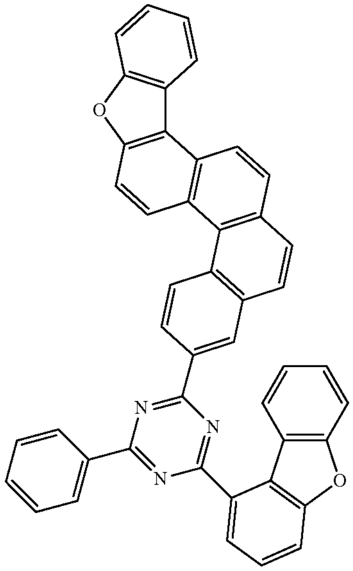
C-247
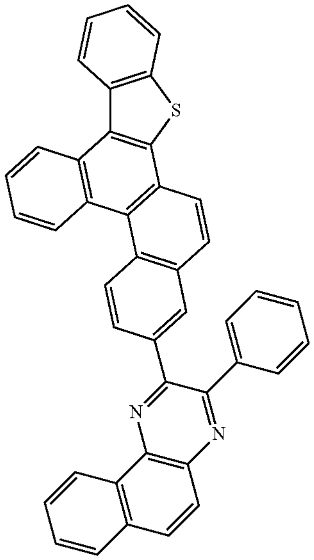
-continued
C-248
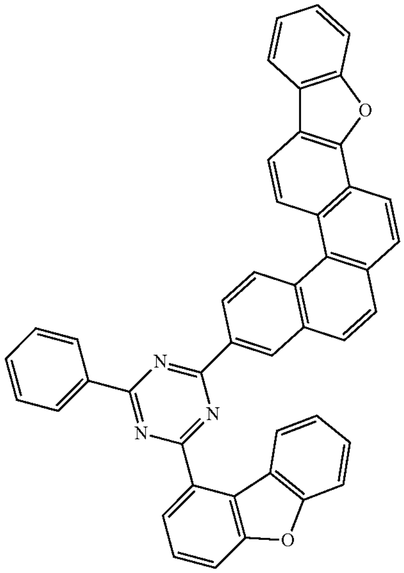
C-249
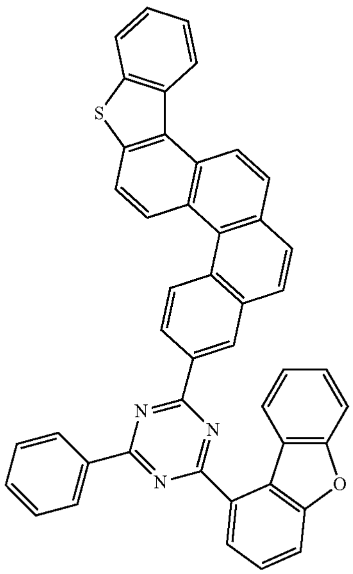

-continued
C-250
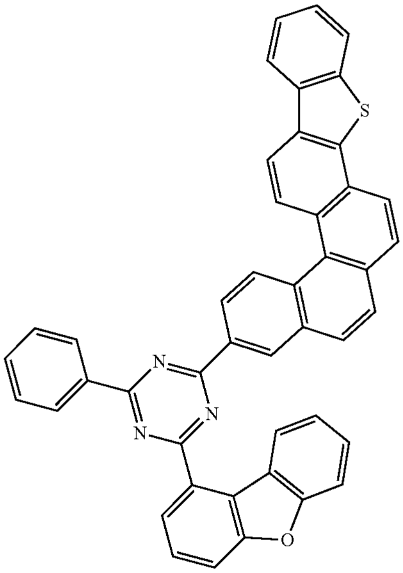
C-251
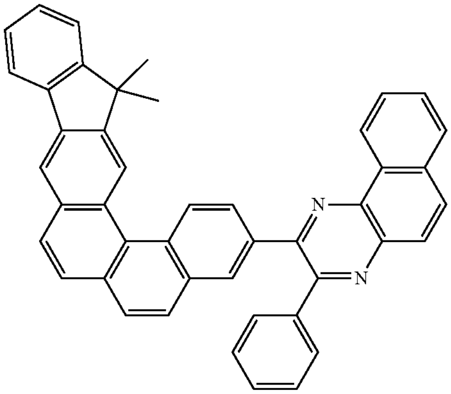
C-252
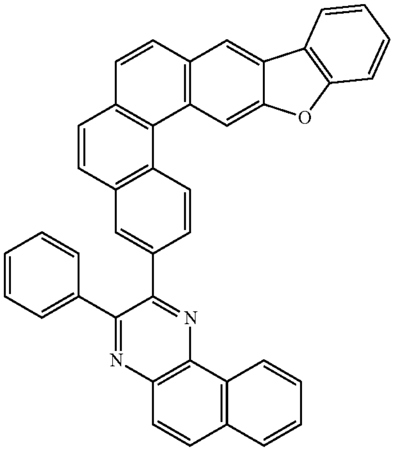
-continued
C-253
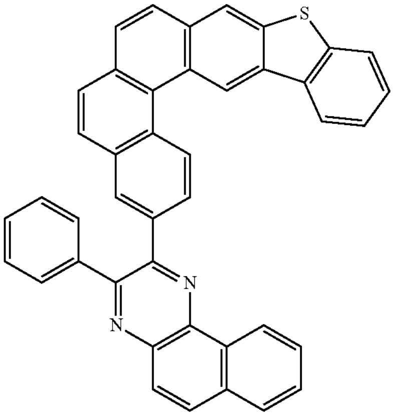
C-254
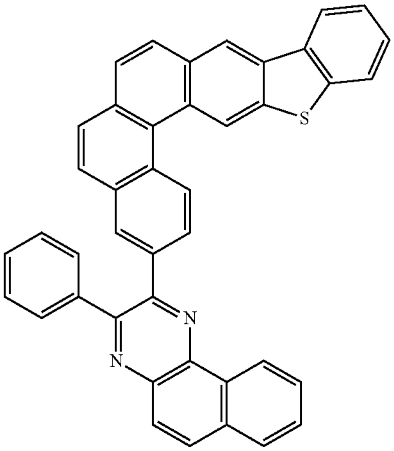
C-255
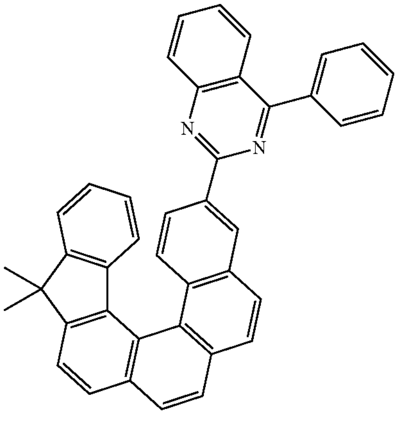

-continued
C-256
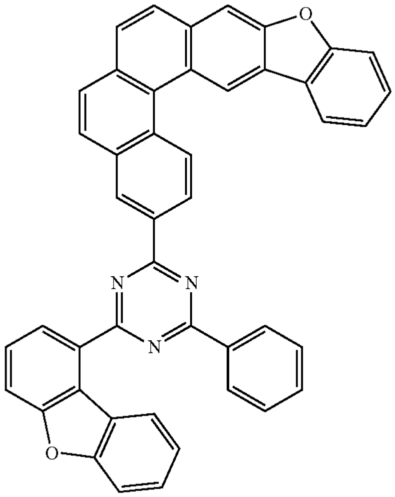
C-257
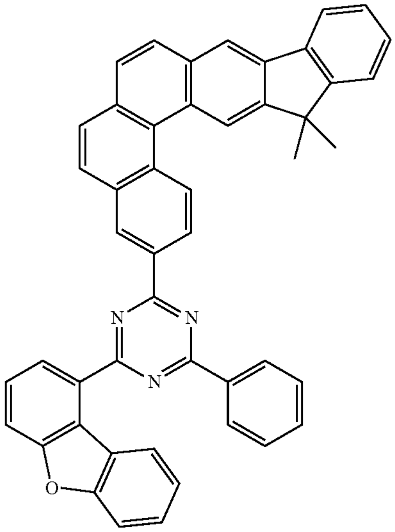
C-258
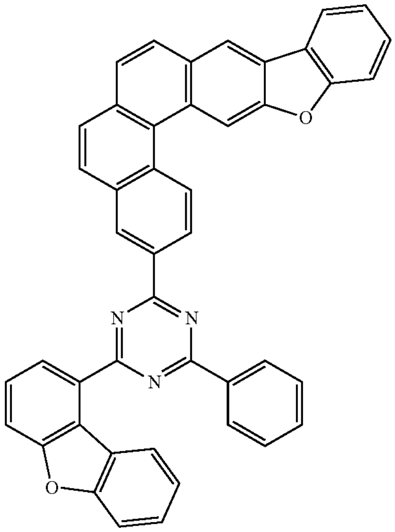
-continued
C-259
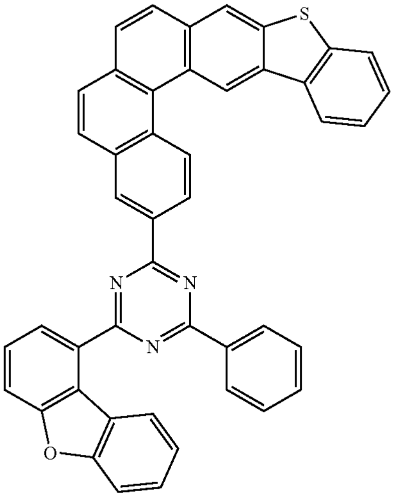
C-260
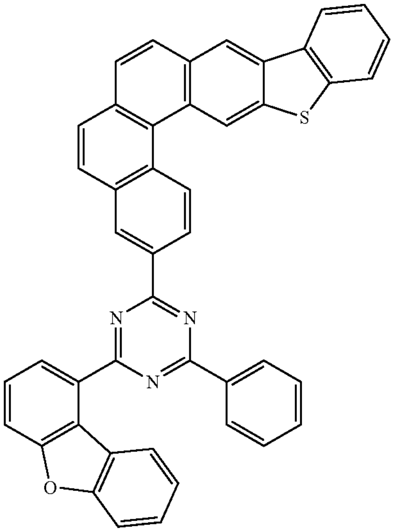
C-261
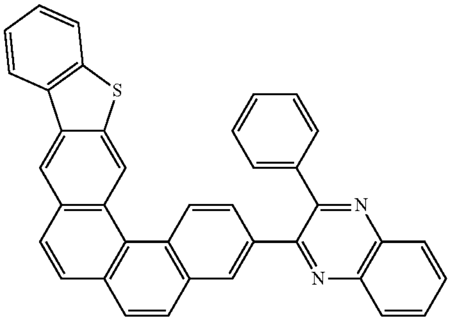

-continued
C-262
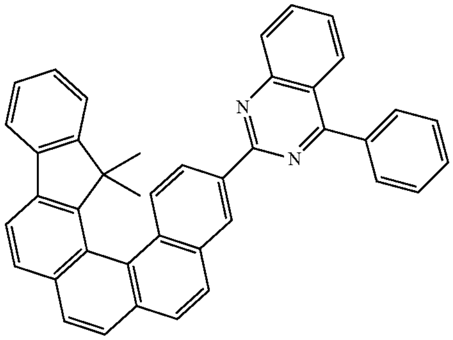
C-263
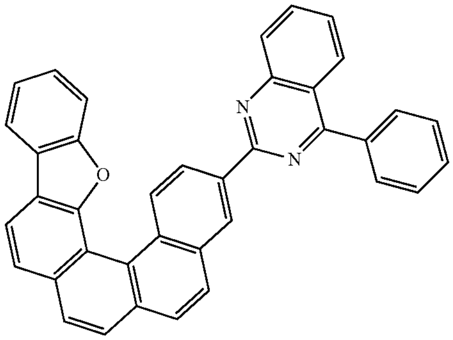
C-264
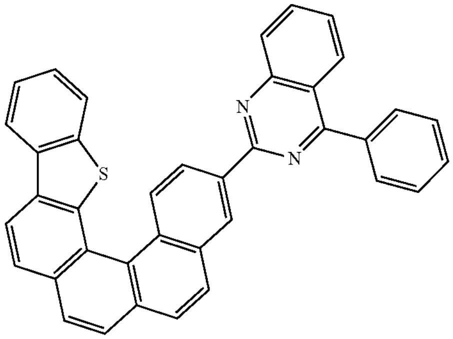
C-265
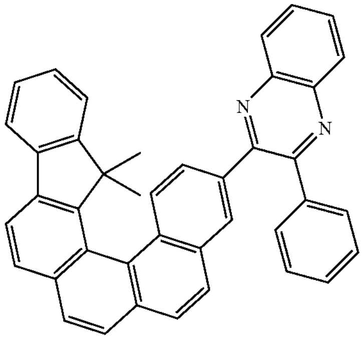
-continued
C-266
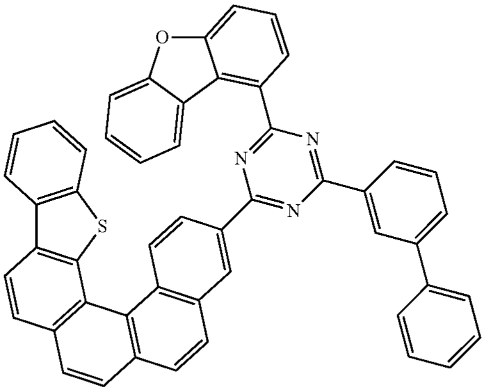
C-267
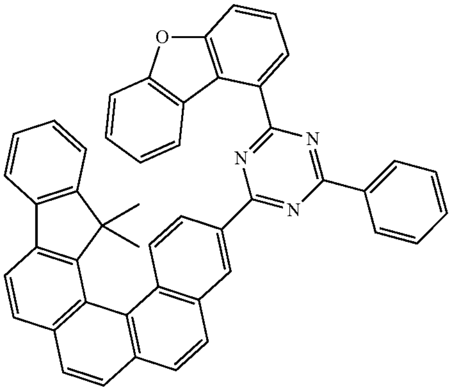
C-268
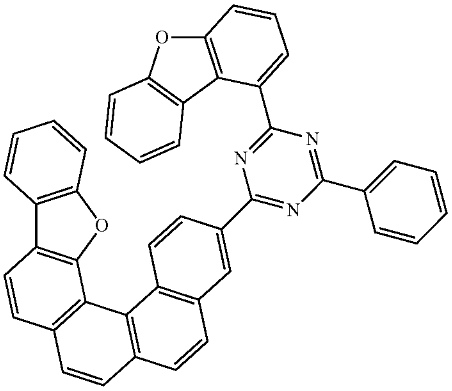
C-269
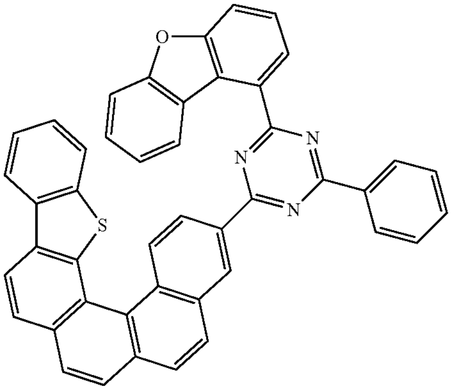

-continued
C-270
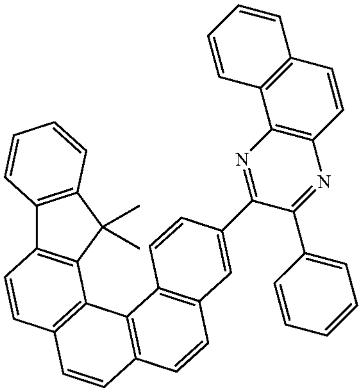
C-271
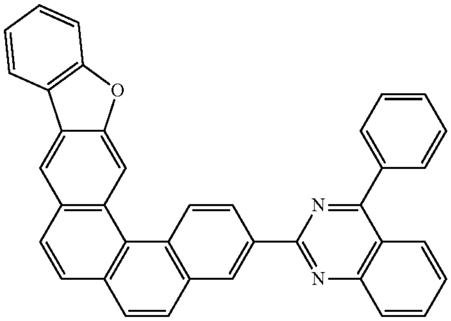
C-272
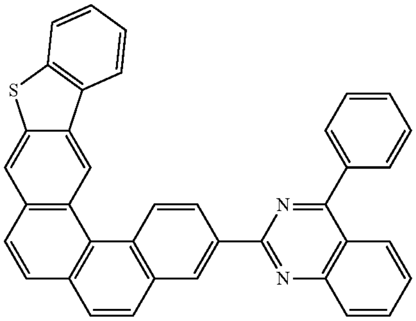
C-273
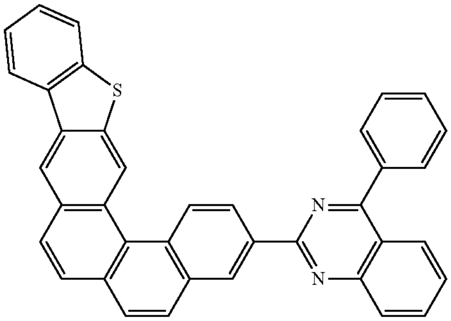
-continued
C-274
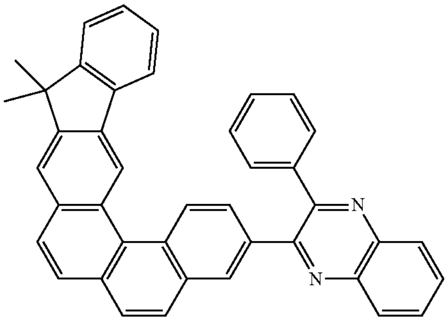
C-275
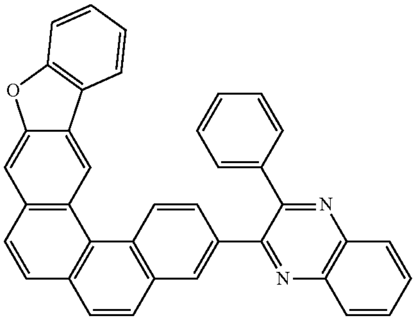
C-276
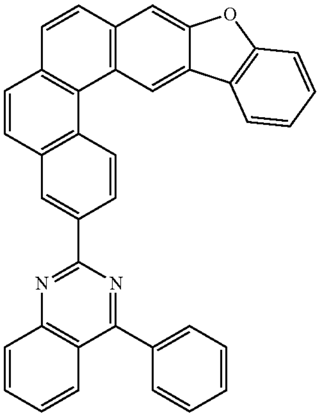
C-277
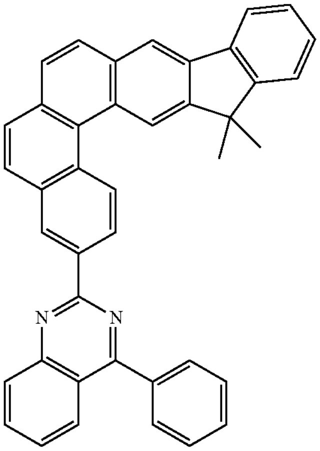

-continued
C-278
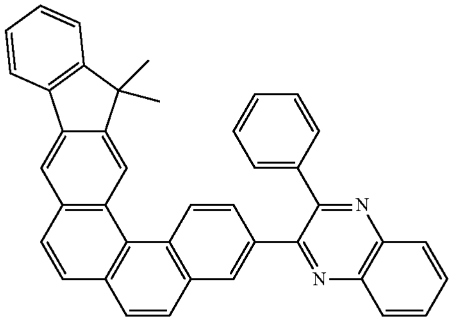
C-279
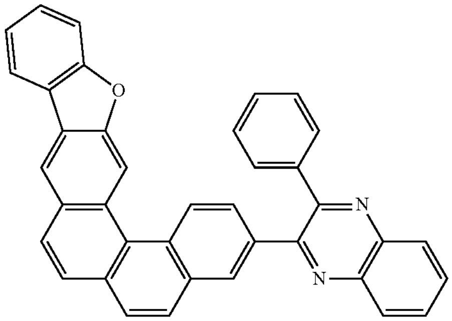
C-280
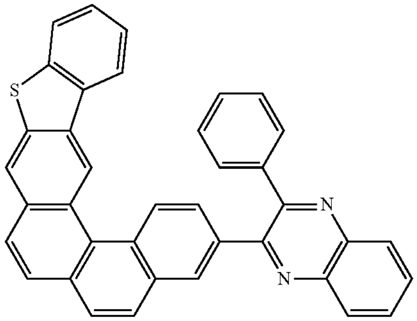
C-281
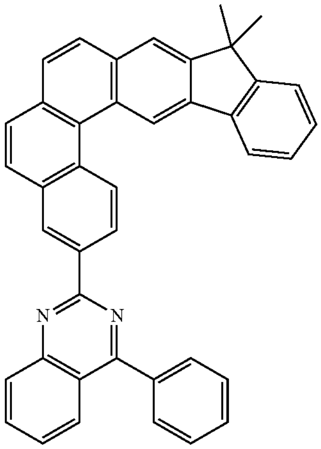
-continued
C-282
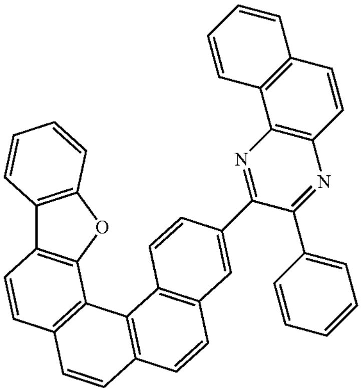
C-283
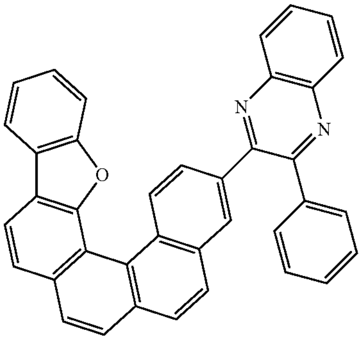
C-284
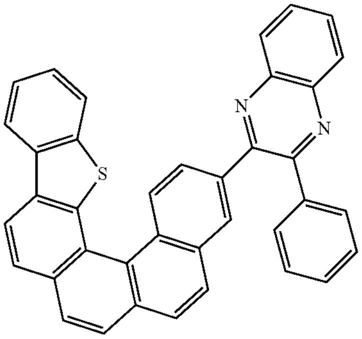
C-285
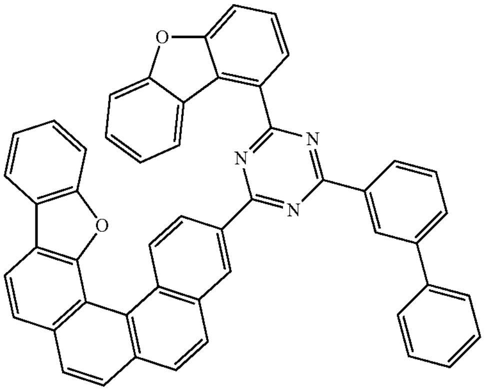

-continued
C-286
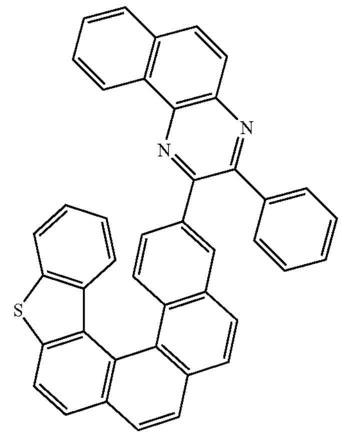
C-287
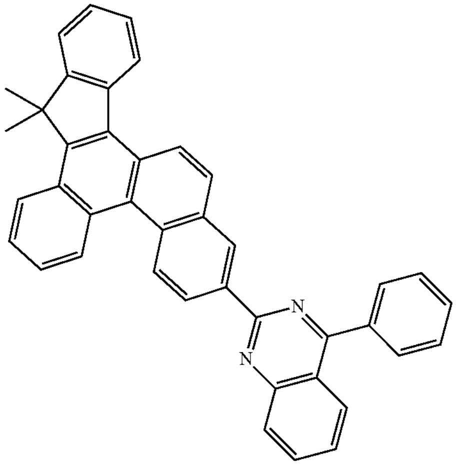
C-288
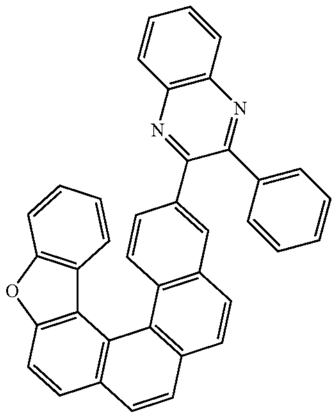
-continued
C-289
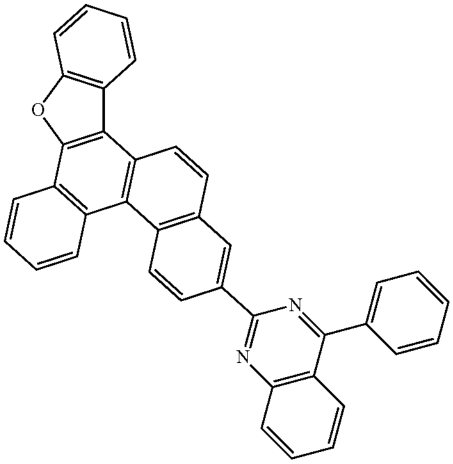
C-290
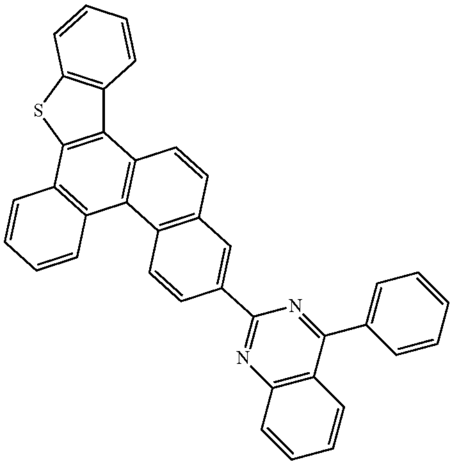
C-291
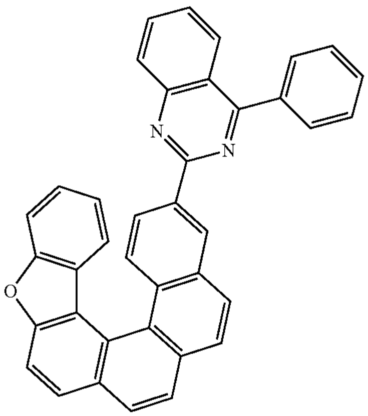

C-293
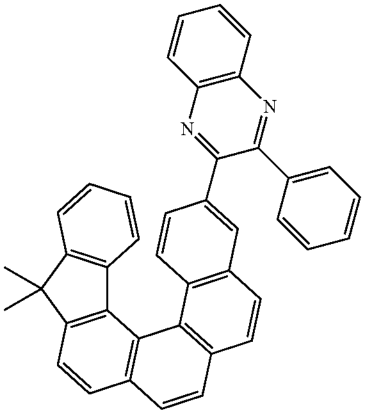
C-294
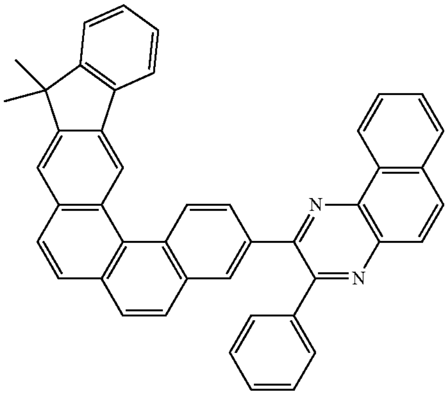
C-295
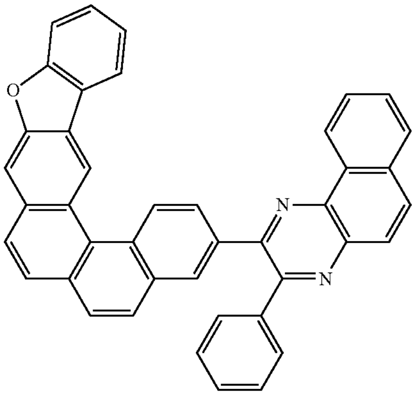
C-296
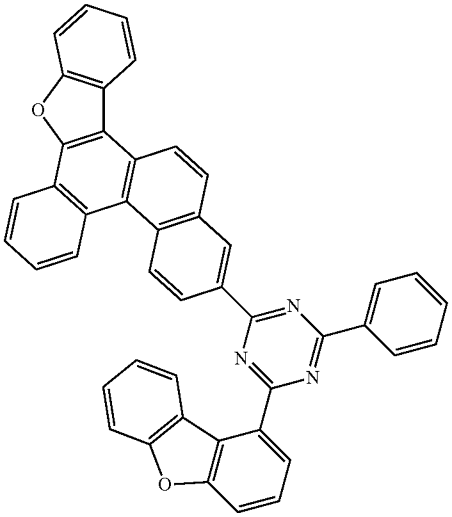
C-297
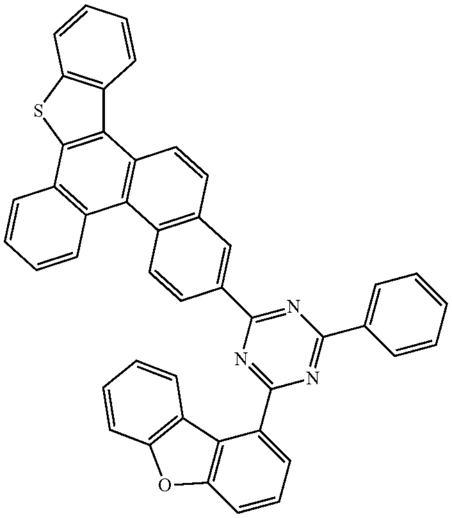
C-298
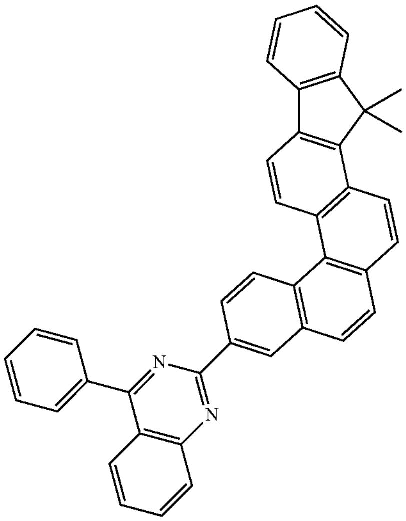

-continued
C-299
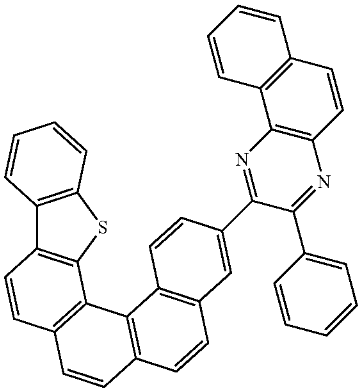
C-300
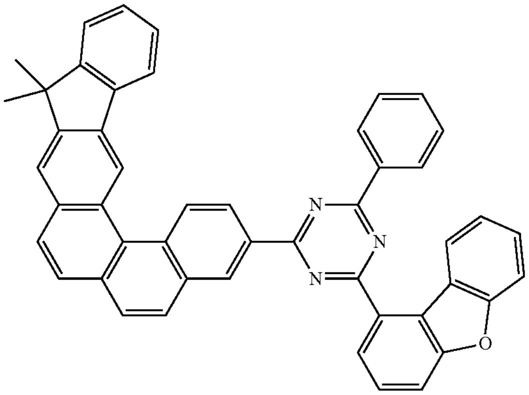
C-301
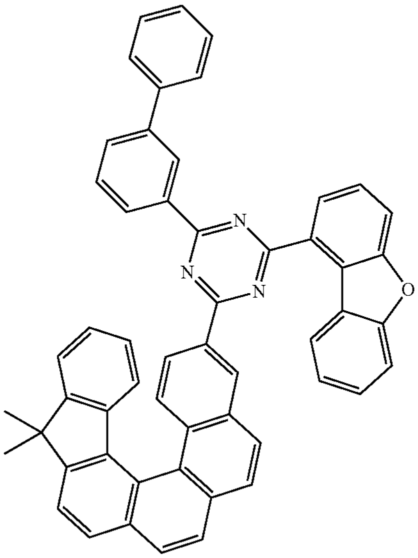
-continued
C-302
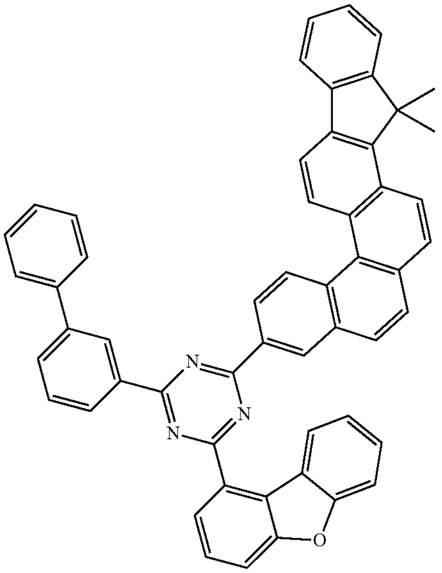
C-303
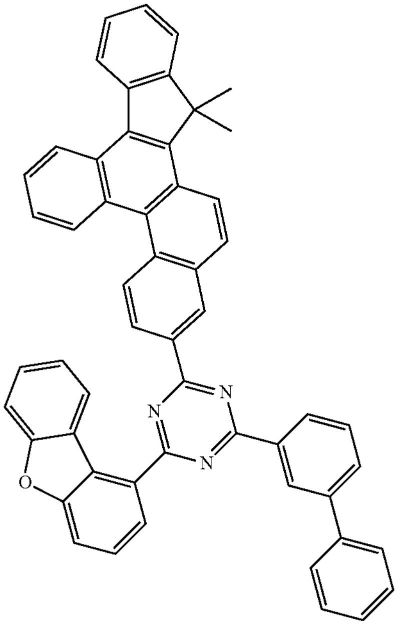

-continued
C-304
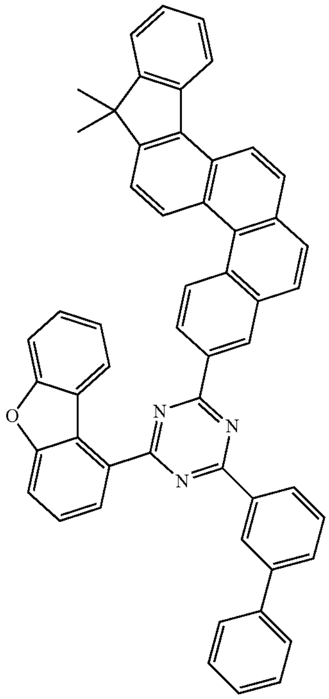
C-305
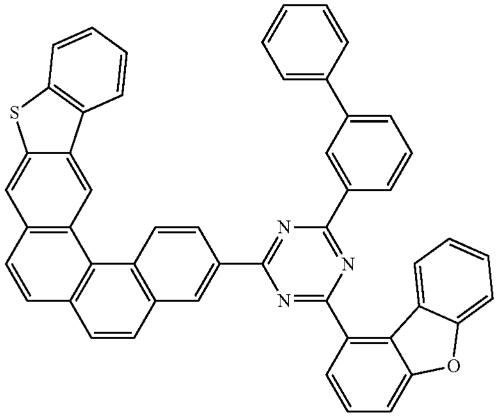
C-306
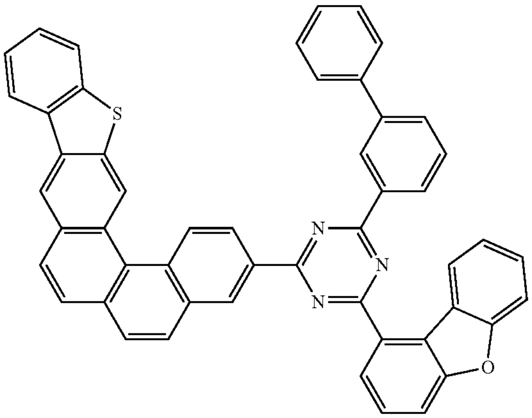
-continued
C-307
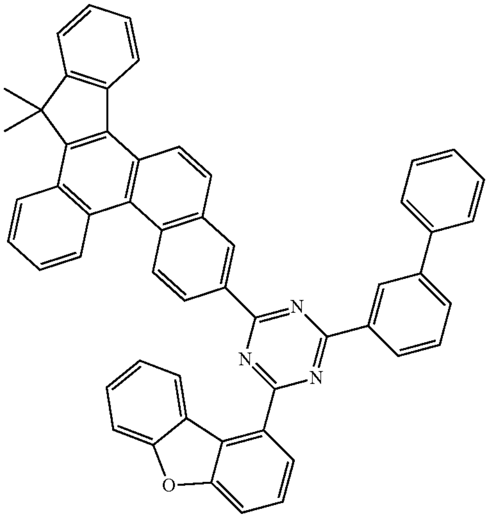
C-308
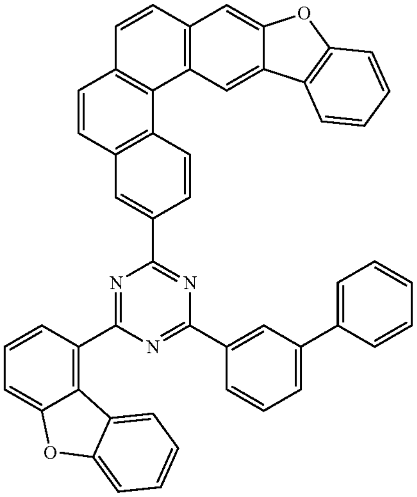
C-309
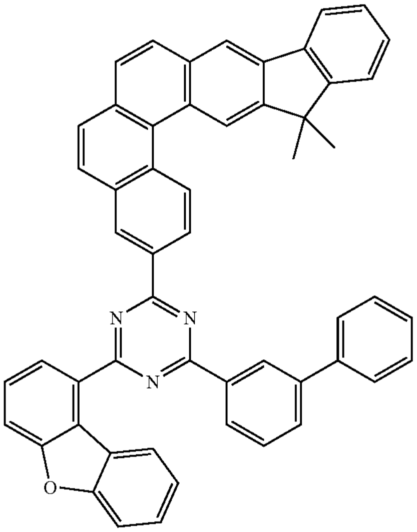

C-310
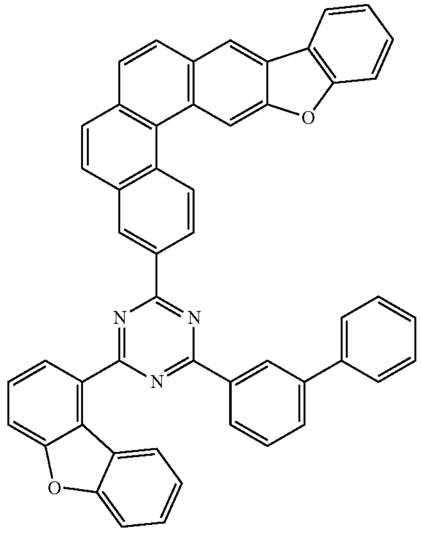
C-311
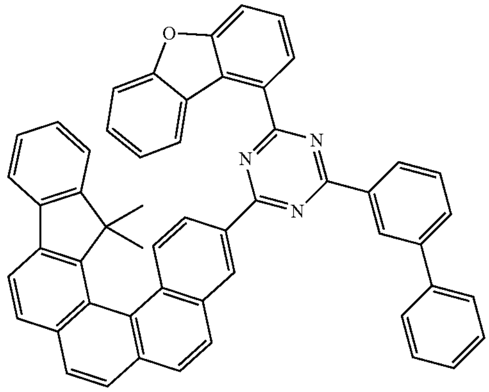
C-312
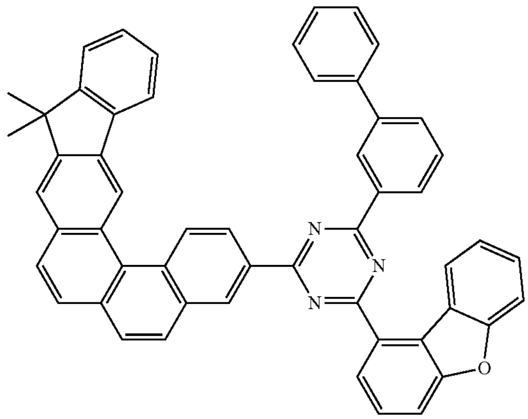
C-313
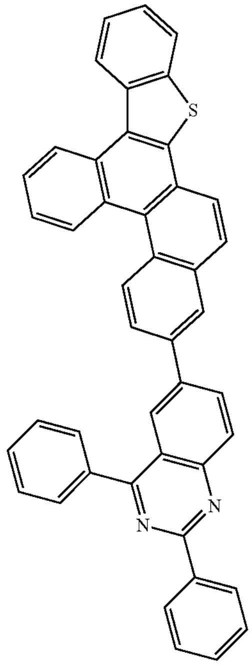
C-314
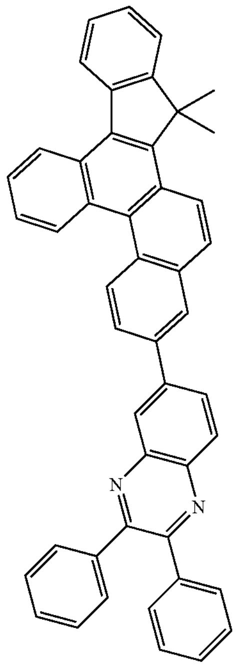

-continued
C-315
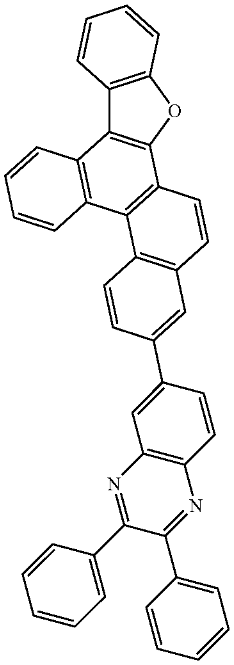
-continued
C-317
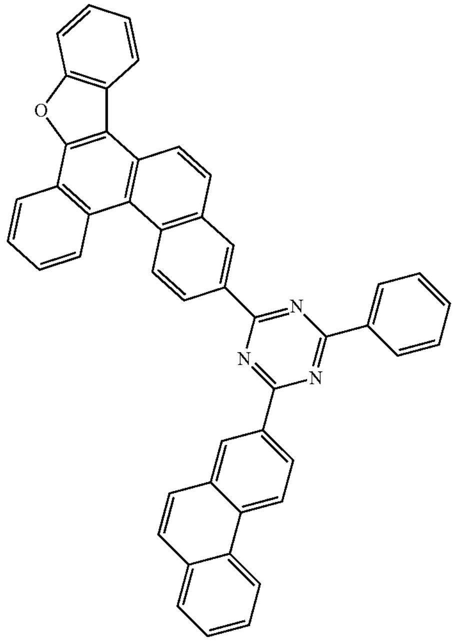
C-316
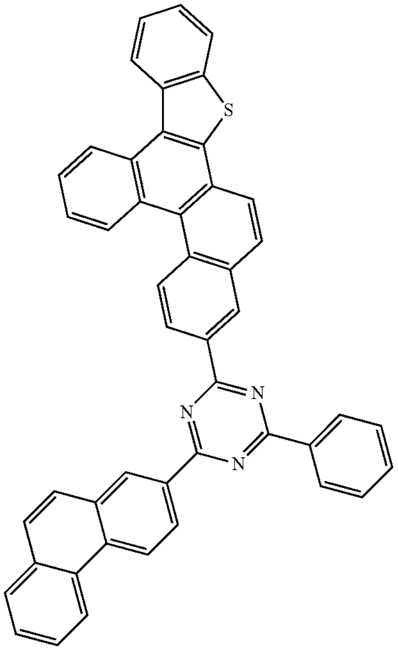
C-318
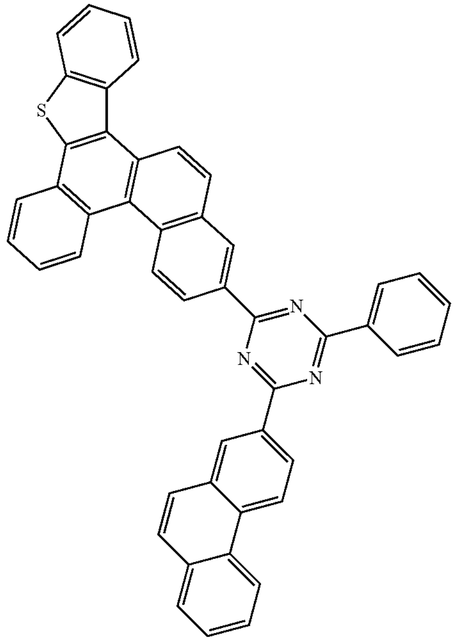

-continued
C-319
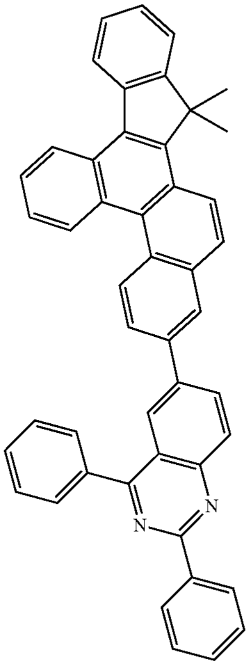
C-320
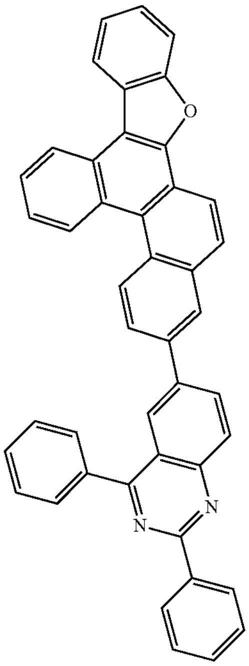
-continued
C-321
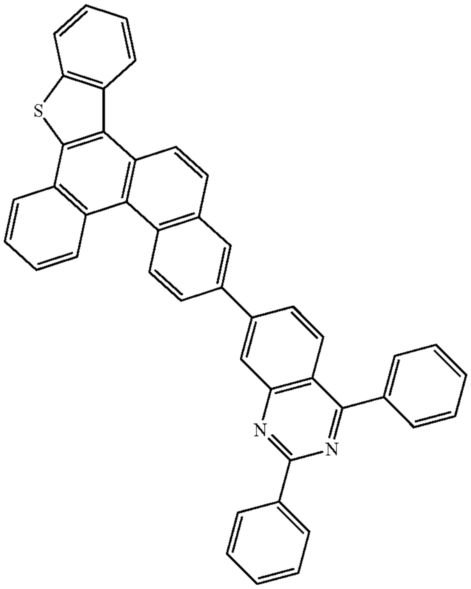
C-322
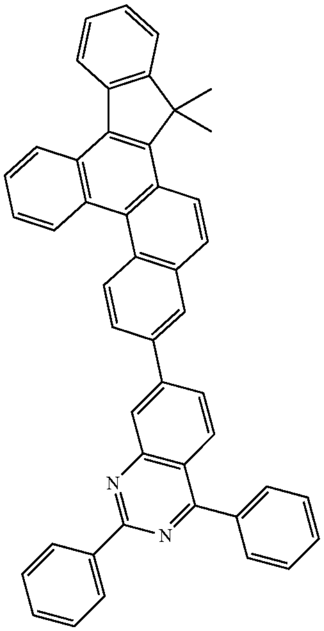

-continued
C-323
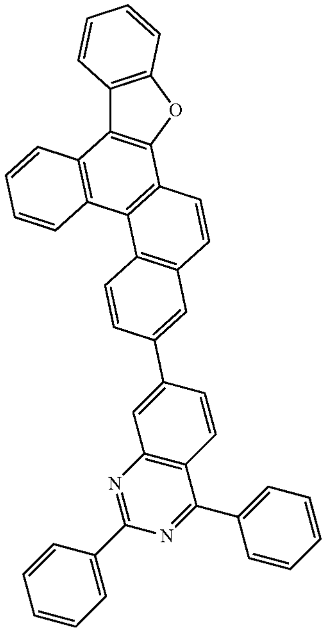
C-324
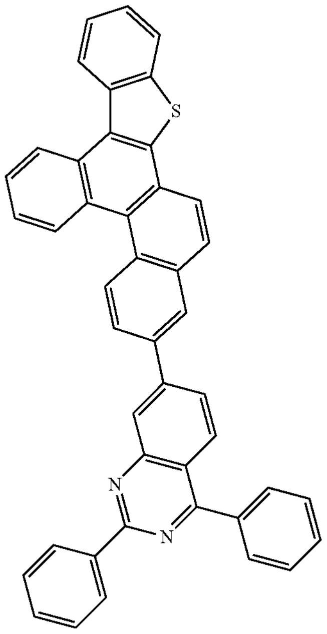
-continued
C-325
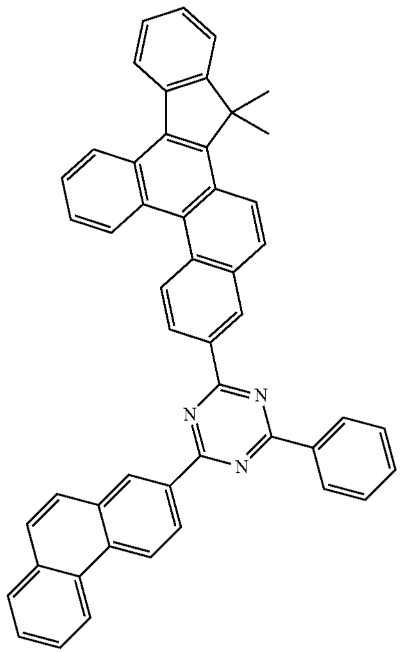
C-326
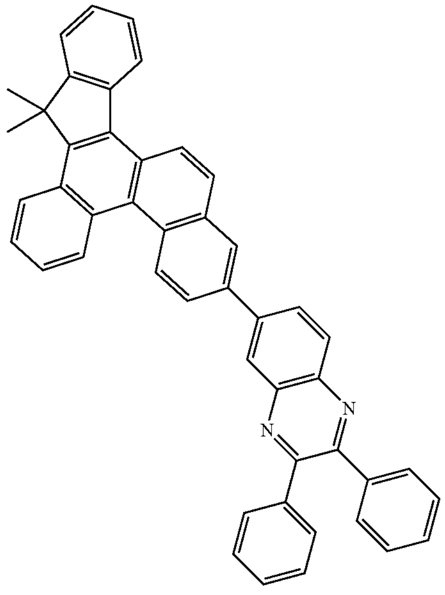

-continued
C-327
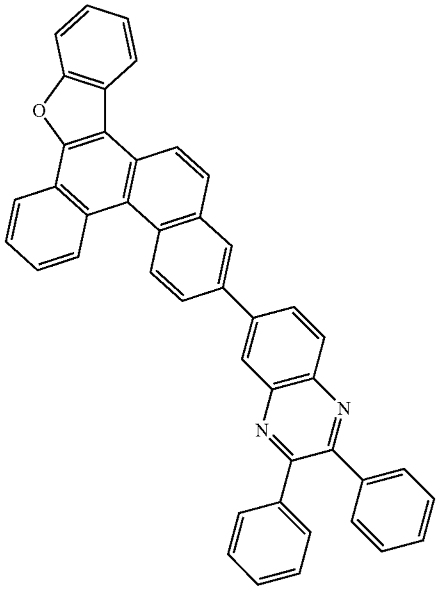
C-328
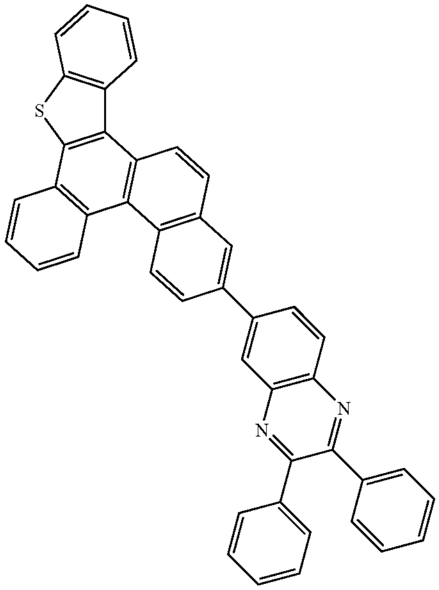
-continued
C-329
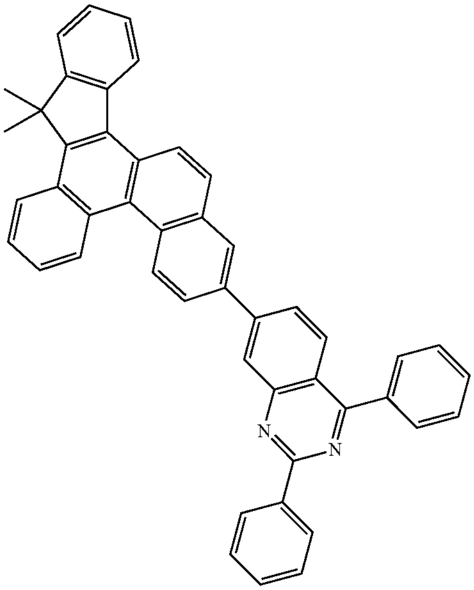
C-330
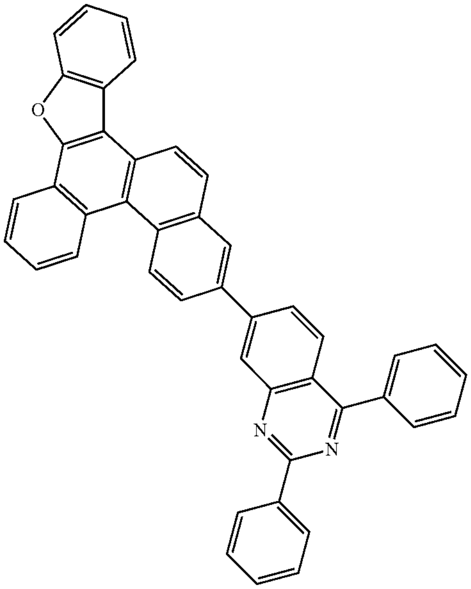
C-331
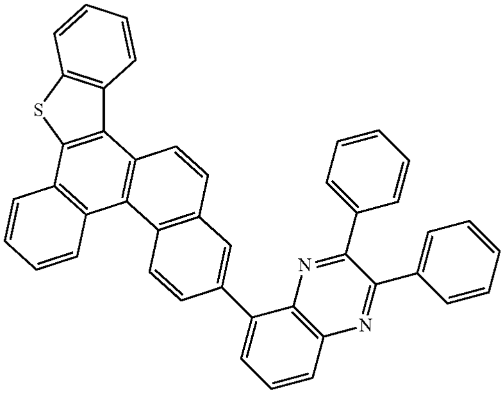

-continued
C-332
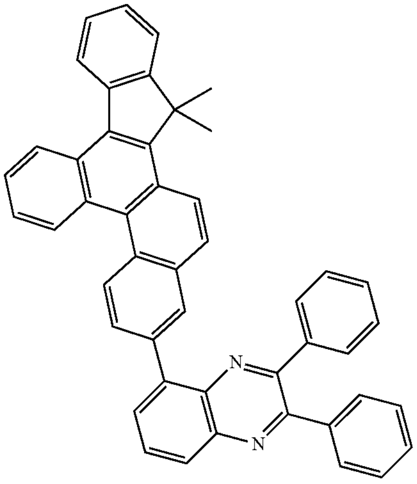
C-333
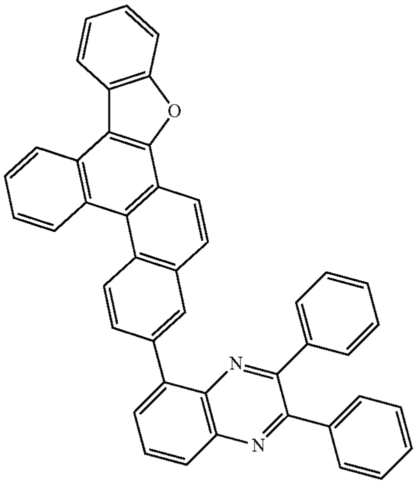
C-334
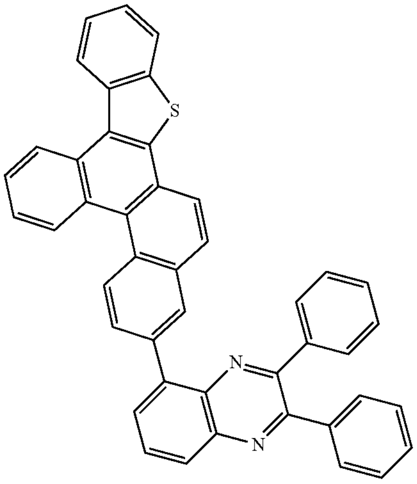
-continued
C-335
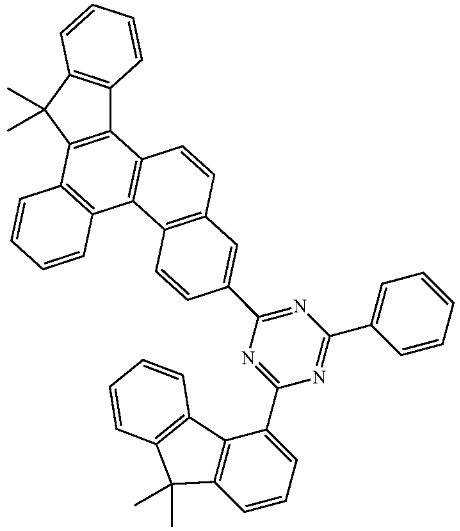
C-336
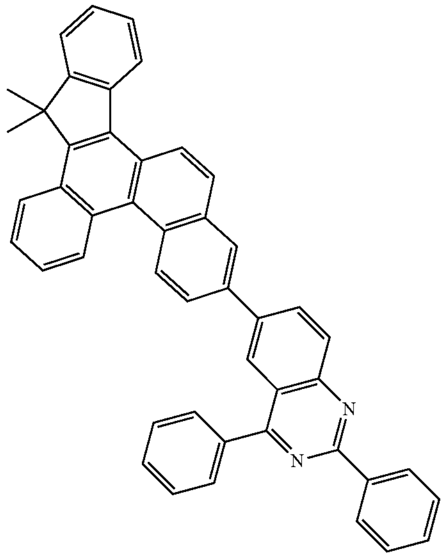
C-337
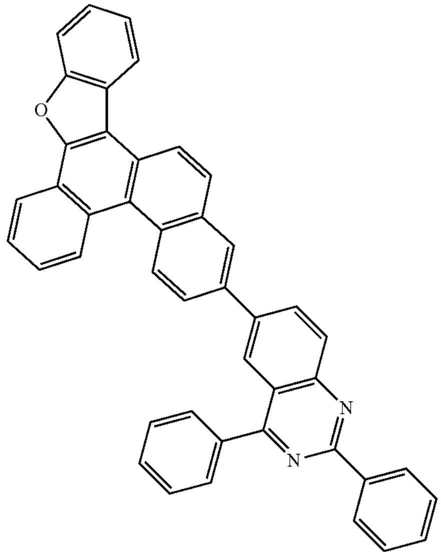

-continued
C-338
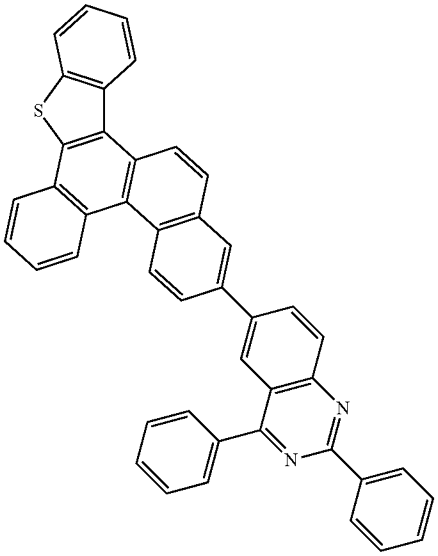
C-339
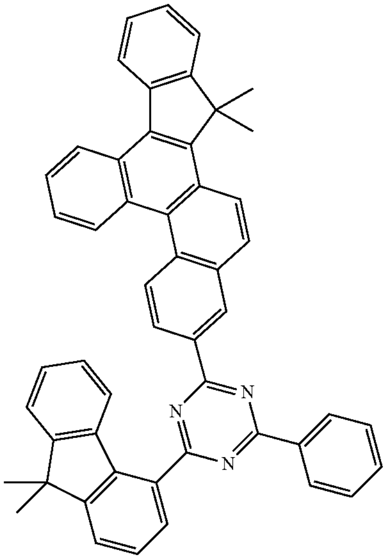
-continued
C-340
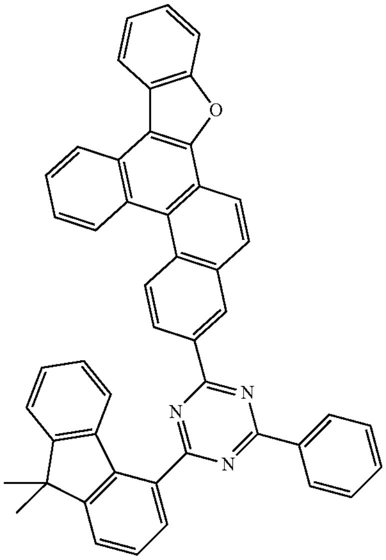
C-341
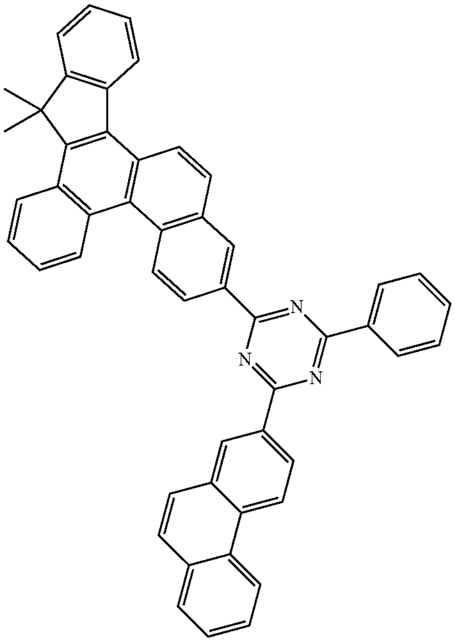

-continued
C-342
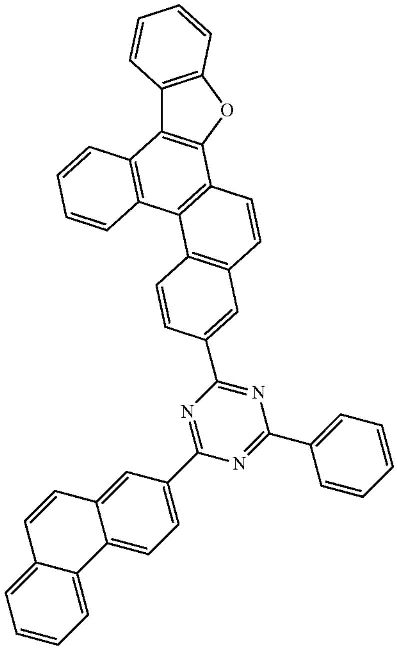
C-343
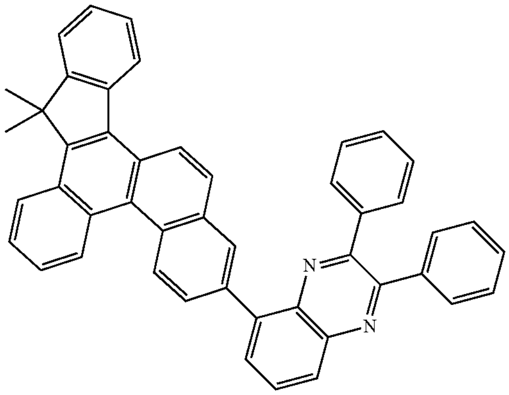
C-344
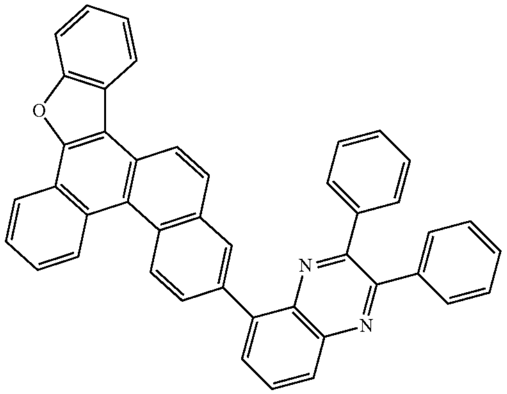
-continued
C-345
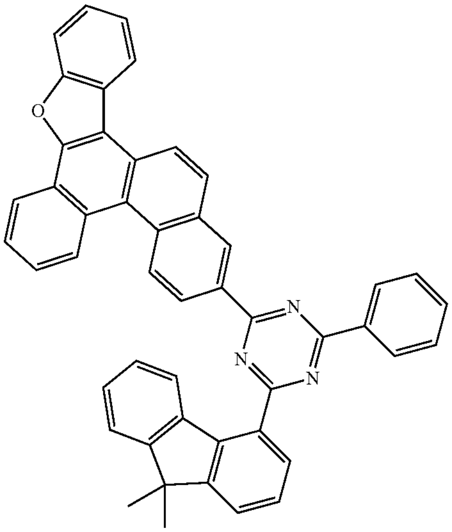
C-346
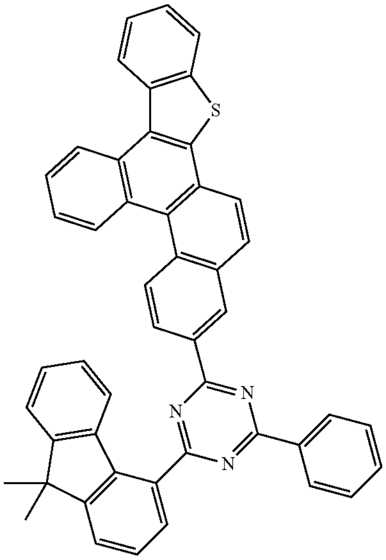

-continued
C-347
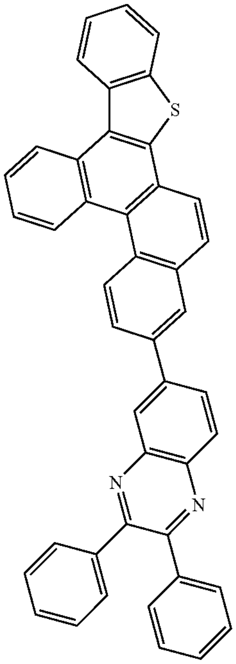
C-348
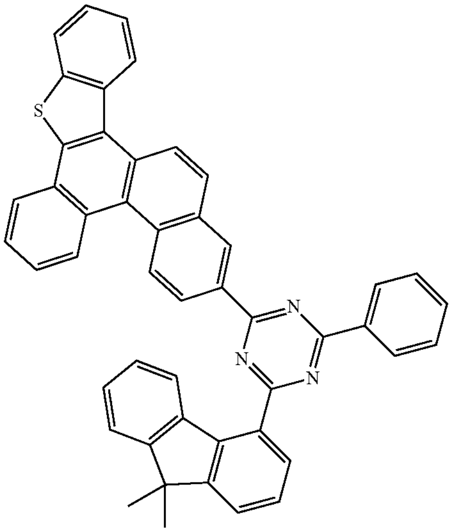
-continued
C-349
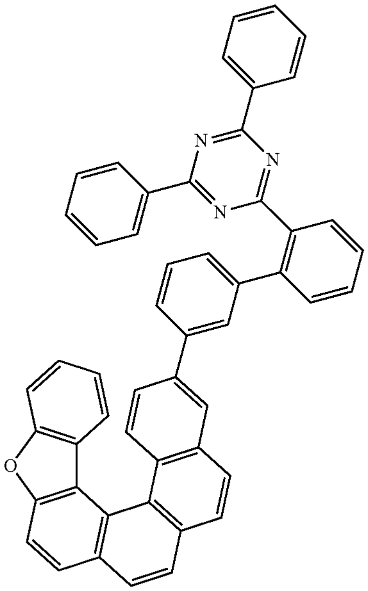
C-350
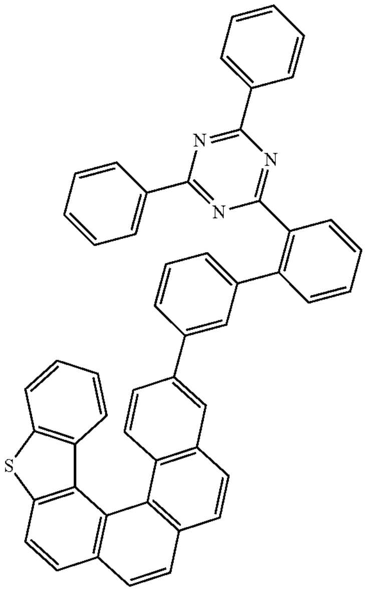
C-351
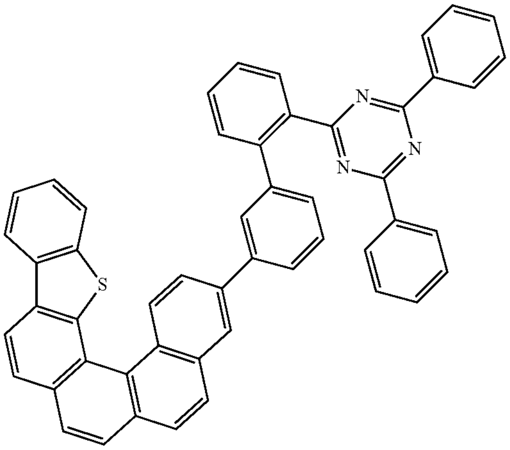

-continued
C-352
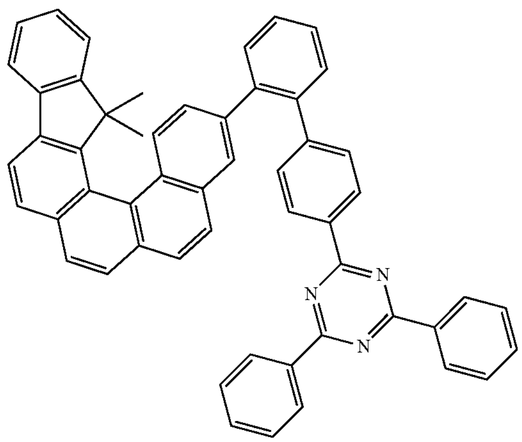
C-353
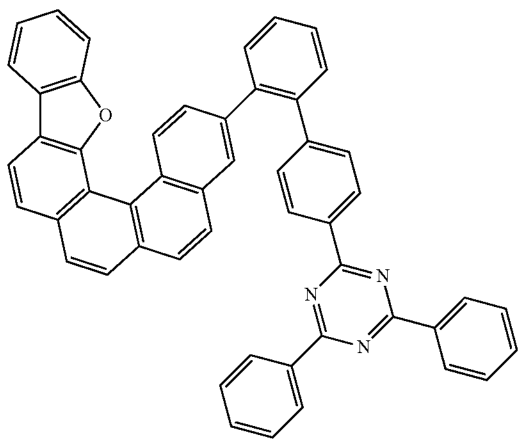
C-354
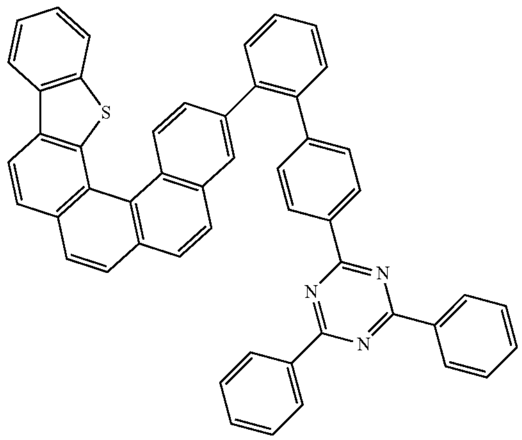
-continued
C-355
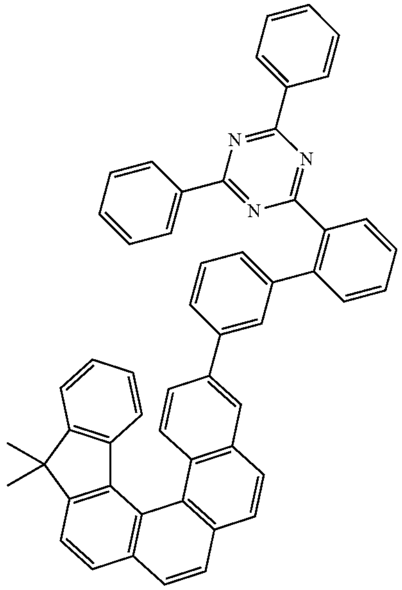
C-356
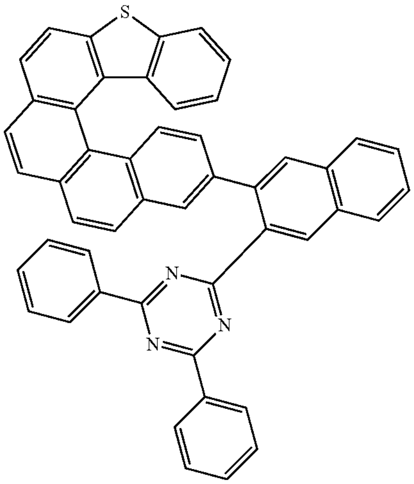
C-357
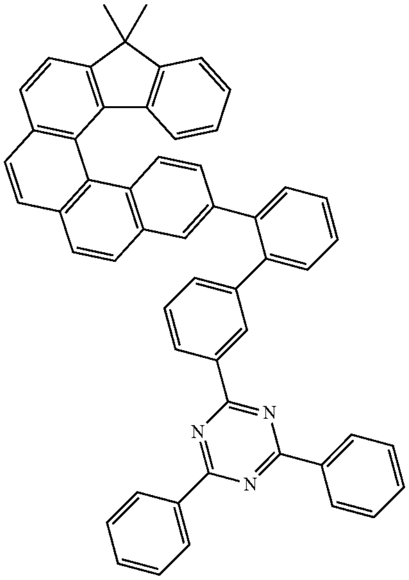

-continued
C-358
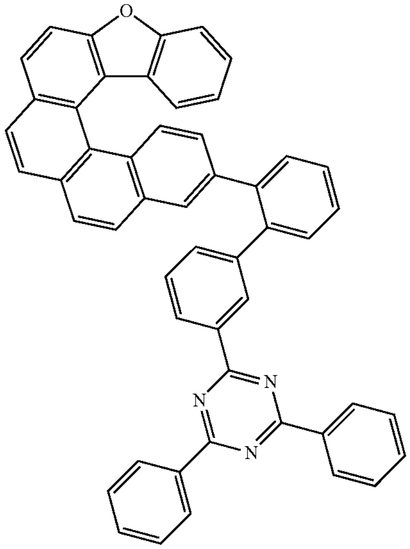
C-359
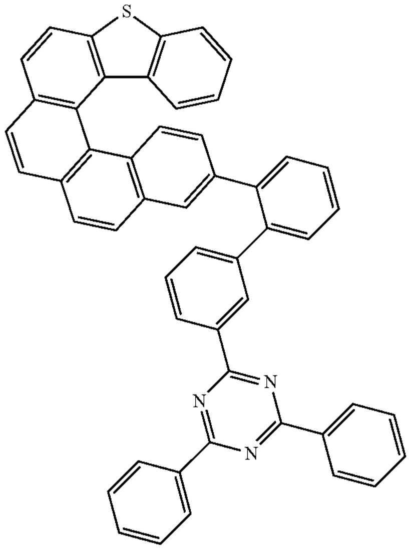
C-360
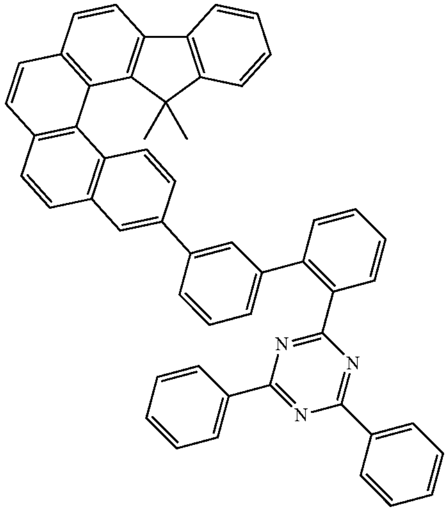
-continued
C-361
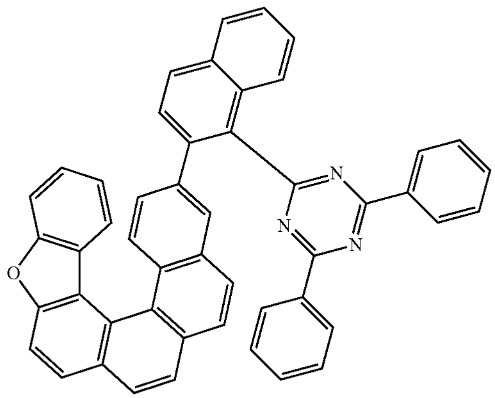
C-362
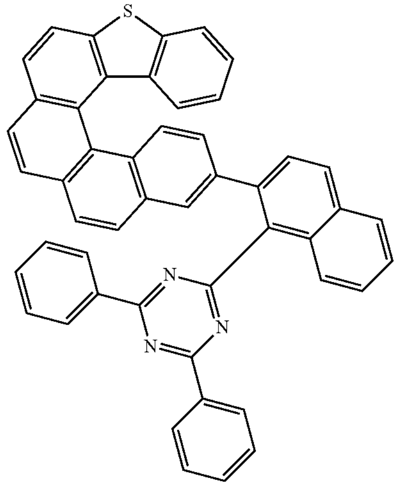
C-363
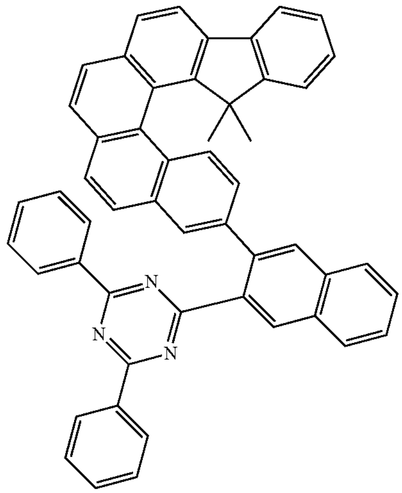

-continued
C-364
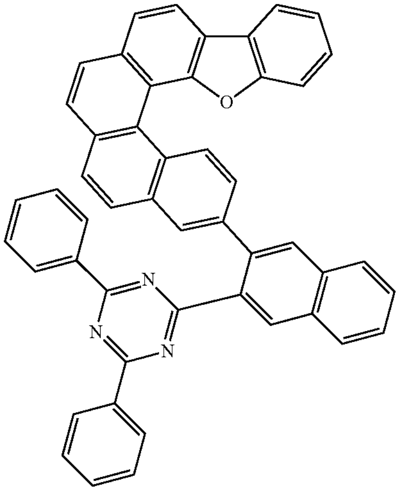
C-365
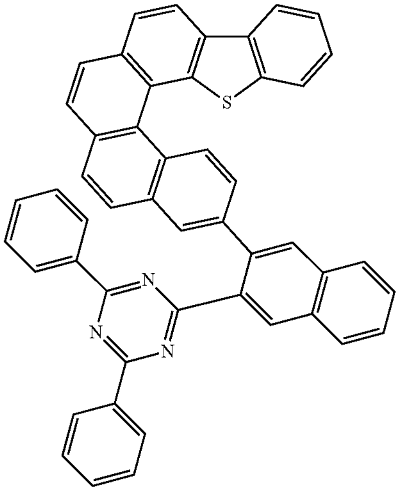
C-366
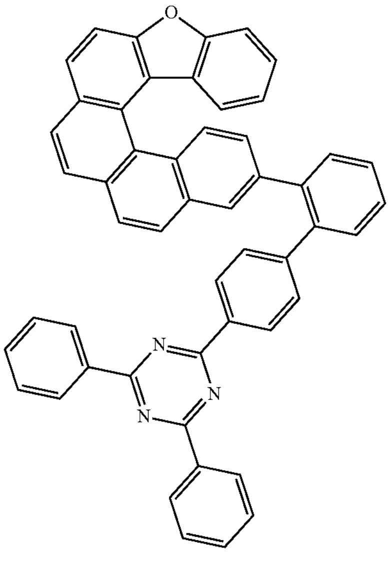
-continued
C-367
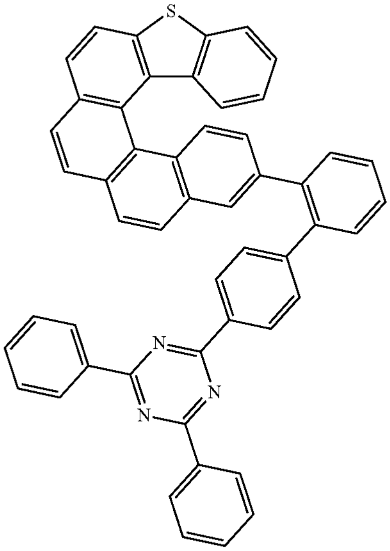
C-368
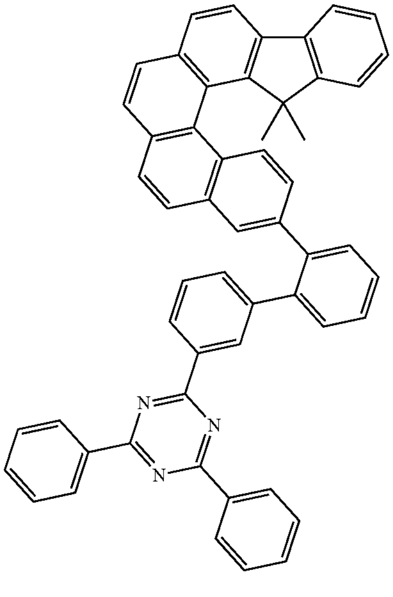

-continued
C-369
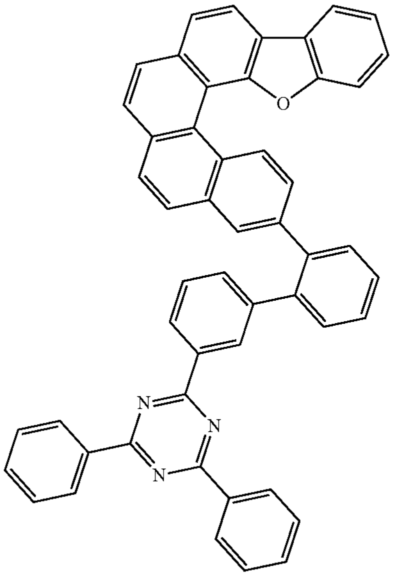
C-370
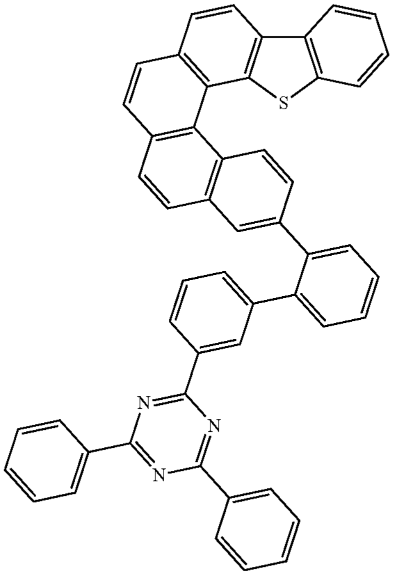
C-371
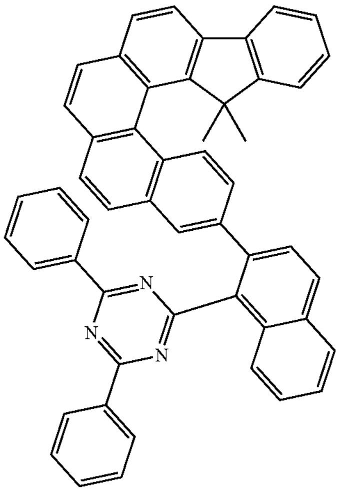
-continued
C-372
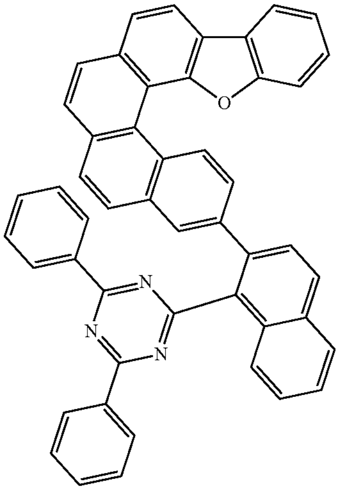
C-373
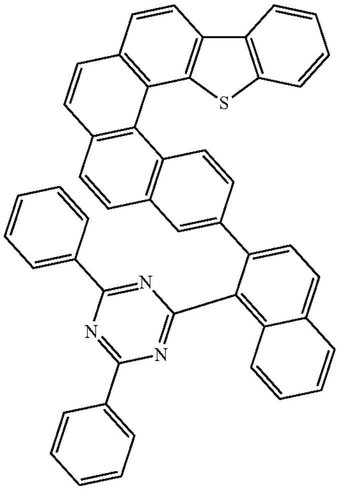
C-374
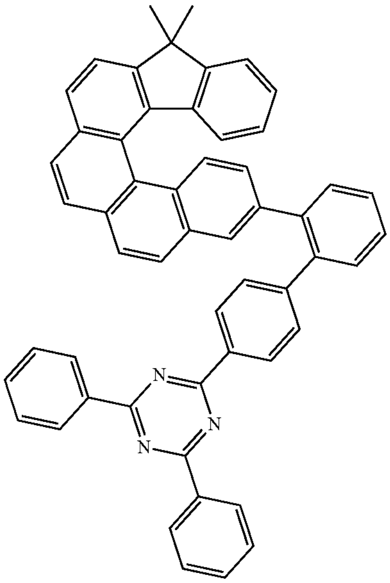

-continued
C-375
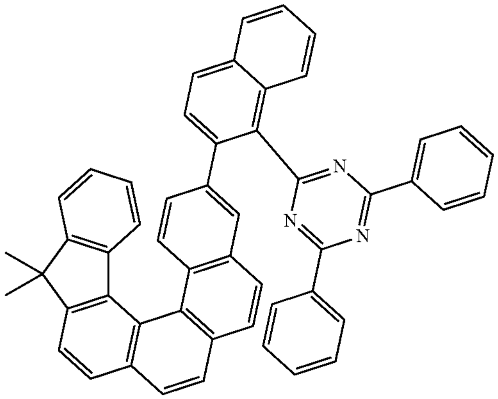
C-376
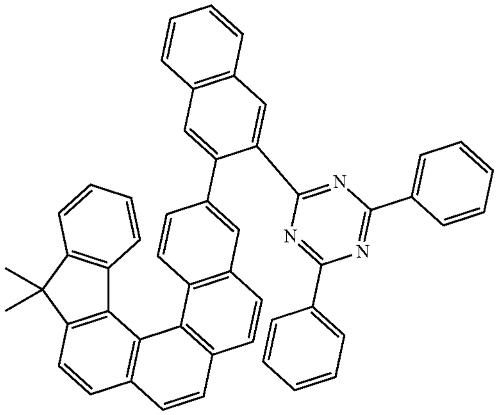
C-377
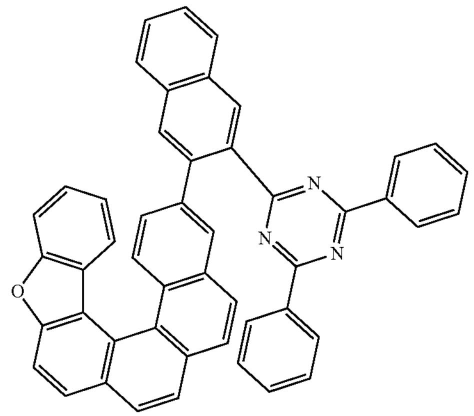
-continued
C-378
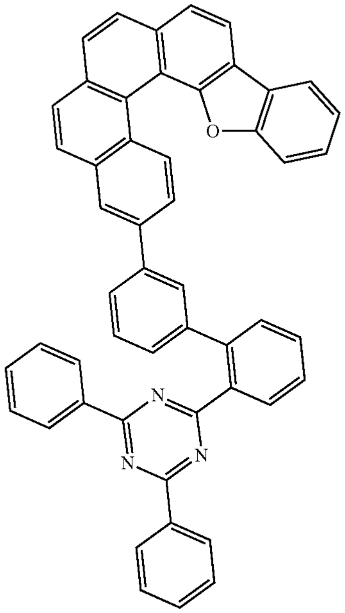
C-379
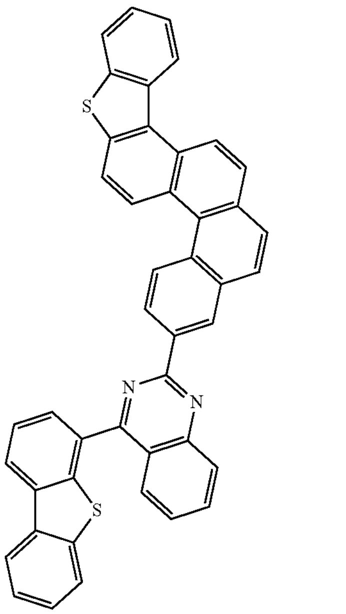

-continued
C-380
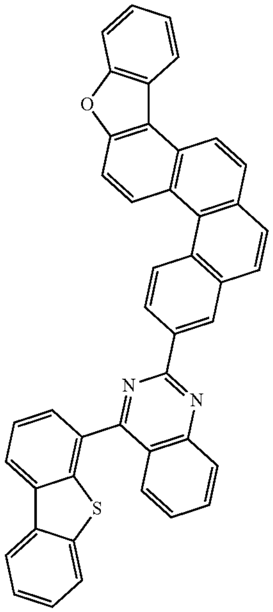
C-381
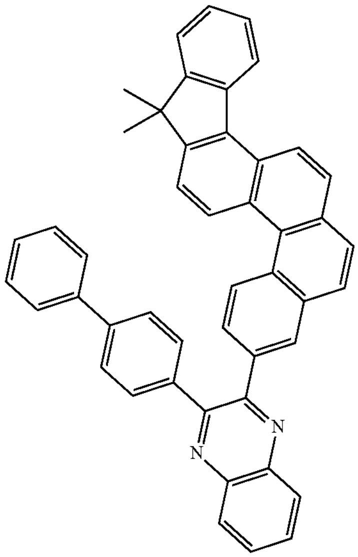
-continued
C-382
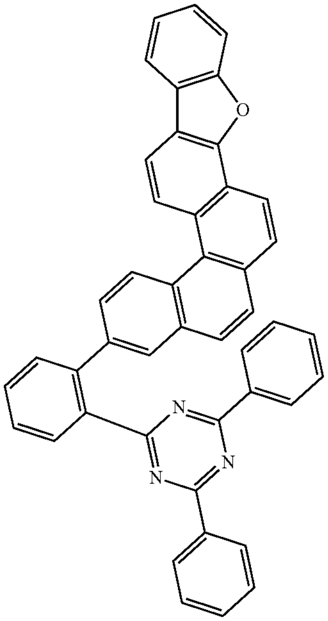
C-383
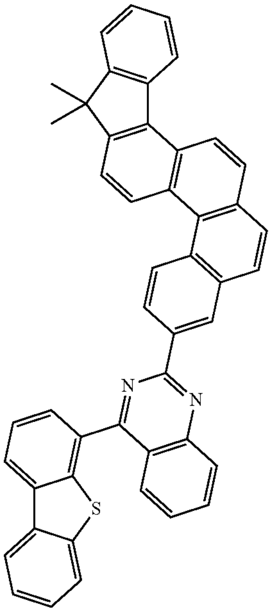

-continued
C-384
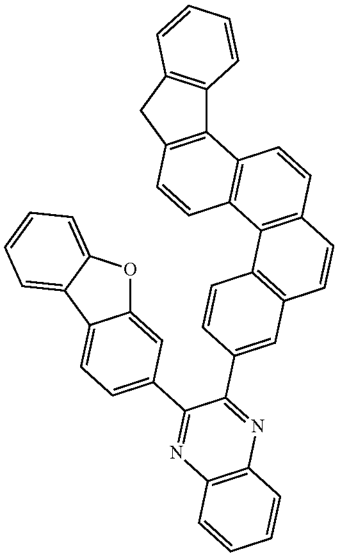
C-385
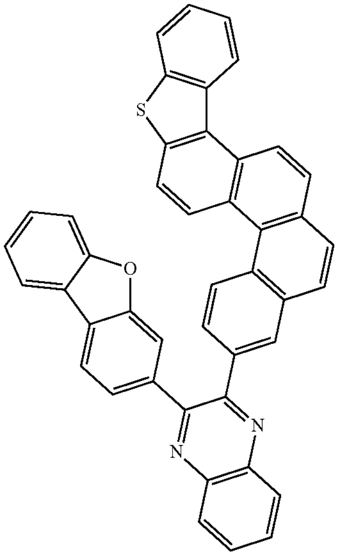
C-386
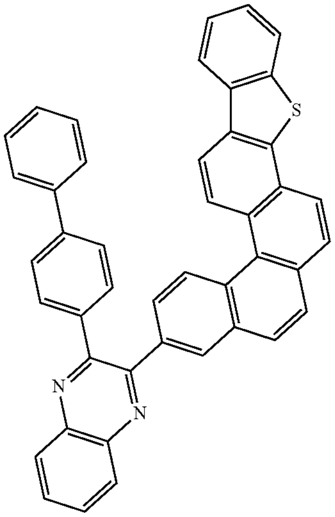
-continued
C-387
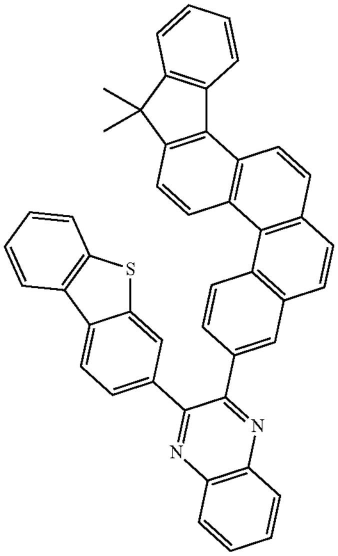
C-388
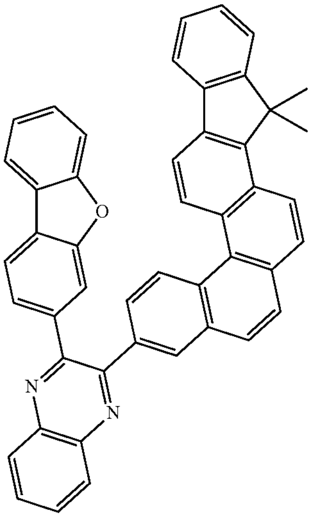
C-389
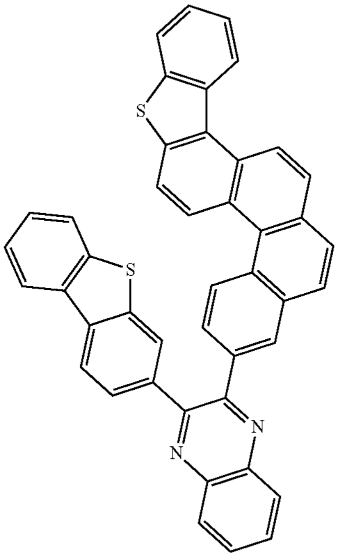

-continued
C-390
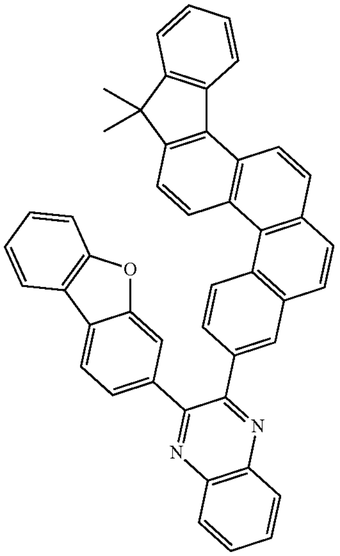
C-391
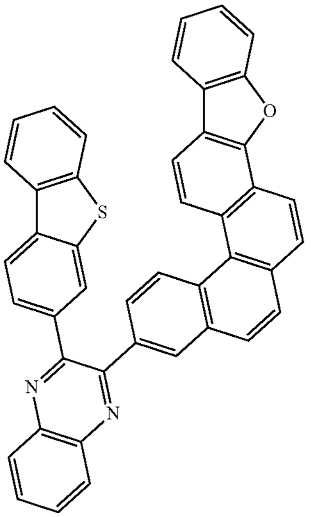
C-392
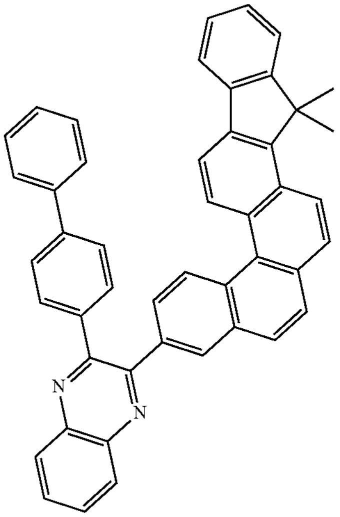
-continued
C-393
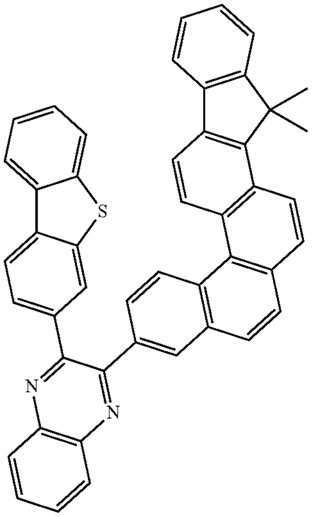
C-394
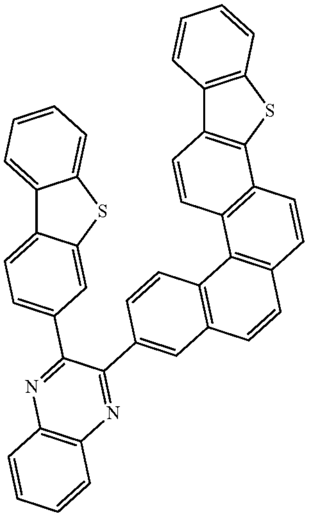
C-395
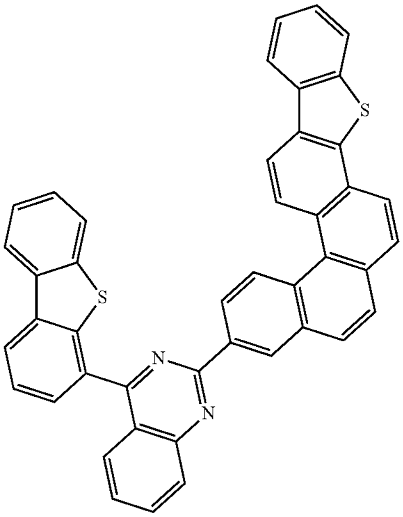

-continued
C-396
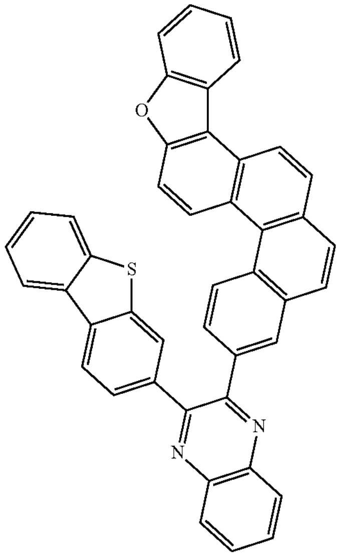
C-397
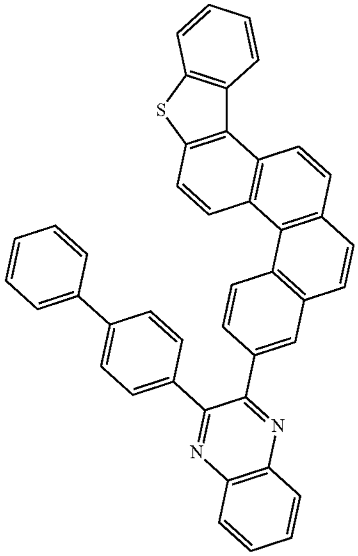
C-398
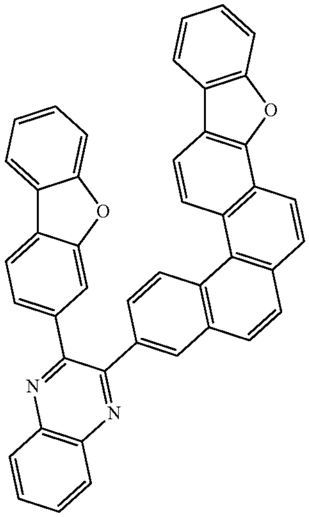
-continued
C-399
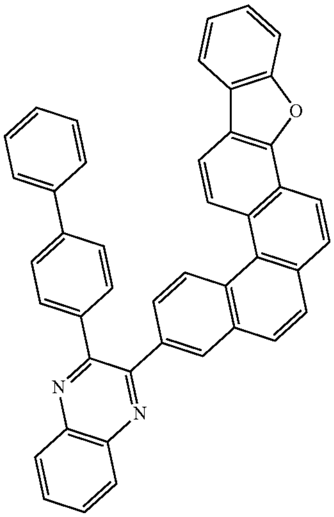
C-400
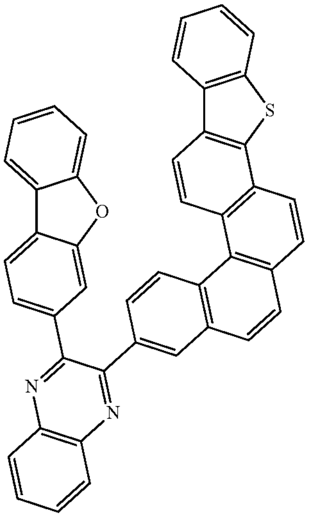
C-401
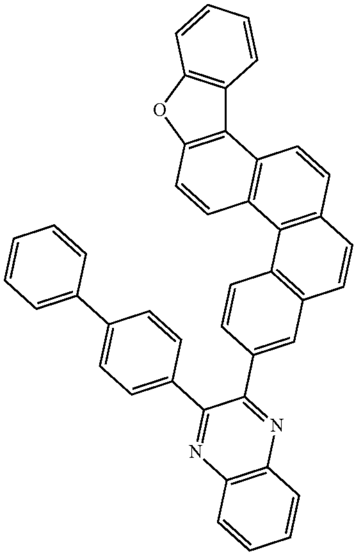

-continued
C-402
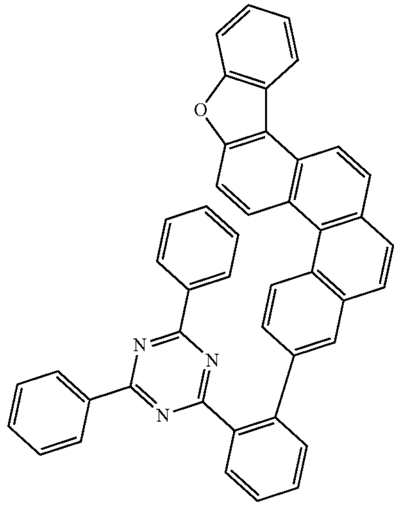
C-403
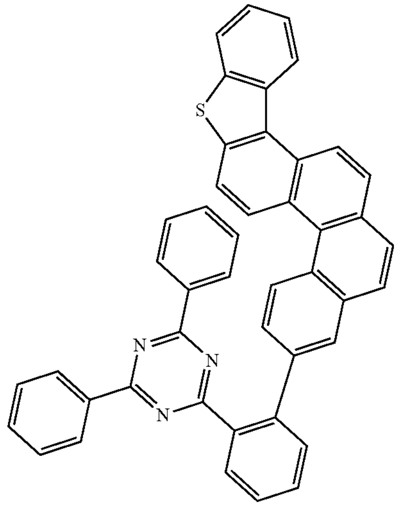
C-404
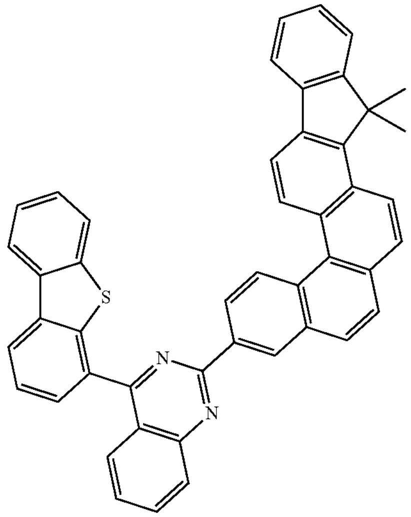
-continued
C-405
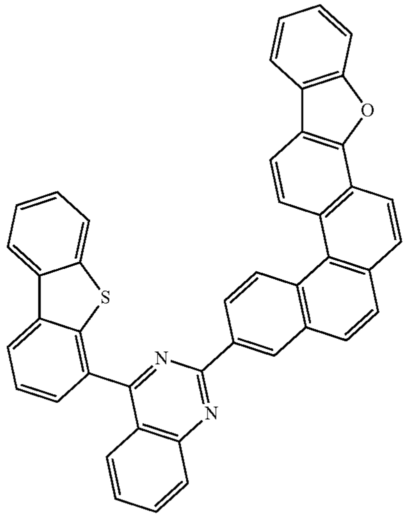
C-406
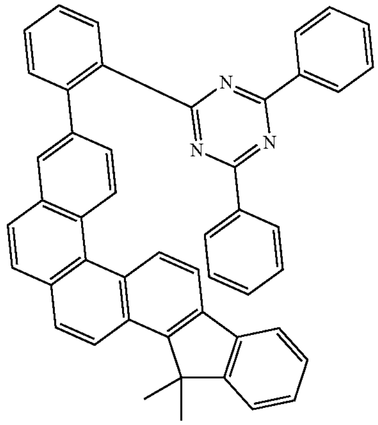
C-407
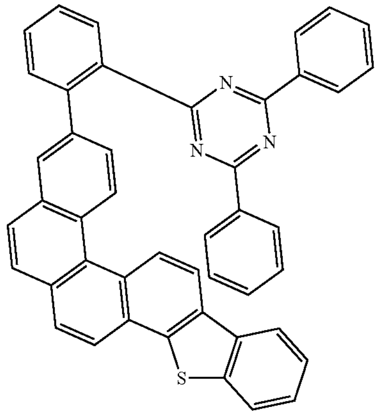

C-408
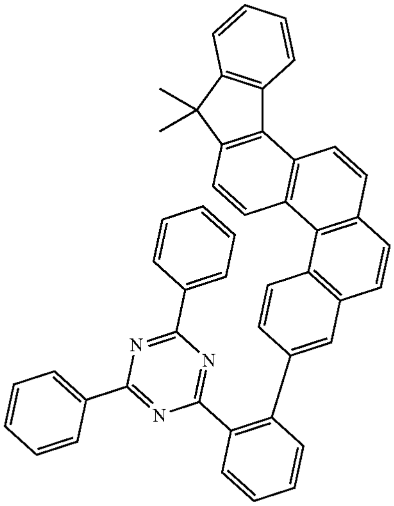
C-410
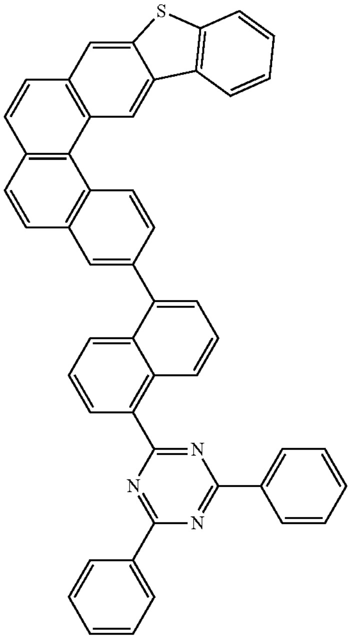
C-409
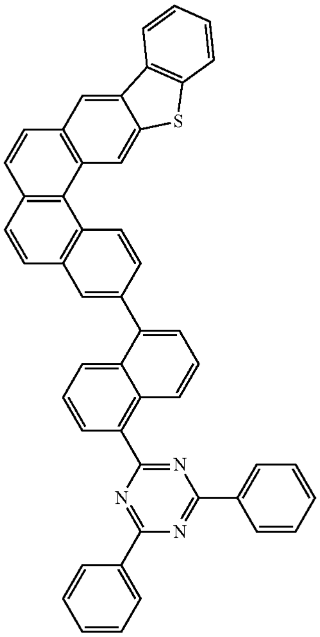
C-411
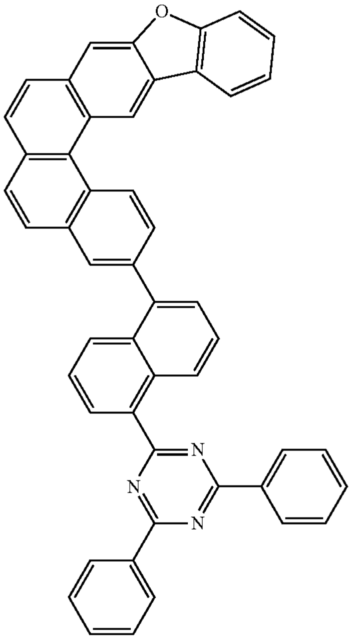

-continued
C-412
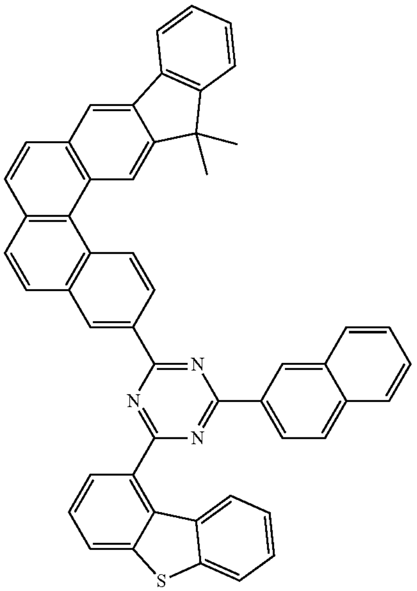
C-413
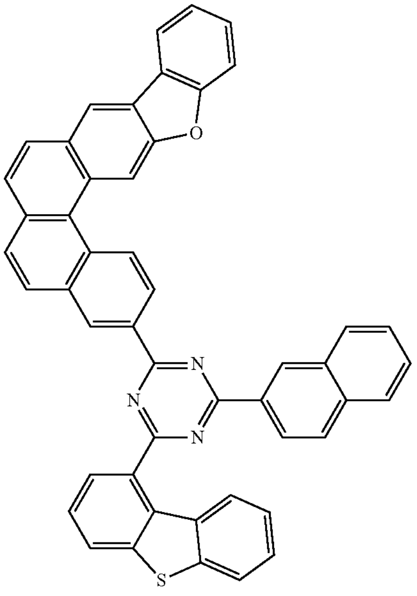
-continued
C-414
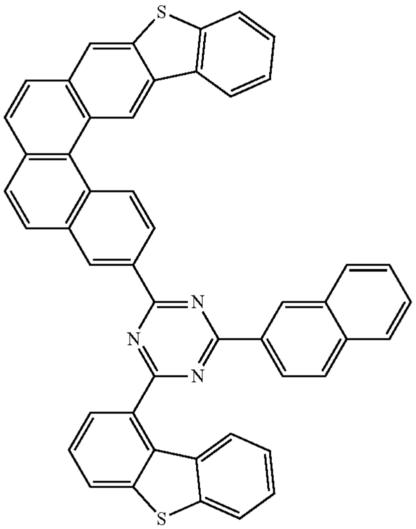
C-415
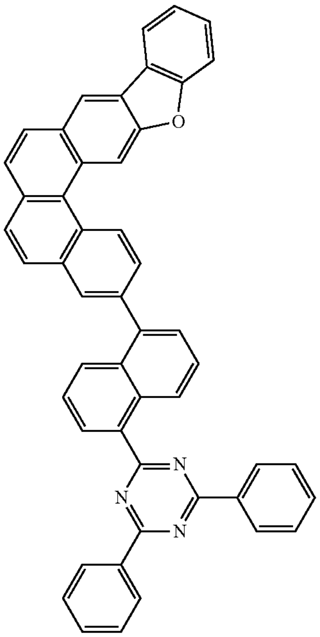

-continued
C-416
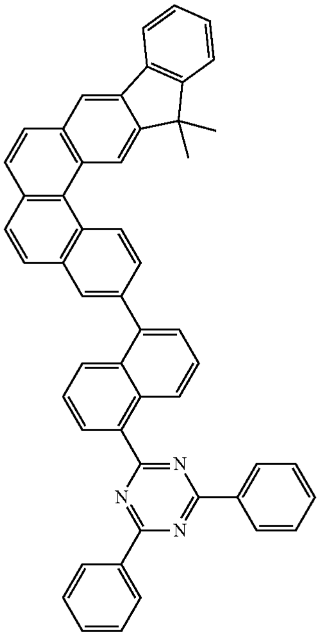
C-418
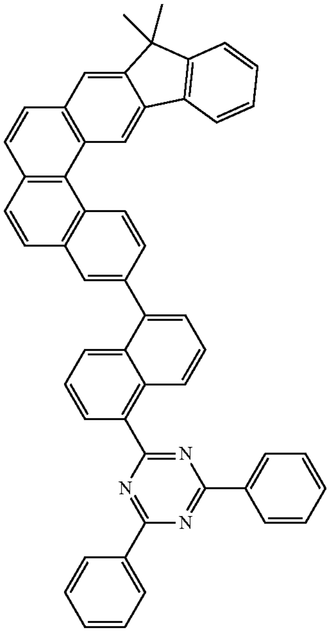
C-419
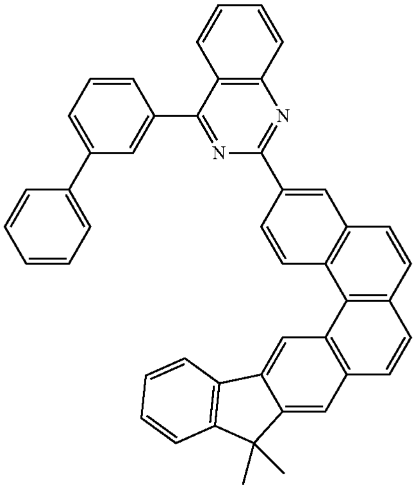
C-417
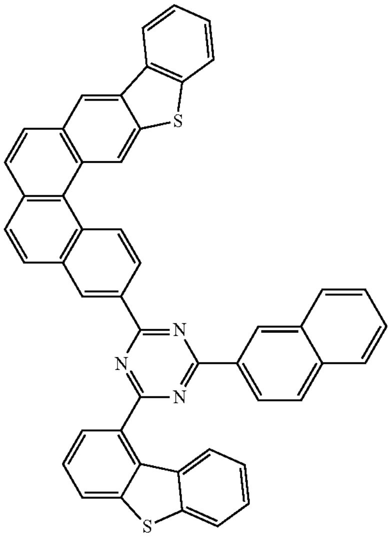
C-420
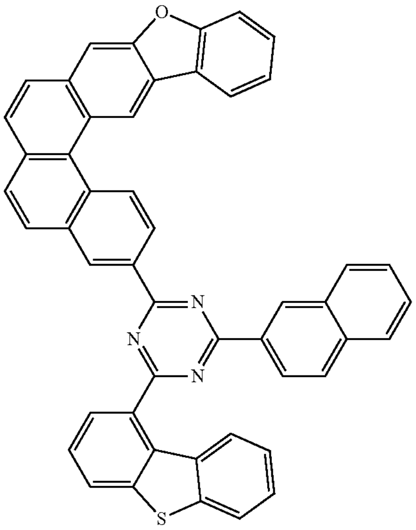

-continued
C-421
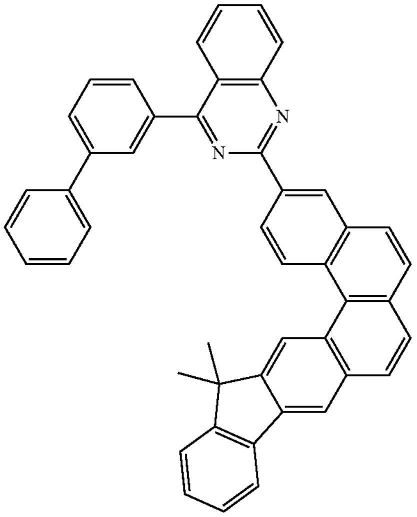
C-422
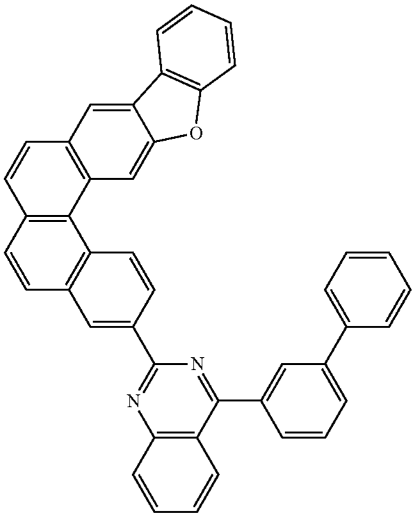
C-423
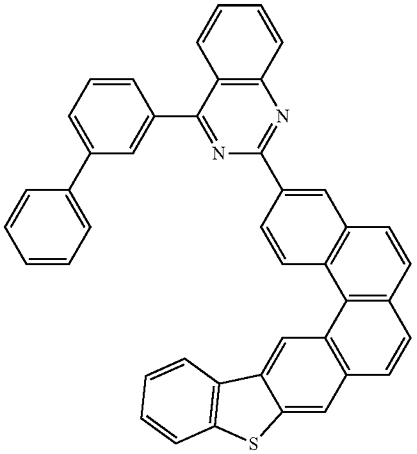
-continued
C-424
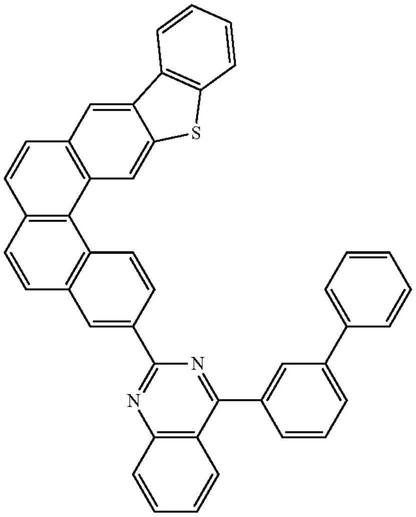
C-425
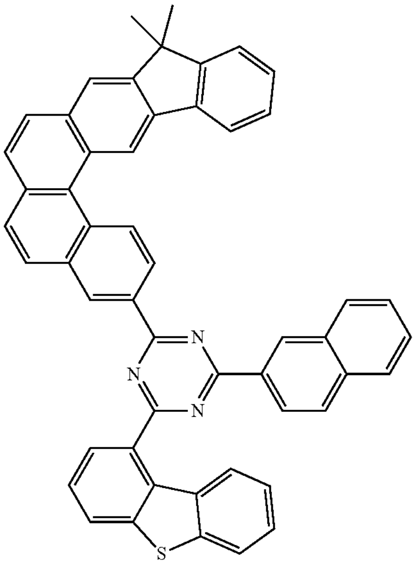
C-426
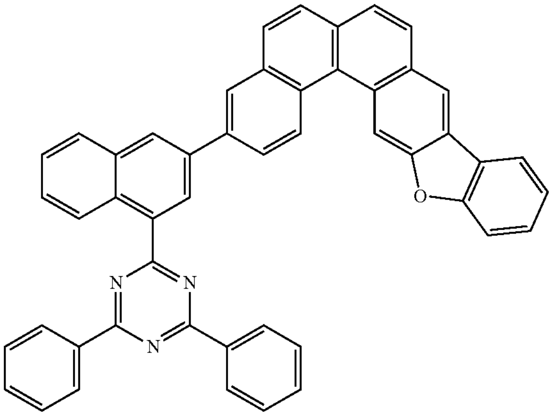

-continued
C-427
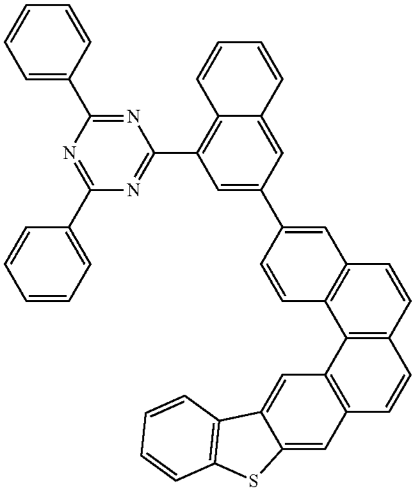
C-428
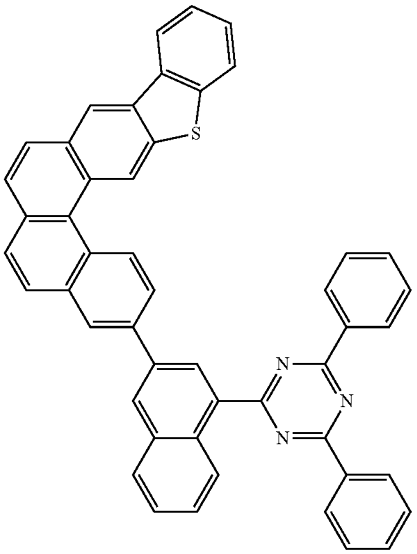
C-429
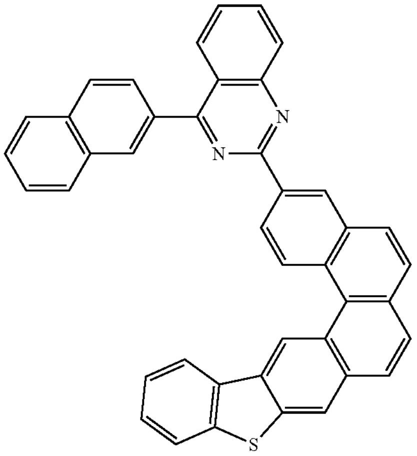
-continued
C-430
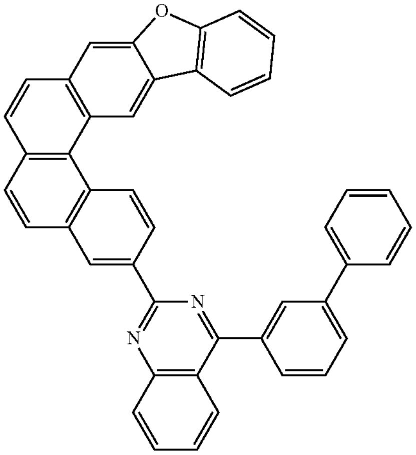
C-431
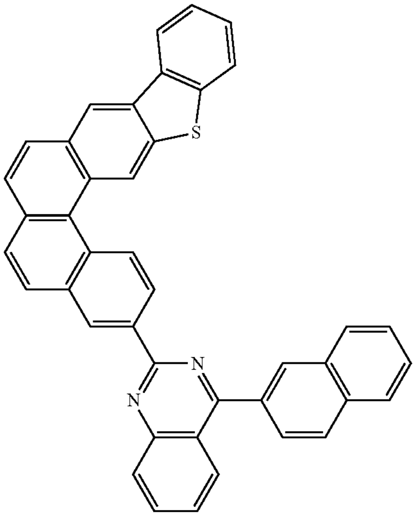
C-432
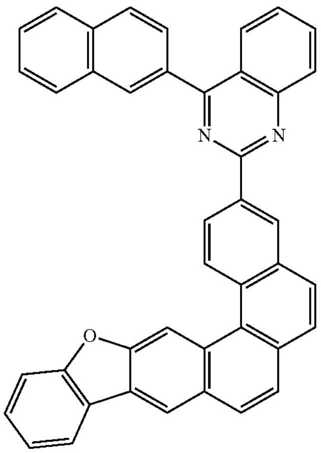

-continued
C-433
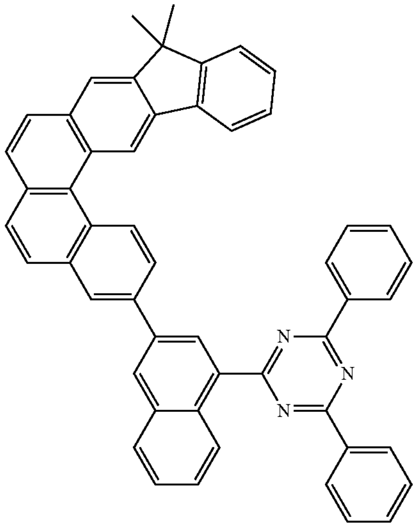
C-434
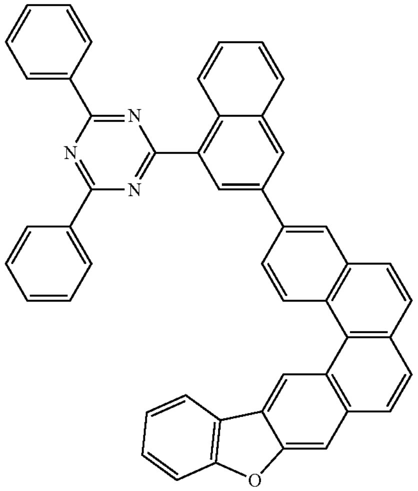
C-435
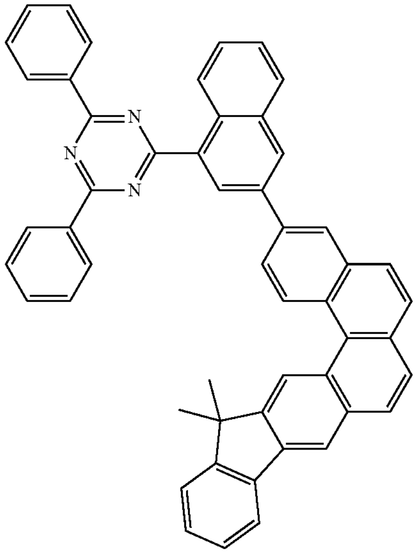
-continued
C-436
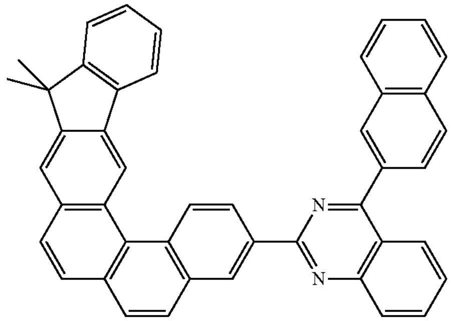
C-437
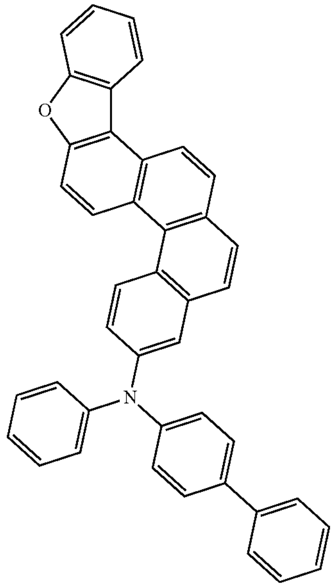
C-438
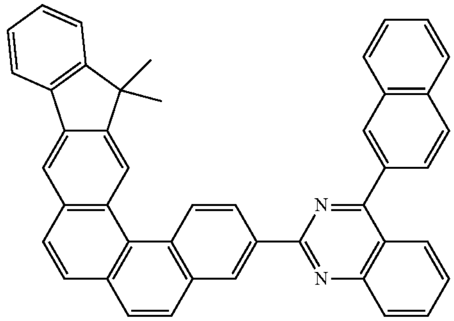

-continued
C-439
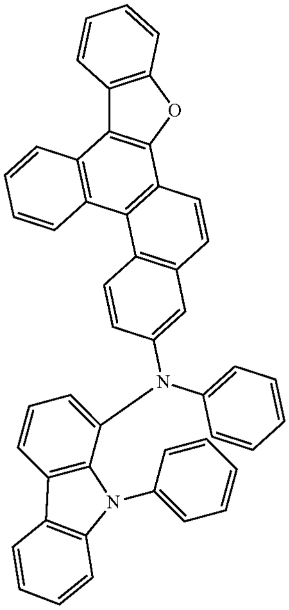
C-440
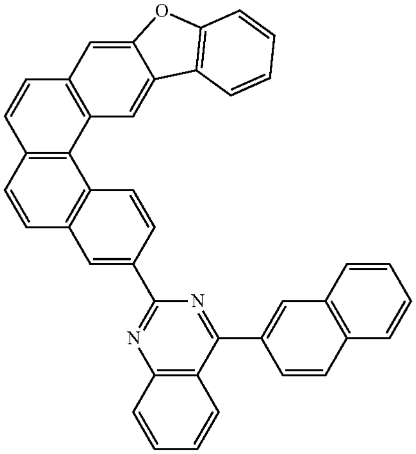
C-441
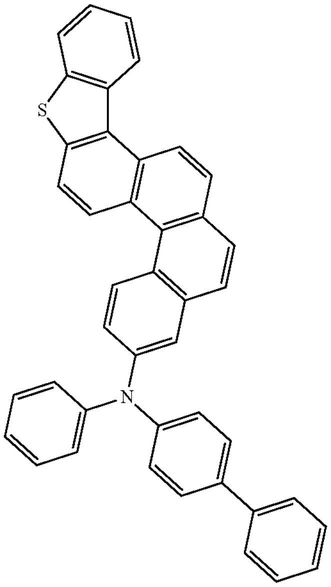
-continued
C-442
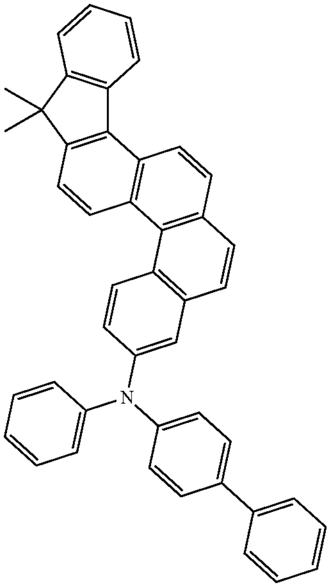
C-443
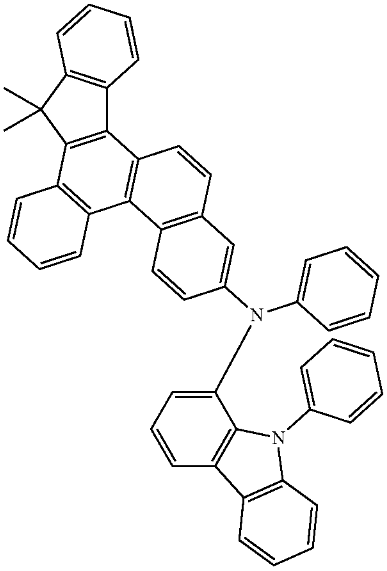

-continued
C-444
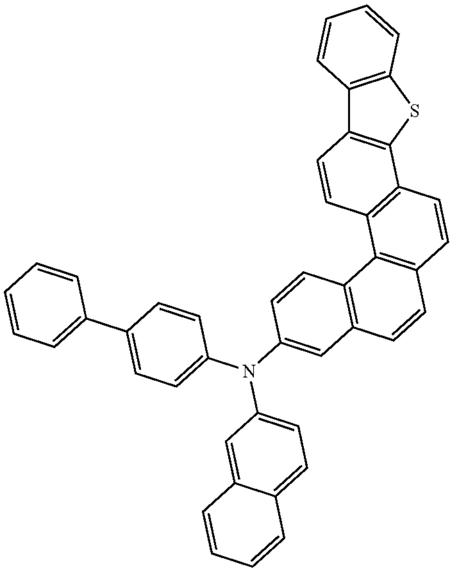
C-445
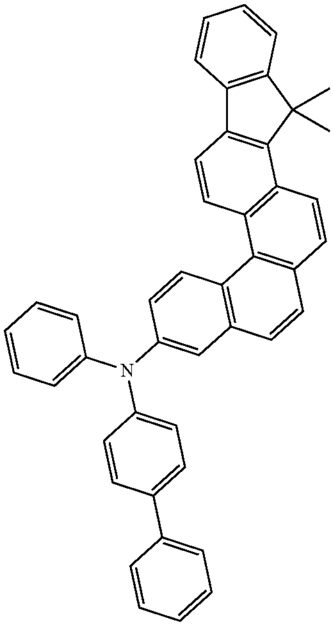
-continued
C-446
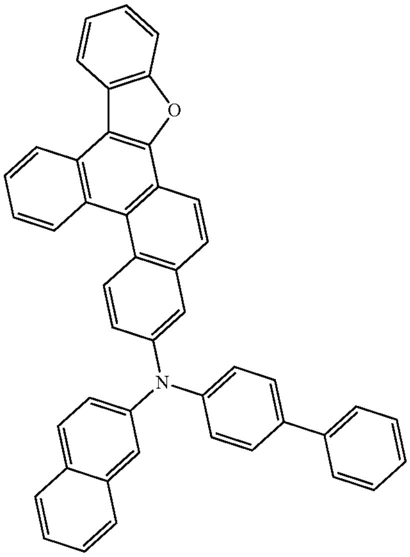
C-447
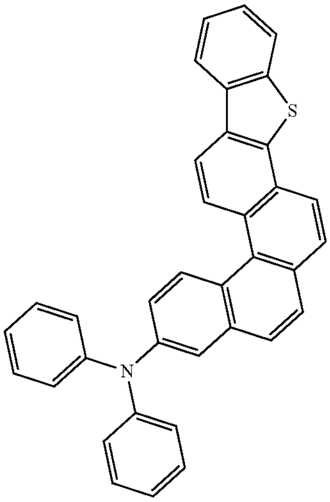
C-448
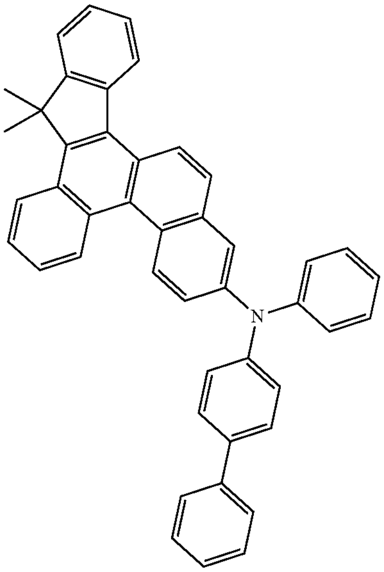

C-449
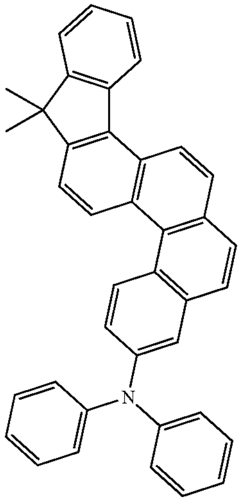
C-450
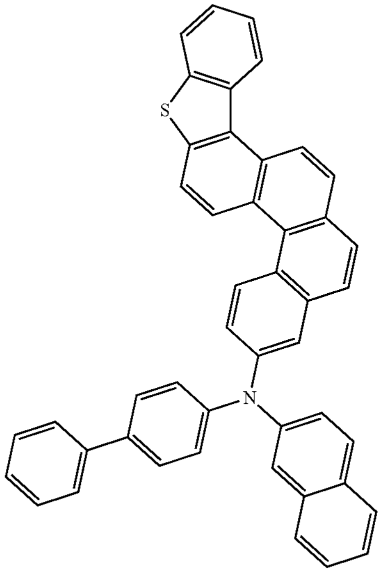
C-451
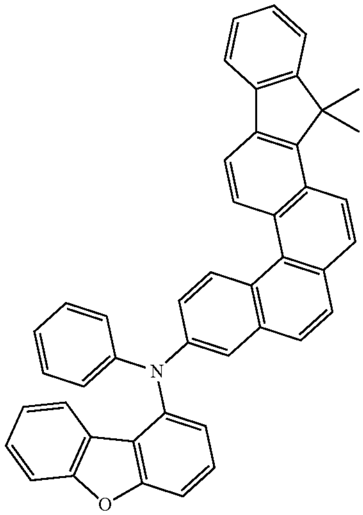
C-452
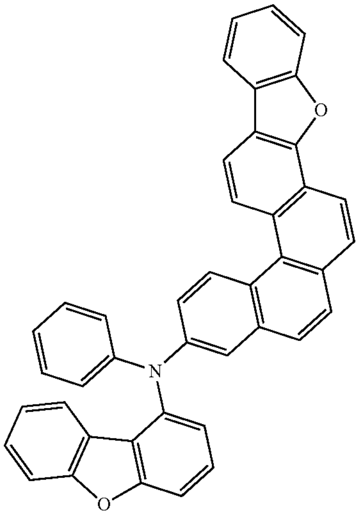
C-453
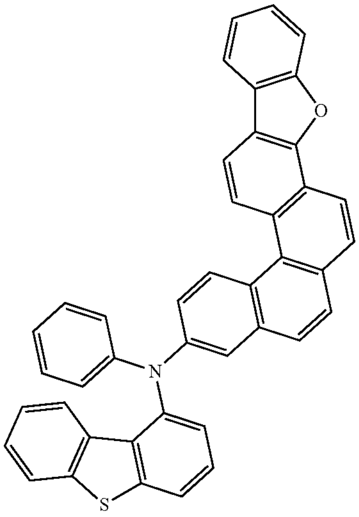
C-454
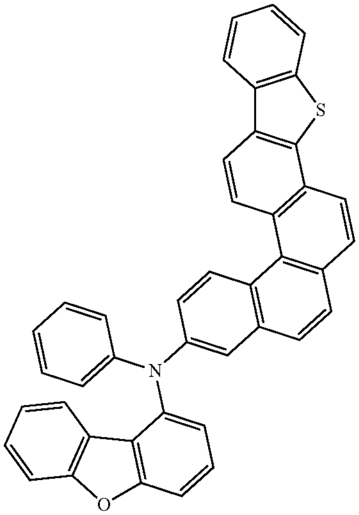

-continued
C-455
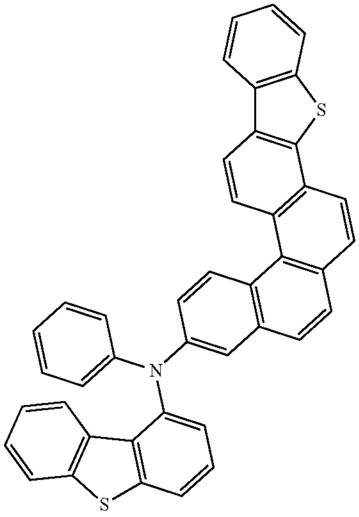
C-456
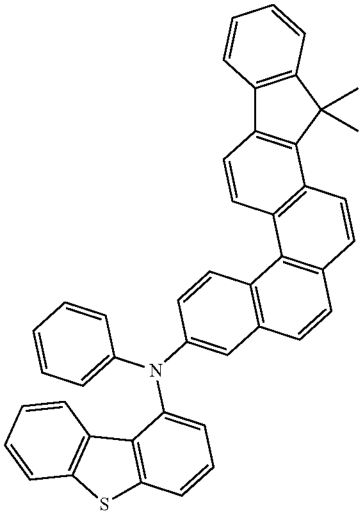
C-457
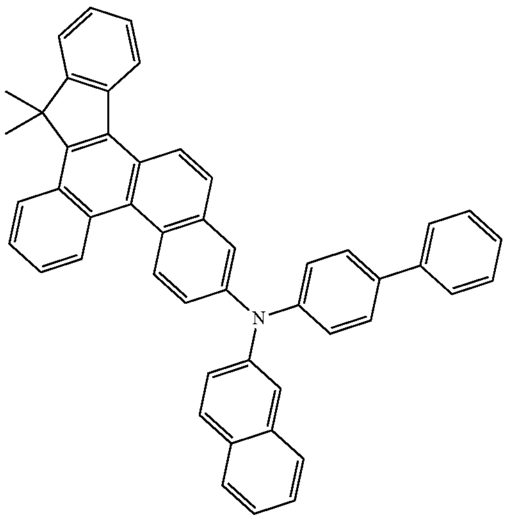
-continued
C-458
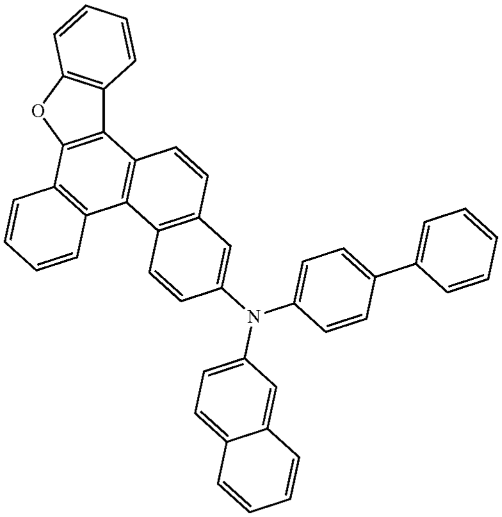
C-459
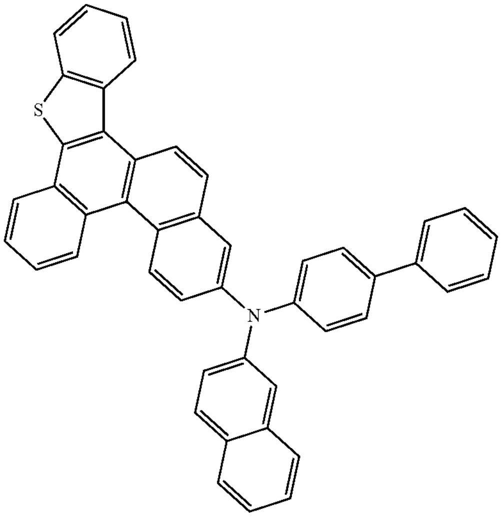
C-460
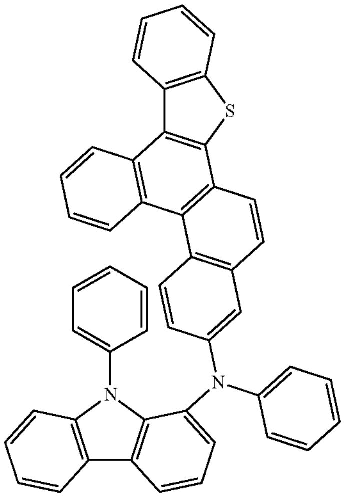

-continued
C-461
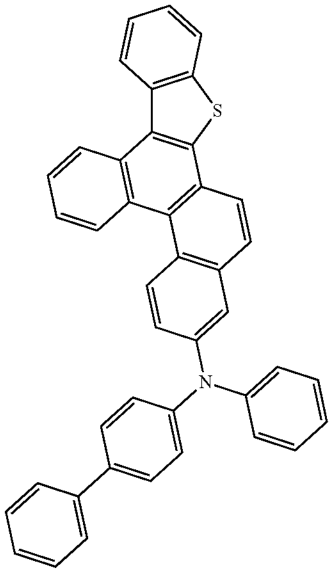
C-462
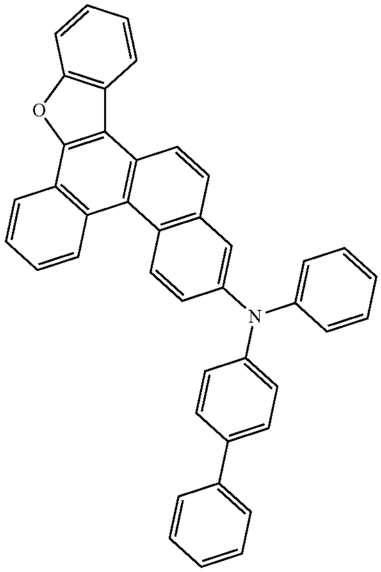
-continued
C-463
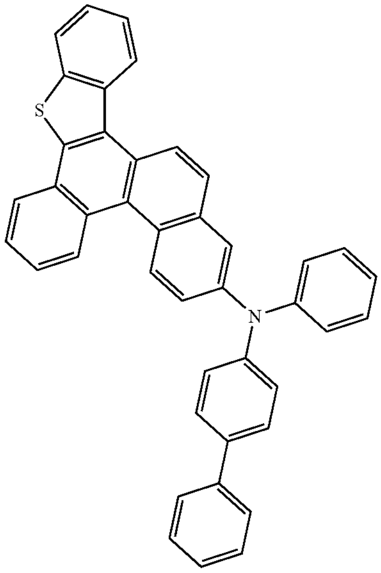
C-464
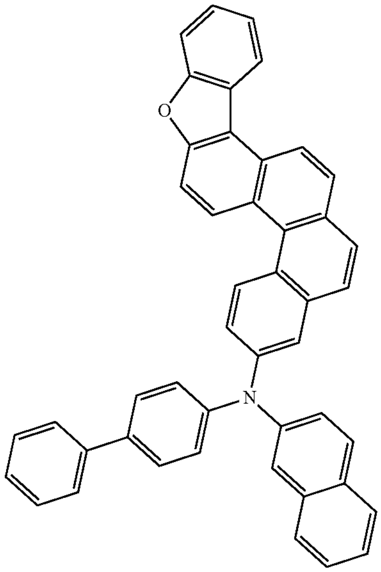

-continued
C-465
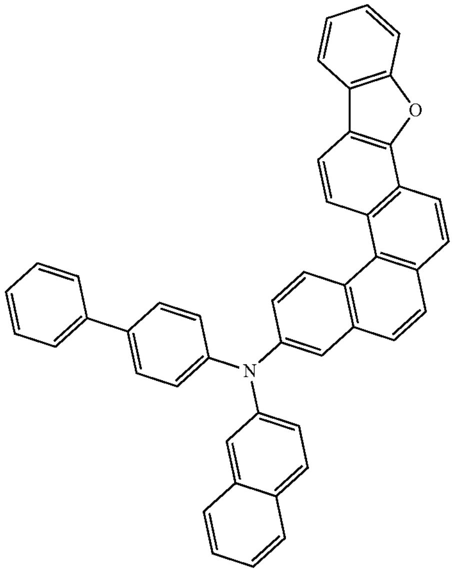
-continued
C-467
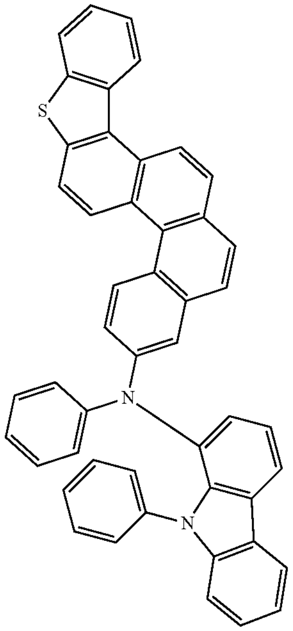
C-466
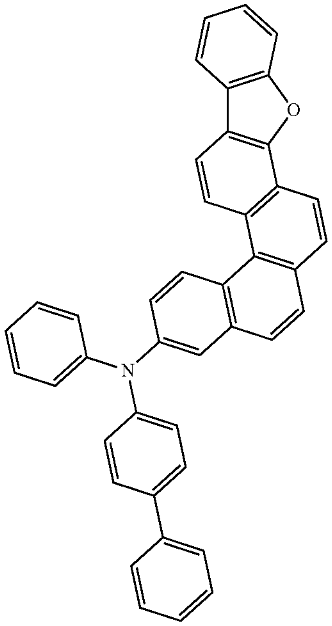
C-468
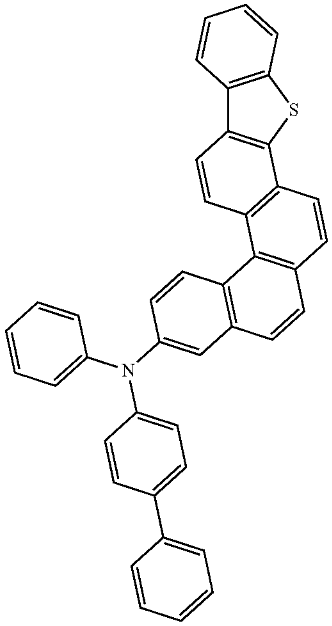

-continued
C-469
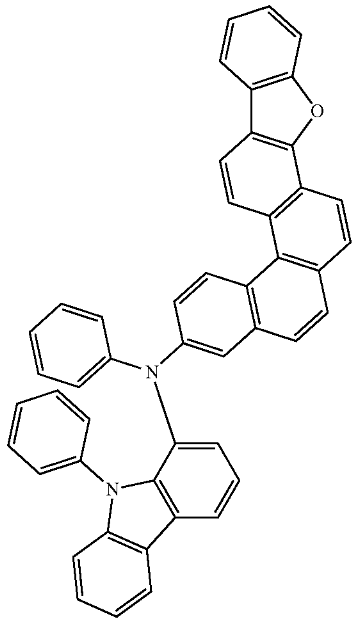
C-470
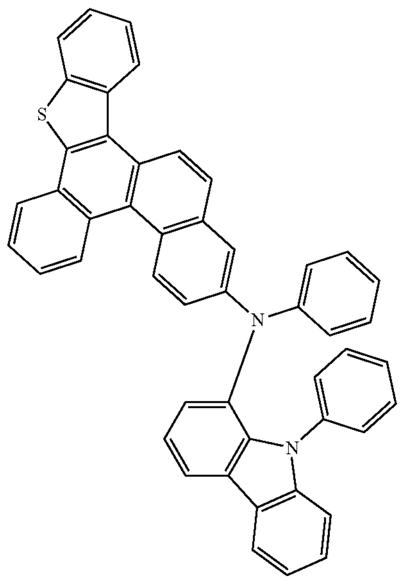
-continued
C-471
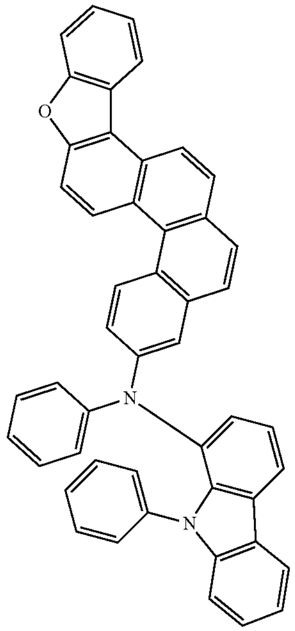
C-472
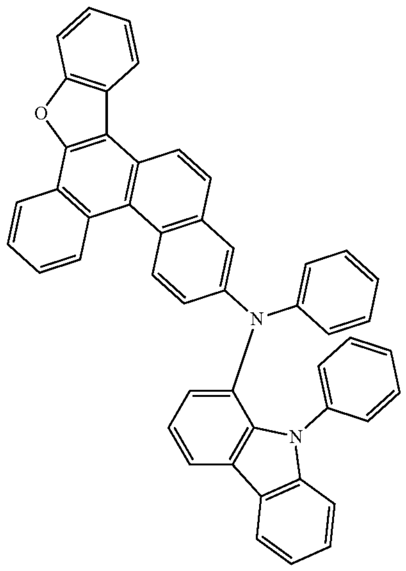

-continued
C-473
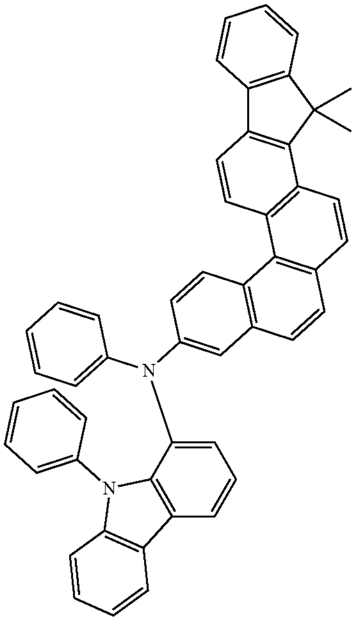
C-474
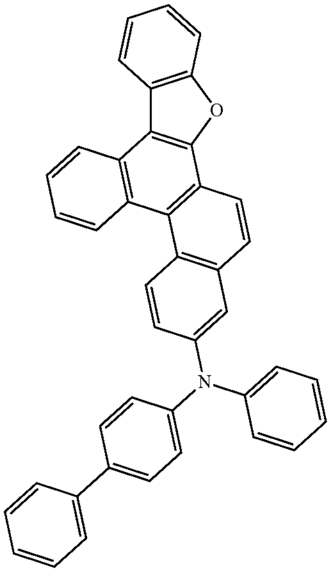
-continued
C-475
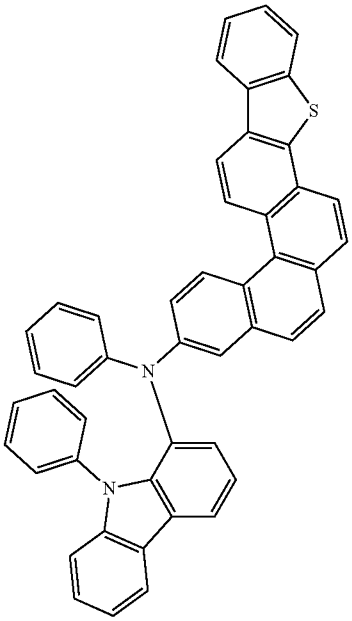
C-476
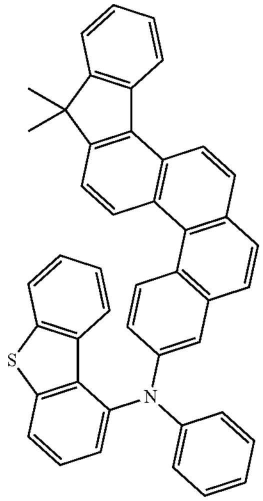
C-477
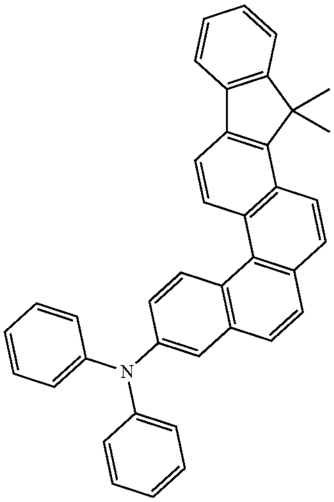

-continued
C-478
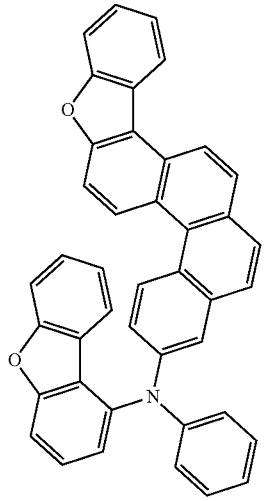
C-479
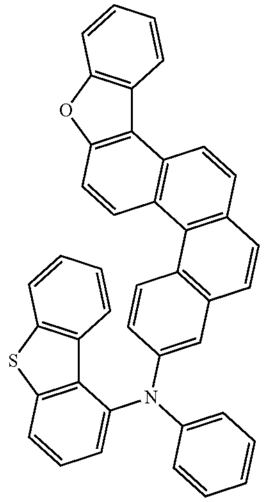
C-480
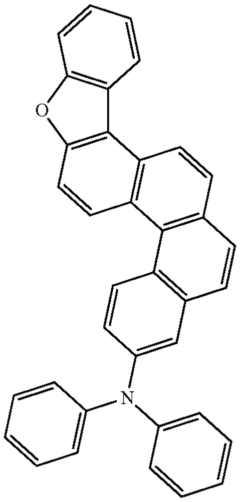
-continued
C-481
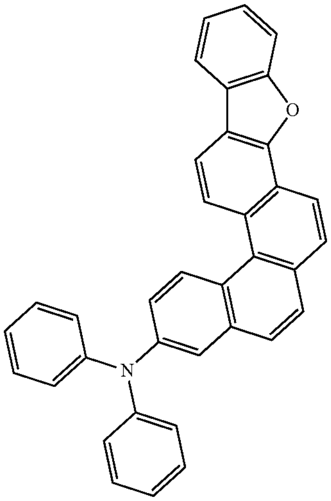
C-482
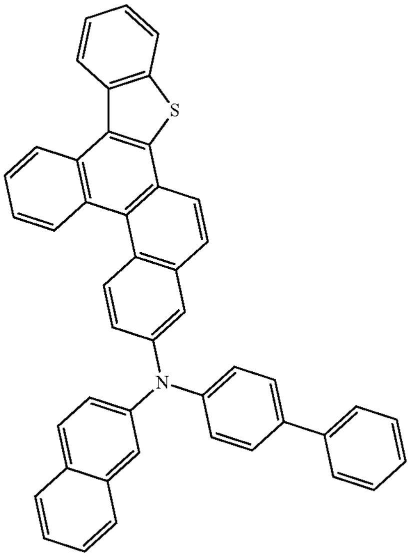
C-483
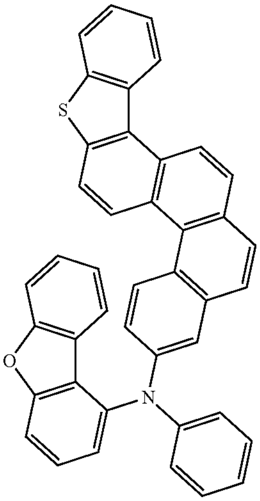

-continued
C-484
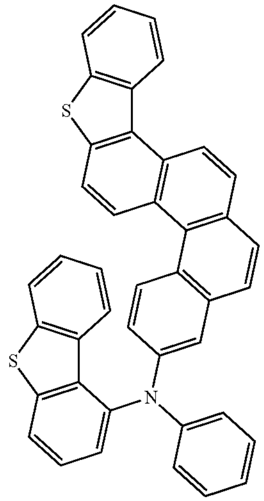
C-485
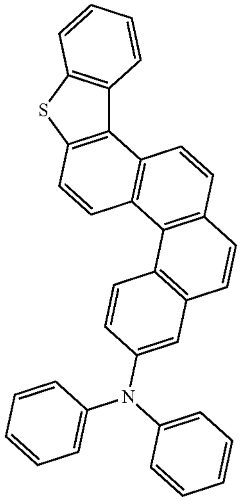
C-486
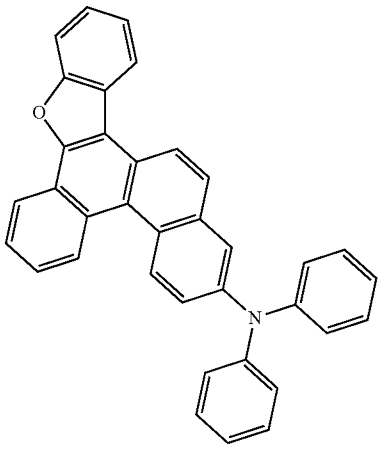
-continued
C-487
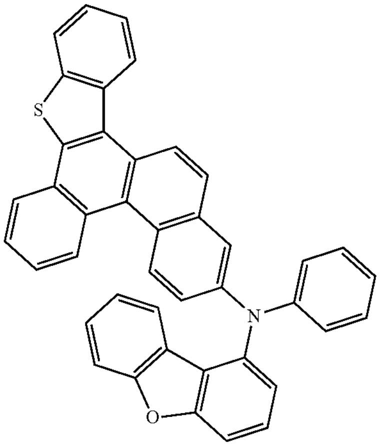
C-488
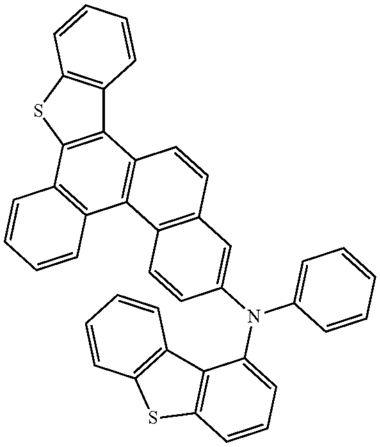
C-489
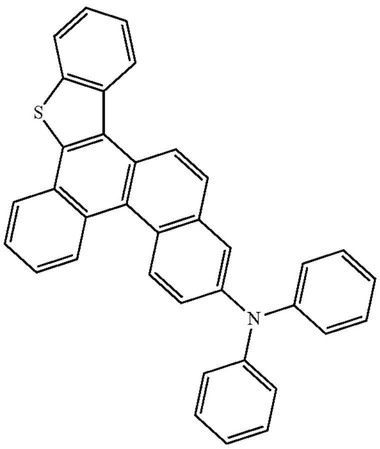

-continued
C-490
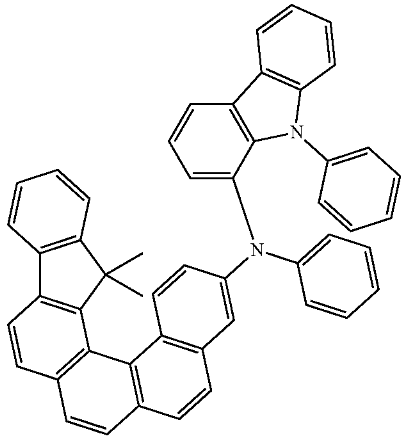
C-491
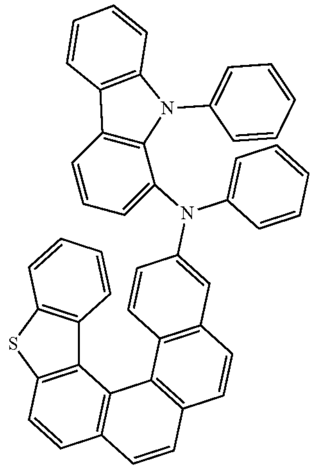
C-492
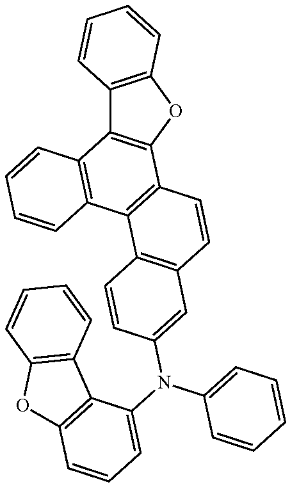
-continued
C-493
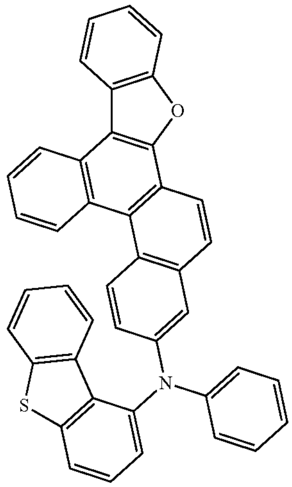
C-494
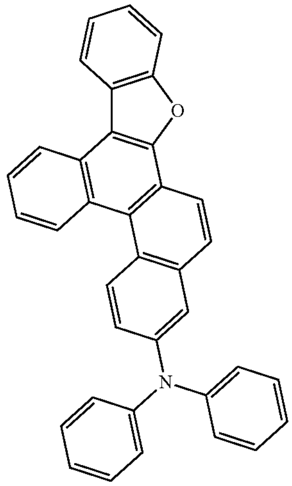
C-495
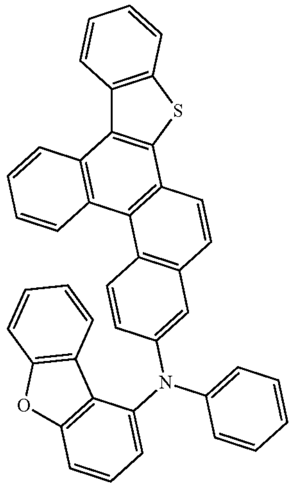

-continued
C-496
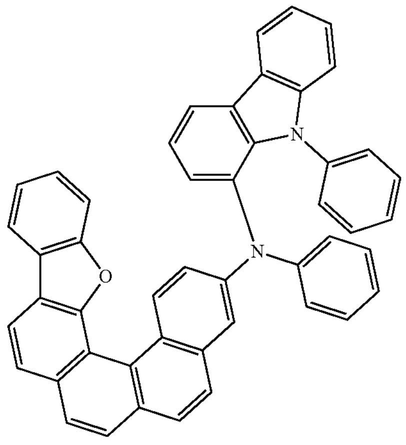
C-497
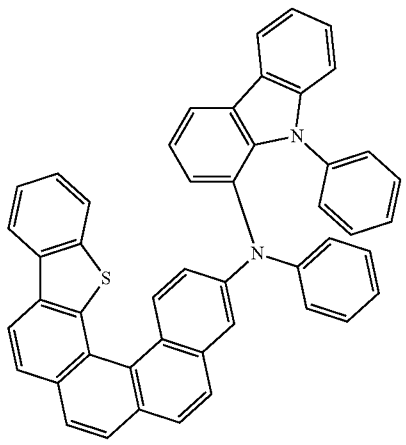
C-498
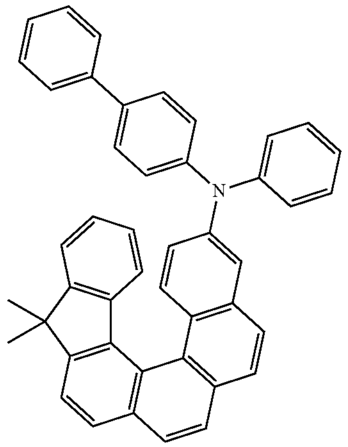
-continued
C-499
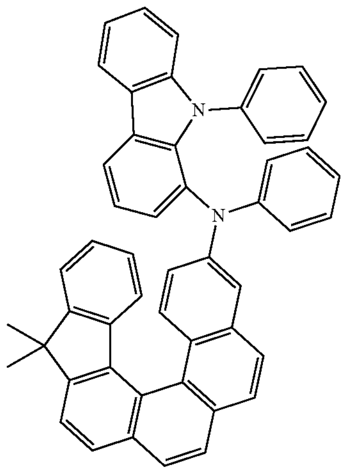
C-500
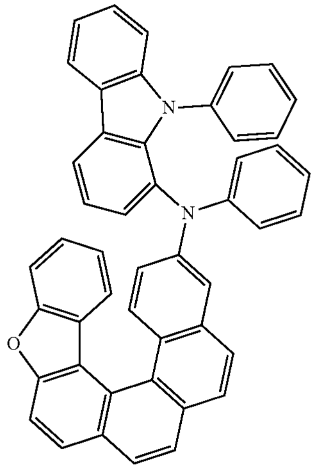
C-501
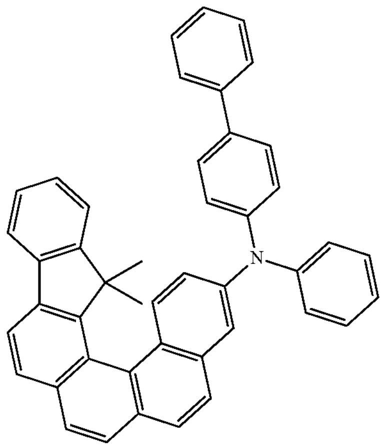

-continued
C-502
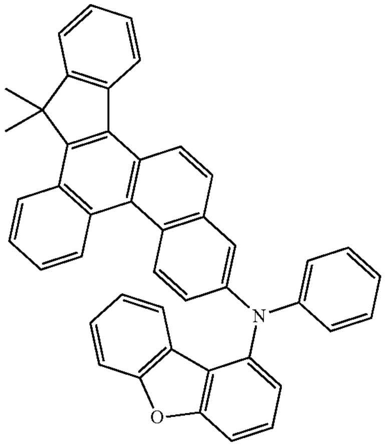
C-503
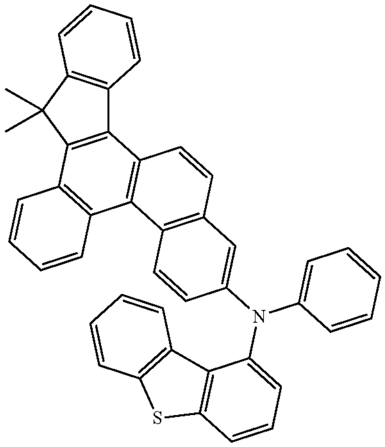
C-504
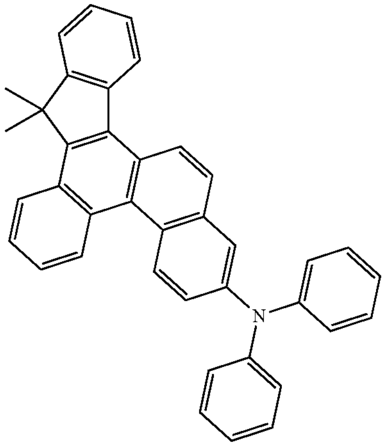
-continued
C-505
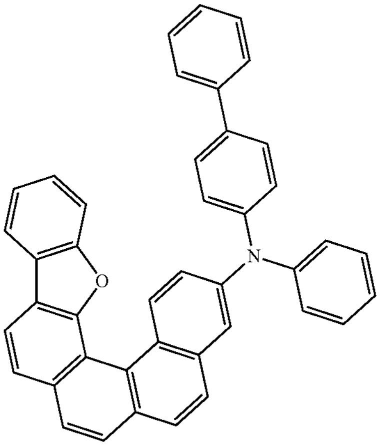
C-506
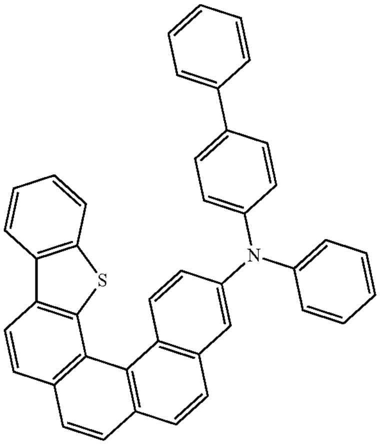
C-507
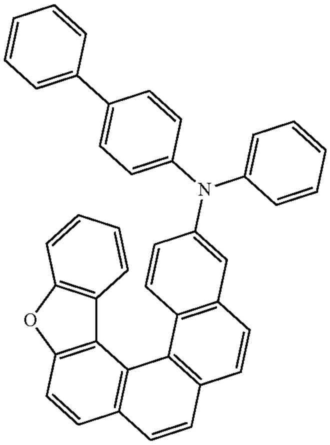

-continued
C-508
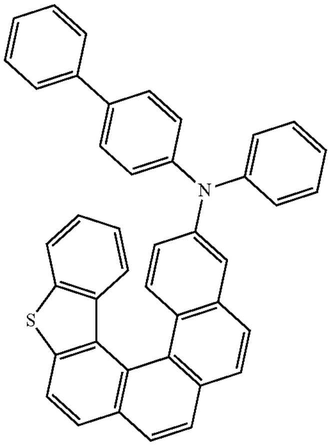
C-509
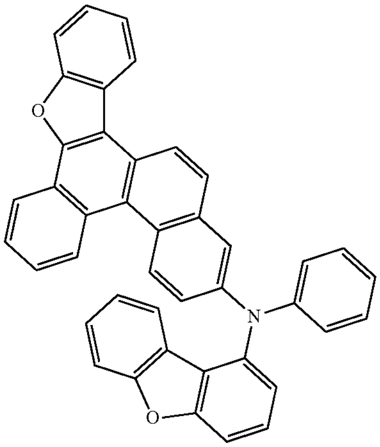
C-510
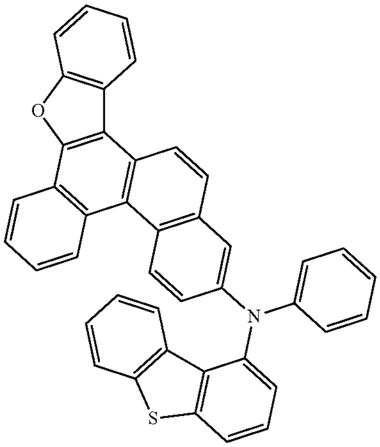
-continued
C-511
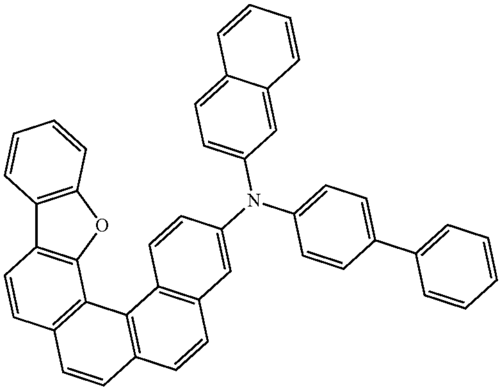
C-512
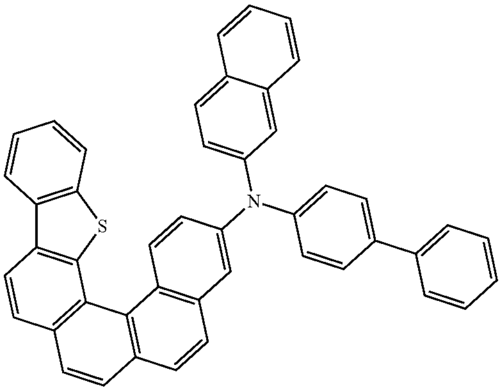
C-513
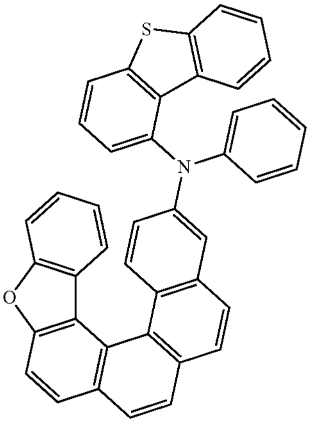

-continued
C-514
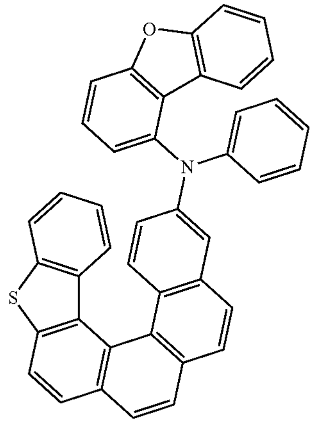
C-515
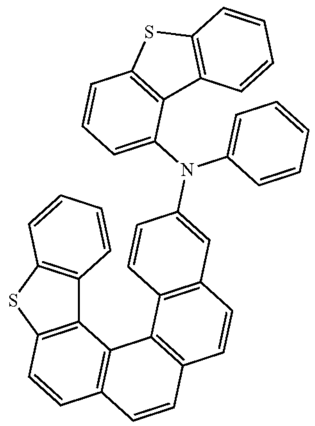
C-516
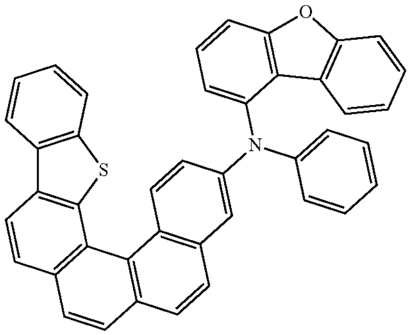
C-517
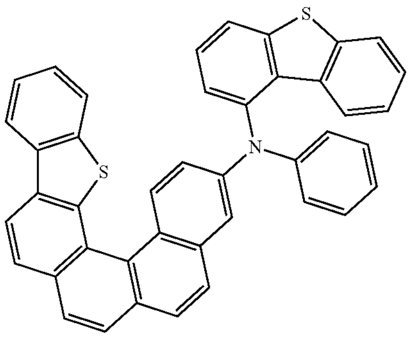
-continued
C-518
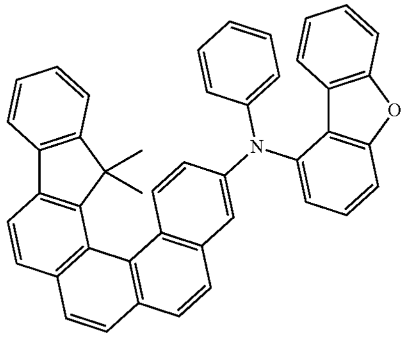
C-519
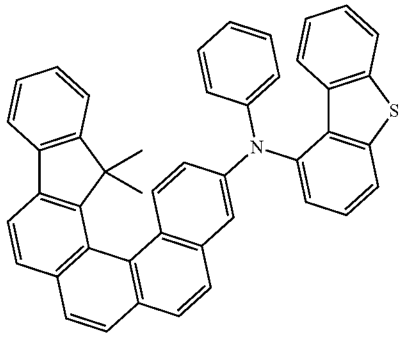
C-520
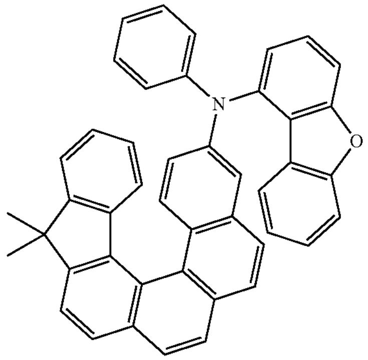
C-521
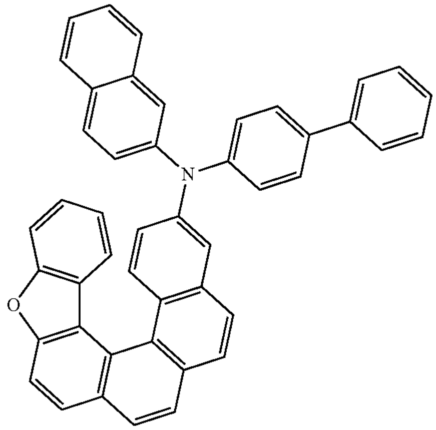

-continued
C-522
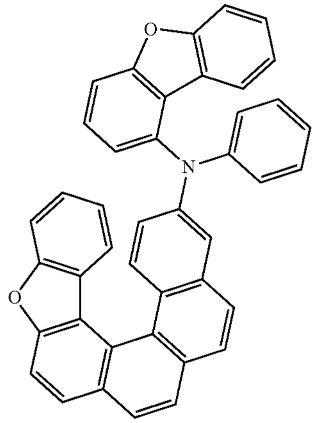
C-523
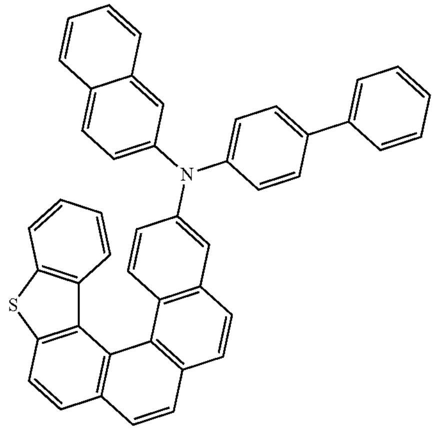
C-524
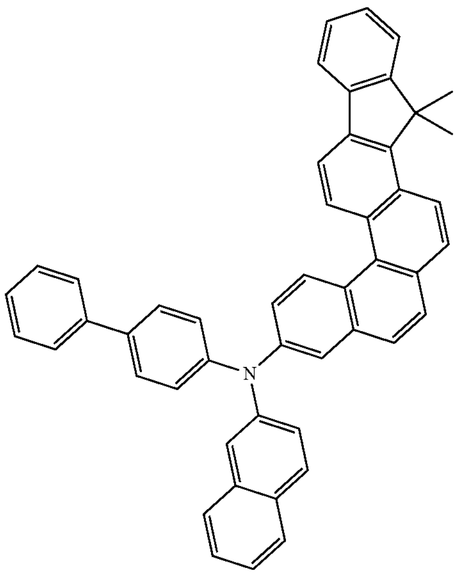
-continued
C-525
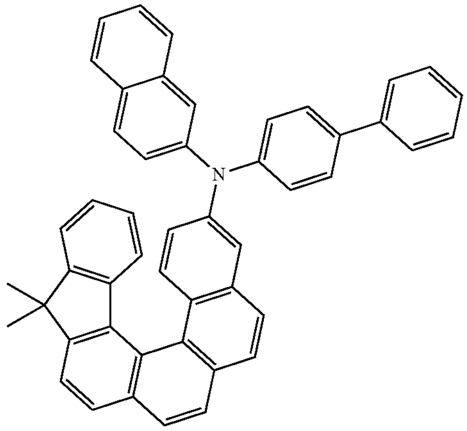
C-526
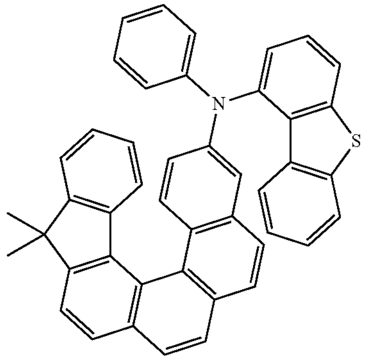
C-527
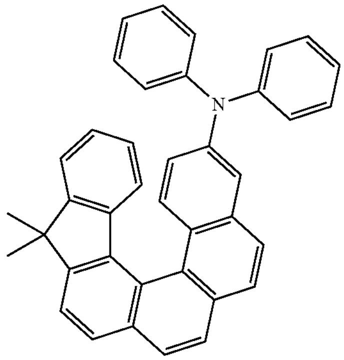
C-528
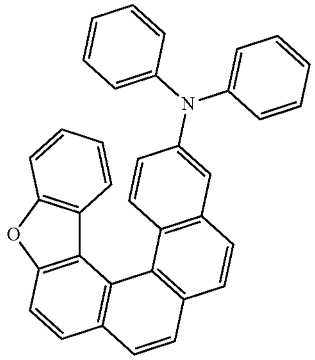

-continued
C-529
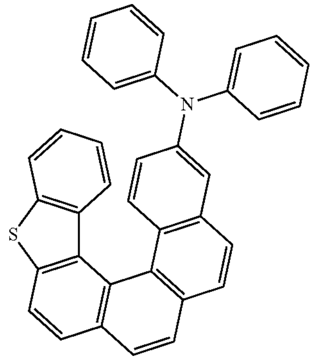
C-530
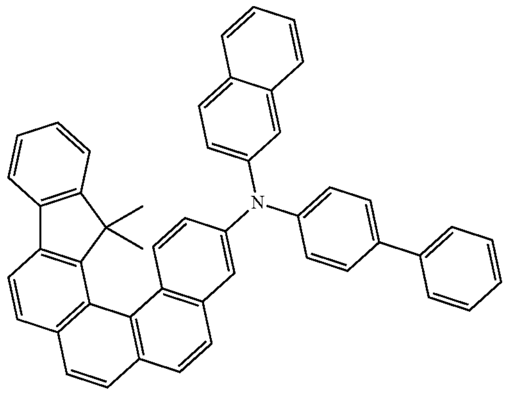
C-531
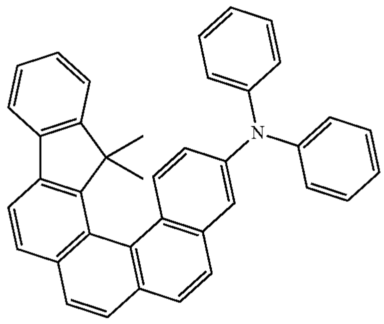
C-532
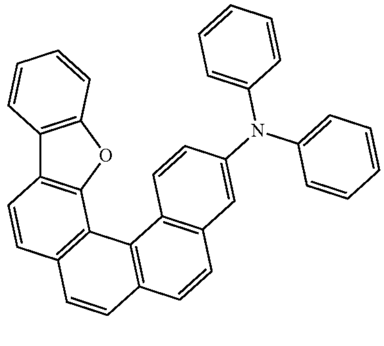
-continued
C-533
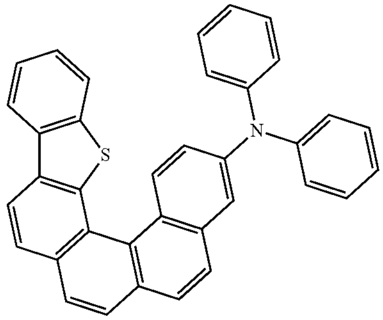
C-534
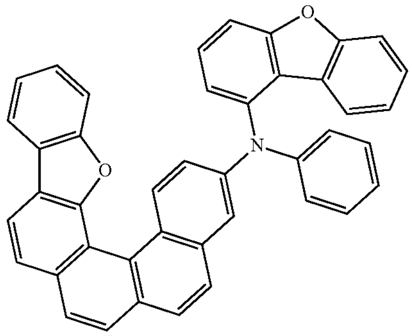
C-535
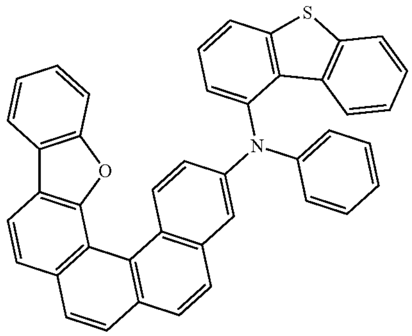
C-536
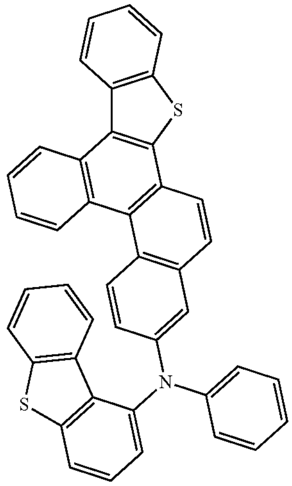

-continued
C-537
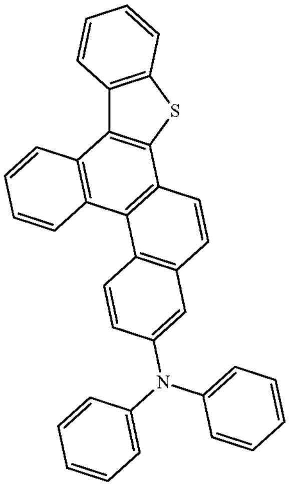
C-538
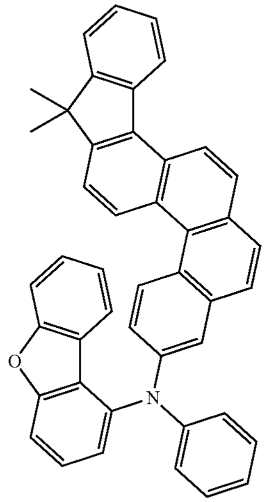
C-539
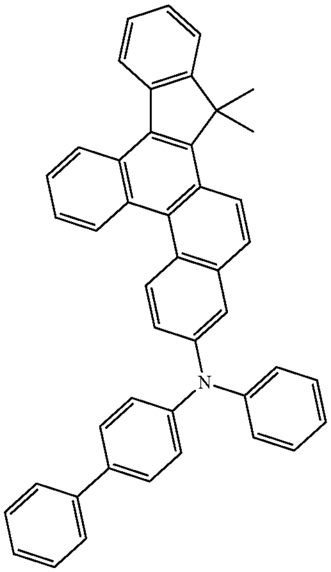
-continued
C-540
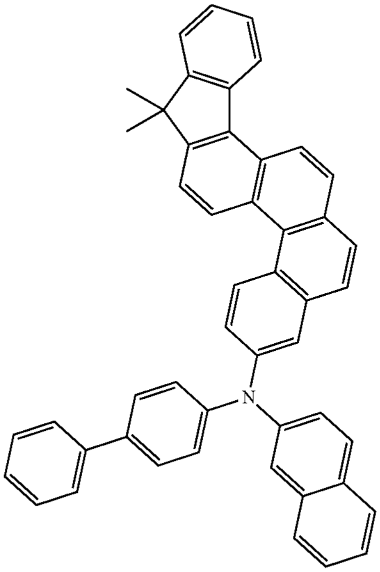
C-541
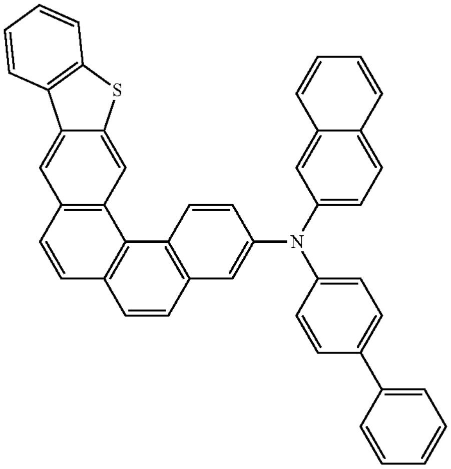
C-542
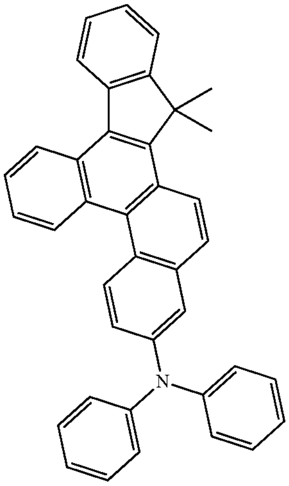

-continued
C-543
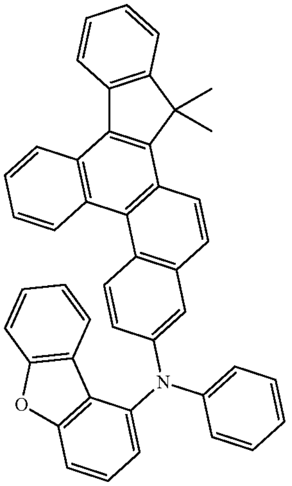
C-544
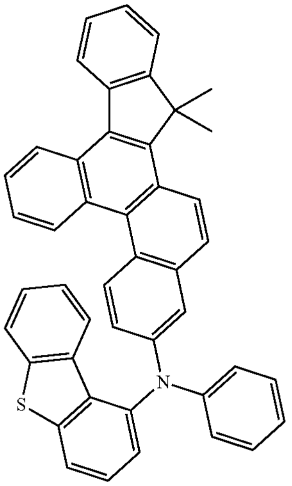
C-545
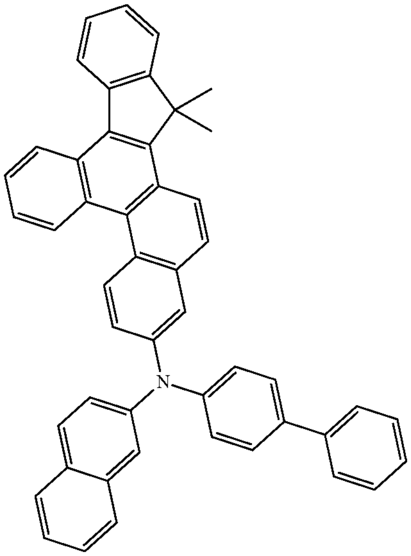
-continued
C-546
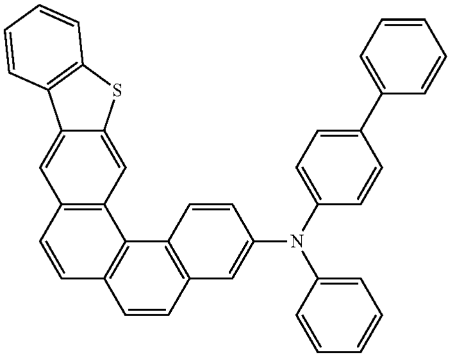
C-547
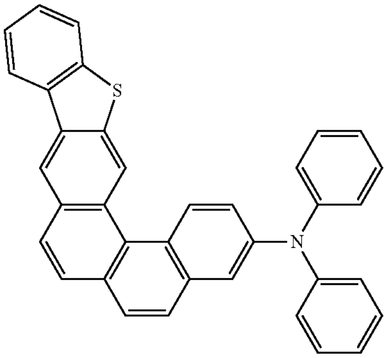
C-548
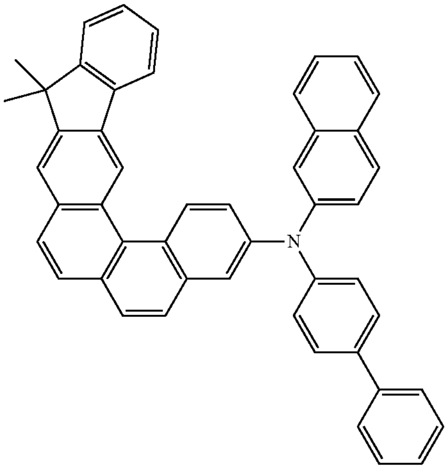

-continued
C-549
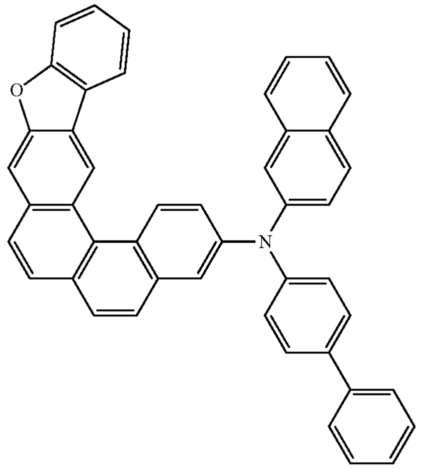
C-550
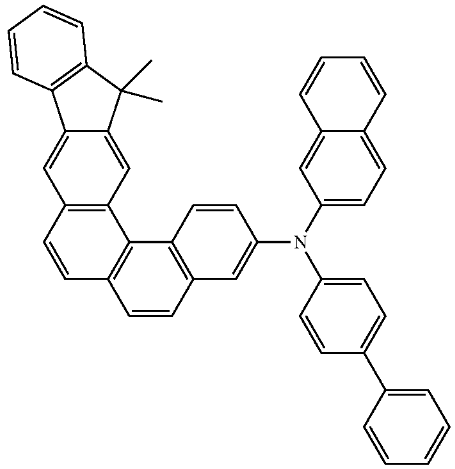
C-551
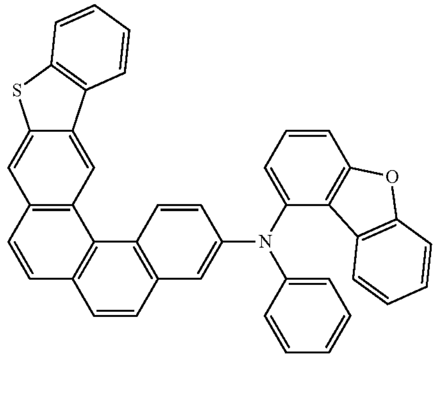
-continued
C-552
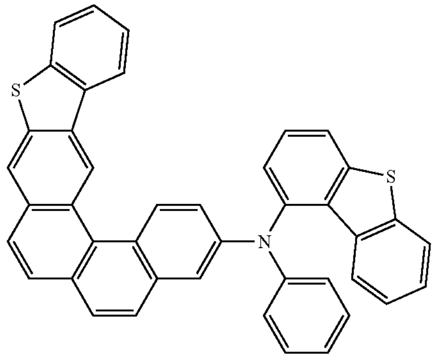
C-553
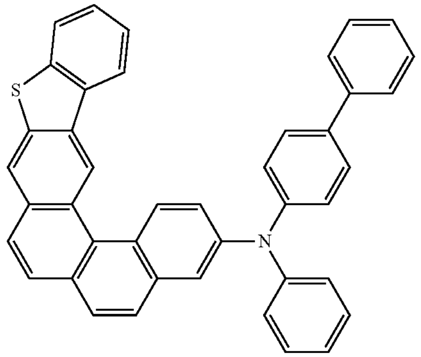
C-554
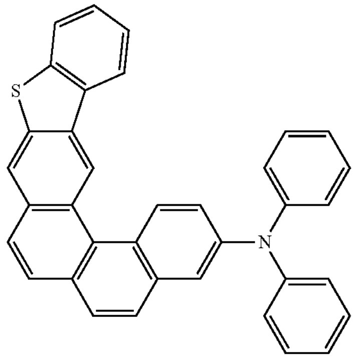
C-555
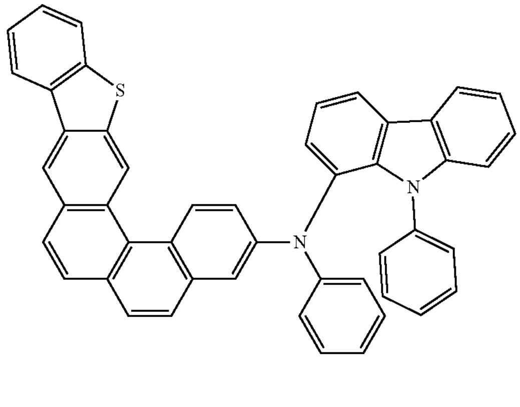

-continued
C-556
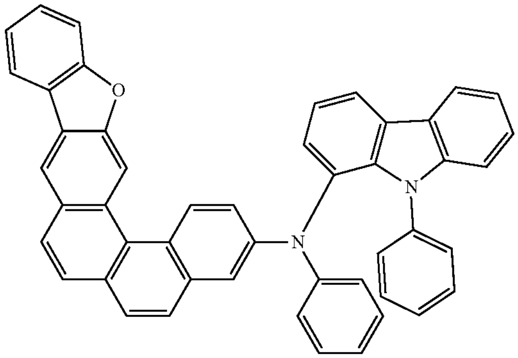
C-557
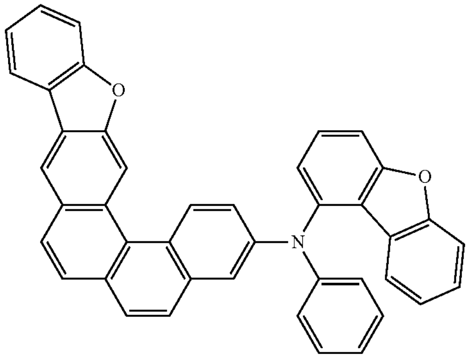
C-558
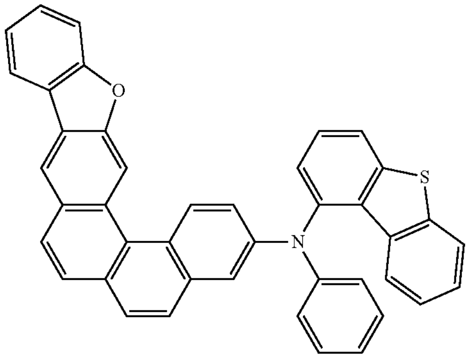
C-559
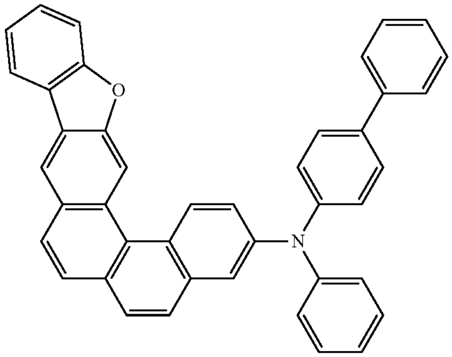
-continued
C-560
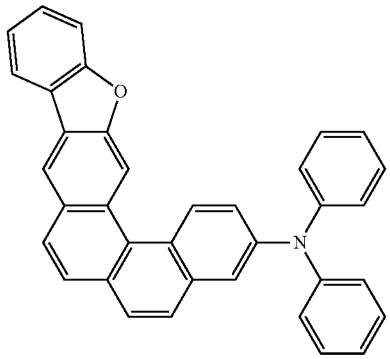
C-561
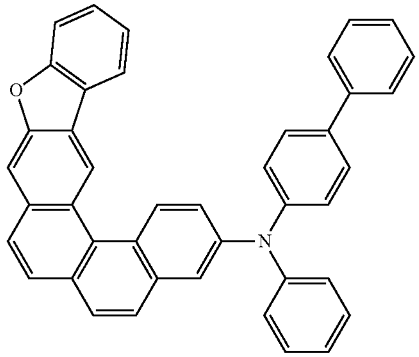
C-562
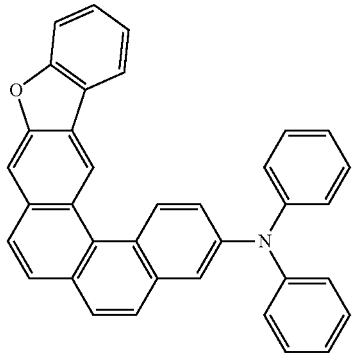
C-563
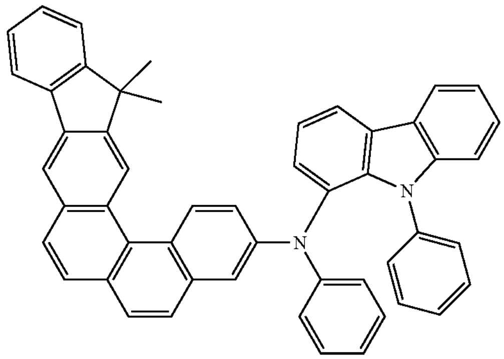

-continued
C-564
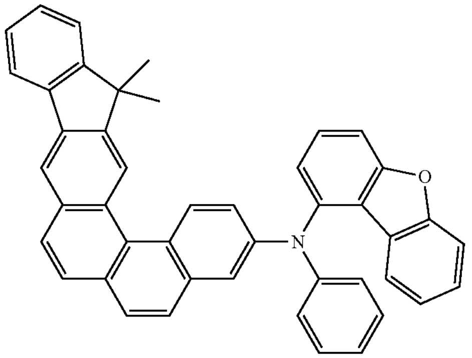
C-565
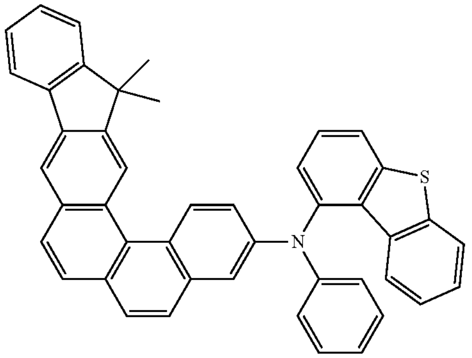
C-566
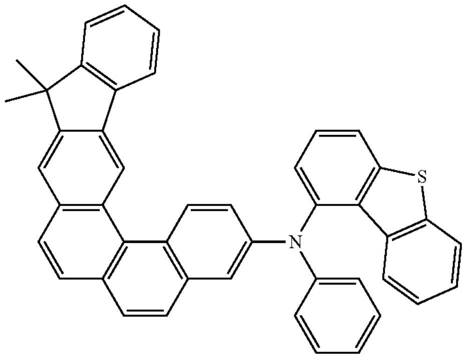
C-567
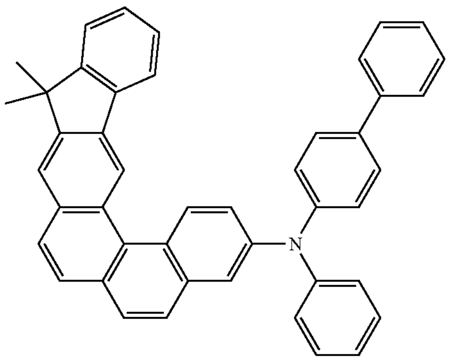
-continued
C-568
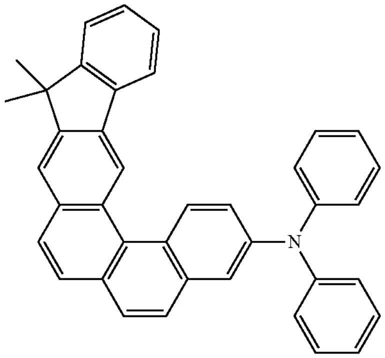
C-569
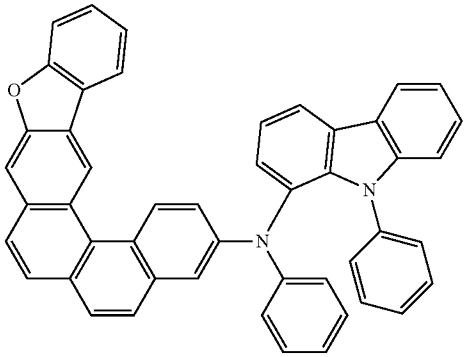
C-570
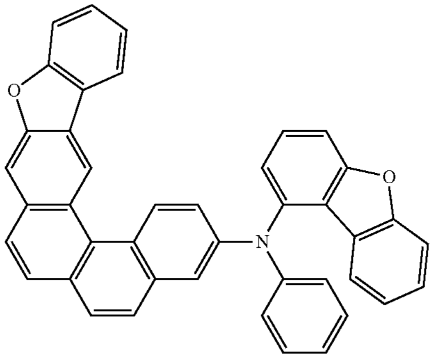
C-571
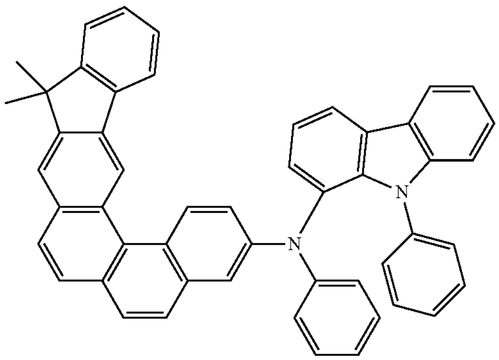

-continued
C-572
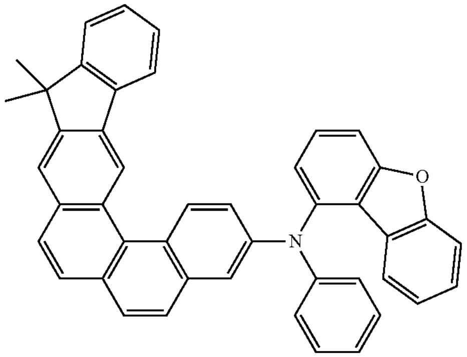
C-573
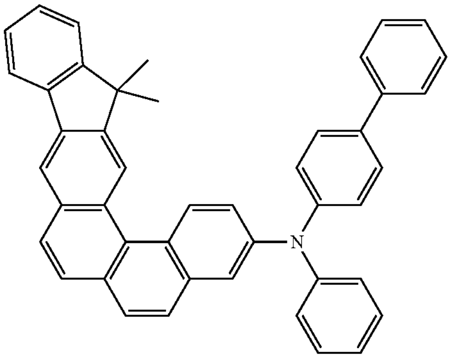
C-574
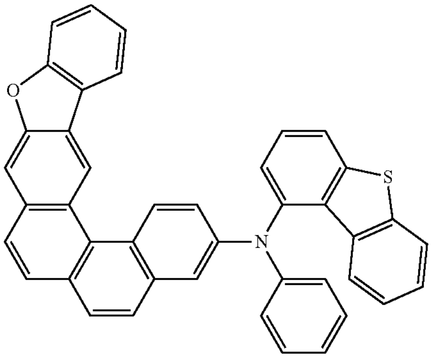
C-575
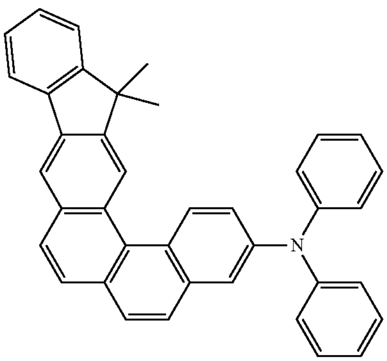
-continued
C-576
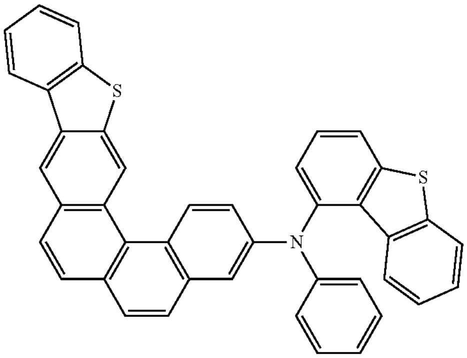
C-577
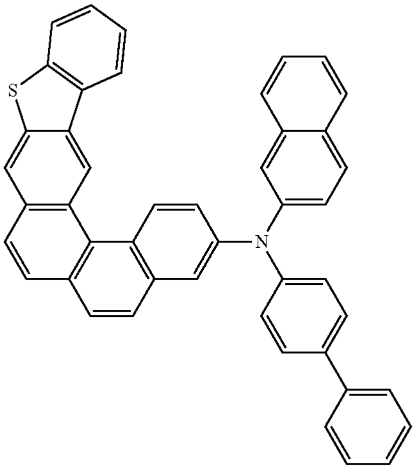
C-578
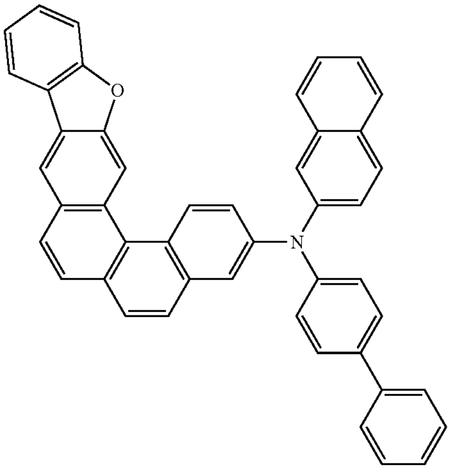

-continued
C-579
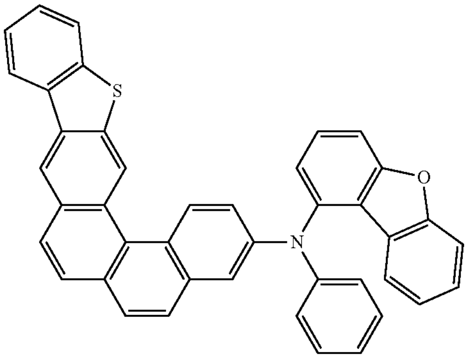
C-580
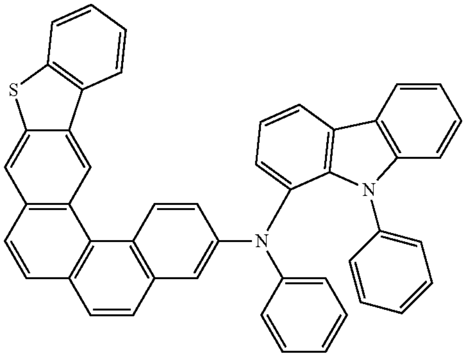
C581
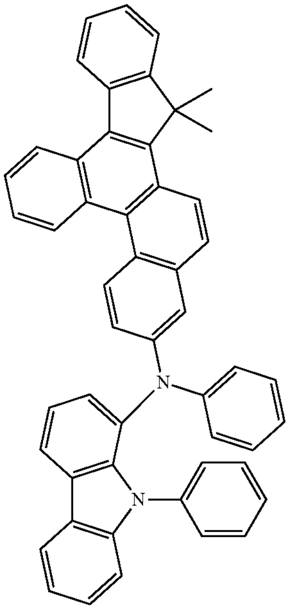
-continued
C582
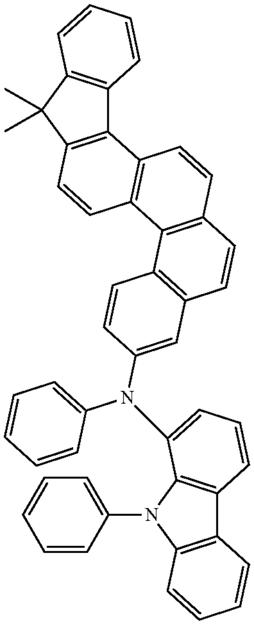
C-583
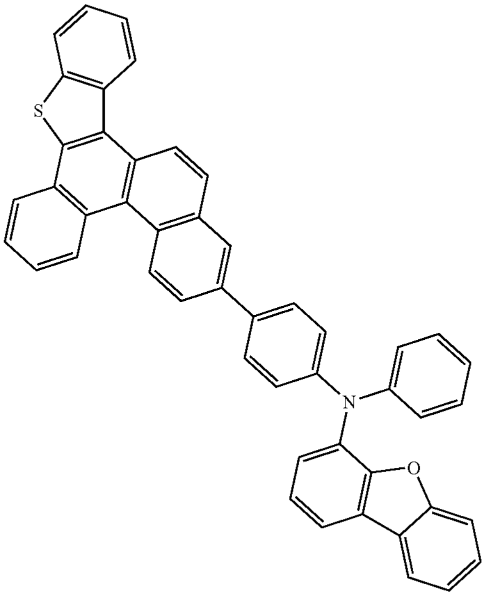

-continued
C-584
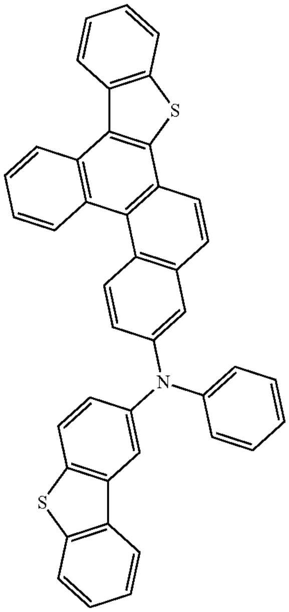
C-585
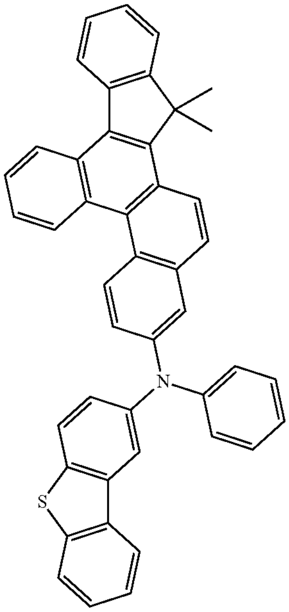
-continued
C-586
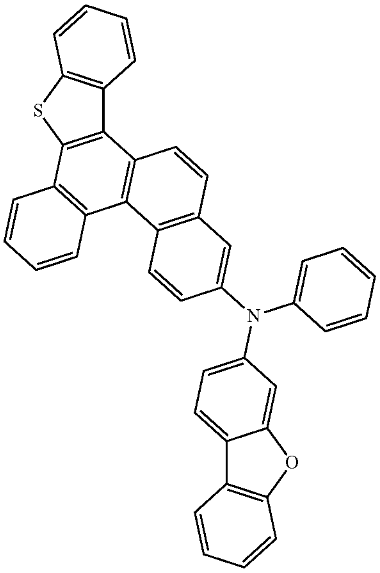
C-587
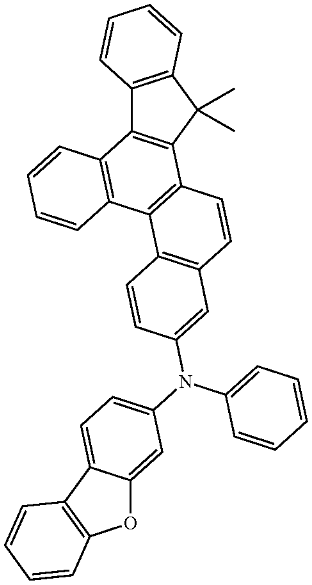

-continued
C-588
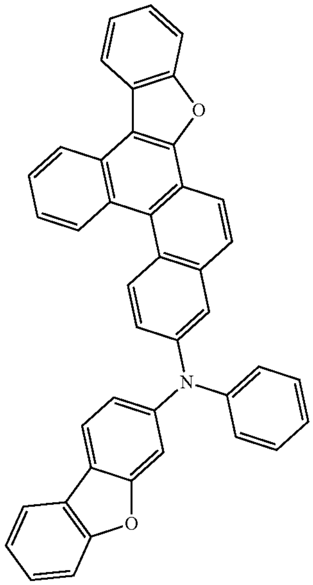
C-589
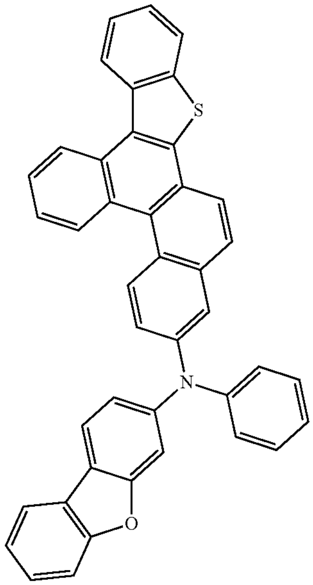
-continued
C-590
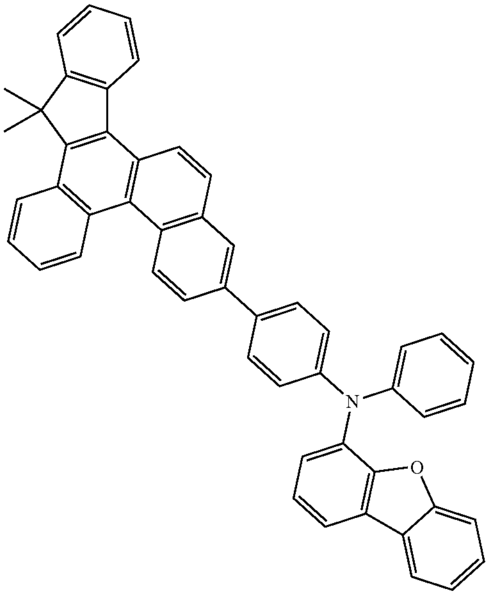
C-591
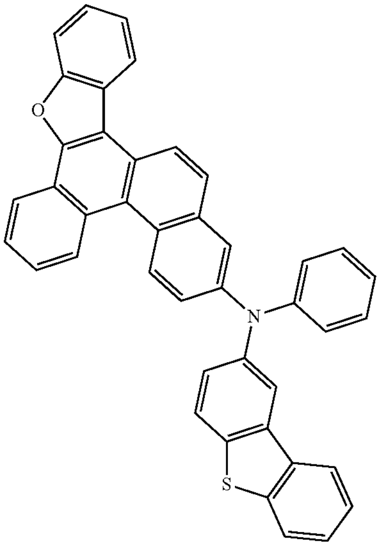

-continued
C-592
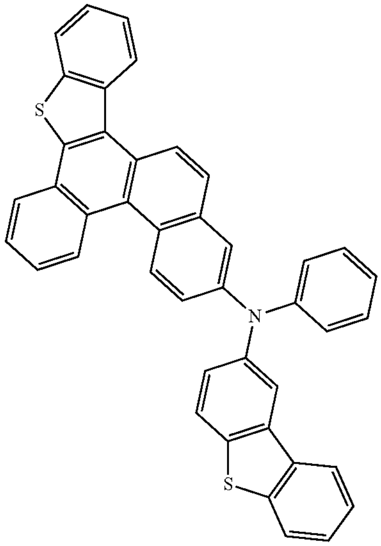
C-593
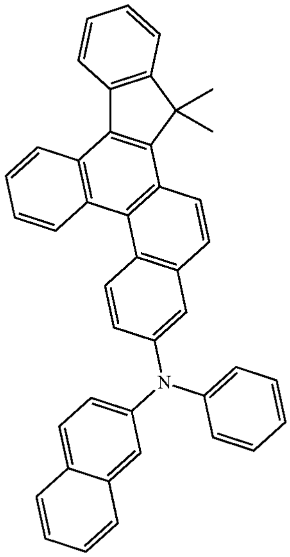
C-594
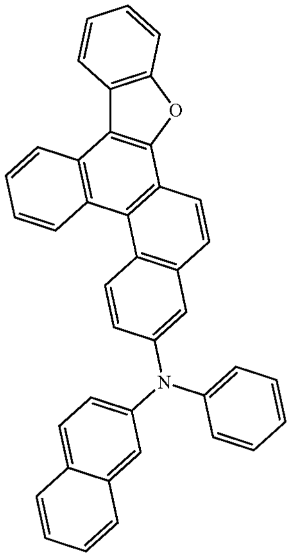
-continued
C-595
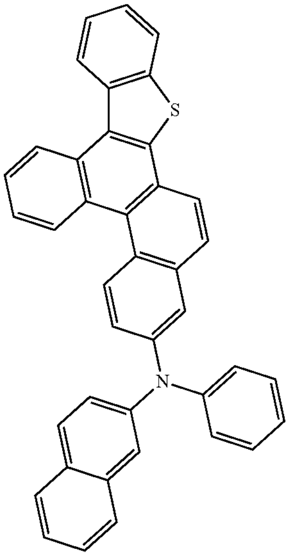
C-596
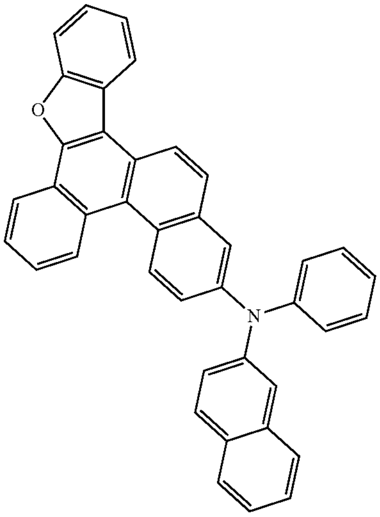
C-597
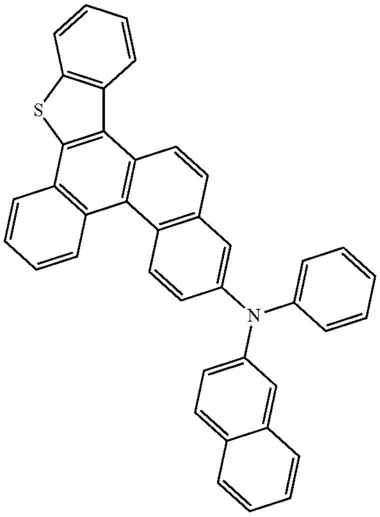

-continued
C-598
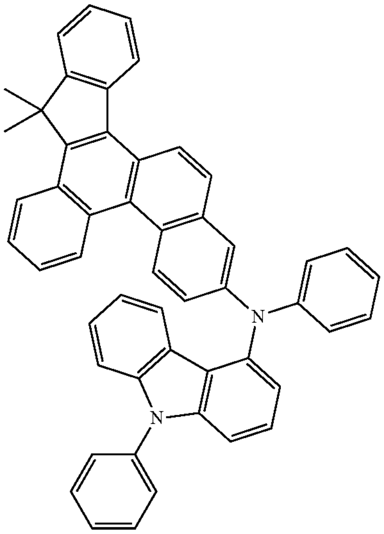
C-599
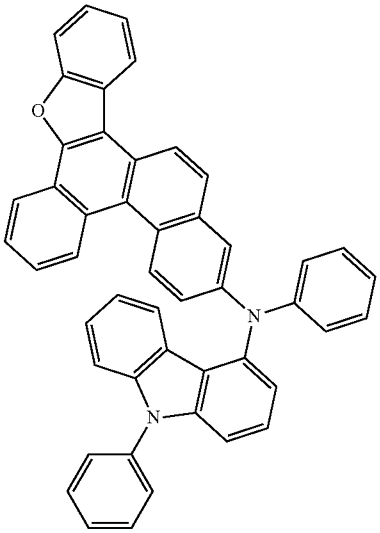
C-600
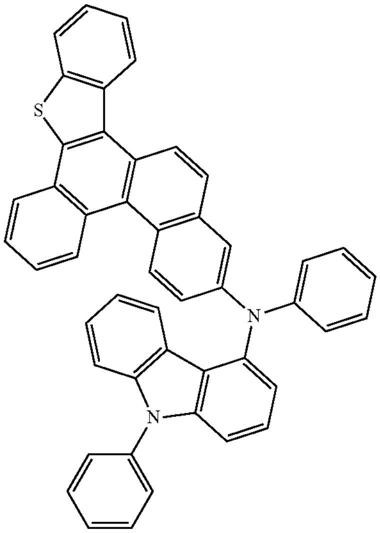
-continued
C-601
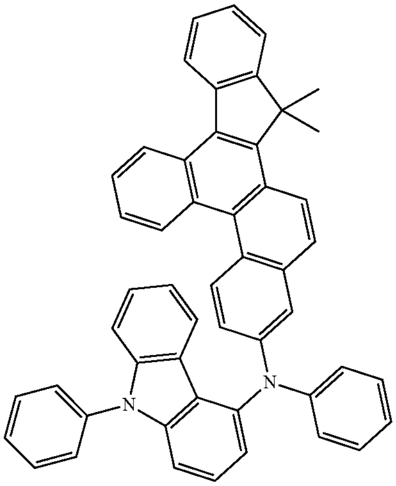
C-602
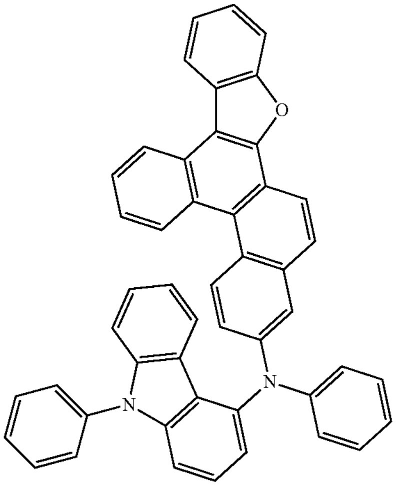
C-603
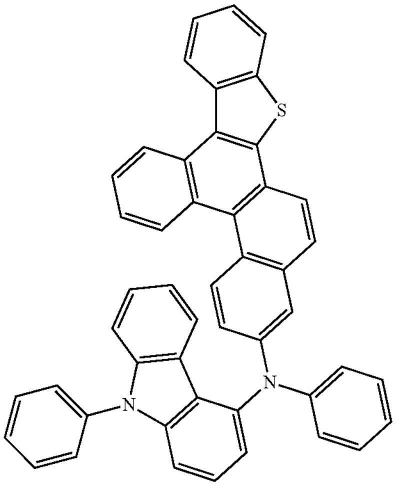

-continued
C-604
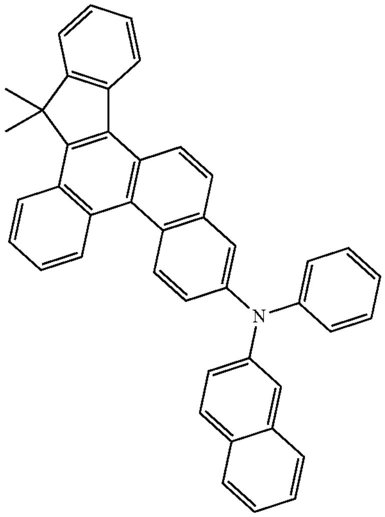
C-605
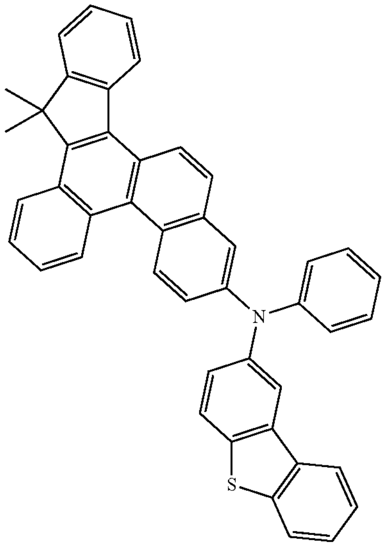
-continued
C-606
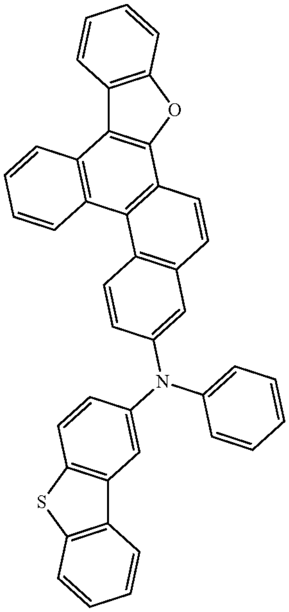
C-607
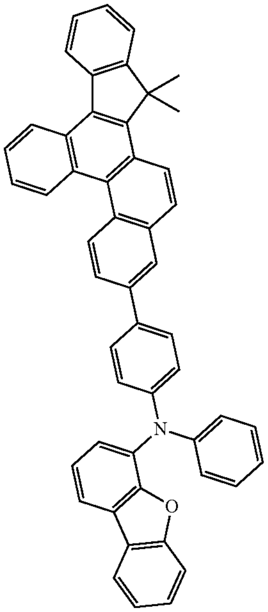

-continued
C-608
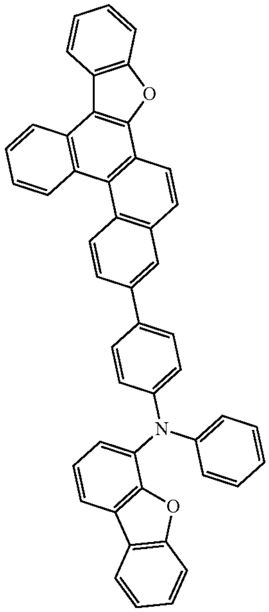
C-609
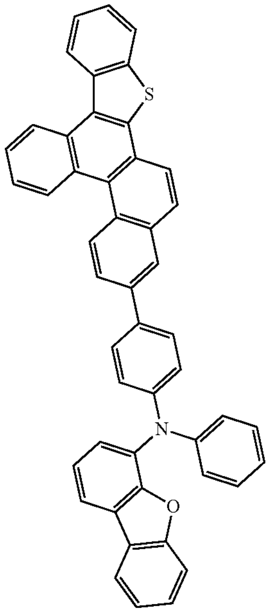
-continued
C-610
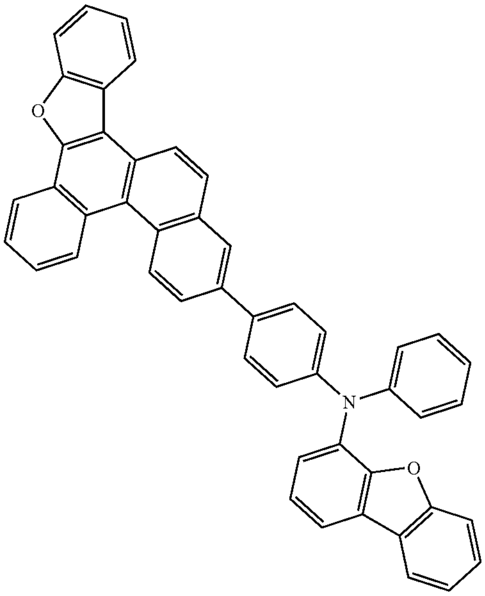
C-611
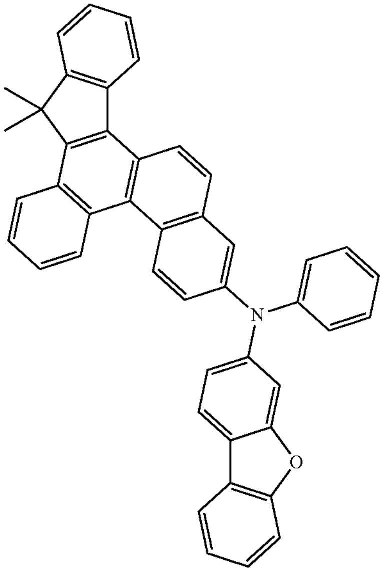

-continued
C-612
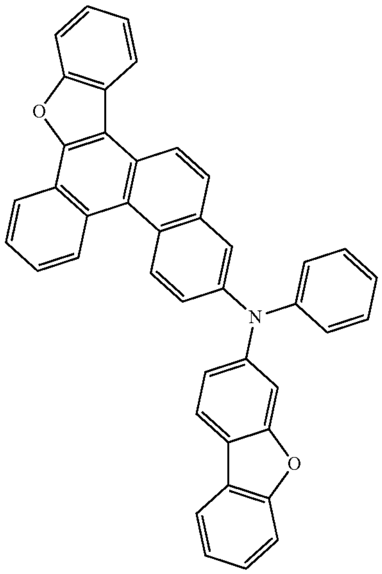
C-613
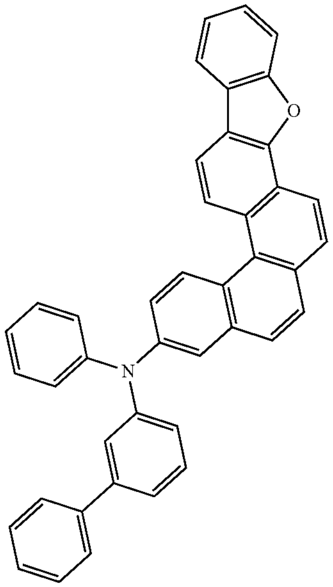
-continued
C-614
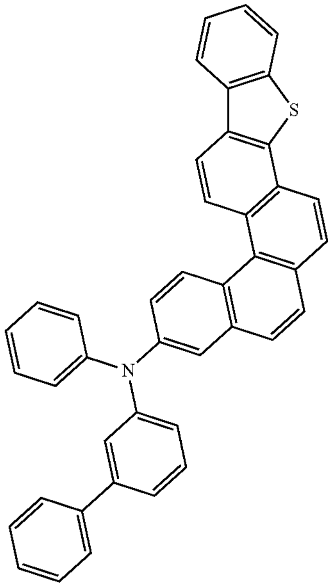
C-615
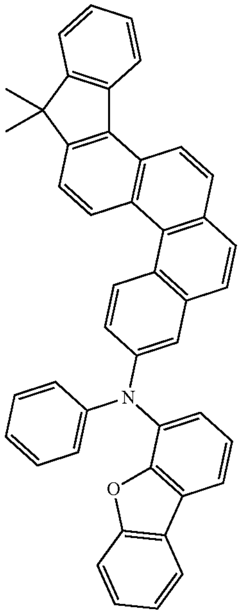

-continued
C-616
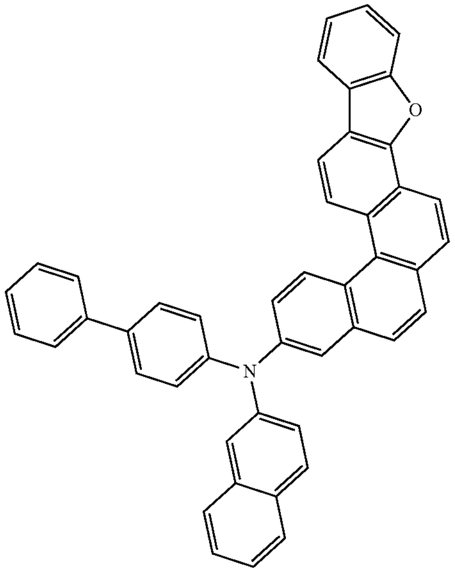
C-617
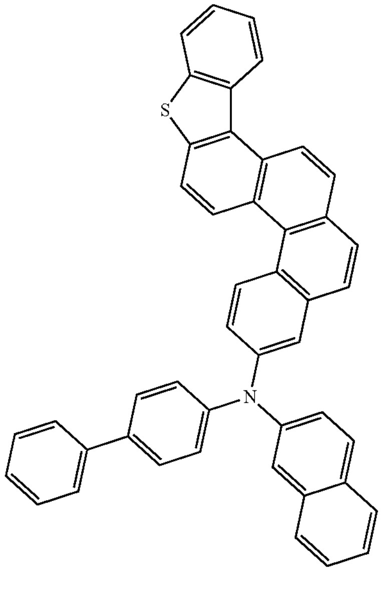
-continued
C-618
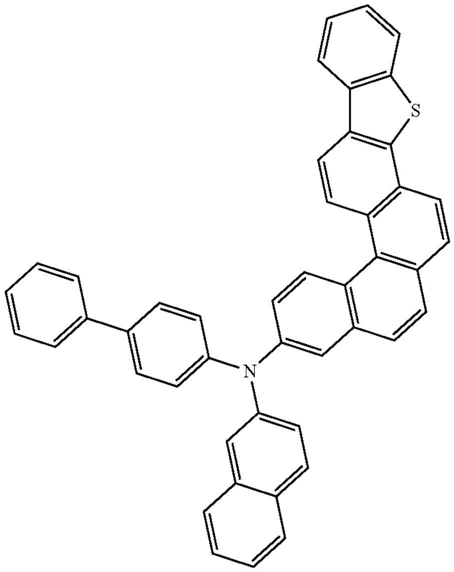
C-619
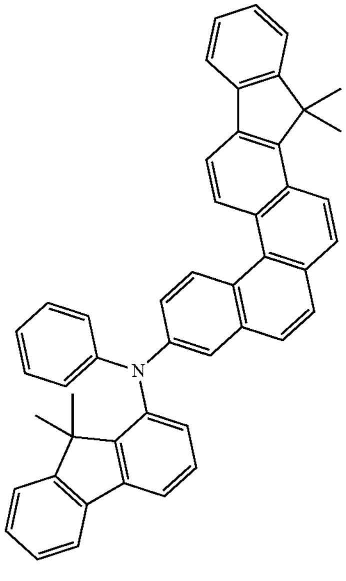

-continued
C-620
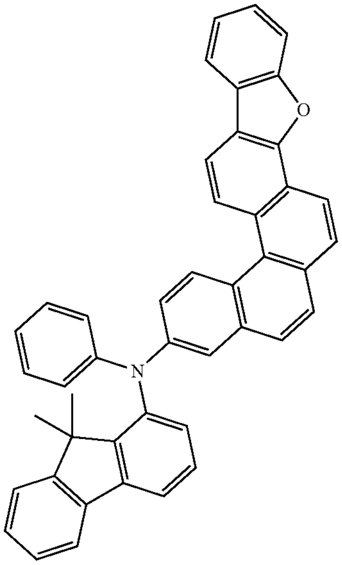
C-621
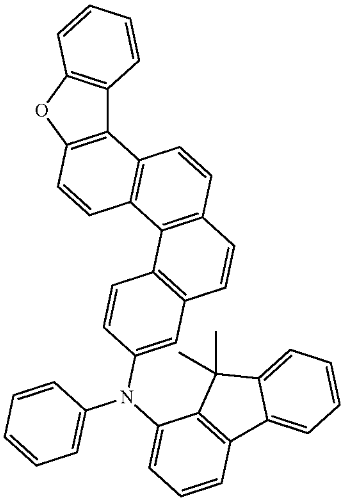
C-622
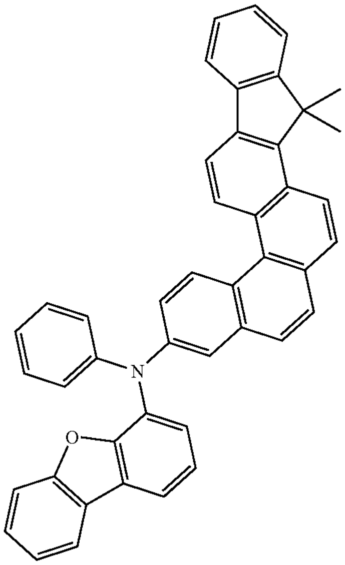
-continued
C-623
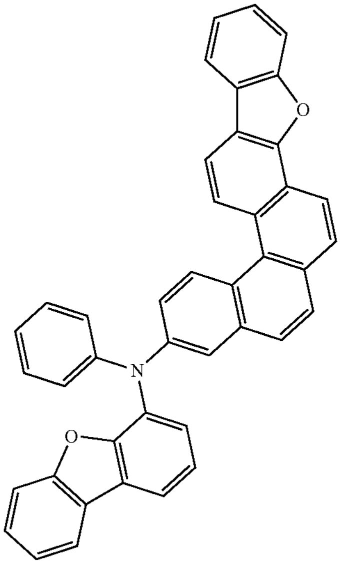
C-624
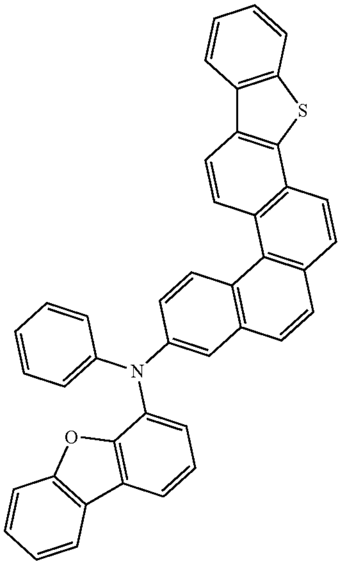

-continued
C-625
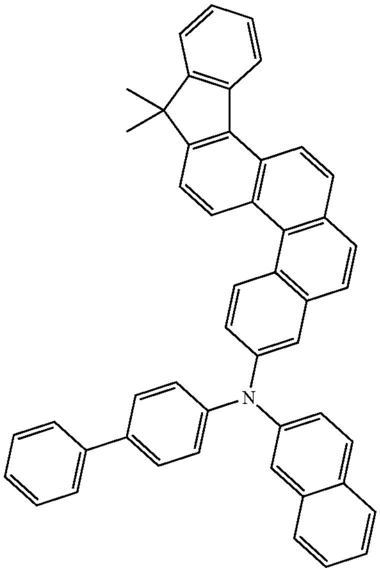
C-626
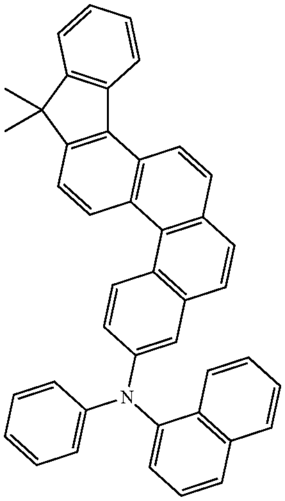
C-627
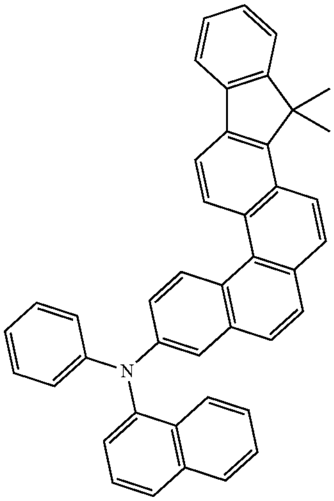
-continued
C-628
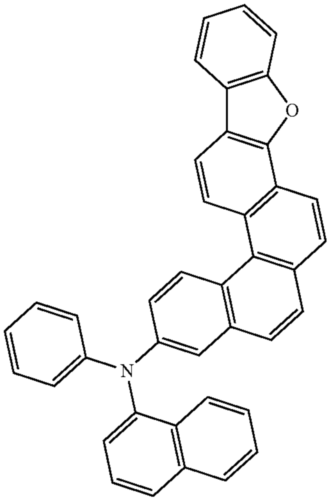
C-629
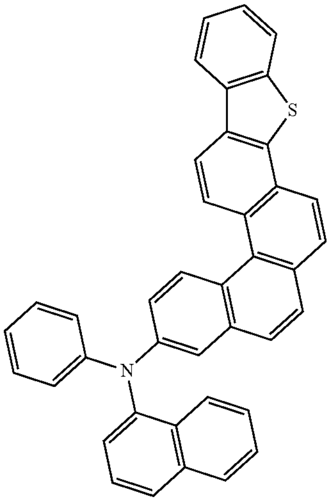
C-630
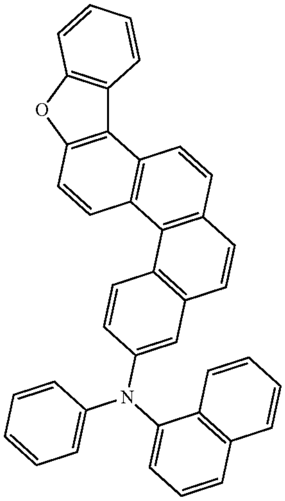

-continued
C-631
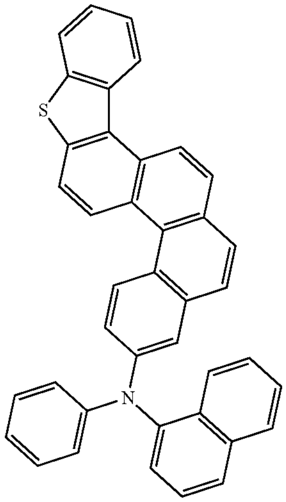
C-632
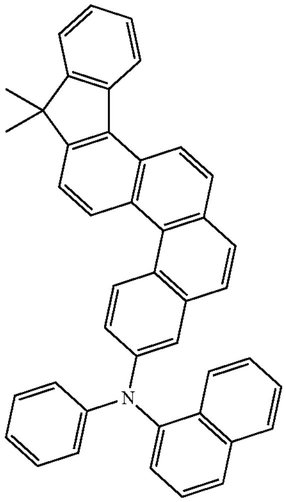
C-633
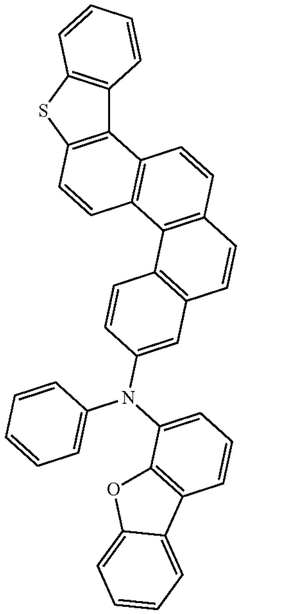
-continued
C-634
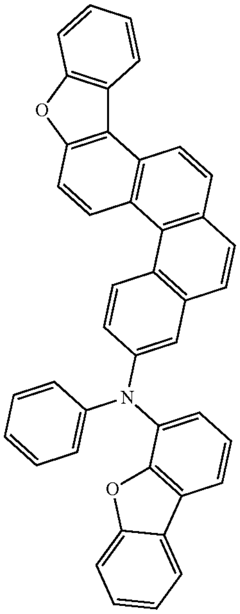
C-635
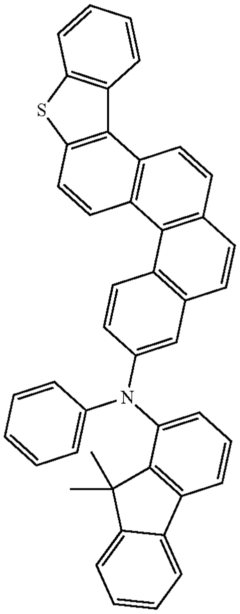

-continued
C-636
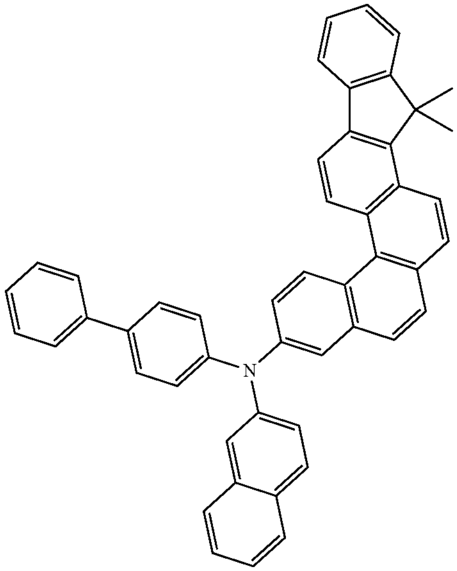
C-637
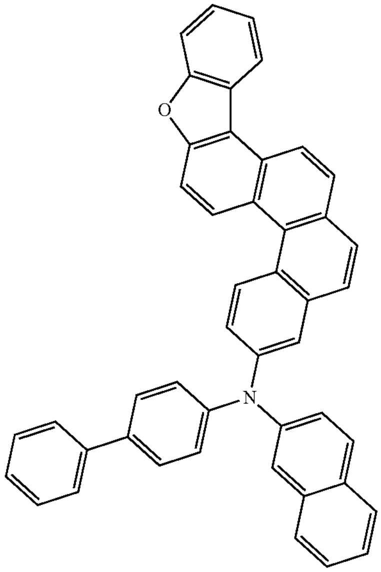
-continued
C-638
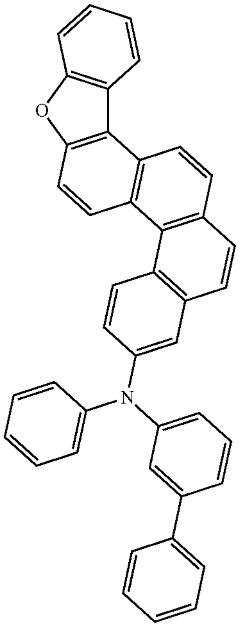
C-639
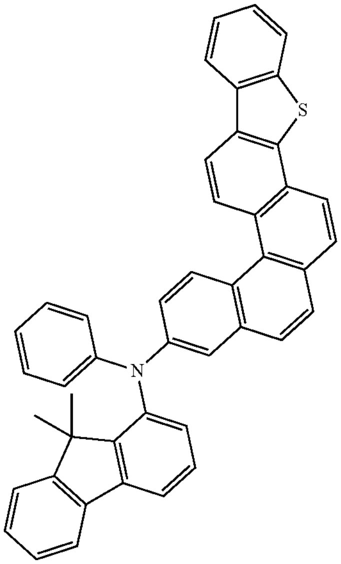

-continued
C-640
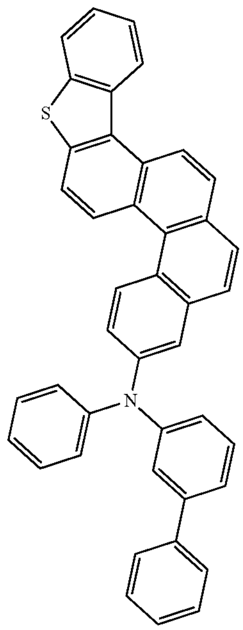
C-641
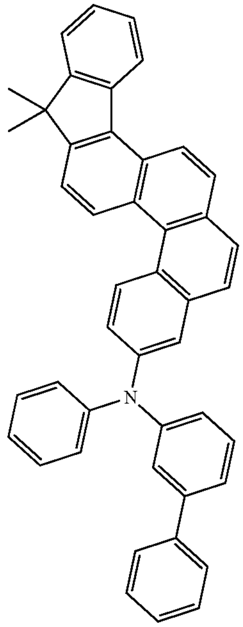
-continued
C-642
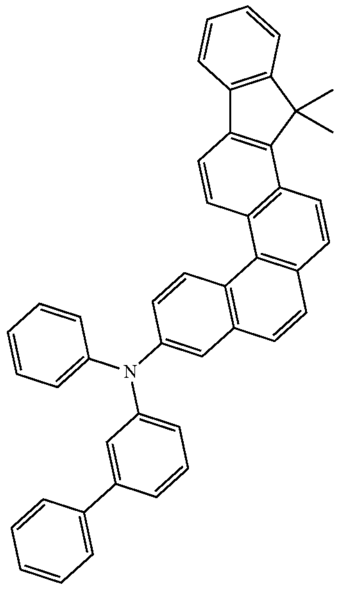
C-643
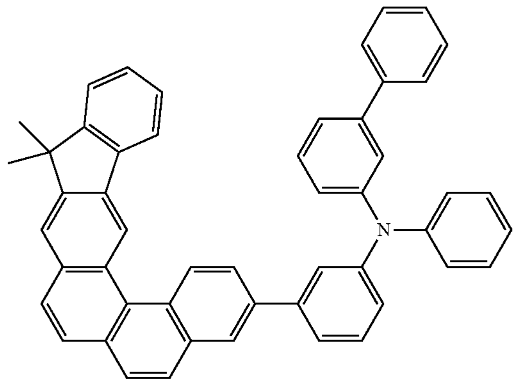
C-644
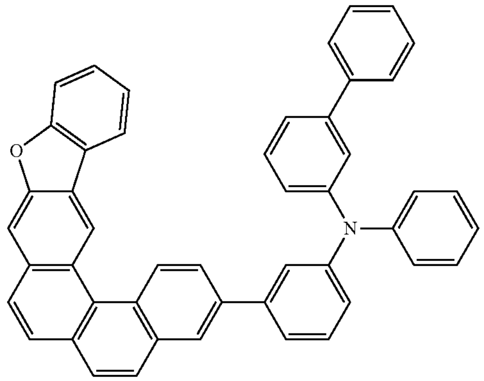

-continued
C-645
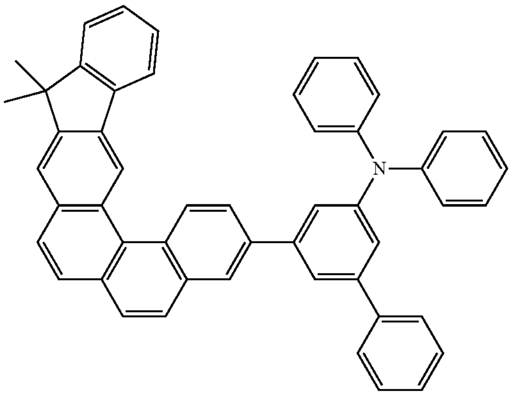
C-646
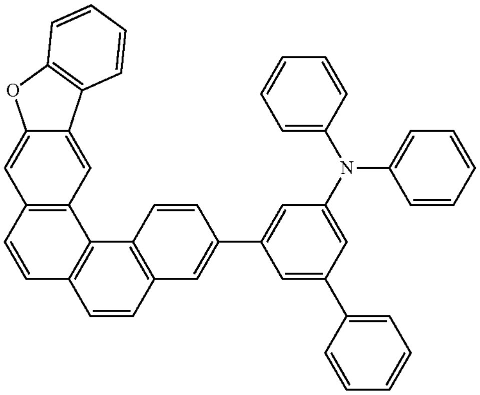
C-647
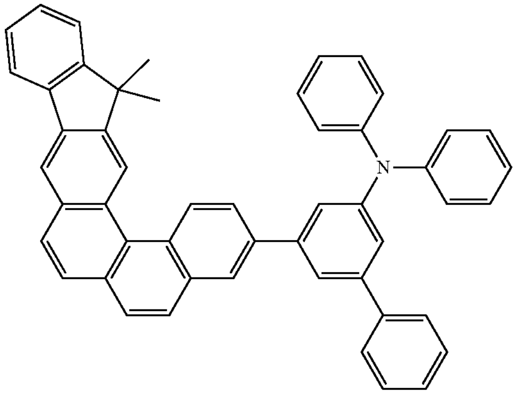
C-648
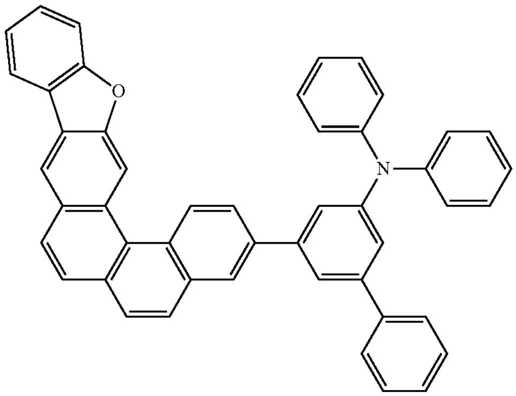
-continued
C-649
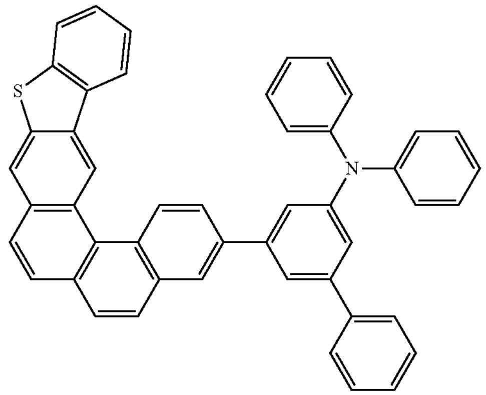
C-650
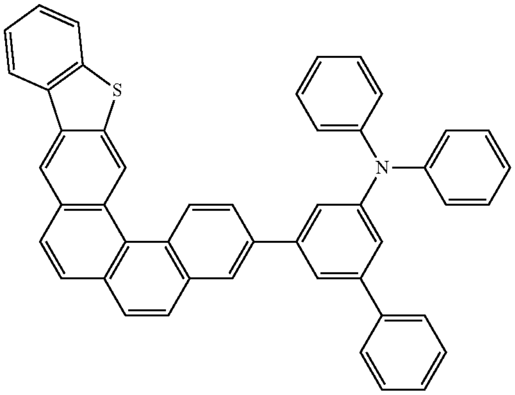
C-651
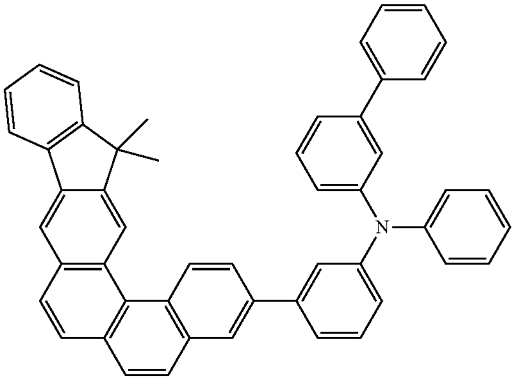
C-652
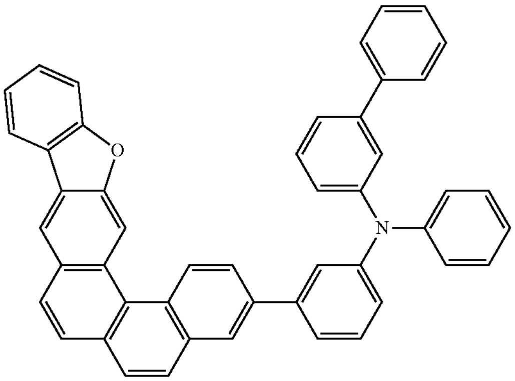

-continued
C-653
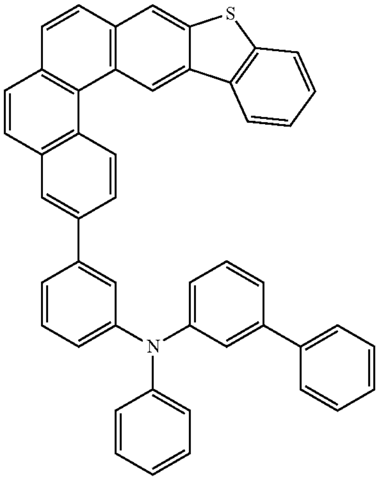
C-654
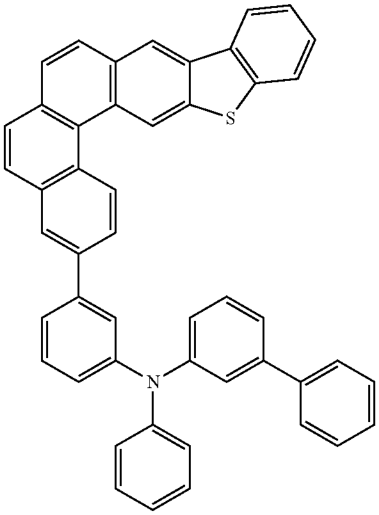
C-655
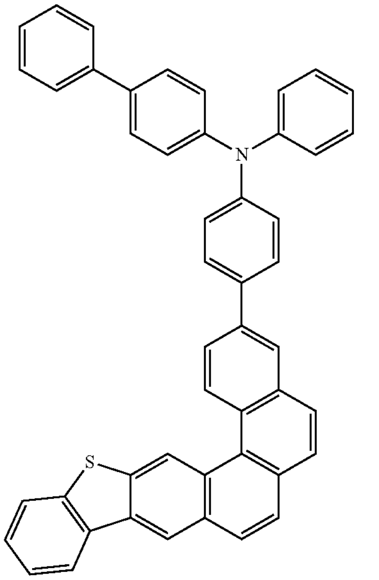
-continued
C-656
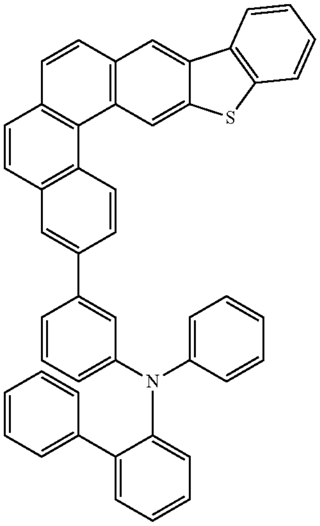
C-657
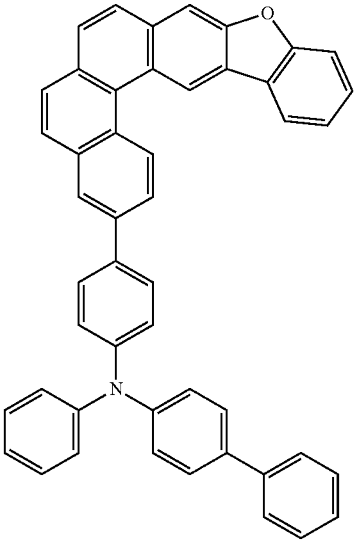
C-658
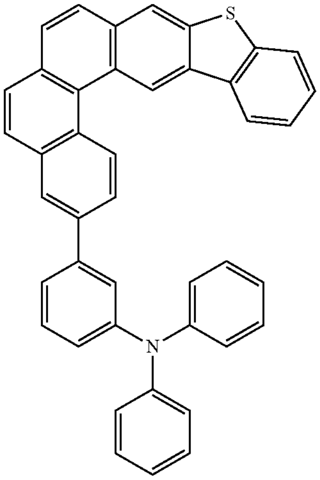

-continued
C-659
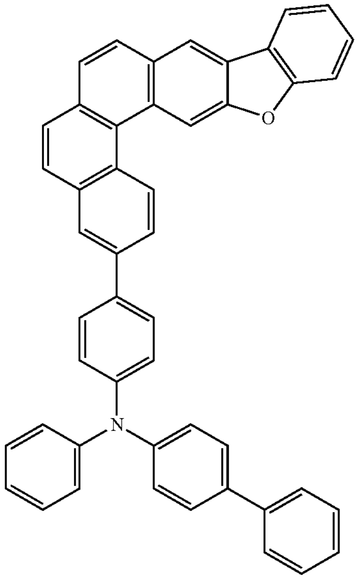
C-660
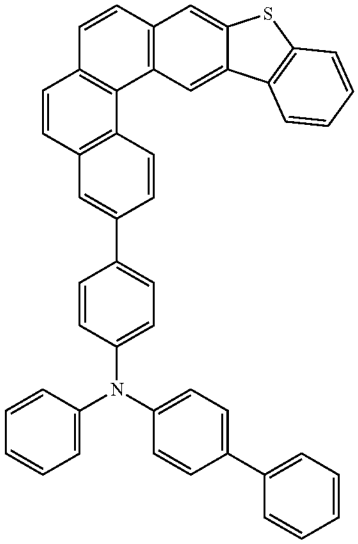
-continued
C-661
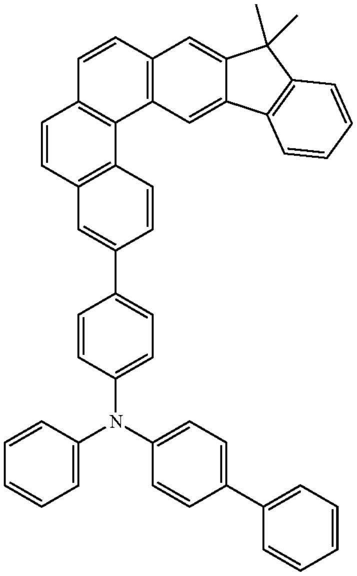
C-662
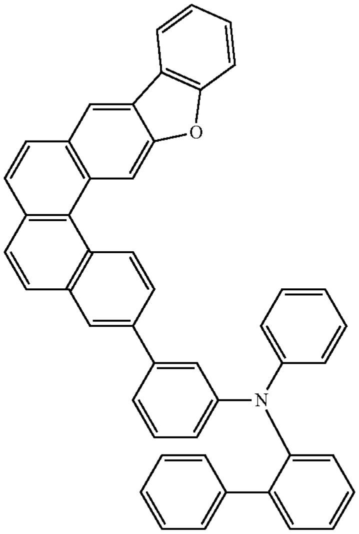

-continued
C-663
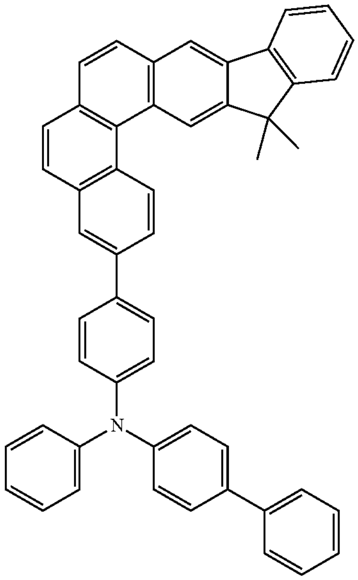
C-664
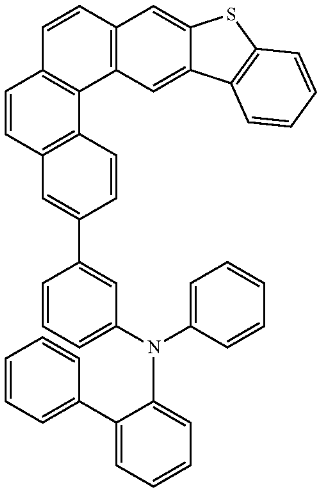
C-665
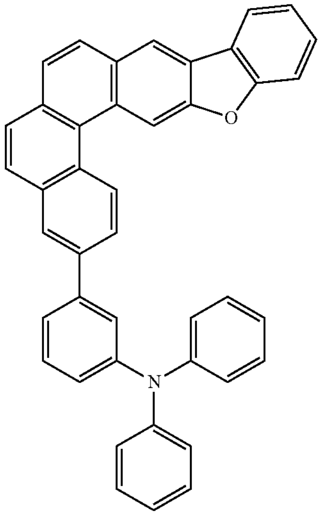
-continued
C-666
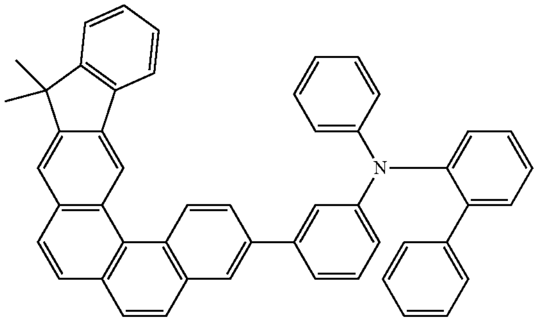
C-667
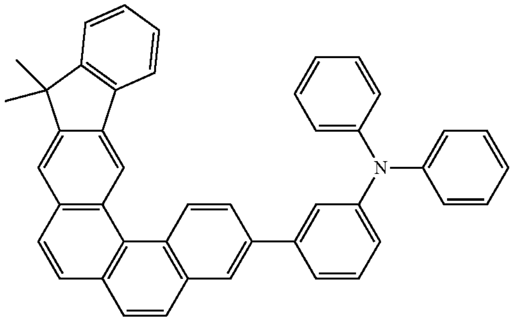
C-668
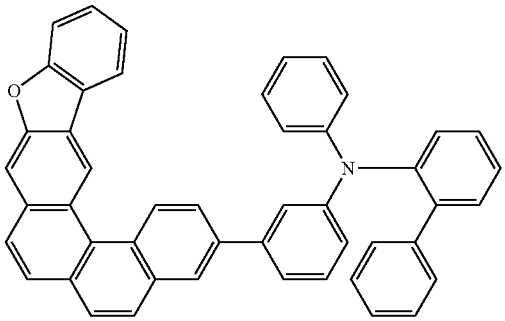
C-669
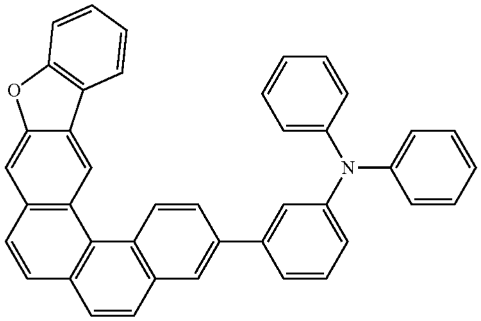

-continued
C-670
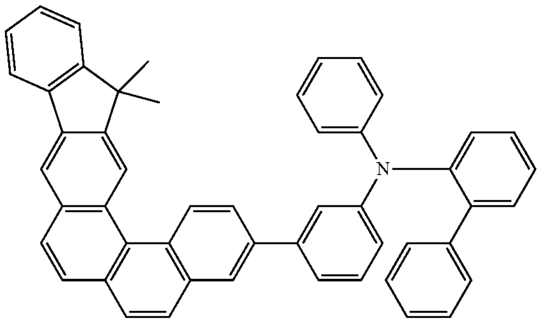
C-671
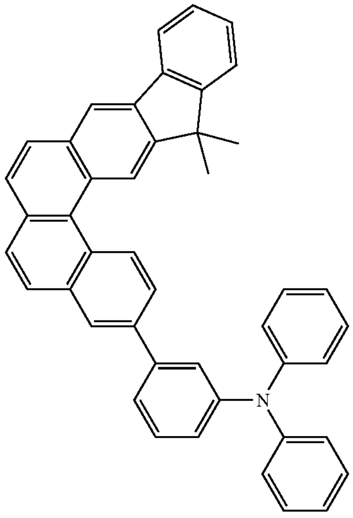
C-672
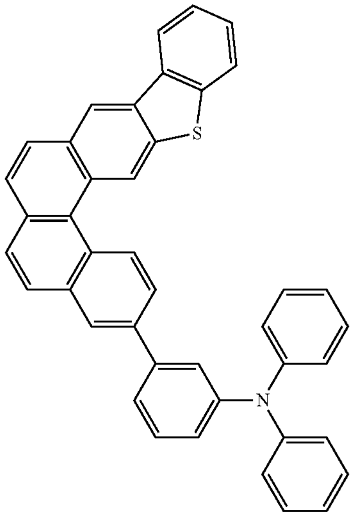
-continued
C-673
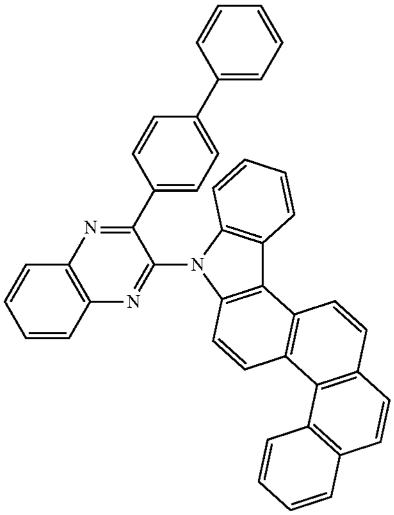
C-674
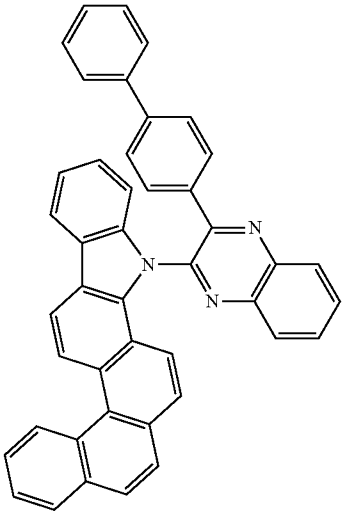
C-675
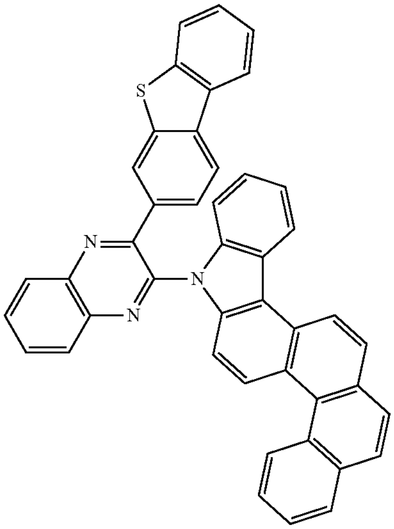

-continued
C-676
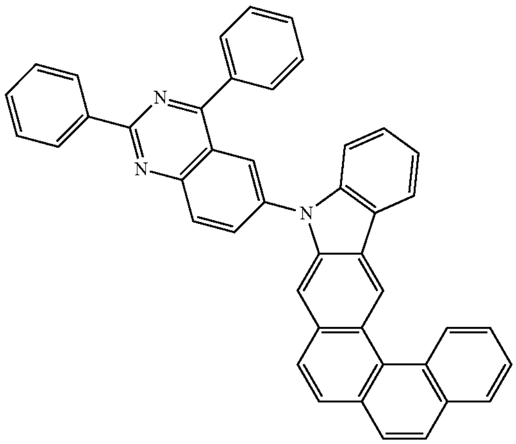
C-677
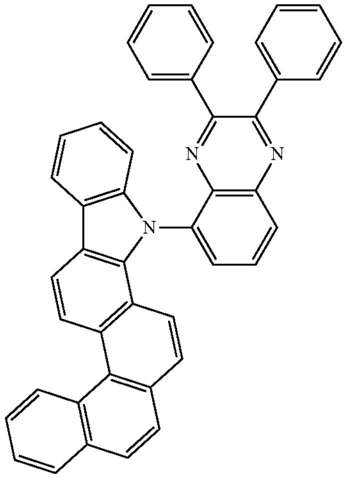
C-678
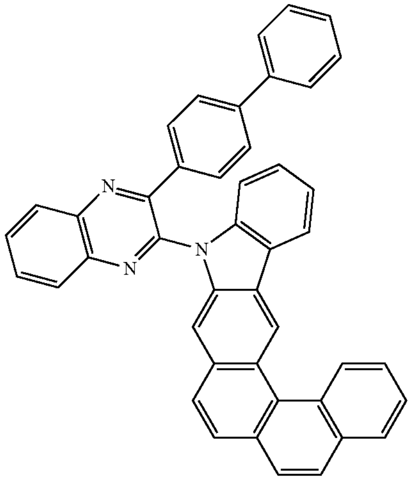
-continued
C-679
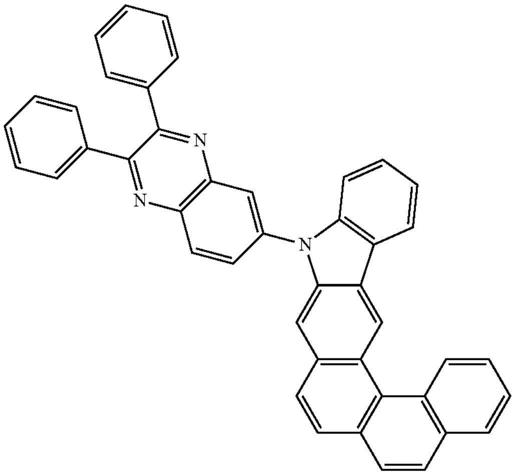
C-680
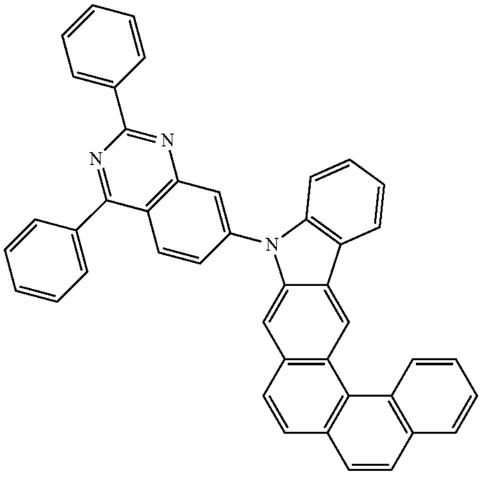
C-681
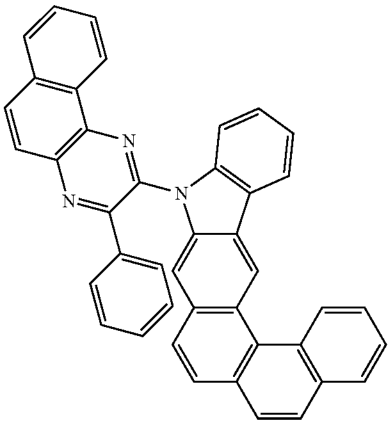

-continued
C-682
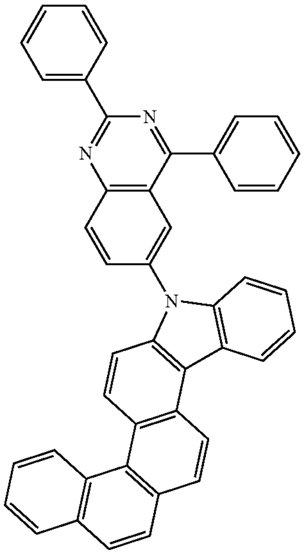
C-683
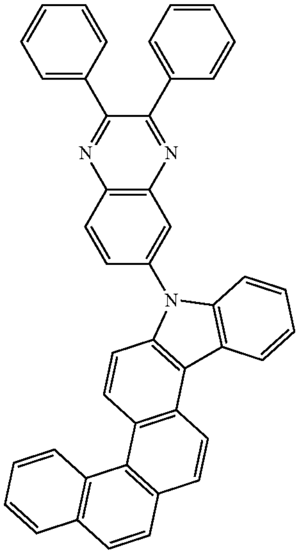
C-684
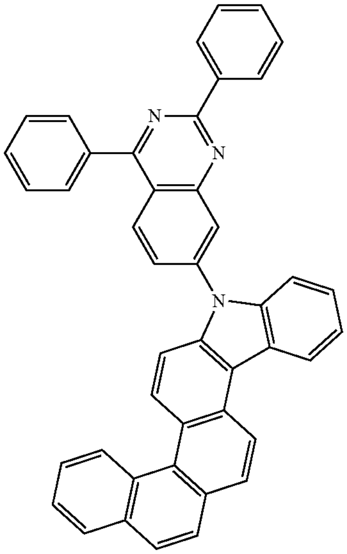
C-685
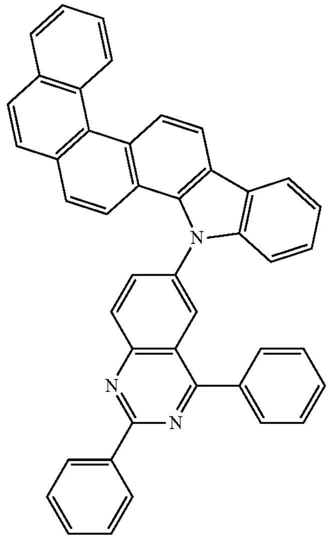
C-686
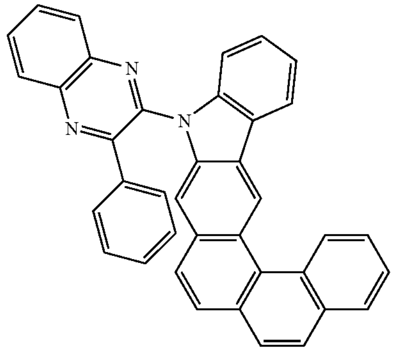
C-687
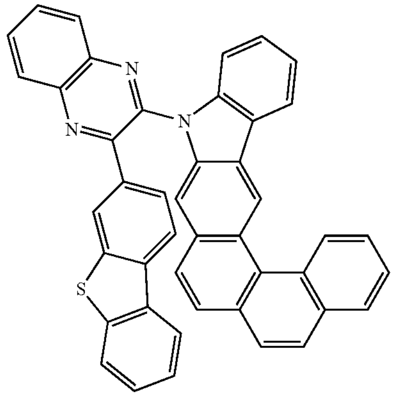

-continued
C-688
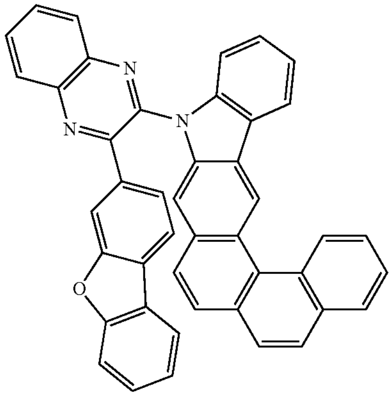
C-689
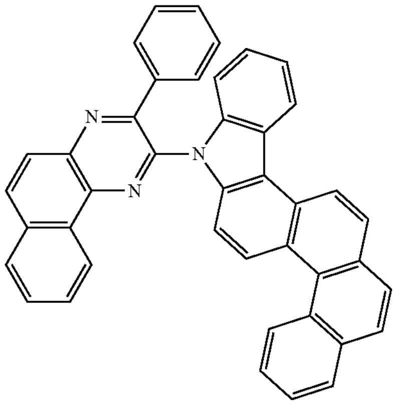
C-690
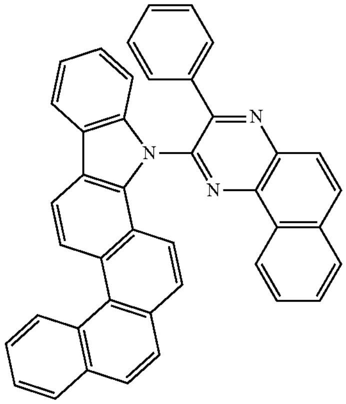
C-691
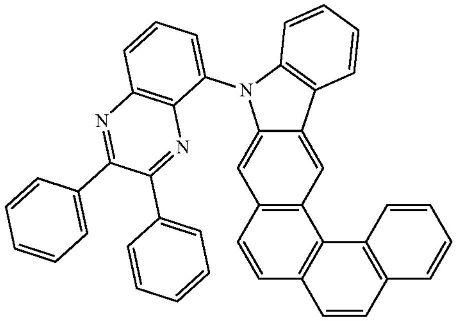
-continued
C-692
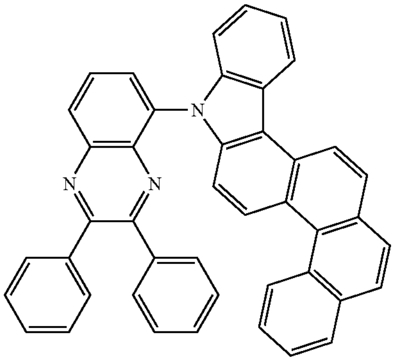
C-693
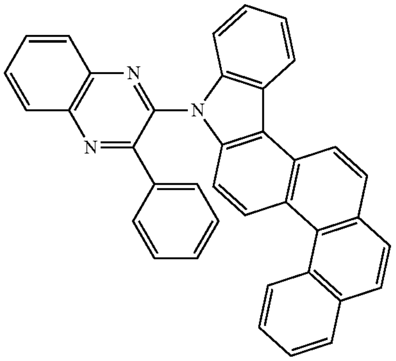
C-694
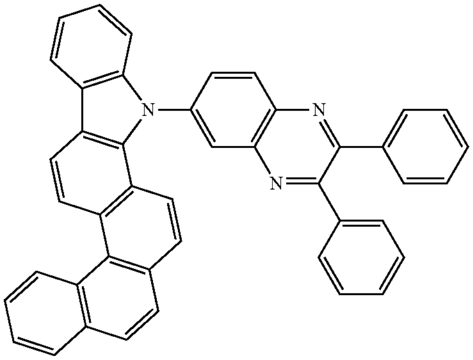
C-695
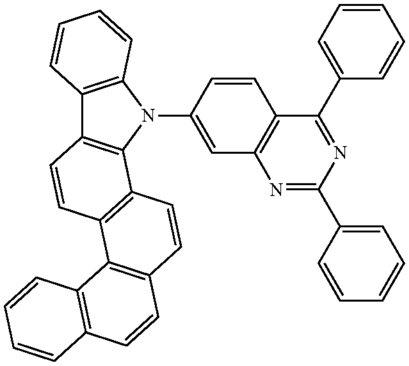

-continued
C-696
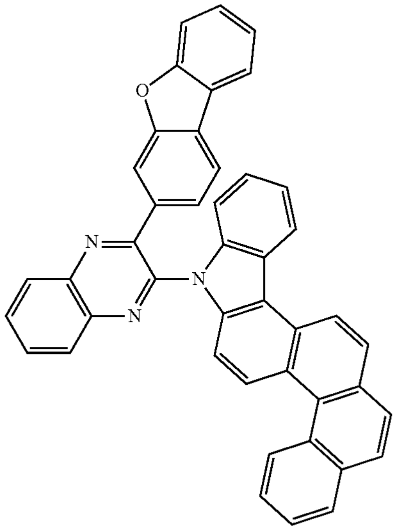
C-697
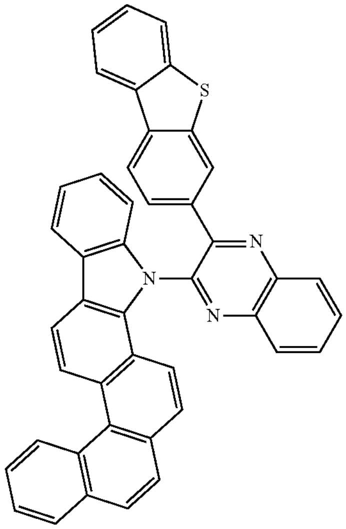
C-698
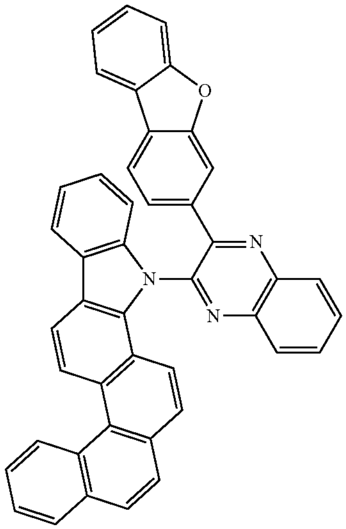
-continued
C-699
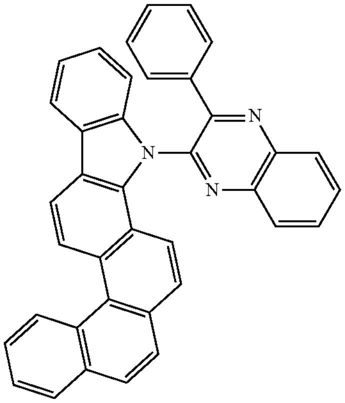
C-700
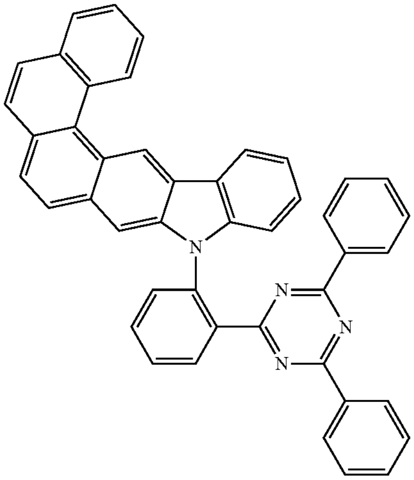
C-701
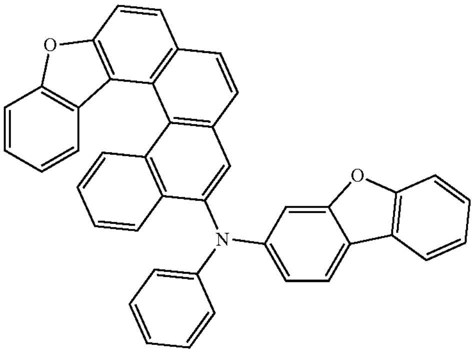

-continued
C-702
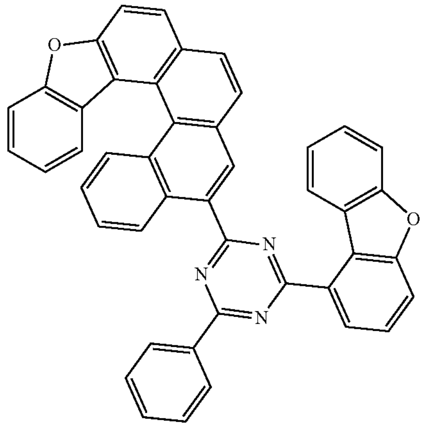
C-703
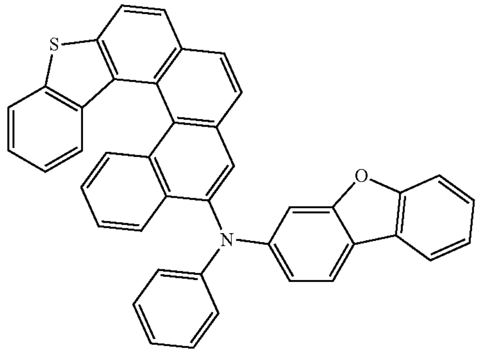
C-704
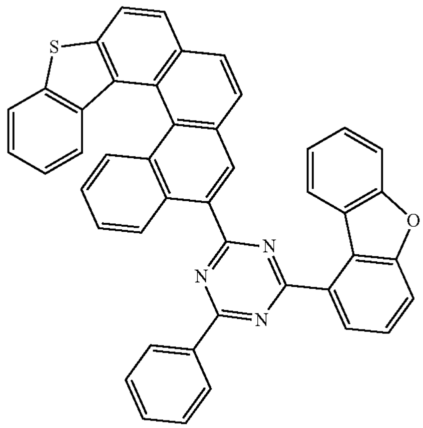
-continued
C-705
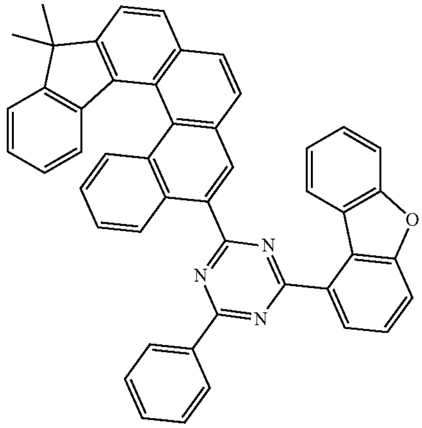
C-706
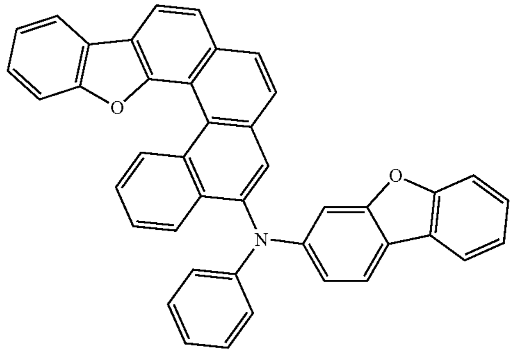
C-707
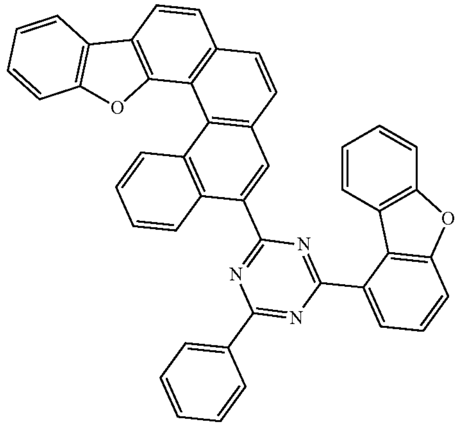
C-708
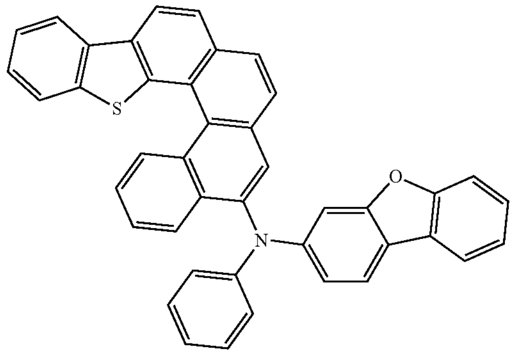

-continued
C-709
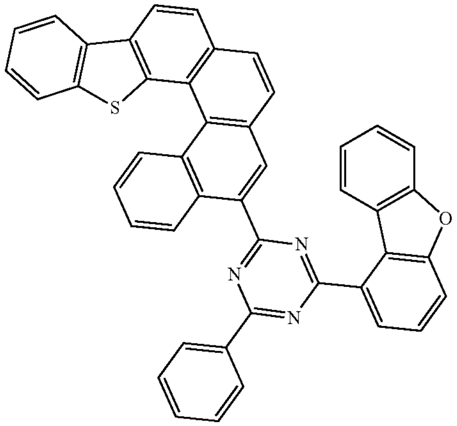
C-710
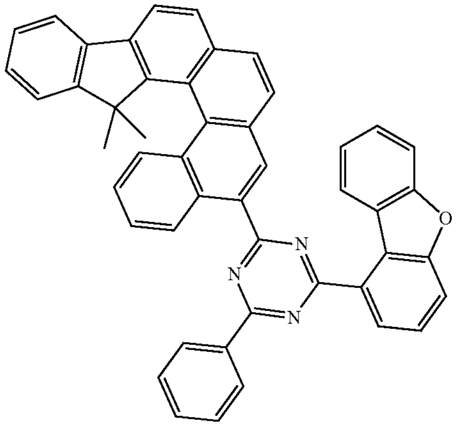
C-711
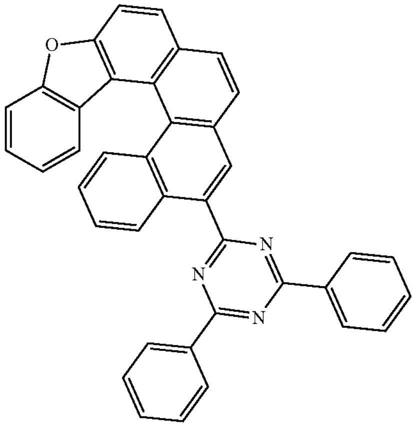
-continued
C-712
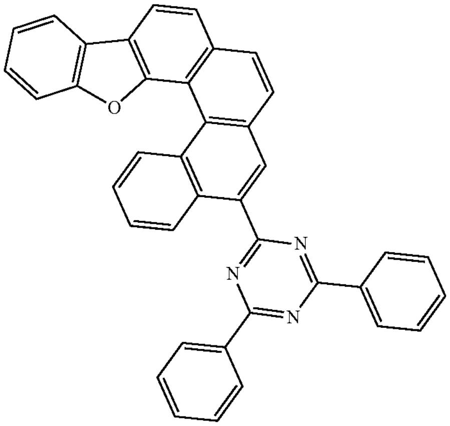
C-713
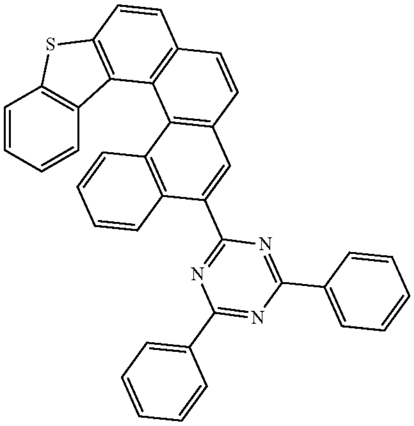
C-714
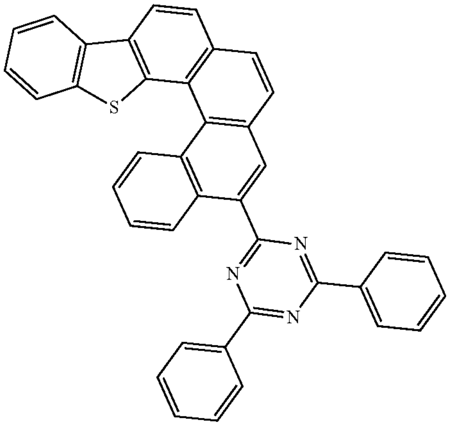
C-715
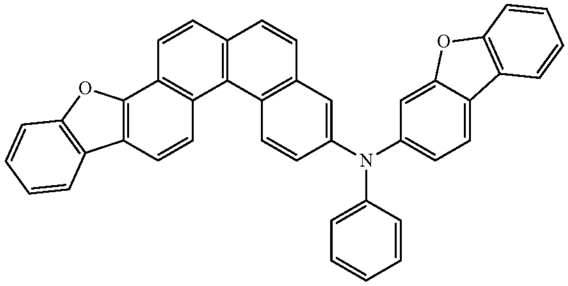

-continued
C-716
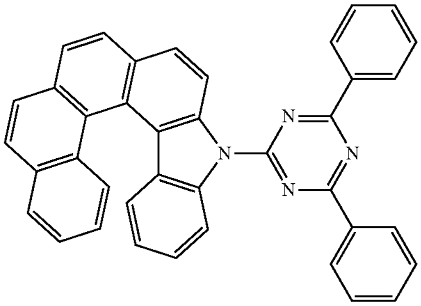
C-717
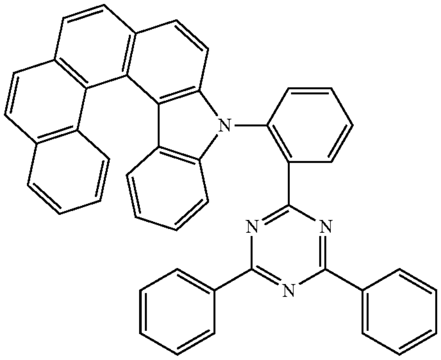
C-718
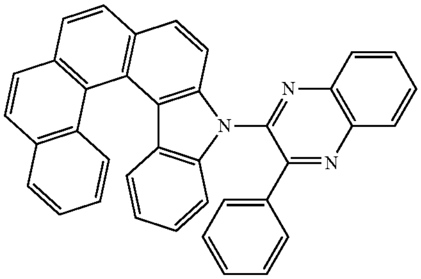
C-719
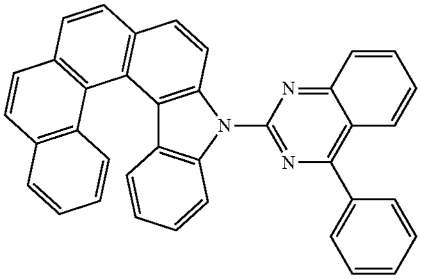
C-720
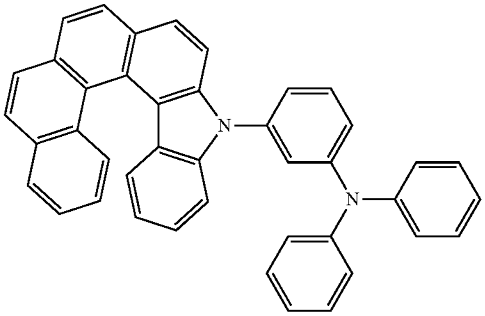
-continued
C-721
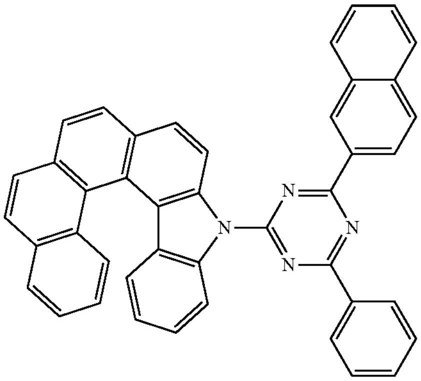
C-722
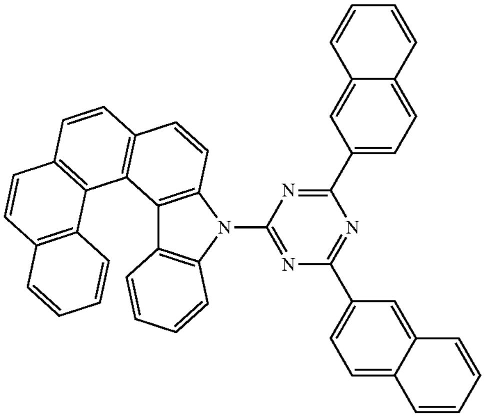
C-723
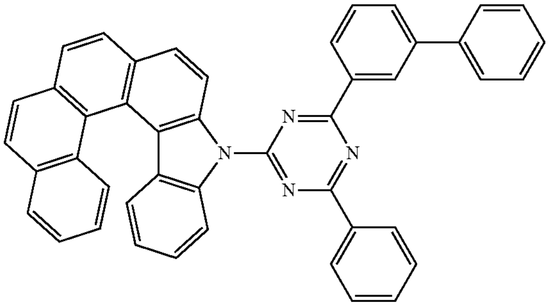
C-724
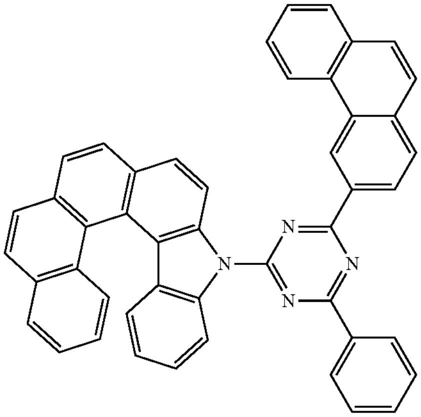

-continued
C-725
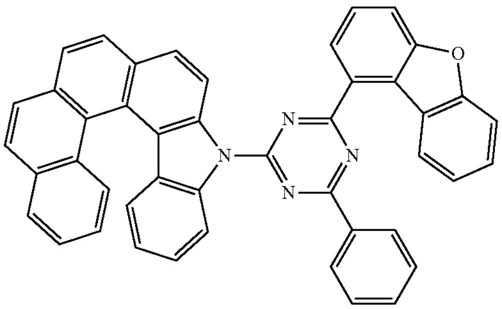
C-726
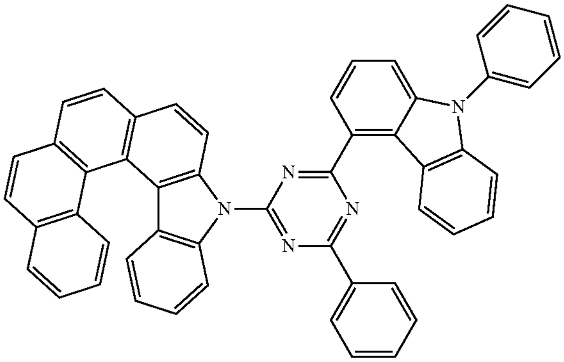
C-727
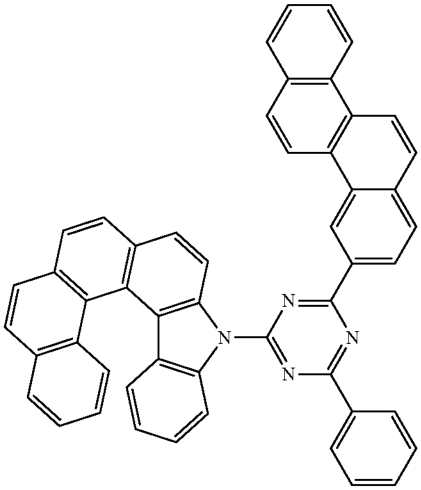
C-728
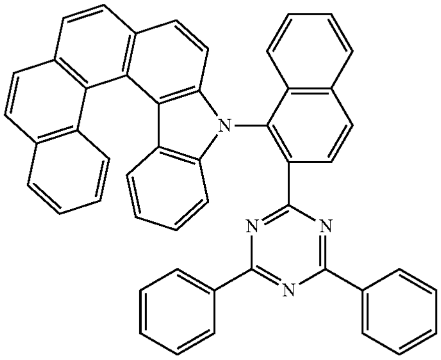
-continued
C-729
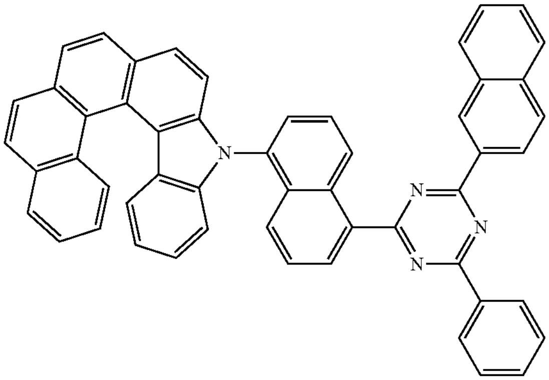
The compound represented by formula 1 of the present disclosure may be produced by a synthetic method known to one skilled in the art, and for example, according to the following reaction schemes 1 to 7.
[Reaction Scheme 1]
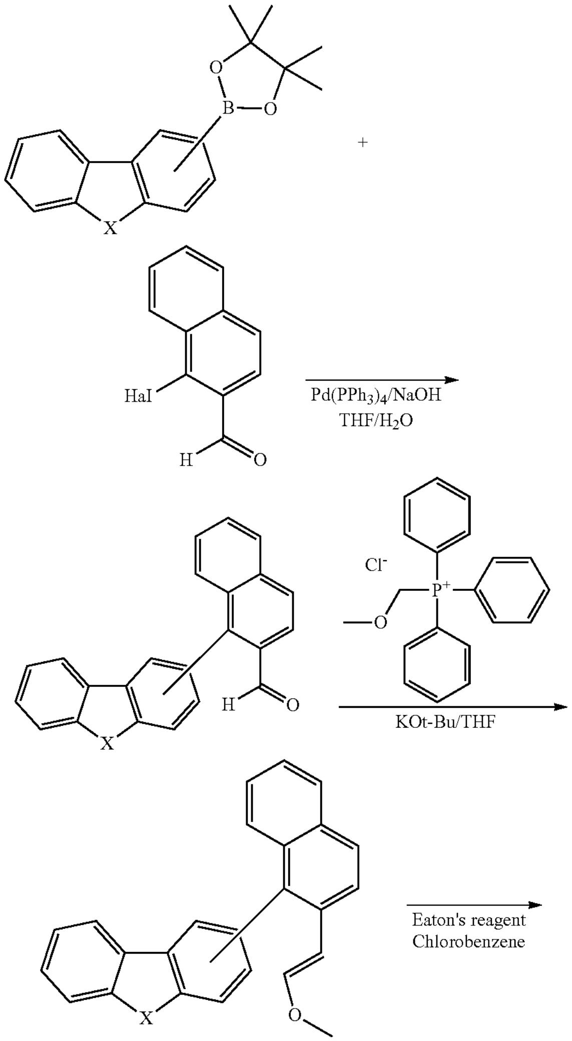

-continued
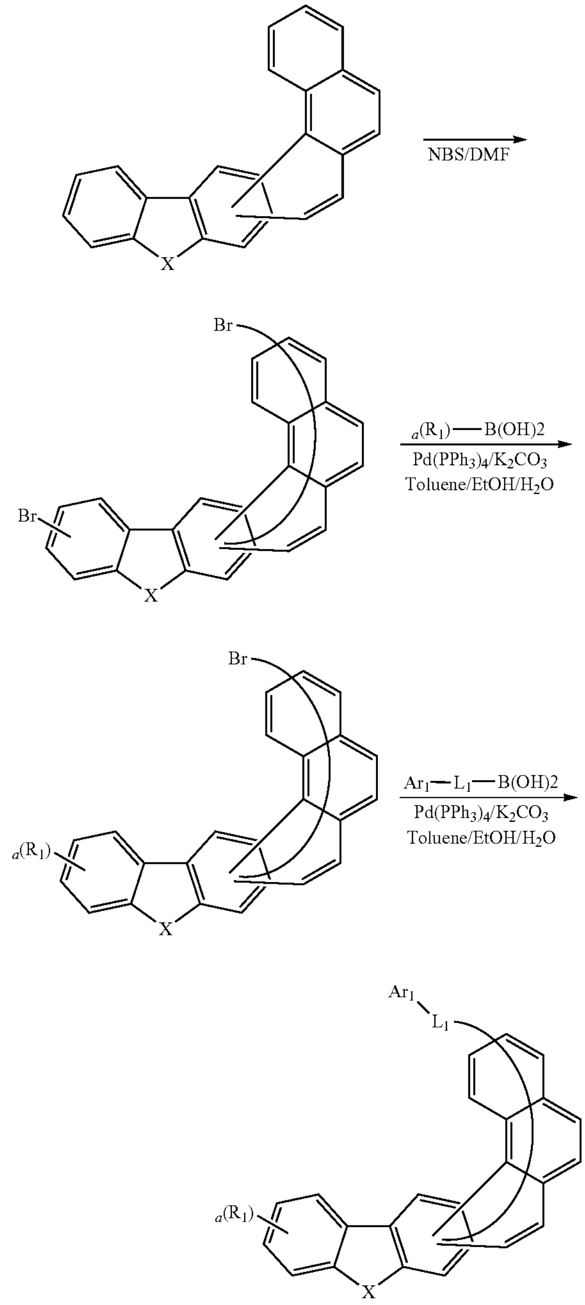
[Reaction Scheme 2]
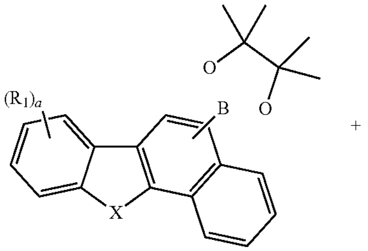
-continued
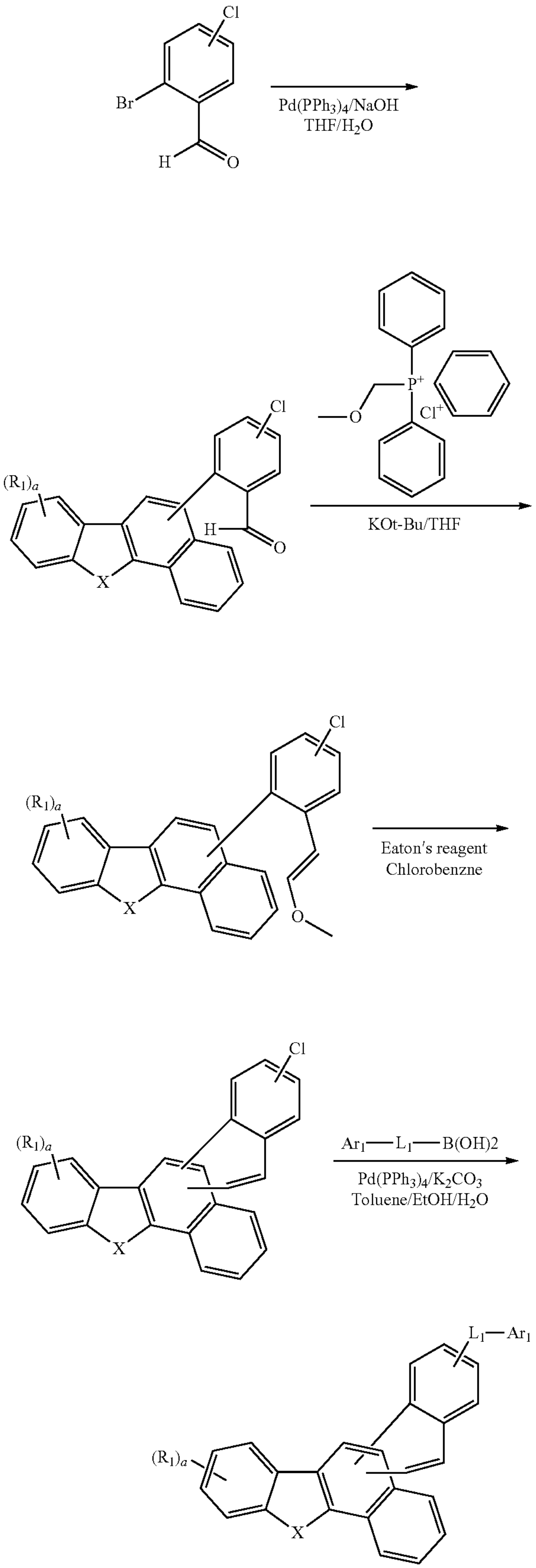

[Reaction Scheme 3]
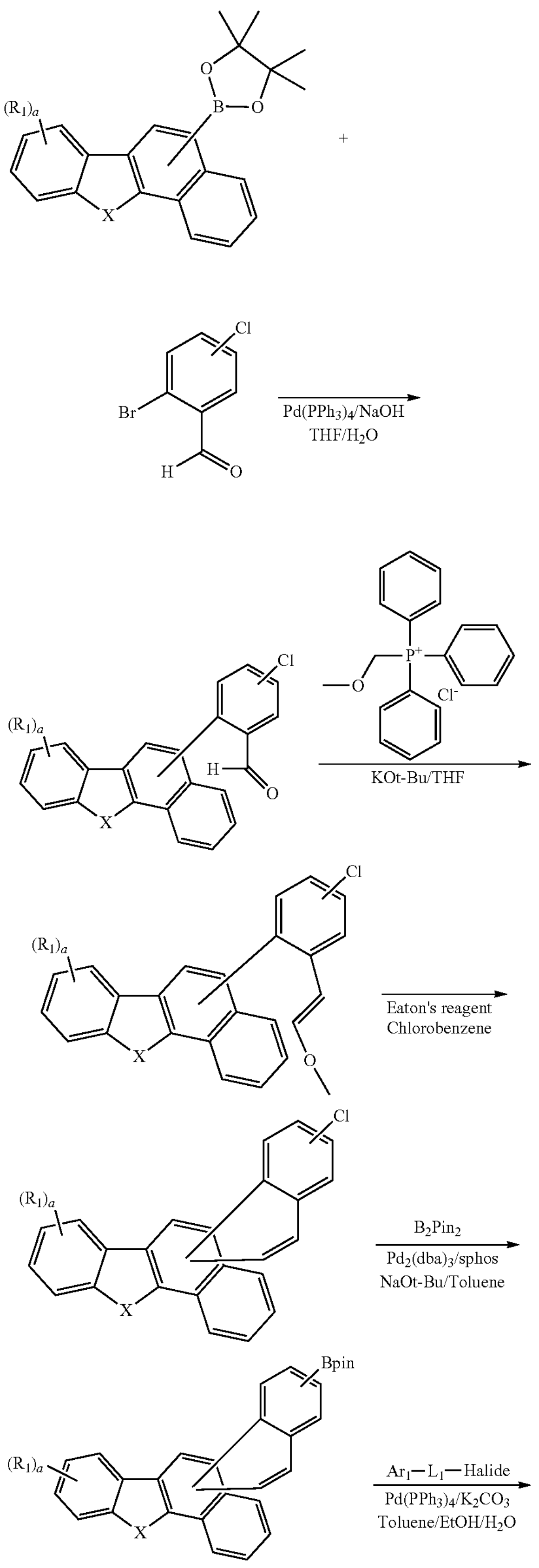
-continued
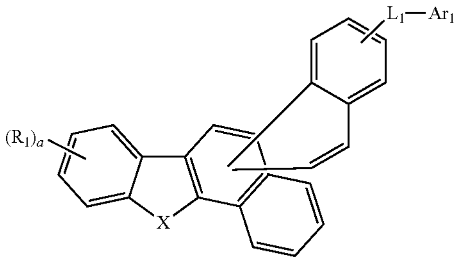
[Reaction Scheme 4]
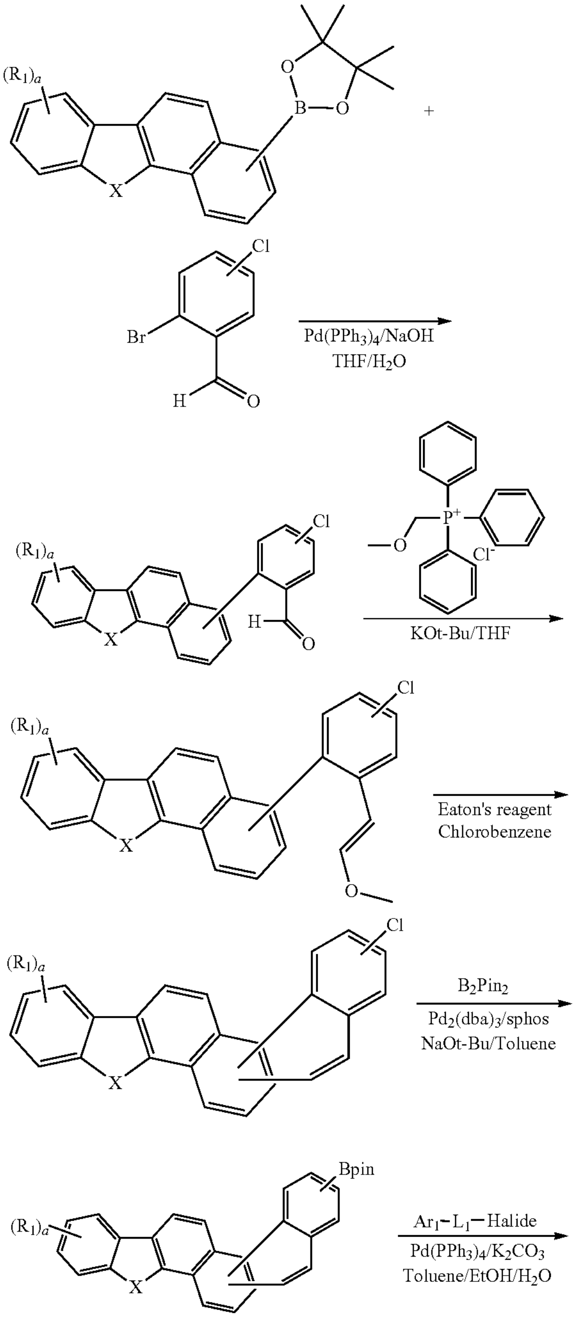

-continued
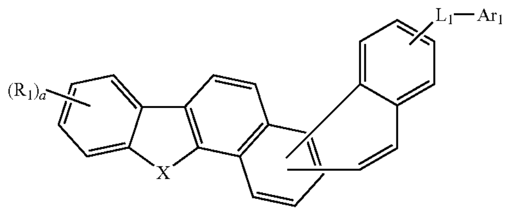
[Reaction Scheme 5]
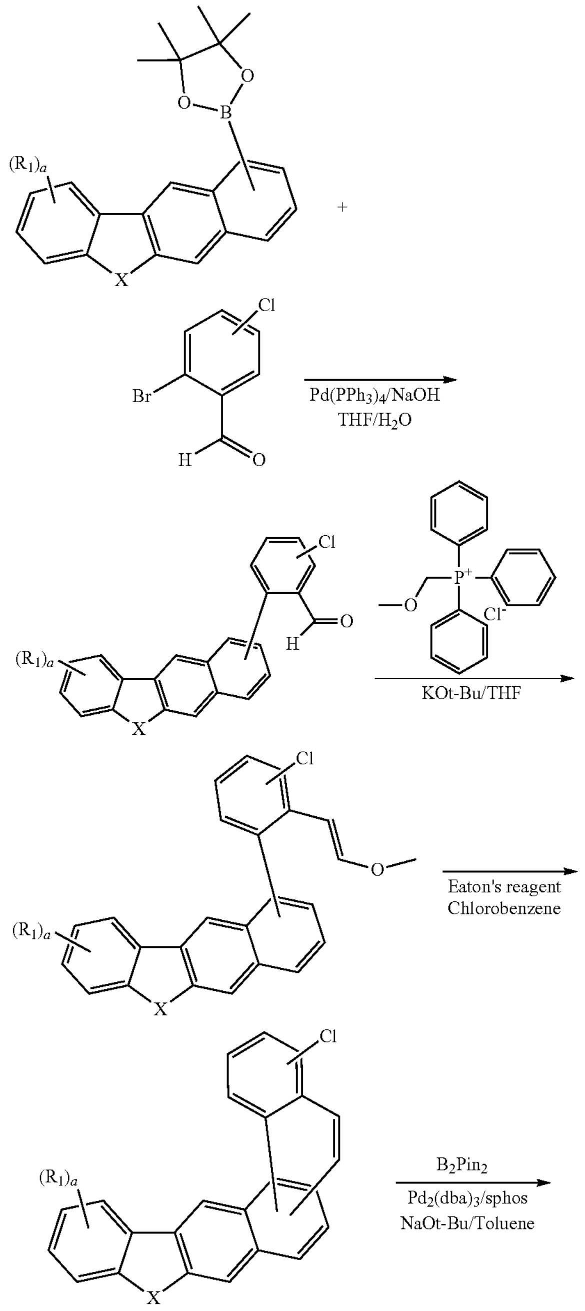
-continued
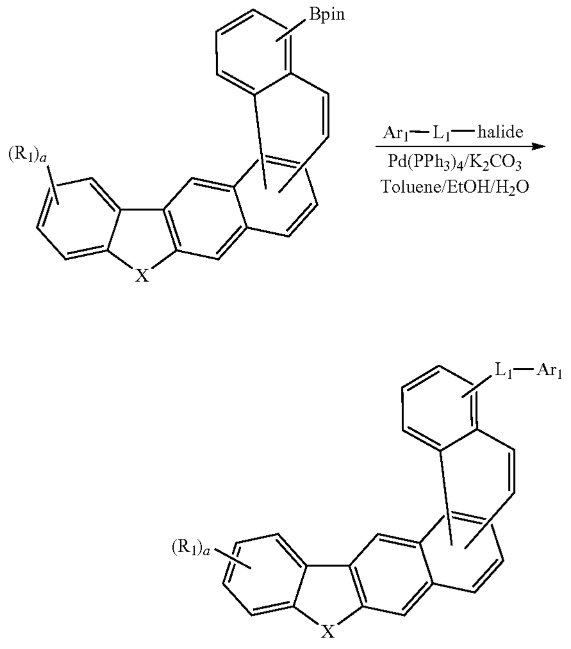
[Reaction Scheme 6]
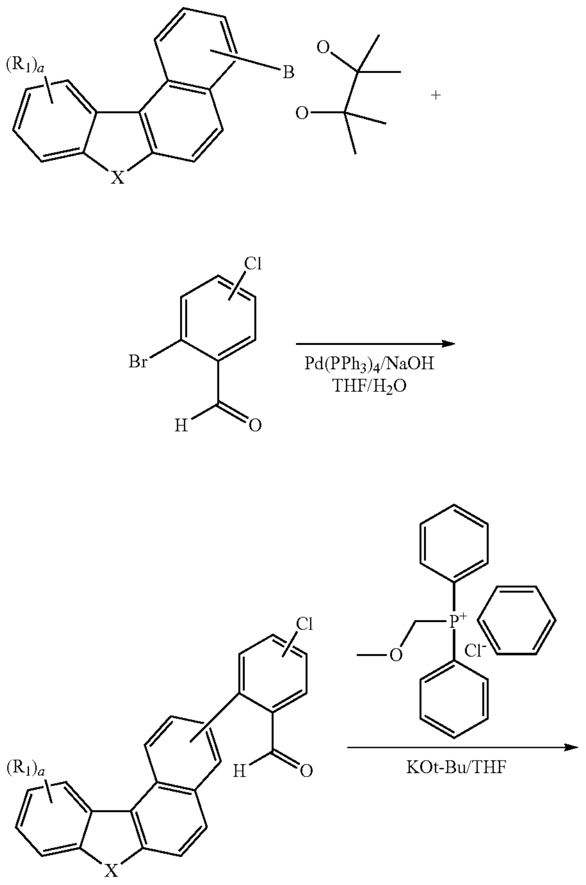

-continued

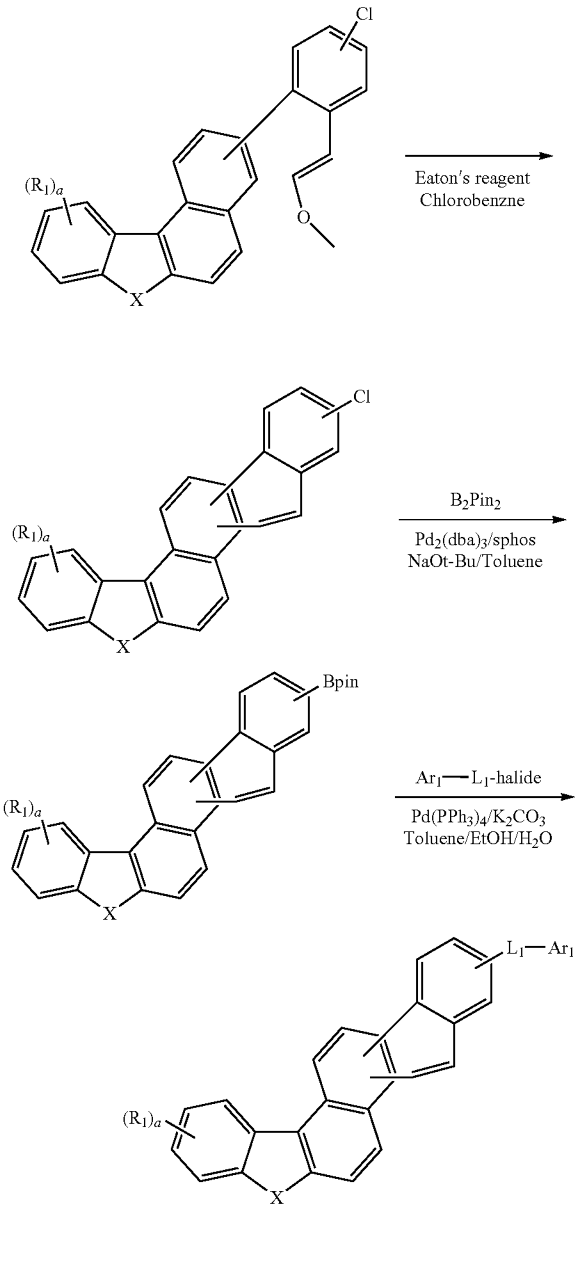

[Reaction Scheme 7]

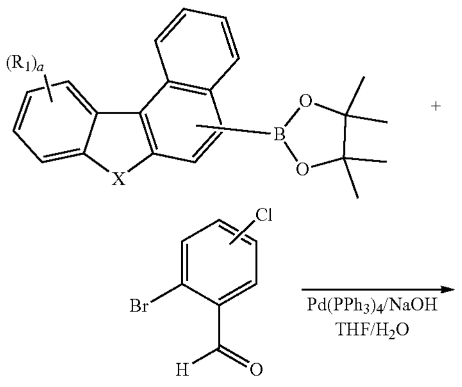

-continued

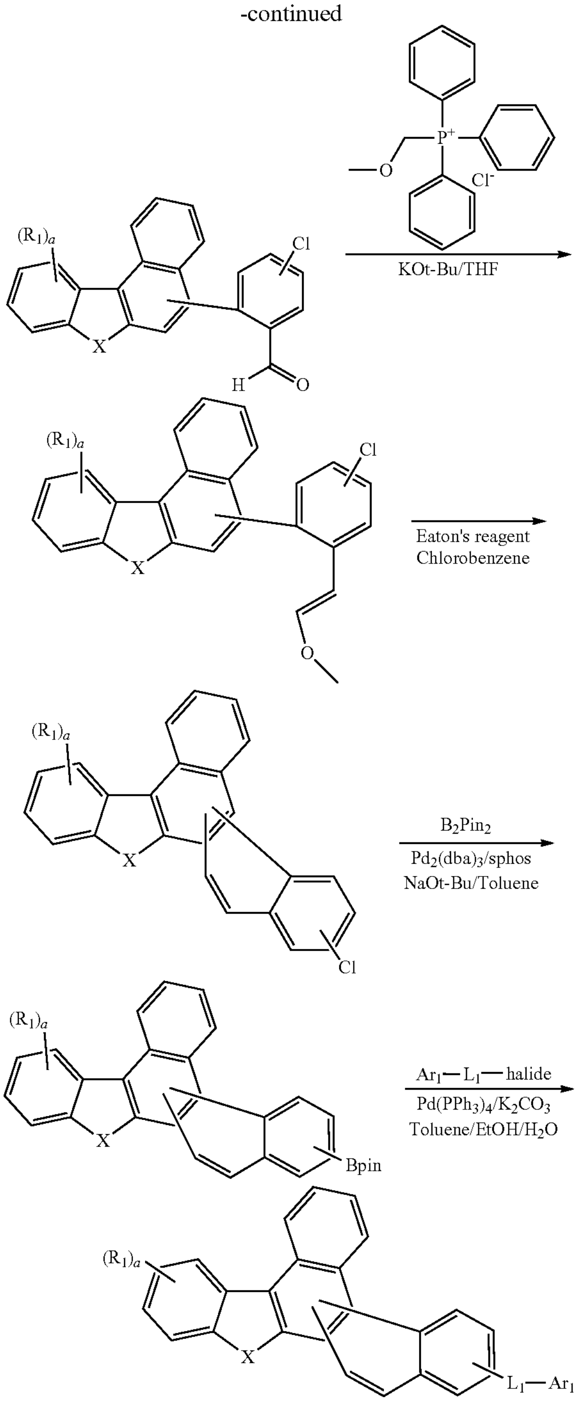

In reaction schemes 1 to 7, X, $R_1$, $L_1$, $Ar_1$, and a are as defined in formula 1, and Hal represents halogen.

Although illustrative synthesis examples of the compound represented by formula 1 are described above, one skilled in the art will be able to readily understand that all of them are based on a Suzuki cross-coupling reaction, a Wittig reaction, a Miyaura borylation reaction, an Ullmann reaction, a Buchwald-Hartwig cross-coupling reaction, an N-arylation reaction, an H-mont-mediated etherification reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the reactions above proceed even when substituents which are defined in formula 1 above, but are not specified in the specific synthesis examples, are bonded.

The hole transport zone of the present disclosure may consist of one or more layer selected from the group consisted of a hole transport layer, a hole injection layer, an electron blocking layer, and a hole auxiliary layer. Each layer may consist of one or more layer.

According to one embodiment of the present disclosure, the hole transport zone may comprise a hole transport layer. In addition, the hole transport zone may comprise a hole transport layer, and further comprise one or more layer of a hole injection layer, an electron blocking layer, and a hole auxiliary layer.

The present disclosure provides an organic electroluminescent material comprising the compound represented by formula 1, and an organic electroluminescent device comprising the organic electroluminescent material.

The organic electroluminescent material may consist of the compound according to the present disclosure alone, or may further comprise conventional materials included in organic electroluminescent materials.

The organic electroluminescent compound of formula 1 of the present disclosure may be comprised in one or more layer of the light-emitting layer, hole injection layer, hole transport layer, hole auxiliary layer, light-emitting auxiliary layer, electron transport layer, electron buffer layer, electron injection layer, interlayer, hole blocking layer, and electron blocking layer; preferably, the light-emitting layer. When used in a light-emitting layer, the organic electroluminescent compound of formula 1 of the present disclosure may be comprised as a host material. Preferably, the light-emitting layer may further comprise one or more dopant. If necessary, the organic electroluminescent compound of the present disclosure may be used as a co-host material. That is, the light-emitting layer may further include an organic electroluminescent compound other than the organic electroluminescent compound represented by formula 1 of the present disclosure (first host material) as a second host material. In this case, the weight ratio between the first host material and the second host material is in the range of 1:99 to 99:1. When two or more materials are included in one layer, mixed deposition may be performed to form a layer, or co-deposition may be performed separately at the same time to form a layer.

According to one embodiment of the present disclosure, when the organic electroluminescent compound of formula 1 of the present disclosure is comprised in a light-emitting layer, the light-emitting layer may further comprise a compound represented by the following formula 2:

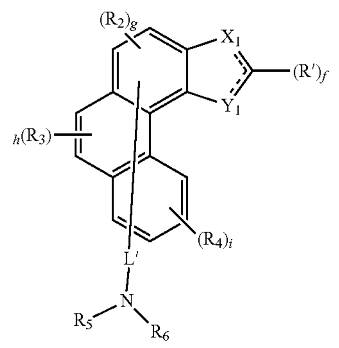

(2)

wherein $X_1$ and $Y_1$ each independently represent —N═, —$NR_7$—, —O—, or —S—, with the proviso that any one of $X_1$ and $Y_1$ represents —N═, and the other of $X_1$ and $Y_1$ represents —$NR_7$—, —O—, or —S—;

R' represents a substituted or unsubstituted (C6-C30)aryl, or a substituted or unsubstituted (3- to 30-membered) heteroaryl;

$R_2$ to $R_7$ each independently represent hydrogen, deuterium, a halogen, a cyano, a substituted or unsubstituted (C1-C30)alkyl, a substituted or unsubstituted (C6-C30) aryl, a substituted or unsubstituted (3- to 30-membered) heteroaryl, a substituted or unsubstituted (C3-C30) cycloalkyl, a substituted or unsubstituted (C1-C30) alkoxy, a substituted or unsubstituted tri(C1-C30) alkylsilyl, a substituted or unsubstituted di(C1-C30) alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), a substituted or unsubstituted mono- or di-(C1-C30)alkylamino, a substituted or unsubstituted mono- or di-(C2-C30)alkenylamino, a substituted or unsubstituted (C1-C30) alkyl(C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl (C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino; or may be linked to an adjacent substituent to form a ring(s);

L' represents a single bond, a substituted or unsubstituted (C6-C30)arylene, or a substituted or unsubstituted (3- to 30-membered)heteroarylene; and f represents 1, g and h each independently represent 1 or 2, i represents an integer of 1 to 4, where if each of g to i is an integer of 2 or more, each of $R_2$ to each of $R_4$ may be the same or different.

In formula 2, $X_1$ and $Y_1$ each independently represent —N═, —$NR_7$—, —O—, or —S—, with the proviso that any one of $X_1$ and $Y_1$ represents —N═, and the other of $X_1$ and $Y_1$ represents —$NR_7$—, —O—, or —S—. According to one embodiment, any one of $X_1$ and $Y_1$ represents —N═, and the other represents —O—, or —S—. For example, $X_1$ represents —N═, and $Y_1$ represents —O—; $X_1$ represents —O—, and $Y_1$ represents —N═; or $X_1$ represents —S—, and $Y_1$ represents —N═. In formula 2, R' represents a substituted or unsubstituted (C6-C30)aryl, or a substituted or unsubstituted (3- to 30-membered)heteroaryl. According to one embodiment, R' represents a substituted or unsubstituted (C6-C30)aryl, or a substituted or unsubstituted (5- to 25-membered)heteroaryl. According to another embodiment, R' represents a substituted or unsubstituted (C6-C30) aryl, or a substituted or unsubstituted (5- to 20-membered) heteroaryl. For example, R' represents an unsubstituted phenyl, an unsubstituted biphenyl, an unsubstituted naphthyl, a fluorenyl substituted with a methyl(s), a benzofluorenyl substituted with a methyl(s), an unsubstituted dibenzofuranyl, an unsubstituted dibenzothiophenyl, a spiro [fluorene-fluoren]yl, a spiro[fluorene-benzofluoren]yl, or an unsubstituted pyridyl.

In formula 2, $R_2$ to $R_7$ each independently represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30) cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), a substituted or unsubstituted mono- or di-(C1-C30)alkylamino, a substituted or unsubstituted mono- or di-(C2-C30)alkenylamino, a substituted or unsubstituted (C1-C30)alkyl (C2-C30)alkenylamino, a substituted or unsubstituted mono- or di-(C6-C30)arylamino, a substituted or unsubstituted (C1-C30)alkyl(C6-C30)arylamino, a substituted or unsubstituted mono- or di-(3- to 30-membered)heteroarylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl (3- to 30-membered)heteroarylamino; or may be linked to an adjacent substituent to form a ring(s). According to one embodiment, $R_2$ to $R_7$ each independently represent hydrogen, a substituted or unsubstituted (C6-C25)aryl, a substituted or unsubstituted (3- to 25-membered)heteroaryl, or a substituted or unsubstituted mono- or di-(C6-C25)arylamino; or may be linked to an adjacent substituent to form a substituted or unsubstituted mono- or polycyclic (C3-C30) alicyclic or aromatic ring(s), whose carbon atom(s) may be replaced with at least one heteroatom selected from nitrogen, oxygen, and sulfur. According to another embodiment, $R_2$ to $R_7$ each independently represent hydrogen, a substituted or unsubstituted (C6-C25)aryl, a substituted or unsubstituted (5- to 25-membered)heteroaryl, a substituted or unsubstituted di(C6-C18)arylamino, a substituted or unsubstituted mono- or di-(3- to 30-membered)heteroarylamino, or a substituted or unsubstituted (C6-C30)aryl(3- to 30-membered)heteroarylamino; or may be linked to an adjacent substituent to form a substituted or unsubstituted mono- or polycyclic (C3-C25) alicyclic or aromatic ring(s), whose carbon atom(s) may be replaced with at least one heteroatom selected from nitrogen and sulfur, and the heteroaryl may contain at least one heteroatom selected from the group consisting of B, N, O, S, Si, and P. Specifically, R', $R_5$, and $R_6$ each independently represent a substituted or unsubstituted phenyl, a substituted or unsubstituted naphthyl, a substituted or unsubstituted biphenyl, a substituted or unsubstituted terphenyl, a substituted or unsubstituted phenanthrenyl, a substituted or unsubstituted fluorenyl, a substituted or unsubstituted benzofluorenyl, a substituted or unsubstituted triphenylenyl, a substituted or unsubstituted spirobifluorenyl, a substituted or unsubstituted pyridyl, a substituted or unsubstituted triazinyl, a substituted or unsubstituted pyrimidinyl, a substituted or unsubstituted quinolyl, a substituted or unsubstituted quinazolinyl, a substituted or unsubstituted quinoxalinyl, a substituted or unsubstituted benzoquinazolinyl, a substituted or unsubstituted benzoquinoxalinyl, a substituted or unsubstituted benzofuropyrimidinyl, a substituted or unsubstituted carbazolyl, a substituted or unsubstituted dibenzothiophenyl, a substituted or unsubstituted benzothiophenyl, a substituted or unsubstituted dibenzofuranyl, a substituted or unsubstituted benzofuranyl, a substituted or unsubstituted naphthyridinyl, a substituted or unsubstituted benzonaphthofuranyl, or a substituted or unsubstituted benzonaphthothiophenyl. For example, at least one of $R_5$ and $R_6$ each independently represent a substituted or unsubstituted phenyl, a substituted or unsubstituted o-biphenyl, a substituted or unsubstituted m-biphenyl, a substituted or unsubstituted p-biphenyl, a substituted or unsubstituted fluorenyl, a substituted or unsubstituted naphthyl, a substituted or unsubstituted phenanthrenyl, a substituted or unsubstituted dibenzofuranyl, a substituted or unsubstituted dibenzothiophenyl, or a substituted or unsubstituted benzofluorenyl. For example, R' may be a phenyl, a biphenyl, or a pyridyl; $R_2$ and $R_3$ may be hydrogen; $R_4$ may be hydrogen or a phenyl; $R_5$ and $R_6$ each independently may be a substituted phenyl, a naphthyl, a biphenyl, a phenanthrenyl, a dimethylfluorenyl, a diphenylfluorenyl, a naphthylphenyl, a phenylnaphthyl, a dimethylbenzofluorenyl, a terphenyl, a spirobifluorenyl, a benzofuranyl, a benzothiophenyl, a dibenzothiophenyl, a dibenzofuranyl unsubstituted or substituted with a phenyl(s), a carbazolyl substituted with a phenyl(s), or a benzonaphthofuranyl; and the substituent(s) of the substituted phenyl may be at least one selected from the group consisting of a phenyl substituted with at least one of deuterium, a methyl(s), and a tert-butyl(s); an anthracenyl; a fluoranthenyl; a phenylfluorenyl; a cyclohexyl; a pyridyl substituted with a phenyl(s); phenoxazinyl; and a benzimidazolyl substituted with a phenyl(s).

In formula 2, f represents 1 or 2, preferably, 1; g and h each independently represent 1 or 2, preferably, 1; i represents an integer of 1 to 4, preferably, 1 or 2. If each of g to i is an integer of 2 or more, each of $R_2$ to each of $R_4$ may be the same or different.

In formula 2, L' represents a single bond, a substituted or unsubstituted (C6-C30)arylene, or a substituted or unsubstituted (3- to 30-membered)heteroarylene. According to one embodiment of the present disclosure, L' represents a single bond, or a substituted or unsubstituted (C6-C18) arylene. According to another embodiment of the present disclosure, L' represents a single bond, or an unsubstituted (C6-C12)arylene. For example, L' represents a single bond, or an unsubstituted phenylene.

The compound represented by formula 2 may be one selected from the following compounds, but is not limited thereto.

H1-1

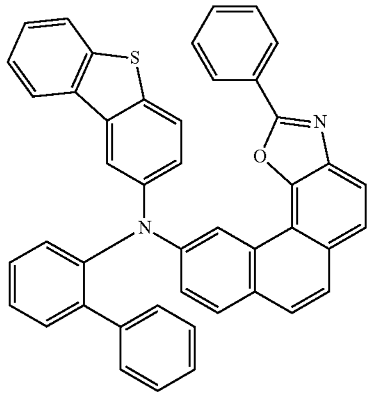

-continued
H1-2
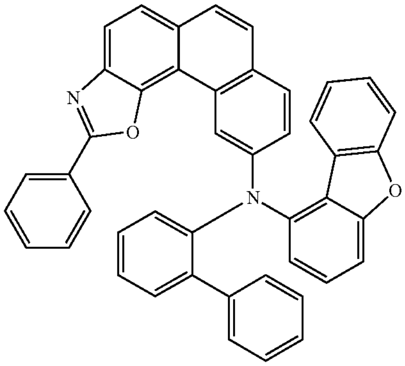
H1-3
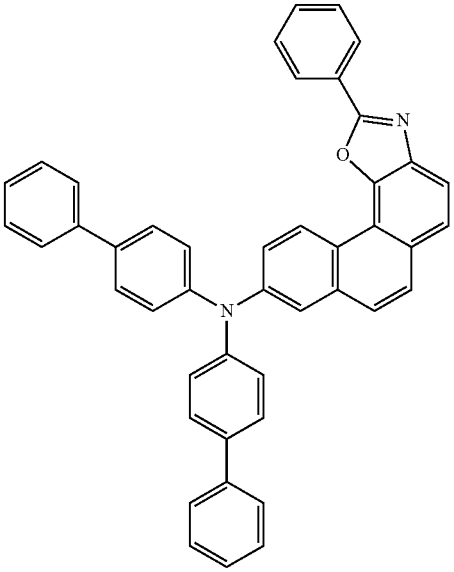
H1-4
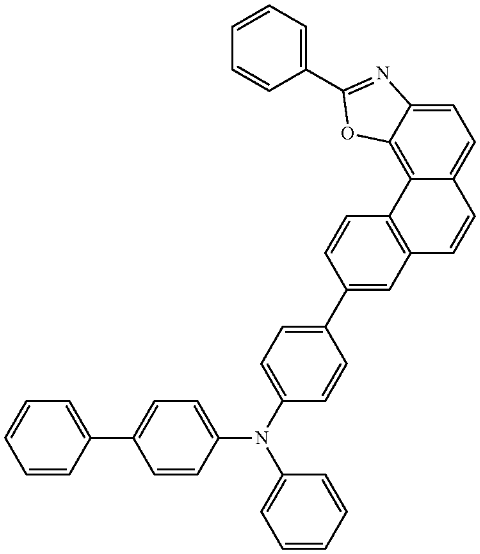
-continued
H1-5
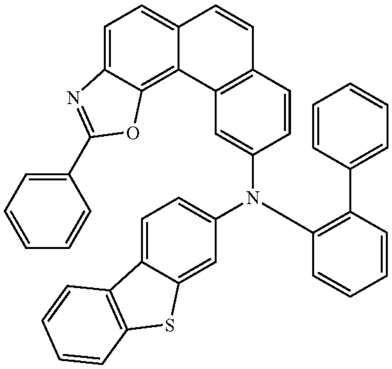
H1-6
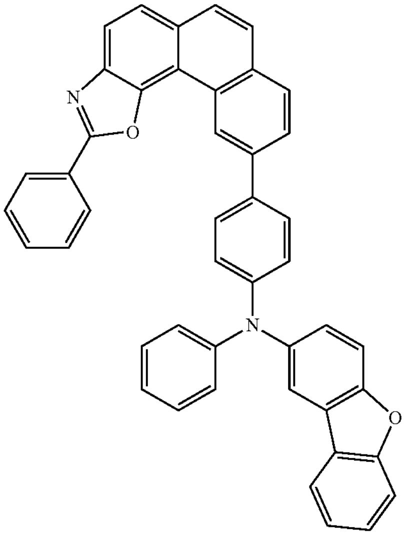
H1-7
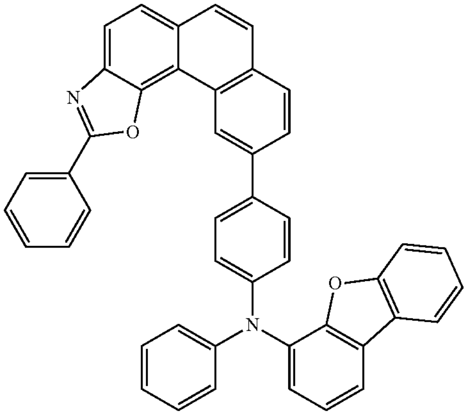

-continued
H1-8
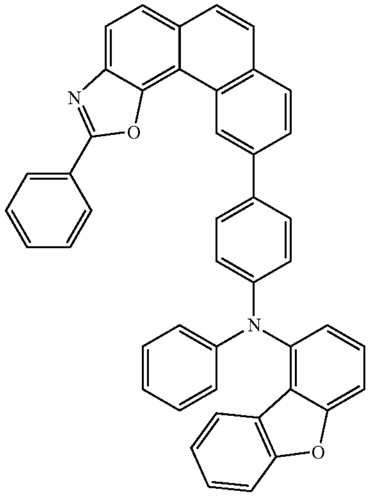
H1-9
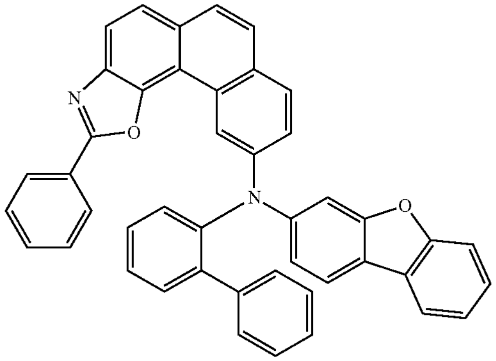
H1-10
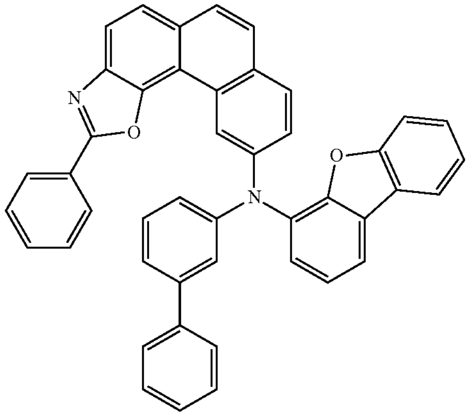
-continued
H1-11
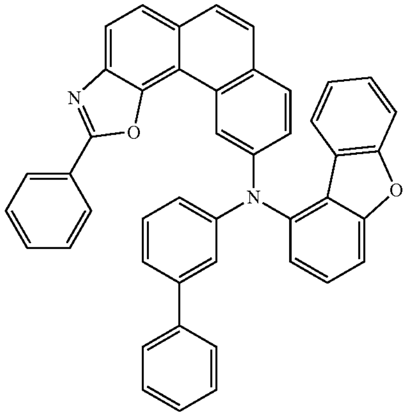
H1-12
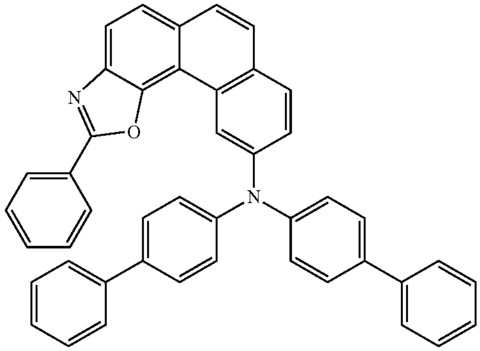
H1-13
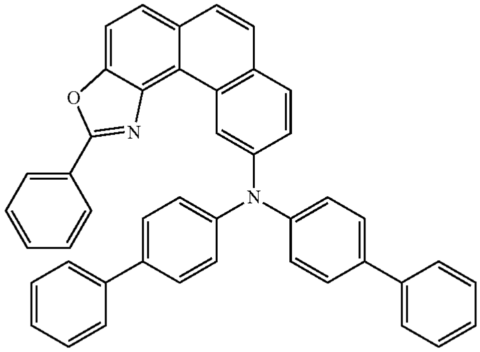
H1-14
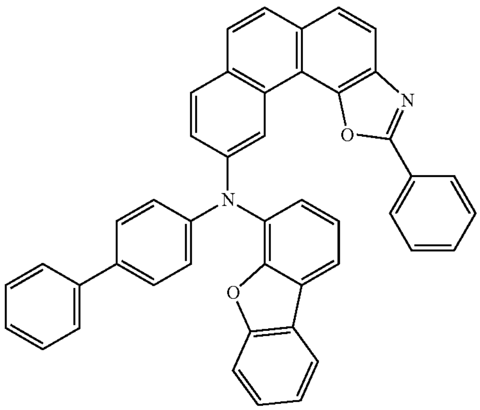

H1-15
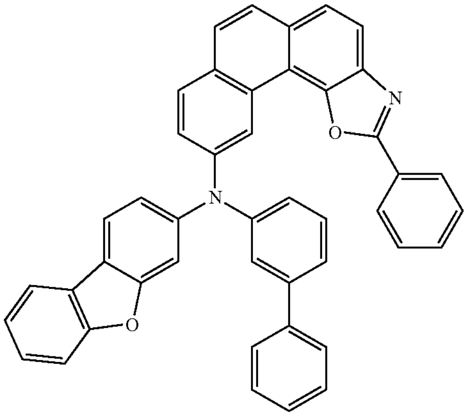
H1-16
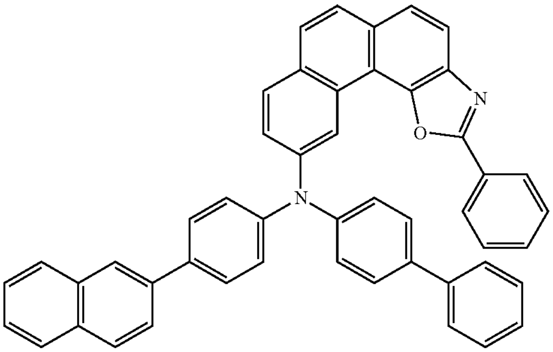
H1-17
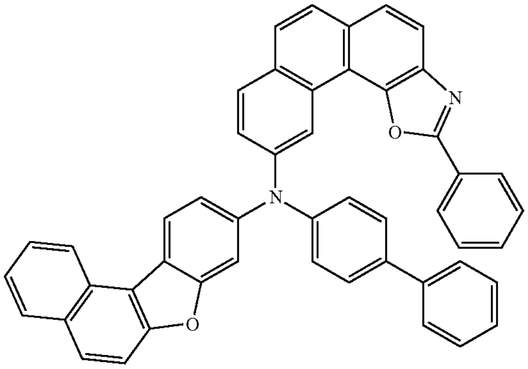
H1-18
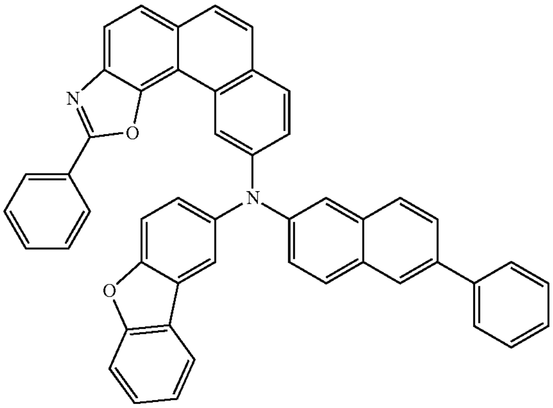
H1-19
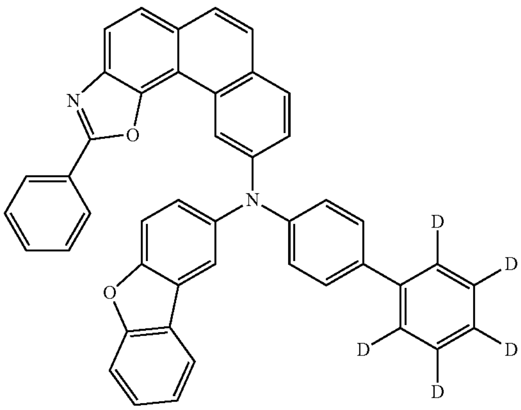
H1-20
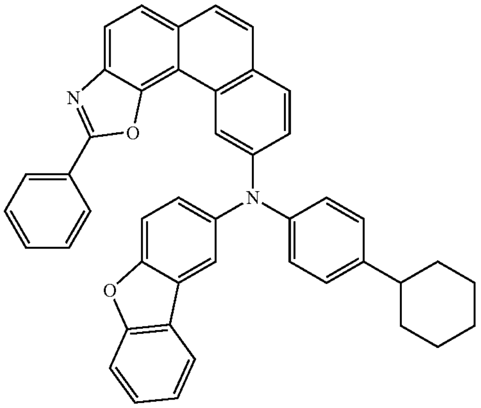
H1-21
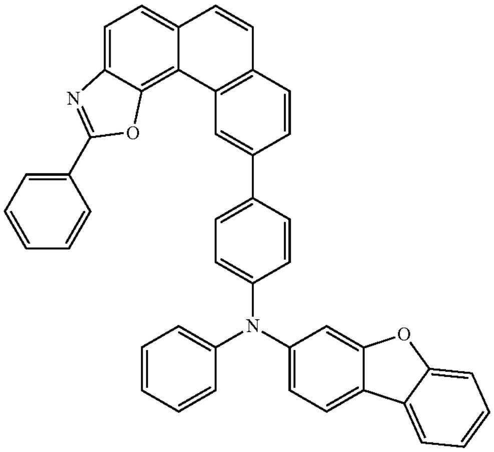

-continued
H1-22
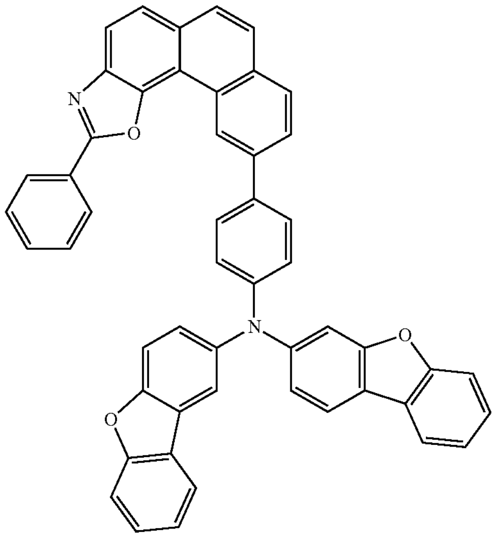
H1-23
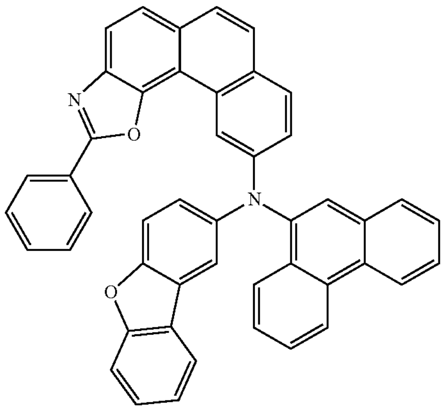
H1-24
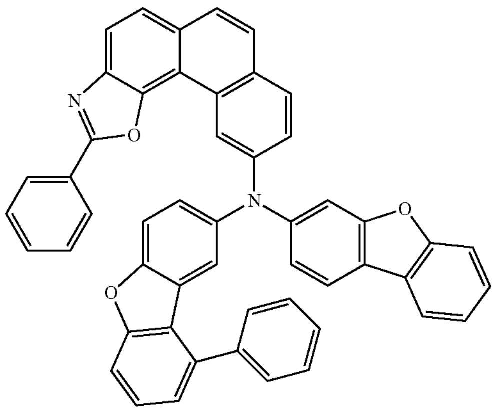
-continued
H1-25
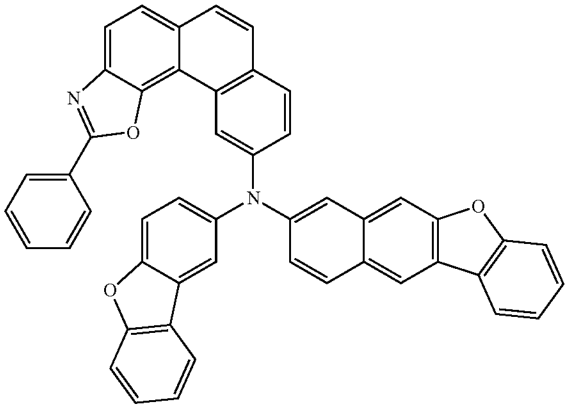
H1-26
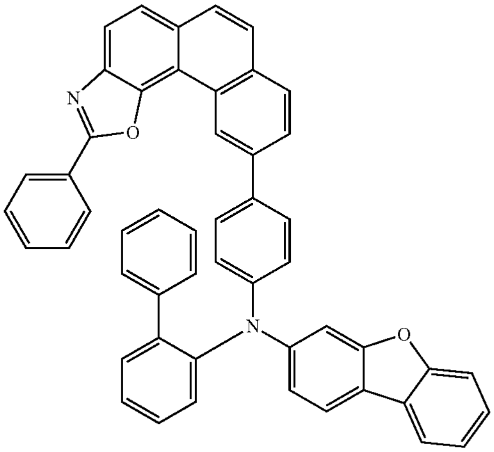
H1-27
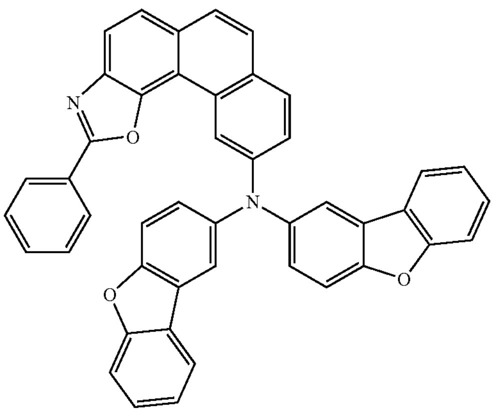

-continued
H1-28
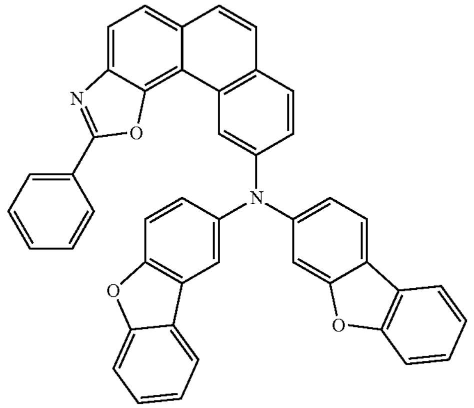
H1-29
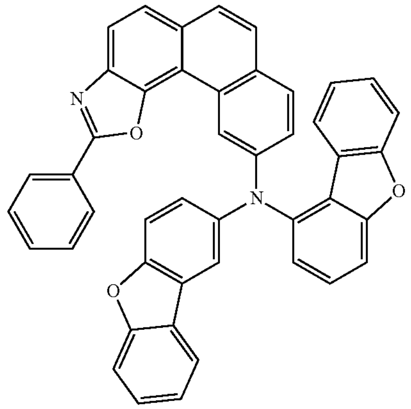
H1-30
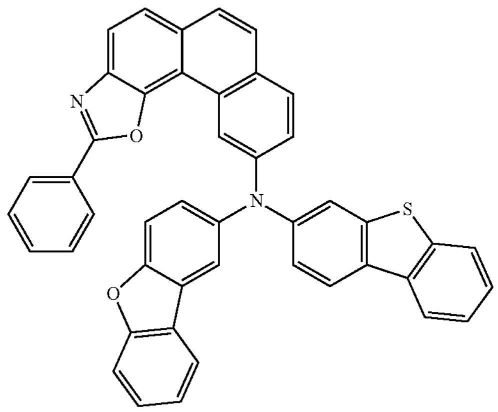
-continued
H1-31
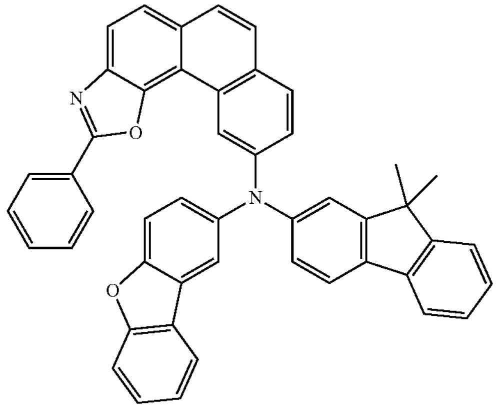
H1-32
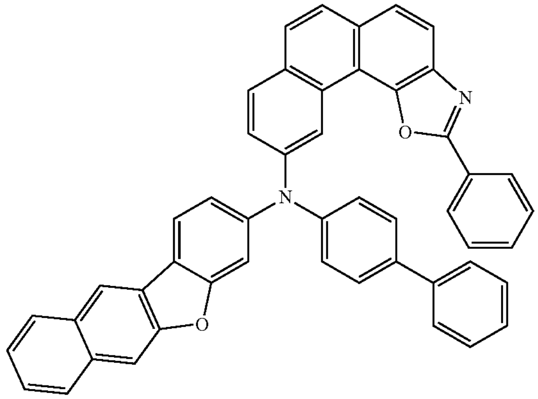
H1-33
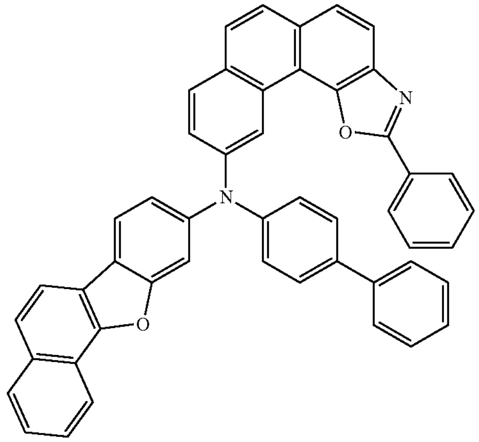

H1-34
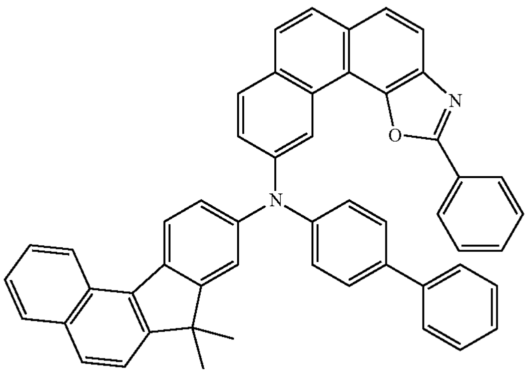
H1-35
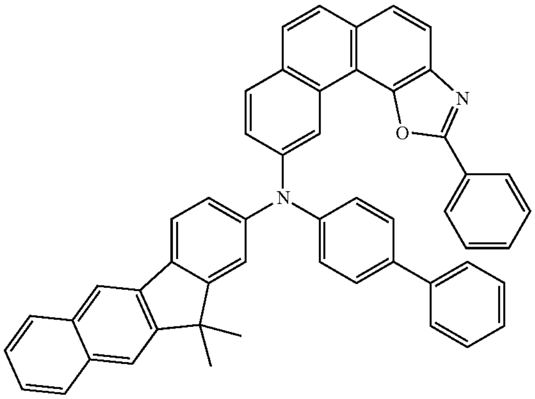
H1-36
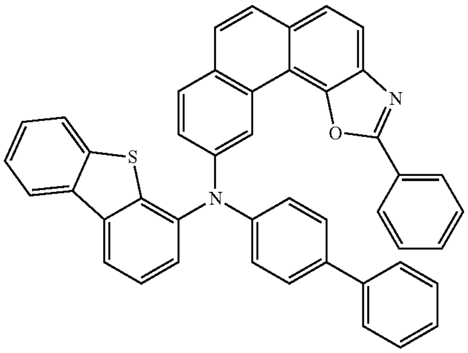
H1-37
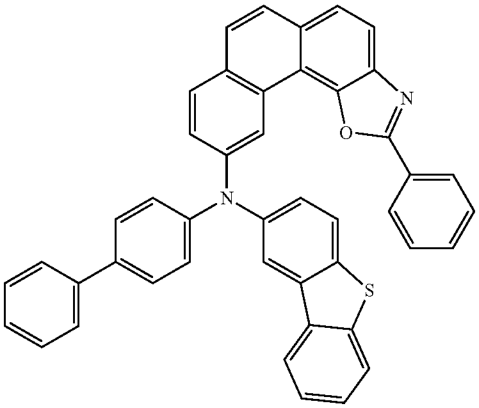
H1-38
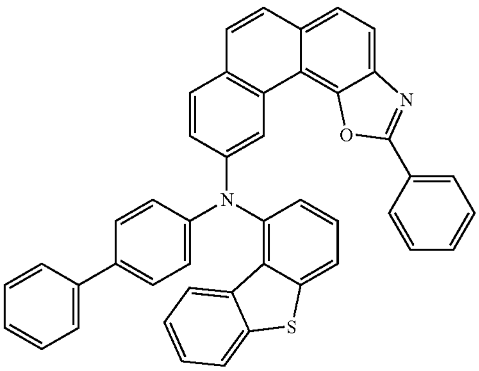
H1-39
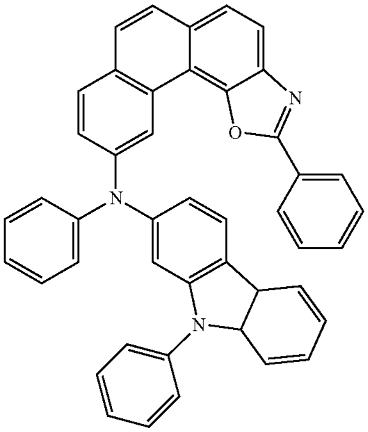
H1-40
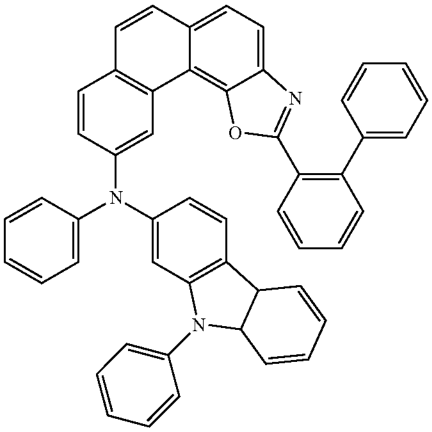
H1-41
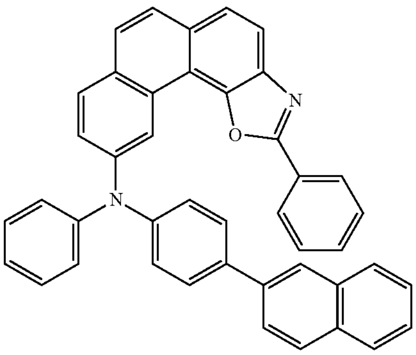

-continued
H1-42
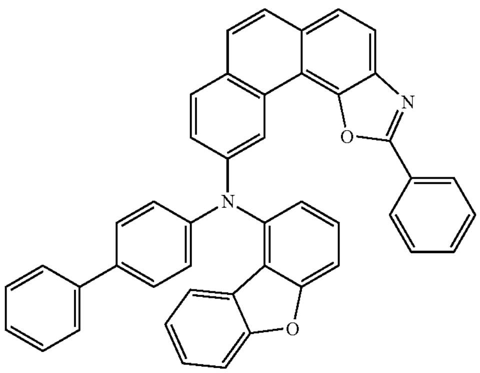
H1-43
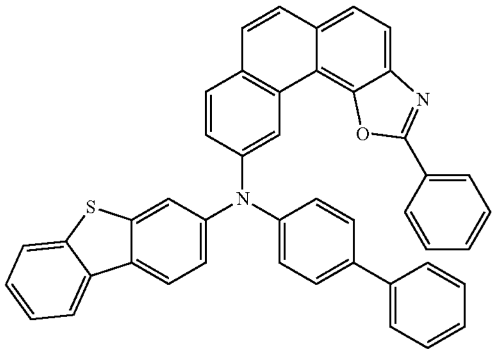
H1-44
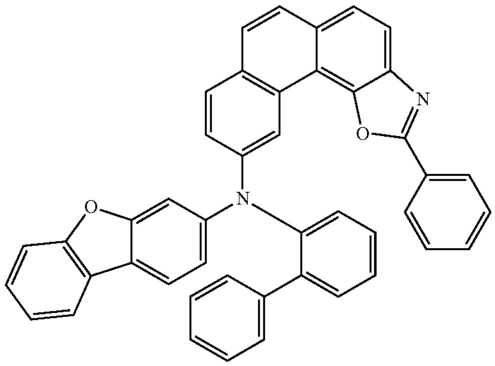
H1-45
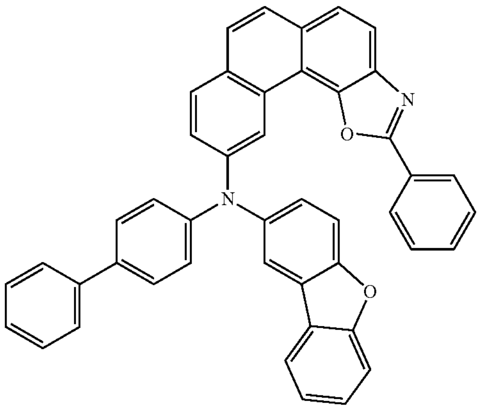
-continued
H1-46
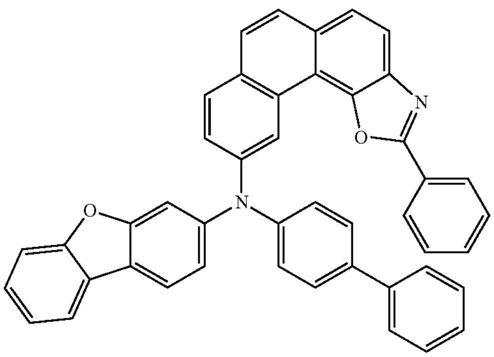
H1-47
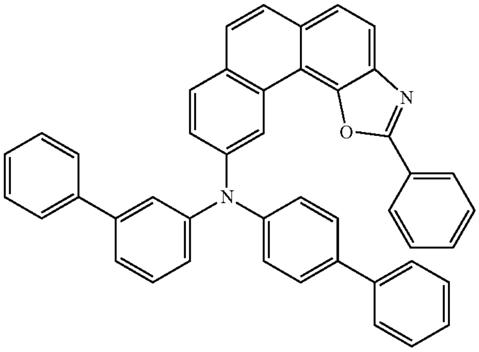
H1-48
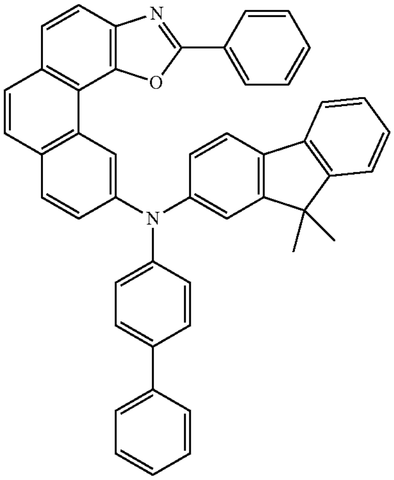
H1-49
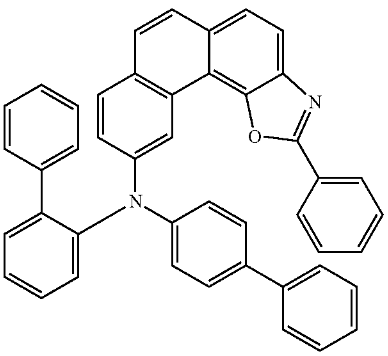

H1-50
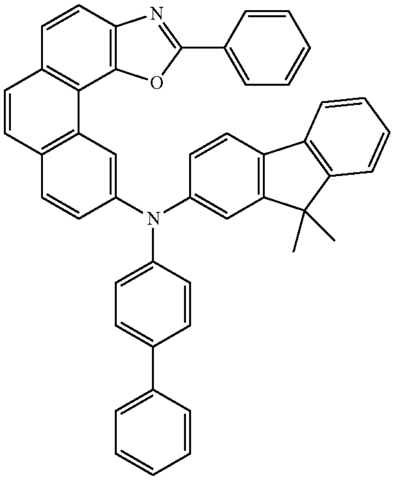
H1-51
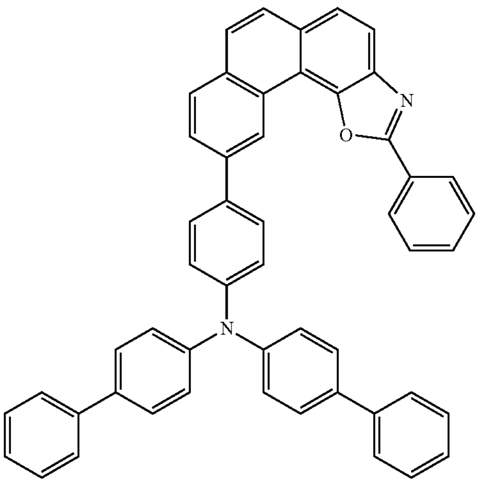
H1-52
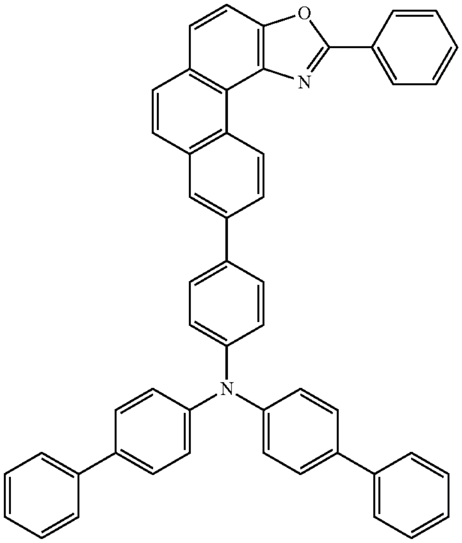
H1-53
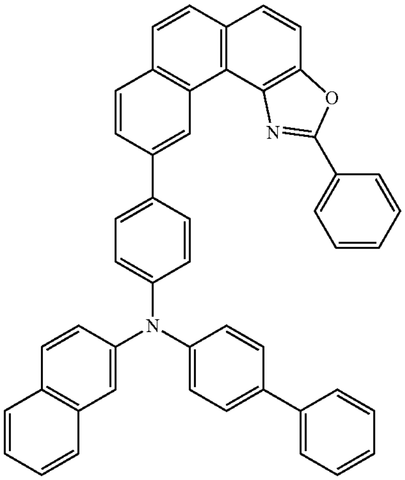
H1-54
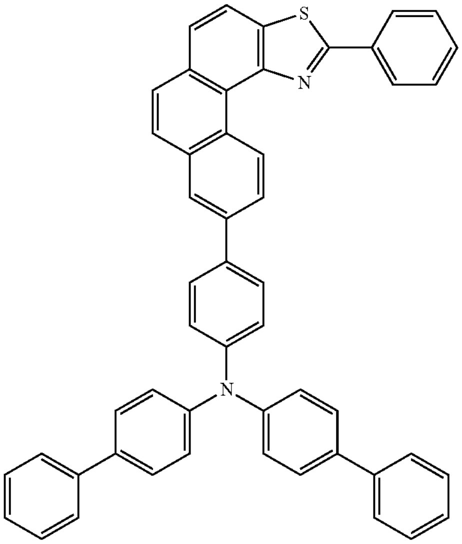
H1-55
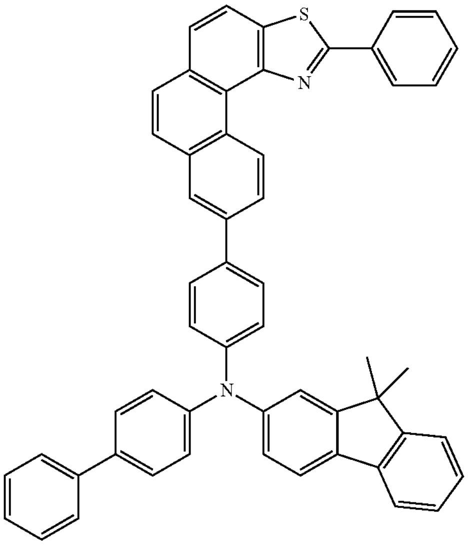

-continued
H1-56
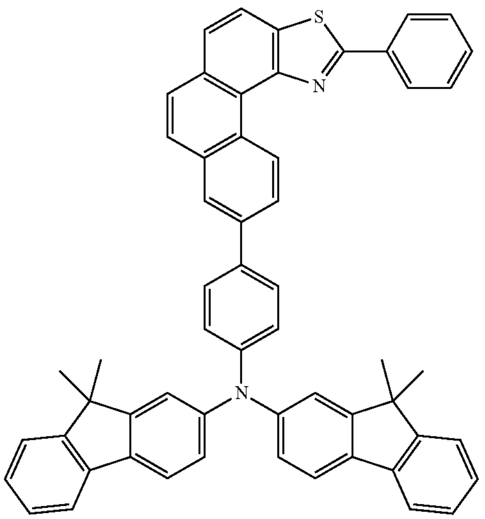
H1-57
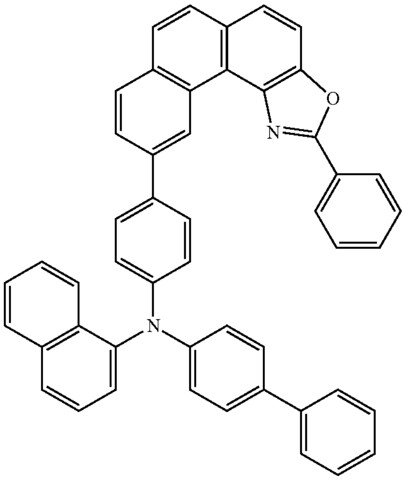
H1-58
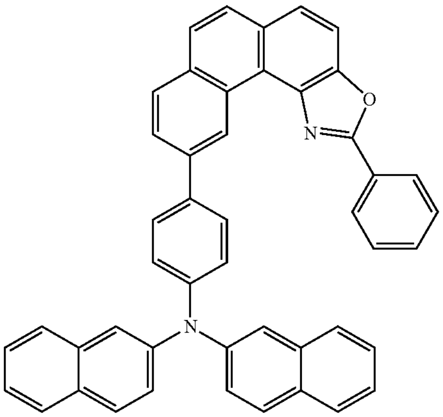
-continued
H1-59
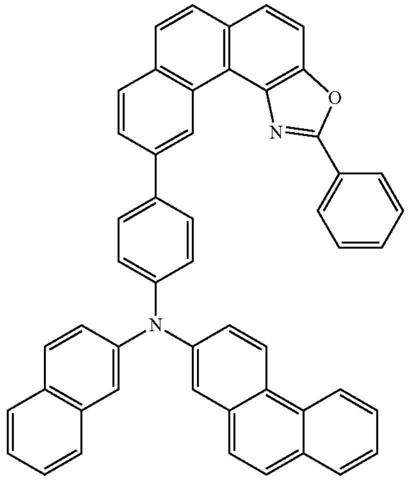
H1-60
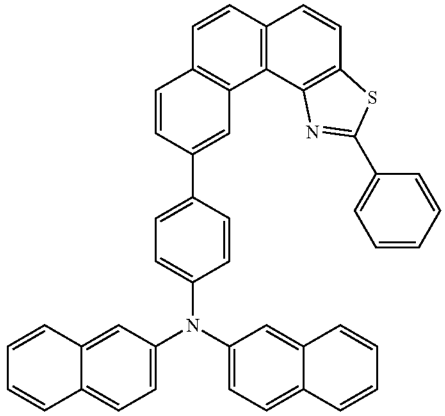
H1-61
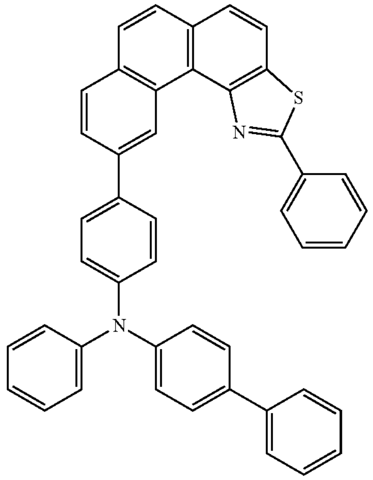

-continued
H1-62
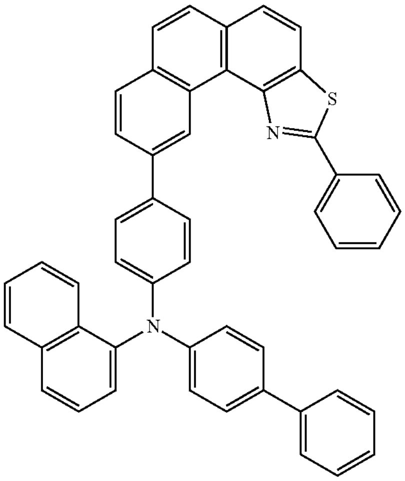
H1-63
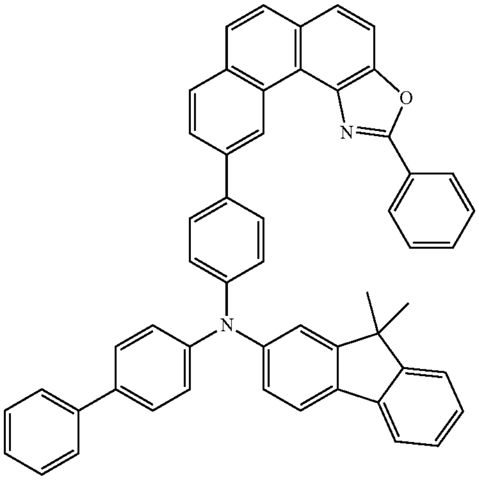
H1-64
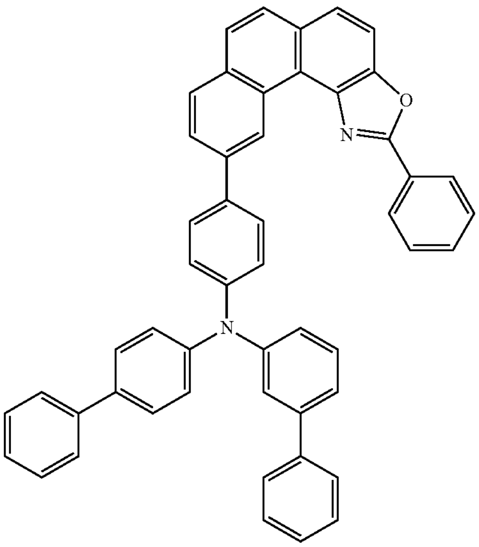
-continued
H1-65
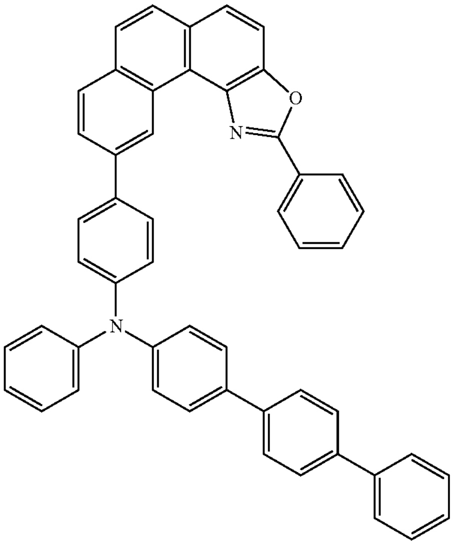
H1-66
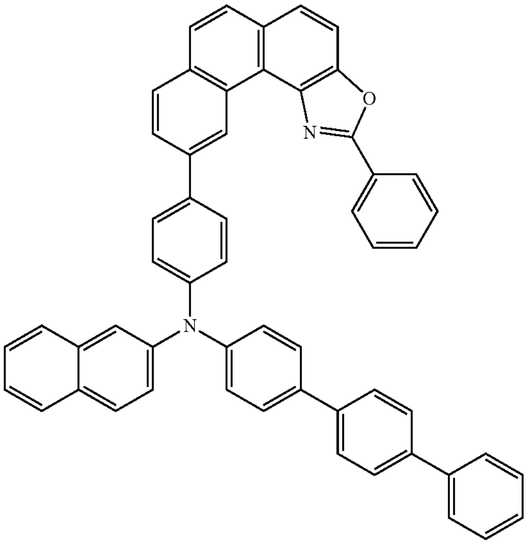
H1-67
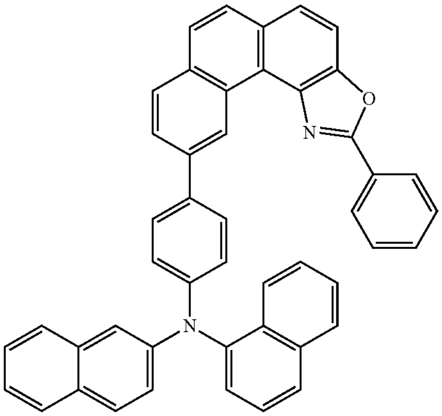

-continued
H1-68
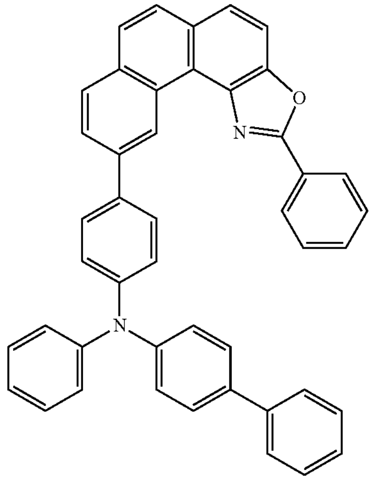
H1-69
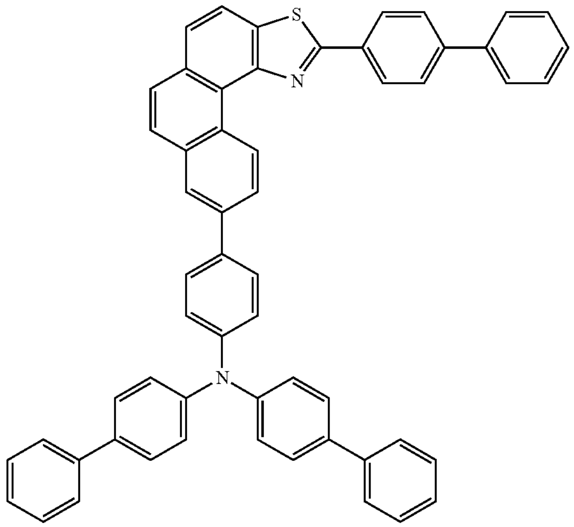
H1-70
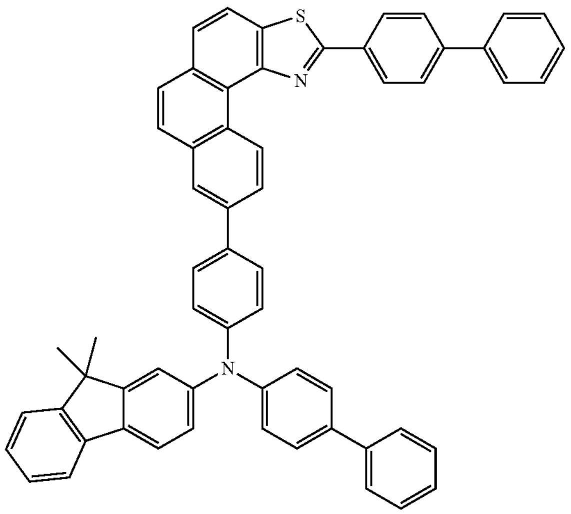
-continued
H1-71
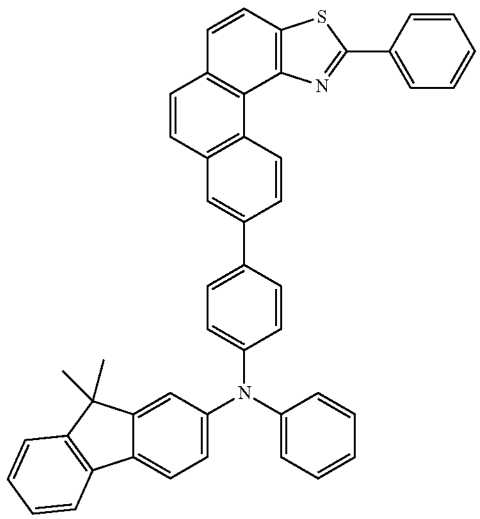
H1-72
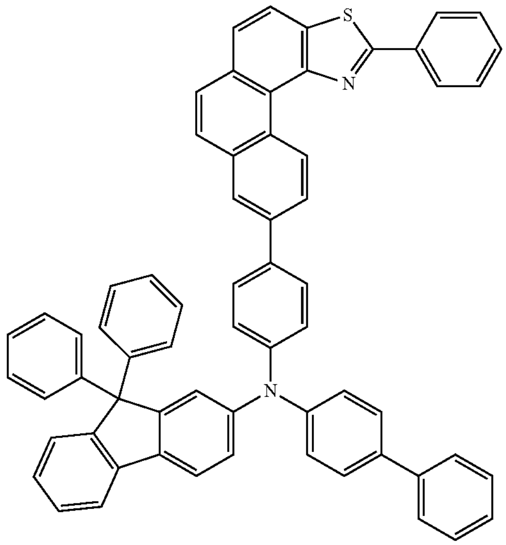
H1-73
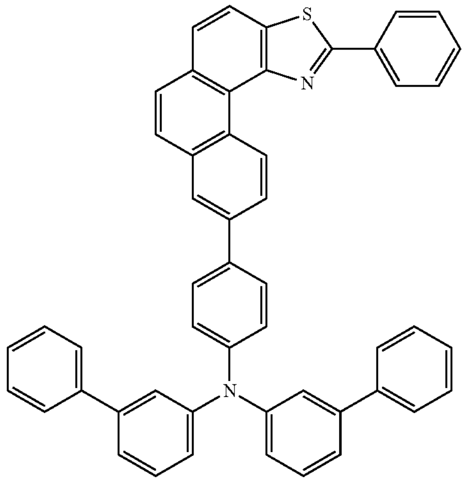

-continued
H1-74
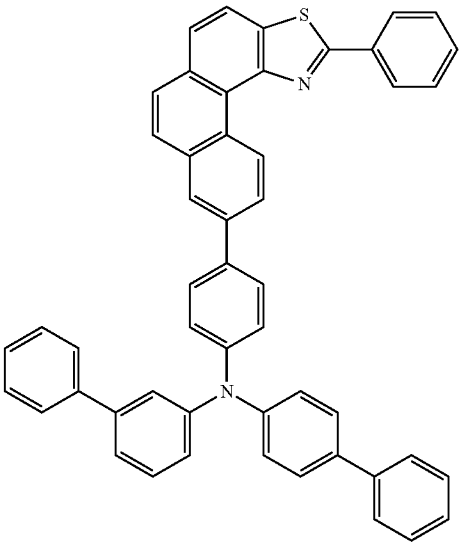
H1-75
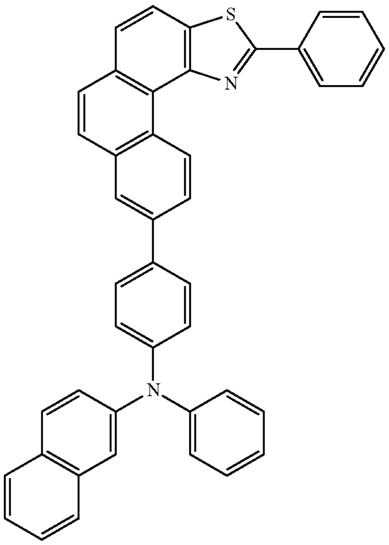
H1-76
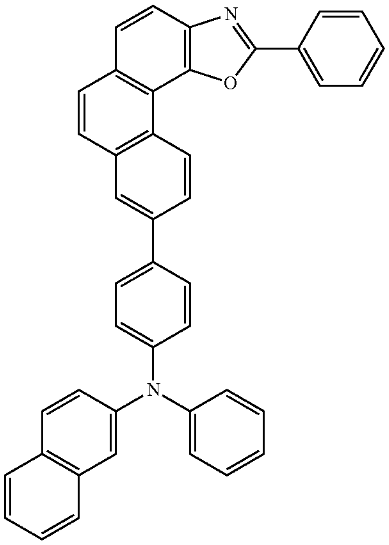
-continued
H1-77
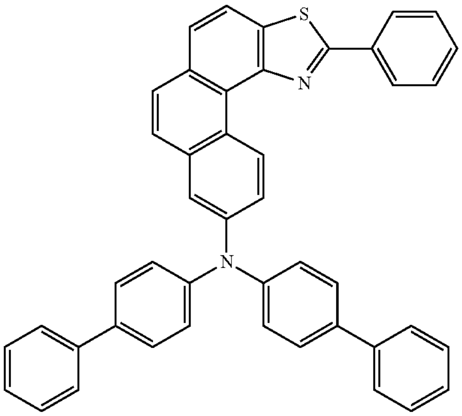
H1-78
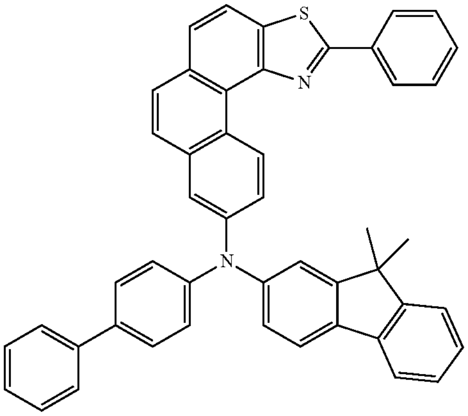
H1-79
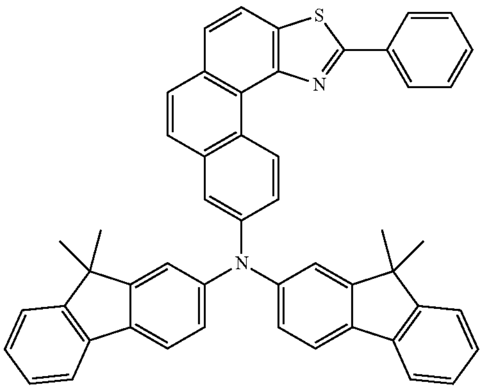

-continued
H1-80
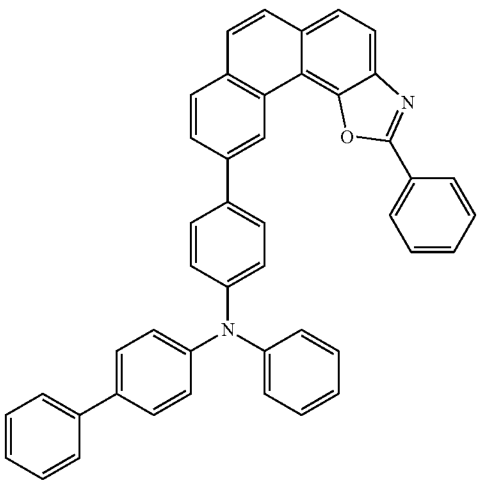
H1-81
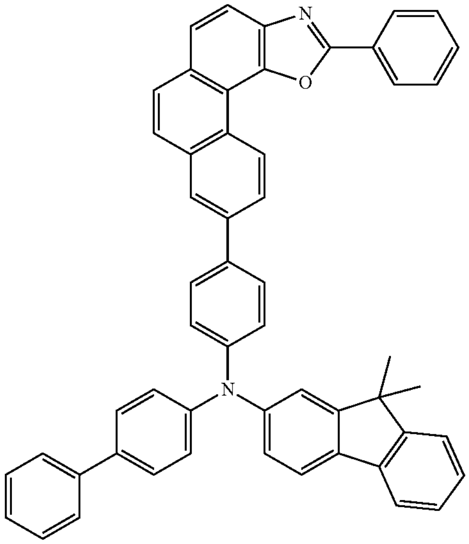
H1-82
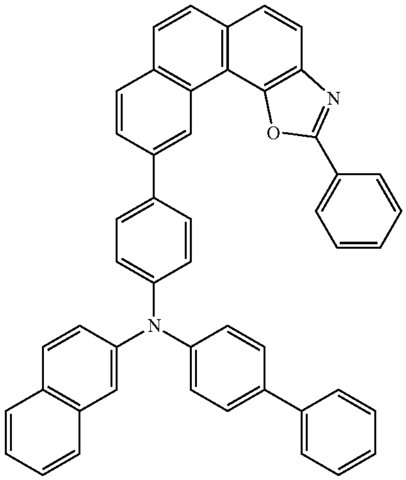
-continued
H1-83
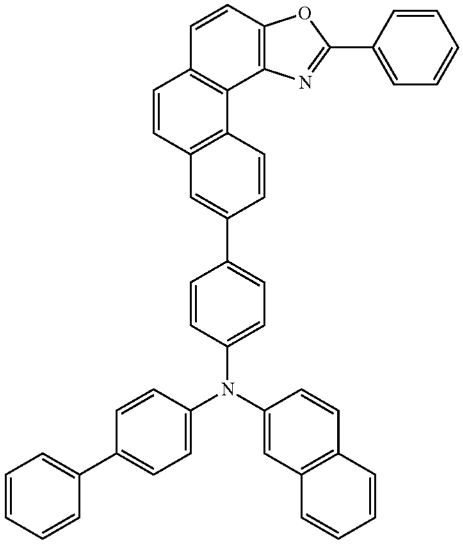
H1-84
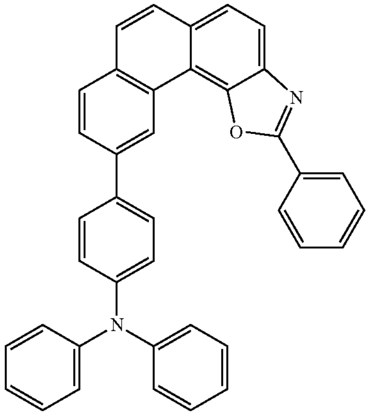
H1-85
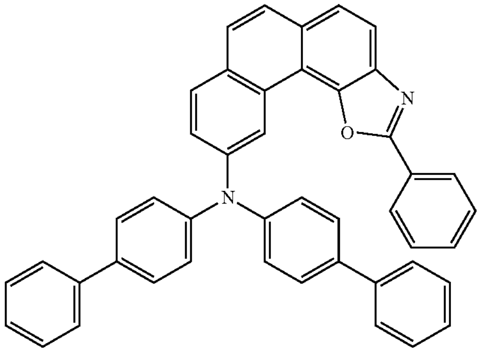

-continued
H1-86
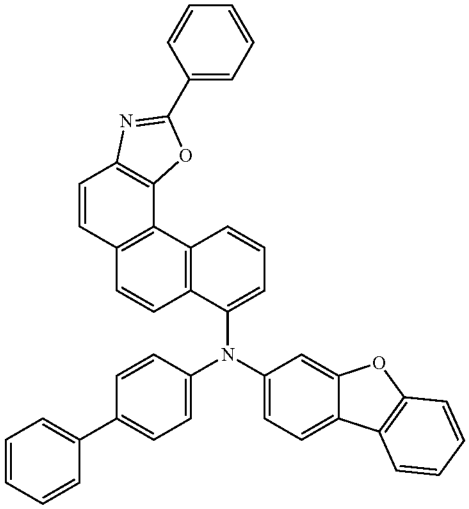
H1-87
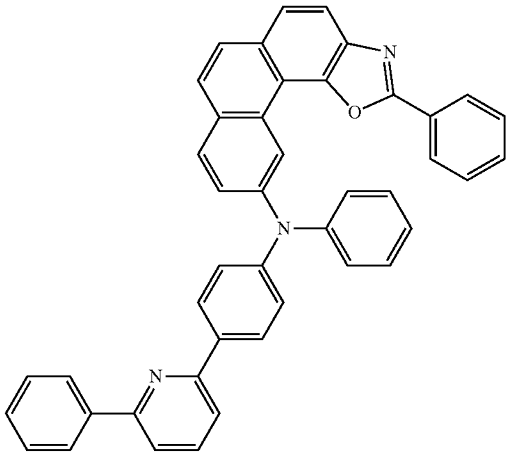
H1-88
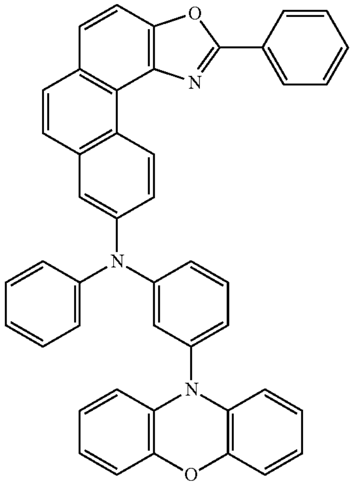
-continued
H1-89
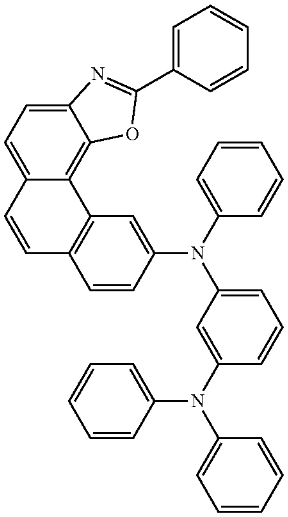
H1-90
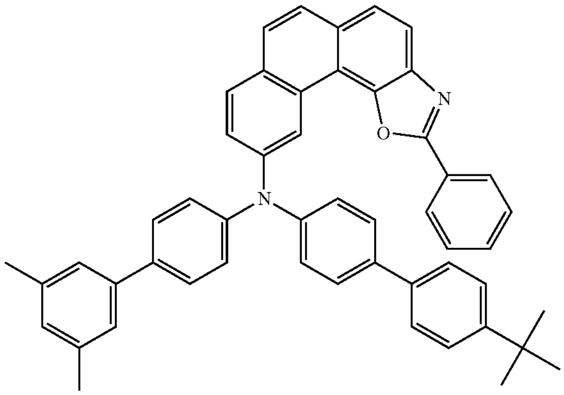
H1-91
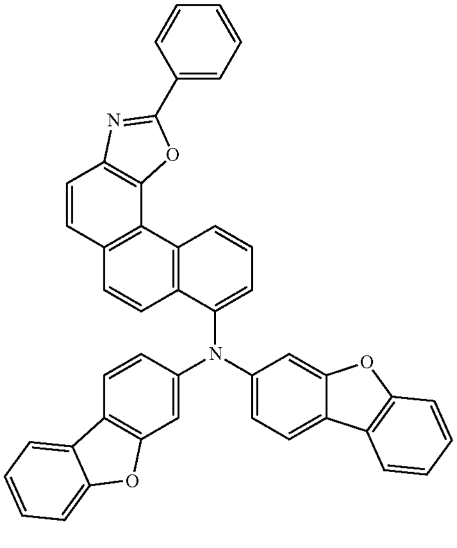

-continued
H1-92
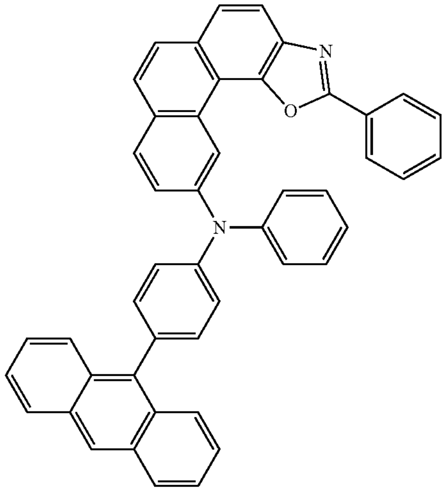
H1-93
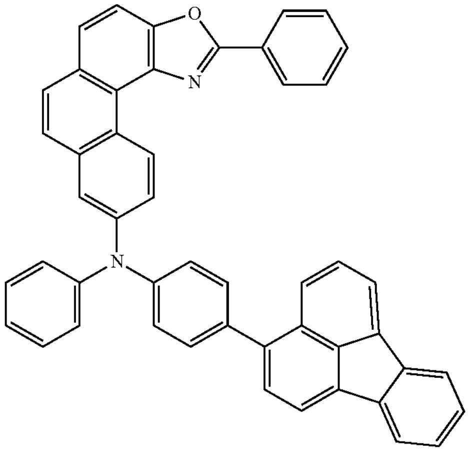
H1-94
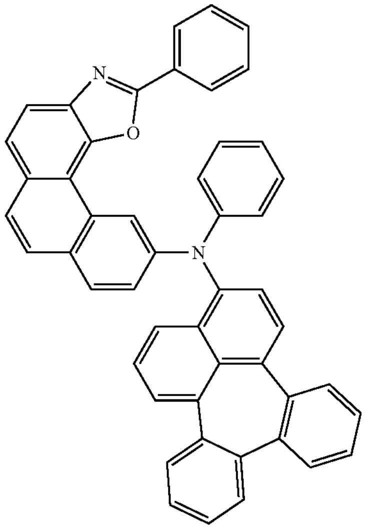
H1-95
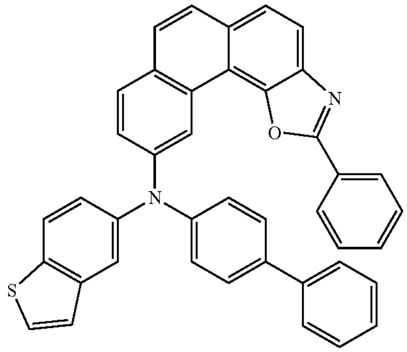
H1-96
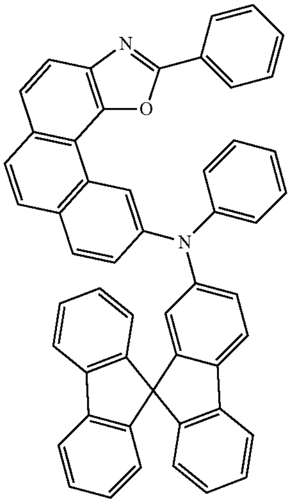
H1-97
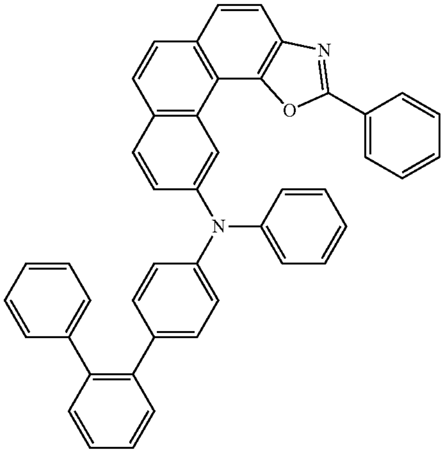

-continued
H1-98
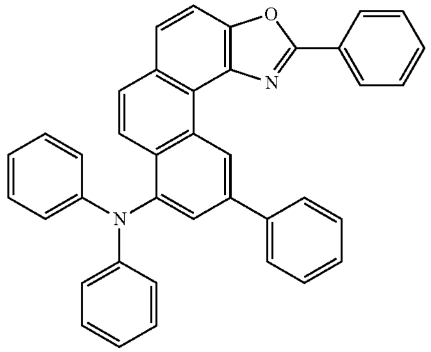
H1-99
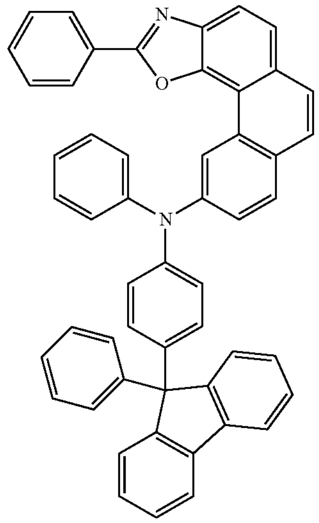
H1-100
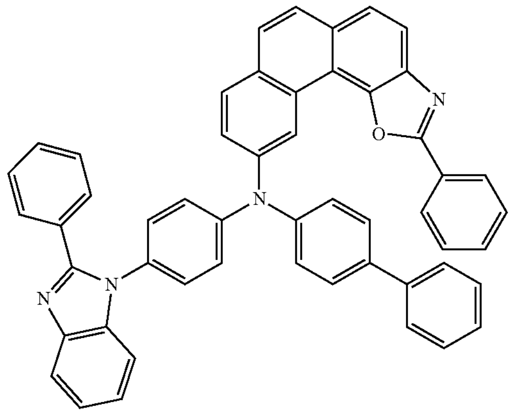
-continued
H1-101
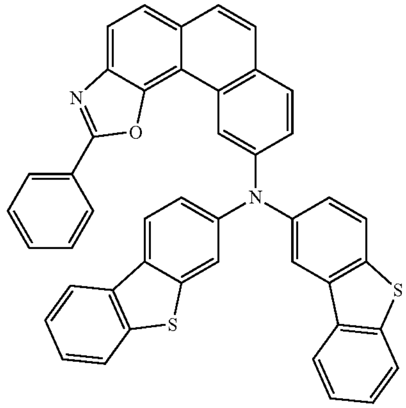
H1-102
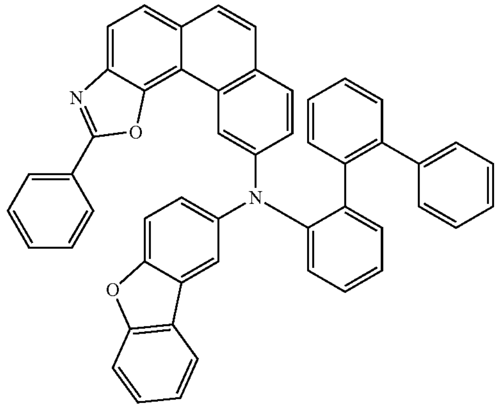
H1-103
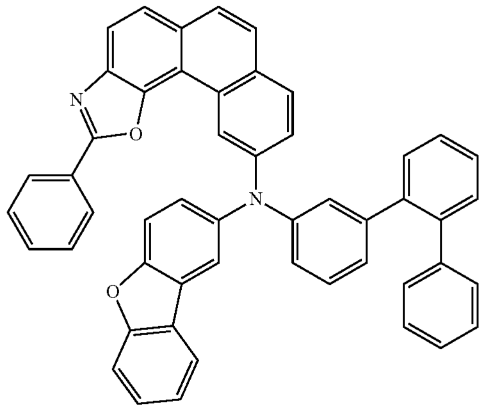

-continued
H1-104
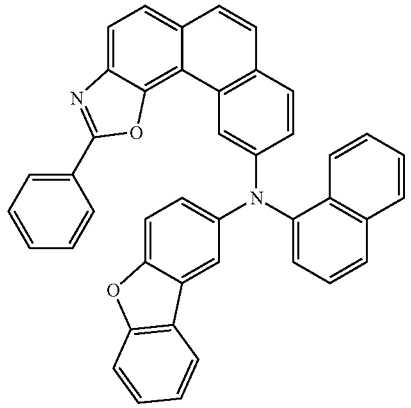
H1-105
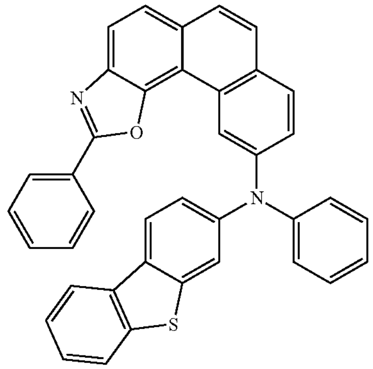
H1-106
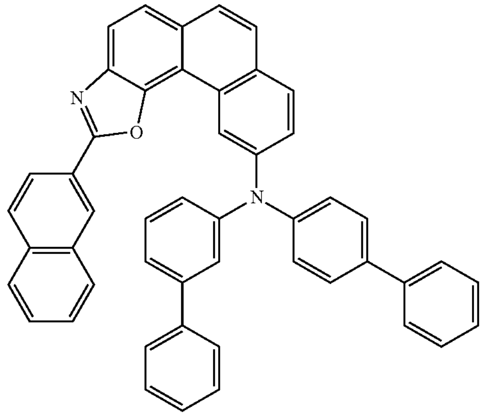
-continued
H1-107
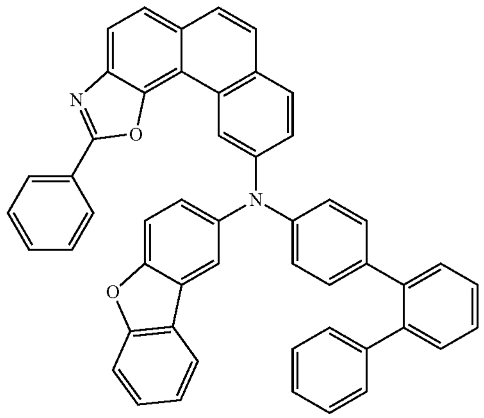
H1-108
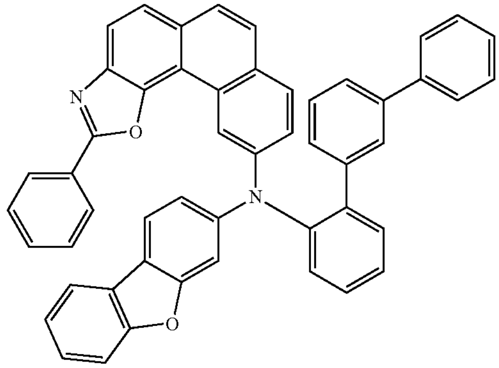
H1-109
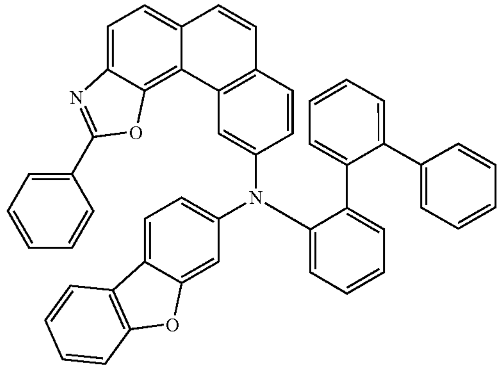
H1-110
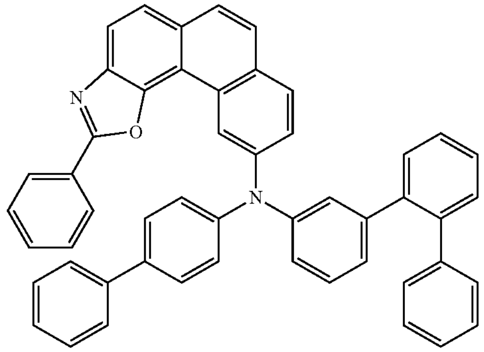

-continued
H1-111
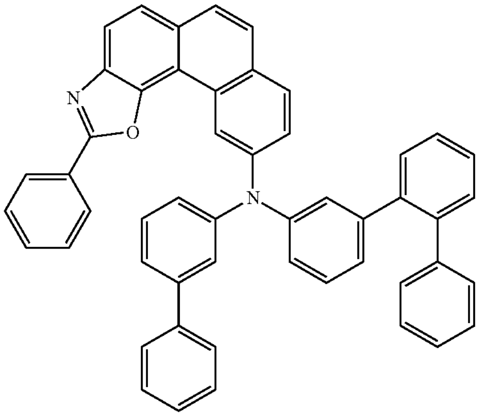
H1-112
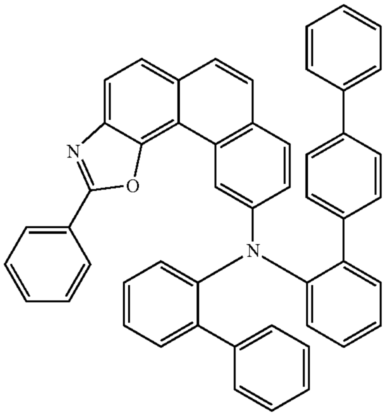
H1-113
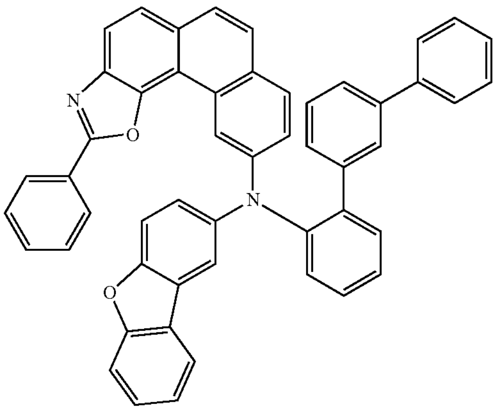
-continued
H1-114
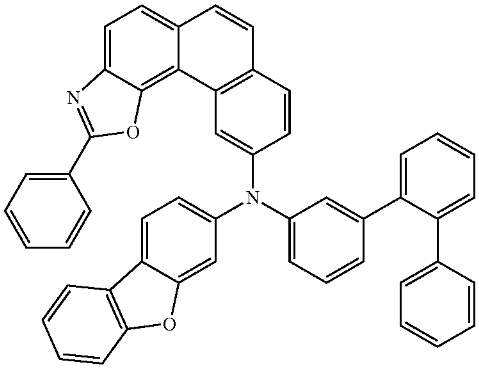
H1-115
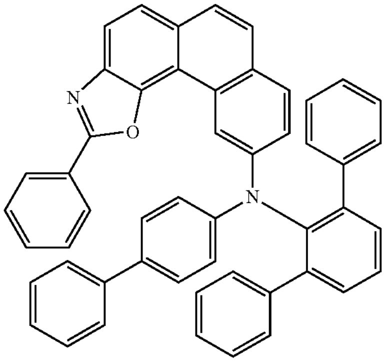
H1-116
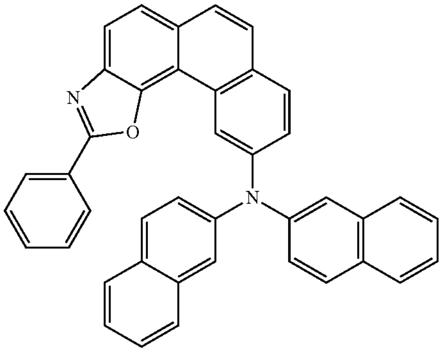
H1-117
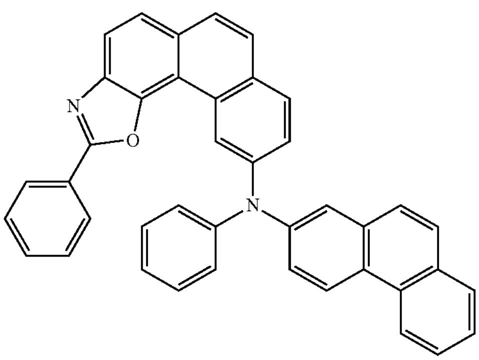

-continued
H1-118
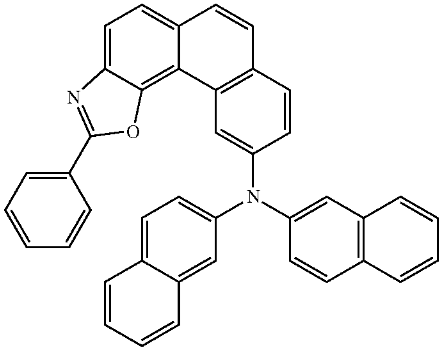
H1-119
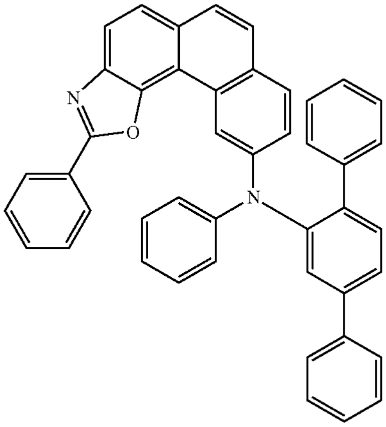
H1-120
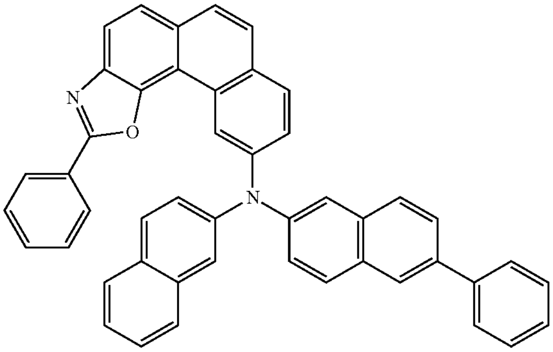
H1-121
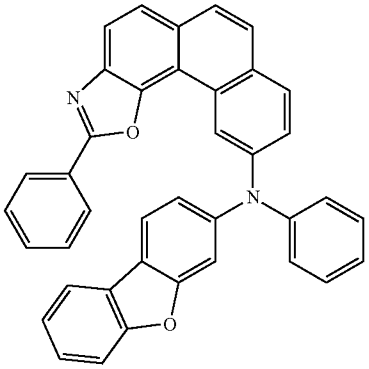
-continued
H1-122
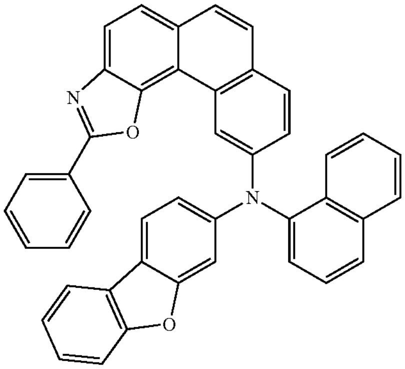
H1-123
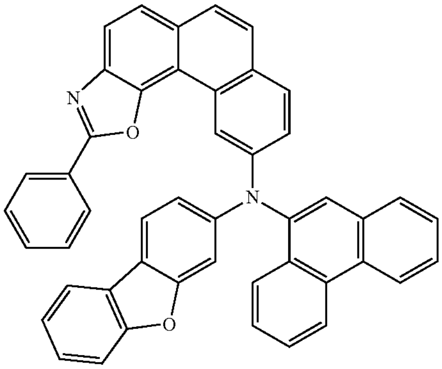
H1-124
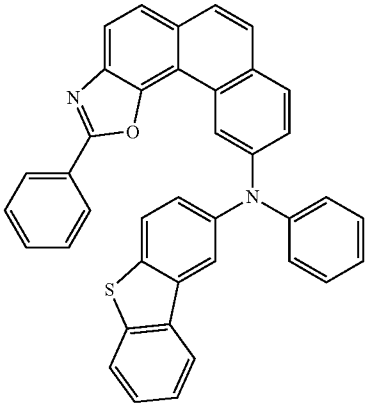
H1-125
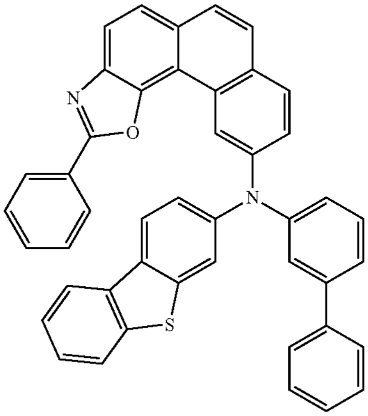

-continued

H1-126

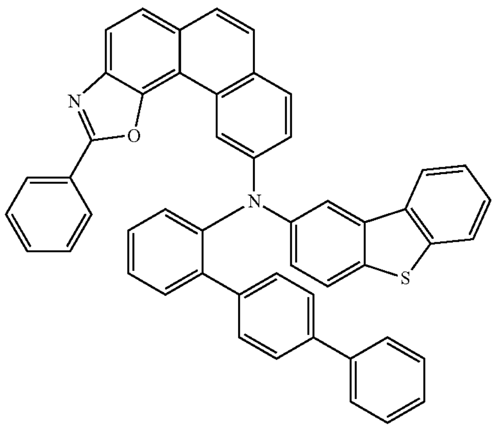

H1-127

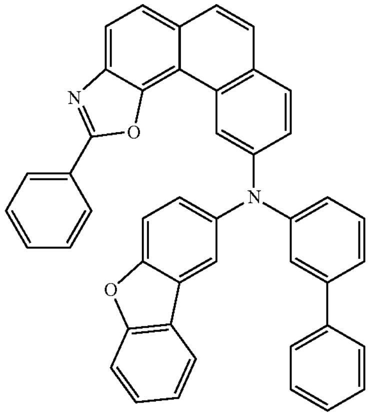

According to another embodiment of the present disclosure, when the organic electroluminescent compound of formula 1 of the present disclosure is comprised in a light-emitting layer, the light-emitting layer may further comprise a compound represented by the following formula 3:

$$HAr\text{-}((L_2)_e\text{-}Ar_2)_d \quad (3)$$

wherein

HAr represents a substituted or unsubstituted (3- to 20-membered)heteroaryl containing a nitrogen atom(s);

$L_2$ each independently represents a substituted or unsubstituted (C6-C30)arylene;

$Ar_2$ each independently represents a substituted or unsubstituted (C6-C30)aryl, or the following formula 4, with the proviso that at least one of $Ar_2$ represents formula 4:

(4)

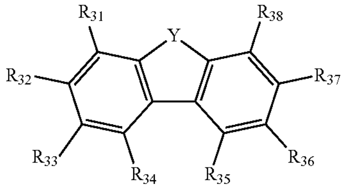

Y represents O, S, $CR_{41}R_{42}$, N—*, or $NR_{43}$;

$R_{41}$ to $R_{43}$ each independently represent a substituted or unsubstituted (C1-C30)alkyl, or a substituted or unsubstituted (C6-C30)aryl, or $R_{41}$ and $R_{42}$ may be linked to each other to form a ring;

$R_{31}$ to $R_{38}$ each independently represent a site linked to $L_2$; or represent hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), or $-L_4-N(Ar_3)(Ar_4)$; or may be linked to an adjacent substituent to form a ring(s);

$L_4$ each independently represents a single bond, a substituted or unsubstituted (C6-C30)arylene, or a substituted or unsubstituted (3- to 30-membered)heteroarylene;

$Ar_3$ and $Ar_4$ each independently represent hydrogen, a substituted or unsubstituted (C1-C30)alkyl, a substituted or unsubstituted (C2-C30)alkenyl, a substituted or unsubstituted fused ring group of a (C3-C30) aliphatic ring(s) and a (C6-C30) aromatic ring(s), a substituted or unsubstituted (C6-C30)aryl, or a substituted or unsubstituted (3- to 30-membered)heteroaryl;

d represents an integer of 1 to 3, where if d is an integer of 2 or more, each of $((L_2)$. —$Ar_2)$ may be the same or different;

e represents an integer of 0 to 2, where if e is 2, each of $L_2$ may be the same or different; and

* represents a site linked to $L_2$.

In formula 3, HAr represents a substituted or unsubstituted (3- to 20-membered)heteroaryl containing a nitrogen atom(s). According to one embodiment of the present disclosure, HAr represents a substituted or unsubstituted (3- to 15-membered)heteroaryl containing a nitrogen atom(s). According to another embodiment of the present disclosure, HAr represents an unsubstituted (5- to 15-membered)heteroaryl containing a nitrogen atom(s). Specifically, HAr may be a pyridyl, a pyrimidinyl, a triazinyl, a quinolyl, a quinazolinyl, a quinoxalinyl, a naphthyridinyl, a pyridopyrazinyl, a benzoquinazolinyl, a benzoquinoxalinyl, a benzofuropyrimidinyl, etc.

In formula 3, $L_2$ each independently represents a substituted or unsubstituted (C6-C30)arylene. According to one embodiment of the present disclosure, $L_2$ each independently represents a substituted or unsubstituted (C6-C20) arylene. According to another embodiment, $L_2$ each independently represents an unsubstituted (C6-C20)arylene. Specifically, $L_2$ each independently may be a phenylene, a naphthylene, a biphenylene, a benzophenanthrenylene, etc.

In formula 3, $Ar_2$ each independently represents a substituted or unsubstituted (C6-C30)aryl, or formula 4, with the proviso that at least one of $Ar_2$ represents formula 4. According to one embodiment of the present disclosure, $Ar_2$ each independently represents a (C6-C30)aryl substituted with a (5- to 15-membered)heteroaryl substituted with a (C6-C12) aryl(s); a (C6-C30)aryl substituted with a di(C6-C12)arylamino(s); an unsubstituted (C6-C30)aryl; or formula 4. Specifically, $Ar_2$ each independently may be a phenyl, a naphthyl, a phenylnaphthyl, a naphthylphenyl, a biphenyl, a terphenyl, a phenanthrenyl, a triphenylenyl, a chrysenyl, a benzophenanthrenyl unsubstituted or substituted with a phenyl(s), a phenyl substituted with a phenylquinoxalinyl(s), a phenyl substituted with a diphenylamino(s), etc., or formula 4.

In formula 4, Y represents 0, S, $CR_{41}R_{42}$. N—*, or $NR_4$; and * represents a site linked to $L_2$.

In formula 4, $R_{41}$ to $R_{43}$ each independently represent a substituted or unsubstituted (C1-C30)alkyl, or a substituted or unsubstituted (C6-C30)aryl, or $R_{41}$ and $R_{42}$ may be linked to each other to form a ring. According to one embodiment of the present disclosure, $R_{41}$ to $R_{43}$ each independently represent a substituted or unsubstituted (C1-C6)alkyl, or a substituted or unsubstituted (C6-C12)aryl, or $R_{41}$ and $R_{42}$ may be linked to each other to form a ring. According to another embodiment of the present disclosure, $R_{41}$ to $R_{43}$ each independently represent an unsubstituted (C1-C6)alkyl, or an unsubstituted (C6-C12)aryl, or $R_{41}$ and $R_{42}$ may be linked to each other to form a ring. Specifically, $R_{41}$ to $R_{43}$ may each independently represent a methyl, a phenyl, etc., or $R_{41}$ and $R_{42}$ may be linked to each other to form a fluorene ring.

In formula 4, $R_{31}$ to Rae each independently represent a site linked to $L_2$; or represent hydrogen, deuterium, a halogen, a cyano, a substituted or unsubstituted (C1-C30) alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted fused ring group of a (C3-C30) aliphatic ring(s) and a (C6-C30) aromatic ring(s), or $-L_4-N(Ar_3)(Ar_4)$; or may be linked to an adjacent substituent to form a ring(s). According to one embodiment of the present disclosure, $R_{31}$ to $R_{38}$ each independently, represent a site linked to $L_2$; or represent hydrogen, or a substituted or unsubstituted (C6-C20)aryl; or may be linked to an adjacent substituent to form a ring(s). According to another embodiment of the present disclosure, $R_{31}$ to $R_{38}$ each independently represent a site linked to $L_2$; or represent hydrogen, or an unsubstituted (C6-C18)aryl; or may be linked to an adjacent substituent to form a ring(s). For example, $R_{31}$ to $R_{38}$ each independently may be a site linked to $L_2$; or may be hydrogen, a phenyl, a naphthyl, a biphenyl, a naphthylphenyl, a phenylnaphthyl, etc.; or may be linked to an adjacent substituent to form a benzene ring.

$L_4$ represents a single bond, a substituted or unsubstituted (C6-C30)arylene, or a substituted or unsubstituted (3- to 30-membered)heteroarylene.

$Ar_3$ and $Ar_4$ each independently represent hydrogen, a substituted or unsubstituted (C1-C30)alkyl, a substituted or unsubstituted (C2-C30)alkenyl, a substituted or unsubstituted fused ring group of a (C3-C30) aliphatic ring(s) and a (C6-C30) aromatic ring(s), a substituted or unsubstituted (C6-C30)aryl, or a substituted or unsubstituted (3- to 30-membered)heteroaryl.

In formula 3, d represents an integer of 1 to 3, where if d is an integer of 2 or more, each of $((L_2)_e-Ar_2)$ may be the same or different. For example, d may be an integer of 2 or 3, and each of $((L_2)_e-Ar_2)$ may be the same or different.

In formula 3, e represents an integer of 0 to 2, where if e is 2, each of $L_2$ may be the same or different.

The compound represented by formula 3 may be one selected from the following compounds, but is not limited thereto.

H2-1

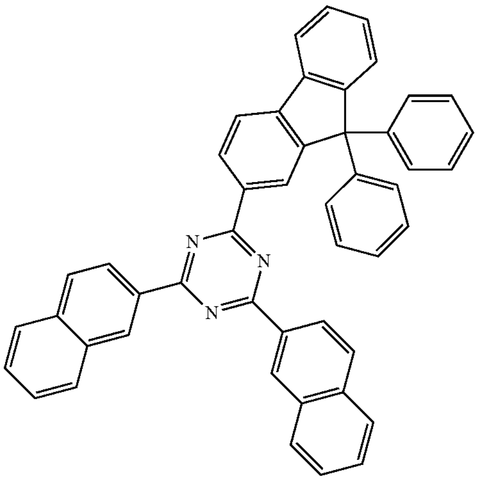

H2-2

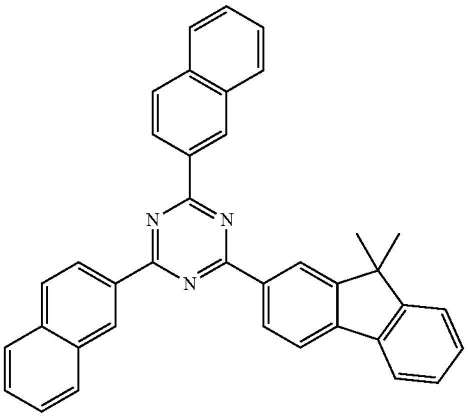

H2-3

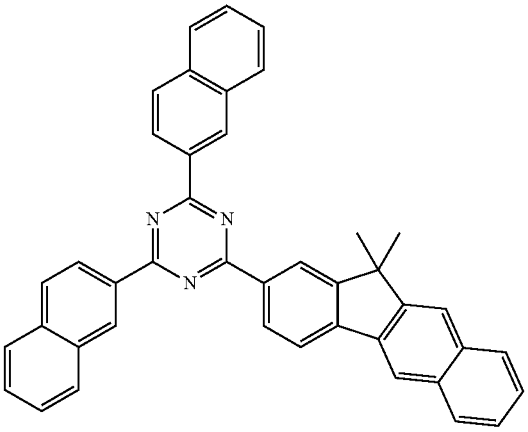

-continued
H2-4
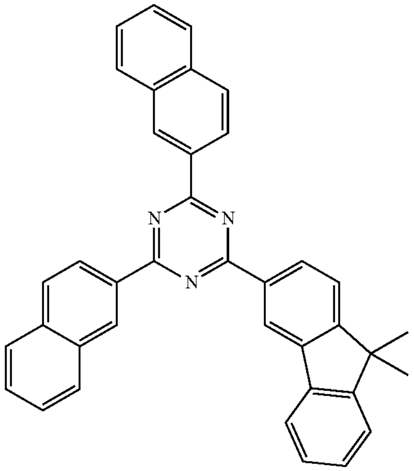
H2-5
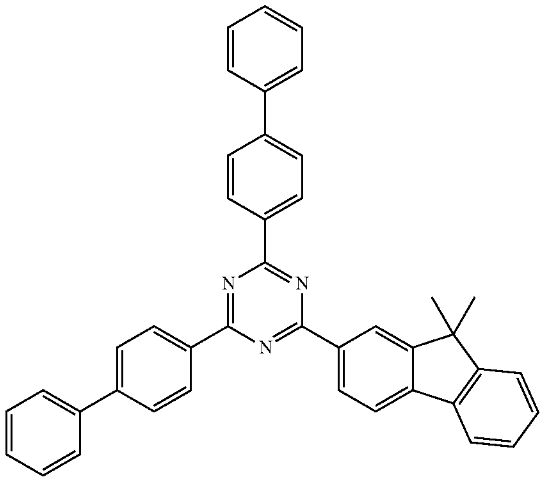
H2-6
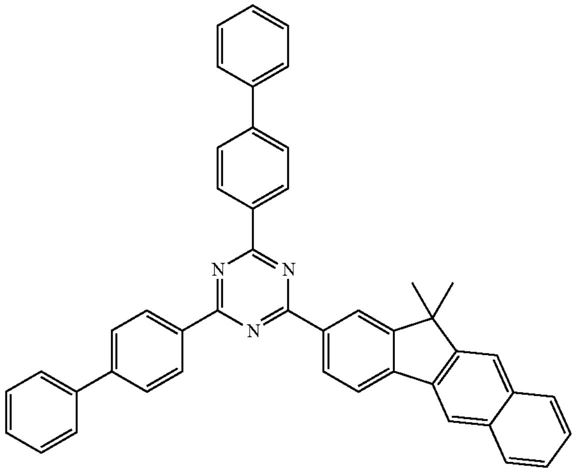
-continued
H2-7
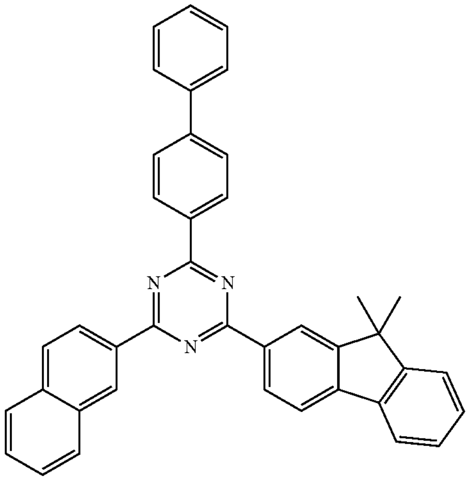
H2-8
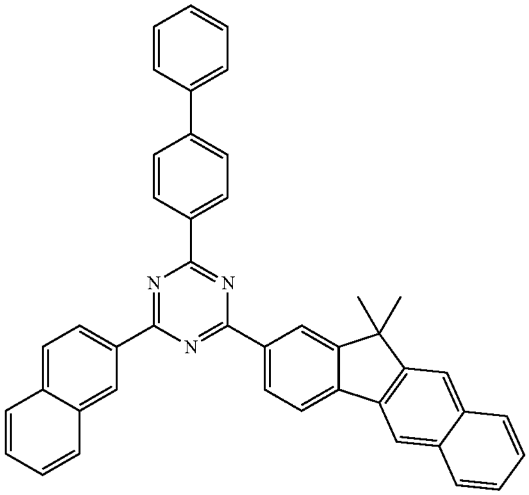
H2-9
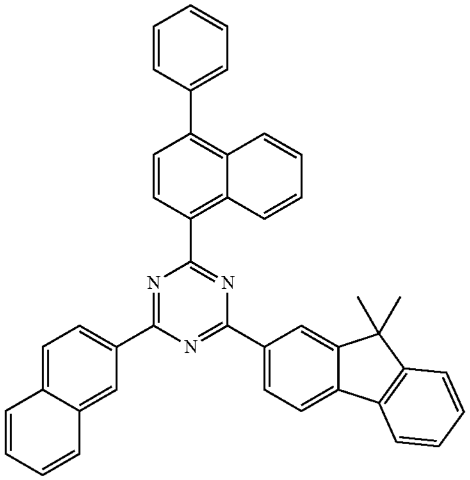

-continued
H2-10
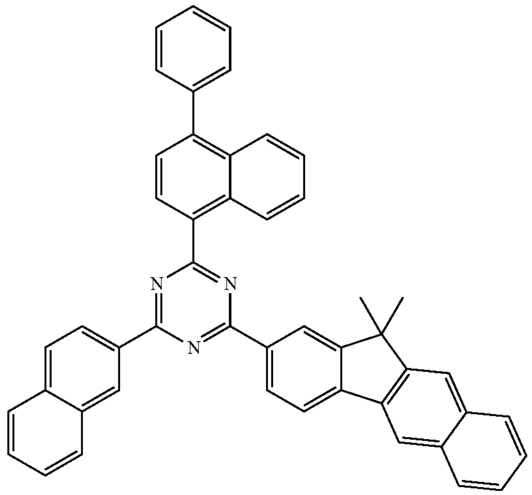
H2-11
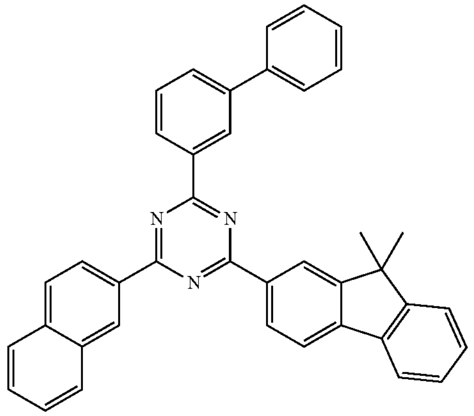
H2-12
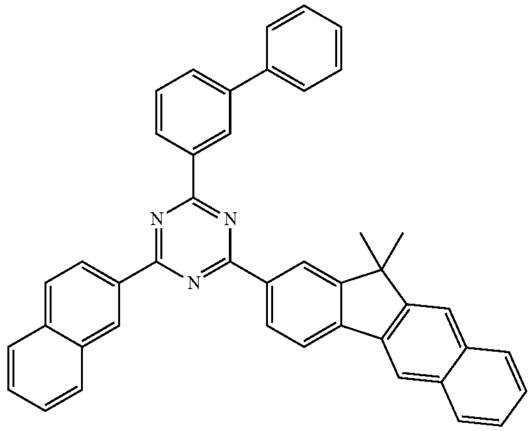
-continued
H2-13
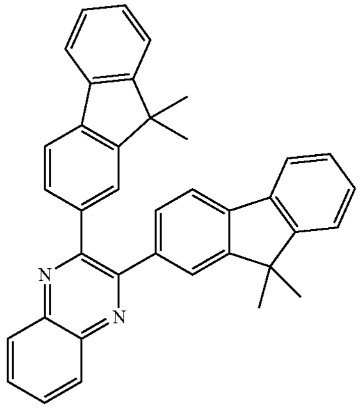
H2-14
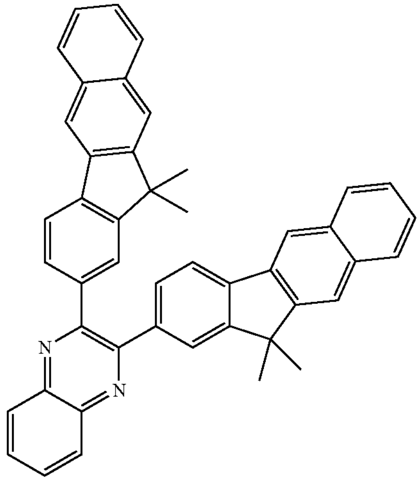
H2-15
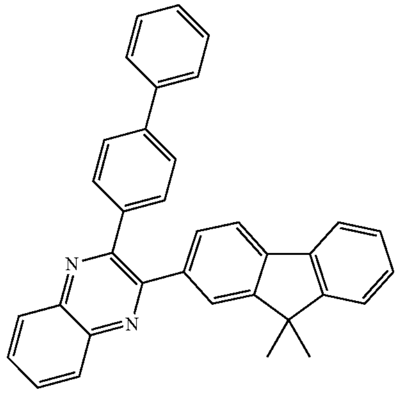

-continued
H2-16
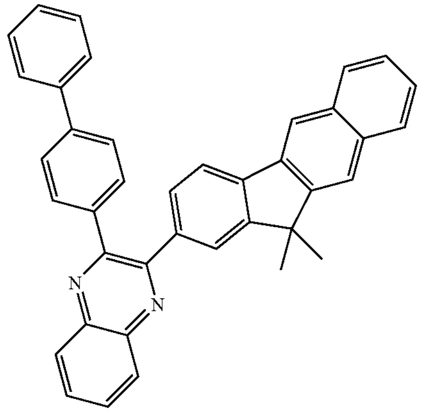
H2-17
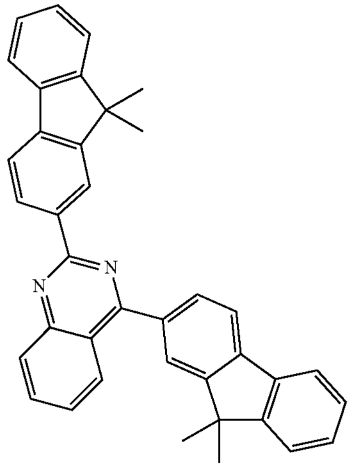
H2-18
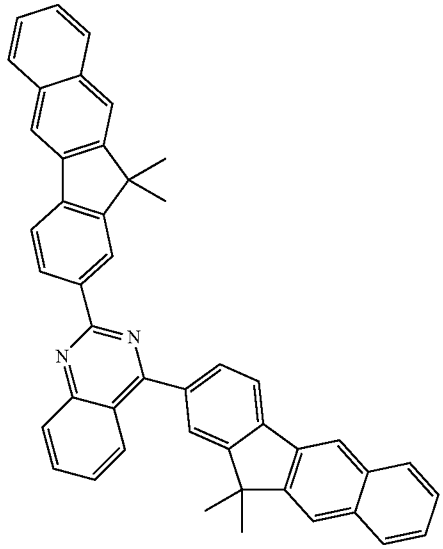
-continued
H2-19
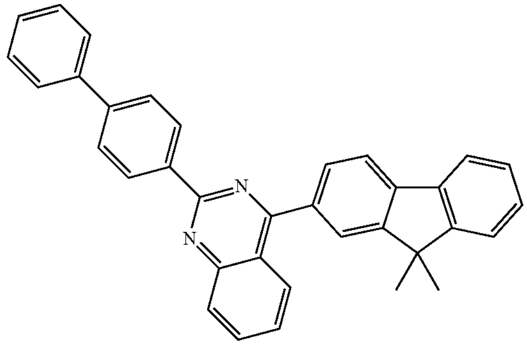
H2-20
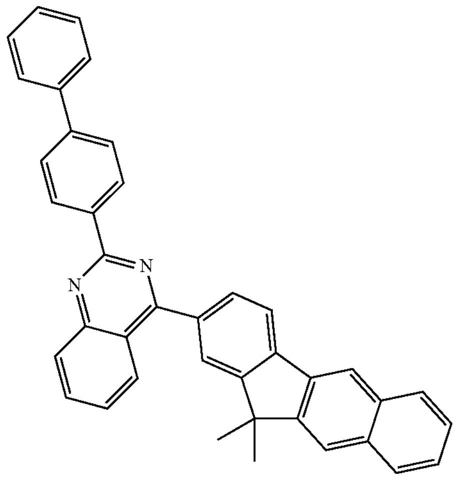
H2-21
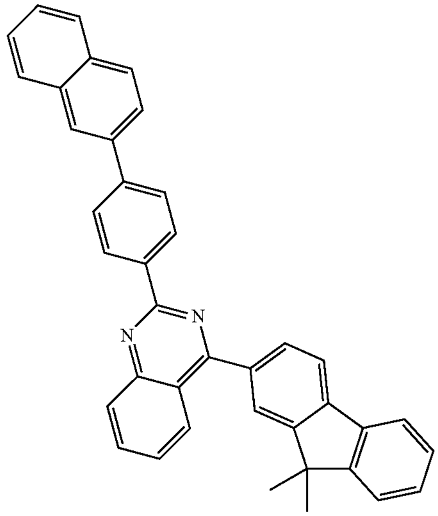

-continued
H2-22
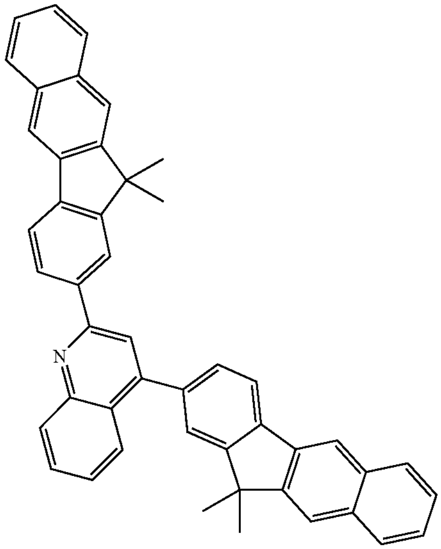
H2-23
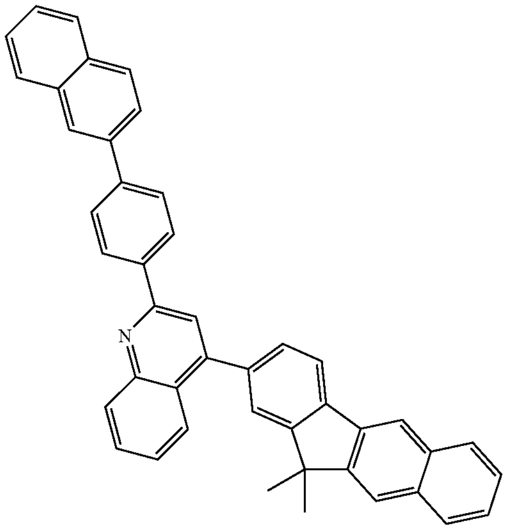
H2-24
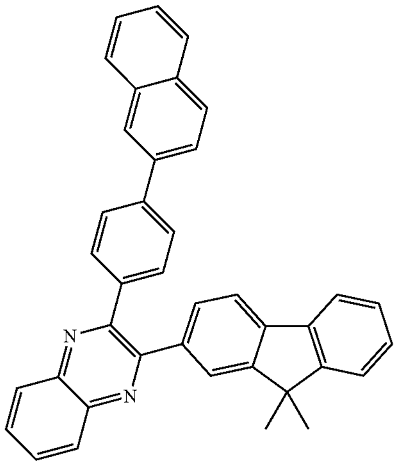
-continued
H2-25
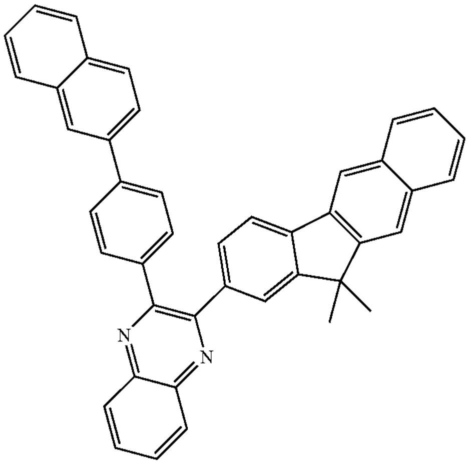
H2-26
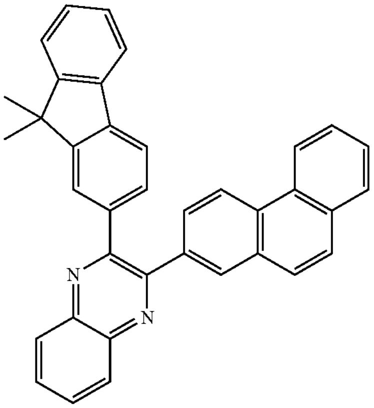
H2-27
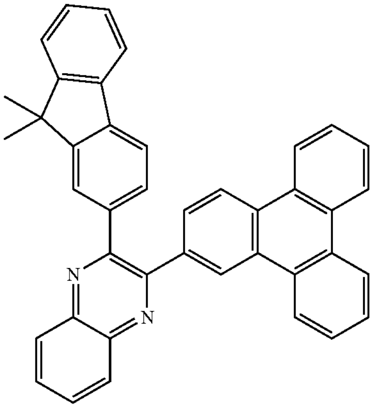

-continued
H2-28
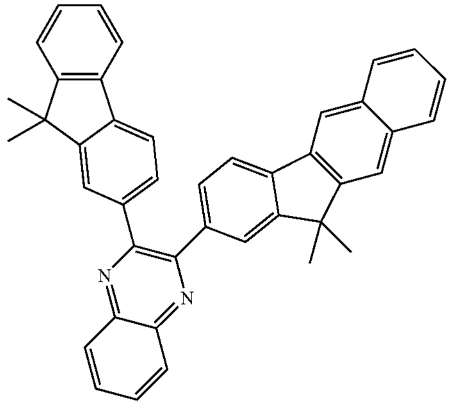
H2-29
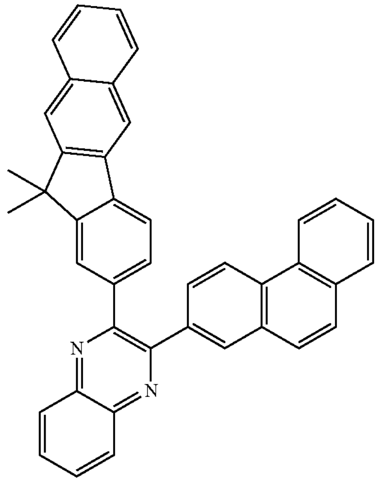
H2-30
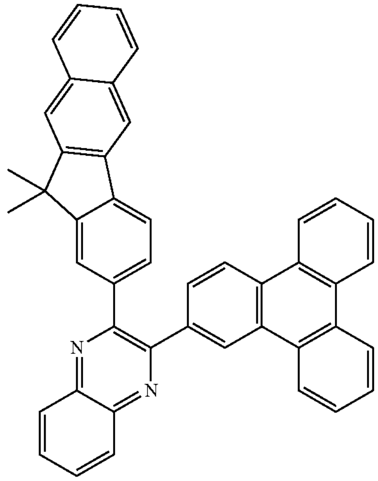
-continued
H2-31
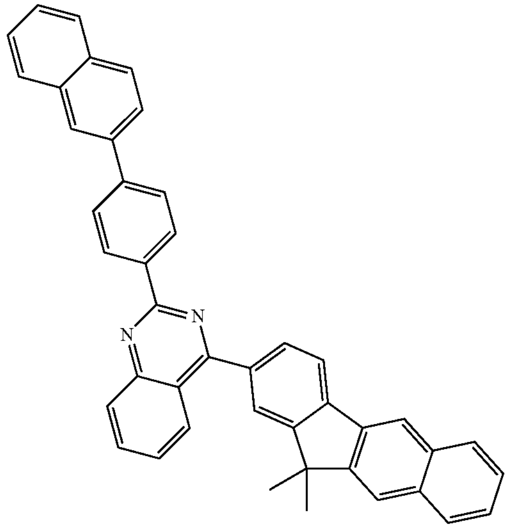
H2-32
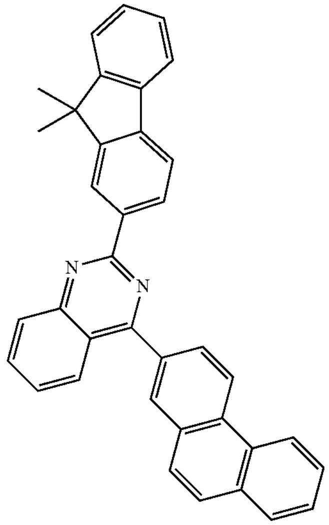
H2-33
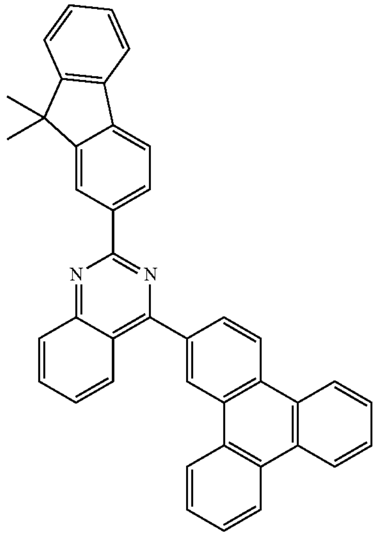

-continued
H2-34
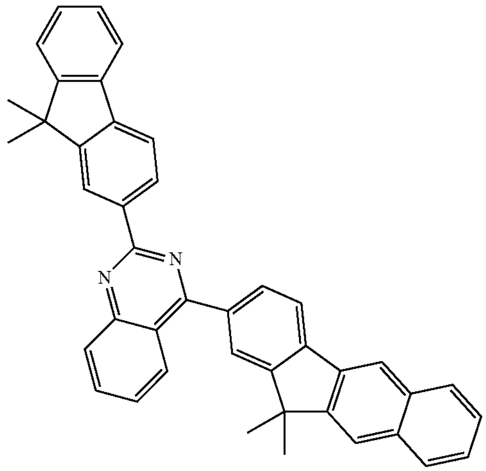
H2-35
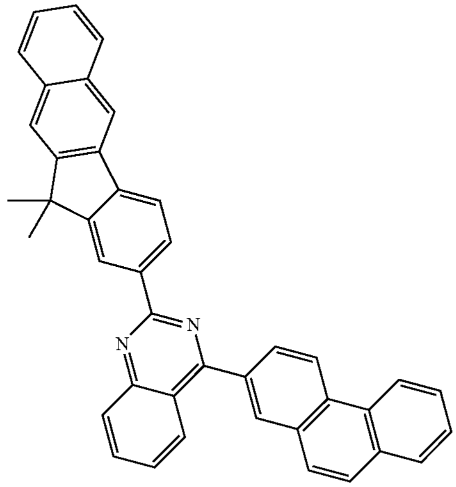
H2-36
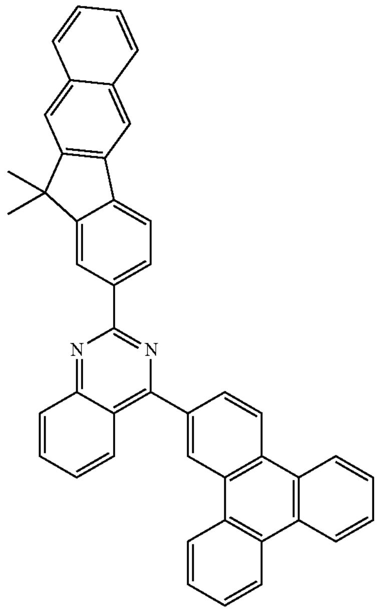
-continued
H2-37
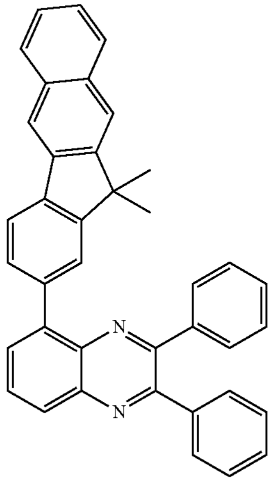
H2-38
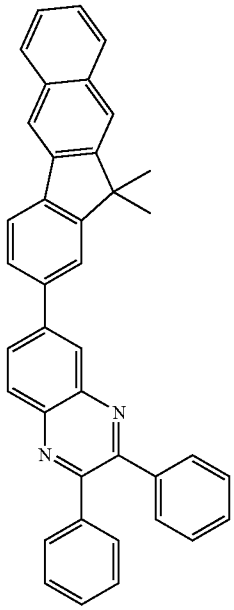

-continued
H2-39
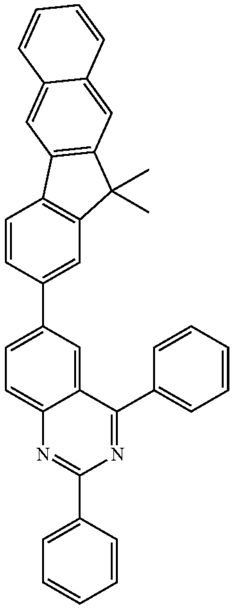
H2-40
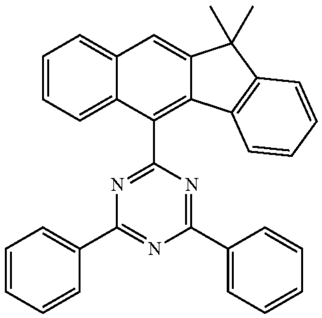
H2-41
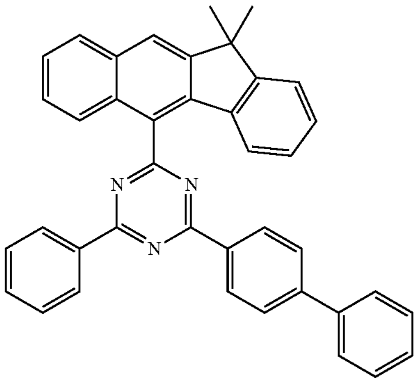
H2-42
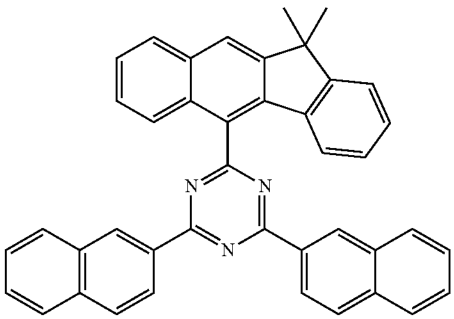
-continued
H2-43
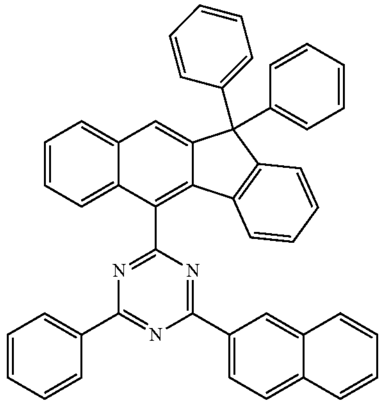
H2-44
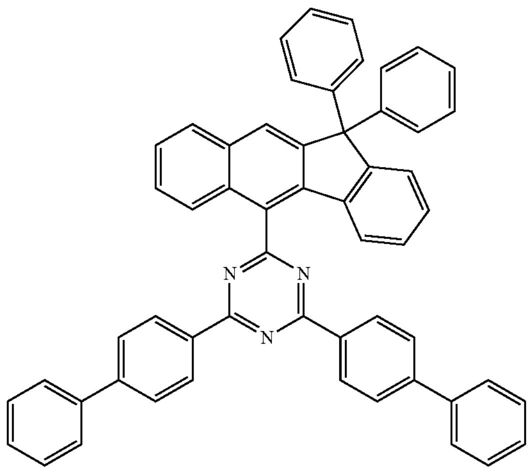
H2-45
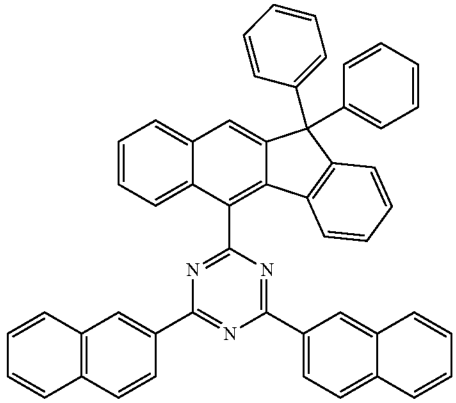
H2-46
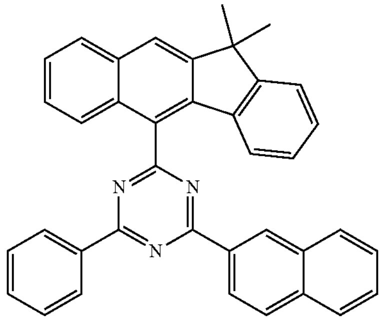

-continued
H2-47
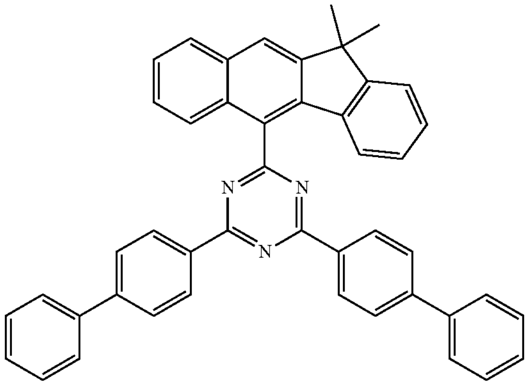
H2-48
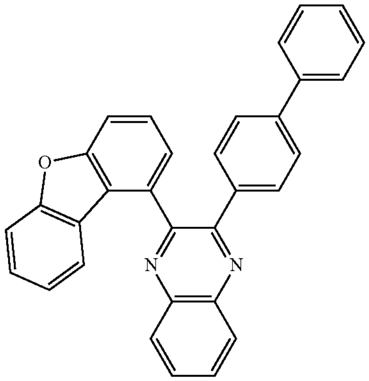
H2-49
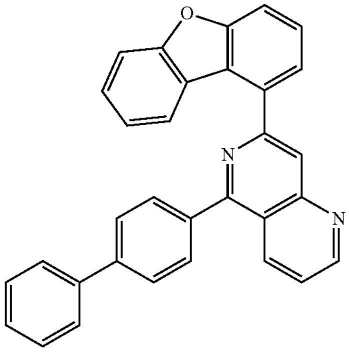
H2-50
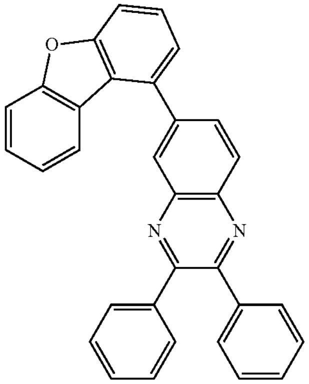
-continued
H2-51
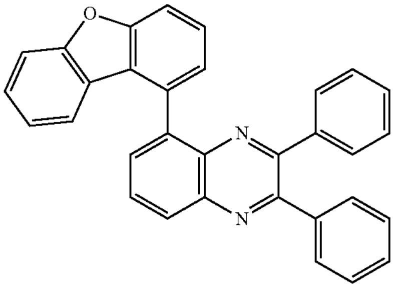
H2-52
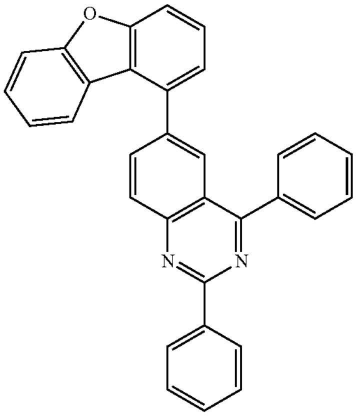
H2-53
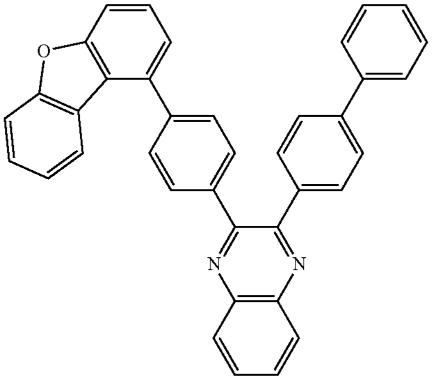
H2-54
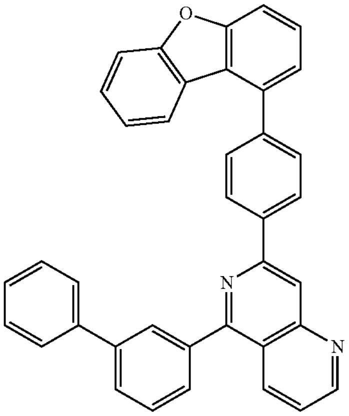

-continued
H2-55
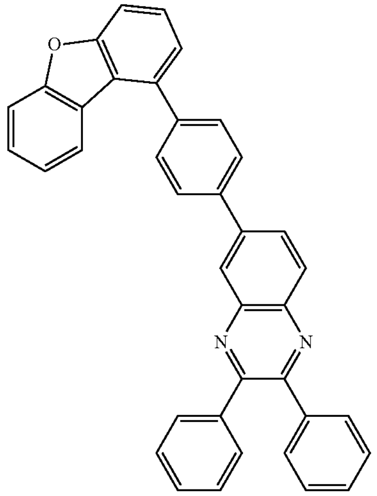
H2-56
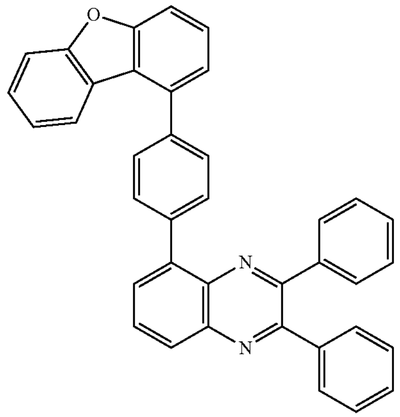
H2-57
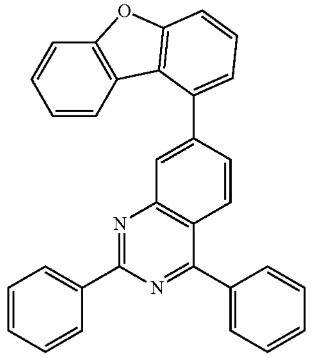
-continued
H2-58
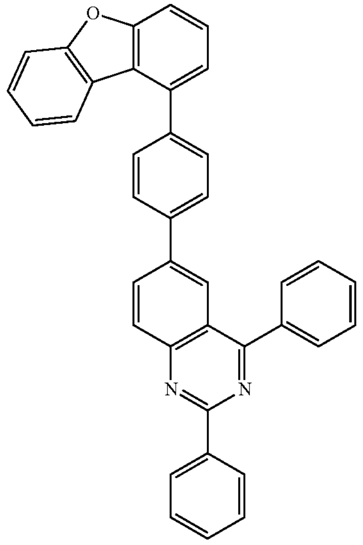
H2-59
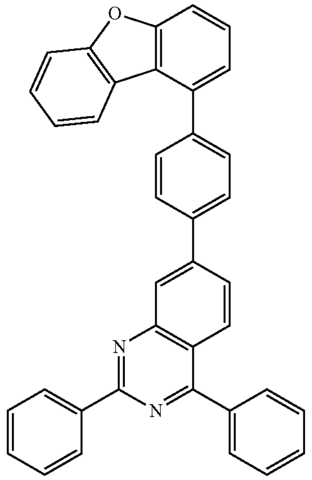
H2-60
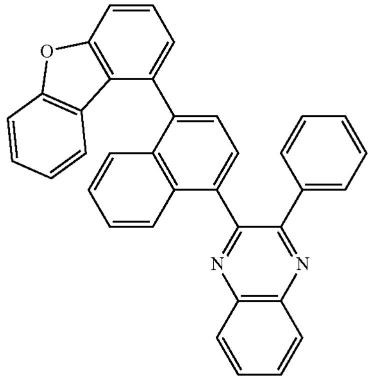

-continued
H2-61
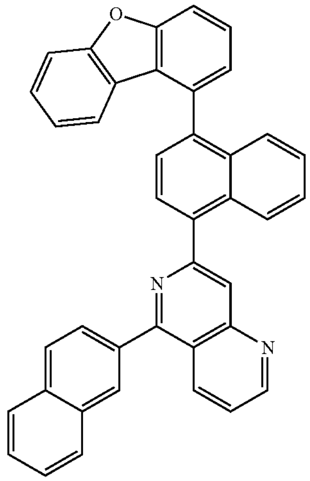
H2-62
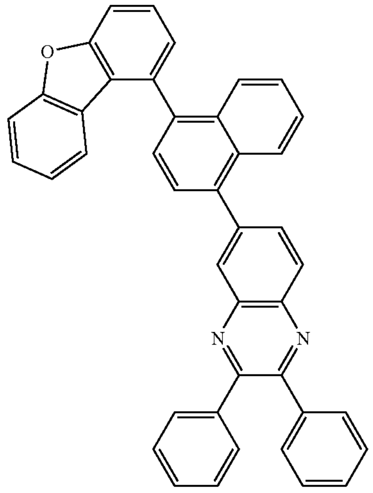
H2-63
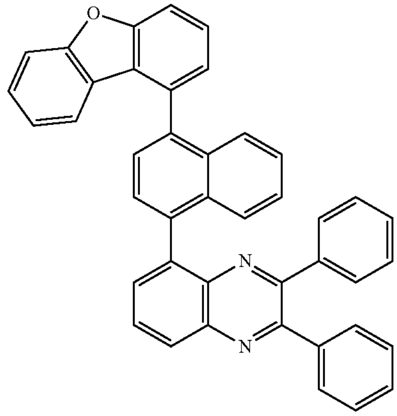
-continued
H2-64
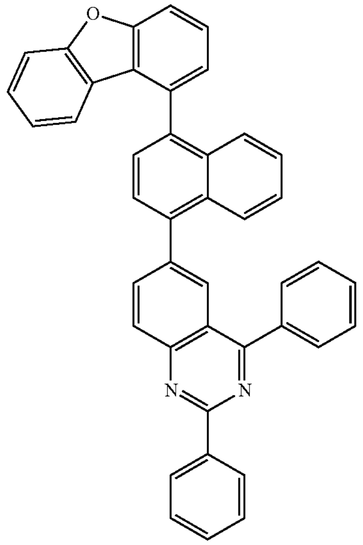
H2-65
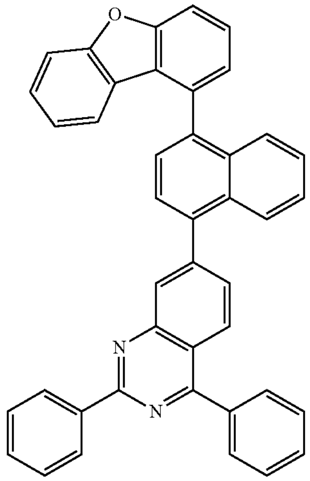
H2-66
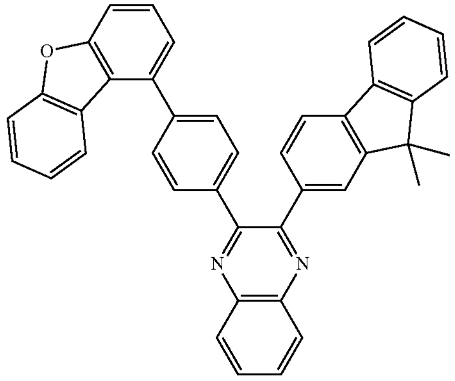

-continued
H2-67
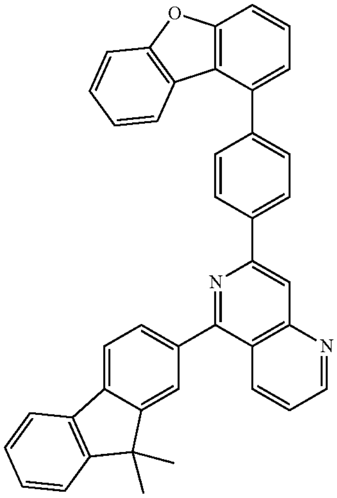
H2-68
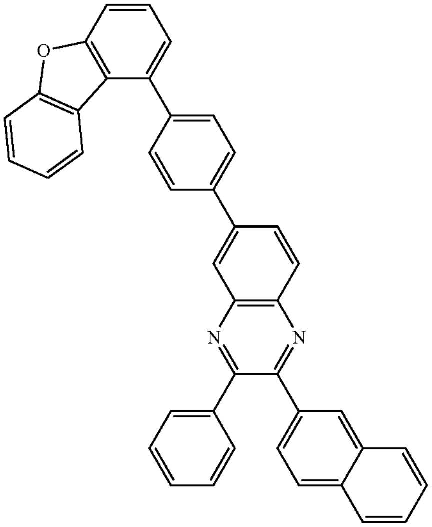
H2-69
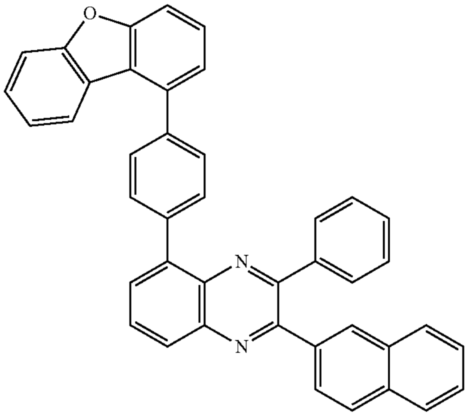
-continued
H2-70
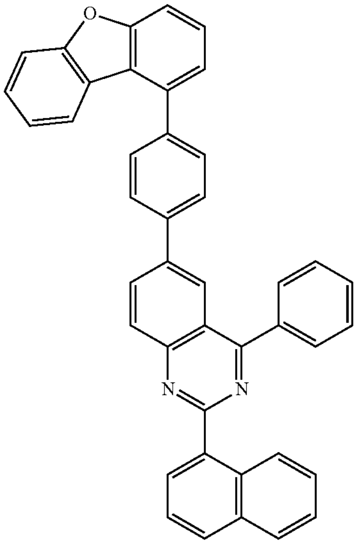
H2-71
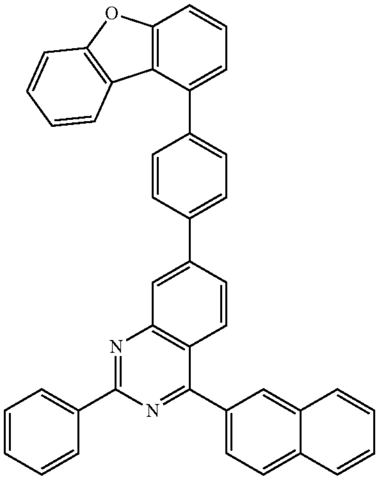
H2-72
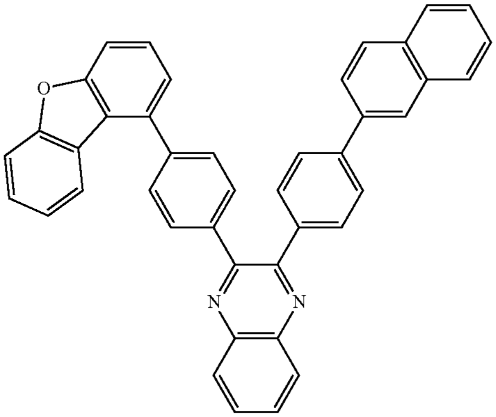

-continued
H2-73
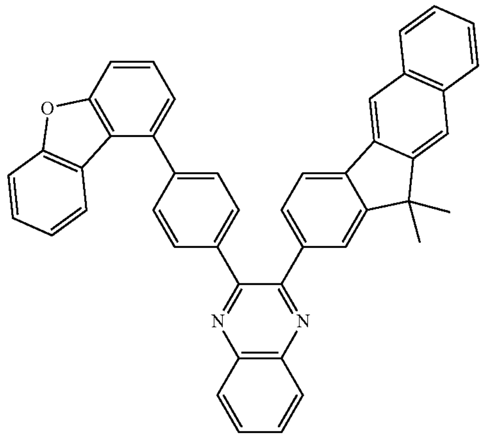
H2-74
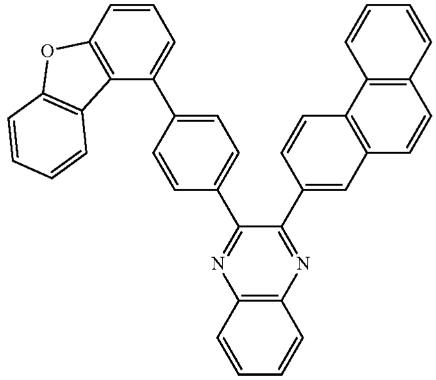
H2-75
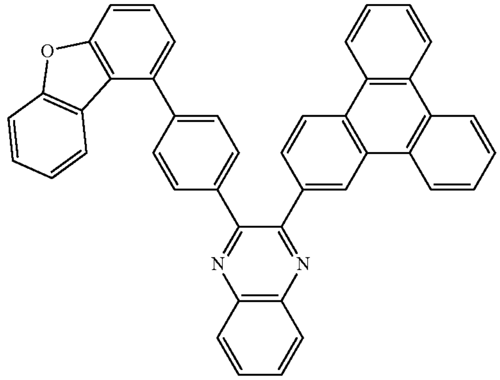
-continued
H2-76
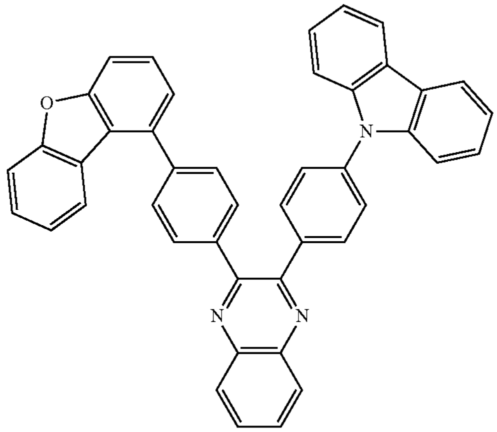
H2-77
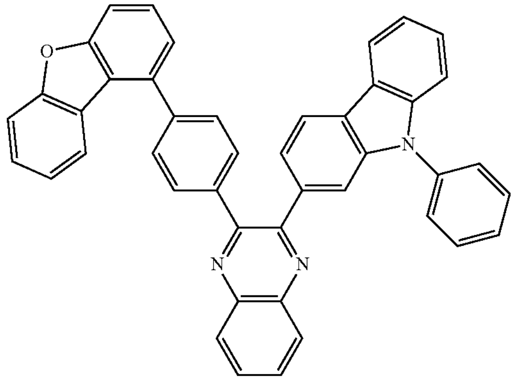
H2-78
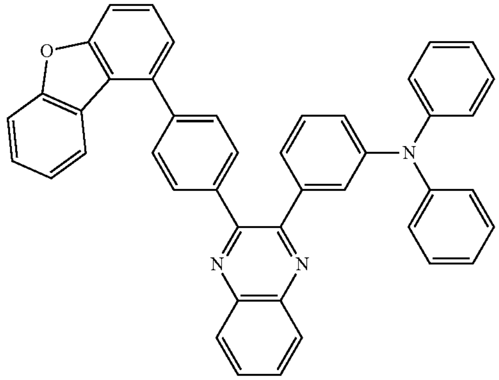

-continued
H2-79
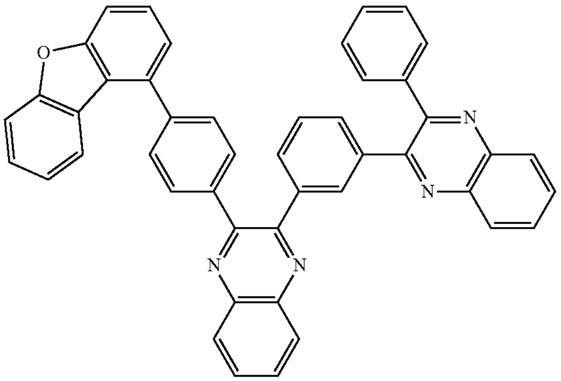
H2-80
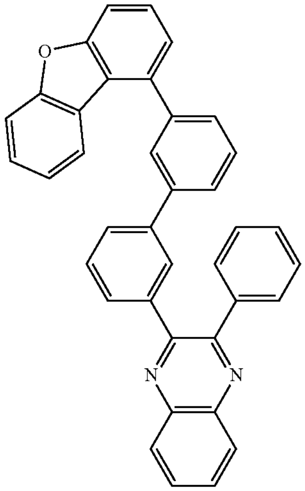
H2-81
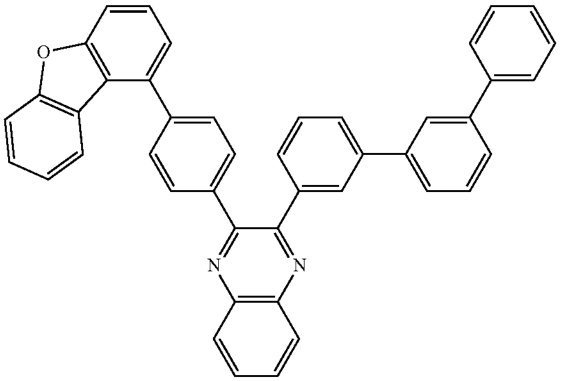
-continued
H2-82
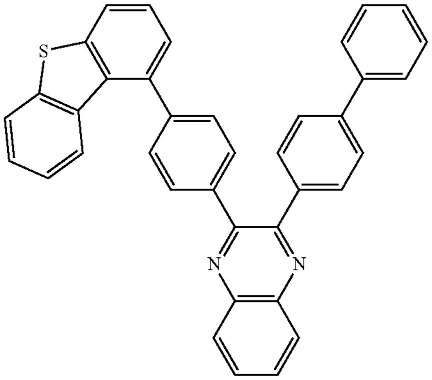
H2-83
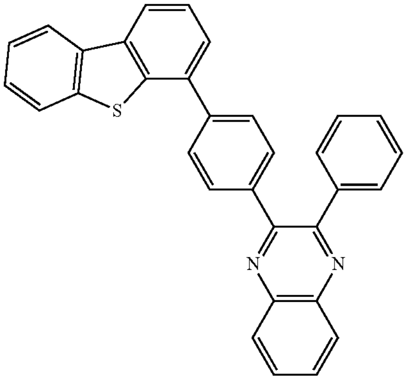
H2-84
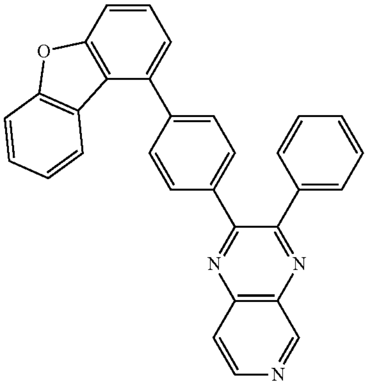
H2-85
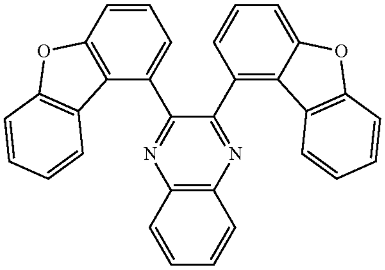

-continued
H2-86
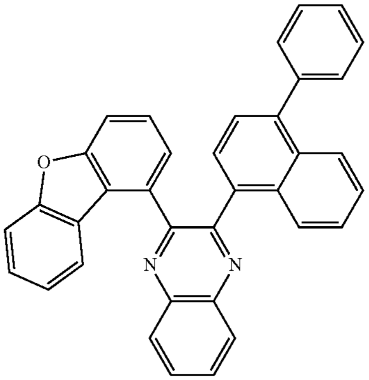
H2-87
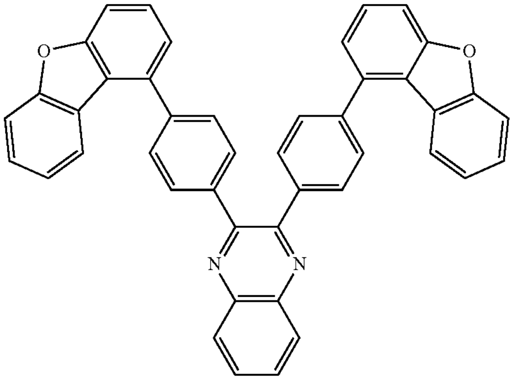
H2-88
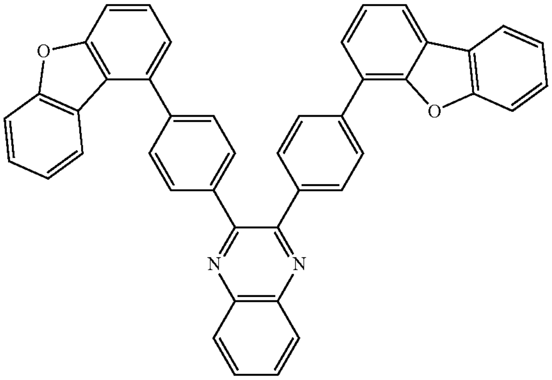
H2-89
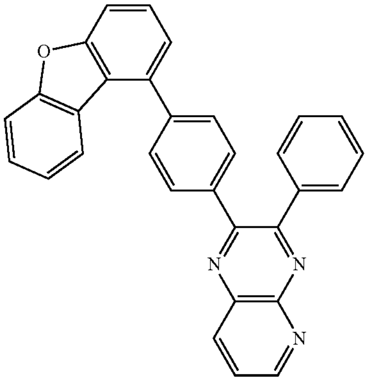
-continued
H2-90
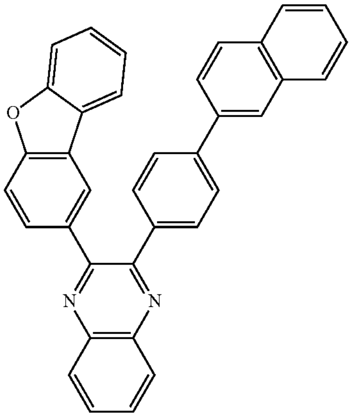
H2-91
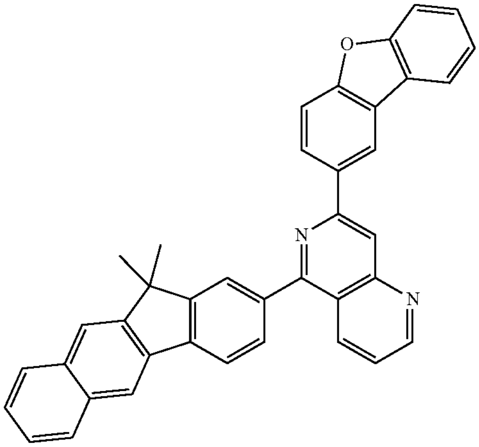
H2-92
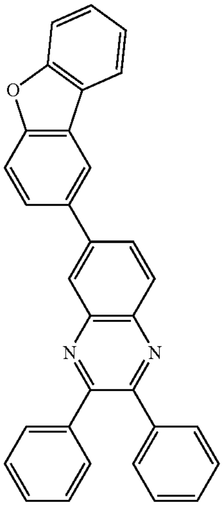

-continued
H2-93
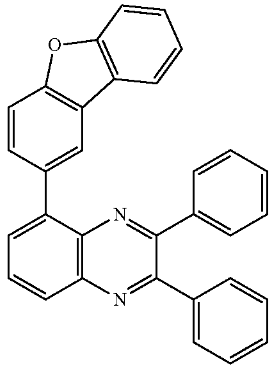
H2-94
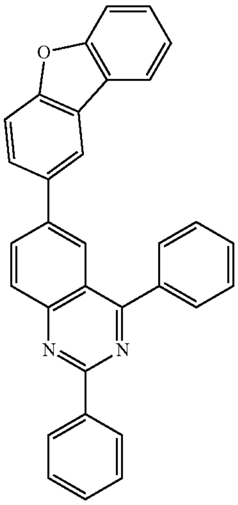
H2-95
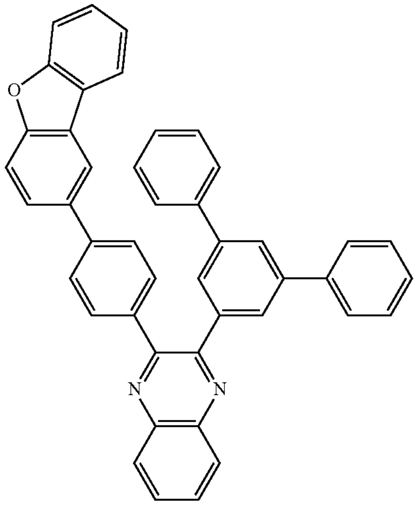
-continued
H2-96
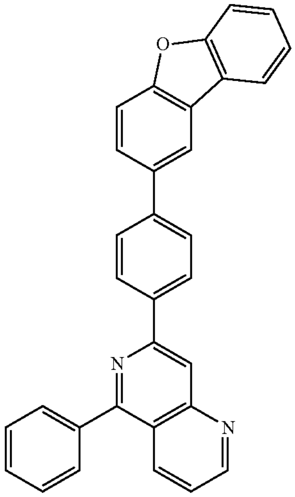
H2-97
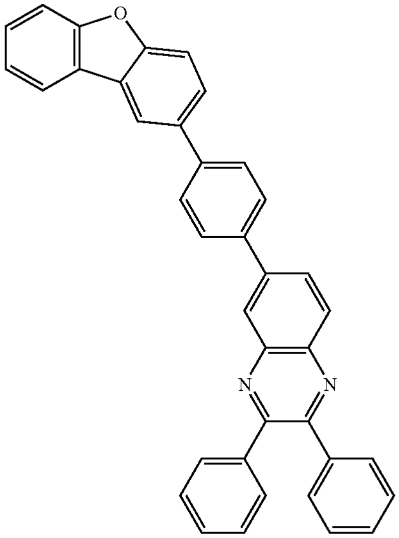
H2-98
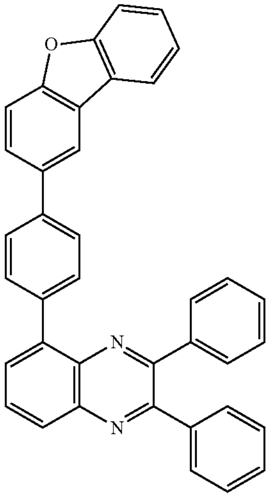

-continued
H2-99
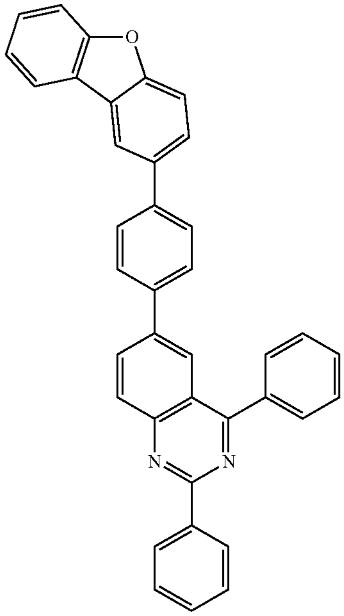
H2-100
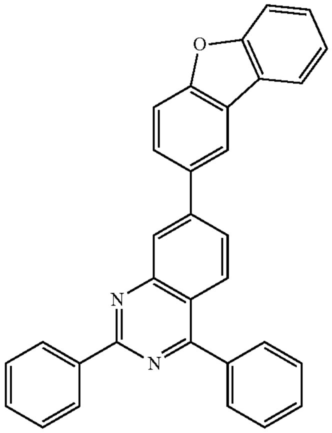
H2-101
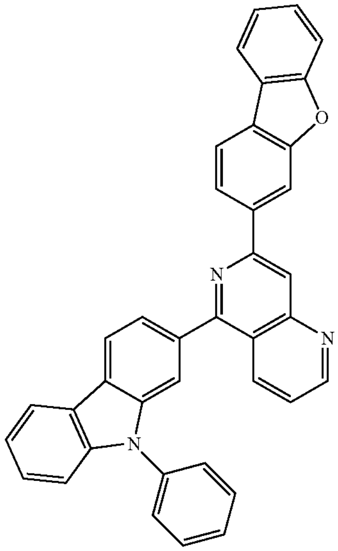
-continued
H2-102
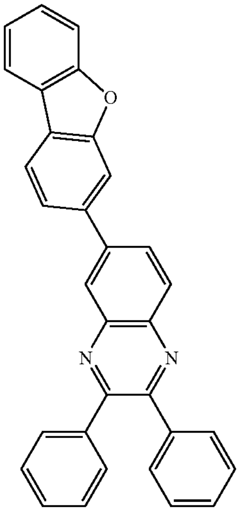
H2-103
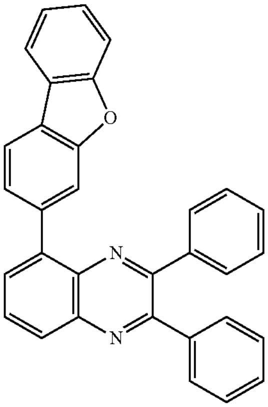
H2-104
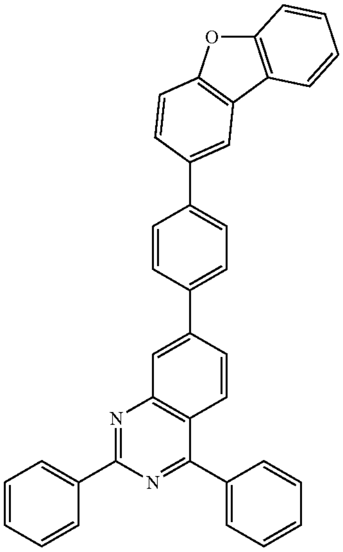

-continued
H2-105
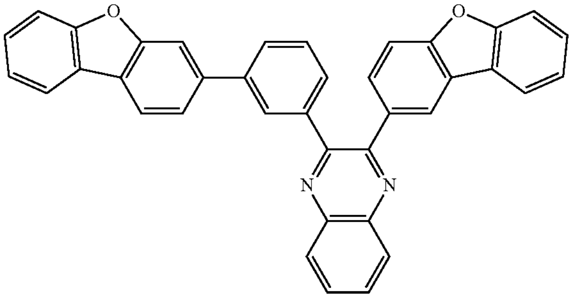
H2-106
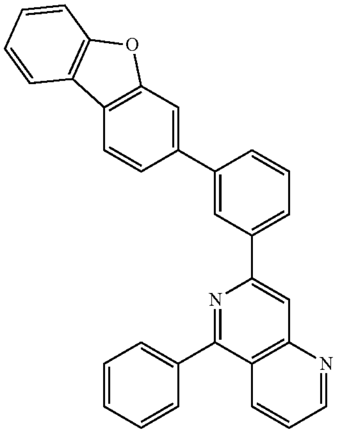
H2-107
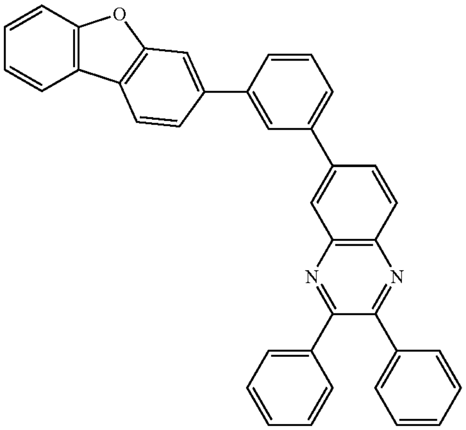
-continued
H2-108
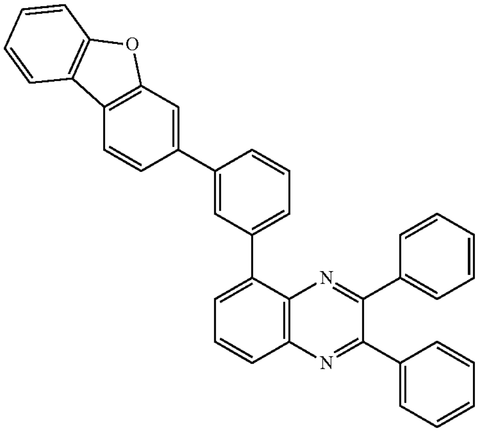
H2-109
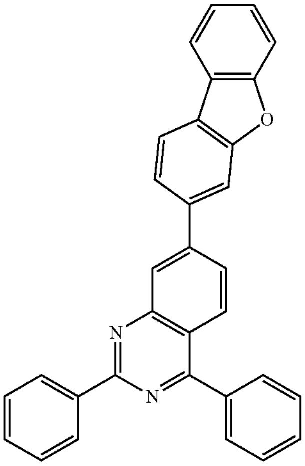
H2-110
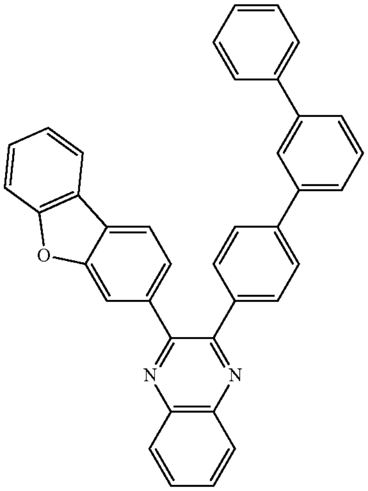

-continued
H2-111
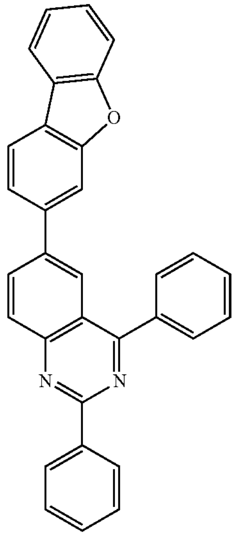
H2-112
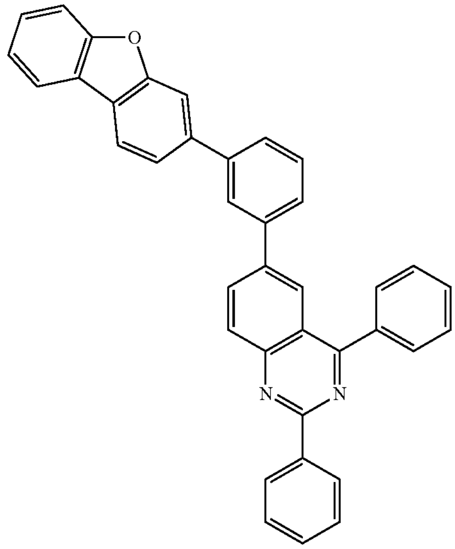
H2-113
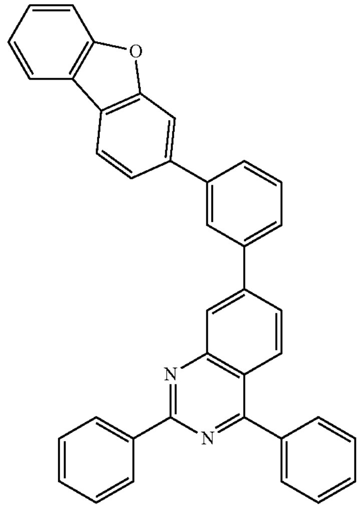
-continued
H2-114
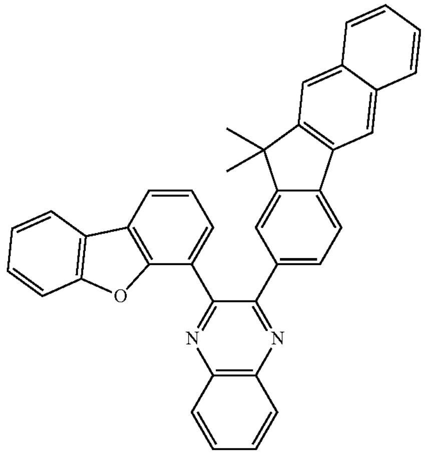
H2-115
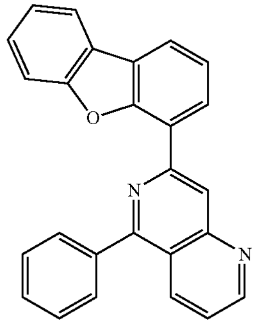
H2-116
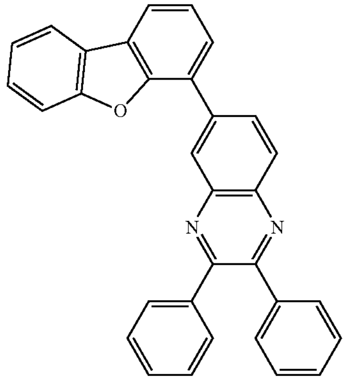
H2-117
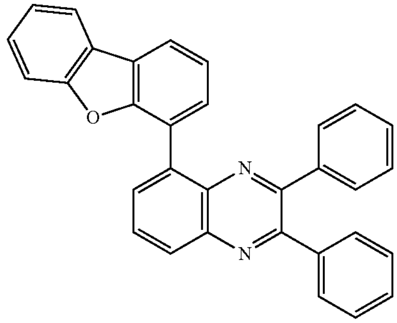

-continued
H2-118
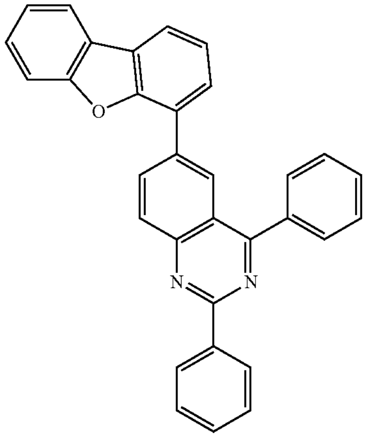
H2-119
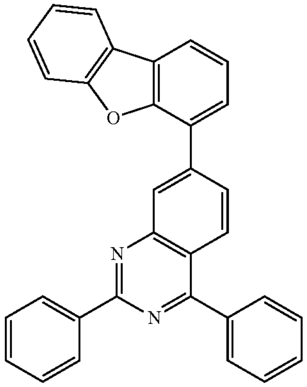
H2-120
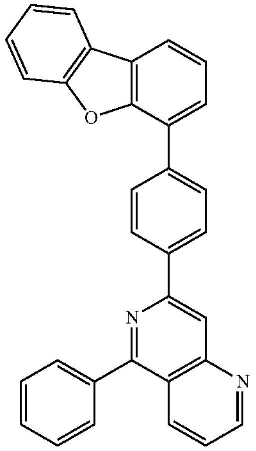
-continued
H2-121
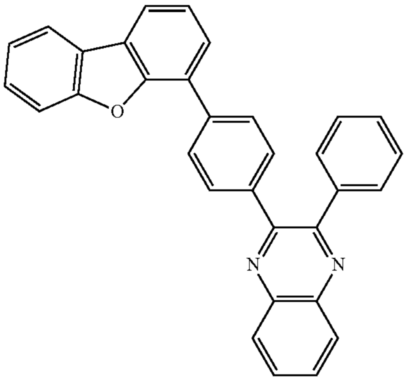
H2-122
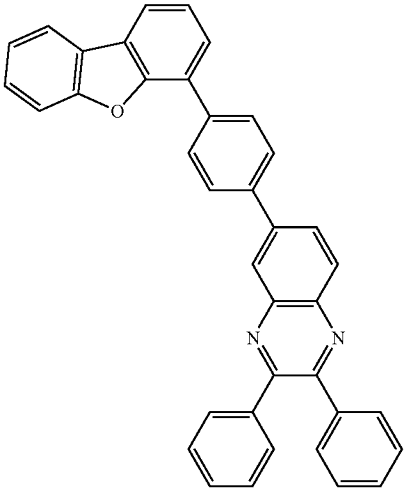
H2-123
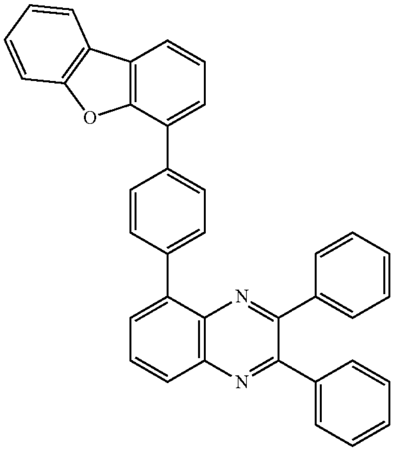

-continued
H2-124
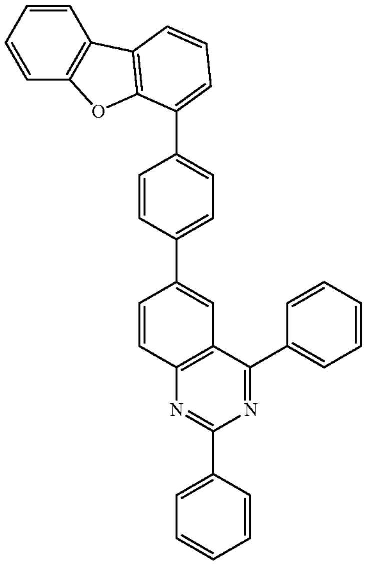
H2-125
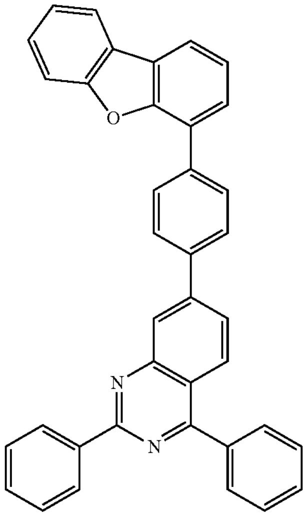
H2-126
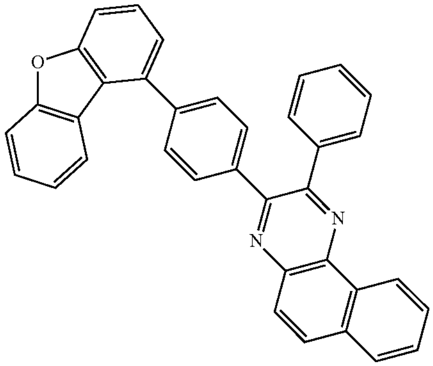
-continued
H2-127
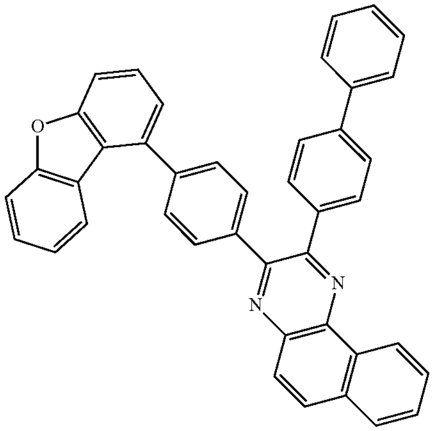
H2-128
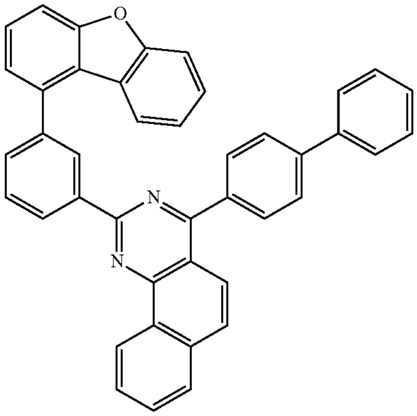
H2-129
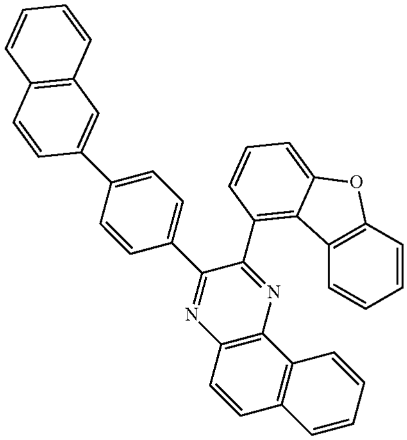

-continued
H2-130
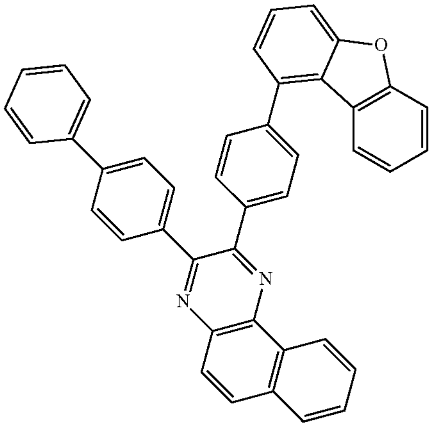
H2-131
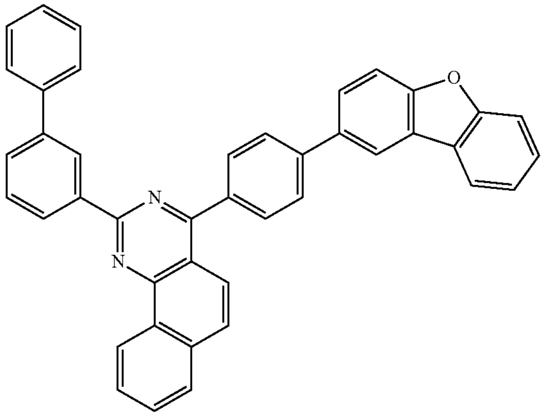
H2-132
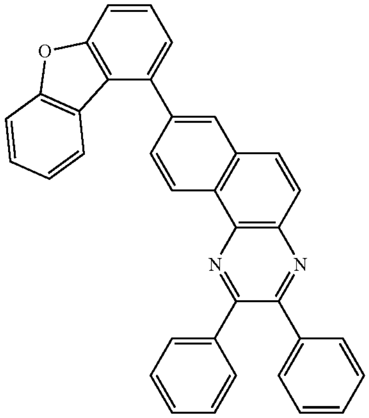
-continued
H2-133
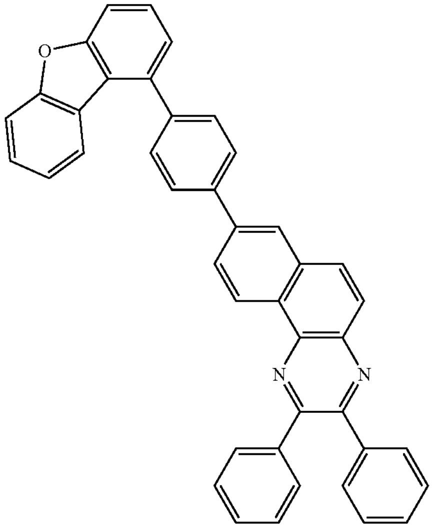
H2-134
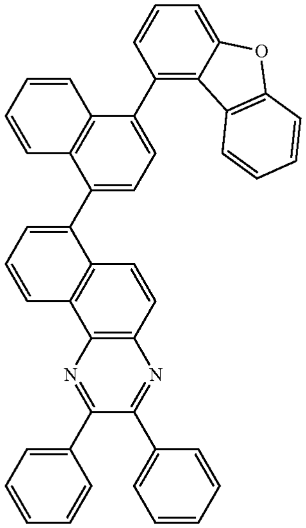
H2-135
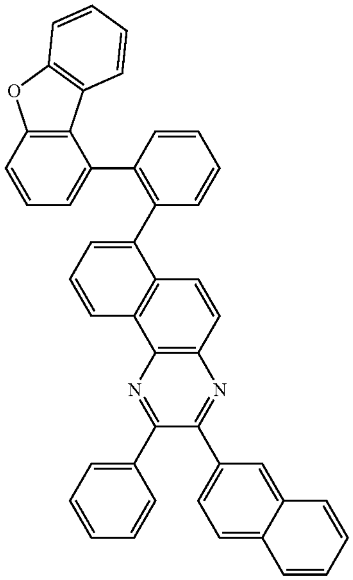

-continued
H2-136
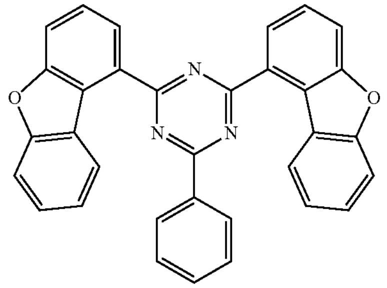
H2-137
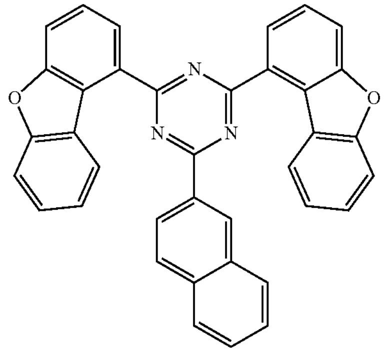
H2-138
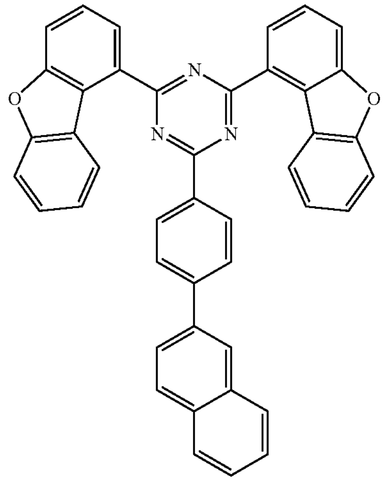
H2-139
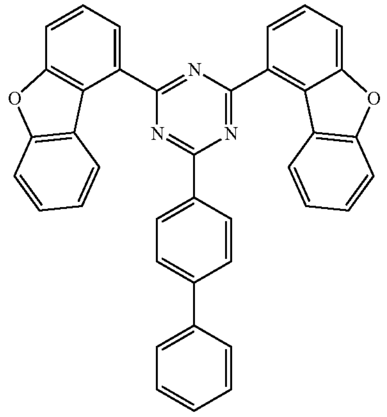
-continued
H2-140
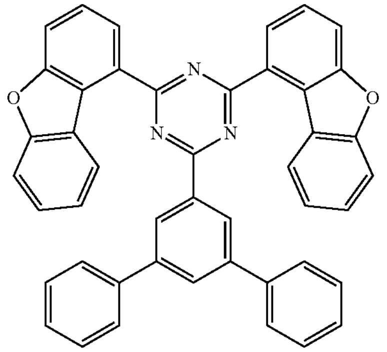
H2-141
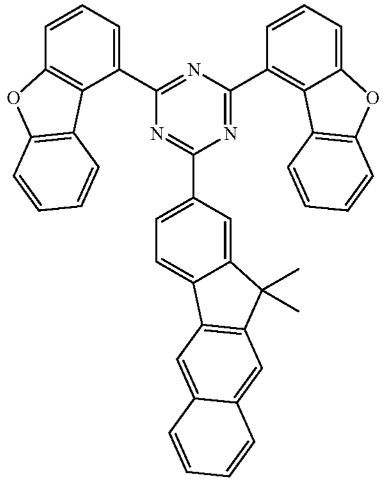
H2-142
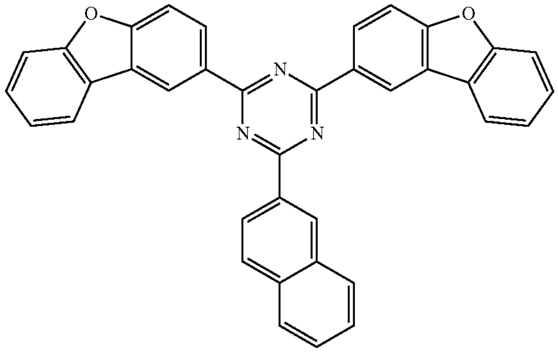

-continued
H2-143
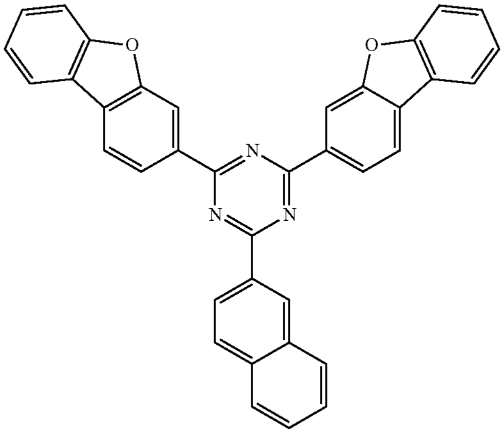
H2-144
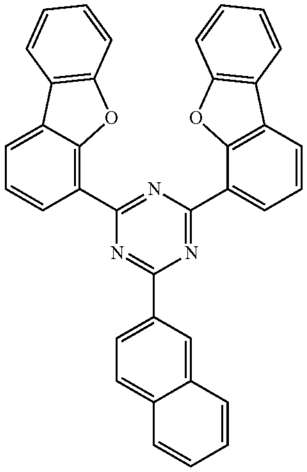
H2-145
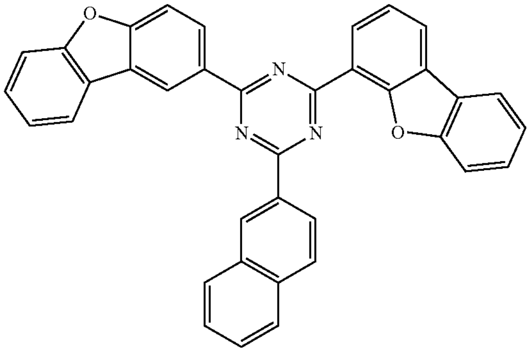
H2-146
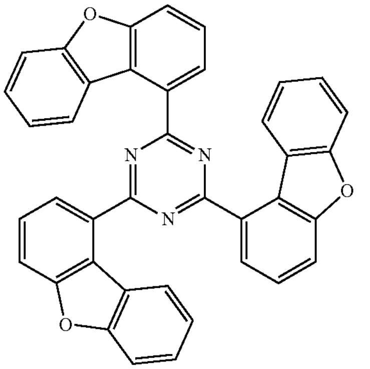
H2-147
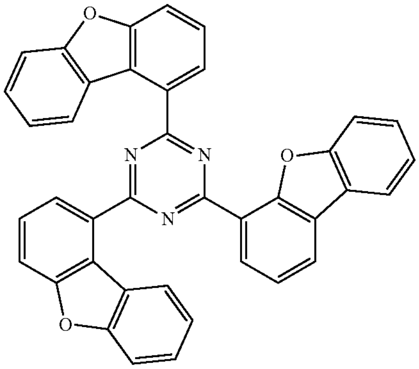
H2-148
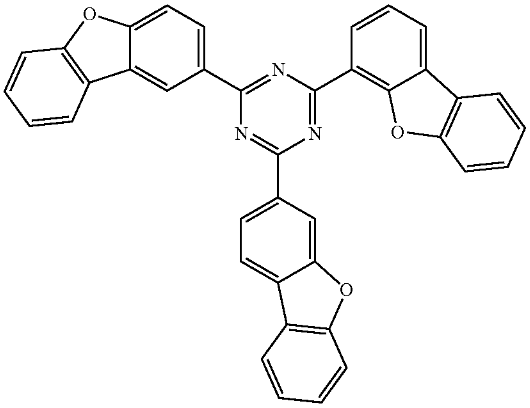
H2-149
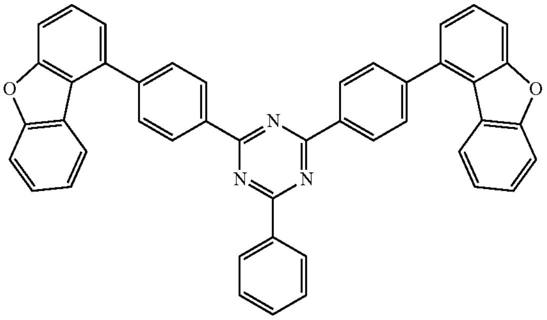

-continued
H2-150
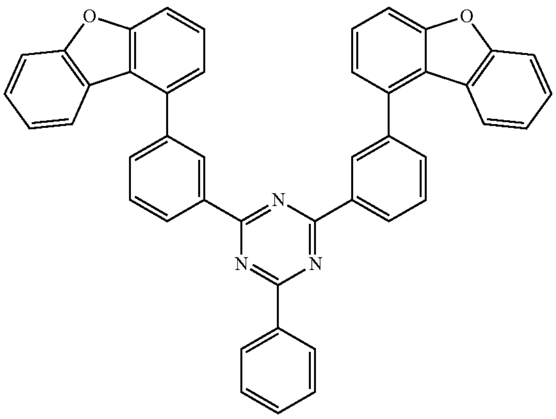
H2-151
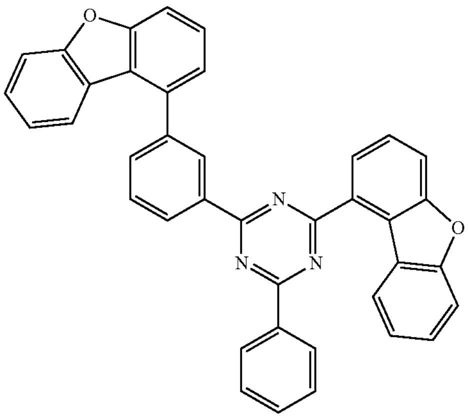
H2-152
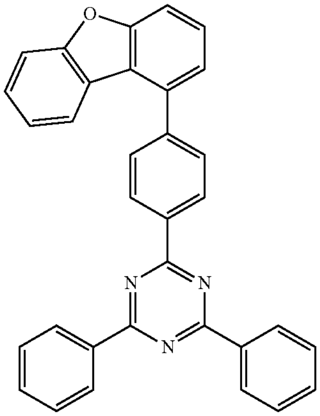
-continued
H2-153
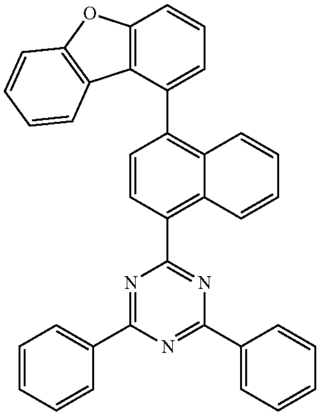
H2-154
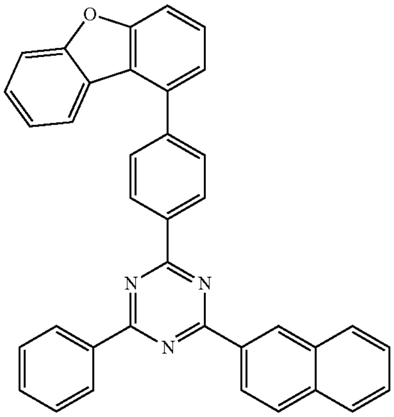
H2-155
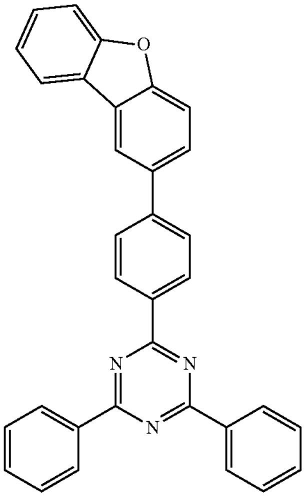

-continued
H2-156
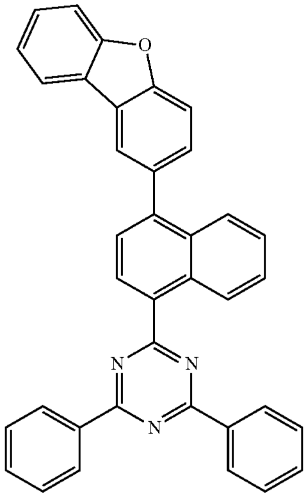
H2-157
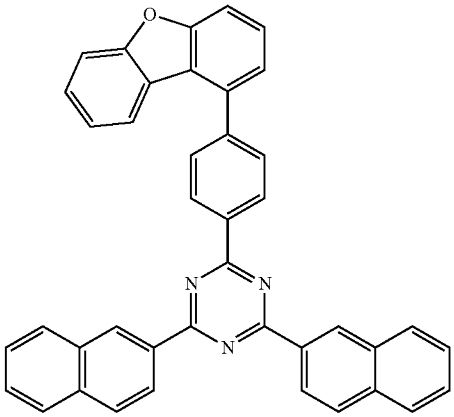
H2-158
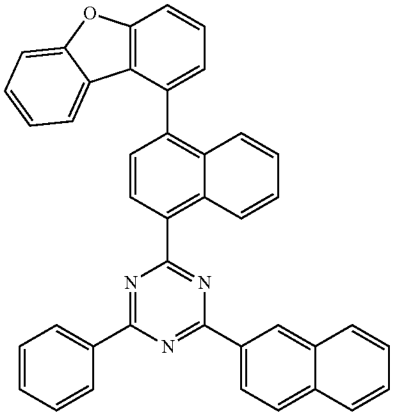
-continued
H2-159
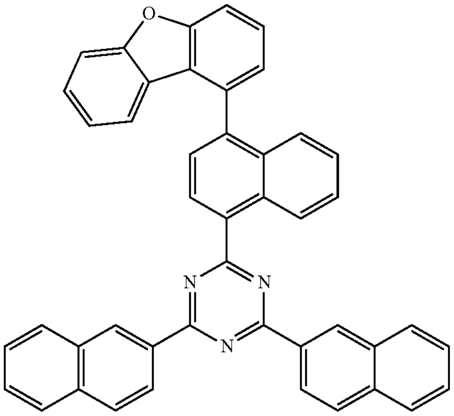
H2-160
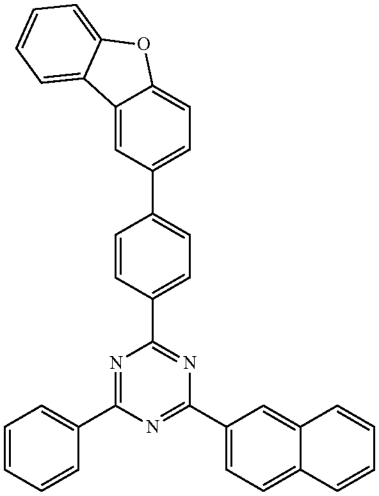
H2-161
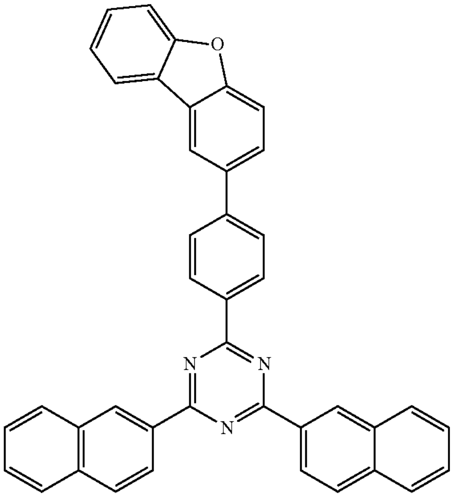

H2-162
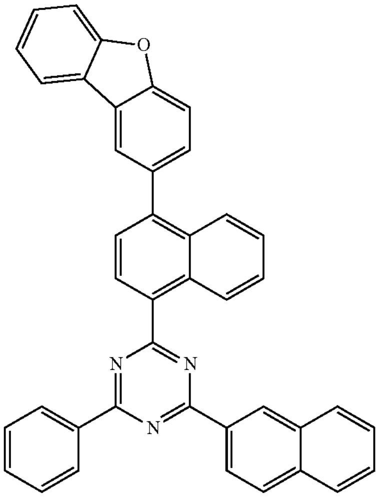
H2-163
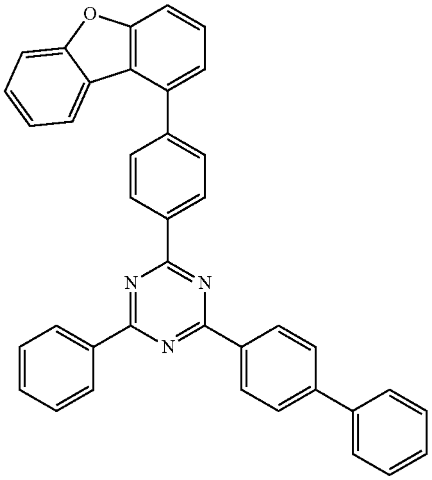
H2-164
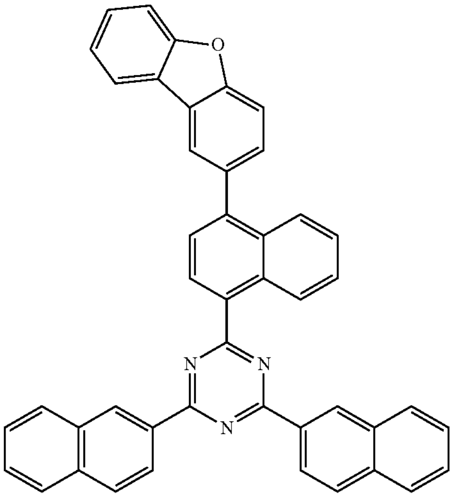
H2-165
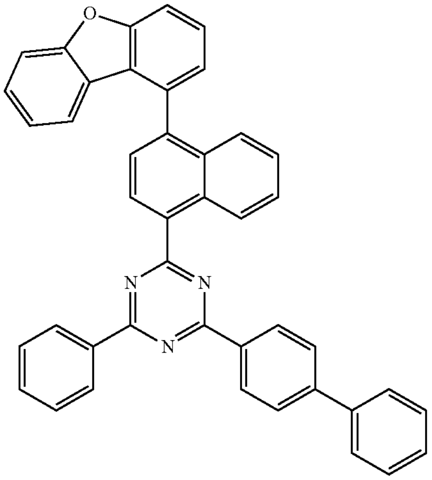
H2-166
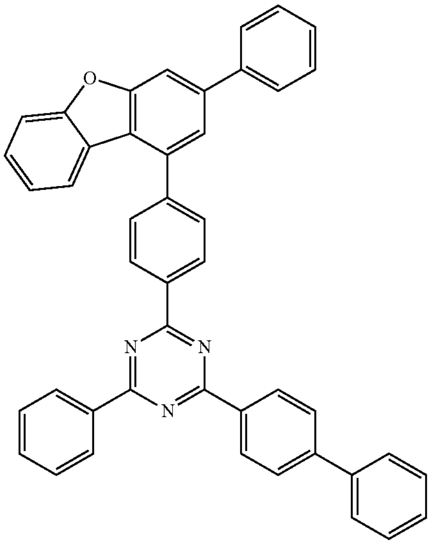
H2-167
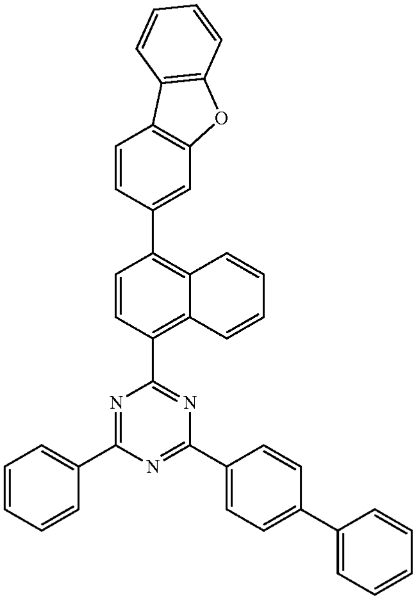

-continued
H2-168
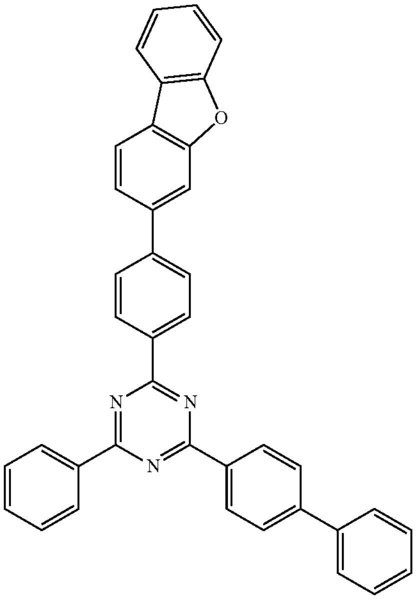
H2-169
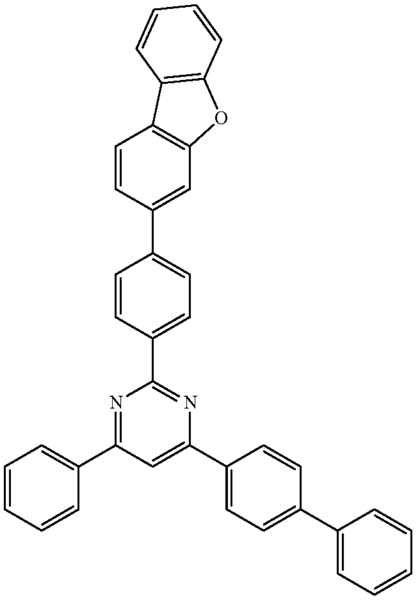
-continued
H2-170
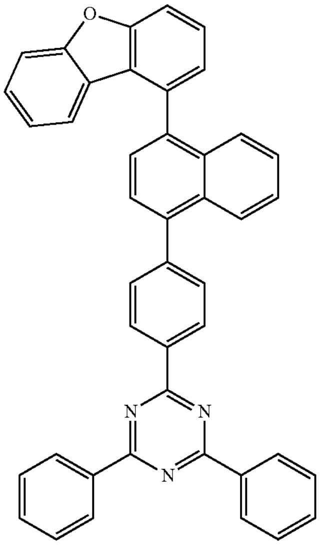
H2-171
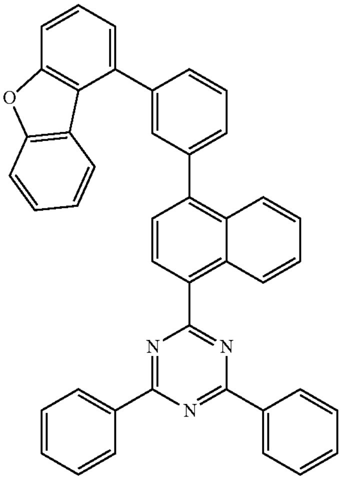
H2-172
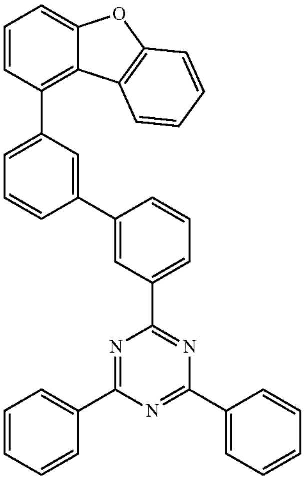

-continued
H2-173
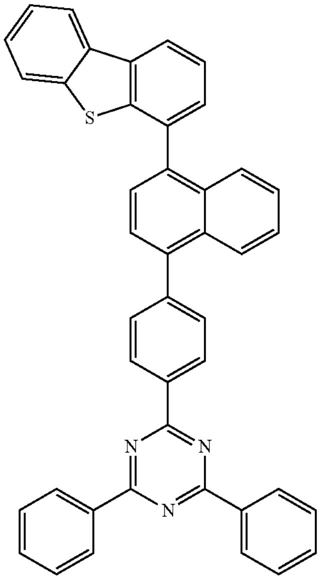
H2-174
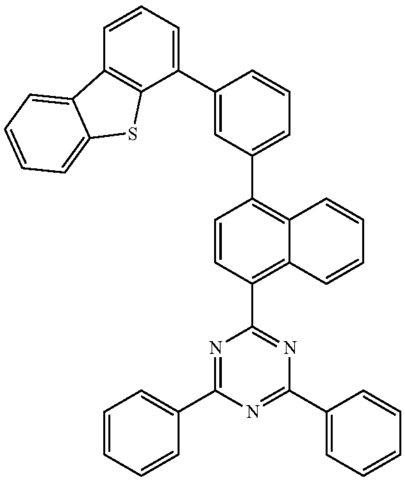
H2-175
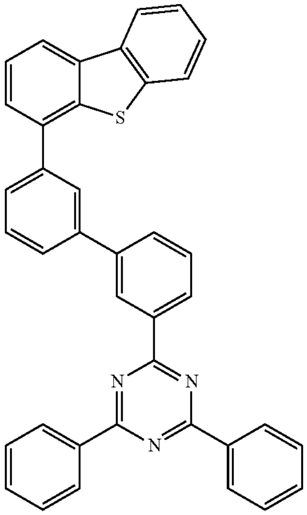
-continued
H2-176
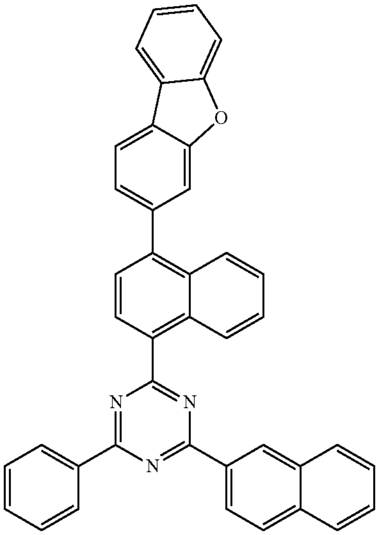
H2-177
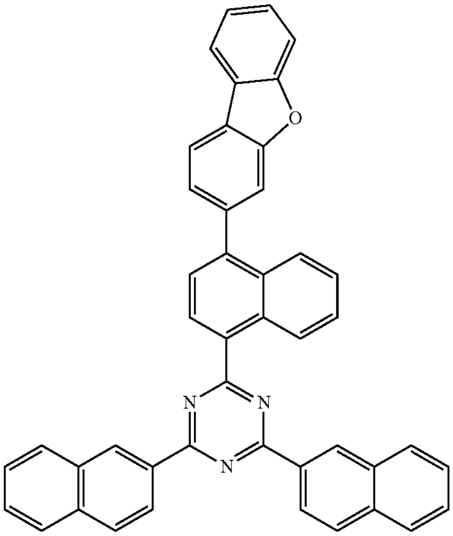
H2-178
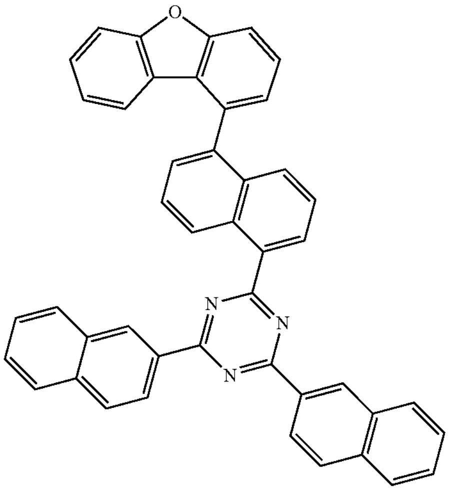

-continued
H2-179
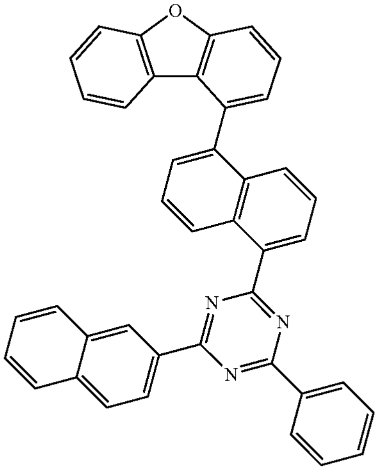
H2-180
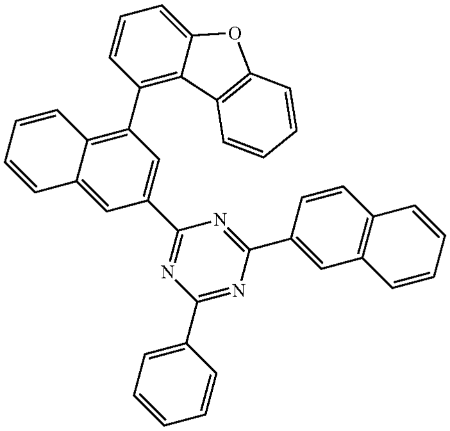
H2-181
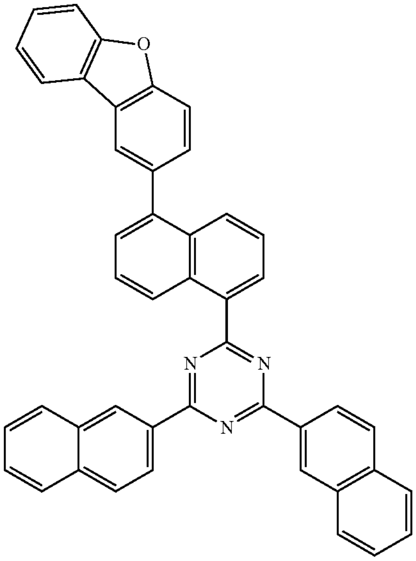
-continued
H2-182
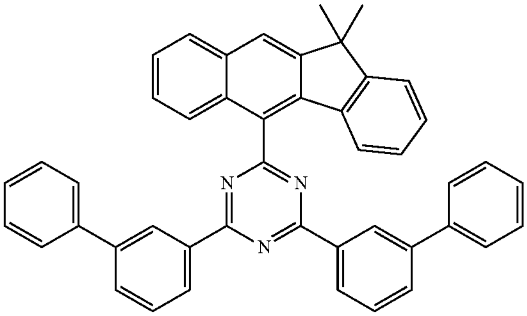
H2-183
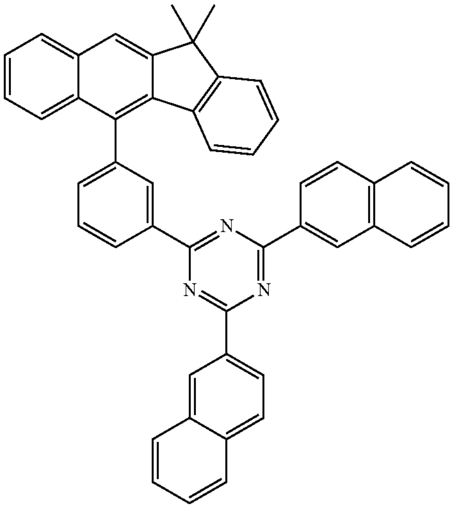
H2-184
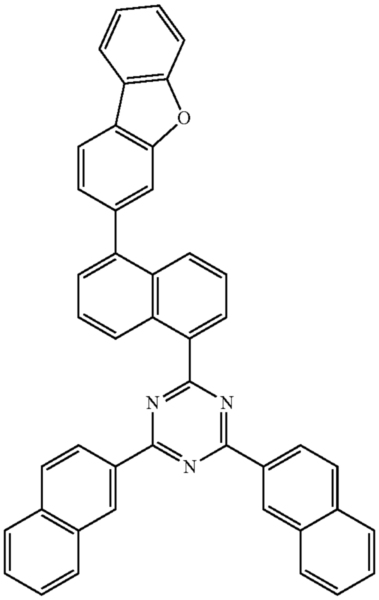

-continued
H2-185
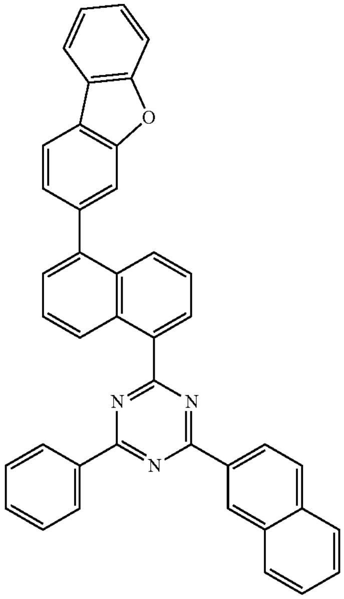
H2-186
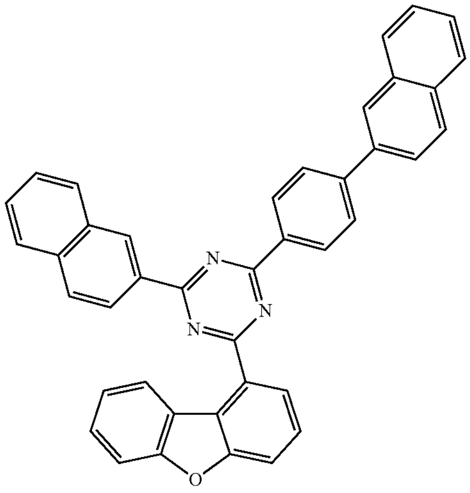
H2-187
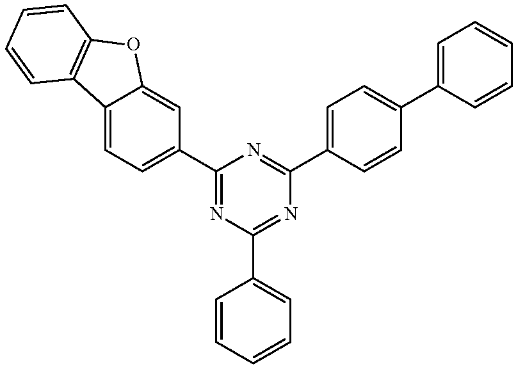
-continued
H2-188
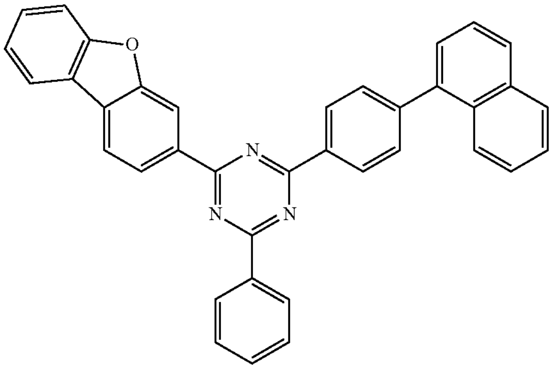
H2-189
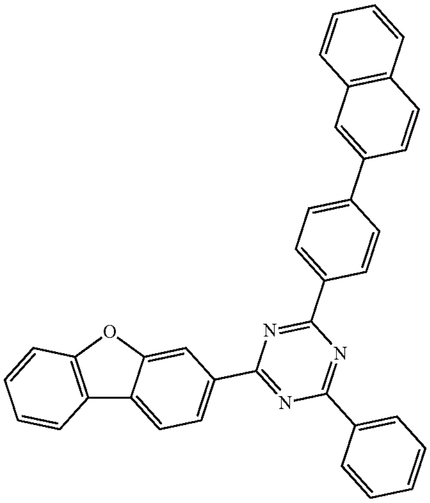
H2-190
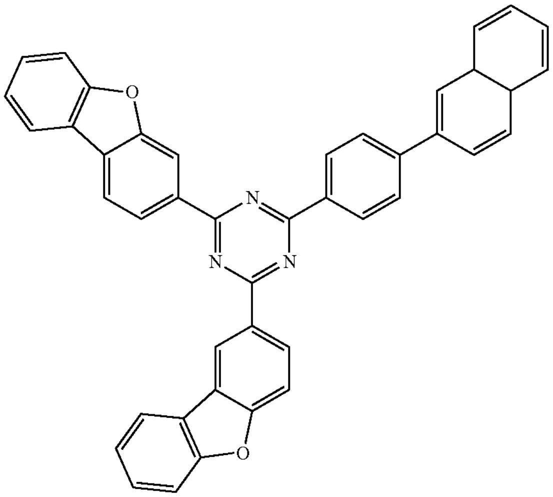

-continued
H2-191
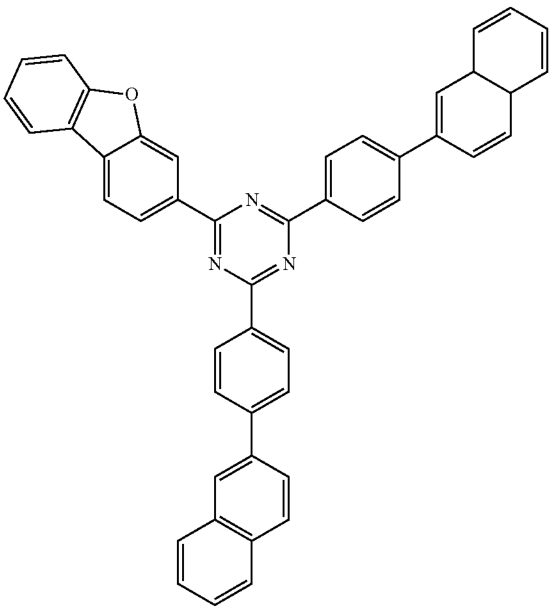
H2-192
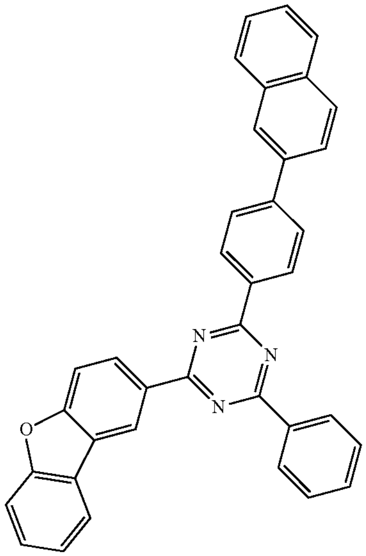
H2-193
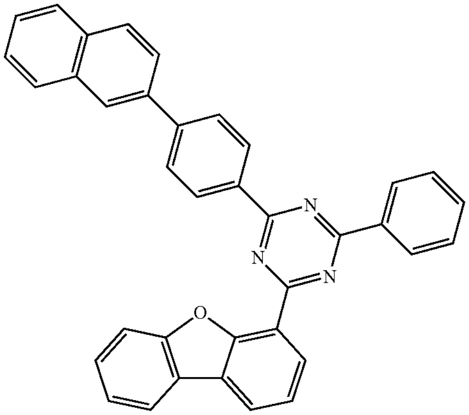
-continued
H2-194
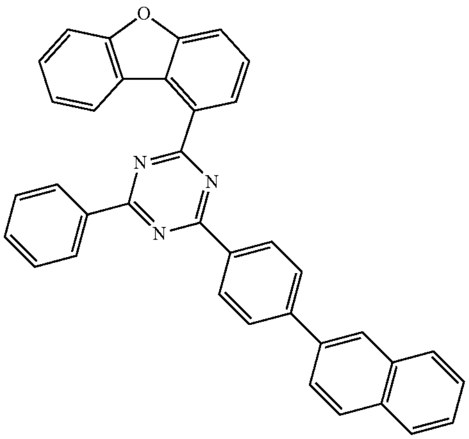
H2-195
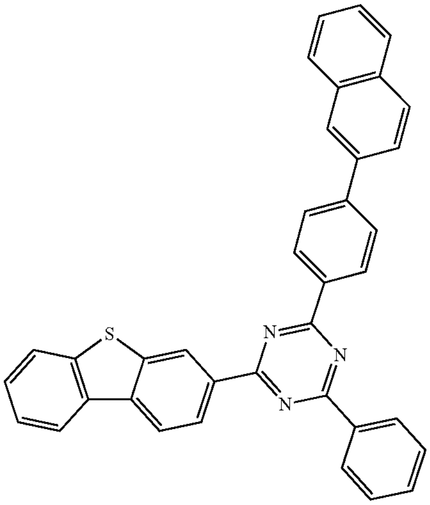
H2-196
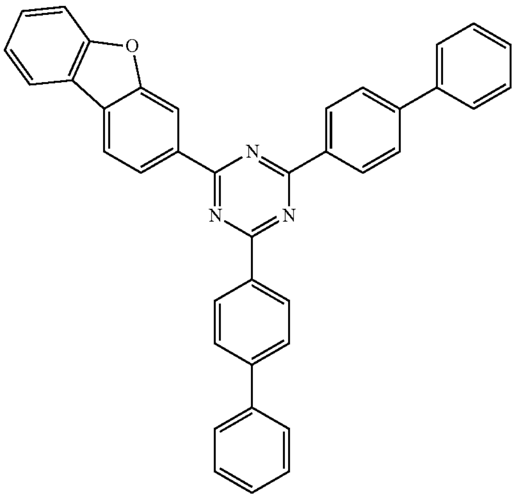

-continued
H2-197
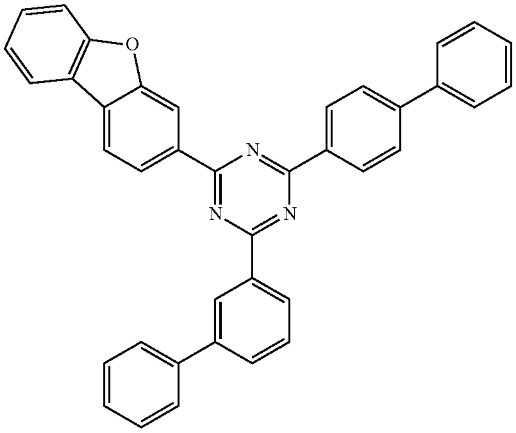
H2-198
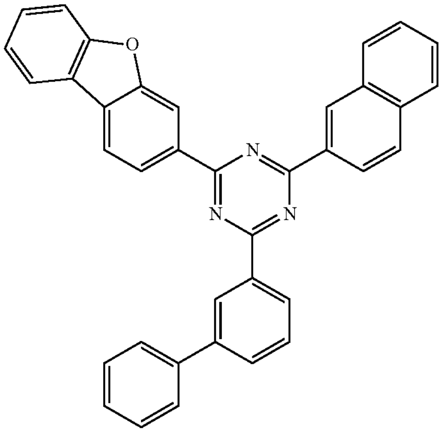
H2-199
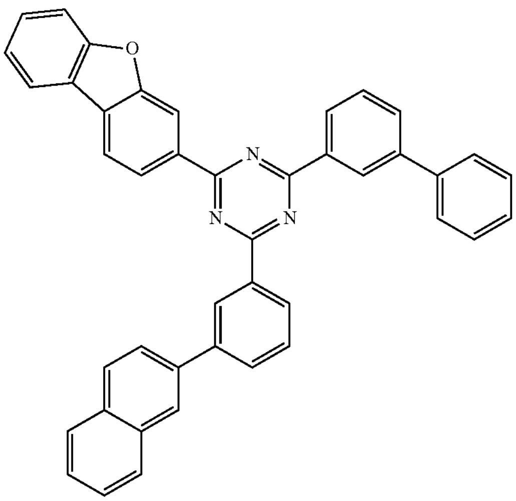
-continued
H2-200
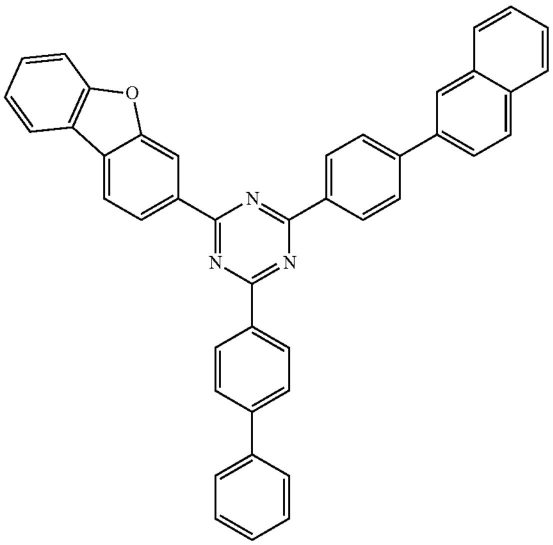
H2-201
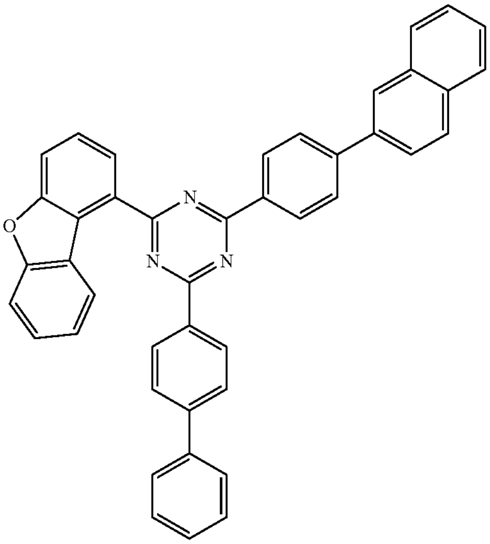
H2-202
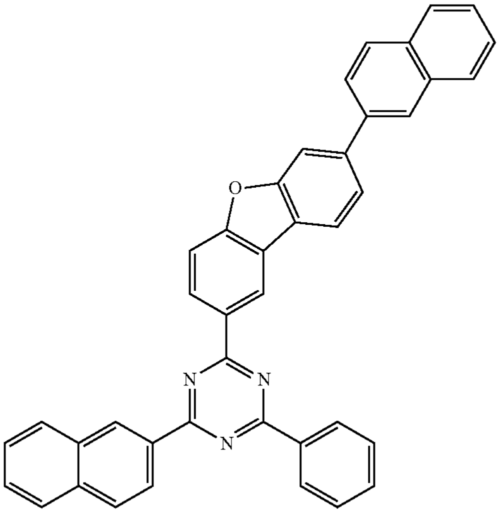

-continued
H2-203
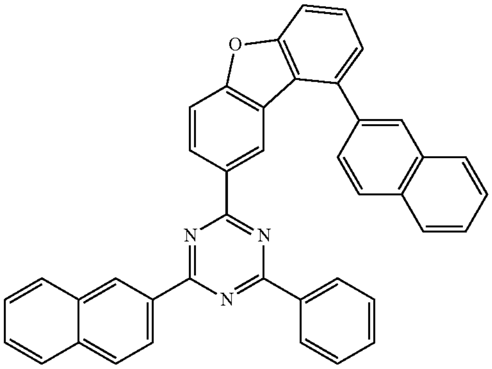
H2-204
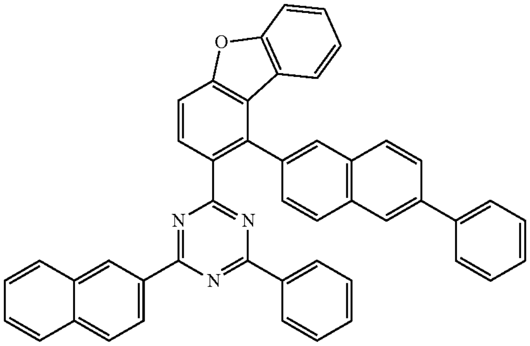
H2-205
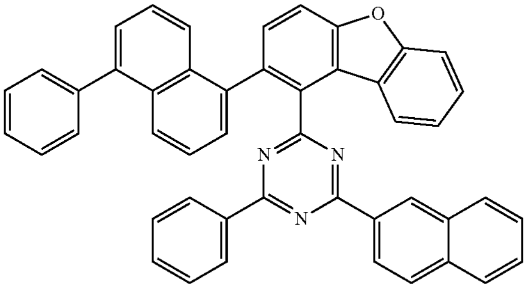
H2-206
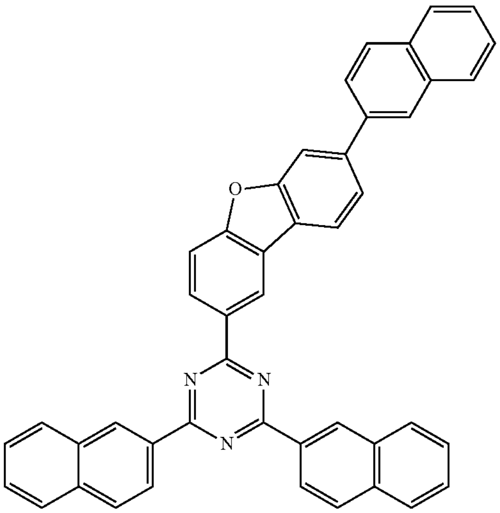
-continued
H2-207
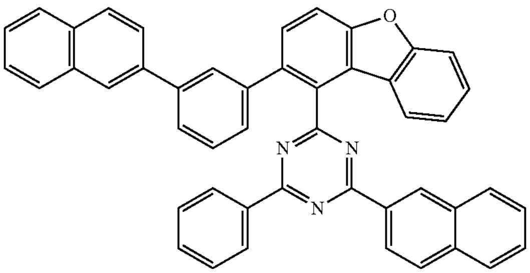
H2-208
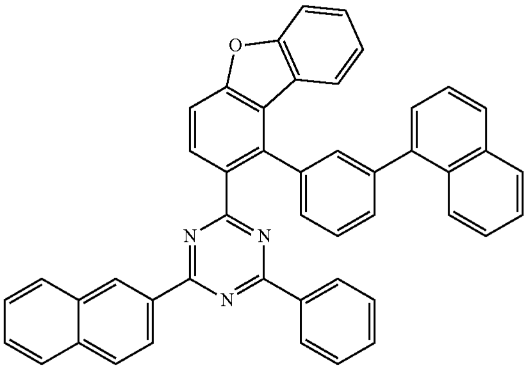
H2-209
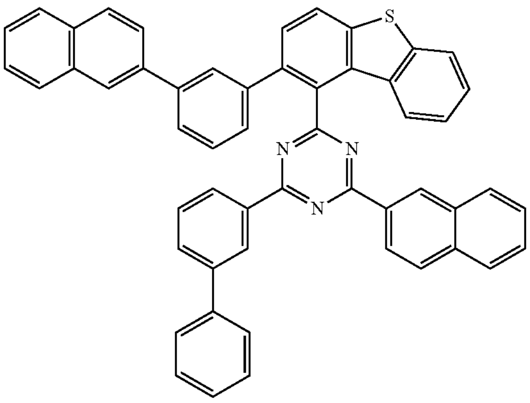
H2-210
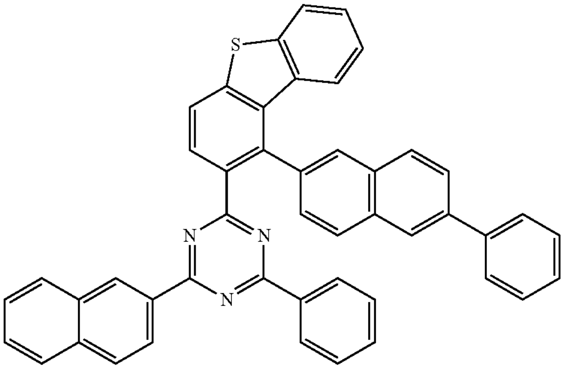

H2-211
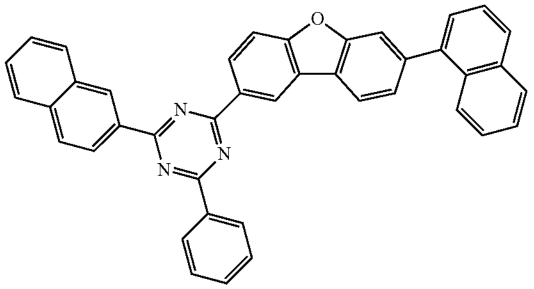
H2-212
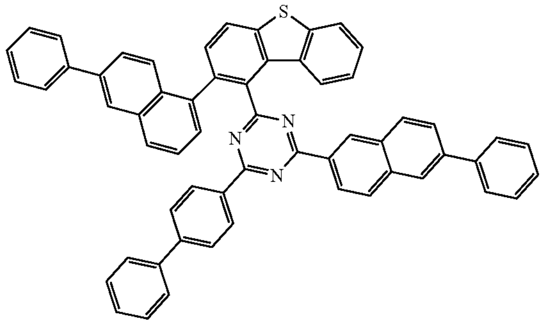
H2-213
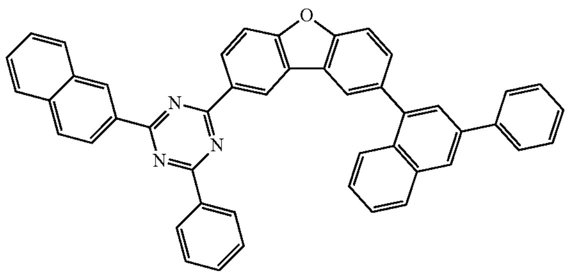
H2-214
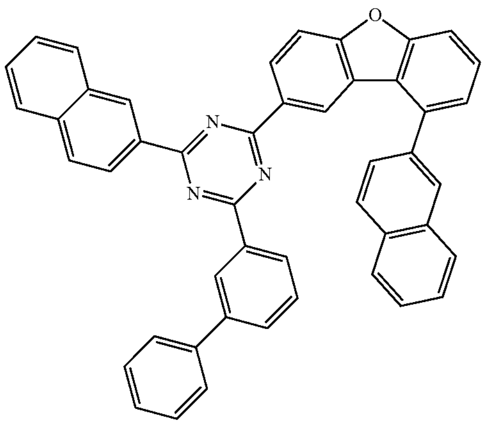
H2-215
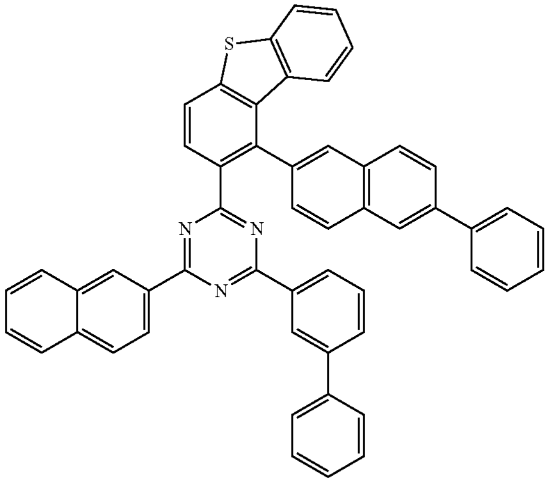
H2-216
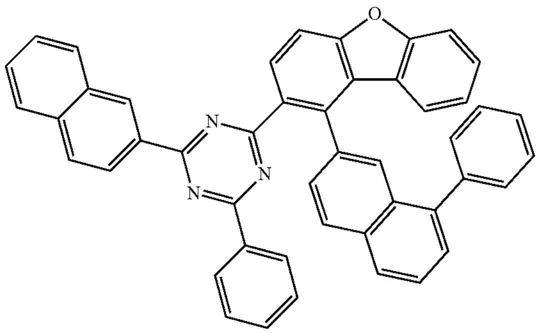
H2-217
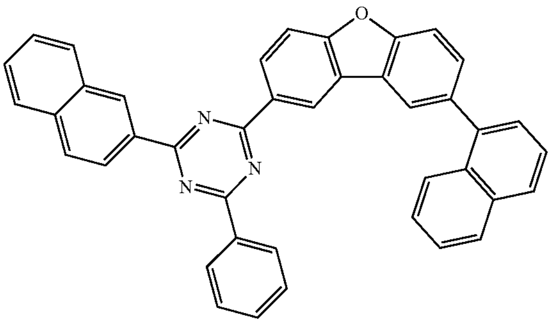

-continued
H2-218
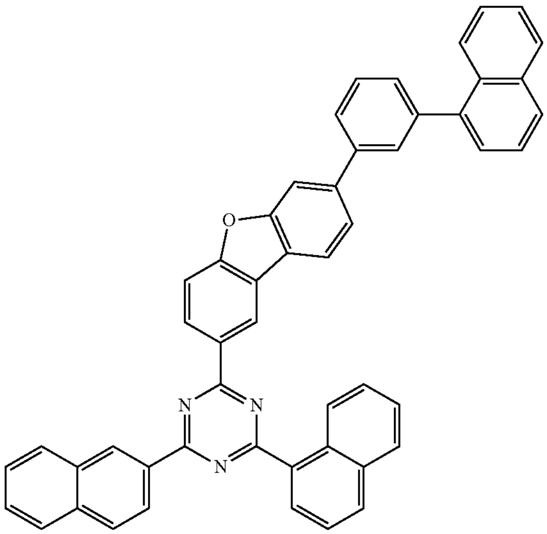
H2-219
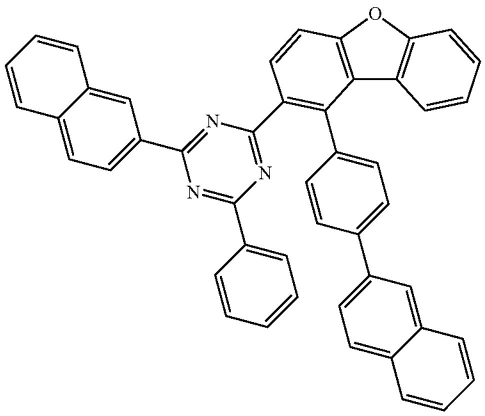
H2-220
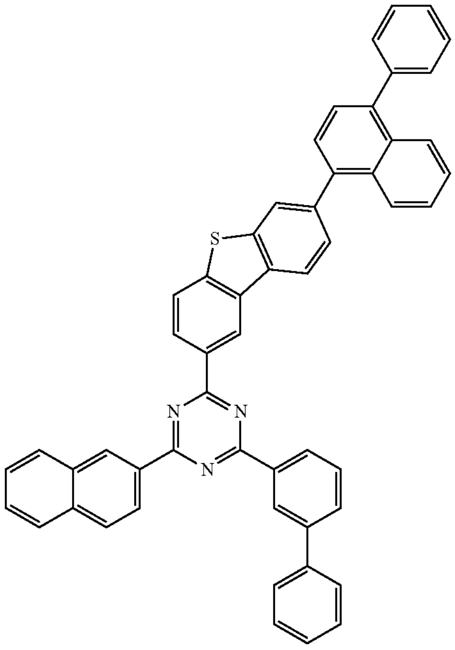
-continued
H2-221
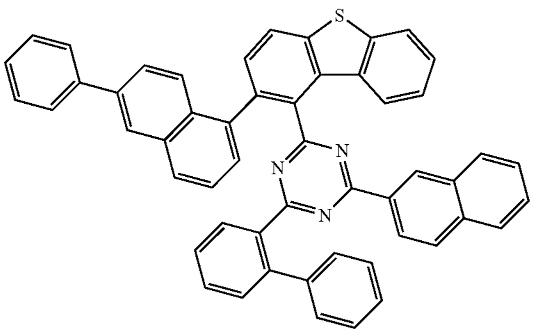
H2-222
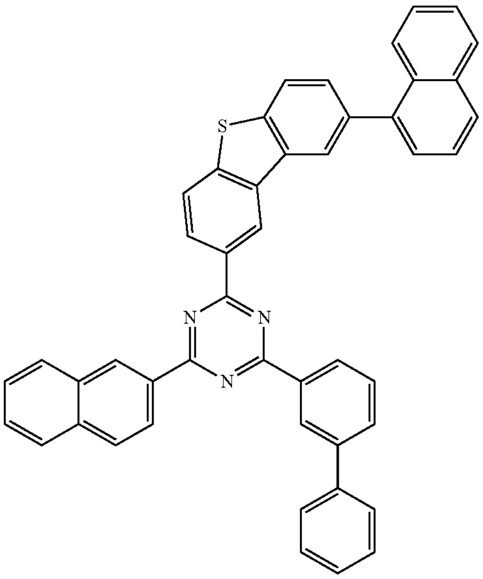
H2-223
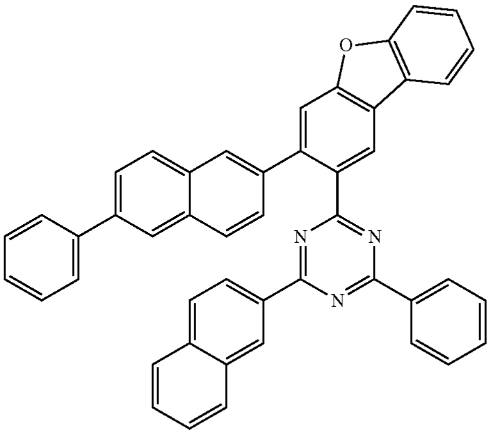

-continued
H2-224
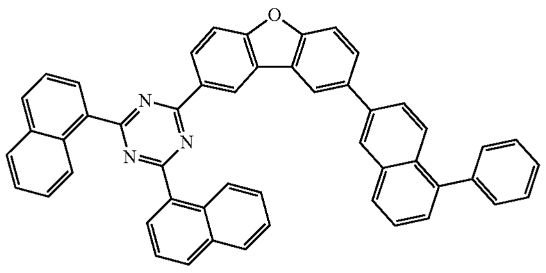
H2-225
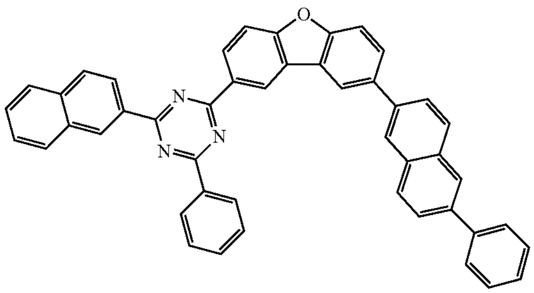
H2-226
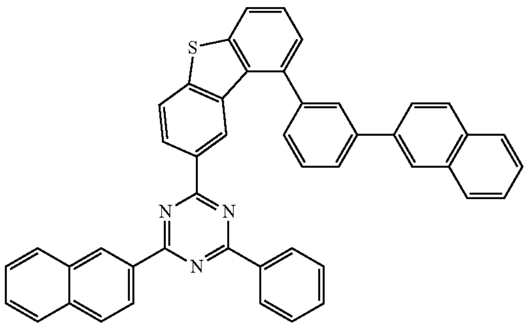
H2-227
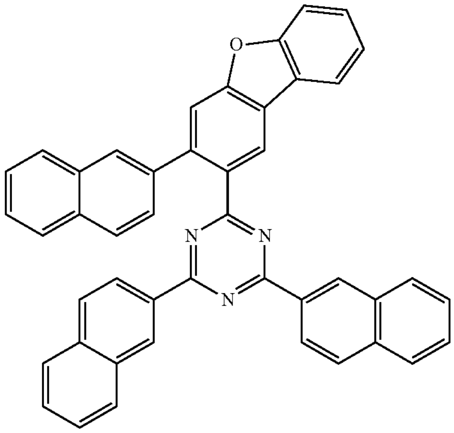
-continued
H2-228
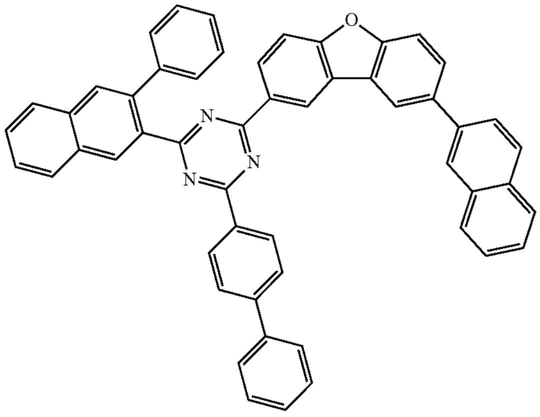
H2-229
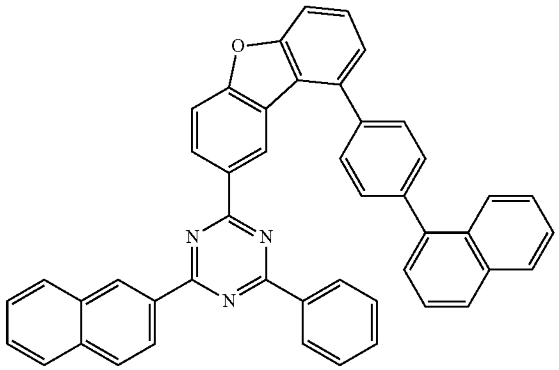
H2-230
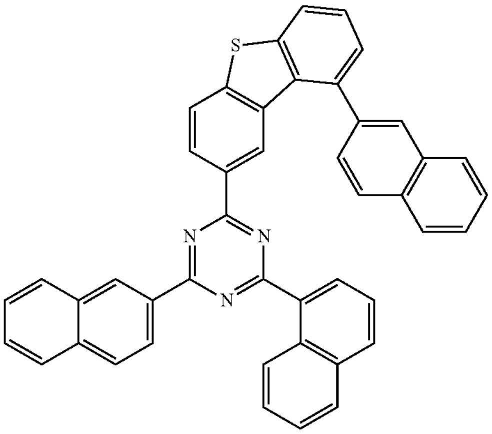

-continued
H2-231
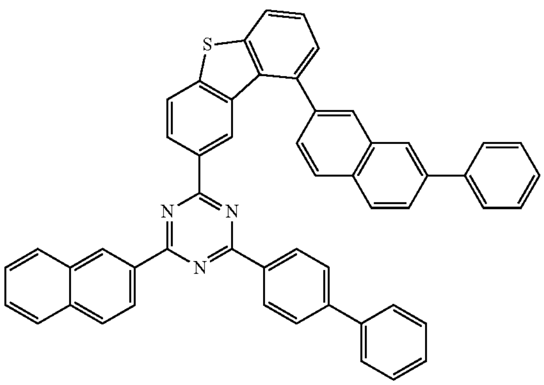
H2-232
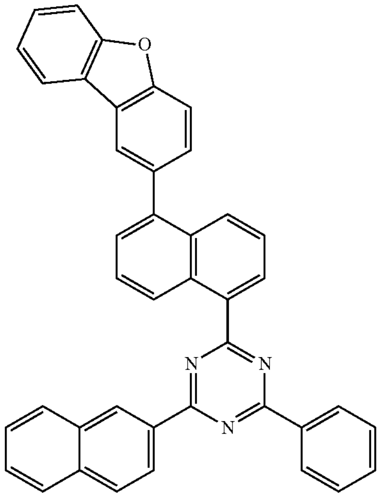
H2-233
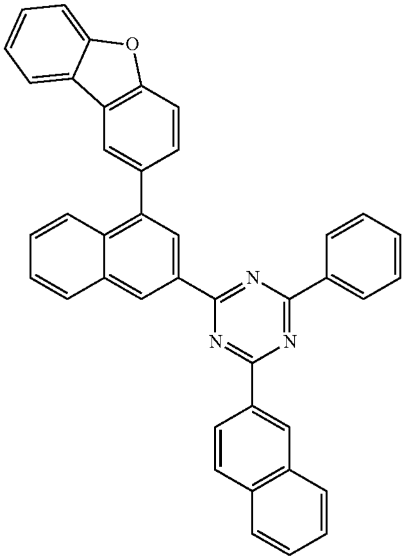
-continued
H2-234
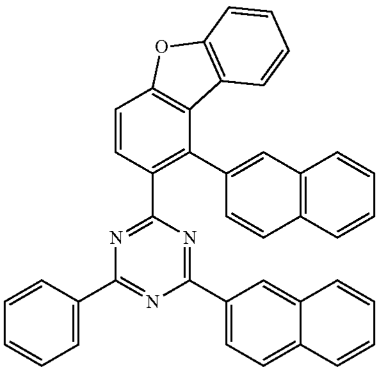
H2-235
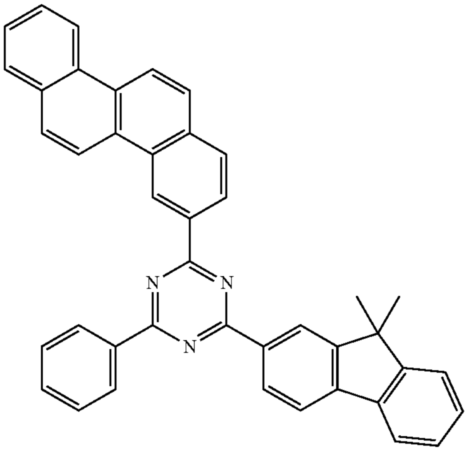
H2-236
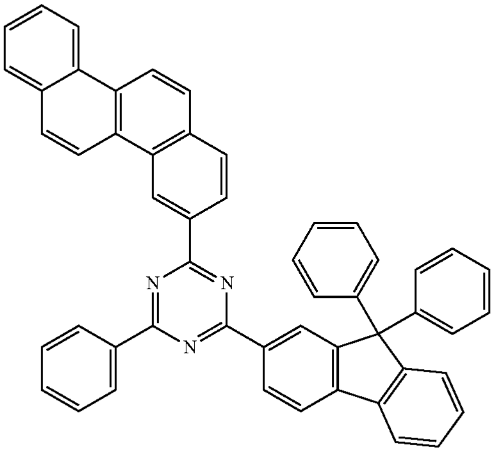

H2-237
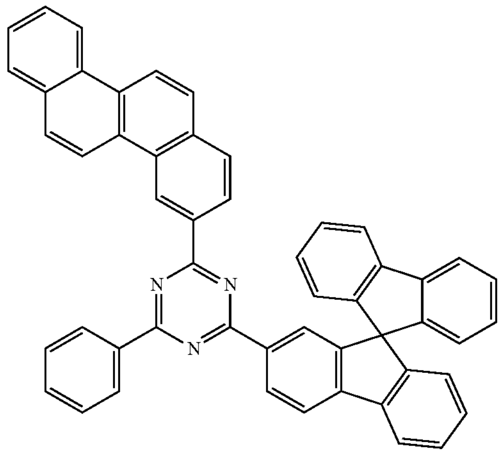
H2-238
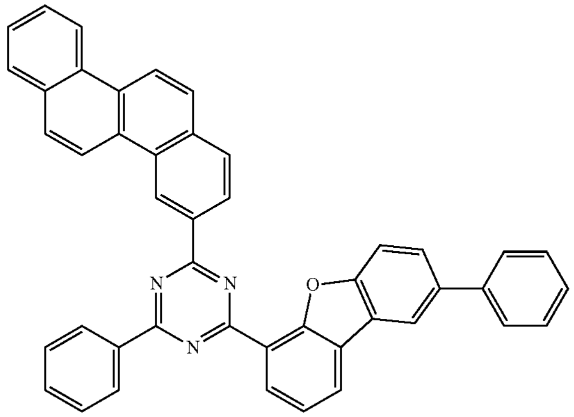
H2-239
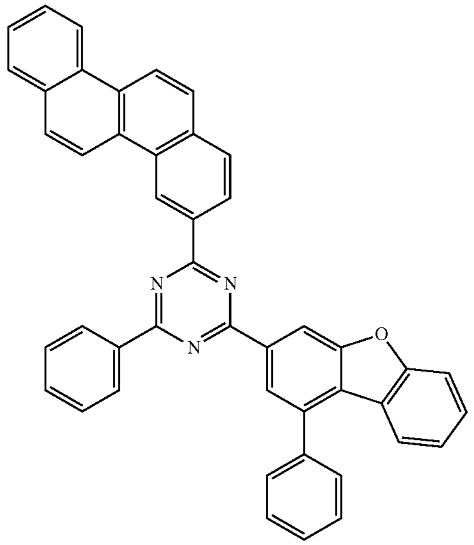
H2-240
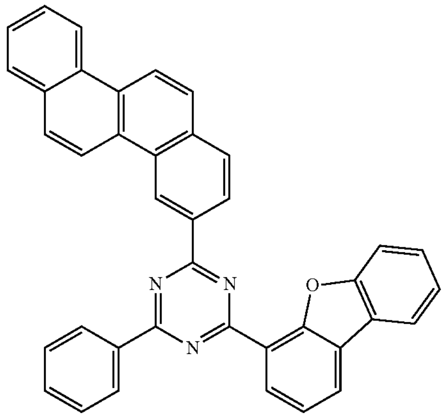
H2-241
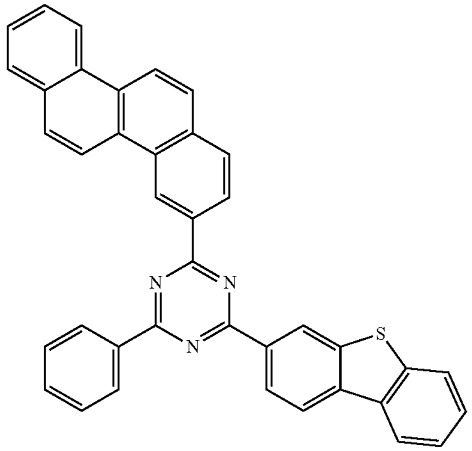
H2-242
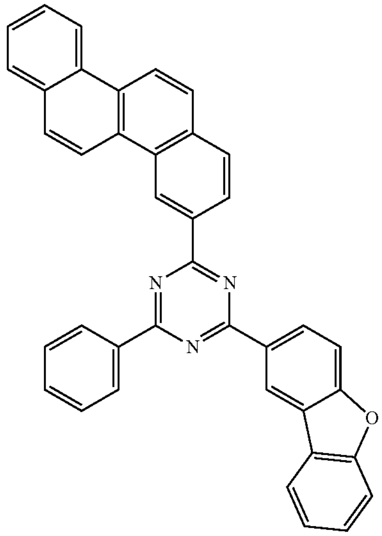

-continued
H2-243
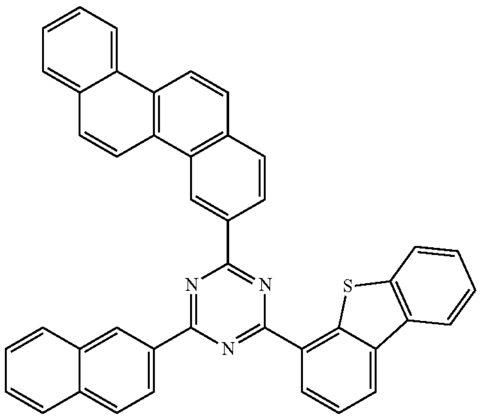
H2-244
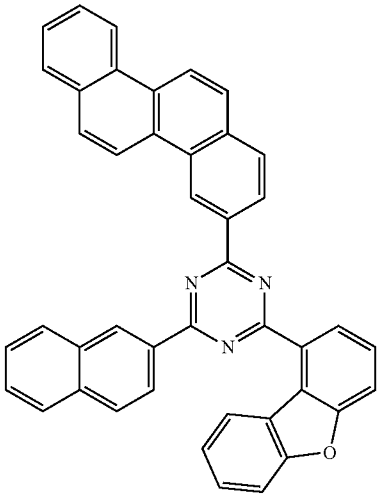
H2-245
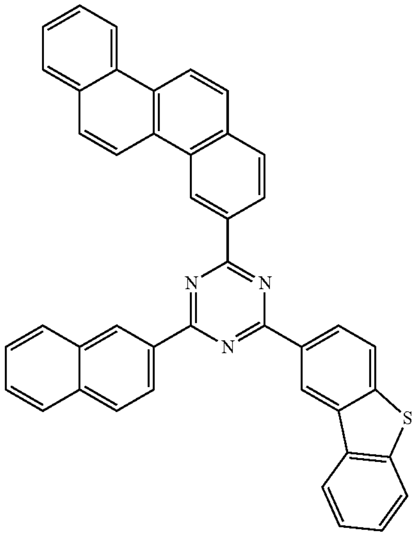
-continued
H2-246
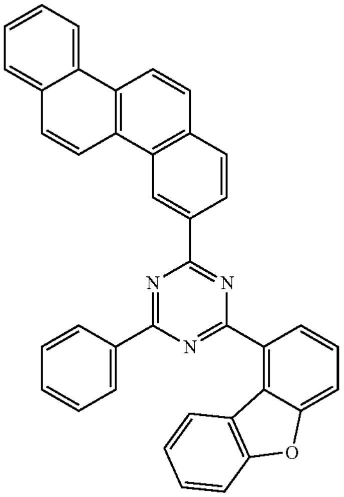
H2-247
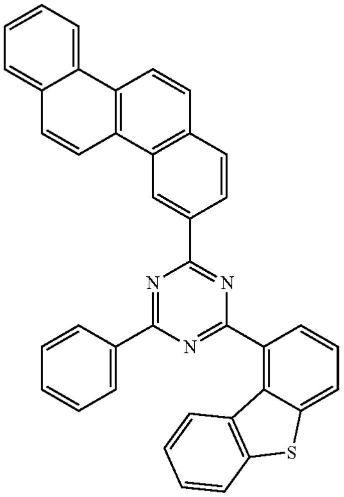
H2-248
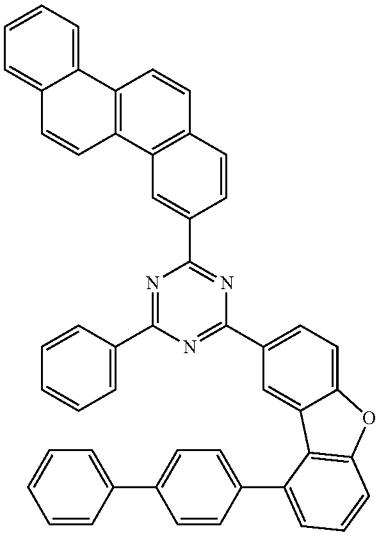

-continued
H2-249
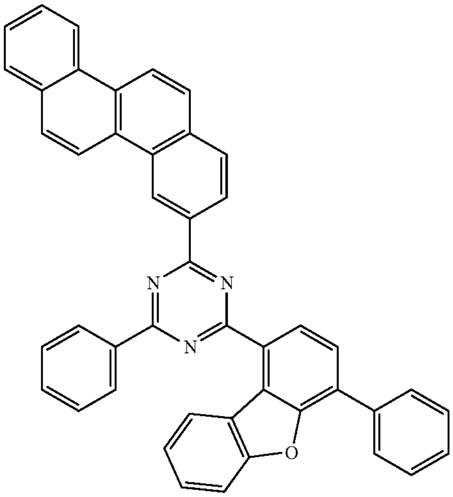
H2-250
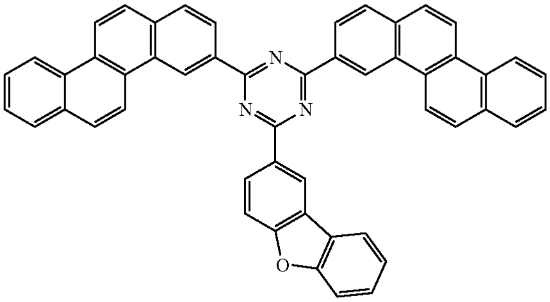
H2-251
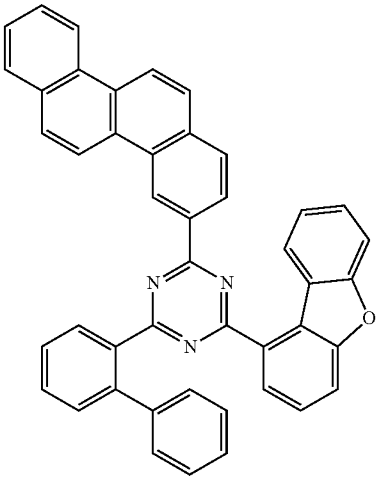
-continued
H2-252
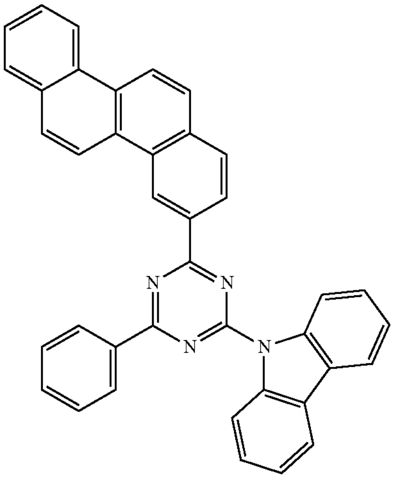
H2-253
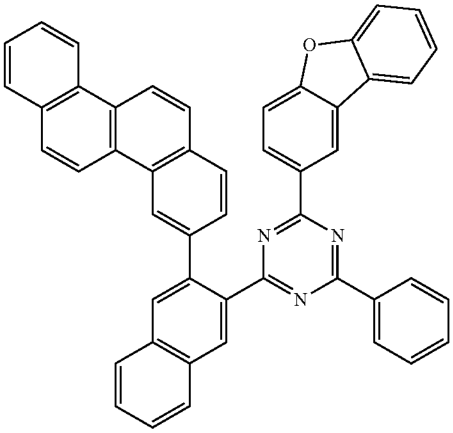
H2-254
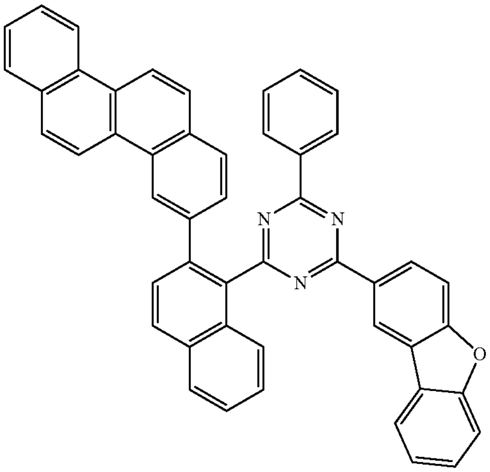

-continued
H2-255
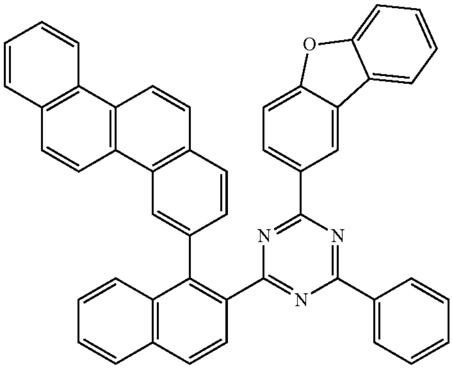
H2-256
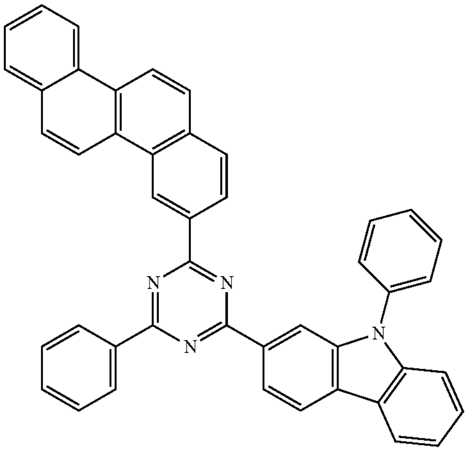
H2-257
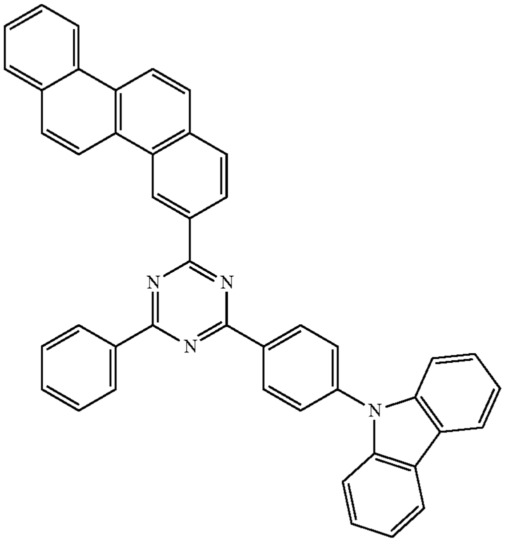
-continued
H2-258
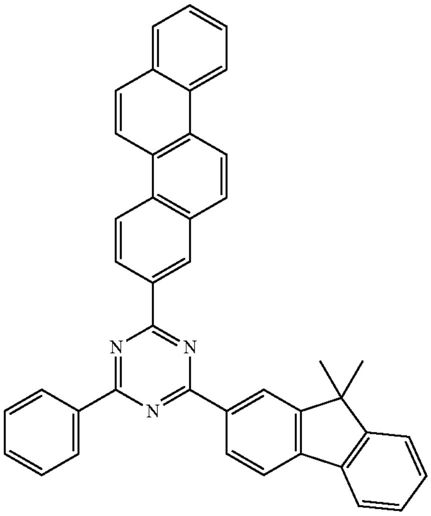
H2-259
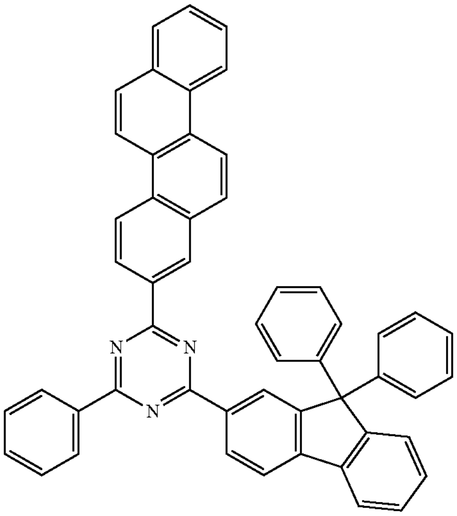
H2-260
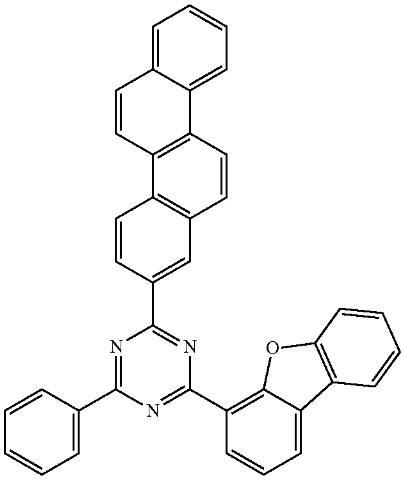

-continued
H2-261
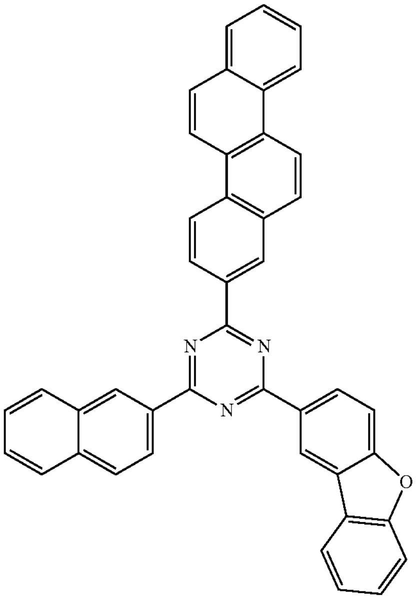
H2-262
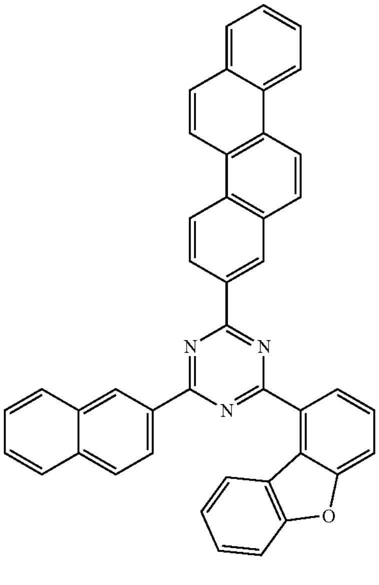
H2-263
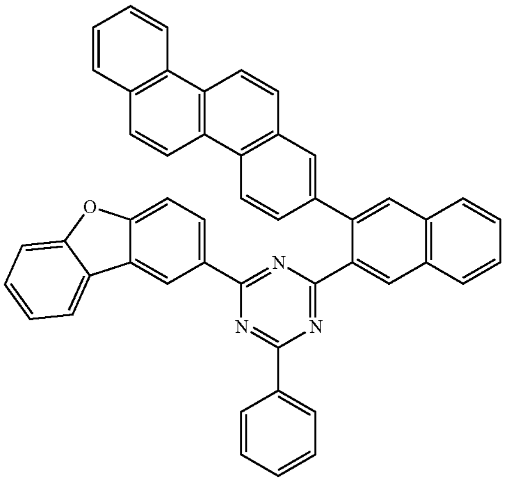
-continued
H2-264
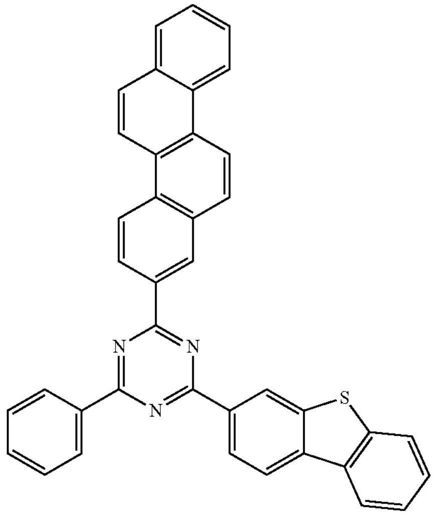
H2-265
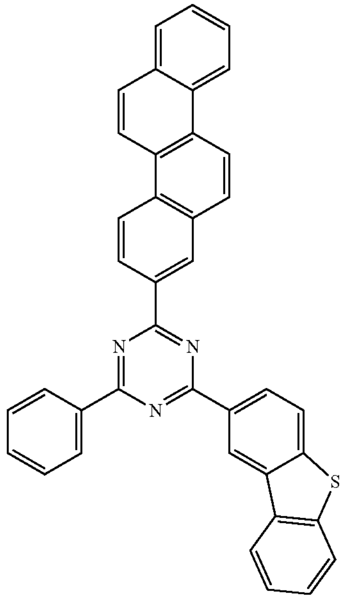

-continued
H2-266
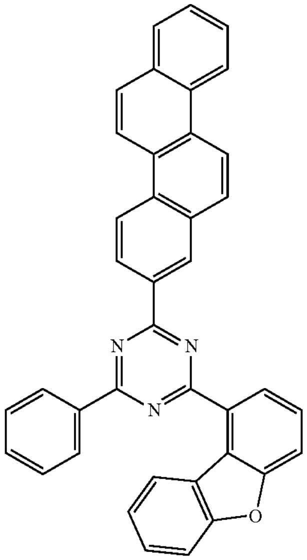
H2-267
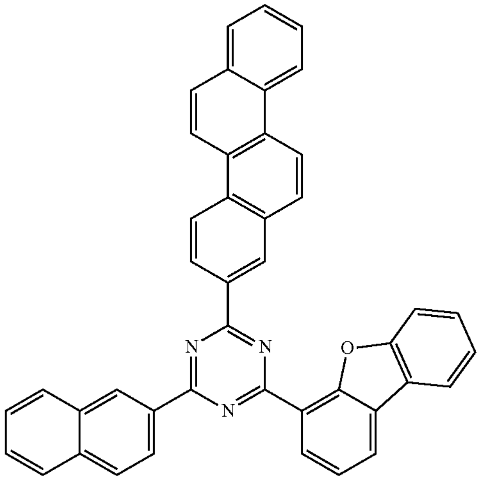
H2-268
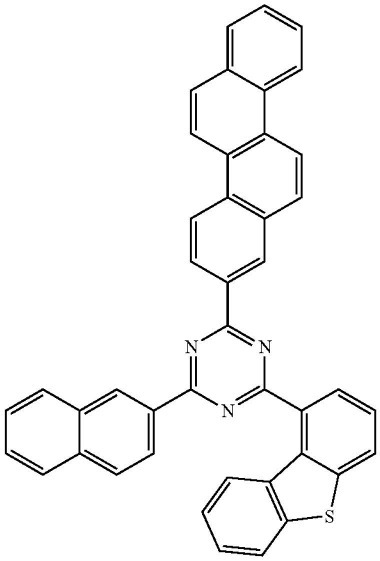
-continued
H2-269
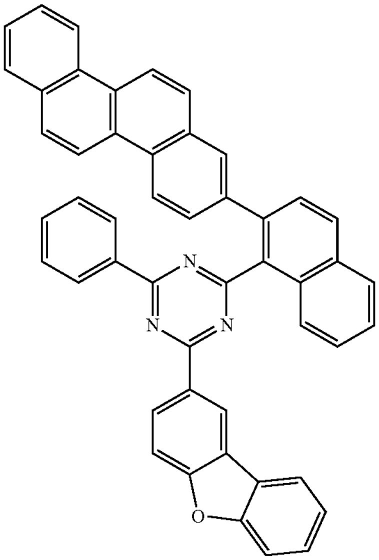
H2-270
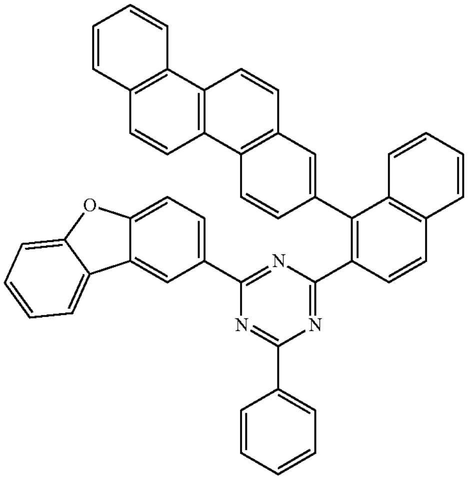
H2-271
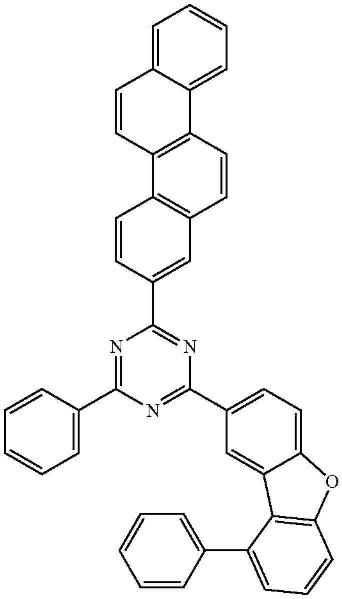

-continued
H2-272
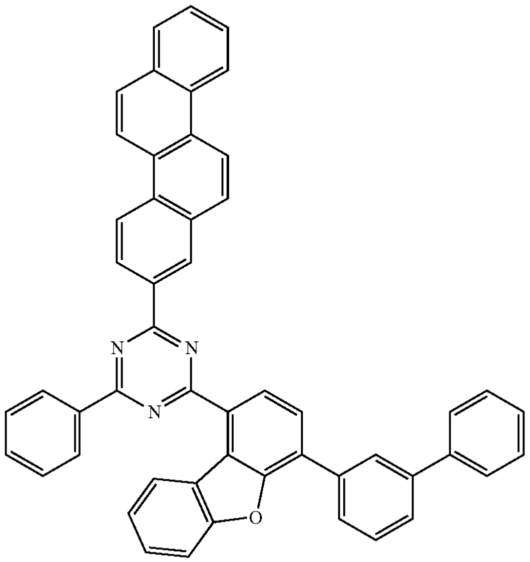
H2-273
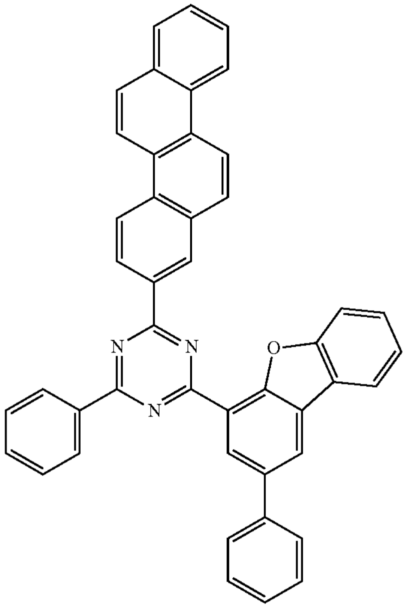
H2-274
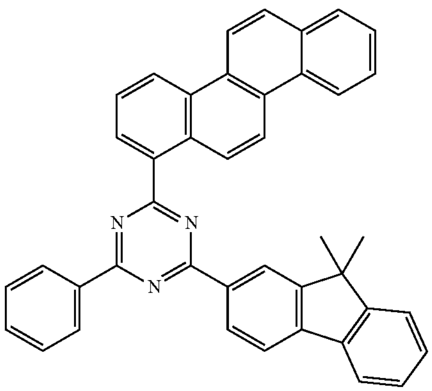
-continued
H2-275
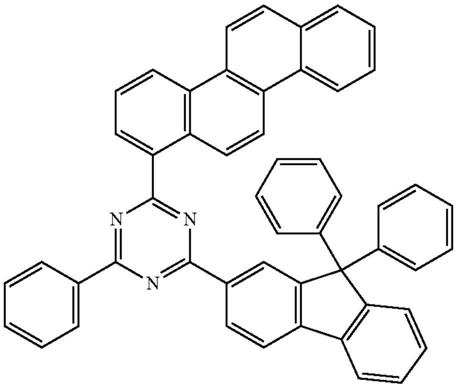
H2-276
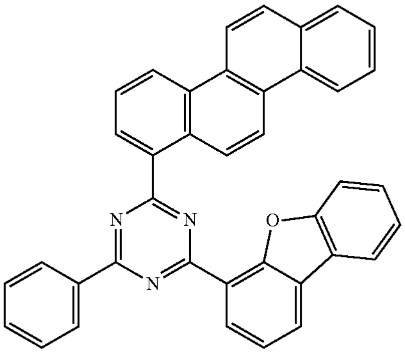
H2-277
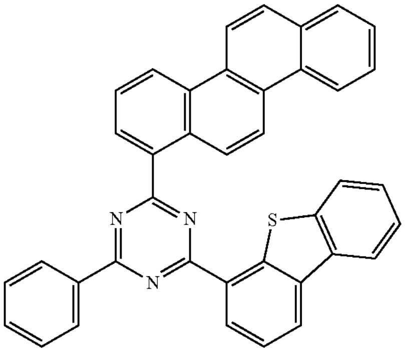
H2-278
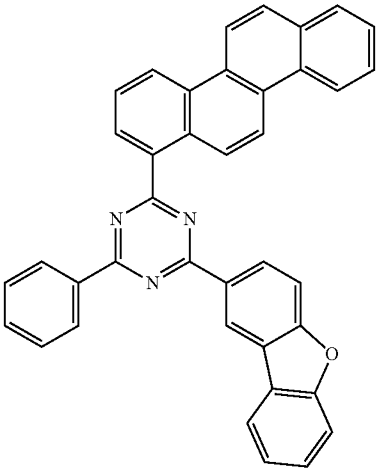

-continued
H2-279
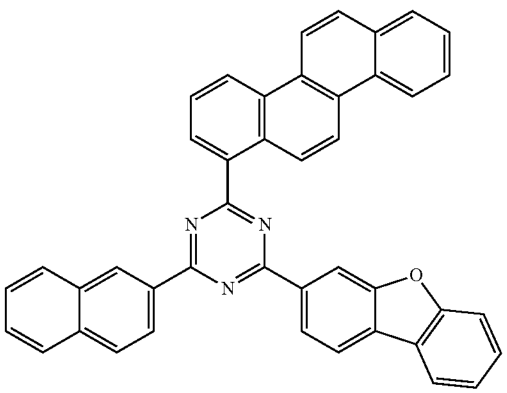
H2-280
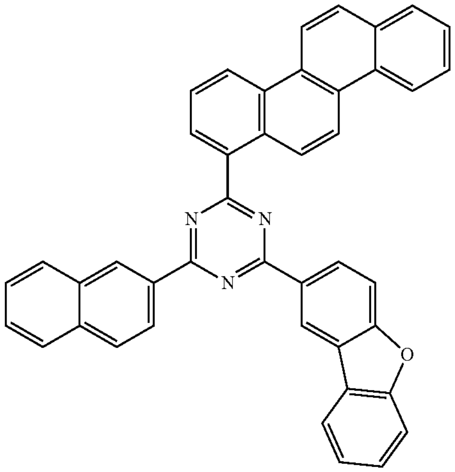
H2-281
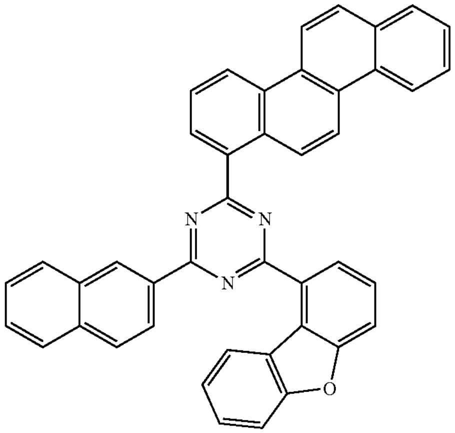
-continued
H2-282
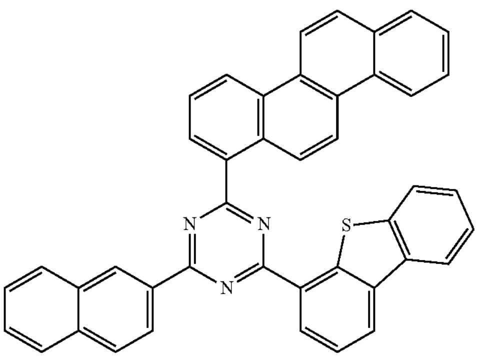
H2-283
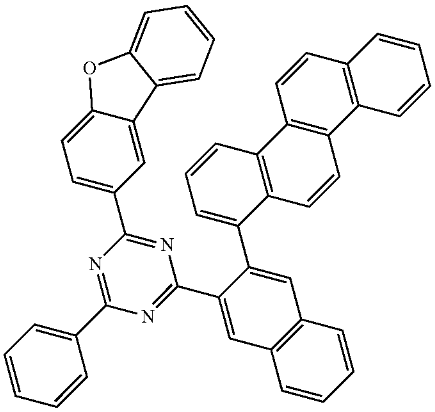
H2-284
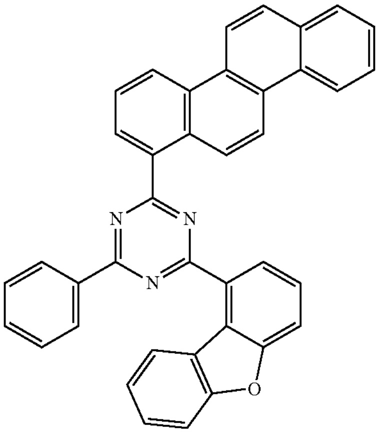
H2-285
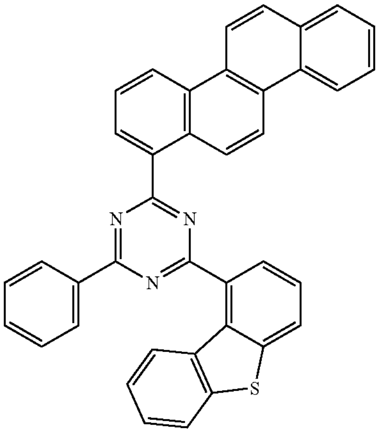

-continued
H2-286
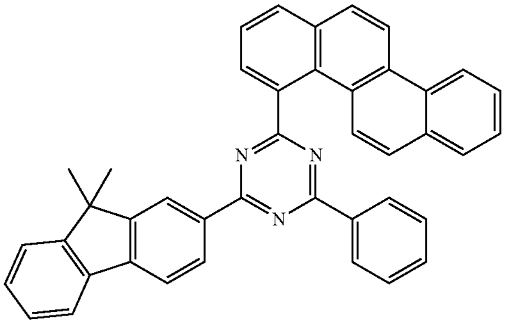
H2-287
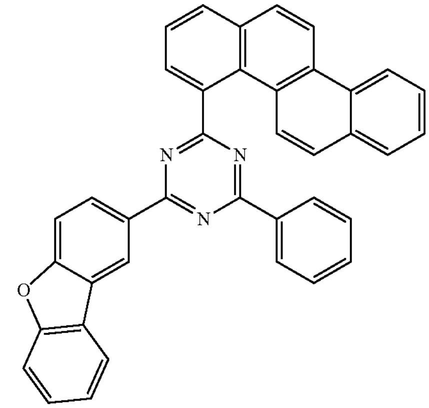
H2-288
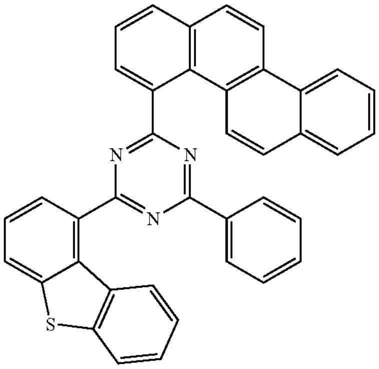
H2-289
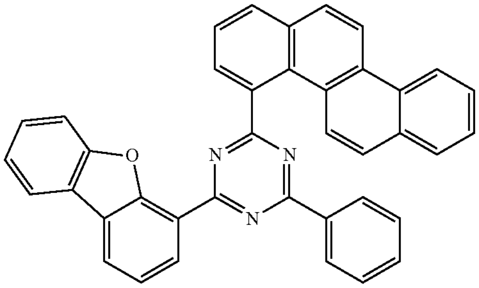
-continued
H2-290
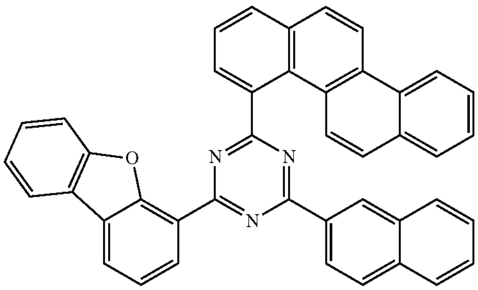
H2-291
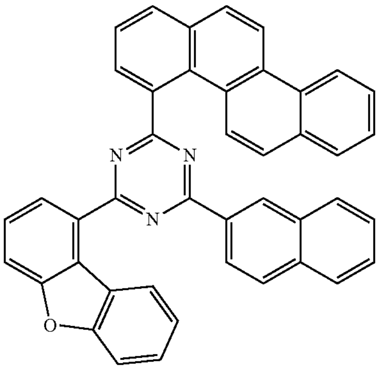
H2-292
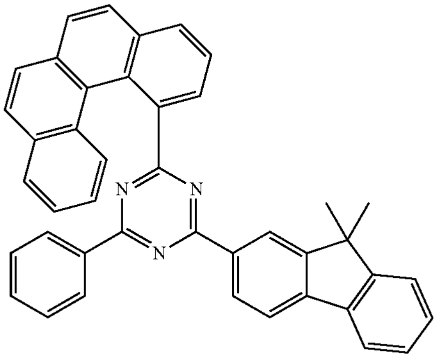
H2-293
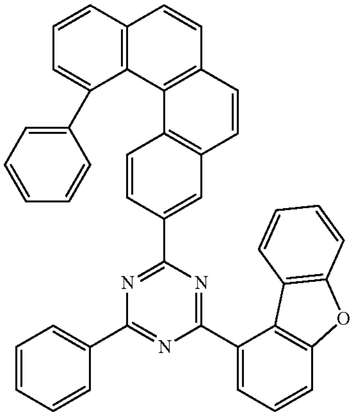

-continued
H2-294
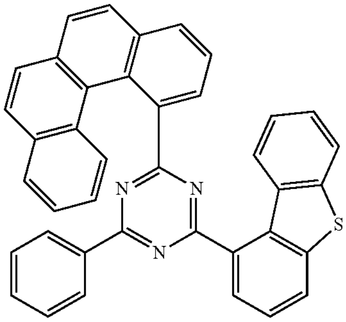
H2-295
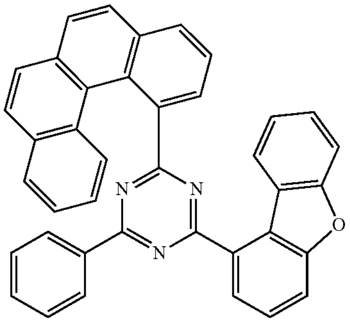
H2-296
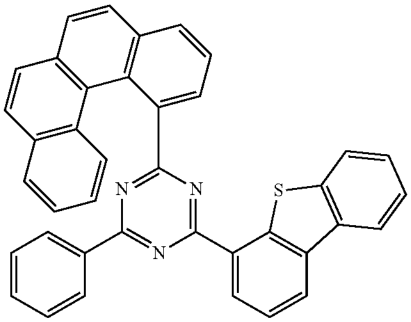
H2-297
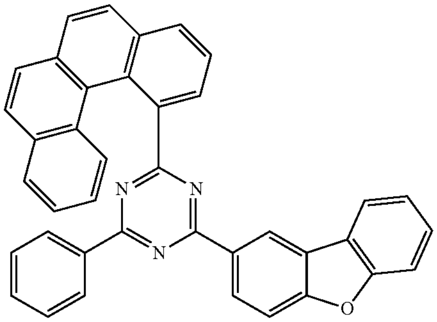
-continued
H2-298
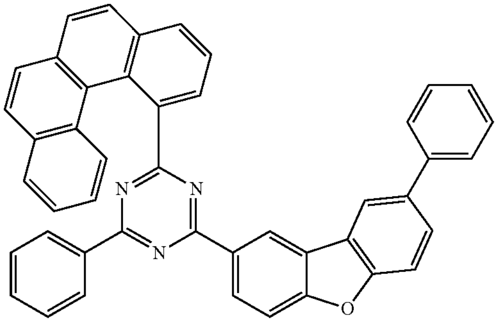
H2-299
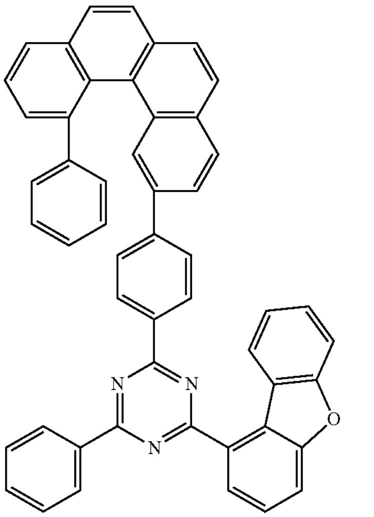
H2-300
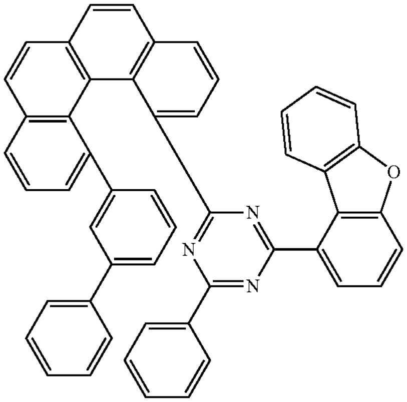

-continued
H2-301
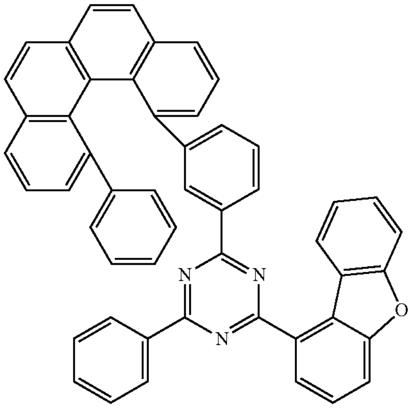
H2-302
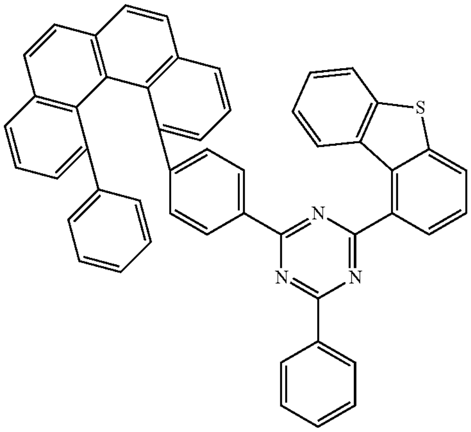
H2-303
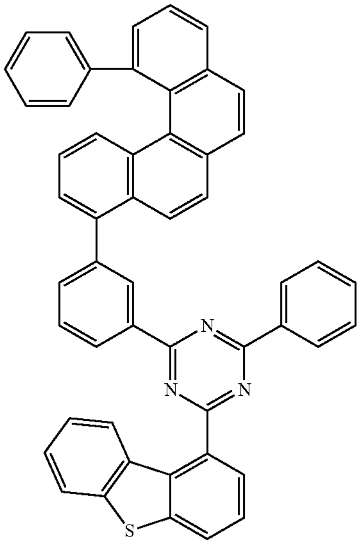
-continued
H2-304
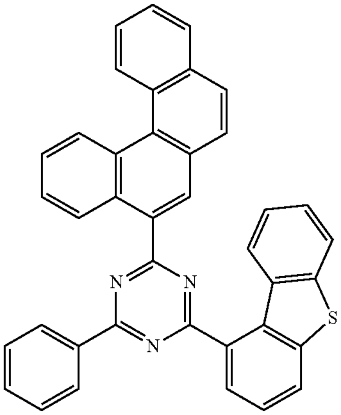
H2-305
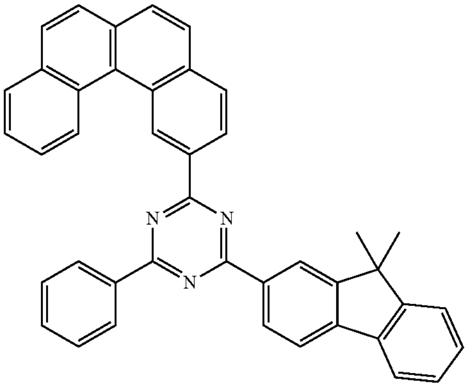
H2-306
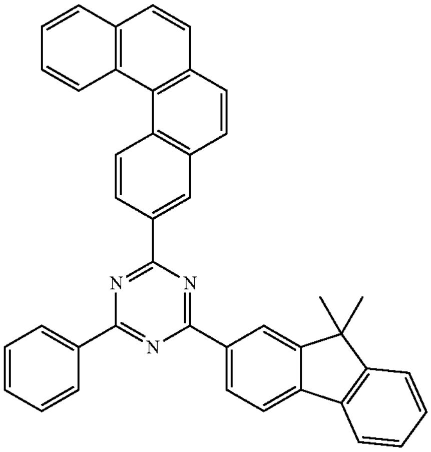
H2-307
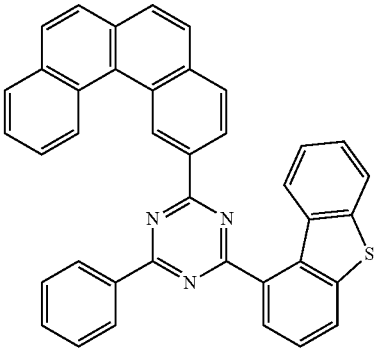

-continued
H2-308
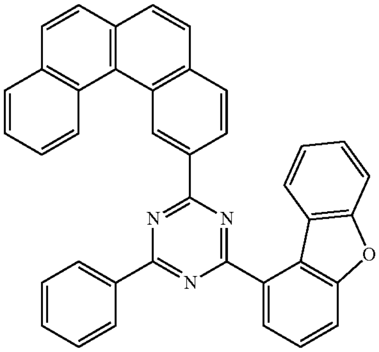
H2-309
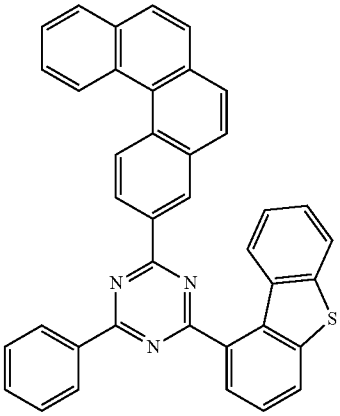
H2-310
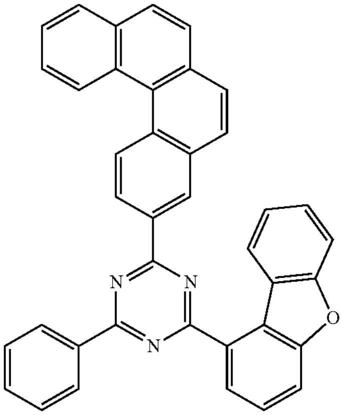
H2-311
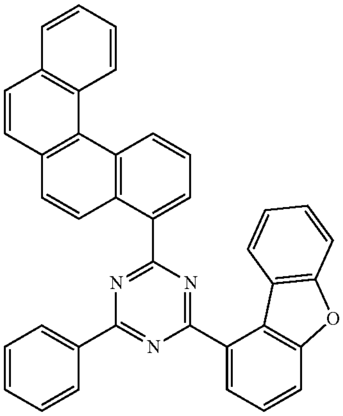
-continued
H2-312
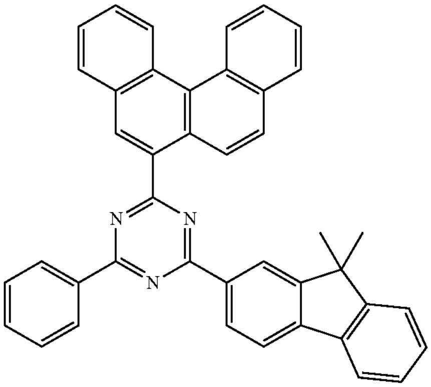
H2-313
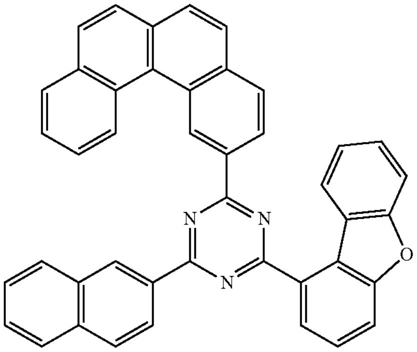
H2-314
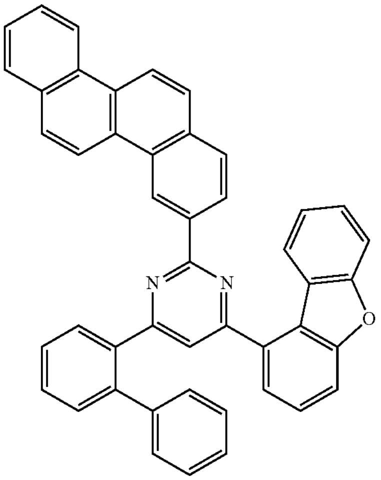
H2-315
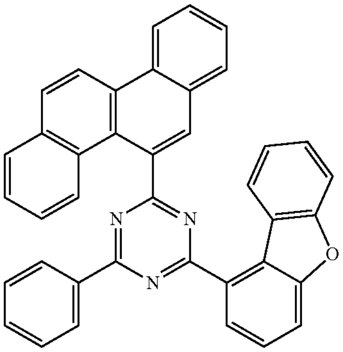

-continued

H2-316

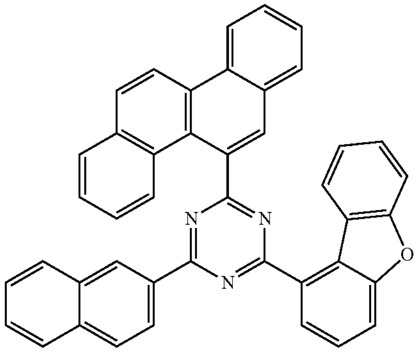

H2-317

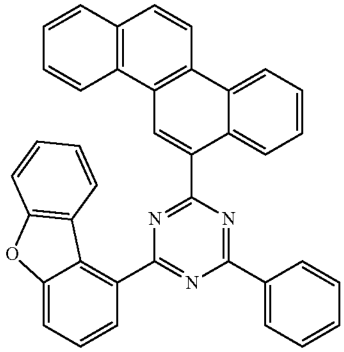

H2-318

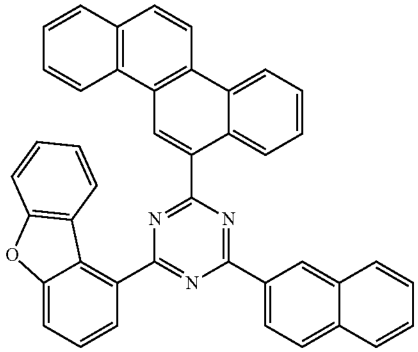

The dopant comprised in the organic electroluminescent device of the present disclosure may be at least one phosphorescent or fluorescent dopant, and is preferably a phosphorescent dopant. The phosphorescent dopant material applied to the organic electroluminescent device of the present disclosure is not particularly limited, but may be preferably selected from the metallated complex compounds of iridium (Ir), osmium (Os), copper (Cu), and platinum (Pt), more preferably selected from ortho-metallated complex compounds of iridium (Ir), osmium (Os), copper (Cu), and platinum (Pt), and even more preferably ortho-metallated iridium complex compounds.

The dopant comprised in the organic electroluminescent device of the present disclosure may comprise a compound represented by the following formula 101, but is not limited thereto.

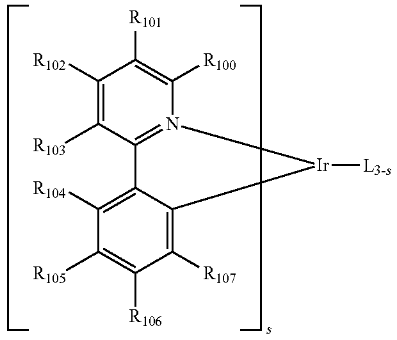

(101)

In formula 101, L is selected from the following structures 1 to 3.

[Structure 1]

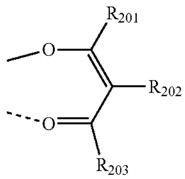

[Structure 2]

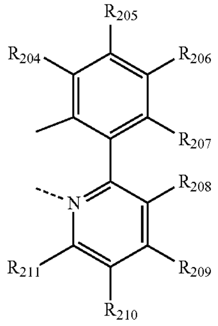

[Structure 3]

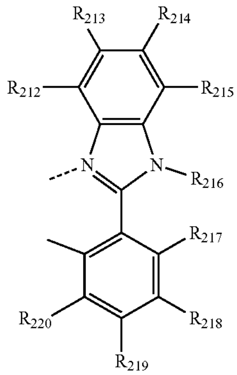

$R_{100}$ to $R_{103}$ each independently represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a cyano, a substituted or unsubstituted (3- to 30-membered)heteroaryl, or a substituted or unsubstituted (C1-C30)alkoxy; or may be linked to an adjacent substituent to form a ring(s), e.g., a substituted or unsubstituted, quinoline, isoquinoline, benzofuropyridine, benzothienopyridine, indenopyridine, benzofuroquinoline, benzothienoquinoline, or indenoquinoline, together with pyridine;

$R_{104}$ to $R_{107}$ each independently represent hydrogen, deuterium, a halogen, a (C1-C30)alkyl unsubstituted or substituted with deuterium and/or a halogen(s), a substituted or unsubstituted (C3-C30)cycloalkyl, a substituted or unsubstituted (C6-C30)aryl, a substituted or unsubstituted (3- to 30-membered)heteroaryl, a cyano, or a substituted or unsubstituted (C1-C30)alkoxy; or may be linked to an adjacent substituent to form a ring(s), e.g., a substituted or unsubstituted, naphthalene, fluorene, dibenzothiophene, dibenzofuran, indenopyridine, benzofuropyridine, or benzothienopyridine, together with benzene;

$R_{201}$ to $R_{220}$ each independently represent hydrogen, deuterium, a halogen, a (C1-C30)alkyl unsubstituted or substituted with deuterium and/or a halogen(s), a substituted or unsubstituted (C3-C30)cycloalkyl, or a substituted or unsubstituted (C6-C30)aryl; or may be linked to an adjacent substituent to form a ring(s); and s represents an integer of 1 to 3.

The specific examples of the dopant compound are as follows, but are not limited thereto.

D-1

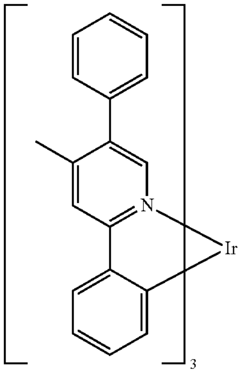

D-2

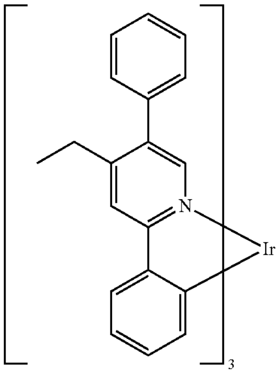

D-3

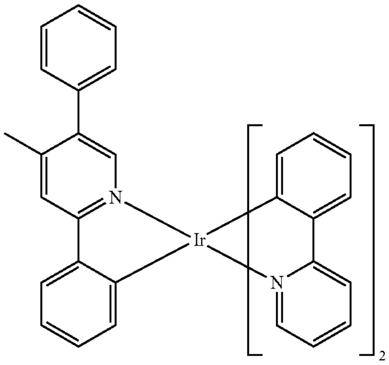

-continued

D-4

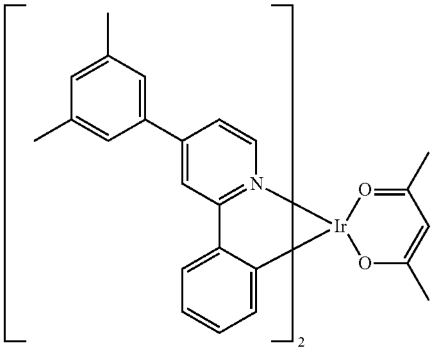

D-5

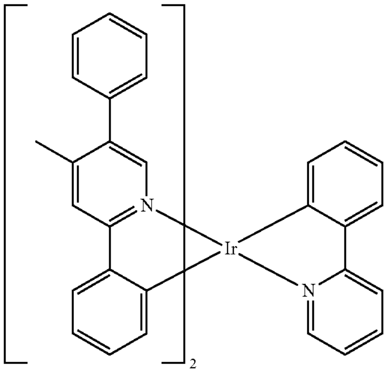

D-6

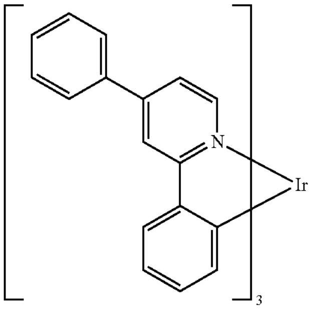

D-7

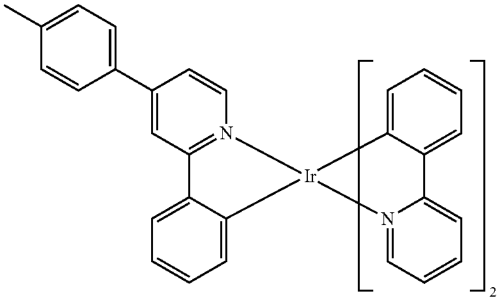

-continued
D-8
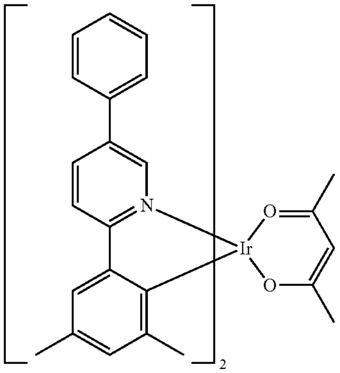
D-9
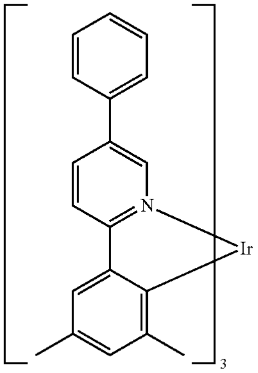
D-10
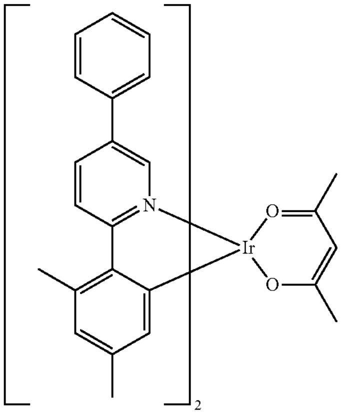
D-11
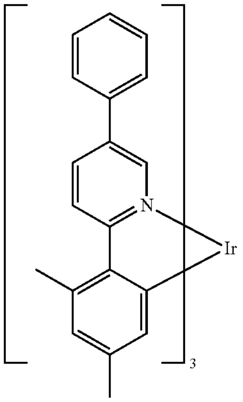
-continued
D-12
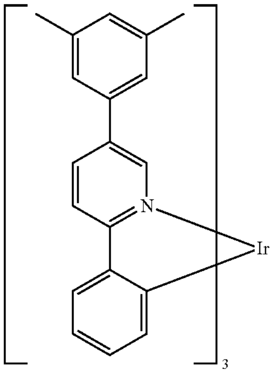
D-13
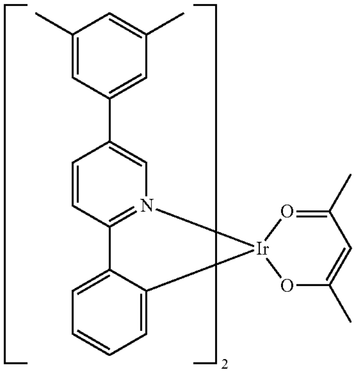
D-14
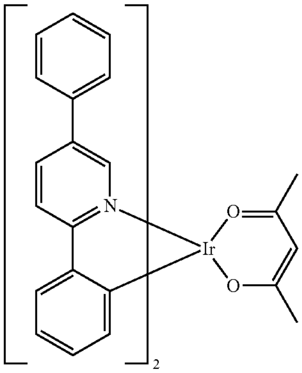
D-15
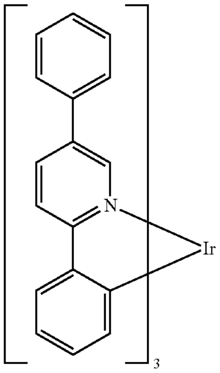

-continued
D-16
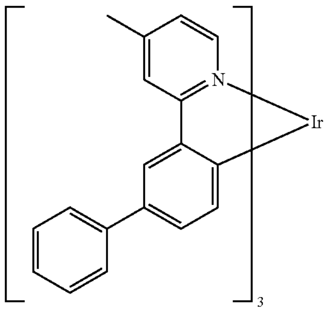
D-17
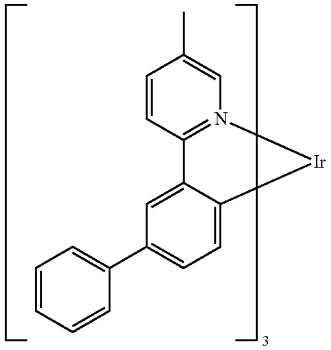
D-18
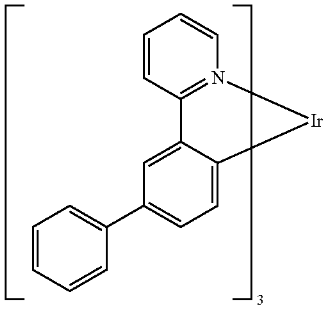
D-19
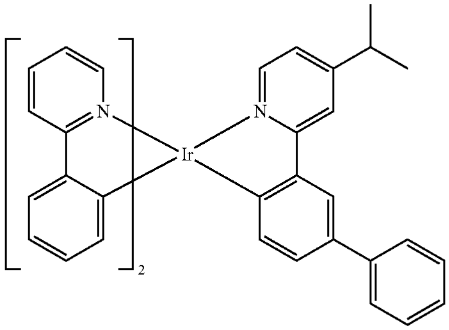
-continued
D-20
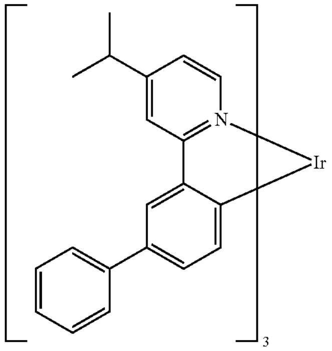
D-21
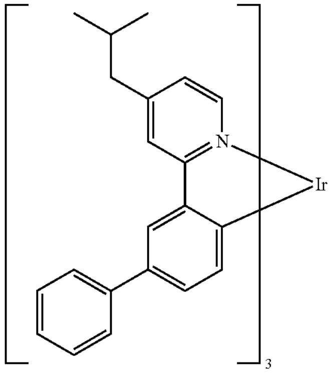
D-22
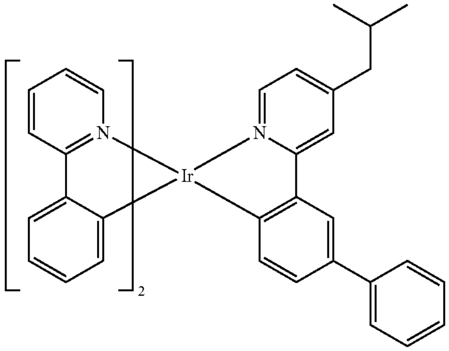
D-23
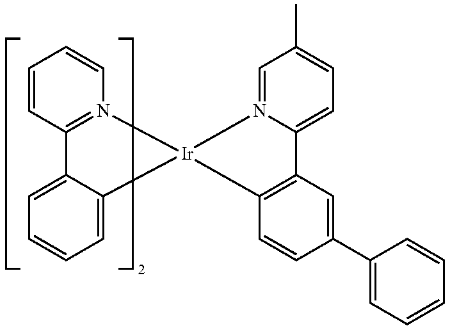

-continued
D-24
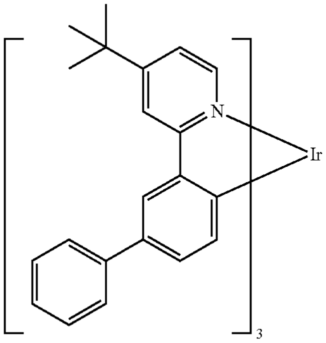
D-25
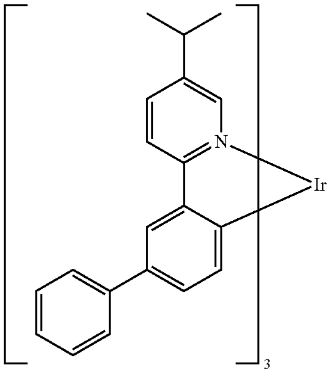
D-26
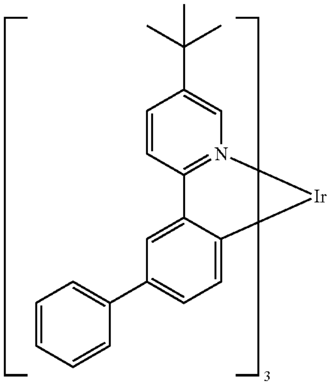
D-27
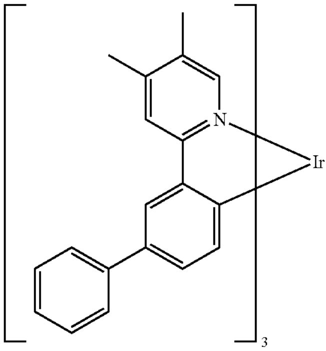
-continued
D-28
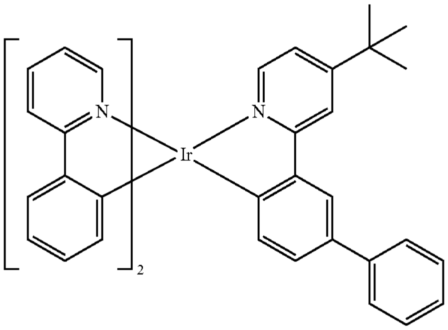
D-29
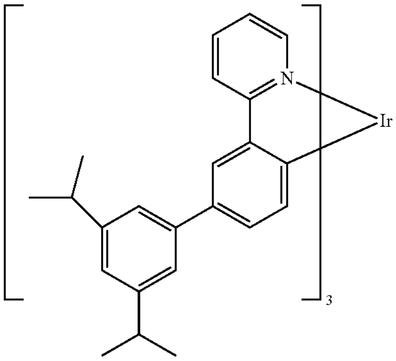
D-30
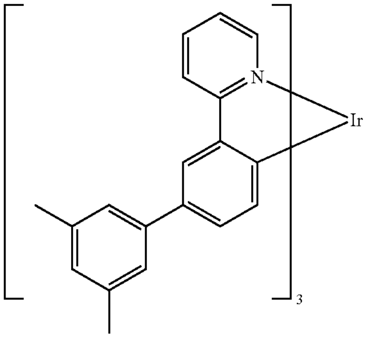
D-31
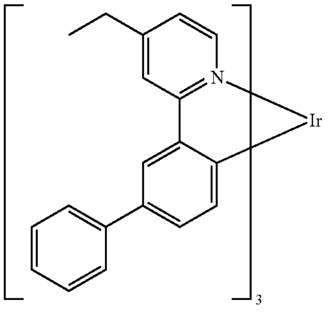
D-32
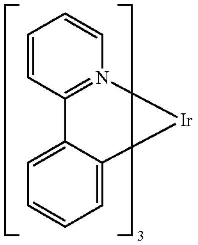

-continued
D-33
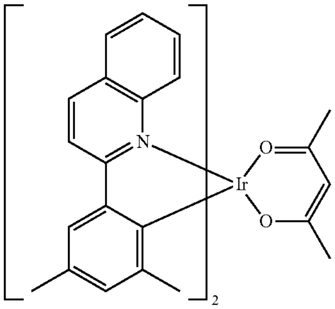
D-34
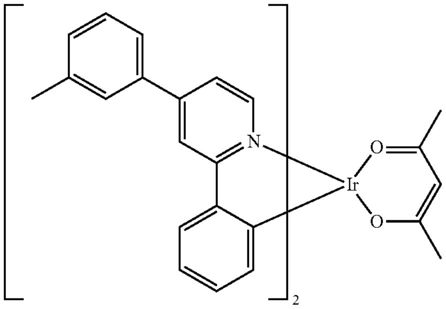
D-35
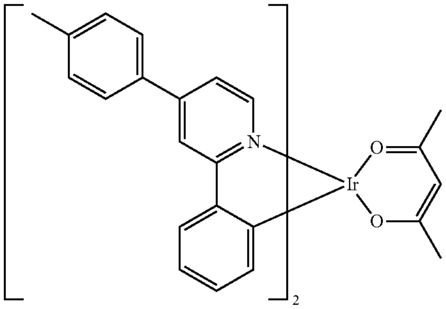
D-36
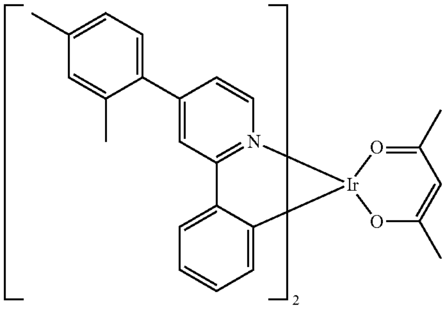
D-37
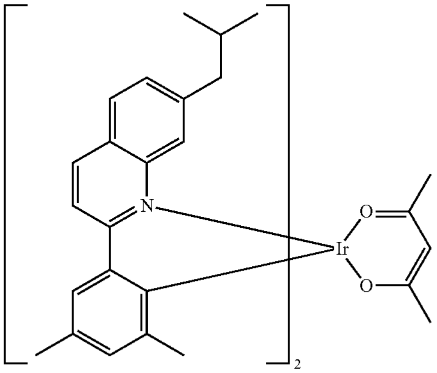
-continued
D-38
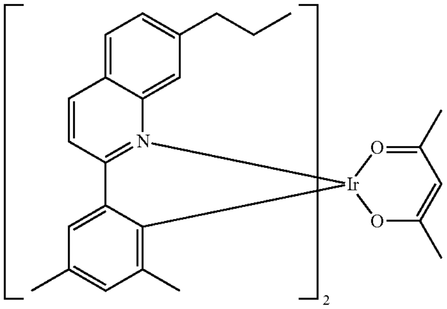
D-39
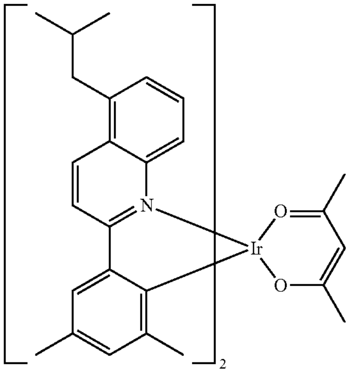
D-40
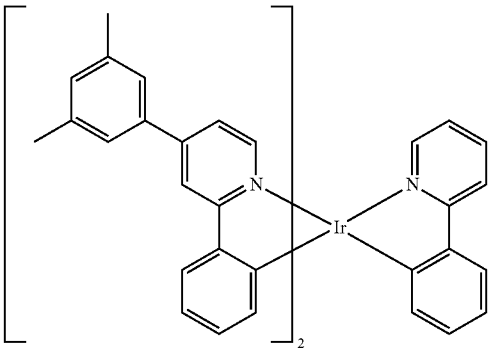
D-41
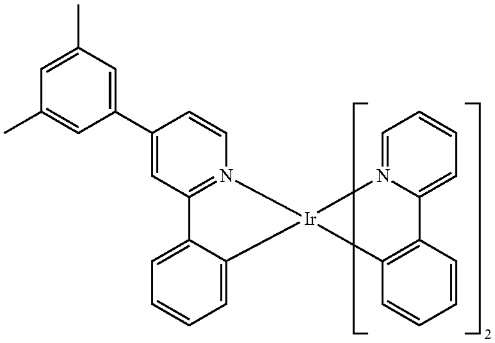

-continued
D-42
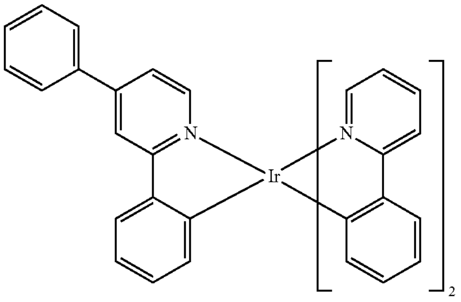
D-43
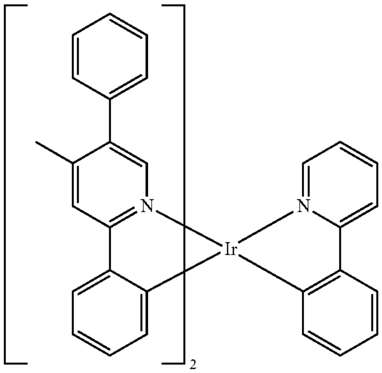
D-44
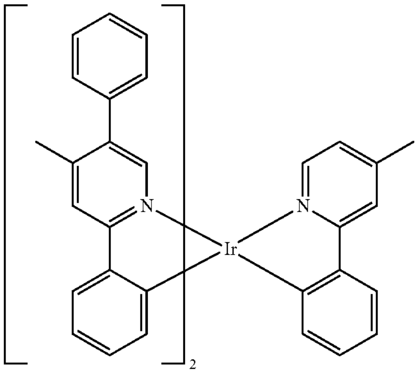
D-45
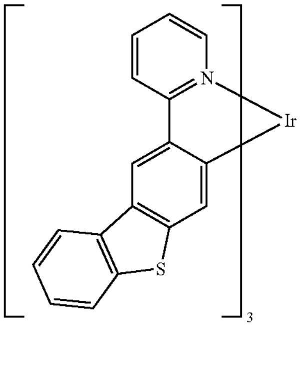
-continued
D-46
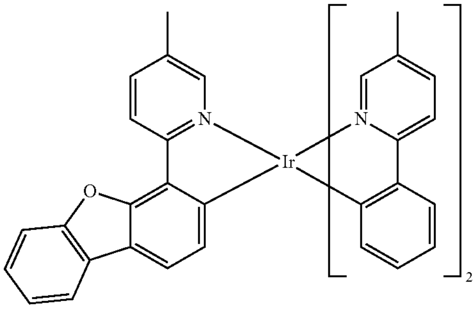
D-47
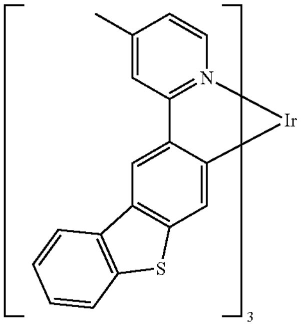
D-48
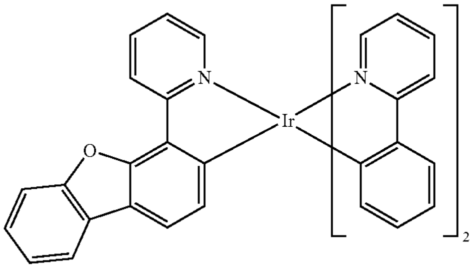
D-49
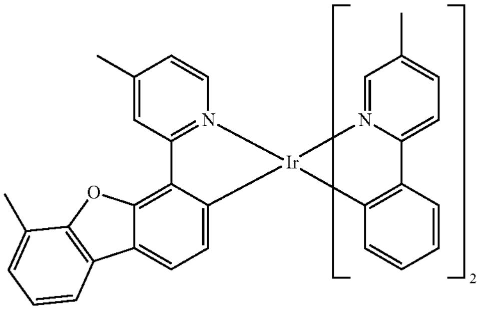
D-50
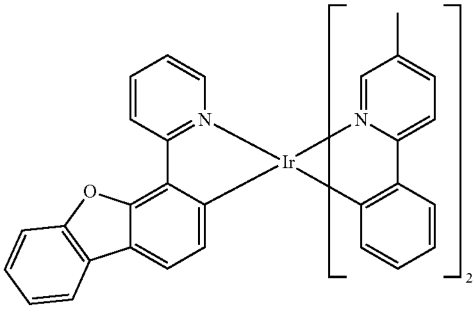

-continued
D-51
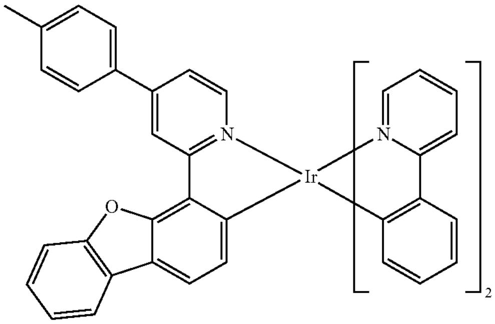
D-52
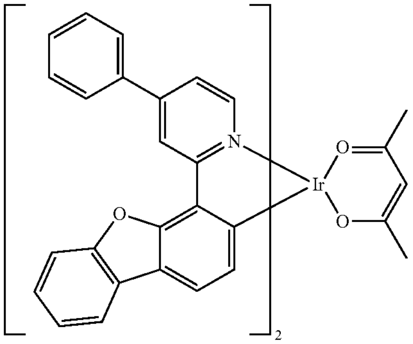
D-53
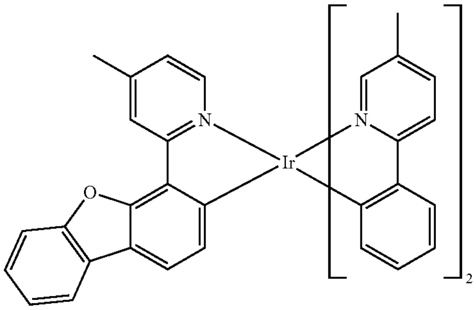
D-54
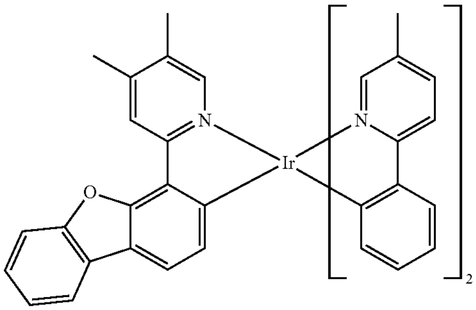
-continued
D-55
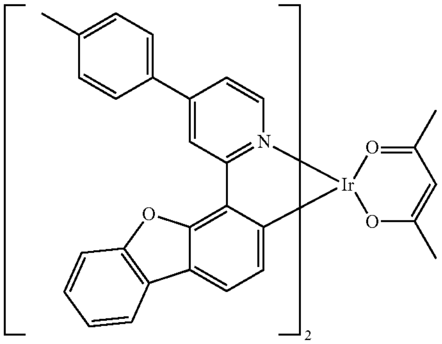
D-56
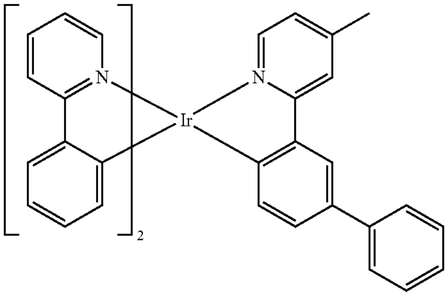
D-57
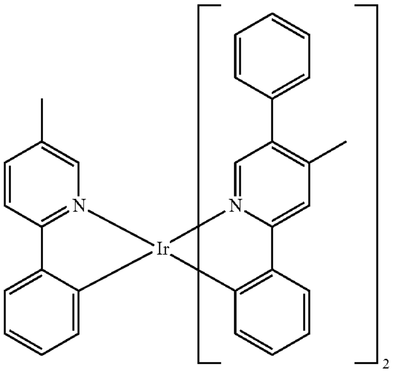
D-58
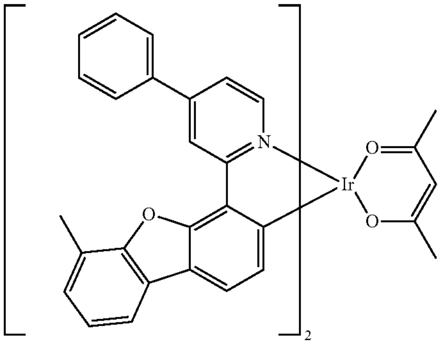

-continued
D-59
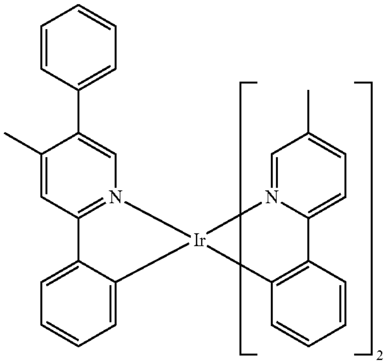
D-60
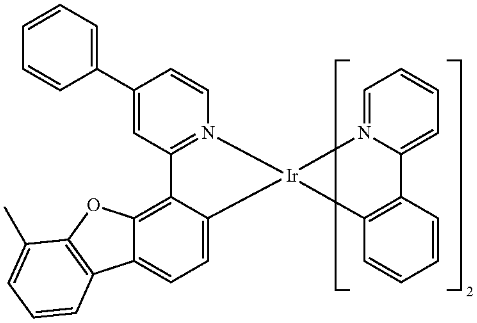
D-61
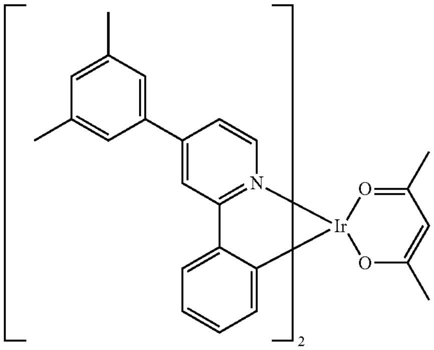
D-62
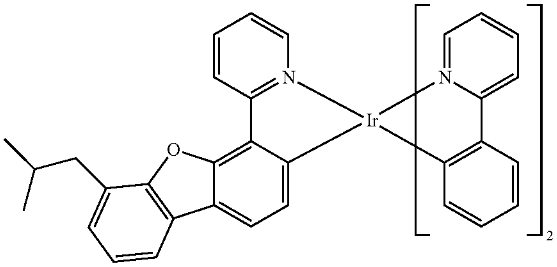
-continued
D-63
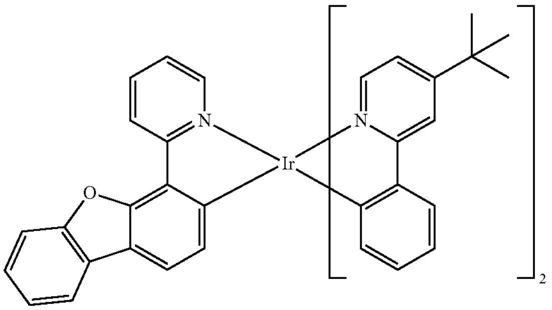
D-64
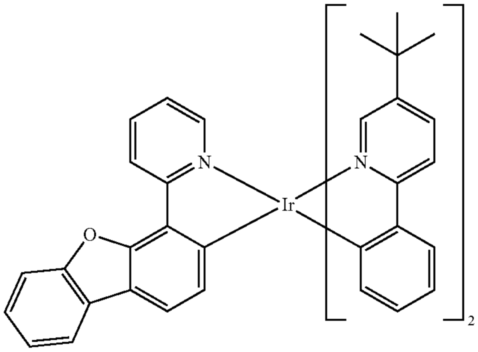
D-65
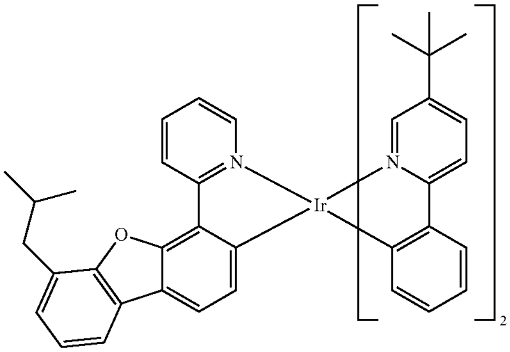
D-66
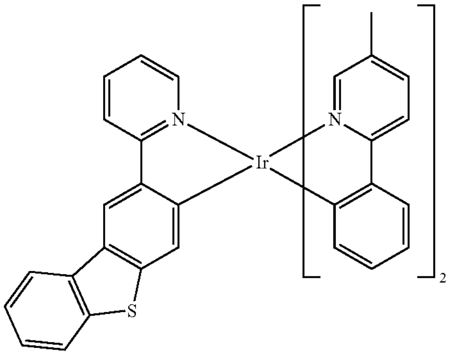

-continued
D-67
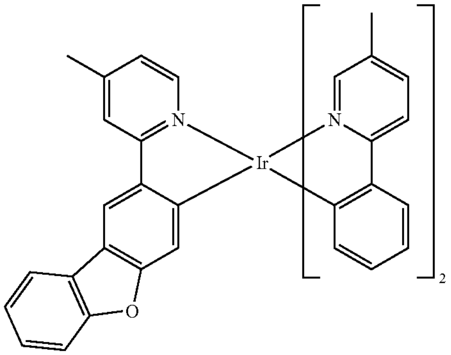
D-68
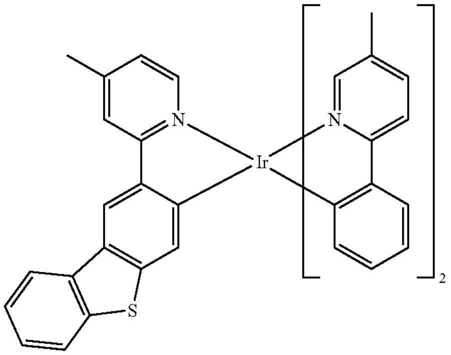
D-69
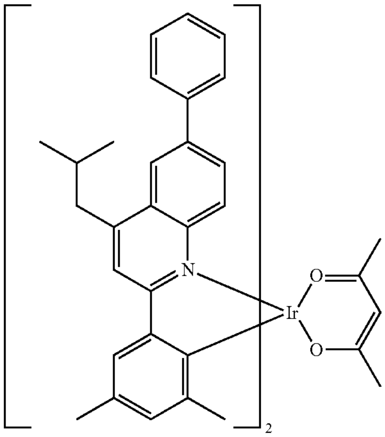
D-70
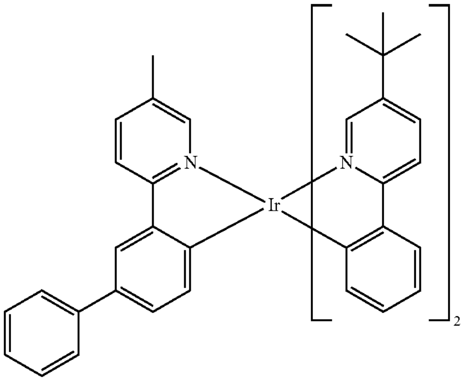
-continued
D-71
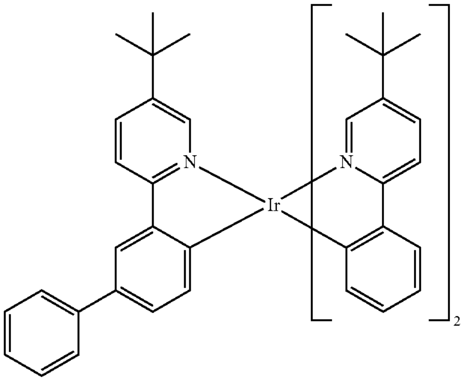
D-72
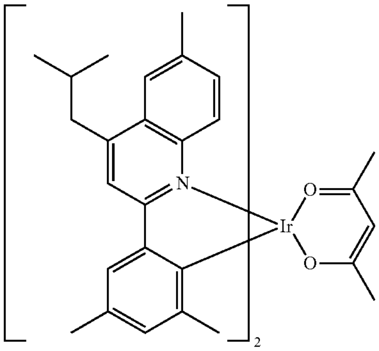
D-73
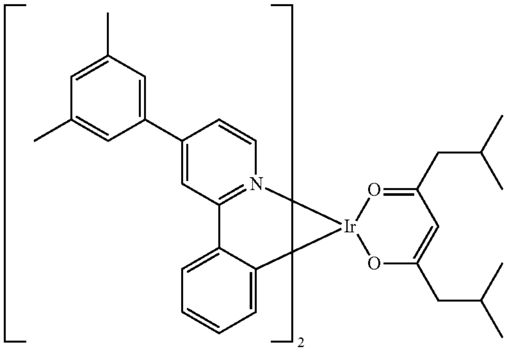
D-74
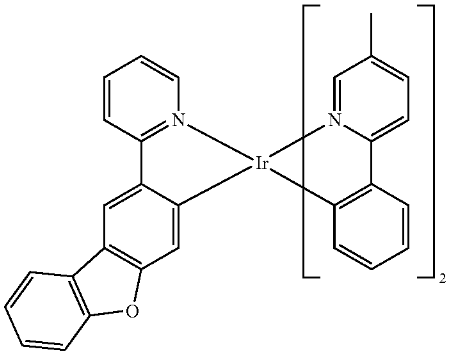

-continued
D-75
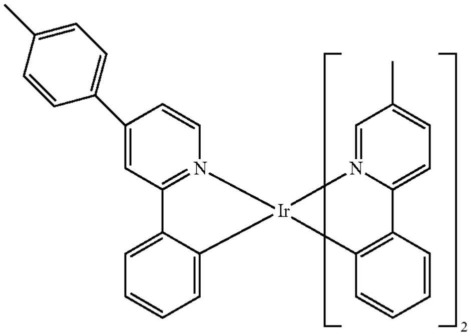
D-76
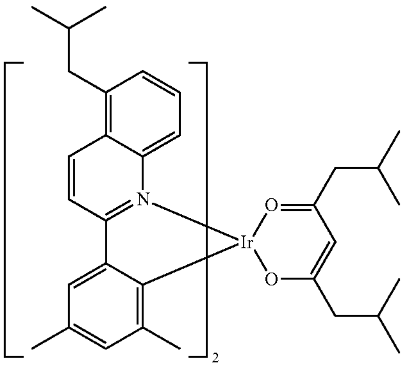
D-77
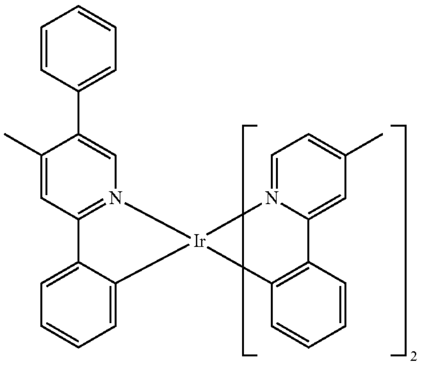
D-78
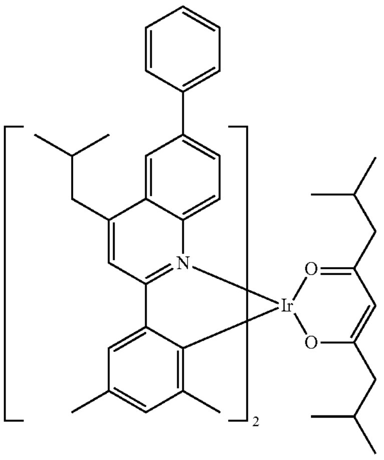
-continued
D-79
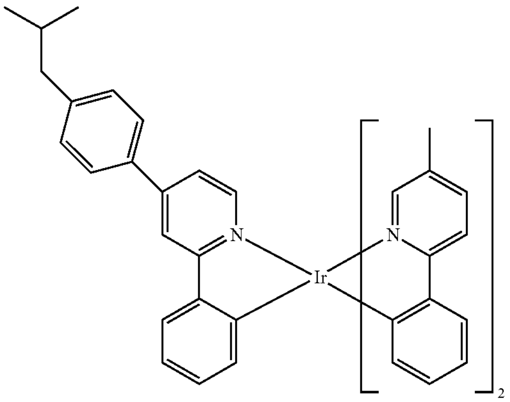
D-80
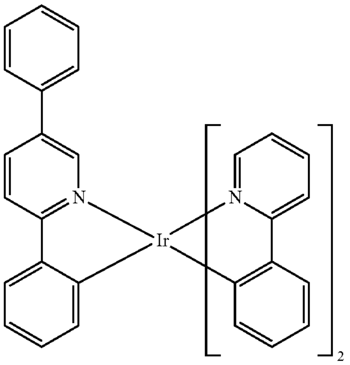
D-81
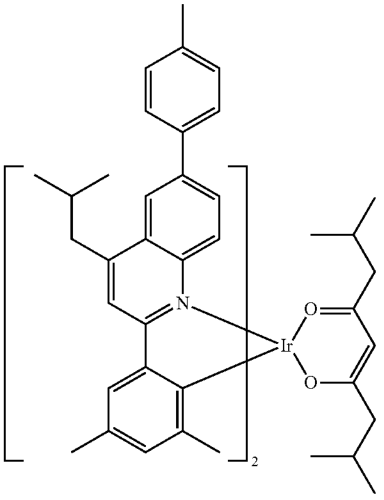

-continued
D-82
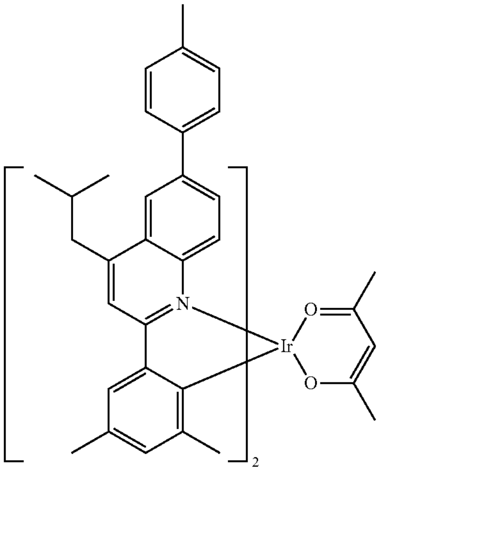
D-83
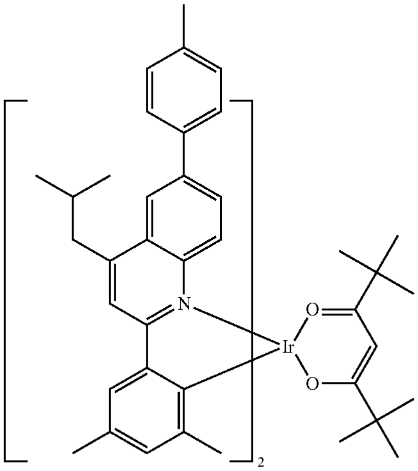
D-84
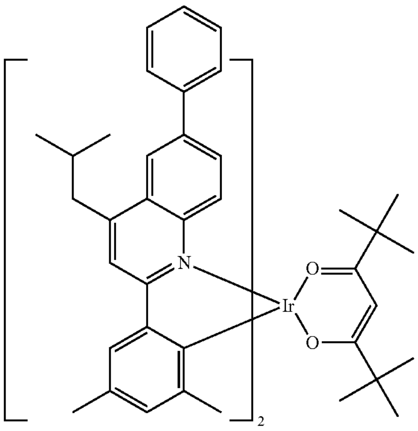
-continued
D-85
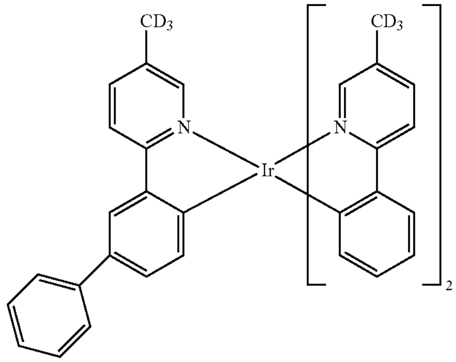
D-86
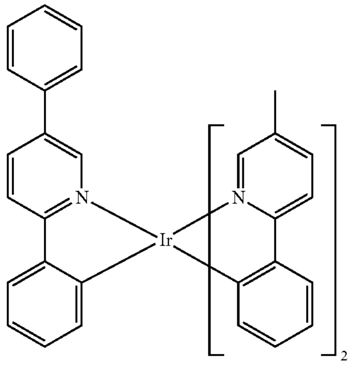
D-87
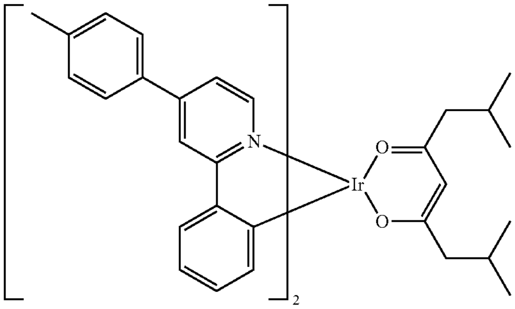
D-88
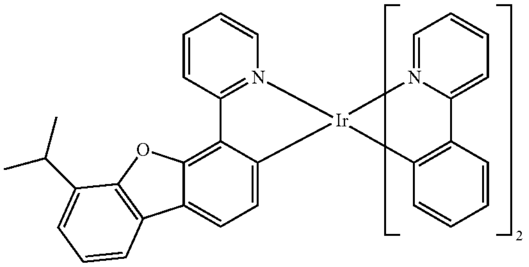

D-89
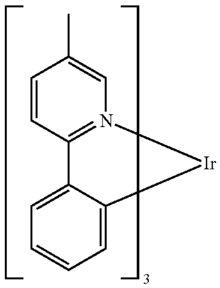
D-90
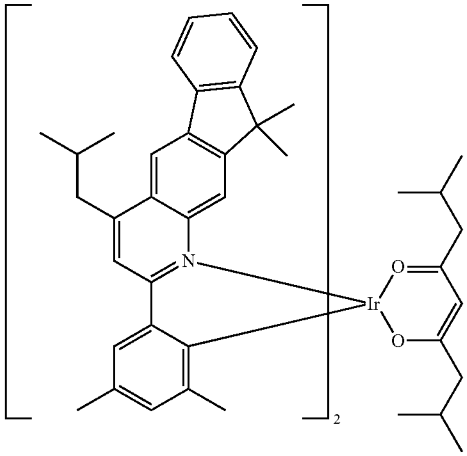
D-91
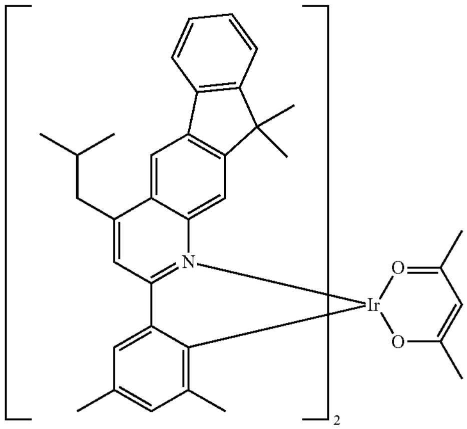
D-92
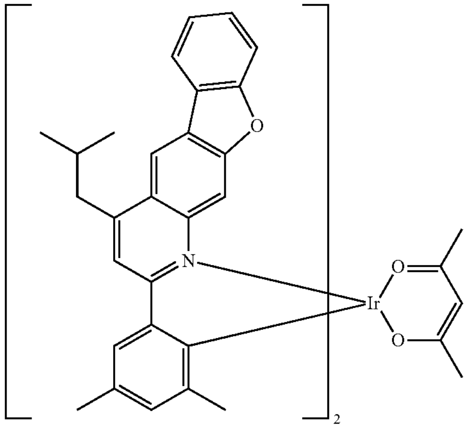
D-93
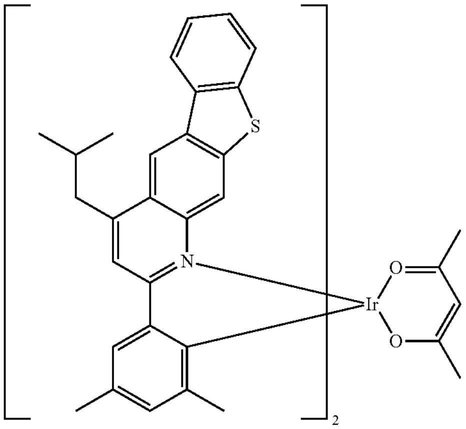
D-94
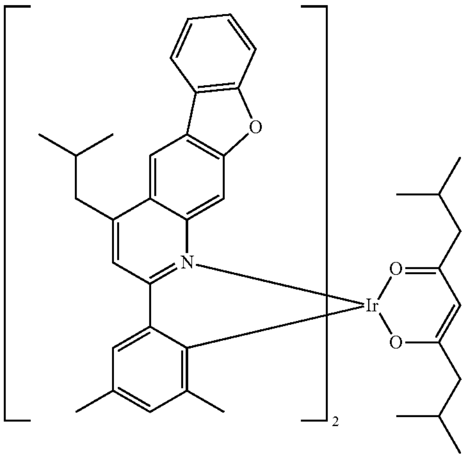
D-95
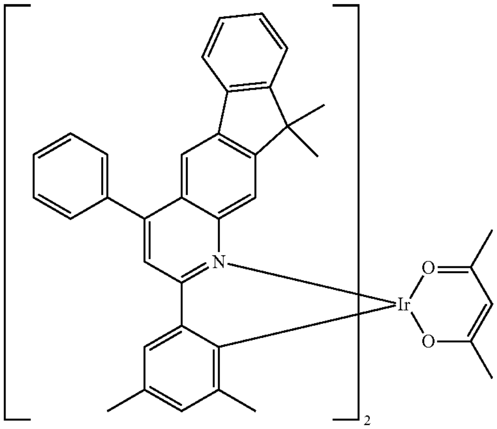

-continued
D-96
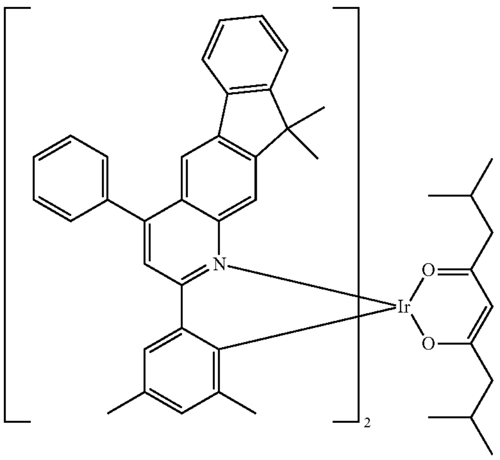
D-97
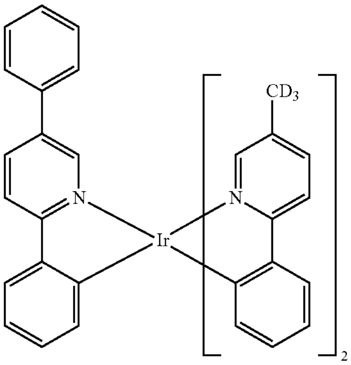
D-98
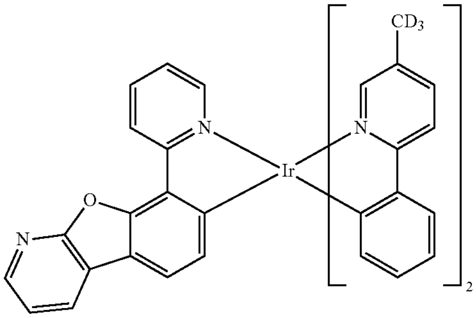
D-99
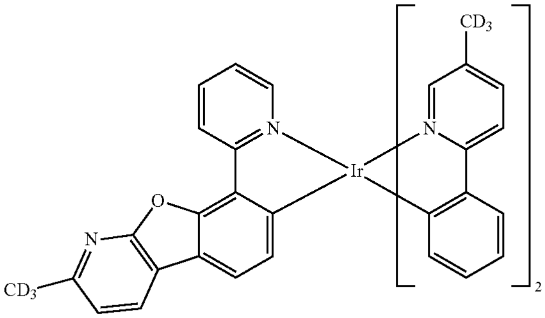
-continued
D-100
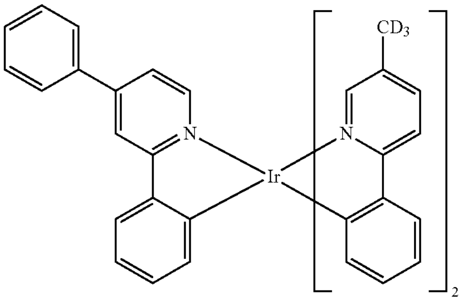
D-101
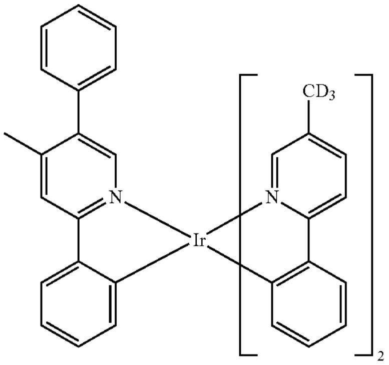
D-102
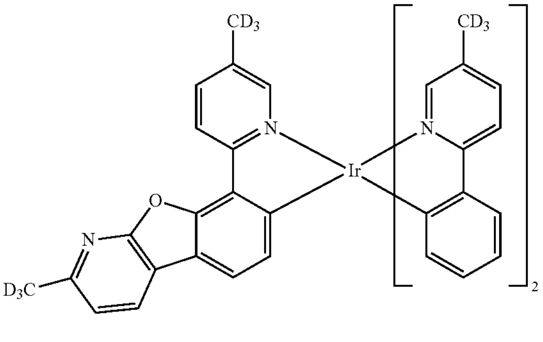
D-103
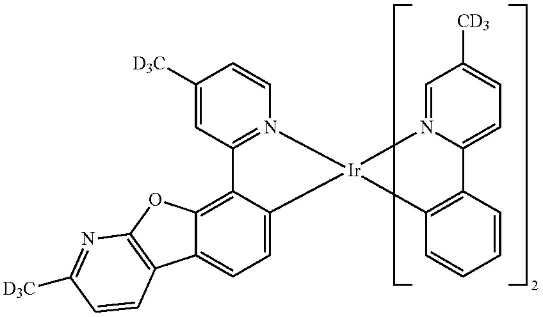

-continued
D-104
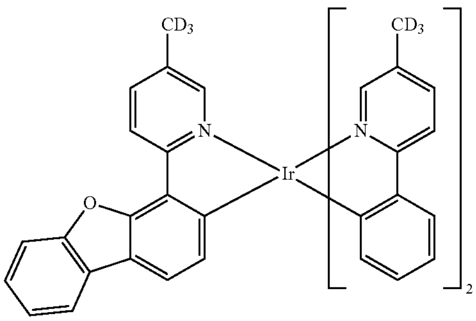
D-105
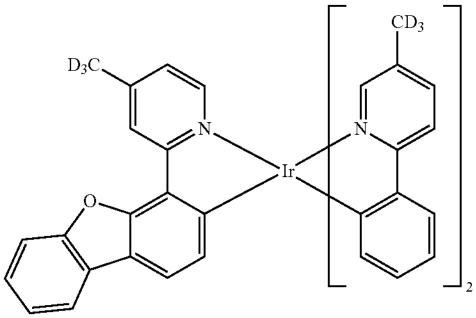
D-106
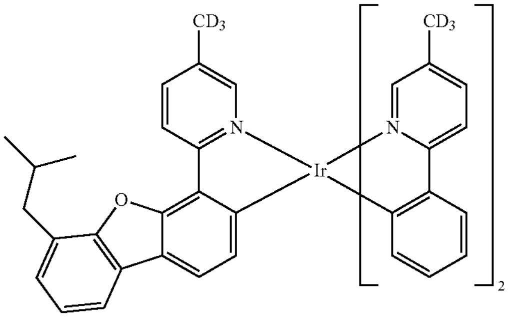
D-107
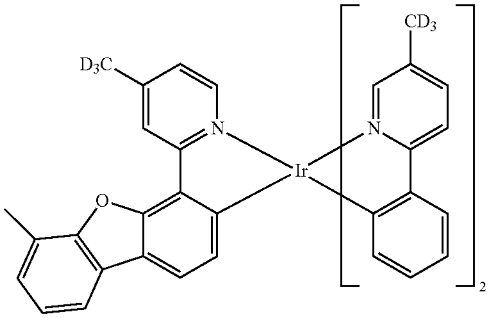
-continued
D-108
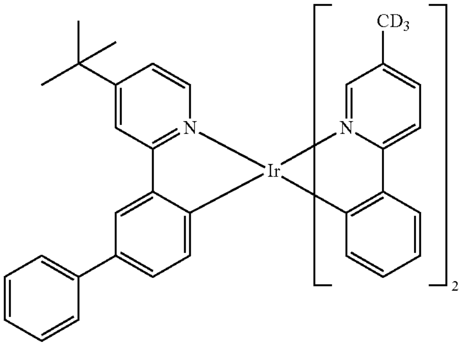
D-109
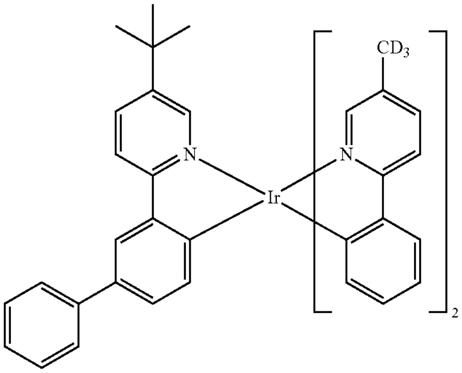
D-110
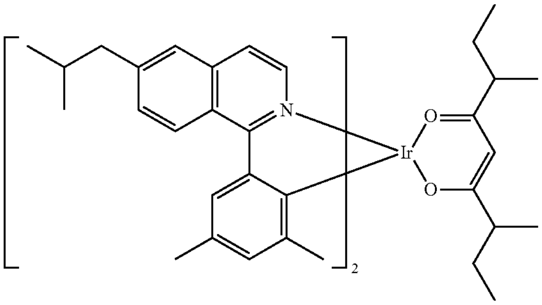
D-111
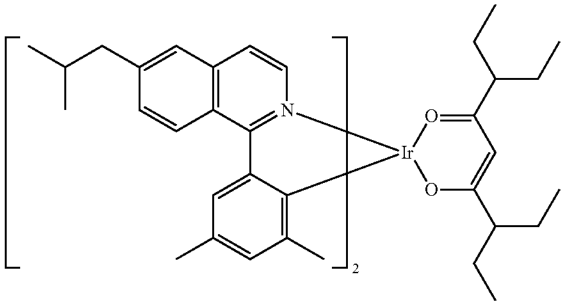

-continued
D-112
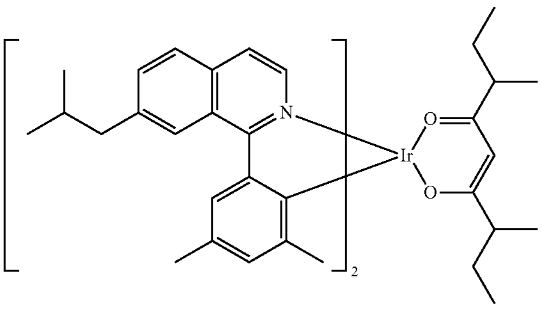
D-113
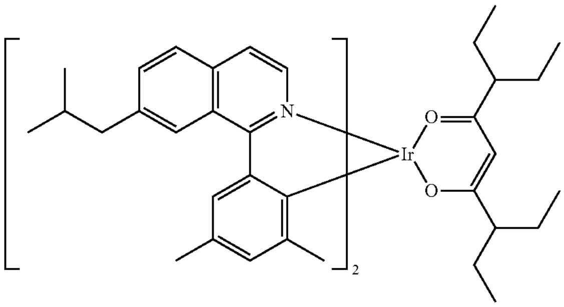
D-114
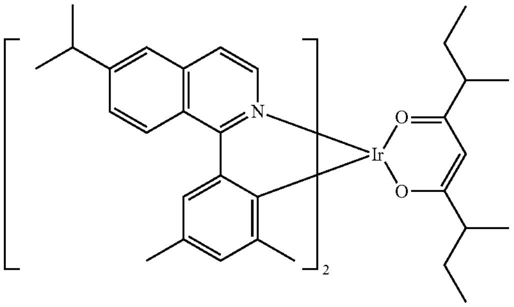
D-115
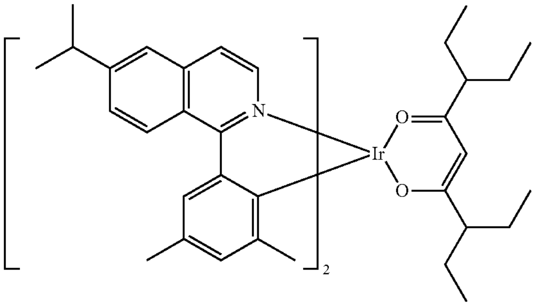
-continued
D-116
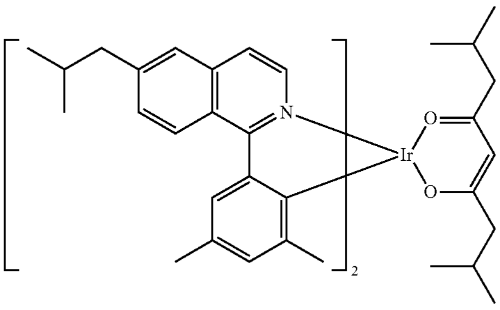
D-117
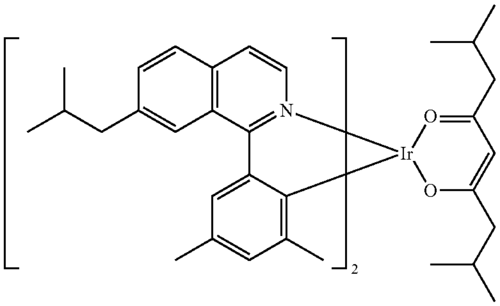
D-118
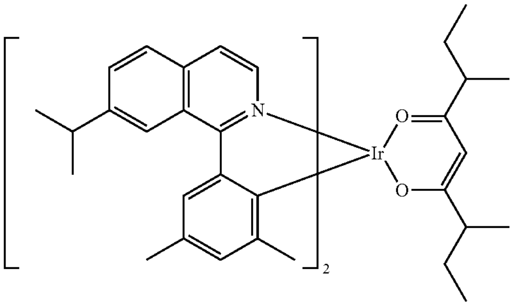
D-119
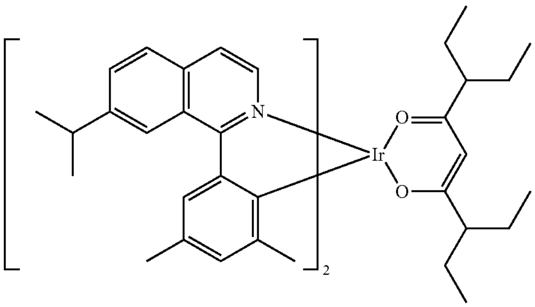

-continued
D-120
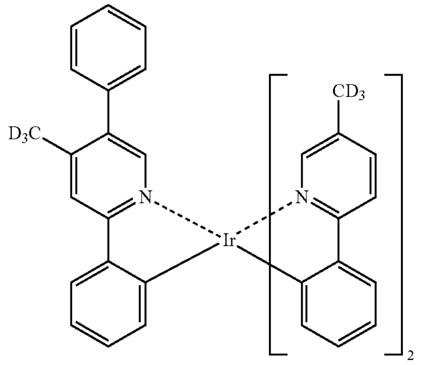
D-121
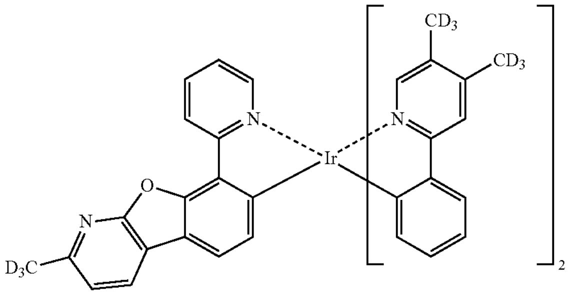
D-122
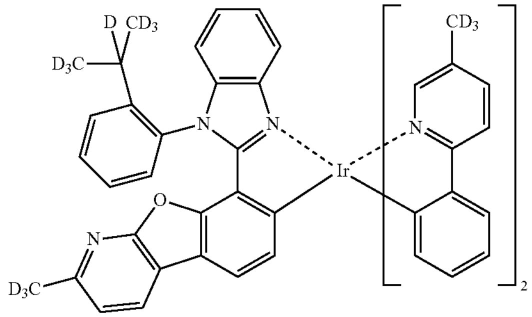
D-123
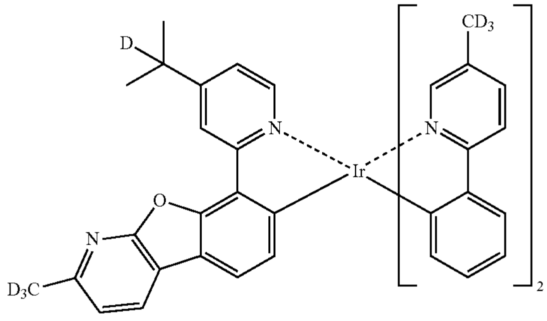
-continued
D-124
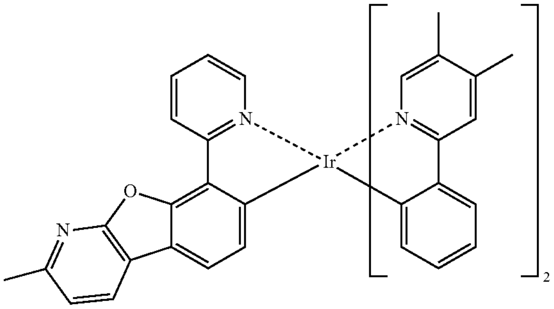
D-125
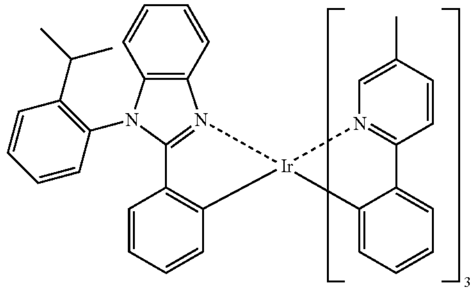
D-126
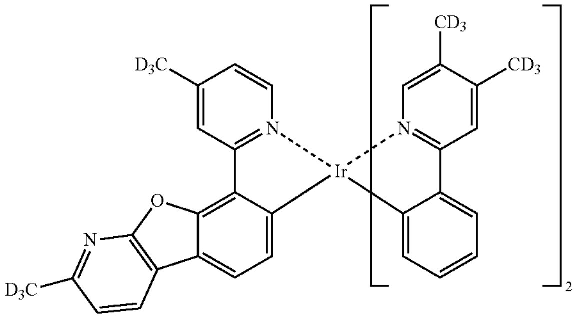
D-127
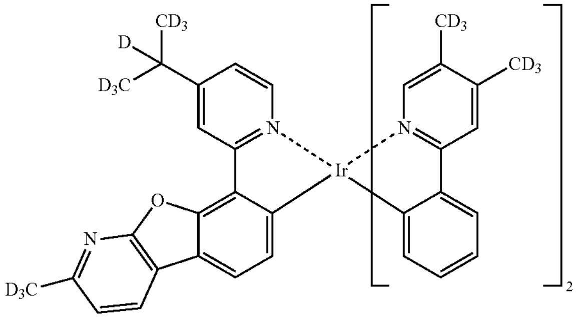

D-128
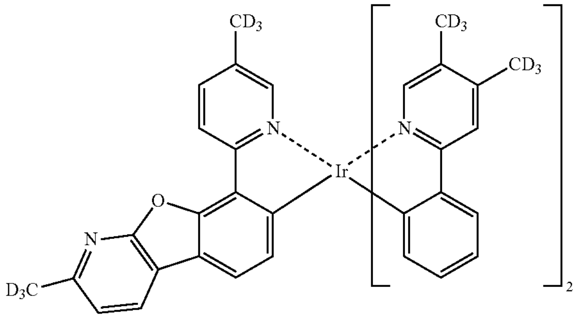
D-129
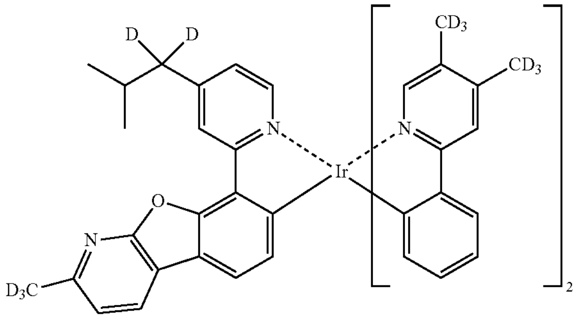
D-130
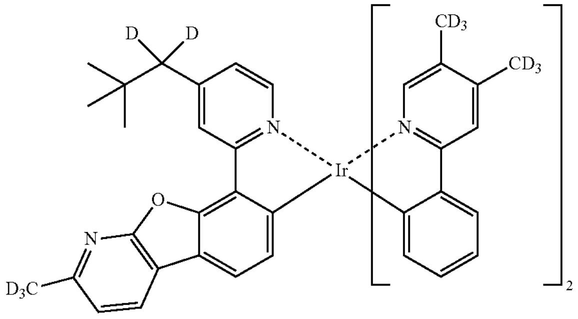
D-131
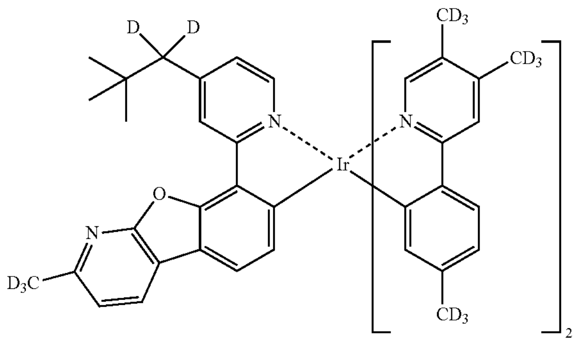
D-132
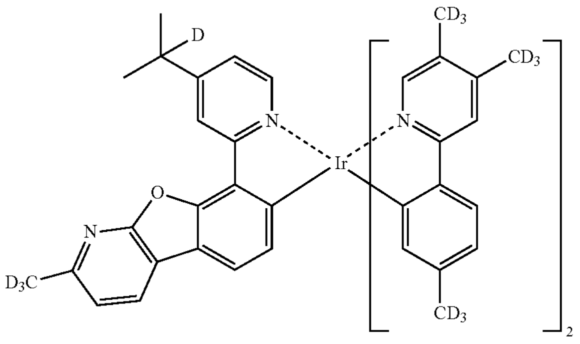
D-133
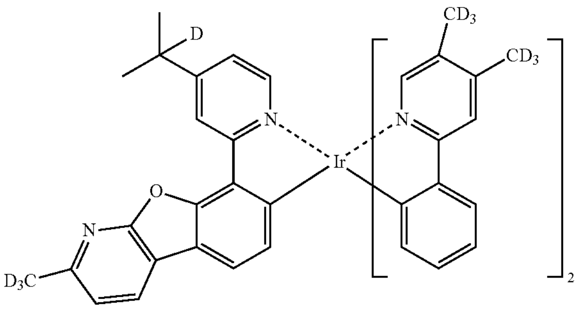
D-134
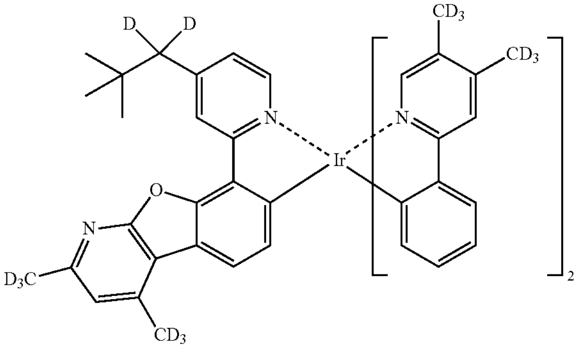
D-135
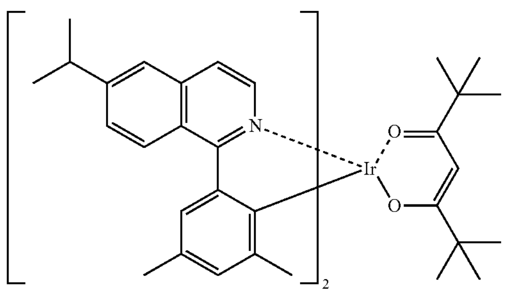

-continued
D-136
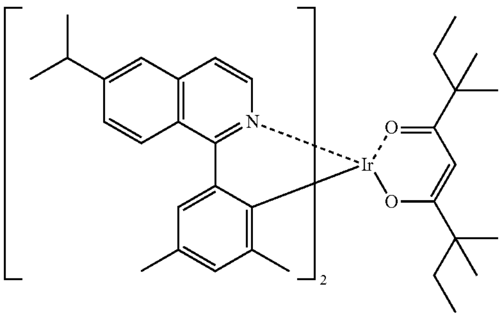
D-137
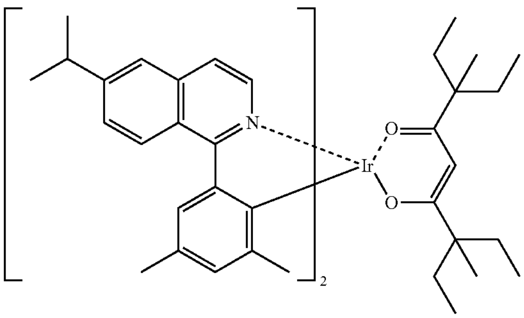
D-138
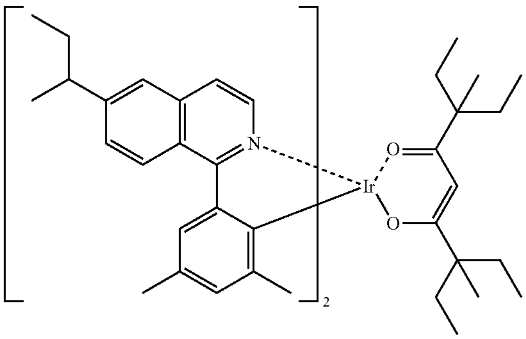
D-139
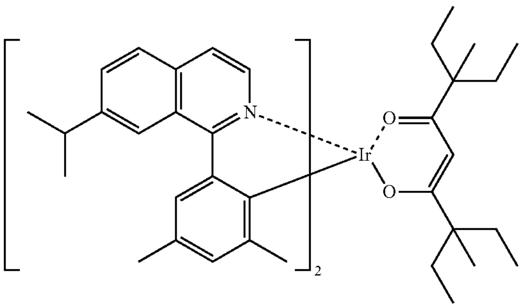
-continued
D-140
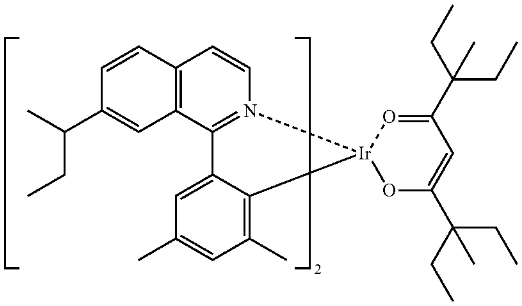
D-141
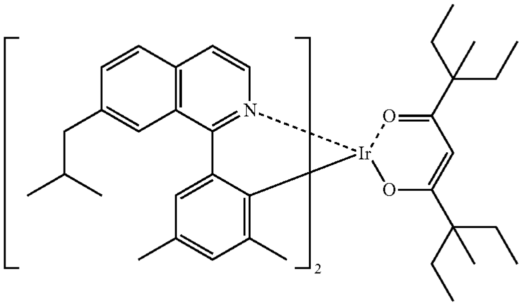
D-142
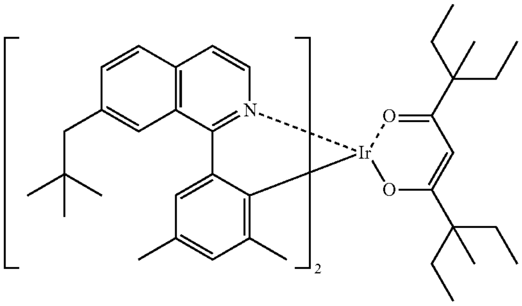
D-143
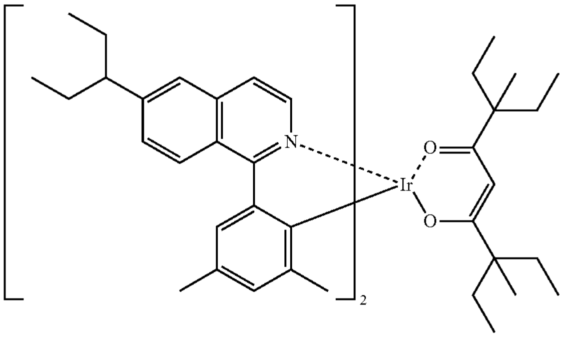

-continued

D-144

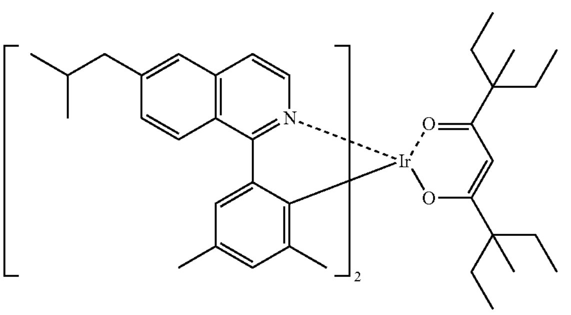

D-145

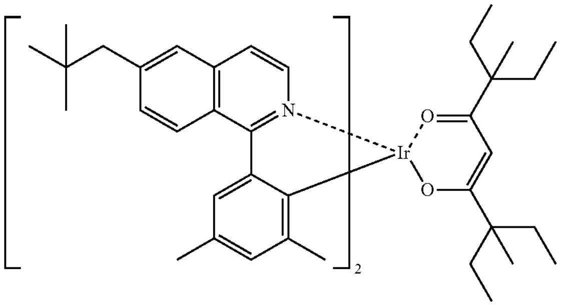

D-146

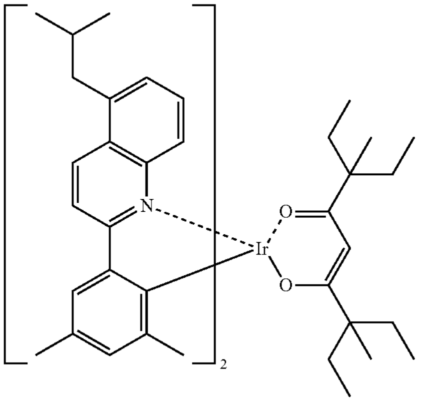

D-147

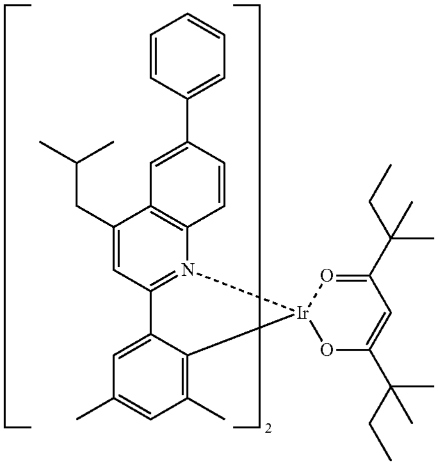

-continued

D-148

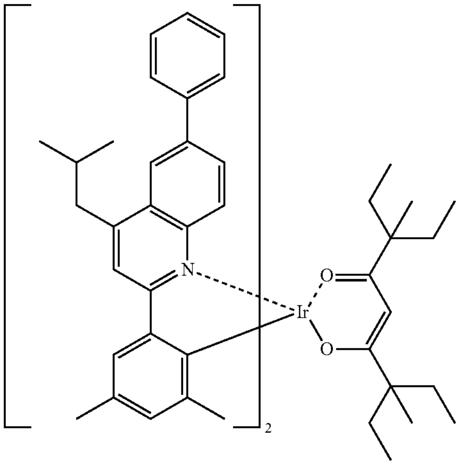

D-149

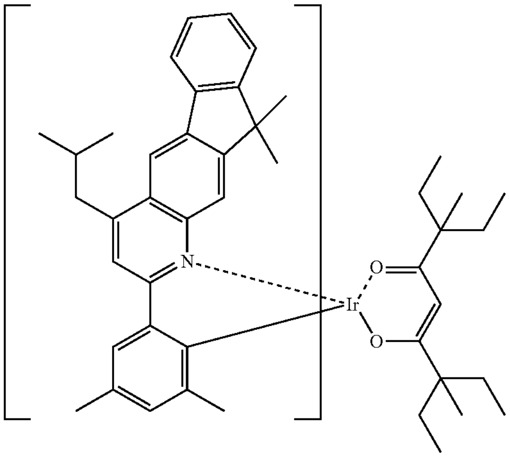

The organic electroluminescent device according to the present disclosure has a first electrode, a second electrode, and at least one organic layer between the first electrode and the second electrode.

One of the first and second electrodes may be an anode, and the other may be a cathode. The organic layer comprises a light-emitting layer and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer. Further, each layer may consist of multilayers.

The first electrode and the second electrode may each be formed with a transmissive conductive material, a transflective conductive material, or a reflective conductive material. The organic electroluminescent device may be a top emission type, a bottom emission type, or both-sides emission type according to the kinds of the material forming the first electrode and the second electrode. In addition, the hole injection layer may be further doped with a p-dopant, and the electron injection layer may be further doped with an n-dopant.

According to one embodiment of the present disclosure, the organic electroluminescent device of the present disclosure may further comprise an azine-based compound besides the organic electroluminescent compound of the present disclosure as at least one of an electron transport material, an electron injection material, an electron buffer material, and a hole blocking material.

In the organic electroluminescent device according to the present disclosure, the organic layer may further comprise at least one compound selected from the group consisting of arylamine-based compounds and styrylarylamine-based compounds.

In addition, in the organic electroluminescent device of the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

The organic electroluminescent device of the present disclosure may emit white light by further including at least one light-emitting layer containing a blue, red, or green light-emitting compound, which is known in the art, besides the compound of the present disclosure. In addition, it may further include a yellow or orange light-emitting layer, if necessary.

In the organic electroluminescent device of the present disclosure, at least one layer selected from a chalcogenide layer, a metal halide layer and a metal oxide layer (hereinafter, "a surface layer") may be preferably placed on an inner surface(s) of one or both electrodes. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. The surface layer may provide operation stability for the organic electroluminescent device. Preferably, the chalcogenide includes $SiO_X$ ($1 \le X \le 2$), $AlO_X$ ($1 \le X \le 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, or an electron blocking layer, or a combination thereof may be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, or an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. Further, the electron blocking layer may be placed between the hole transport layer (or hole injection layer) and the light-emitting layer, and may block overflowing electrons from the light-emitting layer and confine the excitons in the light-emitting layer to prevent light leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

In the organic electroluminescent device of the present disclosure, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to produce an organic electroluminescent device having two or more light-emitting layers, which emits white light.

An organic electroluminescent material according to one embodiment of the present disclosure may be used as light-emitting materials for a white organic light-emitting device. The white organic light-emitting device has been suggested to have various structures such as a parallel arrangement (side-by-side) method, a stacking method, or color conversion material (CCM) method, etc., according to the arrangement of R (red), G (green), B (blue), or YG (yellowish green) light-emitting units. In addition, the organic electroluminescent material according to one embodiment of the present disclosure may also be applied to the organic electroluminescent device comprising a quantum dot (QD).

In order to form each layer of the organic electroluminescent device of the present disclosure, dry film-forming methods such as vacuum evaporation, sputtering, plasma, ion plating, etc., or wet film-forming methods such as ink jet printing, spin coating, dip coating, flow coating, etc., can be used. The first and second host compounds of the present disclosure may be co-evaporated or mixture-evaporated to form a film.

When using a wet film-forming method, a thin film can be formed by dissolving or diffusing the materials forming each layer into any suitable solvent such as ethanol, chloroform, tetrahydrofuran, dioxane, etc. The solvent is not particularly limited as long as the material constituting each layer is soluble or dispersible in the solvents, which do not cause any problems in forming a film.

It is possible to produce a display system, e.g., a display system for smartphones, tablets, notebooks, PCs, TVs, or cars, or a lighting system, e.g., an outdoor or indoor lighting system, by using the organic electroluminescent device of the present disclosure.

Hereinafter, the preparation method of the compound of the present disclosure, and the properties thereof will be explained in detail with reference to the representative compounds of the present disclosure. However, the present disclosure is not limited to the following examples.

Example 1: Preparation of Compound C-686

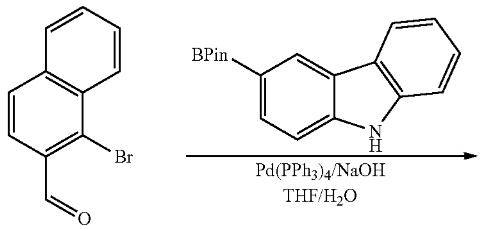

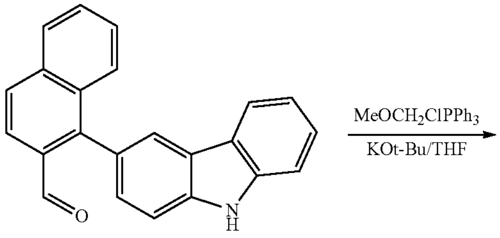

1-1

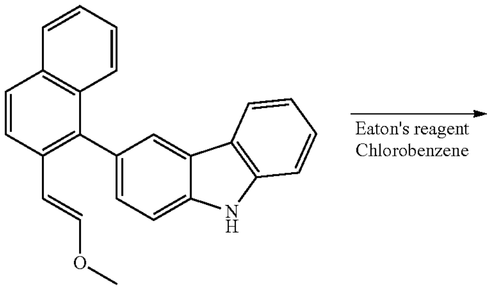

1-2

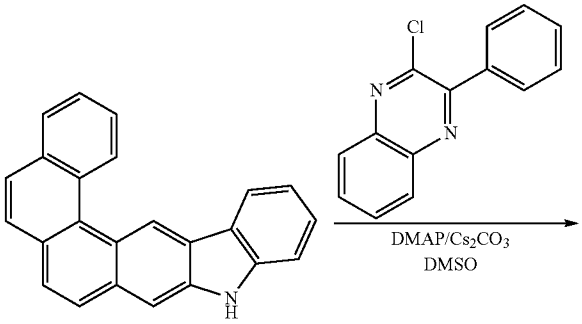

1-3

-continued

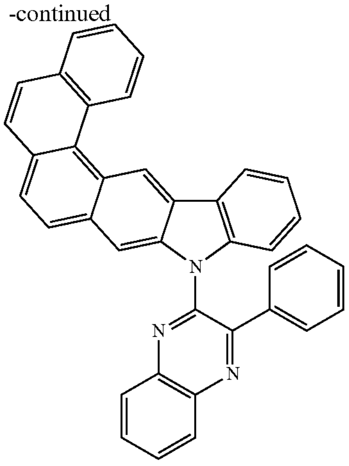

C-686

Synthesis of Compound 1-1

1-bromo-2-naphthaldehyde (20.0 g, 85.1 mmol), 3-(4,4,5,5-tetramethyl-1,3,2-dioxaborolan-2-yl)-9H-carbazole (26.2 g, 51.5 mmol), tetrakis(triphenylphosphine)palladium (0) (2.95 g, 2.55 mmol), NaOH (4.12 g, 255 mmol), 360 mL of tetrahydrofuran (THF), and 90 mL of $H_2O$ were introduced into a flask, and the mixture was stirred under reflux at 90° C. for 1.5 hours. After completion of the reaction, the reaction mixture was neutralized with $NH_4Cl$ aqueous solution, extracted with methylene chloride (MC), and dried with $MgSO_4$. The residue was separated by column chromatography, and the solid obtained by adding MeOH was filtered under reduced pressure to obtain compound 1-1 (20.0 g, yield: 73%).

Synthesis of Compound 1-2

Compound 1-1 (19.0 g, 59.1 mmol), (methoxymethyl) triphenylphosphonium chloride (30.4 g, 88.7 mmol), and 300 mL of THF were introduced into a flask, and while stirring at 0° C., 33.3 mL of a 1 M solution of K-Ot-Bu dissolved in THF was added dropwise thereto. The mixture was stirred for 3 hours, neutralized with $NH_4Cl$, extracted with MC, and dried with $MgSO_4$. The residue was separated by column chromatography, and the solid obtained by adding MeOH was filtered under reduced pressure to obtain compound 1-2 (20.0 g, yield: 97%).

Synthesis of Compound 1-3

Compound 1-2 (66.3 g, 191 mmol), 34 mL of Eaton's reagent, and 950 mL of chlorobenzene were introduced into a flask, and the mixture was stirred under reflux at 180° C. overnight. After completion of the reaction, the reaction mixture was neutralized with $NaHCO_3$, extracted with MC, and dried with $MgSO_4$. The residue was separated by column chromatography, and the solid obtained by adding MeOH was filtered under reduced pressure to obtain compound 1-3 (27 g, yield: 45%).

Synthesis of Compound C-86

Compound 1-3 (10.0 g, 11 mmol), 2-chloro-3-phenylquinoxaline (7.6 g, 31.5 mmol), $Cs_2CO_3$ (10.3 g, 31.5 mmol), dimethylaminopyridine (DMAP) (1.92 g, 0.0158 mmol), and 60 mL of dimethylsulfoxide (DMSO) were introduced into a flask, and the mixture was stirred at 100° C. for 4 hours. After completion of the reaction, the solid obtained by adding $H_2O$ to the mixture was separated by column chromatography, and the solid obtained by adding MeOH was filtered under reduced pressure to obtain compound C-686 (1.3 g, yield: 8%).

| Compound | MW | M.P. |
|---|---|---|
| C-686 | 521.61 | 269° C. |

Example 2: Preparation of Compound C-700

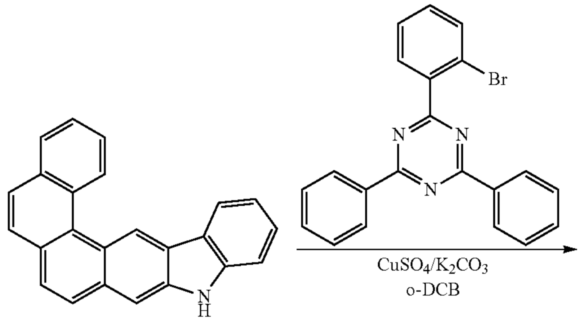

1-3

-continued

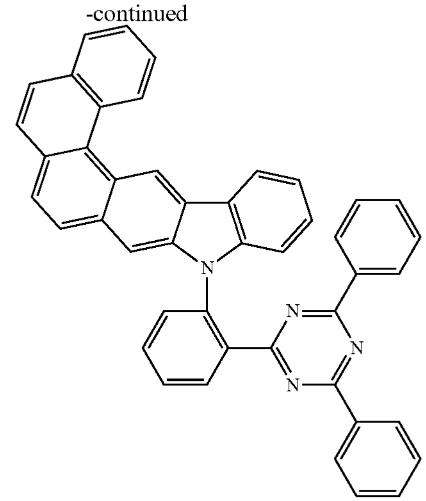

C-700

Compound 1-3 (5.0 g, 15.8 mmol), 2-(2-bromophenyl)-4,6-diphenyl-1,3,5-triazine (6.71 g, 17.3 mmol), $CuSO_4$ (1.0 g, 6.30 mmol), $K_2CO_3$ (4.35 g, 31.5 mmol), and 80 mL of o-dichlorobenzene (o-DCB) were introduced into a flask, and the mixture was stirred under reflux at 180° C. overnight. After completion of the reaction, a solid was obtained by adding MeOH to the mixture, and the solid was dissolved in $CHCl_3$. The residue was separated by column chromatography, and the solid obtained by adding MeOH was filtered under reduced pressure to obtain compound C-700 (2.0 g, yield: 20%).

| Compound | MW | M.P. |
|---|---|---|
| C-700 | 624.73 | 236° C. |

Example 3: Preparation of Compound C-589

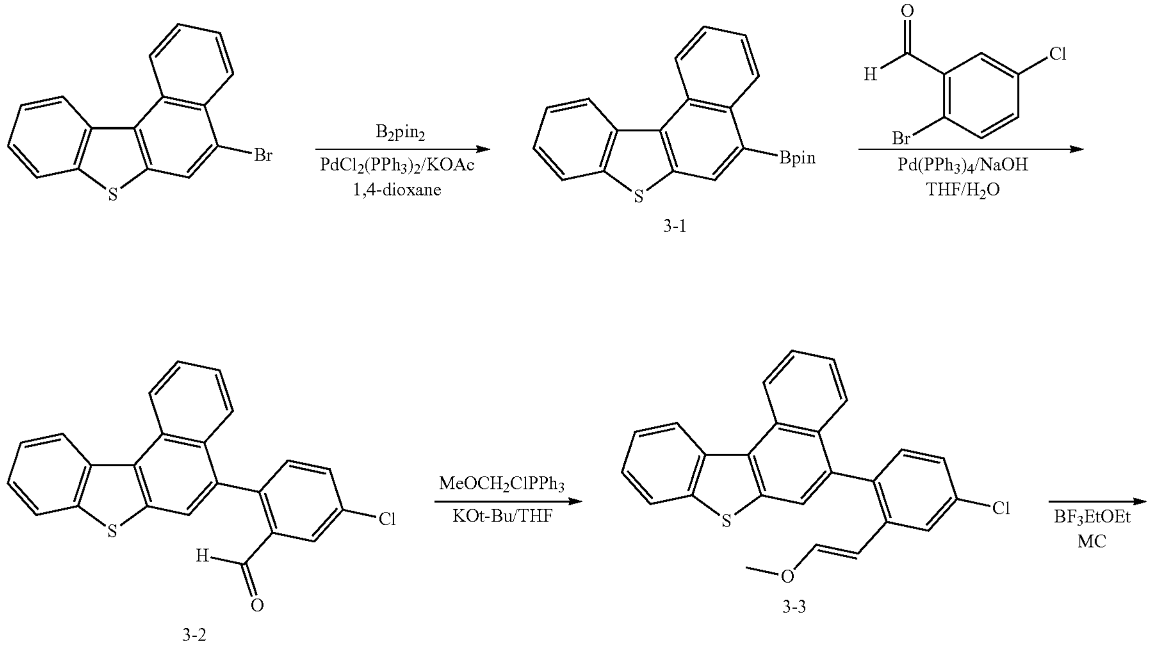

3-1

3-2

3-3

-continued

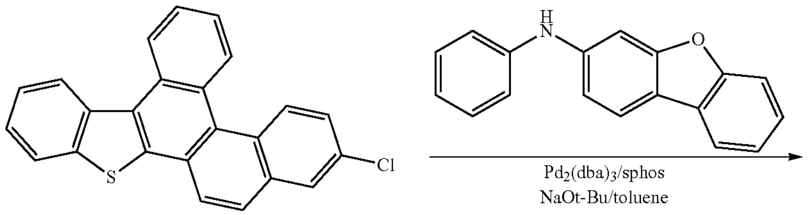

3-4

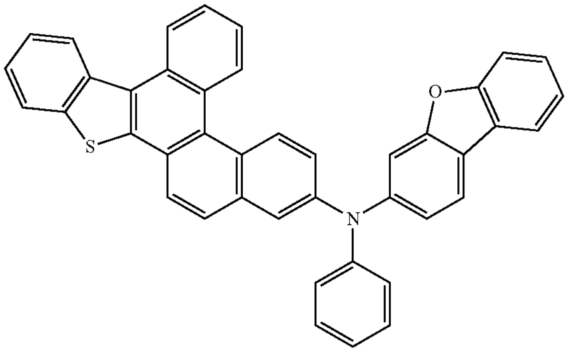

C-589

Synthesis of Compound 3-1

5-bromobenzo[b]naphtho[1,2-d]thiophene (50.0 g, 160 mmol), 4,4,4',4',5,5,5',5'-octamethyl-2,2'-bi(1,3,2-dioxaborolane) (48.6 g, 192 mmol), $PdCl_2(PPh_3)_2$ (5.60 g, 7.98 mmol), KOAc (39.2 g, 399 mmol), and 800 mL of 1,4-dioxane were introduced into a flask, and the mixture was stirred under reflux at 130° C. for 2 hours. After completion of the reaction, the reaction mixture was separated by column chromatography, and the solid obtained by adding MeOH was filtered under reduced pressure to obtain compound 3-1 (41.3 g, yield: 72%).

Synthesis of Compound 3-2

Compound 3-1 (40.3 g, 112 mmol), 2-bromo-5-chlorobenzaldehyde (25.8 g, 117 mmol), tetrakis(triphenylphosphine)palladium(0) (3.88 g, 3.36 mmol), NaOH (13.4 g, 336 mmol), 450 mL of THF, and 150 mL of $H_2O$ were introduced into a flask, and the mixture was stirred under reflux at 130° C. for 2 hours. After completion of the reaction, the reaction mixture was neutralized with an HCl aqueous solution, extracted with EA, and dried with $MgSO_4$. The residue was separated by column chromatography, and the solid obtained by adding MeOH was filtered under reduced pressure to obtain compound 3-2 (26.0 g, yield: 62.3%).

Synthesis of Compound 3-3

Compound 3-2 (25.0 g, 67.0 mmol), (methoxymethyl) triphenylphosphonium chloride (34.6 g, 101 mmol), and 340 mL of THF were introduced into a flask, and while stirring at 0° C., 101 mL of a 1 M solution of K-Ot-Bu dissolved in THF was added dropwise thereto. The mixture was stirred for 3 hours, neutralized with $NH_4Cl$, extracted with MC, and dried with $MgSO_4$. The residue was separated by column chromatography, and the solid obtained by adding MeOH was filtered under reduced pressure to obtain compound 3-3 (37.0 g, yield: 138%).

Synthesis of Compound 3-4

Compound 3-3 (36.0 g, 89.8 mmol) was dissolved in 450 mL of MC in a flask, and while stirring at 0° C., 34 mL of $BF_3$·EtOEt was added dropwise thereto. After completion of the reaction, the reaction mixture was neutralized with $NaHCO_3$, extracted with MC, and dried with $MgSO_4$. The residue was separated by column chromatography, and the solid obtained by adding MeOH was filtered under reduced pressure to obtain compound 3-4 (18.7 g, yield: 56.5%).

Synthesis of Compound C-589

Compound 3-4 (4.50 g, 12.2 mmol), N-phenyldibenzofuran-3-amine (3.32 g, 12.8 mmol), $Pd_2(dba)_3$ (0.559 g, 0.610 mmol), s-phos (0.501 g, 1.22 mmol), NaOt-Bu (2.34 g, 24.4 mmol), and 60 mL of toluene were introduced into a flask, and the mixture was stirred at 140° C. for 2 hours. After completion of the reaction, the mixture was cooled to room temperature, and separated by column chromatography. The solid obtained by adding MeOH was then filtered under reduced pressure to obtain compound C-589 (2.5 g, yield: 34.6%).

| Compound | MW | M.P. |
|---|---|---|
| C-589 | 591.72 | 122.6° C. |

Example 4: Preparation of Compound C-101

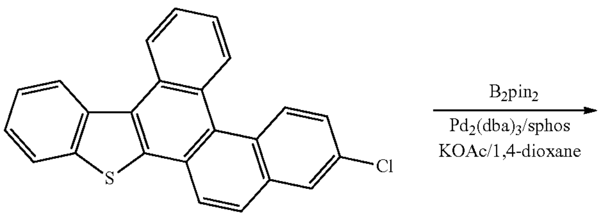

3-4

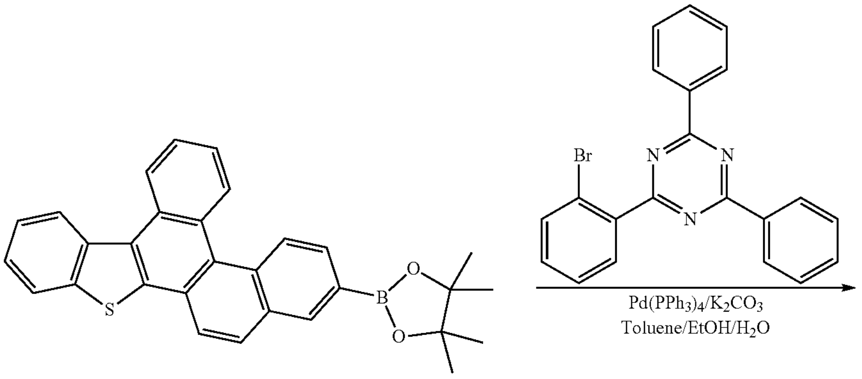

4-1

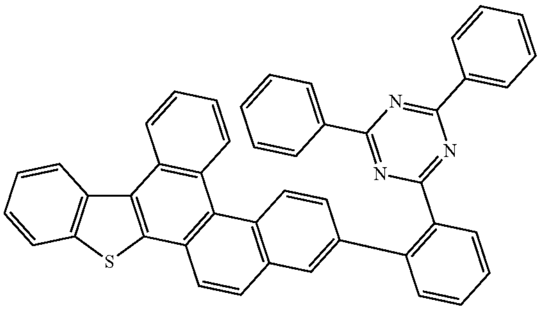

C-101

Synthesis of Compound 4-1

Compound 3-4 (9.0 g, 24.4 mmol), 4,4,4',4',5,5,5',5'-octamethyl-2,2'-bi(1,3,2-dioxaborolane) (8.05 g, 31.7 mmol), $Pd_2(dba)_3$ (1.12 g, 1.22 mmol), s-phos (1.00 g, 2.44 mmol), KOAc (7.18 g, 73.2 mmol), and 110 mL of 1,4-dioxane were introduced into a flask, and the mixture was stirred under reflux at 130° C. for 2 hours. After completion of the reaction, the reaction mixture was separated by column chromatography, and the solid obtained by adding MeOH was filtered under reduced pressure to obtain compound 4-1 (10.0 g, yield: 89%).

Synthesis of Compound C-101

Compound 4-1 (5.0 g, 10.9 mmol), 2-(2-bromophenyl)-4,6-diphenyl-1,3,5-triazine (4.22 g, 10.9 mmol), tetrakis (triphenylphosphine)palladium(0) (0.627 g, 0.543 mmol), $K_2CO_3$ (3.75 g, 27.2 mmol), 50.0 mL of toluene, 25.0 mL of EtOH, and 25.0 mL of $H_2O$ were introduced into a flask, and the mixture was stirred under reflux at 140° C. for 2 hours. After completion of the reaction, the reaction mixture was diluted by adding water, extracted with EA, and dried with $MgSO_4$. The residue was separated by column chromatography, and the solid obtained by adding MeOH was filtered under reduced pressure to obtain compound C-101 (3.0 g, yield: 43.0%).

| Compound | MW | M.P. |
|---|---|---|
| C-101 | 641.79 | 254.6° C. |

Example 5: Preparation of Compound C-715

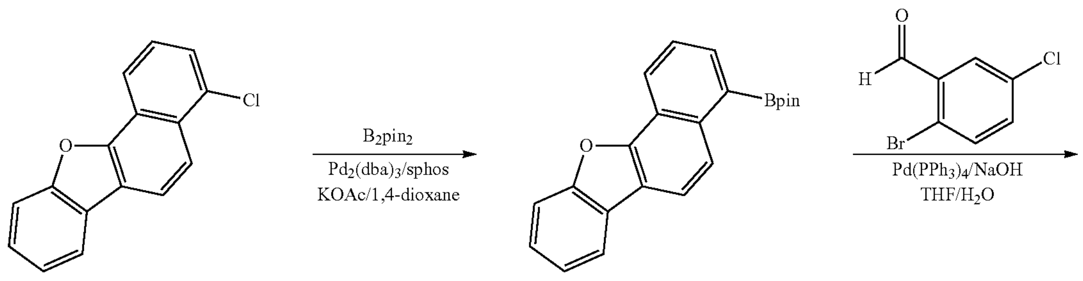

5-1

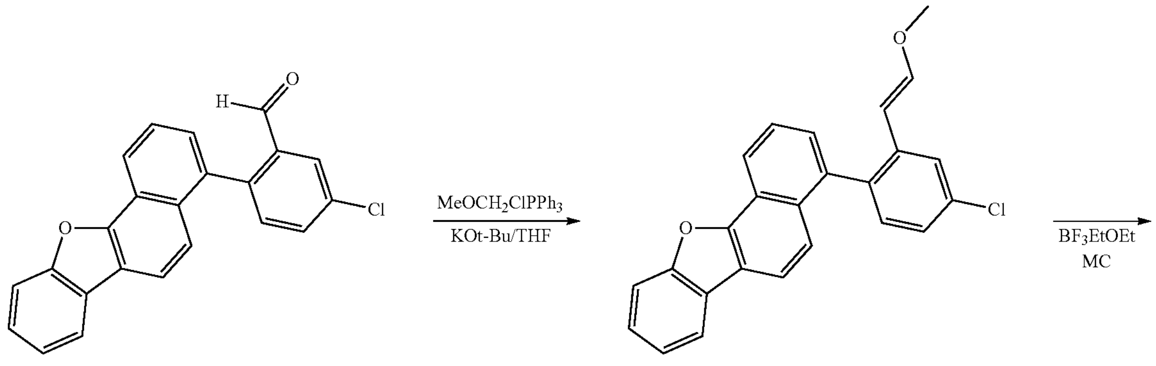

5-2

5-3

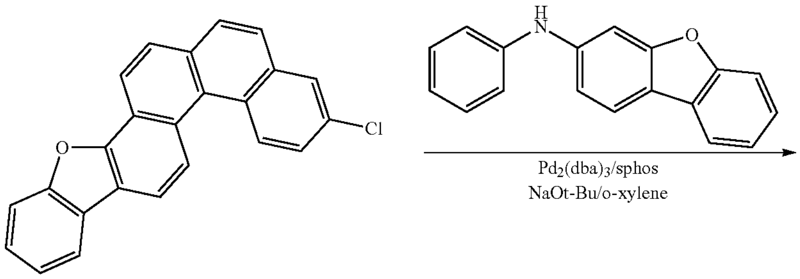

5-4

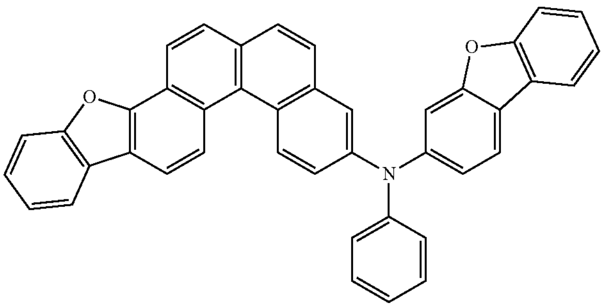

C-715

Synthesis of Compound 5-1

4-chloronaphtho[1,2-b]benzofuran (50.0 g, 198 mmol), 4,4,4',4',5,5,5',5'-octamethyl-2,2'-bi(1,3,2-dioxaborolane) (65.3 g, 257 mmol), $Pd_2(dba)_3$ (9.06 g, 9.89 mmol), s-phos (8.13 g, 19.8 mmol), KOAc (58.3 g, 399 mmol), and 1000 mL of 1,4-dioxane were introduced into a flask, and the mixture was stirred under reflux at 130° C. for 3 hours. After completion of the reaction, the reaction mixture was separated by column chromatography, and the solid obtained by adding MeOH was filtered under reduced pressure to obtain compound 5-1 (51.2 g, yield: 75%).

Synthesis of Compound 5-2

Compound 5-1 (50.2 g, 146 mmol), 2-bromo-5-chlorobenzaldehyde (33.6 g, 153 mmol), tetrakis(triphenylphosphine)palladium(0) (5.06 g, 4.38 mmol), NaOH (17.5 g, 438 mmol), 500 mL of THF, and 250 mL of $H_2O$ were introduced into a flask, and the mixture was stirred under reflux at 130° C. for 2 hours. After completion of the reaction, the reaction mixture was neutralized with an $NH_4Cl$ aqueous solution, extracted with EA, and dried with $MgSO_4$. The residue was separated by column chromatography, and the solid obtained by adding MeOH was filtered under reduced pressure to obtain compound 5-2 (36.0 g, yield: 69.1%).

Synthesis of Compound 5-3

Compound 5-2 (36.0 g, 100.9 mmol), (methoxymethyl) triphenylphosphonium chloride (51.9 g, 151.3 mmol), and 500 mL of THF were introduced into a flask, and while stirring at 0° C., 151.3 mL of a 1 M solution of K-Ot-Bu dissolved in THF was added dropwise thereto. The mixture was stirred for 3 hours, neutralized with $NH_4Cl$, extracted with EA, and dried with $MgSO_4$. The residue was separated by column chromatography, and the solid obtained by adding MeOH was filtered under reduced pressure to obtain compound 5-3 (38.0 g, yield: 98%).

Synthesis of Compound 5-4

Compound 5-3 (37.0 g, 96.1 mmol) was dissolved in 550 mL of MC in a flask, and while stirring at 0° C., 251 mL of $BF_3$-EtOEt was added dropwise thereto. After completion of the reaction, the reaction mixture was neutralized with $NaHCO_3$, extracted with MC, and dried with $MgSO_4$. The residue was separated by column chromatography, and the solid obtained by adding MeOH was filtered under reduced pressure to obtain compound 5-4 (13.6 g, yield: 40.1%).

Synthesis of Compound C-715

Compound 5-4 (4.80 g, 13.6 mmol), N-phenyldibenzofuran-3-amine (3.7 g, 14.3 mmol), $Pd_2(dba)_3$ (0.559 g, 0.680 mmol), s-phos (0.501 g, 1.36 mmol), NaOt-Bu (2.61 g, 27.2 mmol), and 70 mL of o-xylene were introduced into a flask, and the mixture was stirred at 190° C. for 1.5 hours. After completion of the reaction, the mixture was cooled to room temperature, and separated by column chromatography. The solid obtained by adding MeOH was then filtered under reduced pressure to obtain compound C-715 (3.9 g, yield: 49.8%).

| Compound | MW | M.P. |
|---|---|---|
| C-715 | 575.67 | 258.9° C. |

Example 6: Preparation of Compound C-13

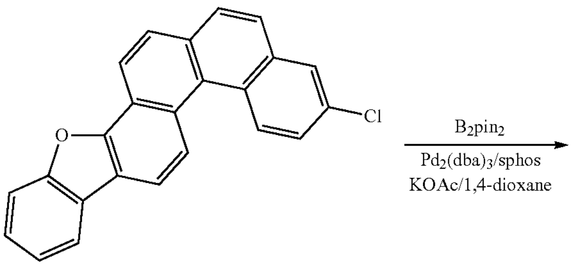

5-4

-continued

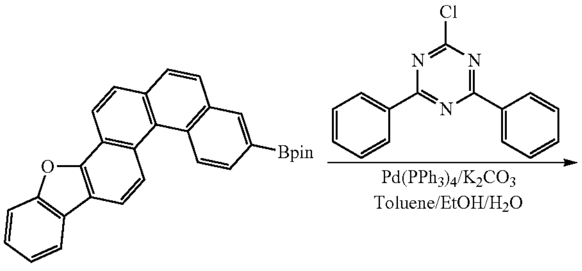

6-1

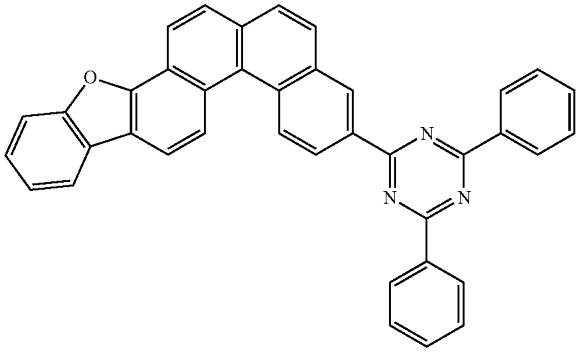

C-13

Synthesis of Compound 6-1

Compound 5-4 (9.0 g, 25.5 mmol), 4,4,4',4',5,5,5',5'-octamethyl-2,2'-bi(1,3,2-dioxaborolane) (8.43 g, 33.2 mmol), $Pd_2(dba)_3$ (1.17 g, 1.28 mmol), s-phos (1.05 g, 2.55 mmol), KOAc (7.50 g, 76.5 mmol), and 130 mL of 1,4-dioxane were introduced into a flask, and the mixture was stirred under reflux at 130° C. for 3 hours. After completion of the reaction, the reaction mixture was separated by column chromatography, and the solid obtained by adding MeOH was filtered under reduced pressure to obtain compound 6-1 (10.5 g, yield: 92.7%).

Synthesis of Compound C-13

Compound 6-1 (5.0 g, 11.3 mmol), 2-chloro-4,6-diphenyl-1,3,5-triazine (3.03 g, 11.3 mmol), tetrakis(triphenylphosphine)palladium(0) (0.650 g, 0.563 mmol), $K_2CO_3$ (3.88 g, 28.1 mmol), 30 mL of toluene, 10 mL of EtOH, and 10 mL of $H_2O$ were introduced into a flask, and the mixture was stirred under reflux at 130° C. for 2 hours. After completion of the reaction, the reaction mixture was filtered and dried. The residue was separated by column chromatography, and the solid obtained by adding MeOH was filtered under reduced pressure to obtain compound C-13 (2.5 g, yield: 40.3%).

| Compound | MW | M.P. |
|---|---|---|
| C-13 | 549.63 | 297.4° C. |

Example 7: Preparation of Compound C-220

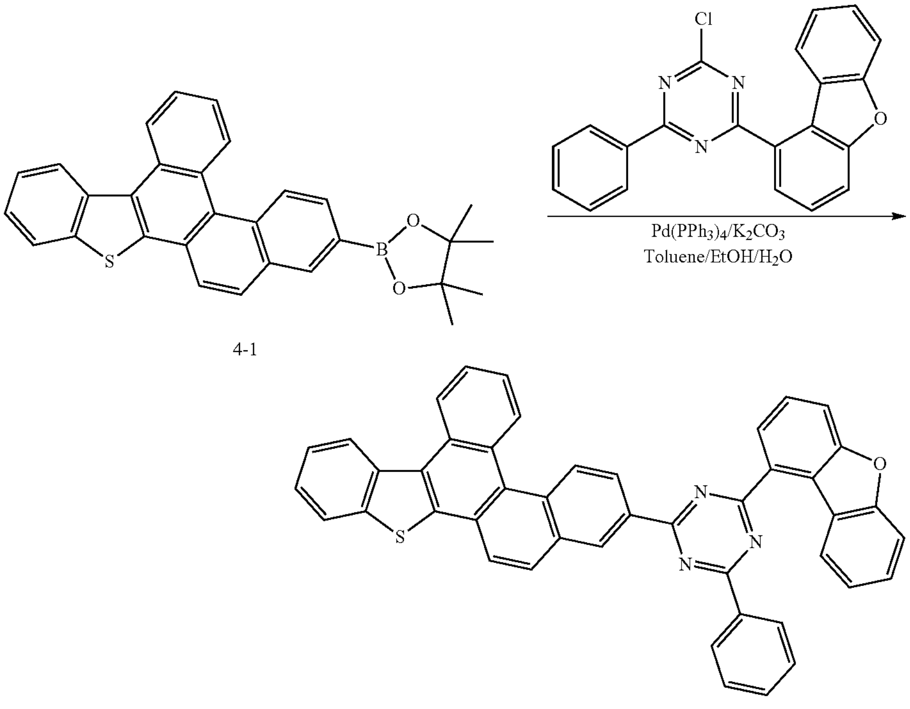

4-1

C-220

Compound 4-1 (4.7 g, 10.2 mmol), 2-chloro-4-(dibenzo[b,d]furan-1-yl)-6-phenyl-1,3,5-triazine (3.84 g, 10.7 mmol), tetrakis(triphenylphosphine)palladium(0) (0.589 g, 0.51 mmol), $K_2CO_3$ (3.52 g, 25.5 mmol), 30.0 mL of toluene, 10.0 mL of EtOH, and 10.0 mL of $H_2O$ were introduced into a flask, and the mixture was stirred under reflux at 140° C. for 2 hours. After completion of the reaction, the reaction mixture was diluted by adding water, extracted with EA, and dried with $MgSO_4$. The residue was separated by column chromatography, and the solid obtained by adding MeOH was filtered under reduced pressure to obtain compound C-220 (3.6 g, yield: 53.8%).

| Compound | MW | M.P. |
| --- | --- | --- |
| C-220 | 655.78 | 346.5° C. |

Device Example 1: Producing a Red Light-Emitting OLED According to the Present Disclosure An OLED comprising a compound according to the present disclosure was produced. A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropyl alcohol. The ITO substrate was then mounted on a substrate holder of a vacuum vapor deposition apparatus. Compound HI-1 was introduced into a cell of the vacuum vapor deposition apparatus, and compound HT-1 was introduced into another cell. The two materials were evaporated at different rates, and compound HI-1 was deposited in a doping amount of 3 wt % based on the total amount of compound HI-1 and compound HT-1 to form a hole injection layer having a thickness of 10 nm on the ITO substrate. Next, compound HT-1 was introduced into a cell of the vacuum vapor deposition apparatus and was evaporated by applying an electric current to the cell, thereby forming a first hole transport layer having a thickness of 80 nm on the hole injection layer. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: Compound C-686 was introduced into one cell of the vacuum vapor depositing apparatus as a host, and compound D-39 was introduced into another cell as a dopant. The two materials were evaporated at different rates, and the dopant was deposited in a doping amount of 3 wt % based on the total amount of the host and dopant to form a light-emitting layer having a thickness of 40 nm on the second hole transport layer. Compound ETL-1 and compound EIL-1 were evaporated as electron transport materials in a weight ratio of 50:50 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the compounds as materials used were purified by vacuum sublimation at $10^{-6}$ torr.

Device Example 2: Producing a Red Light-Emitting OLED According to the Present Disclosure An OLED was produced in the same manner as in Device Example 1, except that compound C-700 was used as the host of the light-emitting layer.

Comparative Example: Producing an OLED Comprising a Comparative Compound as a Host An OLED was produced in the same manner as in Device Example 1, except that compound CBP was used as the host of the light-emitting layer.

The driving voltage, luminous efficiency, and light-emitting color at a luminance of 1,000 nit, and the time taken for luminance to decrease from 100% to 95% at a luminance of 5,000 nit (lifetime; T95) of the OLEDs produced in Device Examples 1 and 2 and the Comparative Example are provided in Table 1 below.

TABLE 1

| | Host | Driving Voltage [V] | Luminous Efficiency [cd/A] | Light-Emitting Color | Lifetime T95 [hr] |
|---|---|---|---|---|---|
| Device Example 1 | C-686 | 3.6 | 33.0 | Red | 143 |
| Device Example 2 | C-700 | 4.1 | 33.7 | Red | 69.2 |
| Comparative Example | CBP | 9.0 | 14.3 | Red | 0.3 |

The OLED comprising the organic electroluminescent compound according to the present disclosure as a host showed lower driving voltage, higher luminous efficiency, and excellent lifetime property compared to the OLED using the compound of the Comparative Example.

Device Examples 3 to 6: Producing a Red Light-Emitting OLED According to the Present Disclosure OLEDs according to the present disclosure were produced. A transparent electrode indium tin oxide (ITO) thin film (10 Ω/sq) on a glass substrate for an OLED (GEOMATEC CO., LTD., Japan) was subjected to an ultrasonic washing with acetone and isopropyl alcohol, sequentially, and then was stored in isopropyl alcohol. The ITO substrate was then mounted on a substrate holder of a vacuum vapor deposition apparatus. Compound HI-1 was introduced into a cell of the vacuum vapor deposition apparatus, and compound HT-1 was introduced into another cell. The two materials were evaporated at different rates, and compound HI-1 was deposited in a doping amount of 3 wt % based on the total amount of compound HI-1 and compound HT-1 to form a hole injection layer having a thickness of 10 nm on the ITO substrate. Next, compound HT-1 was introduced into a cell of the vacuum vapor deposition apparatus and was evaporated by applying an electric current to the cell, thereby forming a first hole transport layer having a thickness of 80 nm on the hole injection layer. Compound HT-2 was then introduced into another cell of the vacuum vapor deposition apparatus and was evaporated by applying an electric current to the cell, thereby forming a second hole transport layer having a thickness of 60 nm on the first hole transport layer. After forming the hole injection layer and the hole transport layers, a light-emitting layer was formed thereon as follows: The first host material and the second host material shown in Table 2 below were introduced into two cells, respectively, of the vacuum vapor depositing apparatus as hosts, and compound D-39 was introduced into another cell as a dopant. The two host materials were evaporated at a rate of 1:1 and the dopant material was simultaneously evaporated at a different rate, and the dopant was deposited in a doping amount of 3 wt % based on the total amount of the hosts and the dopant to form a light-emitting layer having a thickness of 40 nm on the second hole transport layer. Compound ETL-1 and compound EIL-1 were evaporated as electron transport materials in a weight ratio of 50:50 to form an electron transport layer having a thickness of 35 nm on the light-emitting layer. After depositing compound EIL-1 as an electron injection layer having a thickness of 2 nm on the electron transport layer, an Al cathode having a thickness of 80 nm was deposited on the electron injection layer by another vacuum vapor deposition apparatus. Thus, an OLED was produced. All the compounds as materials used were purified by vacuum sublimation at $10^{-6}$ torr.

The driving voltage, luminous efficiency, and light-emitting color at a luminance of 1,000 nit, and the time taken for luminance to decrease from 100% to 95% at a luminance of 5,000 nit (lifetime; T95) of the OLEDs produced in Device Examples 3 to 6 are provided in Table 2 below.

TABLE 2

| | First Host | Second Host | Driving Voltage [V] | Luminous Efficiency [cd/A] | Light-Emitting Color | Lifetime T95 [hr] |
|---|---|---|---|---|---|---|
| Device Example 3 | C-589 | H2-158 | 3.3 | 34.5 | Red | 265 |
| Device Example 4 | C-715 | H2-246 | 3.3 | 33.5 | Red | 555 |
| Device Example 5 | H1-9 | C-13 | 3.1 | 32.6 | Red | 295 |
| Device Example 6 | H1-9 | C-220 | 2.9 | 32.1 | Red | 334 |

The OLED according to the present disclosure showed low driving voltage, high luminous efficiency, and significantly excellent lifetime property.

TABLE 3
| Organic Electroluminescent Material Used in the Device Examples and the Comparative Example | |
|---|---|
| Hole Injection Layer/ Hole Transport Layer | 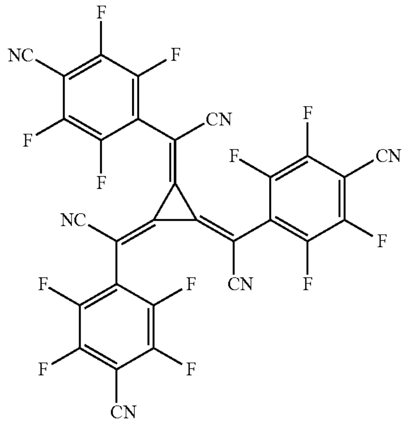 HI-1 |
| | 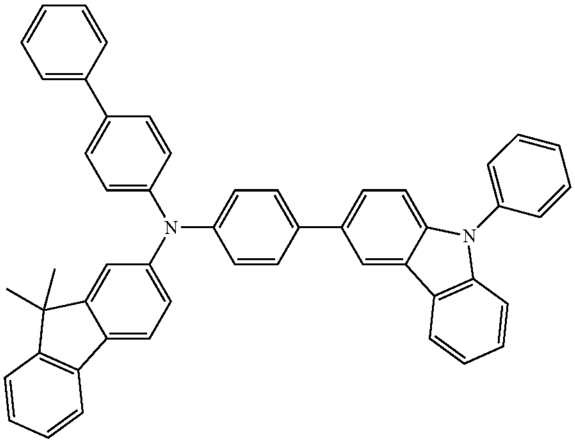 HT-1 |
| | 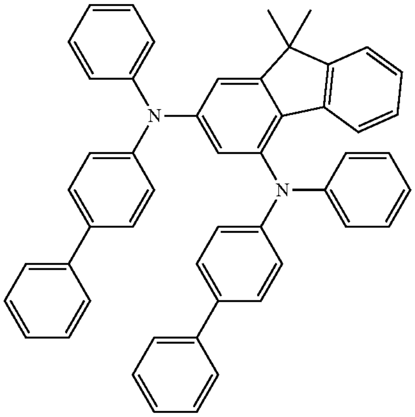 HT-2 |

TABLE 3-continued
| Organic Electroluminescent Material Used in the Device Examples and the Comparative Example | |
|---|---|
| Light-Emitting Layer | 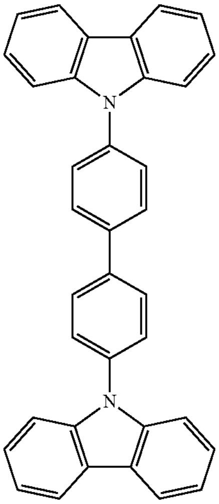 CBP |
| | 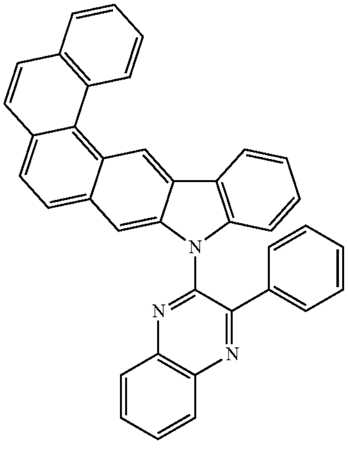 C-686 |
| | 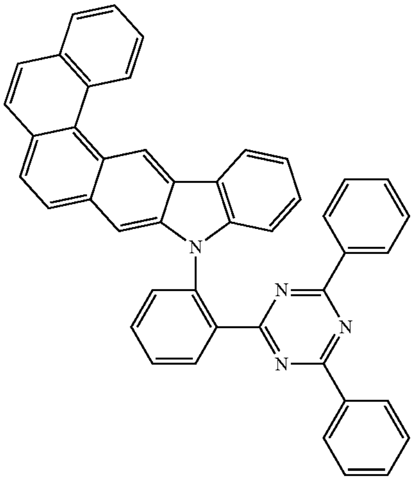 C-700 |

TABLE 3-continued
| Organic Electroluminescent Material Used in the Device Examples and the Comparative Example |
|---|
| 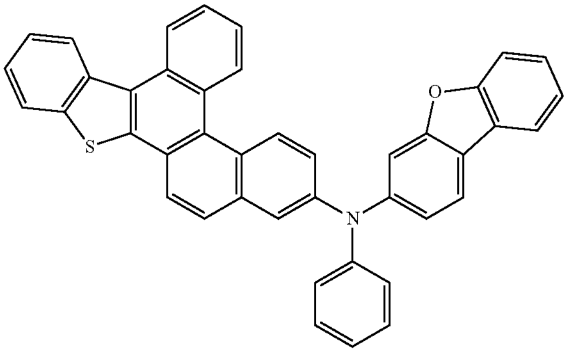 |
| C-589 |
| 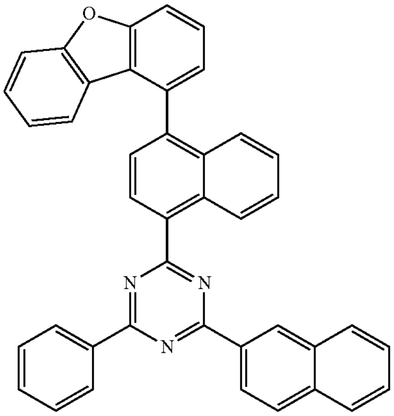 |
| H2-158 |
| 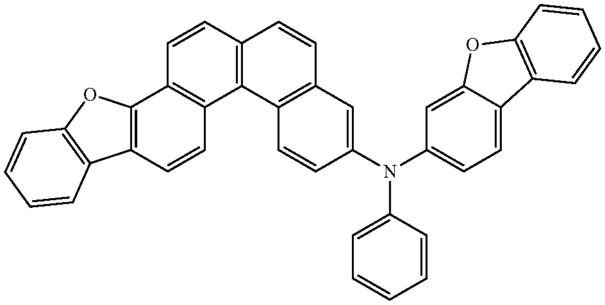 |
| C-715 |

TABLE 3-continued
| Organic Electroluminescent Material Used in the Device Examples and the Comparative Example |
|---|
| 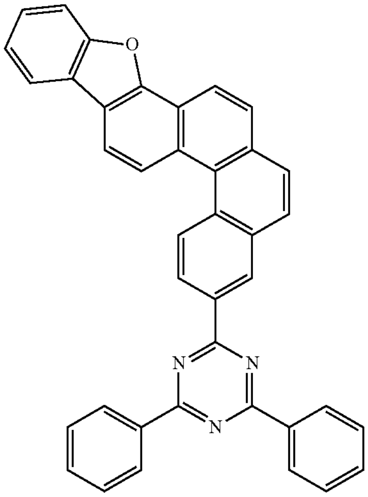 |
| C-13 |
| 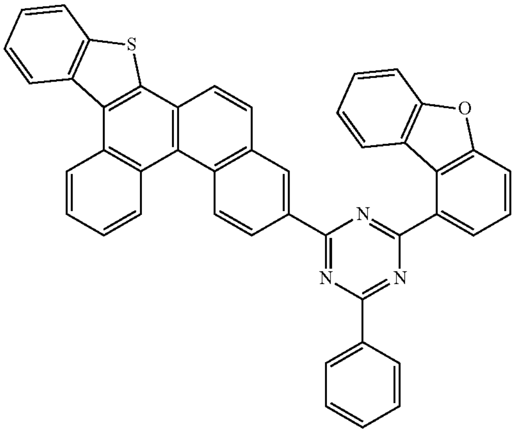 |
| C-220 |
| 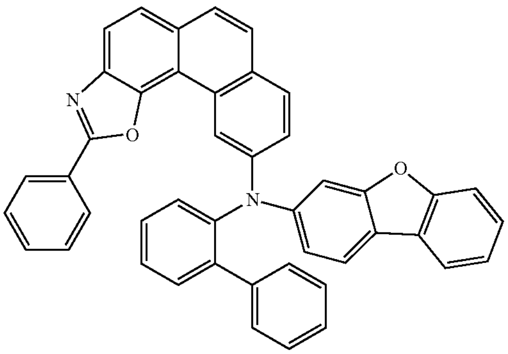 |
| H1-9 |

TABLE 3-continued
| Organic Electroluminescent Material Used in the Device Examples and the Comparative Example | |
|---|---|
| | 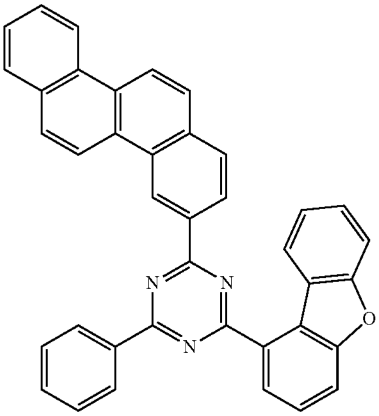<br>H2-246 |
| | 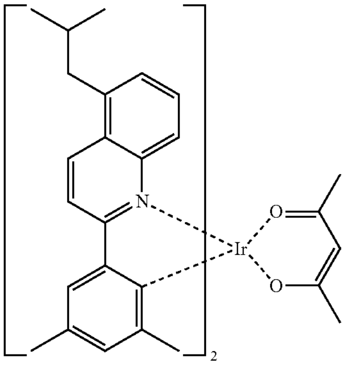<br>D-39 |
| Electron Transport Layer/ Electron Injection Layer | 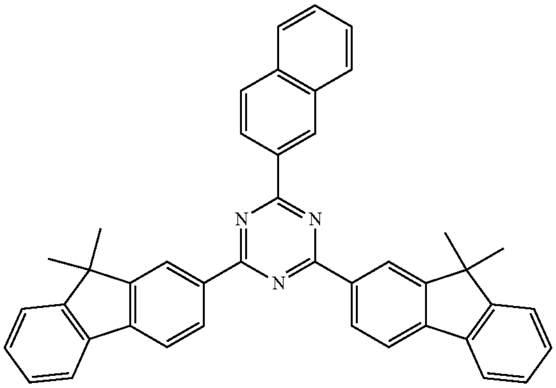<br>ETL-1 |
| | 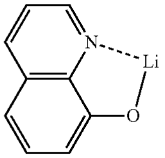<br>EIL-1 |

The invention claimed is:

1. An organic electroluminescent compound represented by the following formula 1:

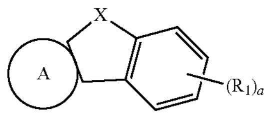

1 wherein when ring A is selected from the following formulas;

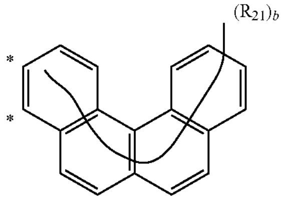

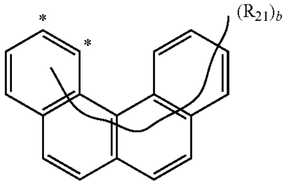

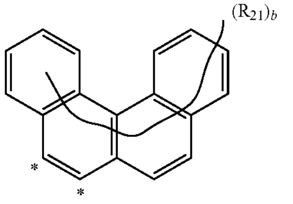

X represents $NR_{11}$, $CR_{12}R_{13}$, O, or S;

$R_1$ each independently represents hydrogen, deuterium, a halogen, or a cyano;

$R_{11}$ represents hydrogen, deuterium, a halogen, a cyano, a substituted or unsubstituted C1-C30 alkyl, a substituted or unsubstituted C3-C30 cycloalkyl, a substituted or unsubstituted 3- to 7-membered heterocycloalkyl, a substituted or unsubstituted C6-C30 aryl, a substituted or unsubstituted 3- to 30-membered heteroaryl, a substituted or unsubstituted silyl, or a substituted or unsubstituted amino;

$R_{12}$ and $R_{13}$ each independently represent a halogen, a cyano, a substituted or unsubstituted C1-C30 alkyl, a substituted or unsubstituted C3-C30 cycloalkyl, a substituted or unsubstituted 3- to 7-membered heterocycloalkyl, a substituted or unsubstituted C6-C30 aryl, a substituted or unsubstituted 3- to 30-membered heteroaryl, a substituted or unsubstituted silyl, or a substituted or unsubstituted amino; or are linked to each other to form a ring;

$R_{21}$ represents $-L_1-Ar_1$, where if $R_{21}$ is plural, each of $R_{21}$ may be the same or different;

$L_1$ each independently represents a single bond, a substituted or unsubstituted C6-C30 arylene aryl, or a substituted or unsubstituted 3- to 30-membered heteroarylene;

$Ar_1$ each independently represents deuterium, a halogen, a cyano, a substituted or unsubstituted C1-C30 alkyl, a substituted or unsubstituted C3-C30 cycloalkyl, a substituted or unsubstituted 3- to 7-membered heterocycloalkyl, a substituted or unsubstituted C6-C30 aryl, a substituted or unsubstituted 3- to 30-membered heteroaryl, a substituted or unsubstituted silyl, or a substituted amino; and a represents an integer of 1 to 4, b represents an integer of 1 to 10, where if and b are an integer of 2 or more, each of $R_1$ and each of $R_{21}$ may be the same or different;

* represents a site fused with the 5-membered ring comprising X;

with the proviso that if X is $NR_{11}$, ring A is not

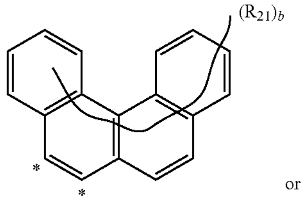

or

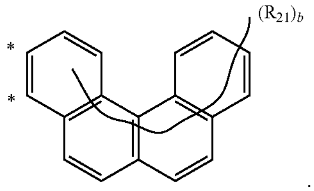

.

2. The organic electroluminescent compound according to claim 1, wherein the substituents of the substituted alkyl, the substituted cycloalkyl, the substituted heterocycloalkyl, the substituted aryl, the substituted arylene, the substituted heteroaryl, the substituted heteroarylene, the substituted silyl, and the substituted amino in $R_{11}$ to $R_{13}$, $L_1$, and $Ar_1$ each independently are at least one selected from the group consisting of deuterium; a halogen; a cyano; a carboxyl; a nitro; a hydroxyl; a phosphine oxide; a C1-C30 alkyl; a haloC1-C30 alkyl; a C2-C30 alkenyl; a C2-C30 alkynyl; a C1-C30 alkoxy; a C1-C30 alkylthio; a C3-C30 cycloalkyl; a C3-C30 cycloalkenyl; a 3- to 7-membered heterocycloalkyl; a C6-C30 aryloxy; a C6-C30 arylthio; a 3- to 30-membered heteroaryl unsubstituted or substituted with a C6-C30 aryls; a C6-C30 aryl unsubstituted or substituted with at least one of a C1-C30 alkyls and a 3- to 30-membered heteroaryls; a triC1-C30 alkylsilyl; a triC6-C30 arylsilyl; a diC1-C30 alkylC6-C30 arylsilyl; a C1-C30 alkyldiC6-C30 arylsilyl; an amino; a mono- or di-C1-C30 alkylamino; a mono- or di-C2-C30 alkenylamino; a mono- or di-C6-C30 arylamino; a mono- or di-3- to 30-membered heteroarylamino; a C1-C30 alkylC2-C30 alkenylamino; a C1-C30 alkylC6-C30 arylamino; a C1-C30 alkyl3- to 30-membered heteroarylamino; a C2-C30 alkenylC6-C30 arylamino; a C2-C30 alkenyl3- to 30-membered heteroarylamino; a C6-C30 aryl3- to 30-membered heteroarylamino; a C1-C30 alkylcarbonyl; a C1-C30 alkoxycarbonyl; a C6-C30 arylcarbonyl; a C6-C30 arylphosphine; a diC6-C30 arylboronyl; a diC1-C30 alkylboronyl; a C1-C30 alkylC6-C30 arylboronyl; a C6-C30 arylC1-C30 alkyl; and a C1-C30 alkylC6-C30 aryl.

3. The organic electroluminescent compound according to claim 1, wherein ring A is selected from the following formulas:

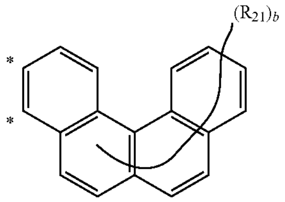

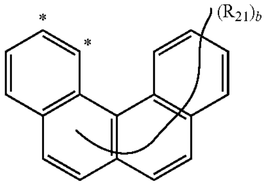

and

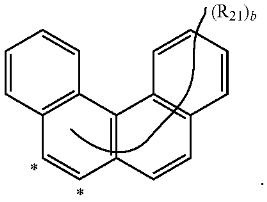

.

4. The organic electroluminescent compound according to claim 1, wherein ring A is selected from the following formulas:

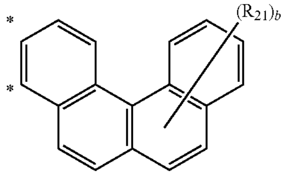

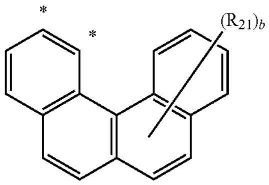

and

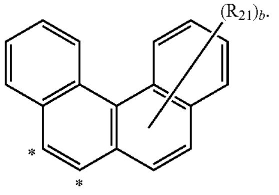

5. The organic electroluminescent compound according to claim 1, wherein ring A is selected from the following formulas:

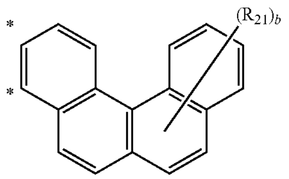

-continued

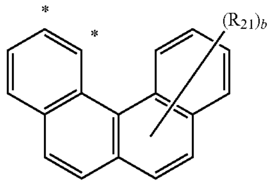

and

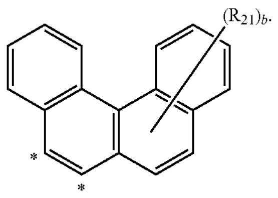

6. The organic electroluminescent compound according to claim 1, wherein $L_1$ each independently represents a single bond, a substituted or unsubstituted phenylene, a substituted or unsubstituted biphenylene, a substituted or unsubstituted terphenylene, a substituted or unsubstituted naphthylene, a substituted or unsubstituted phenanthrenylene, a substituted or unsubstituted triphenylenylene, a substituted or unsubstituted fluorenylene, or a substituted or unsubstituted pyridylene.

7. The organic electroluminescent compound according to claim 1, wherein the substituted or unsubstituted 3- to 30-membered heteroaryl of $R_{11}$ to $R_{13}$ and $Ar_1$ each independently represents a substituted or unsubstituted pyridyl, a substituted or unsubstituted pyrimidinyl, a substituted or unsubstituted triazinyl, a substituted or unsubstituted pyrazinyl, a substituted or unsubstituted quinolyl, a substituted or unsubstituted quinazolinyl, a substituted or unsubstituted quinoxalinyl, a substituted or unsubstituted benzoquinolyl, a substituted or unsubstituted benzoquinazolinyl, a substituted or unsubstituted benzoquinoxalinyl, a substituted or unsubstituted dibenzoquinolyl, a substituted or unsubstituted dibenzoquinazolinyl, a substituted or unsubstituted dibenzoquinoxalinyl, a substituted or unsubstituted indenopyridyl, a substituted or unsubstituted indenopyrimidinyl, a substituted or unsubstituted indenopyrazinyl, a substituted or unsubstituted benzofuropyridyl, a substituted or unsubstituted benzofuropyrimidinyl, a substituted or unsubstituted benzofuropyrazinyl, a substituted or unsubstituted benzothiopyridyl, a substituted or unsubstituted benzothiopyrimidinyl, a substituted or unsubstituted benzothiopyranyl, a substituted or unsubstituted carbazolyl, a substituted or unsubstituted dibenzofuranyl, or a substituted or unsubstituted dibenzothiophenyl.

8. An organic electroluminescent compound selected from the following compounds:

-continued
C-1
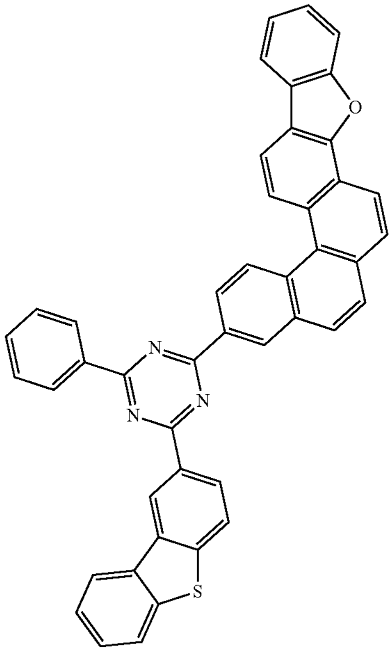
C-3
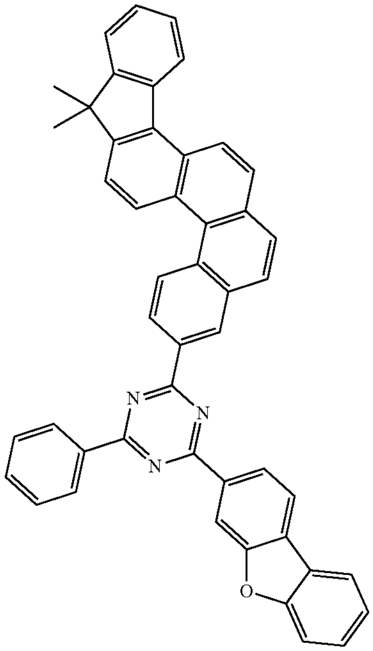
C-2
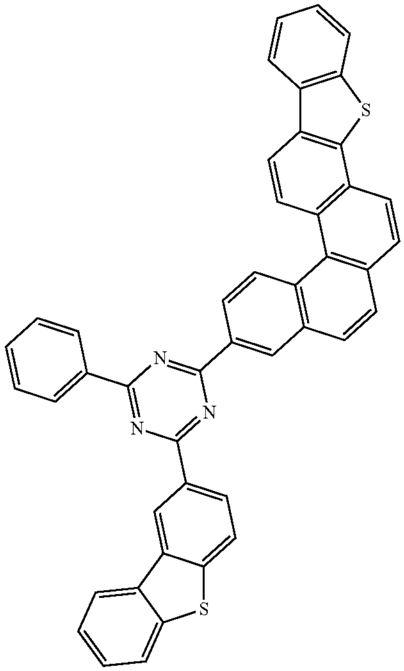
C-4
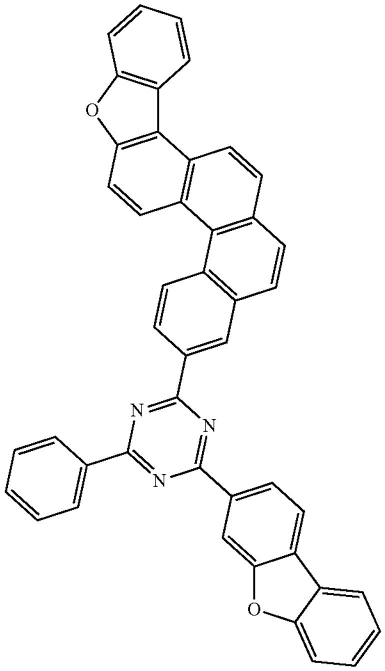

-continued
C-5
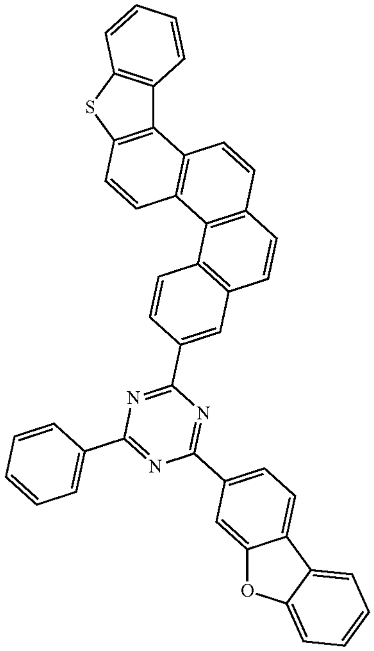
C-7
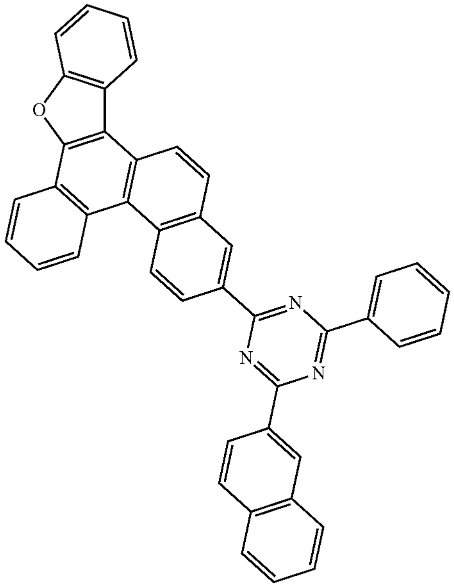
C-6
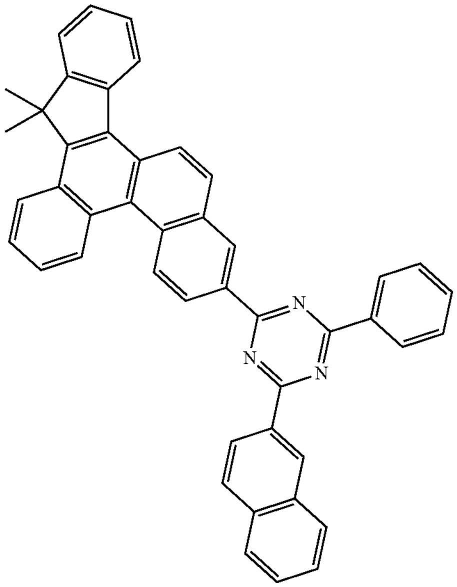
C-8
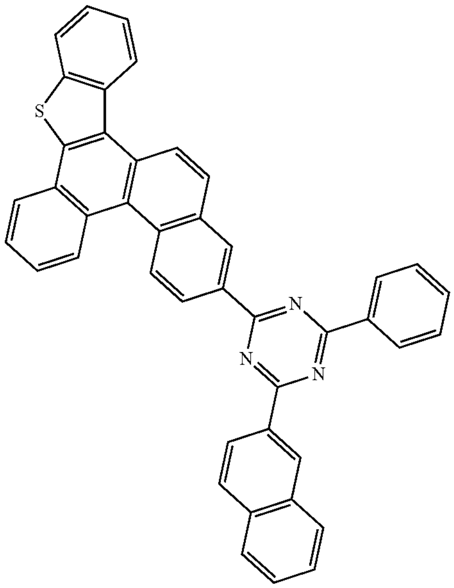

-continued
C-9
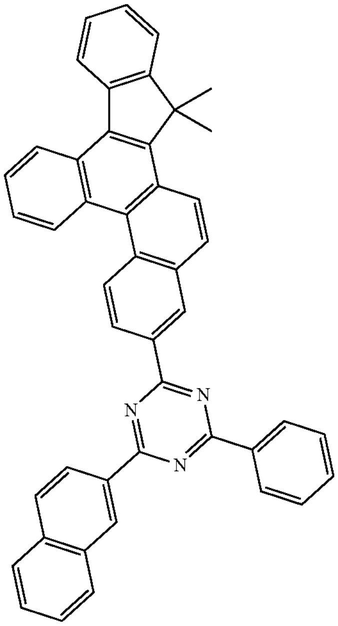
C-10
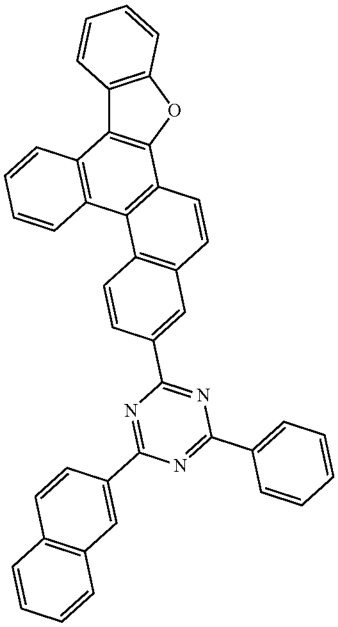
-continued
C-11
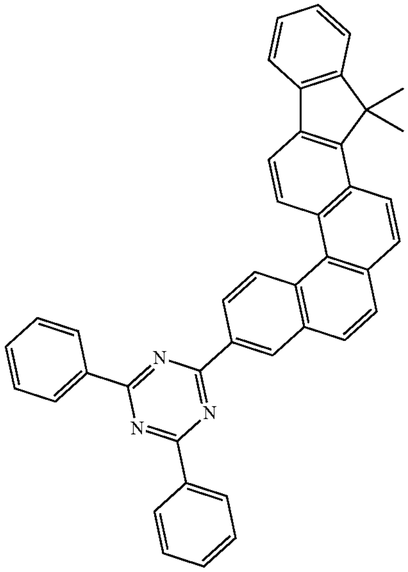
C-12
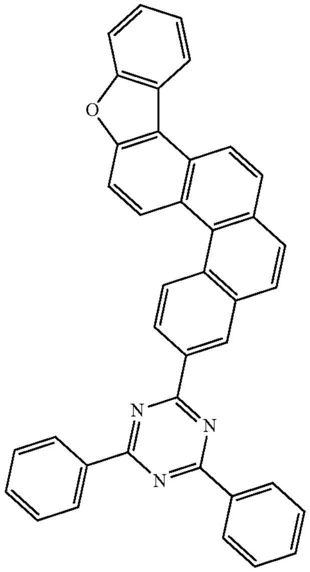

-continued
C-13
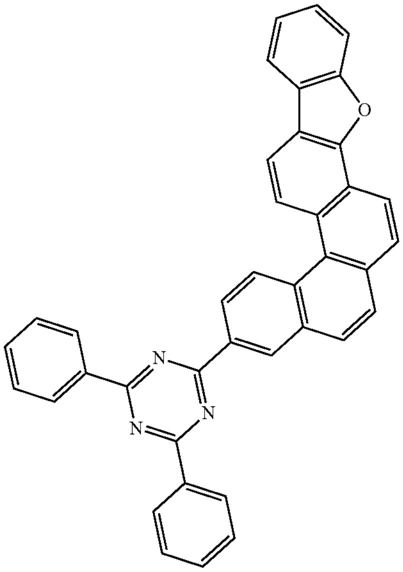
C-14
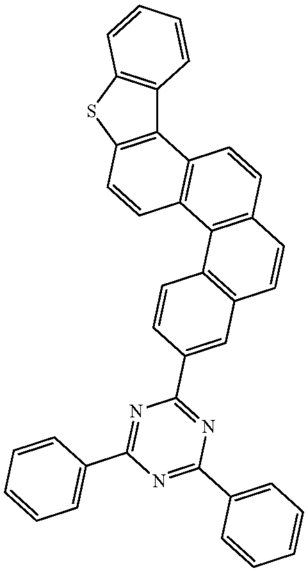
-continued
C-15
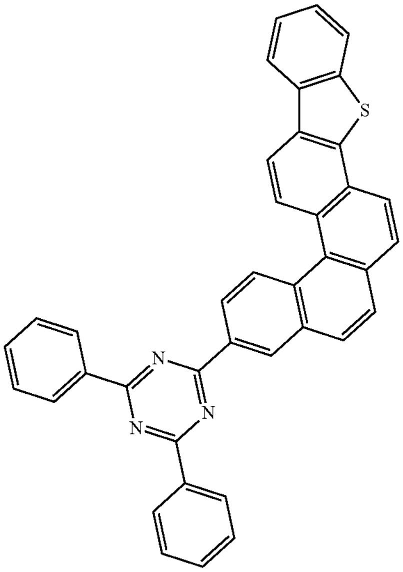
C-16
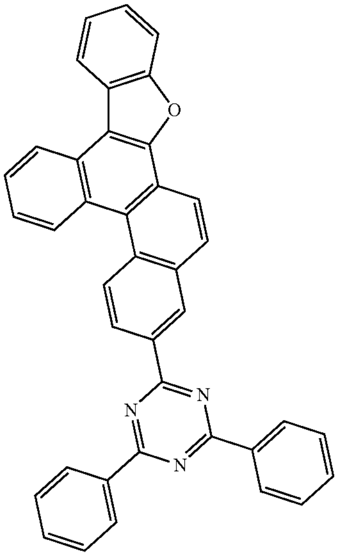

-continued
C-17
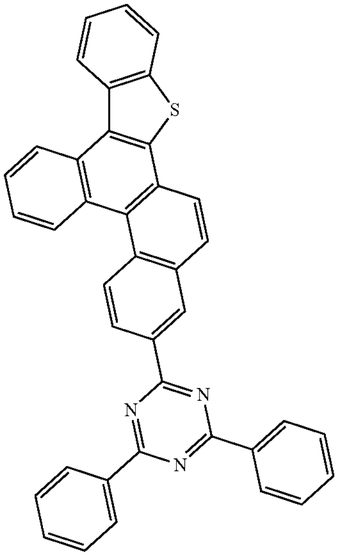
-continued
C-19
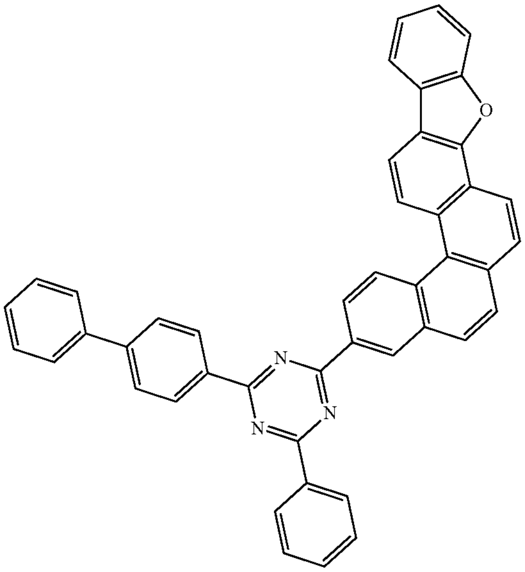
C-18
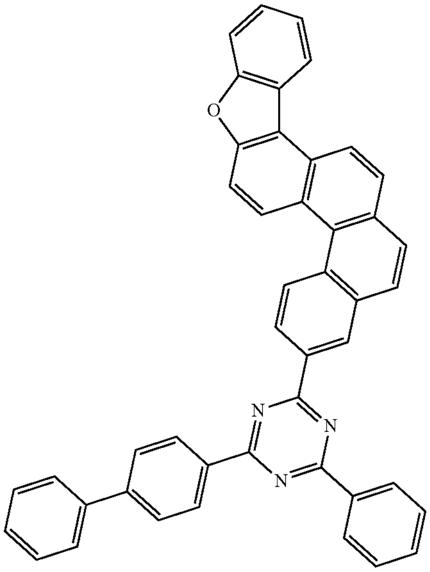
C-20
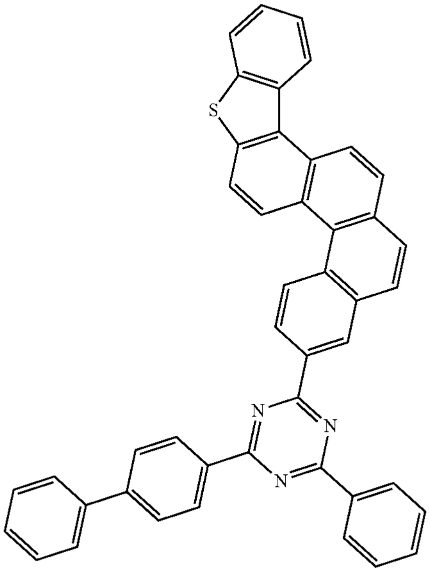

-continued
C-21
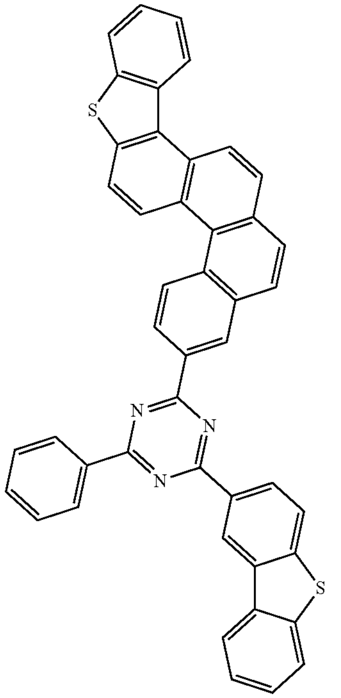
C-22
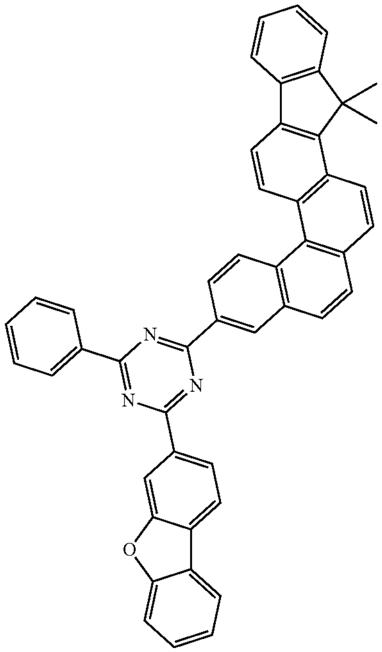
-continued
C-23
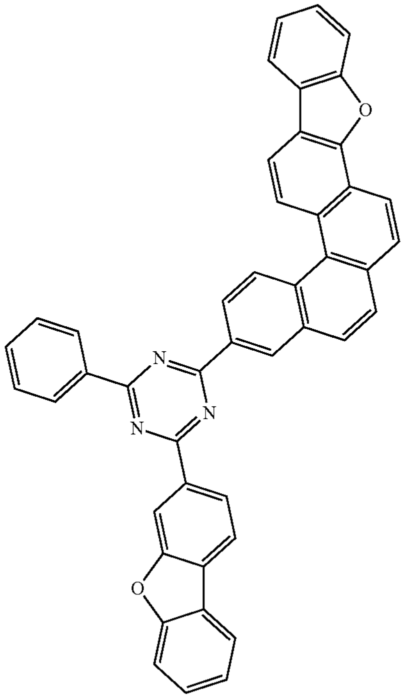
C-24
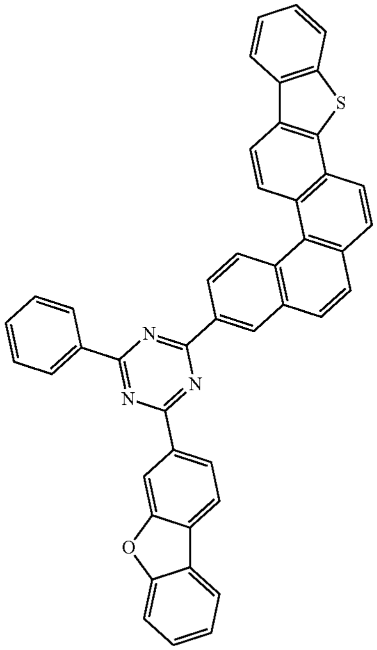

-continued
C-25
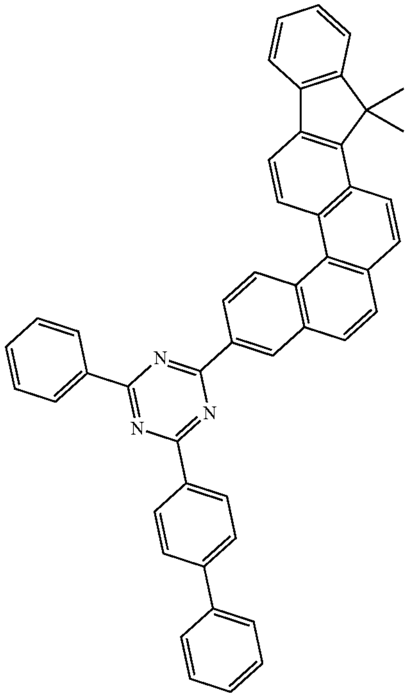
C-26
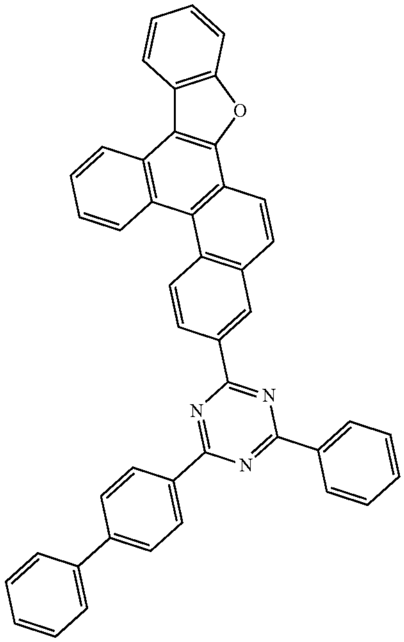
-continued
C-27
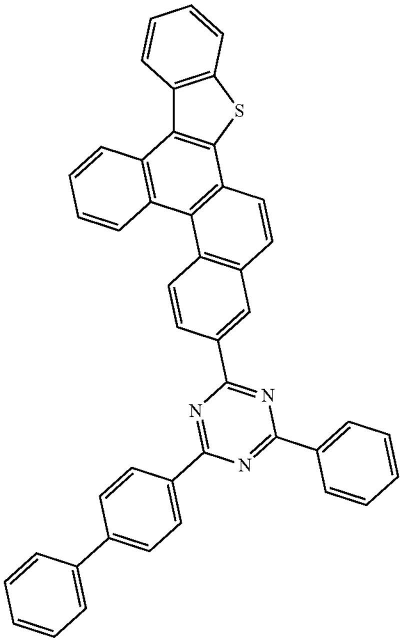
C-28
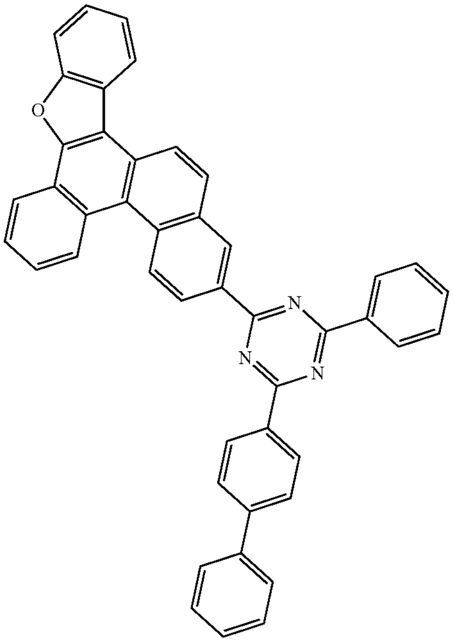

-continued
C-29
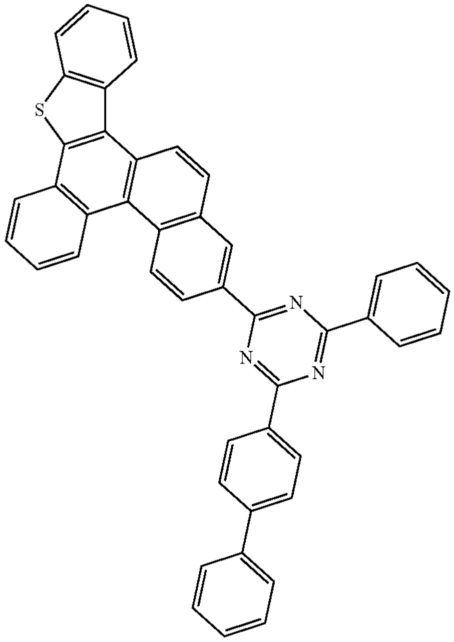
C-30
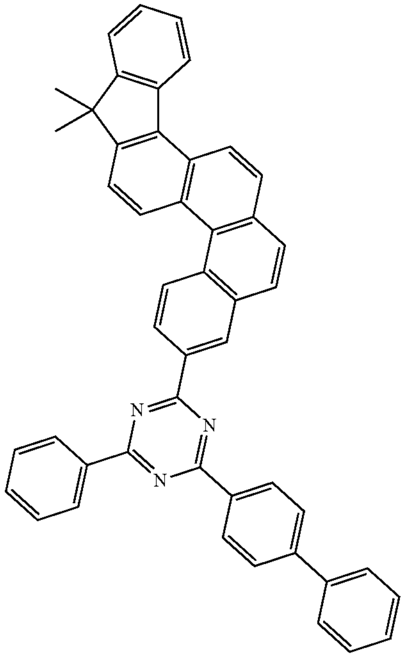
-continued
C-31
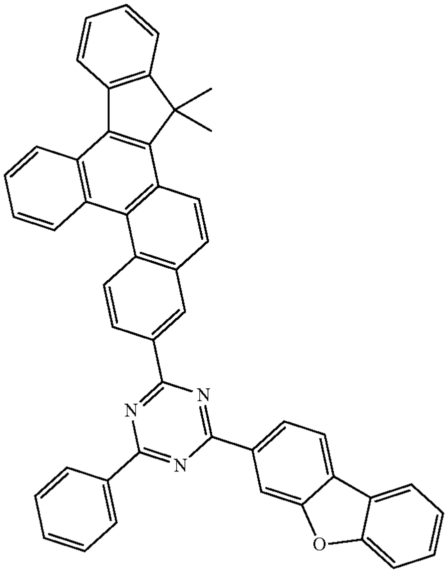
C-32
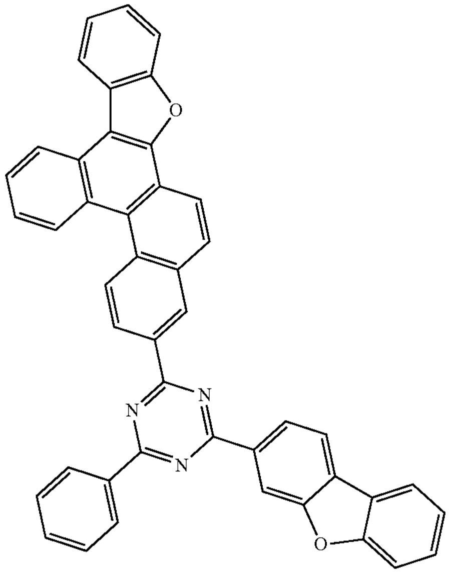

-continued
C-33
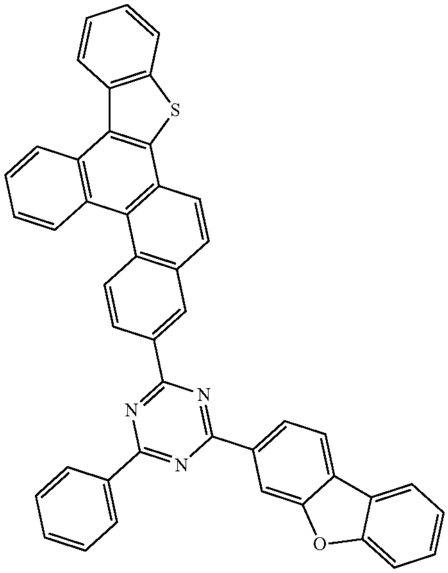
C-34
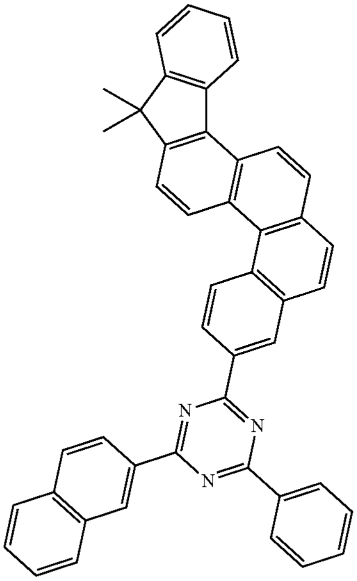
-continued
C-35
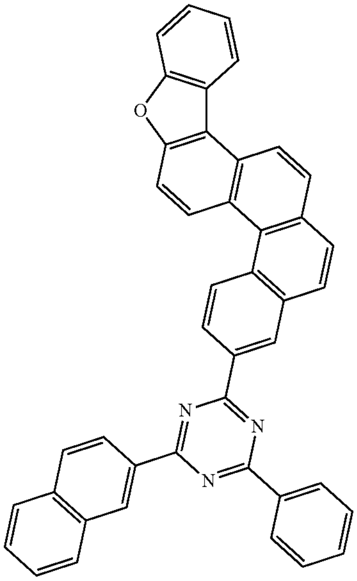
C-36
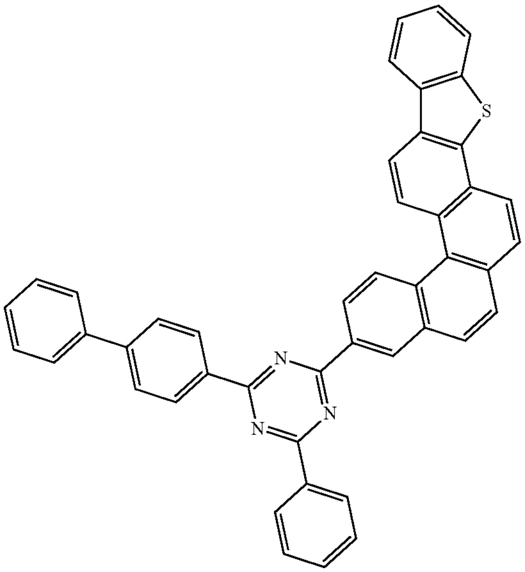

-continued
C-37
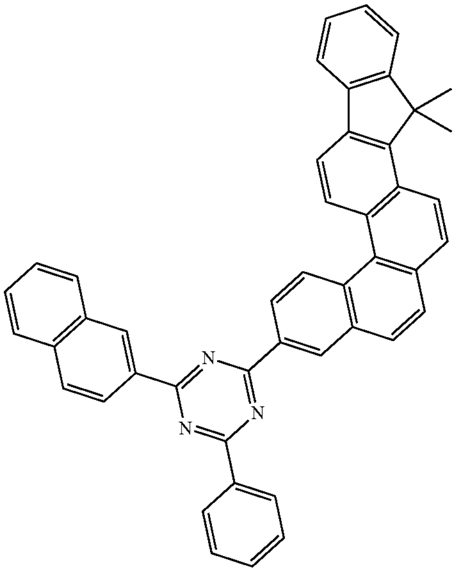
C-38
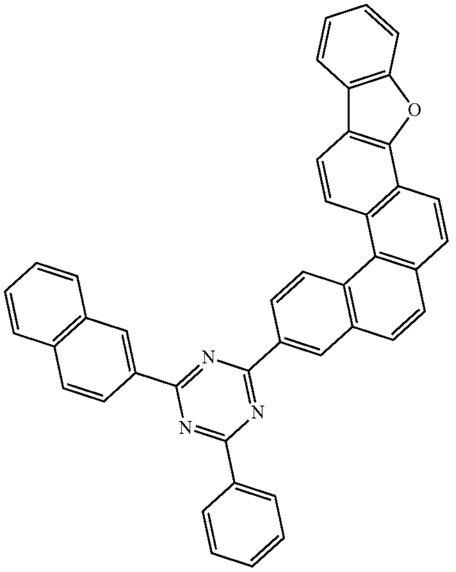
-continued
C-39
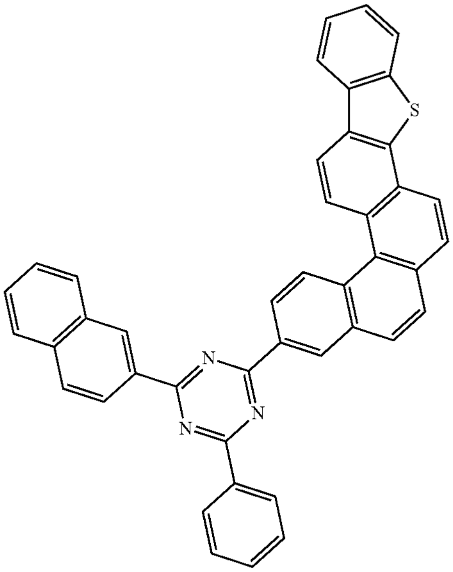
C-40
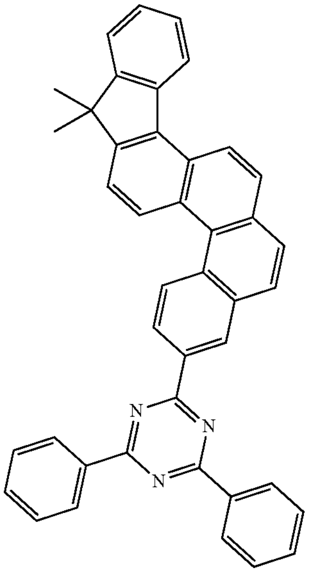
C-41
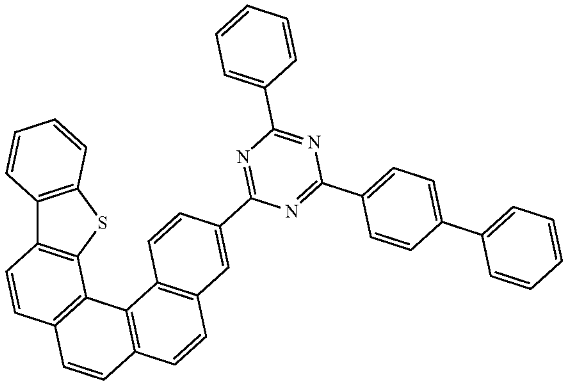

-continued
C-42
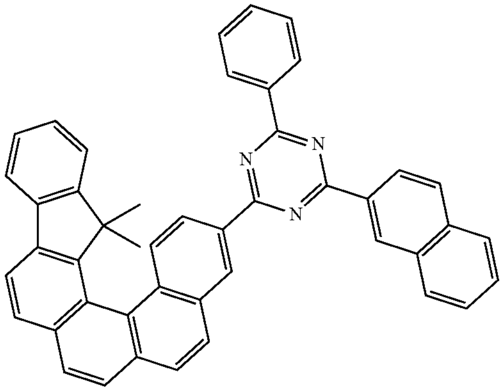
C-43
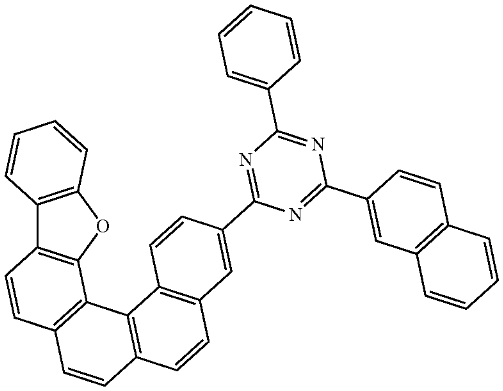
C-44
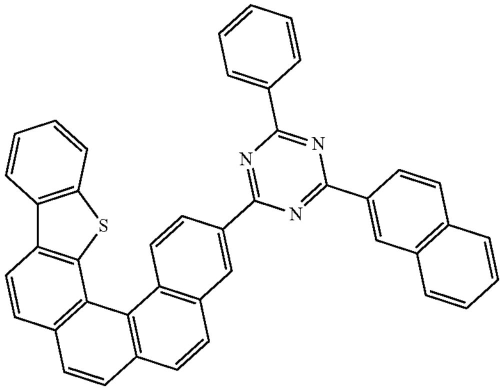
C-45
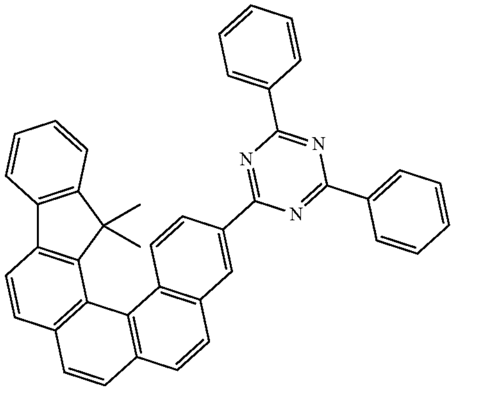
-continued
C-46
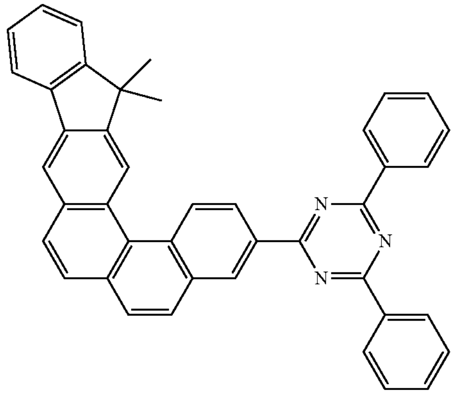
C-47
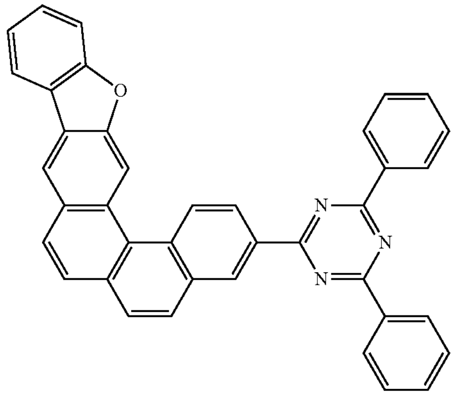
C-48
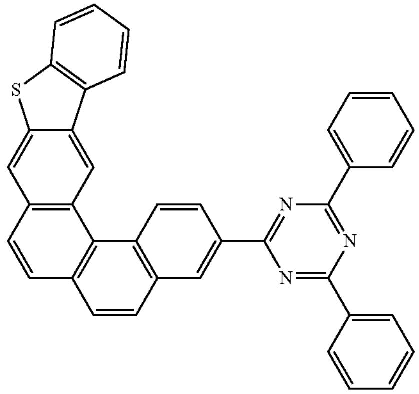
C-49
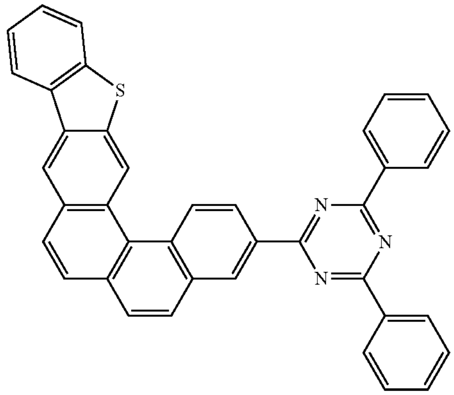

-continued
C-50
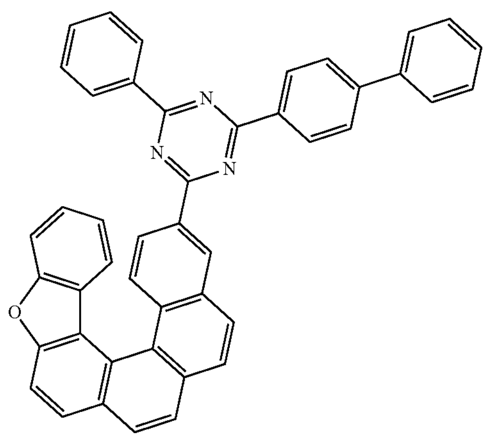
C-51
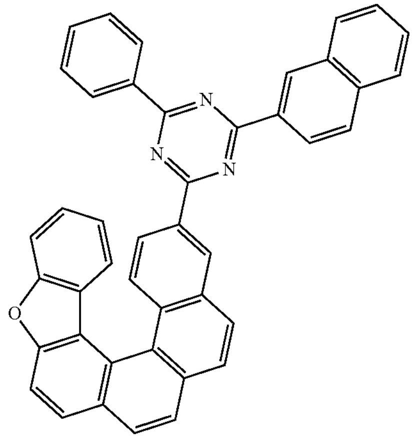
C-52
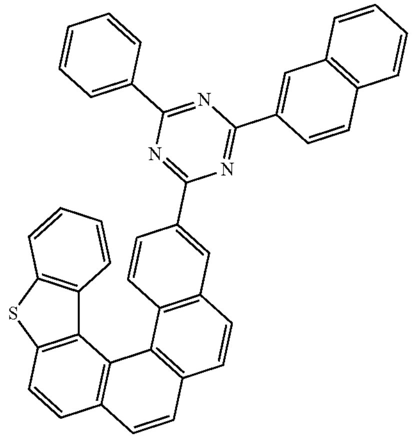
-continued
C-53
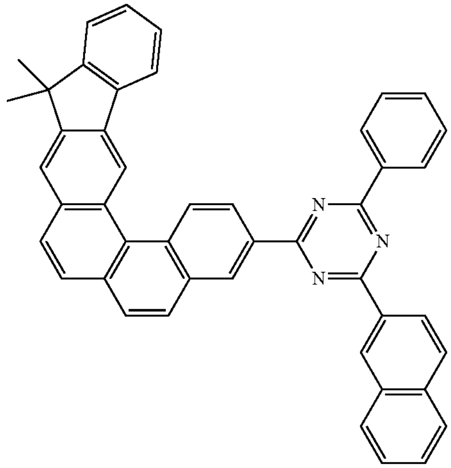
C-54
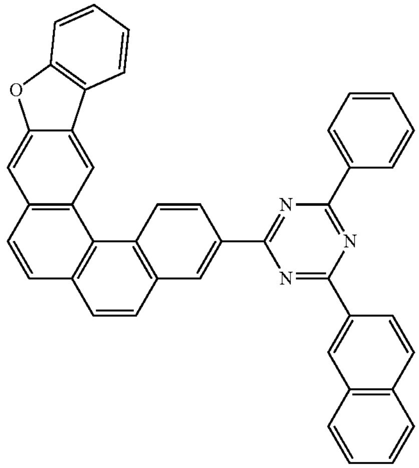
C-55
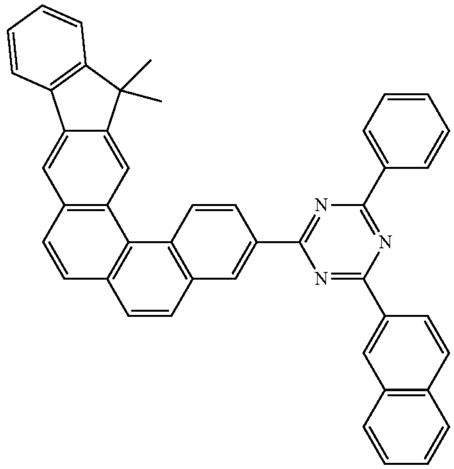

-continued
C-56
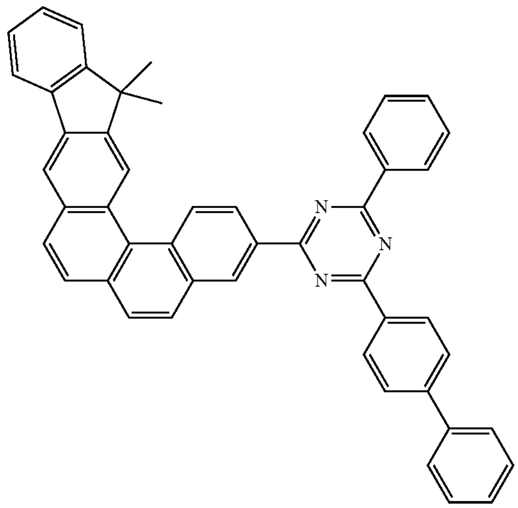
C-57
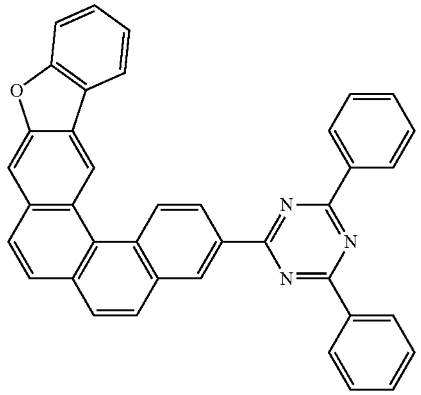
C-58
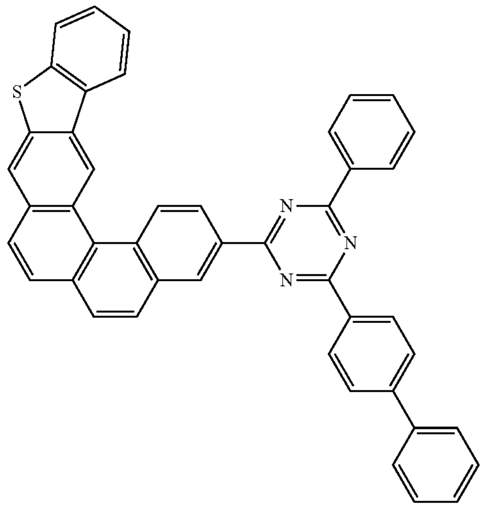
-continued
C-59
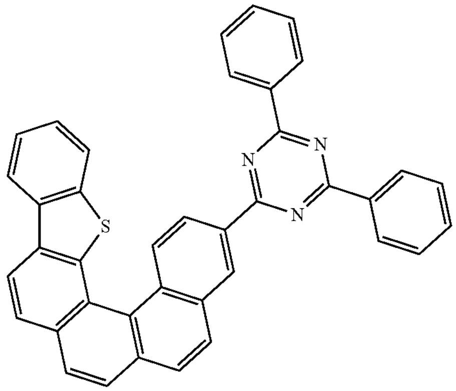
C-60
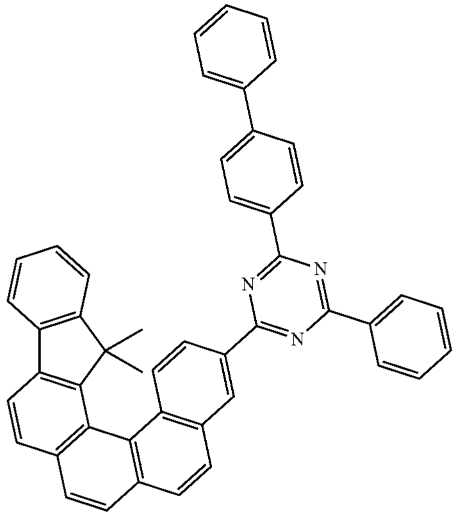
C-61
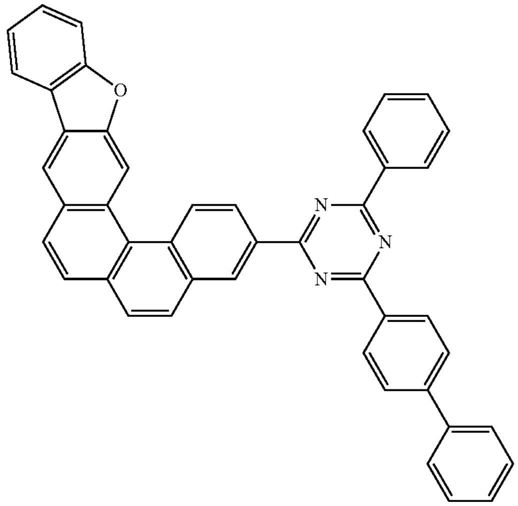

-continued
C-62
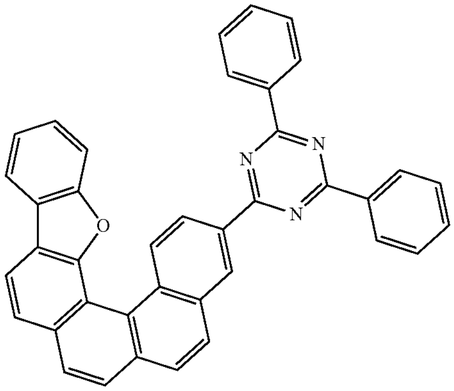
C-63
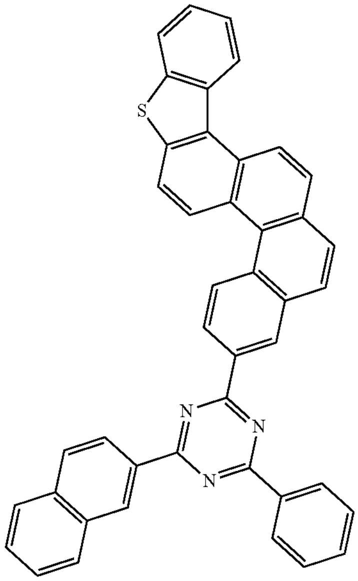
C-64
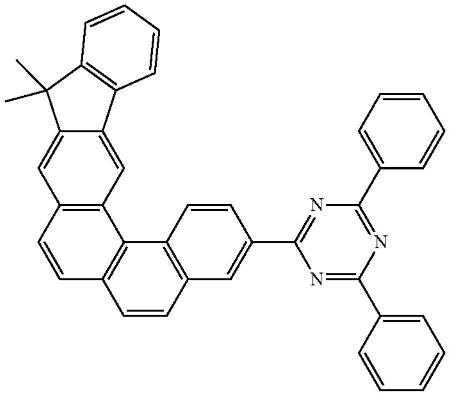
-continued
C-65
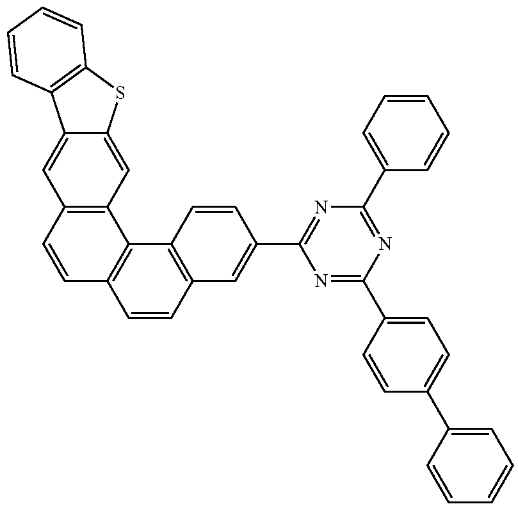
C-66
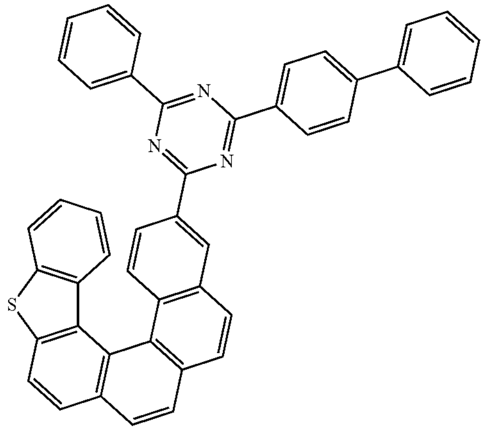
C-67
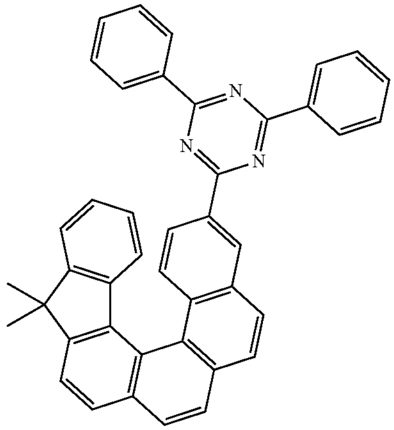

-continued
C-68
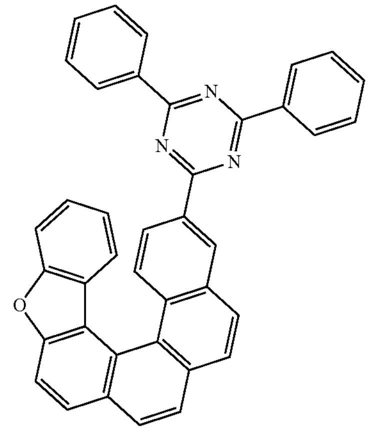
C-69
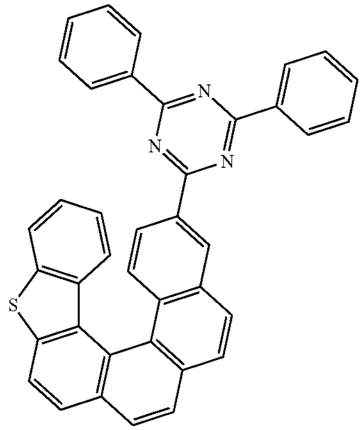
C-70
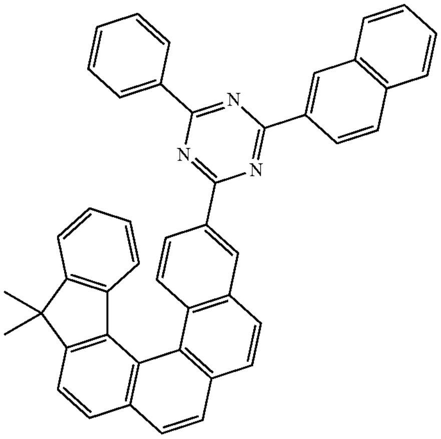
-continued
C-71
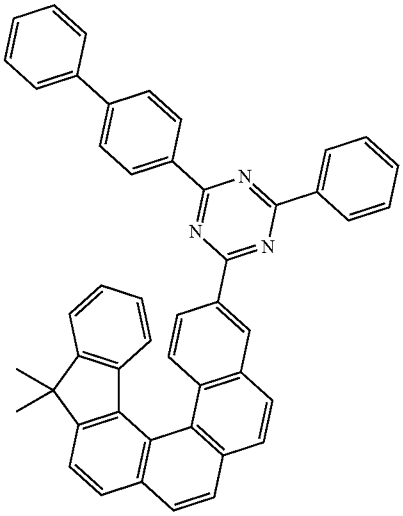
C-72
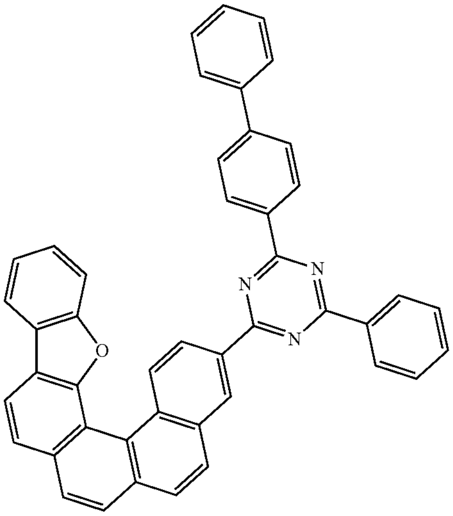
C-73
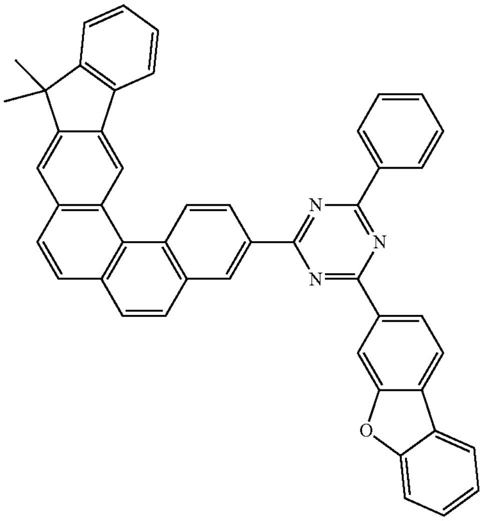

-continued
C-74
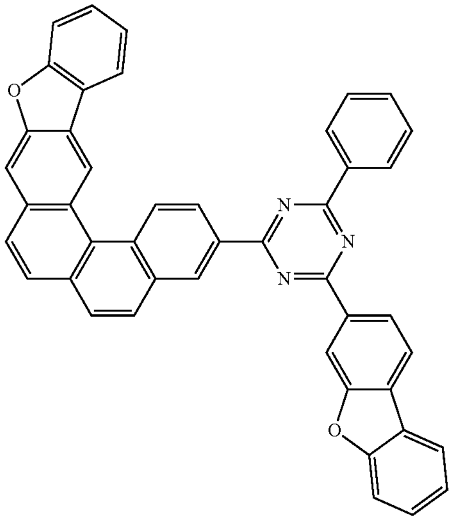
C-75
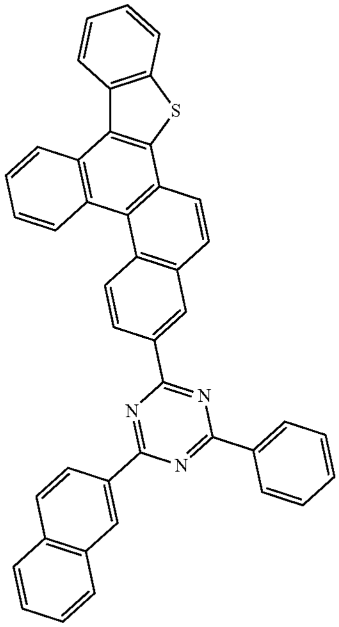
C-76
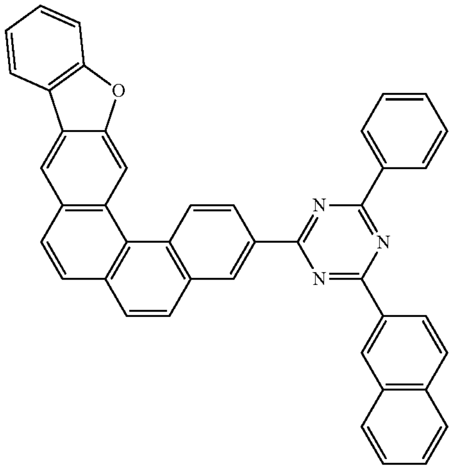
-continued
C-77
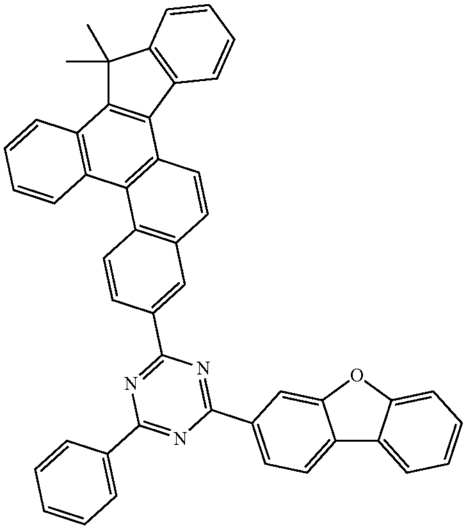
C-78
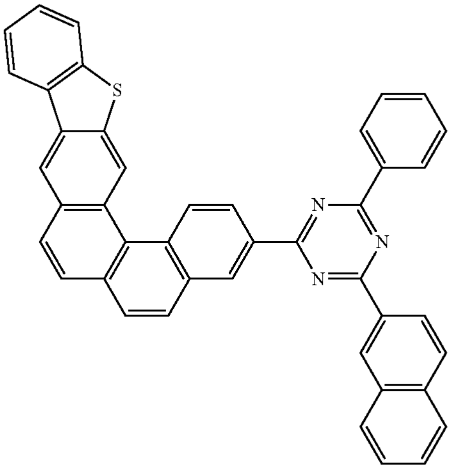
C-79
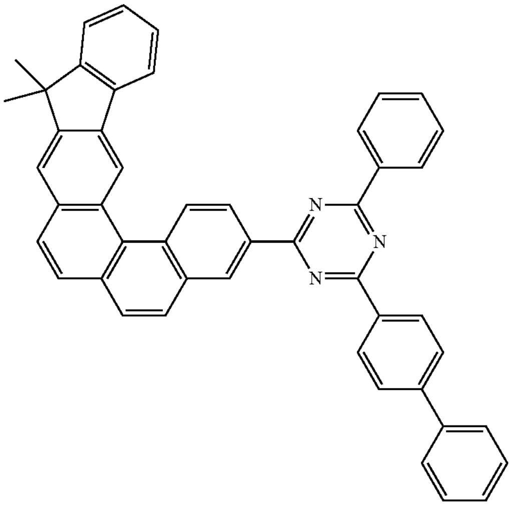

-continued
C-80
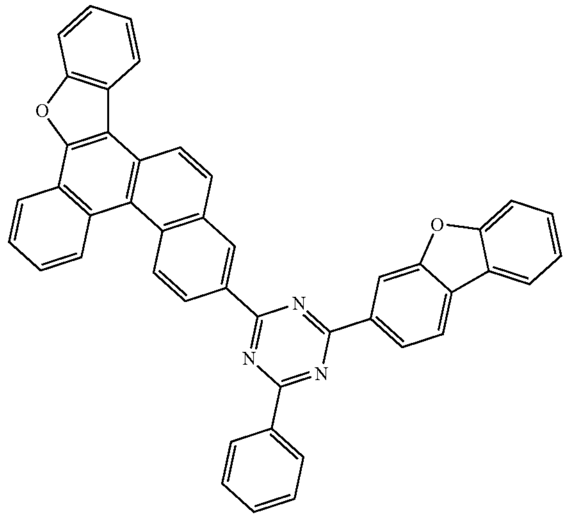
C-81
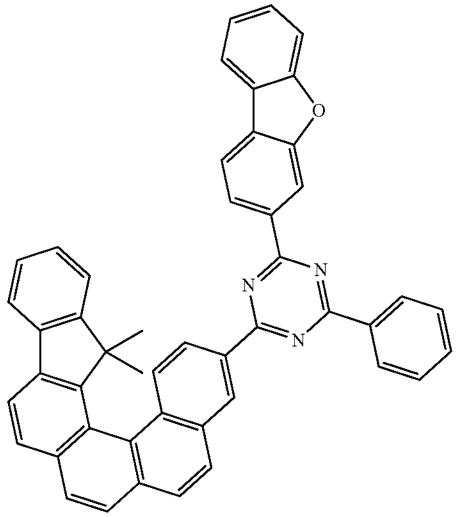
C-82
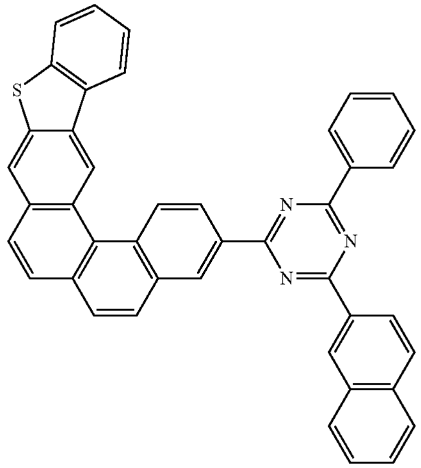
-continued
C-83
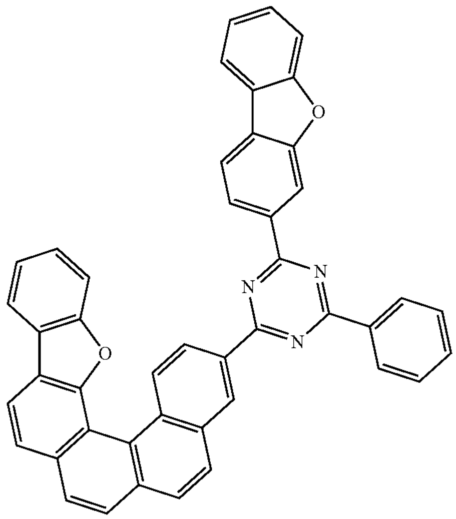
C-84
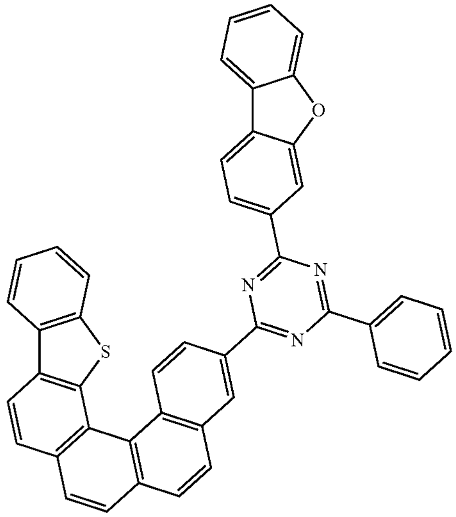
C-85
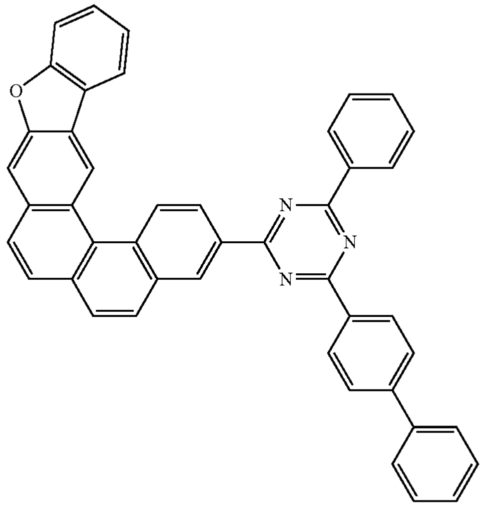

-continued
C-86
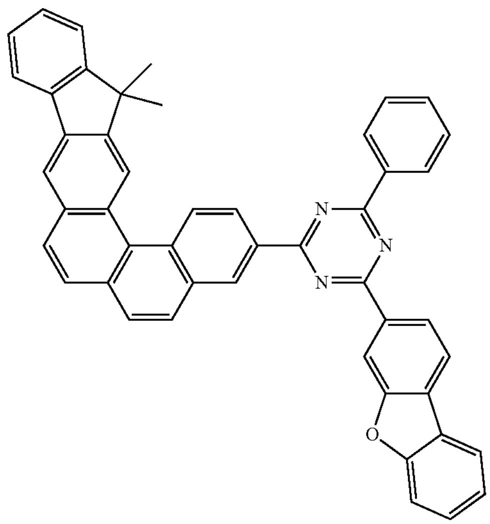
C-87
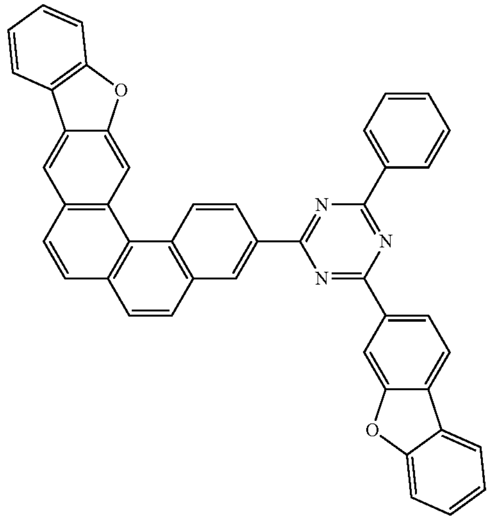
C-88
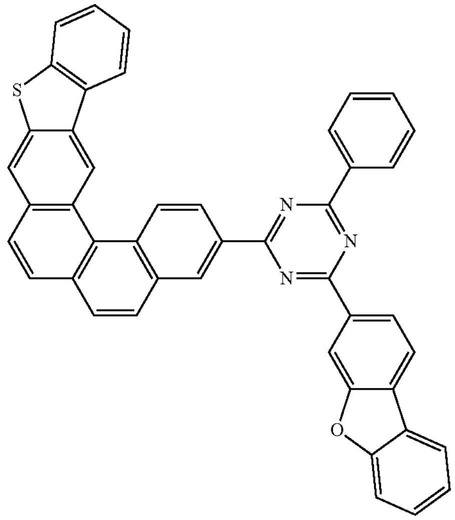
-continued
C-89
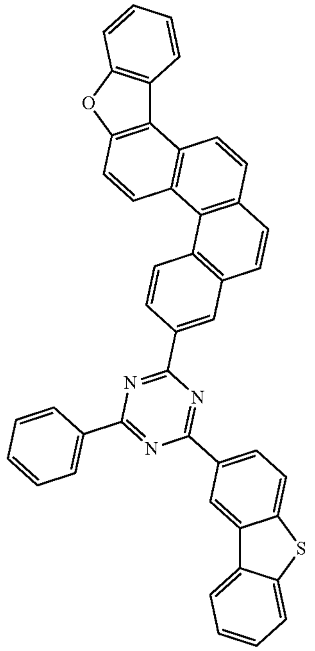
C-90
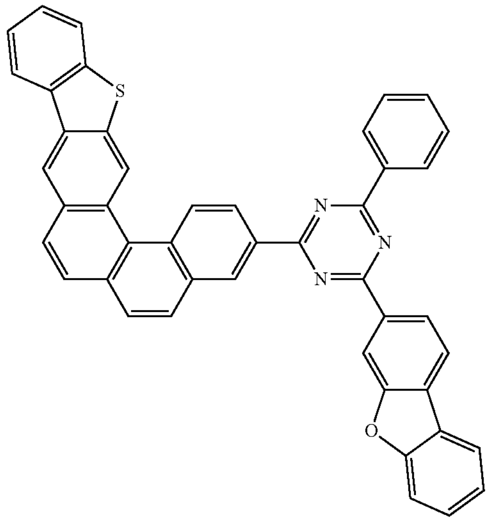

-continued
C-91
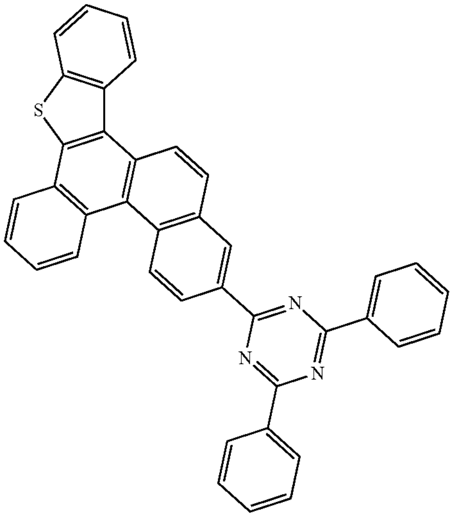
C-92
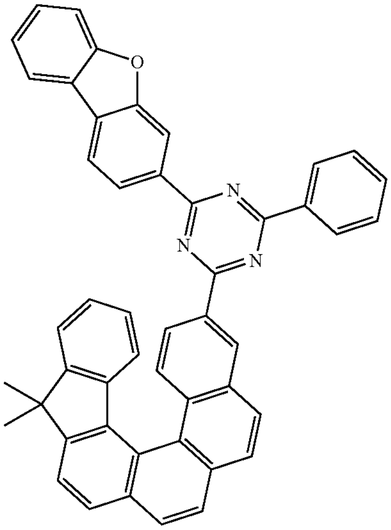
C-93
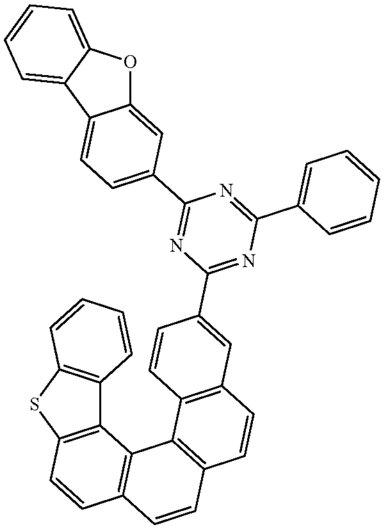
-continued
C-94
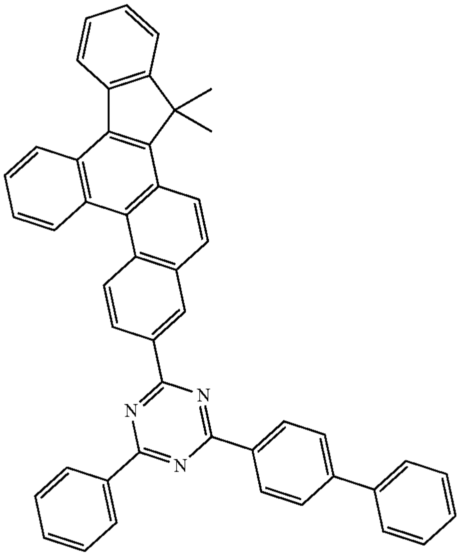
C-95
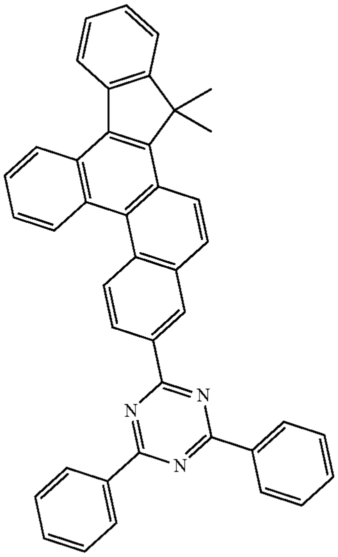
C-96
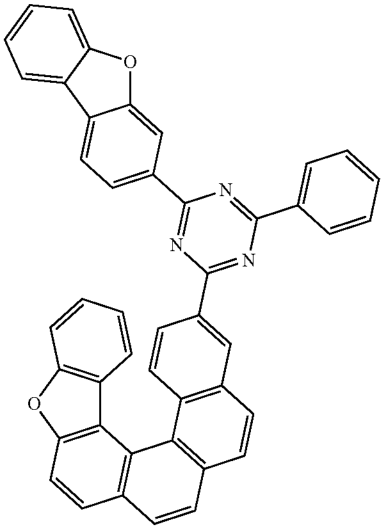

-continued
C-97
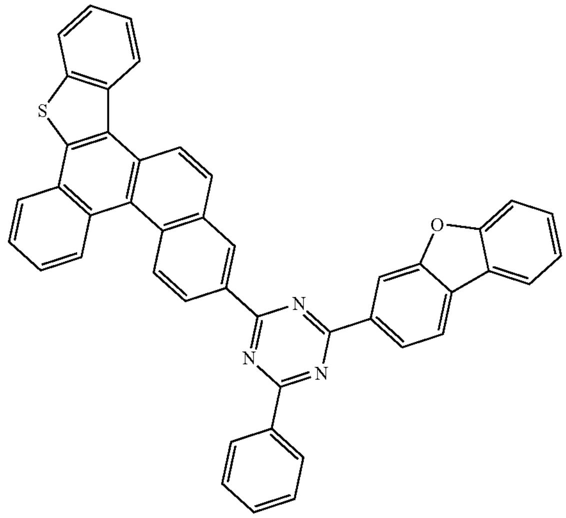
C-98
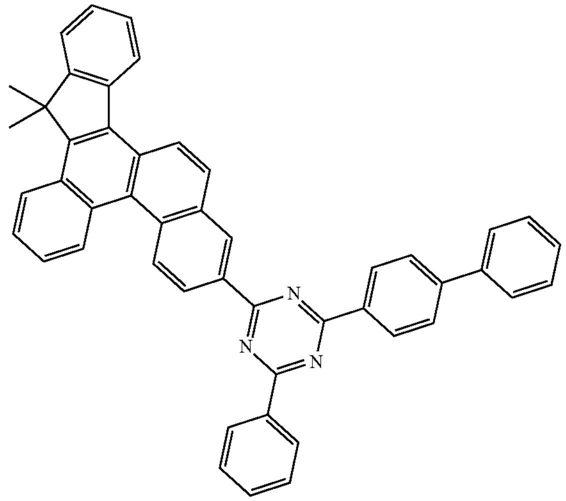
C-99
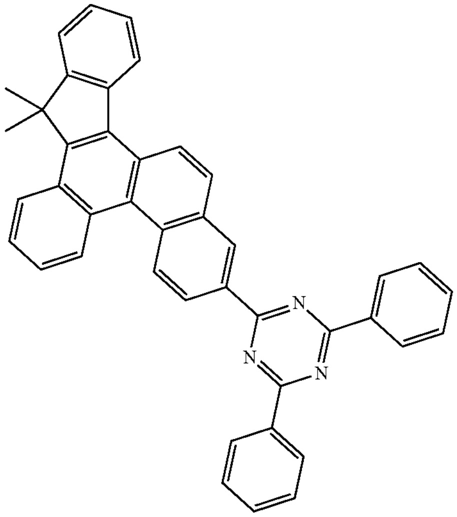
-continued
C-100
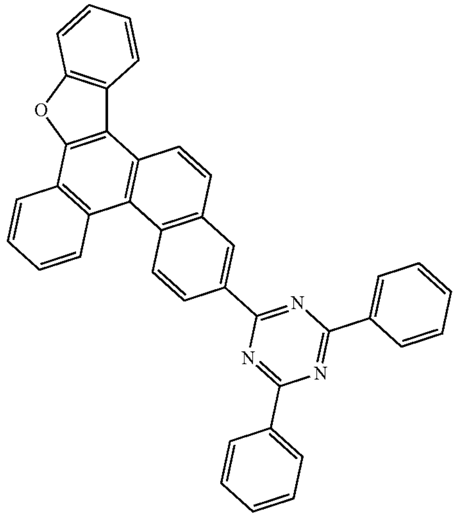
C-101
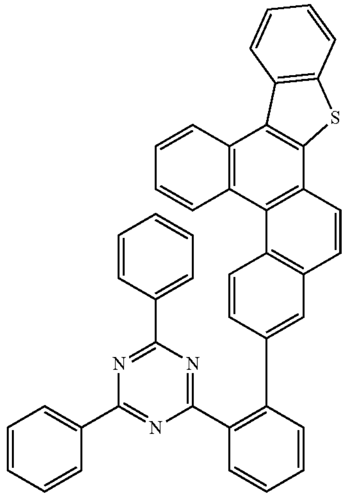

-continued
C-102
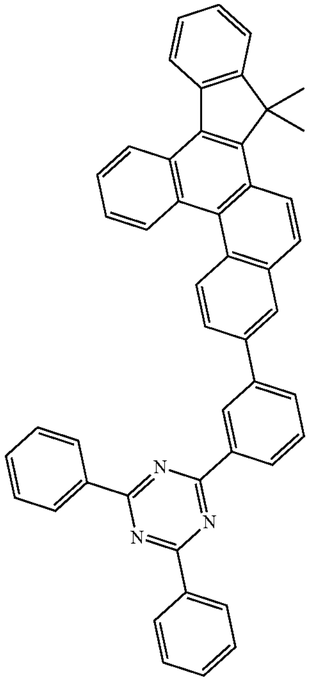
C-103
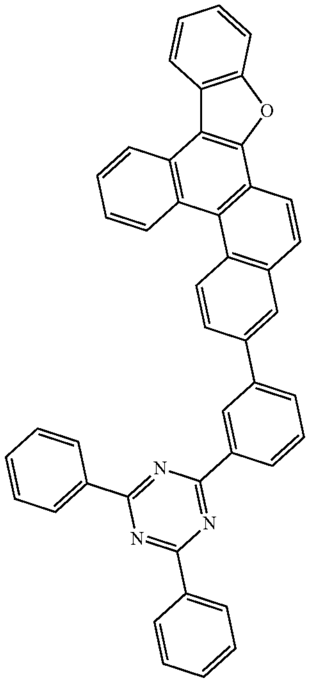
-continued
C-104
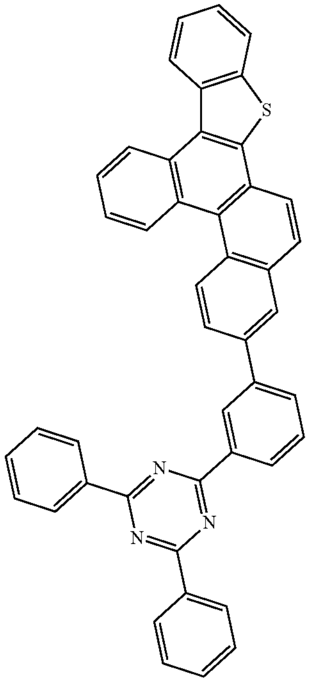
C-105
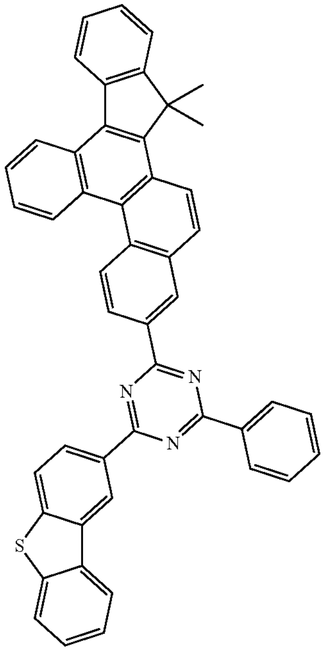

-continued
C-106
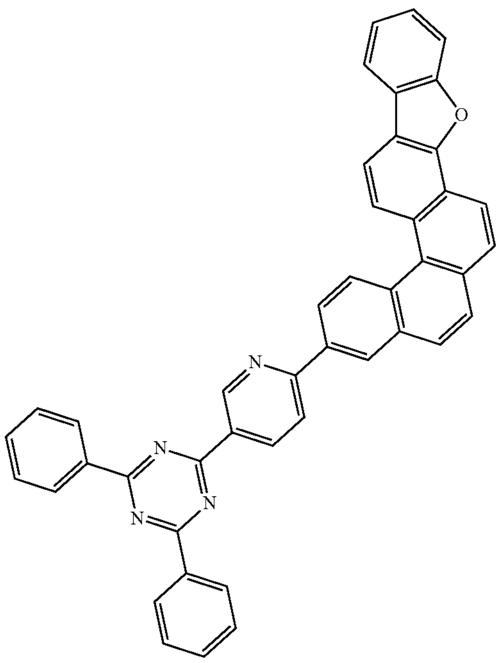
C-107
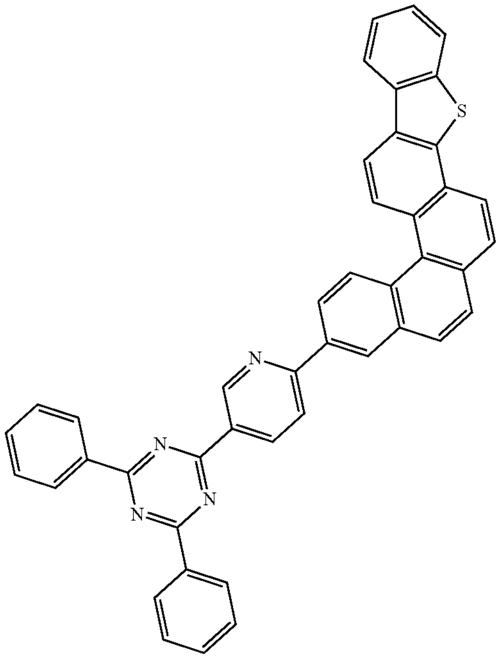
-continued
C-108
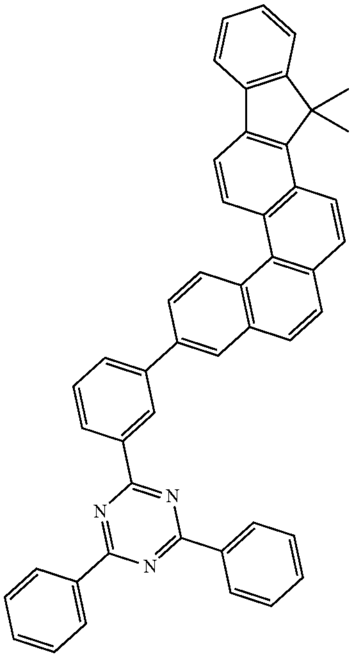
C-109
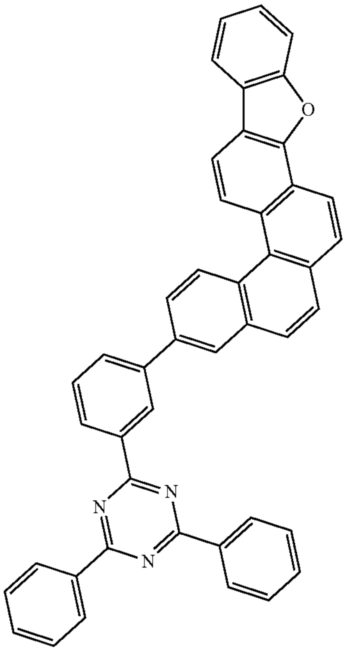

C-110
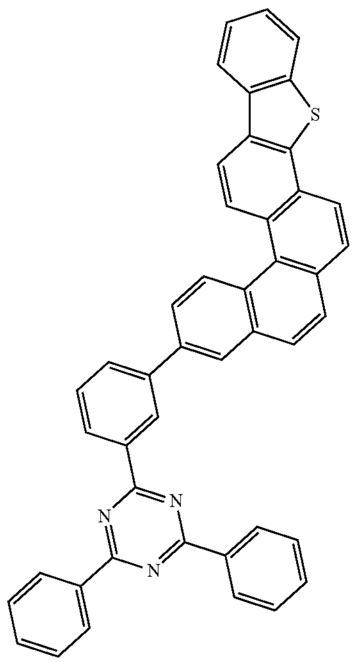
C-111
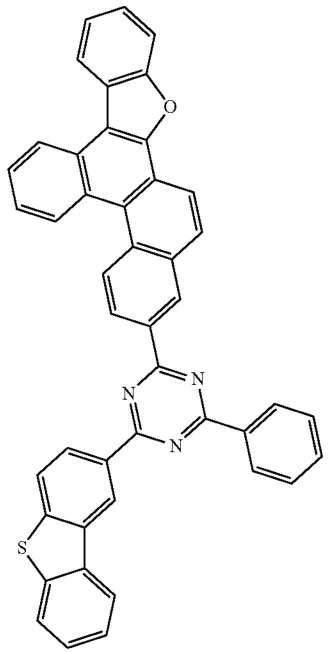
C-112
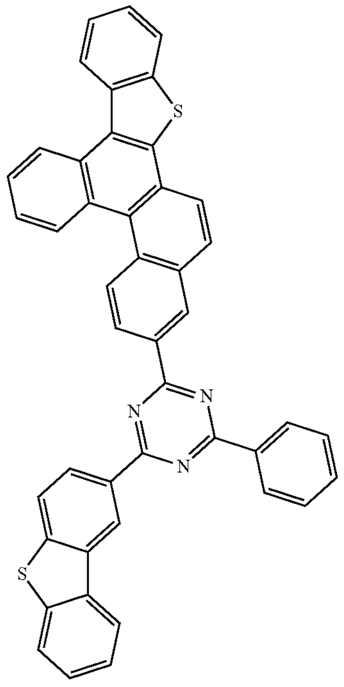
C-113
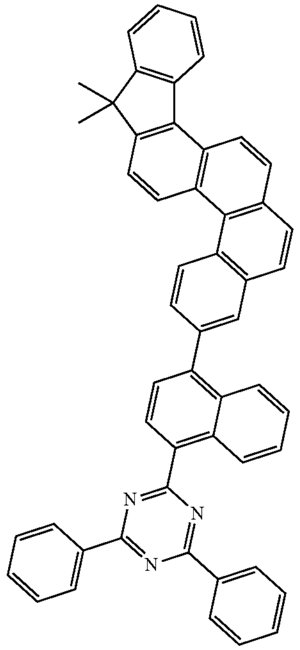

-continued
C-114
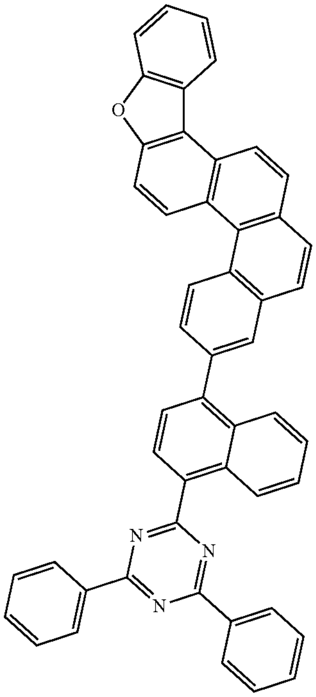
C-115
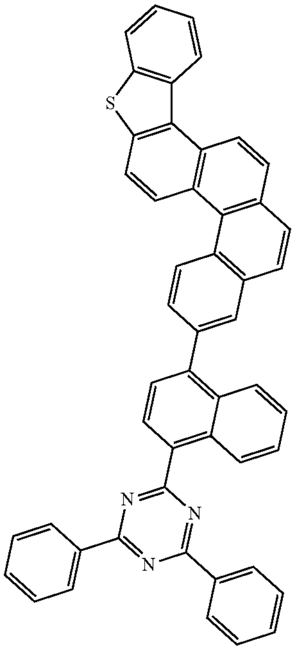
-continued
C-116
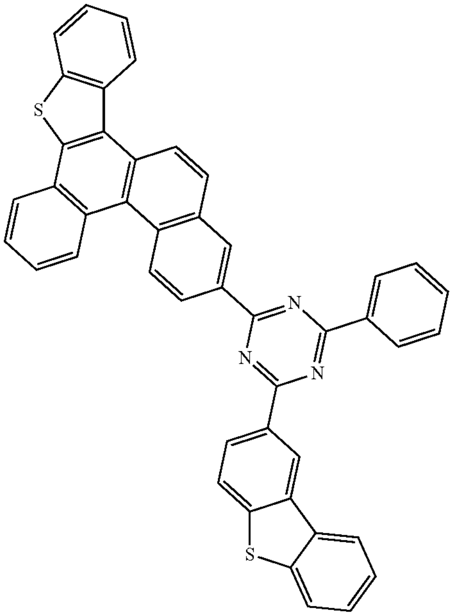
C-117
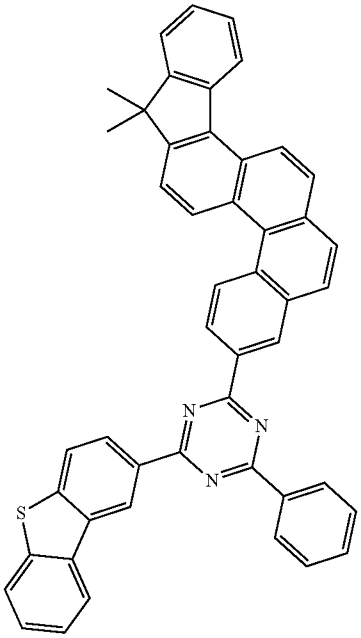

-continued
C-118
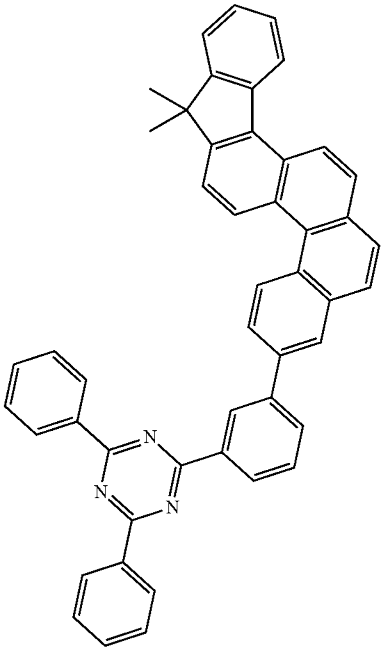
C-119
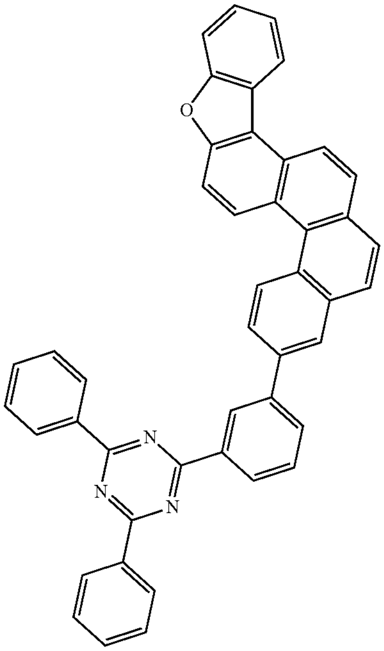
-continued
C-120
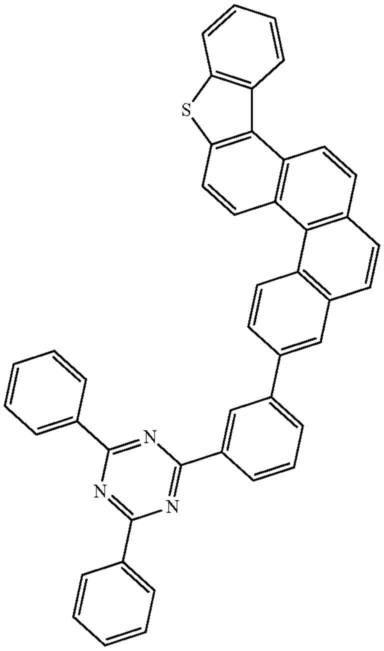
C-121
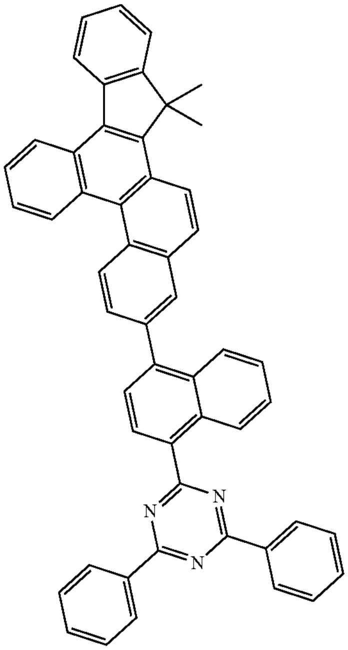

-continued
C-122
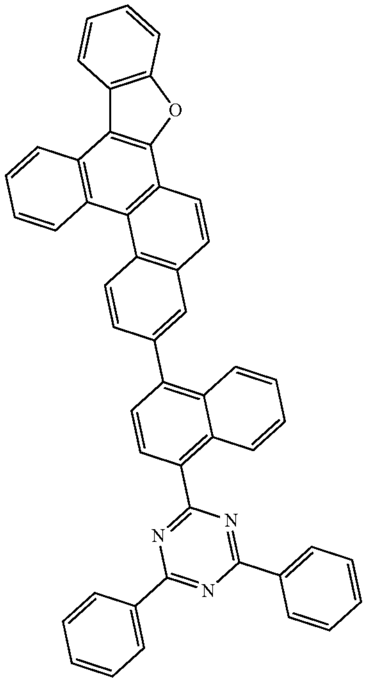
C-123
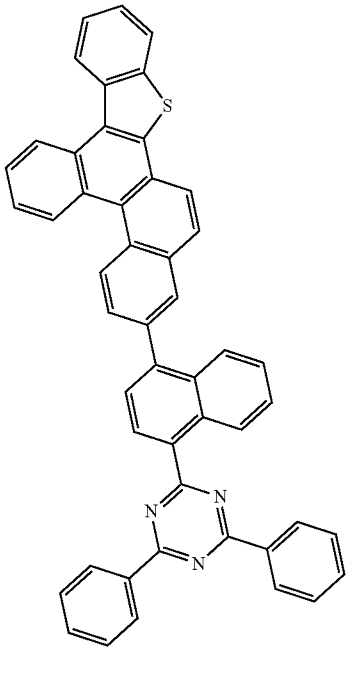
-continued
C-124
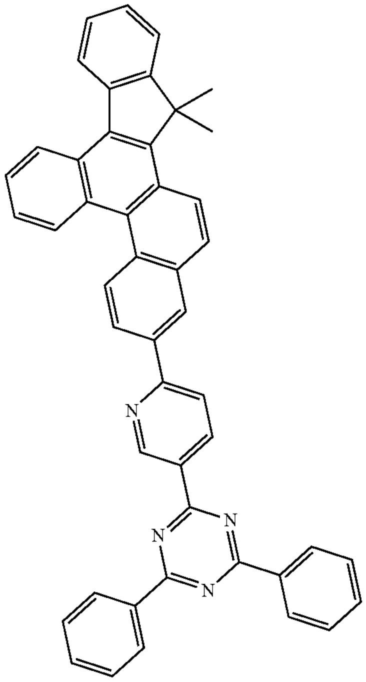
C-125
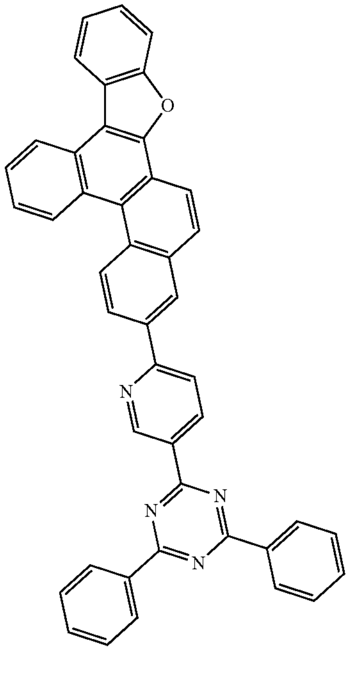

-continued
C-126
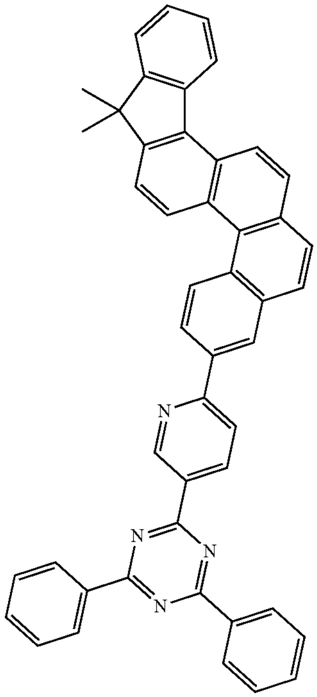
C-127
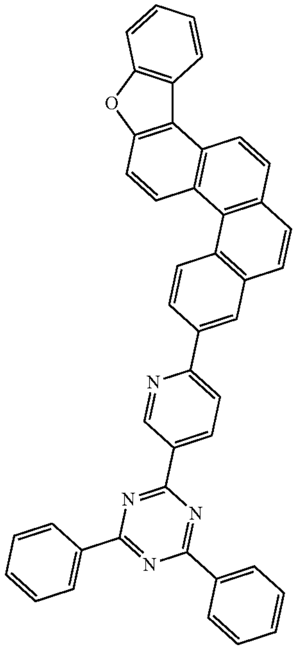
-continued
C-128
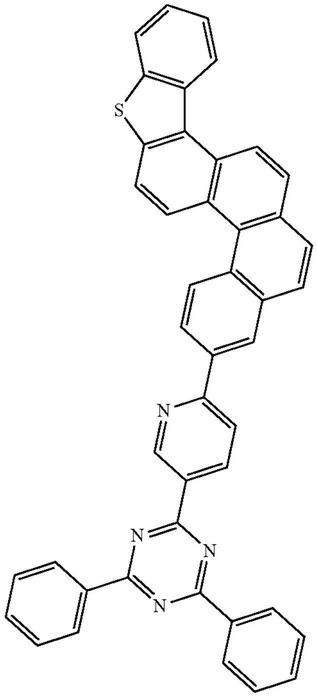
C-129
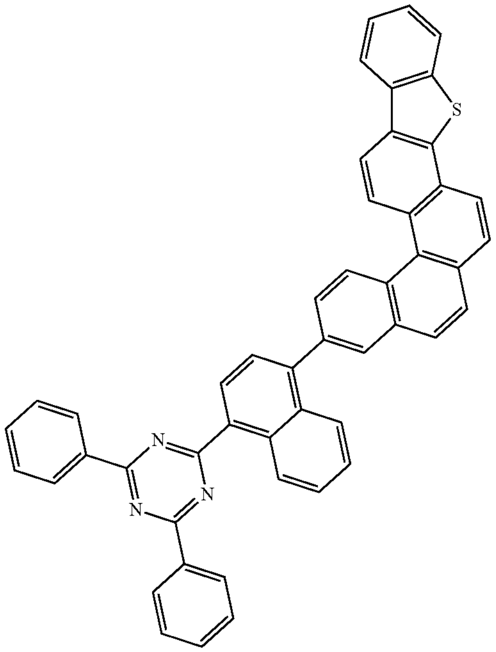

-continued
C-130
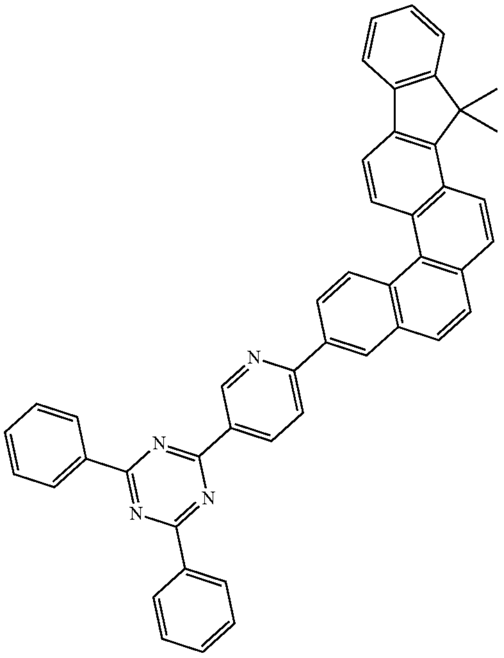
C-131
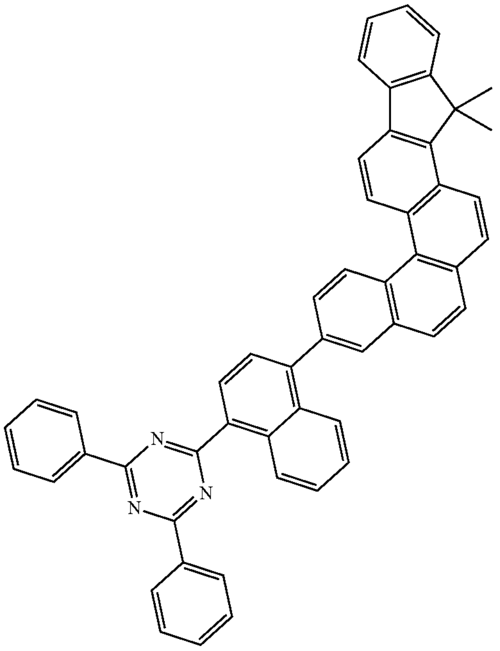
-continued
C-132
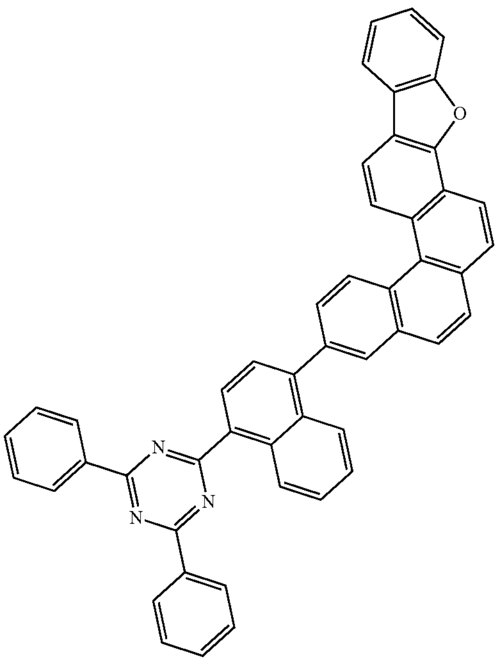
C-133
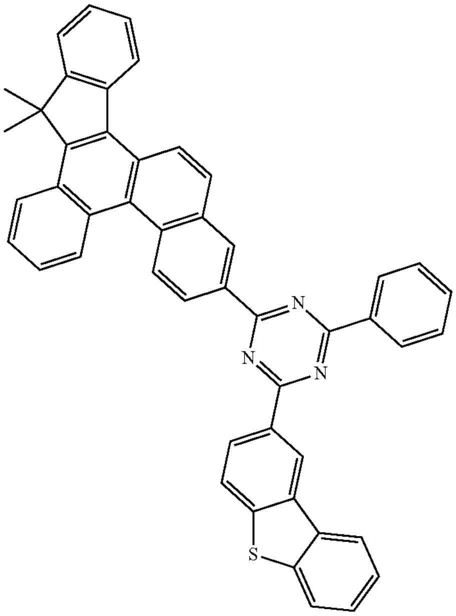

-continued
C-134
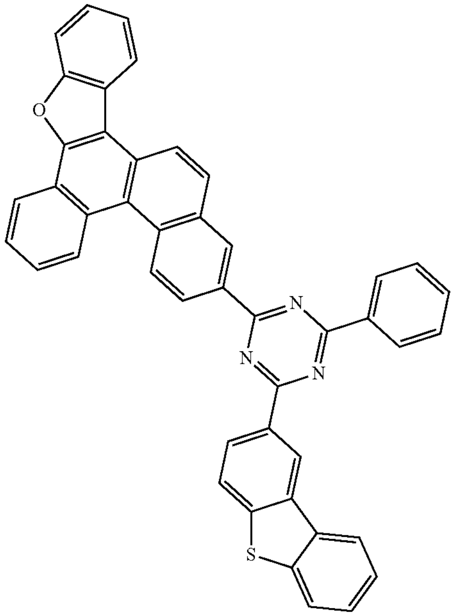
C-135
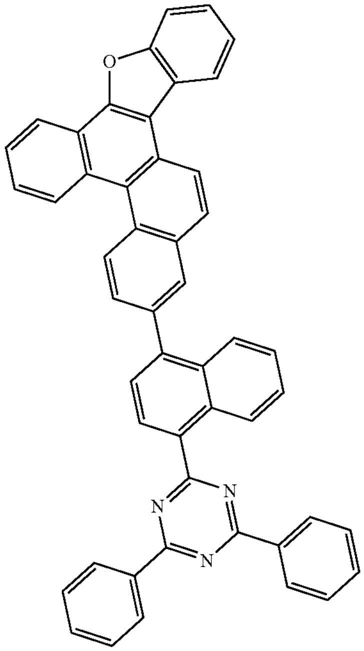
-continued
C-136
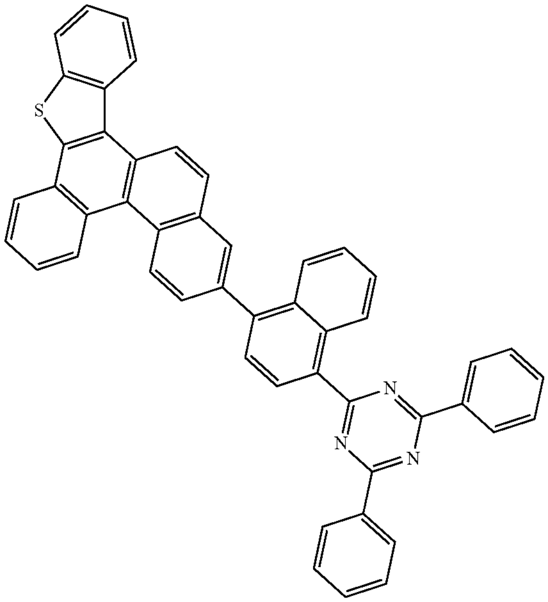
C-137
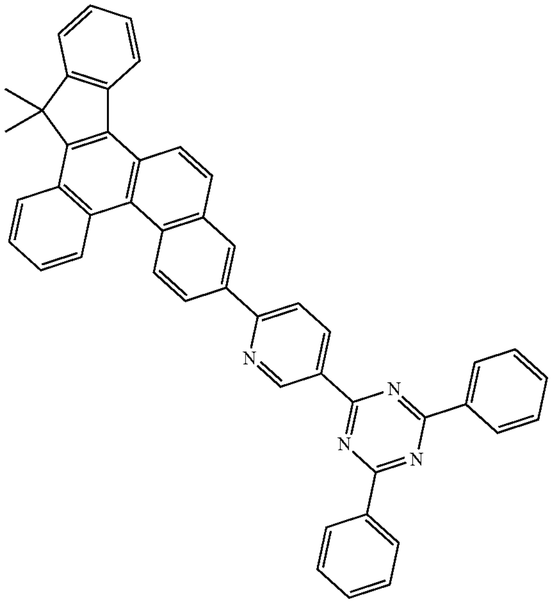

-continued
C-138
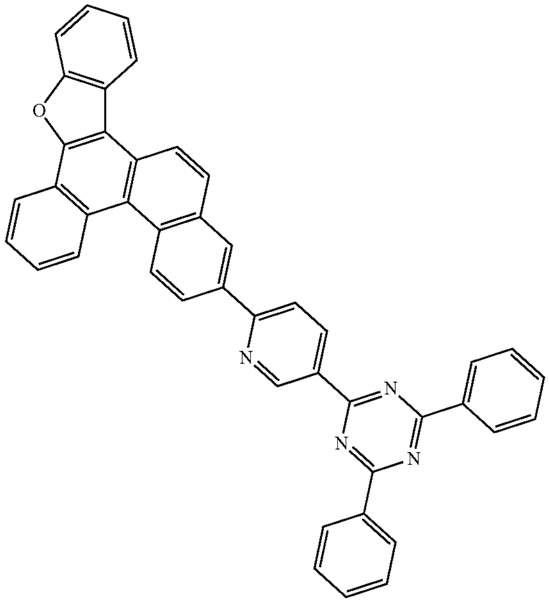
C-139
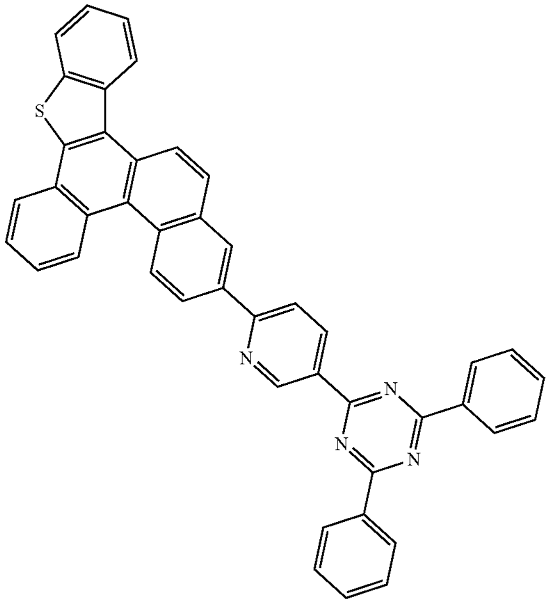
-continued
C-140
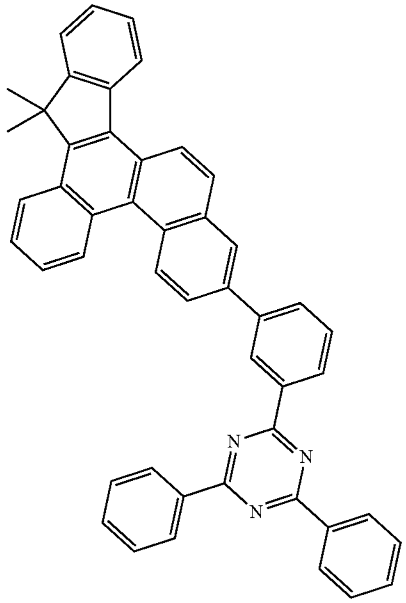
C-141
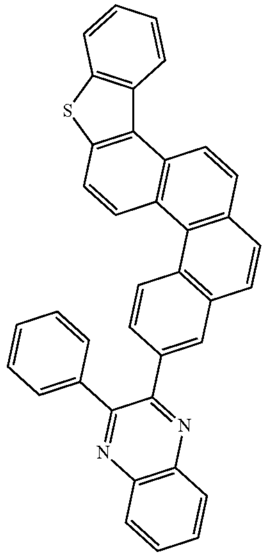

-continued
C-142
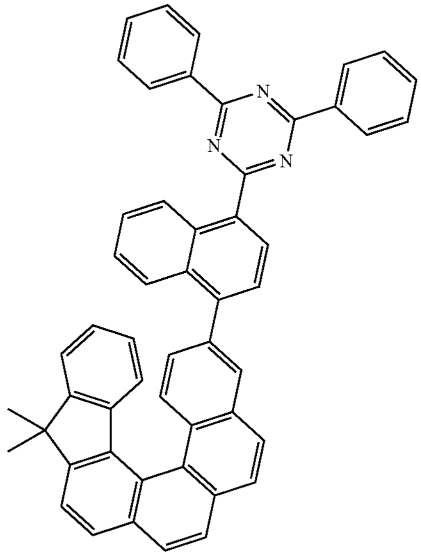
C-143
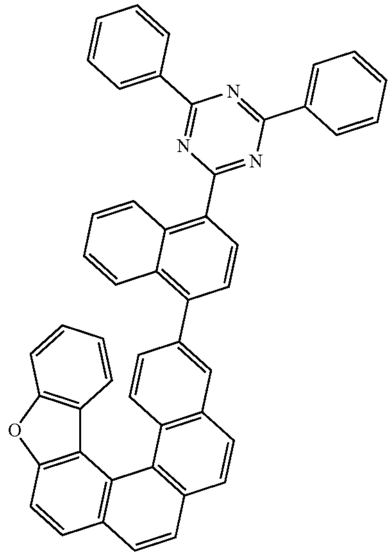
C-144
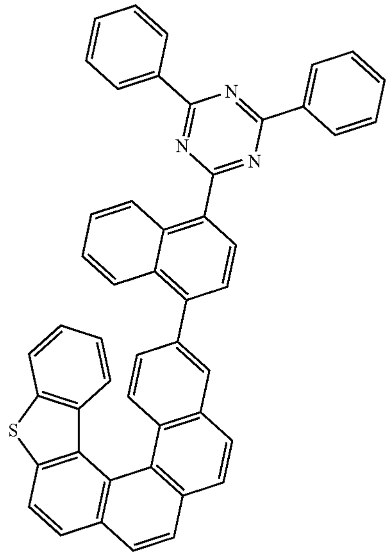
-continued
C-145
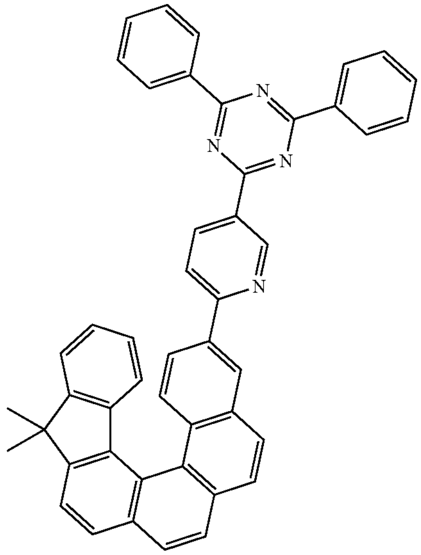
C-146
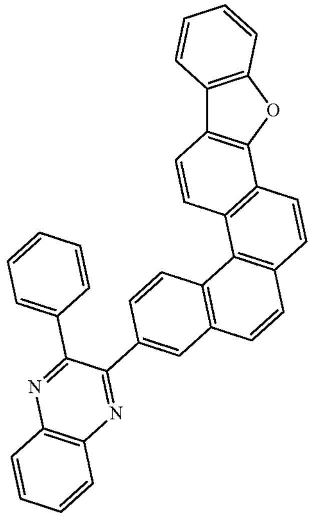
C-147
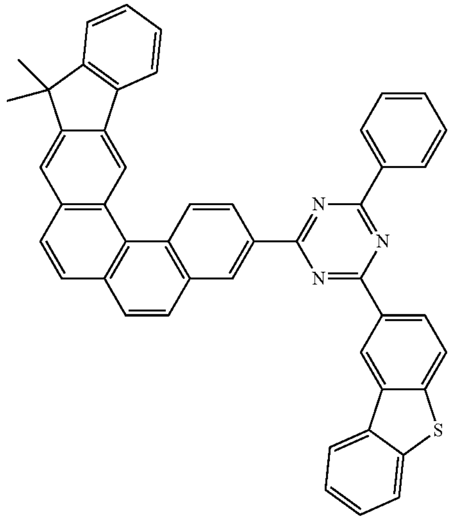

-continued
C-148
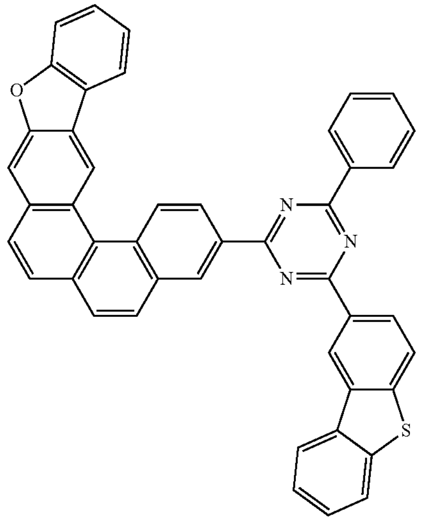
C-149
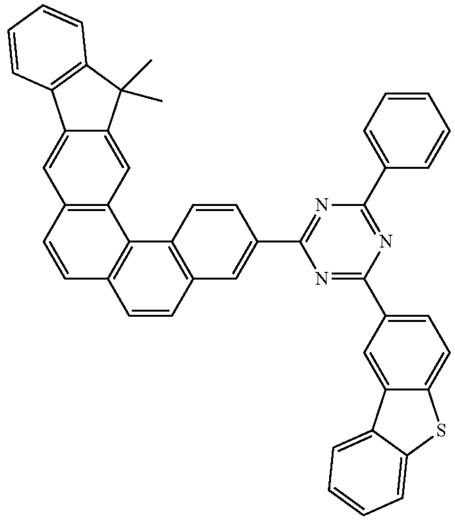
C-150
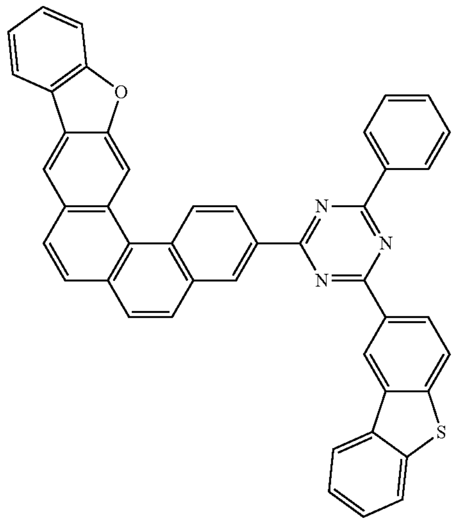
-continued
C-151
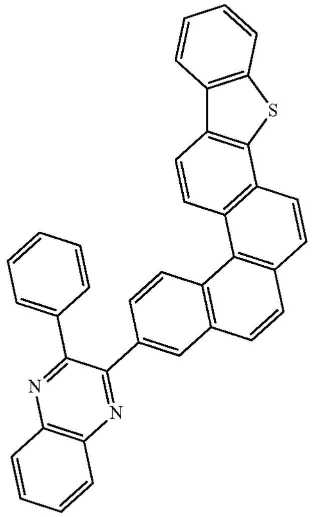
C-152
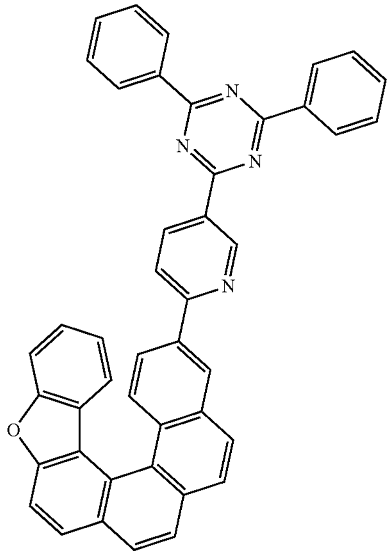
C-153
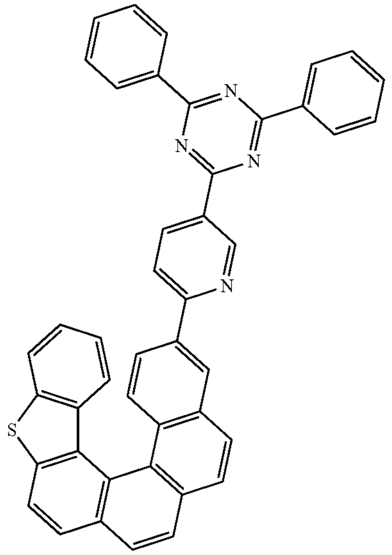

-continued
C-154
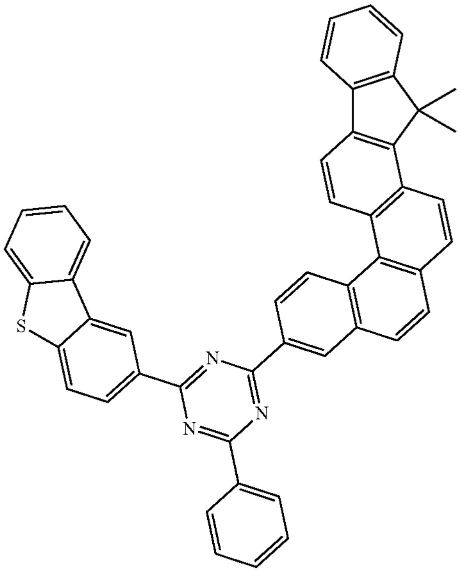
C-155
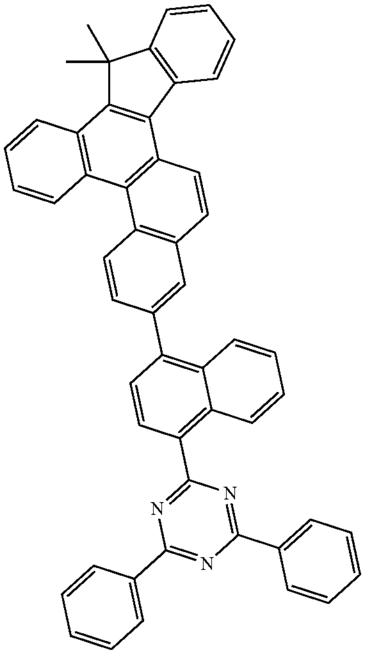
-continued
C-156
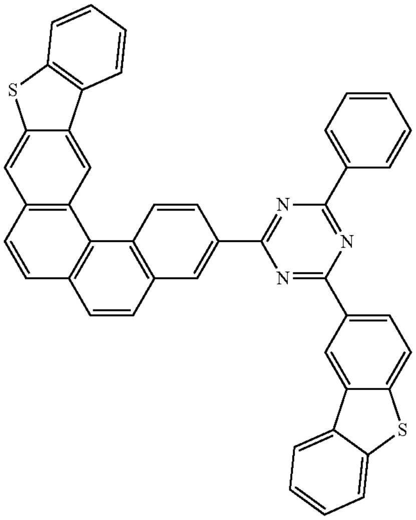
C-157
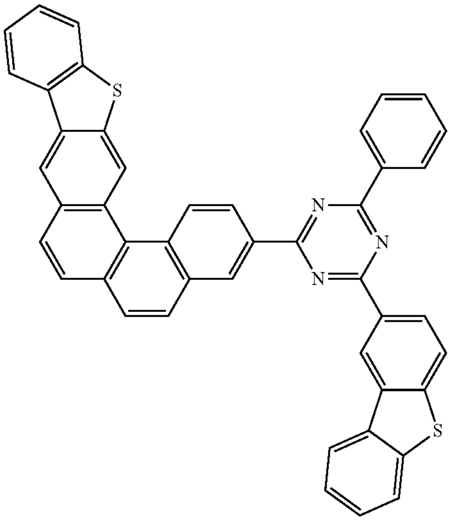
C-158
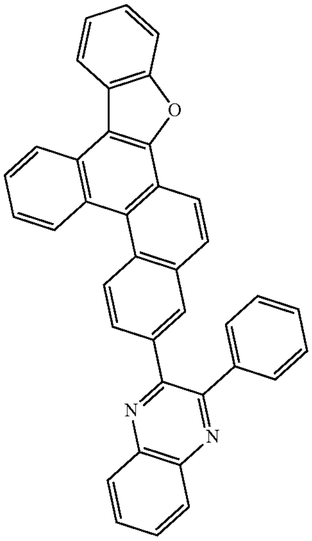

-continued
C-159
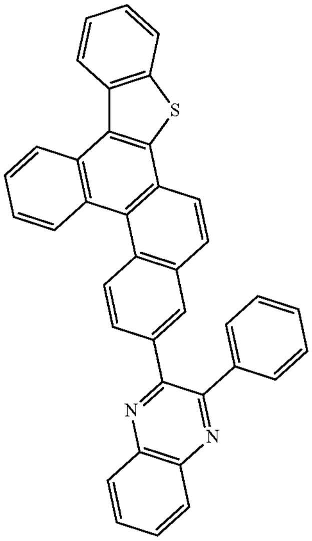
C-160
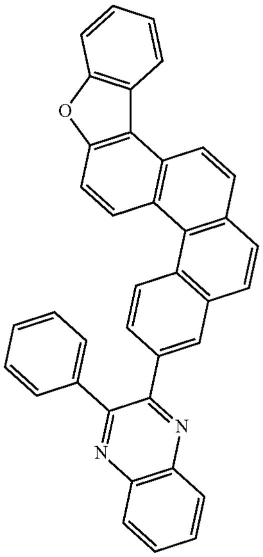
C-161
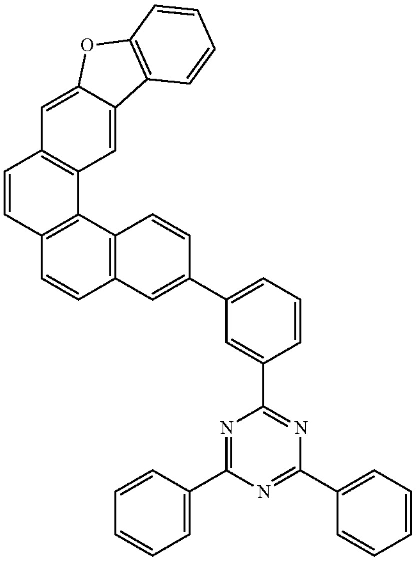
-continued
C-162
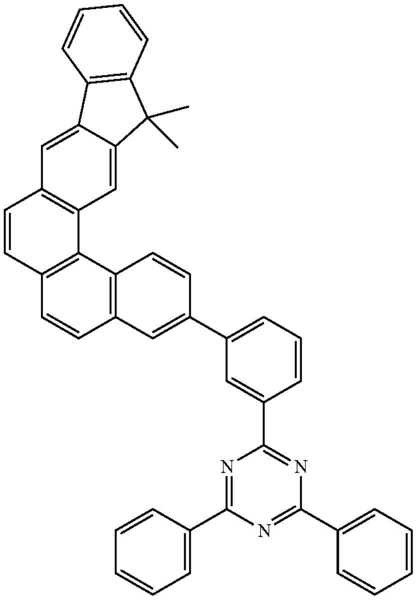
C-163
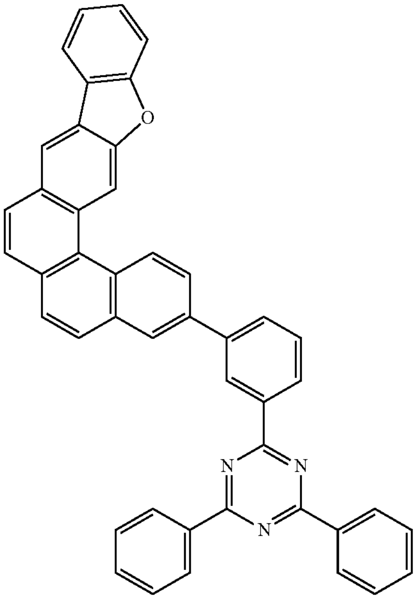

-continued
C-164
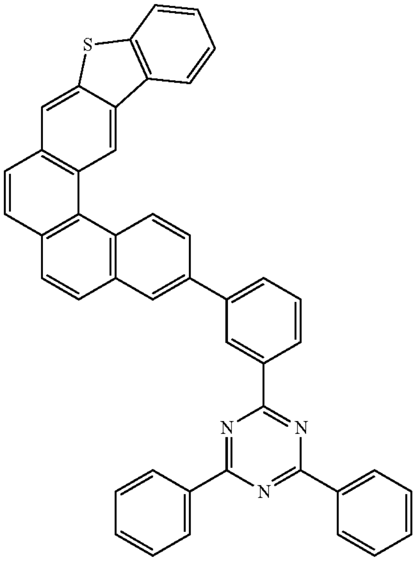
C-165
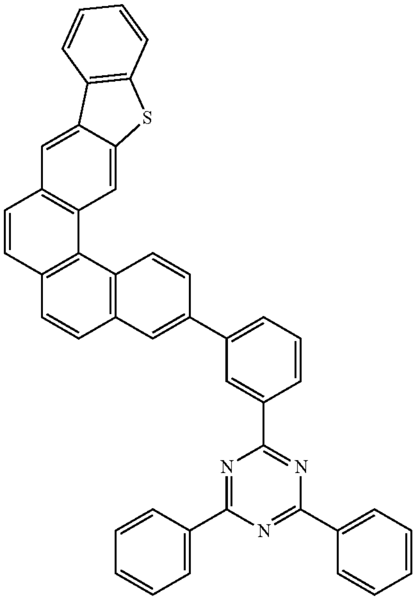
-continued
C-166
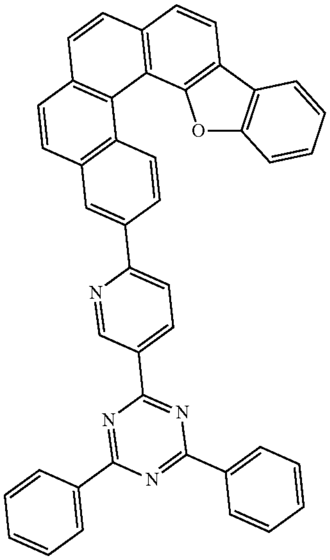
C-167
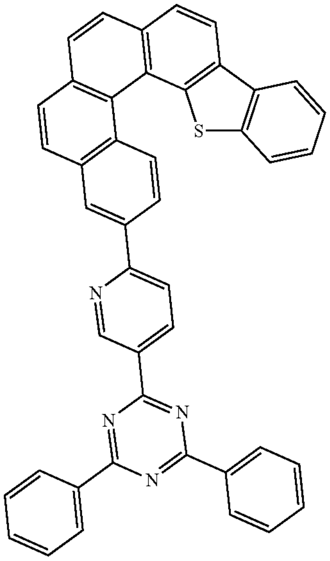
C-168
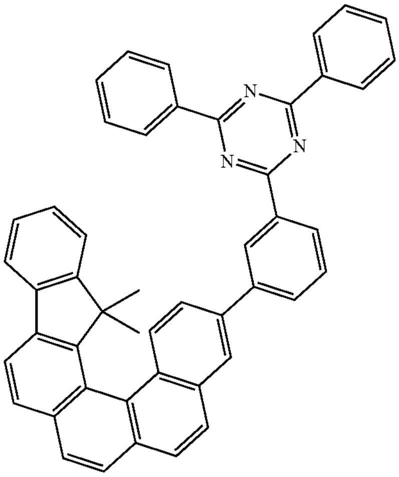

-continued
C-169
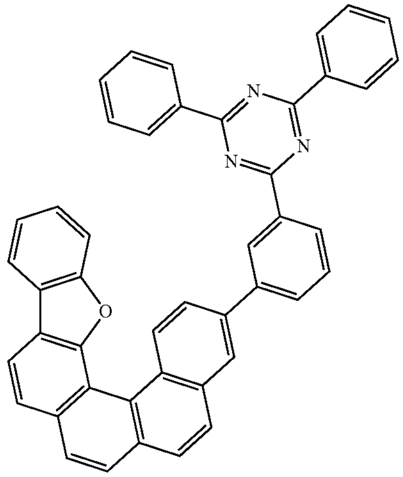
C-170
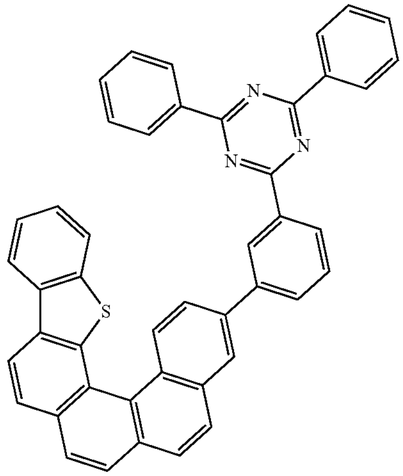
C-171
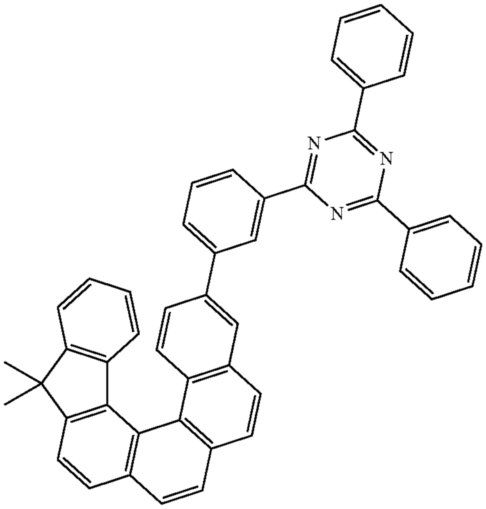
-continued
C-172
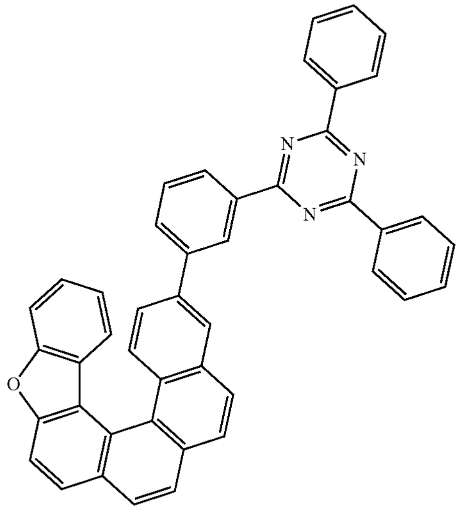
C-173
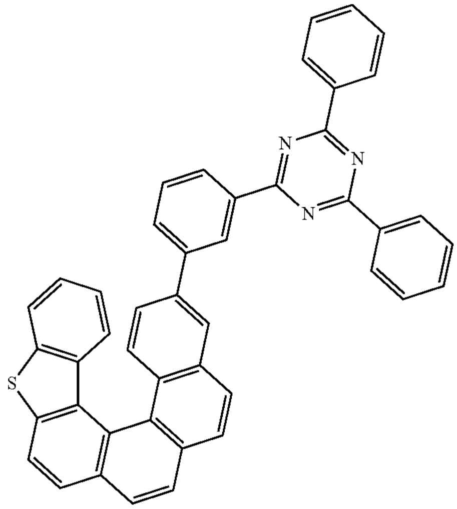
C-174
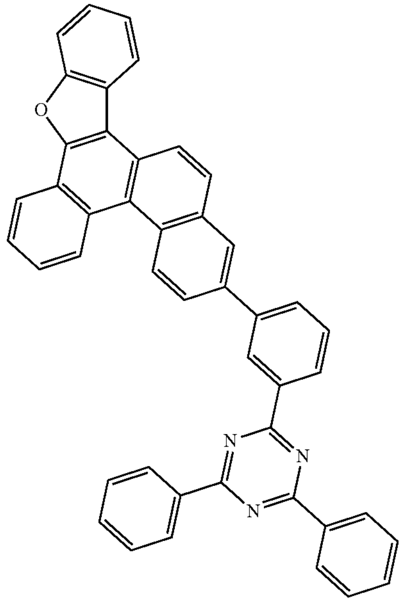

-continued
C-175
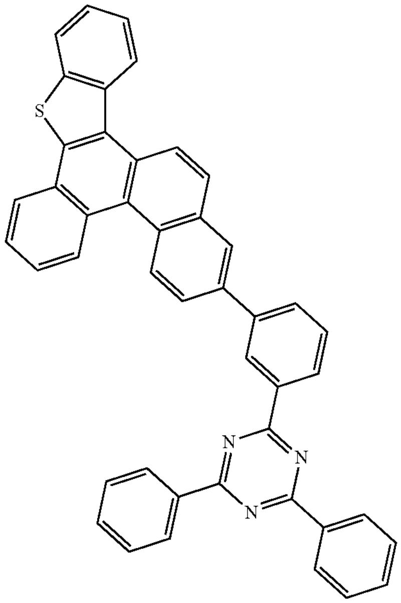
C-176
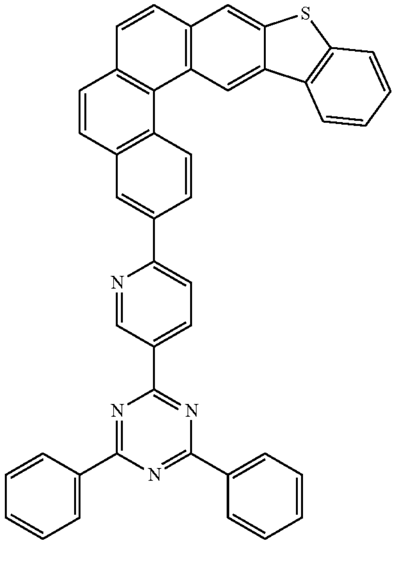
-continued
C-177
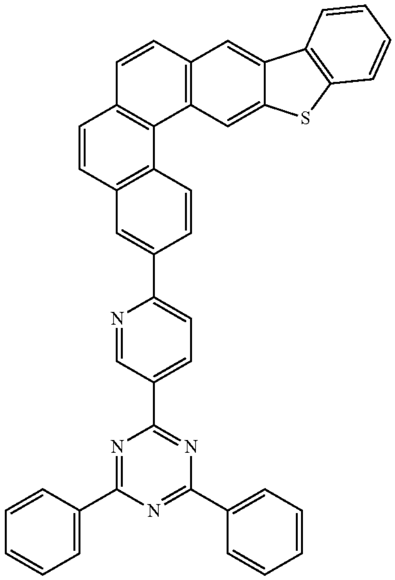
C-178
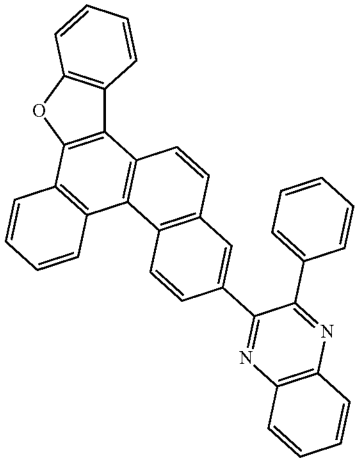
C-179
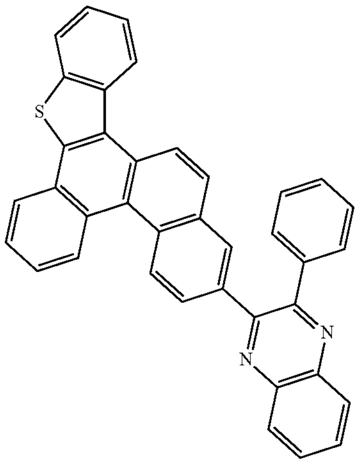

-continued
C-180
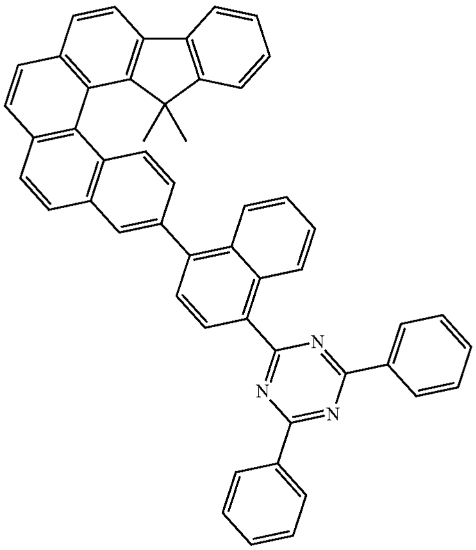
C-181
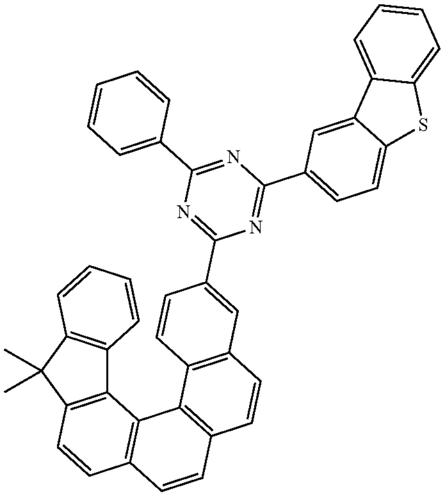
C-182
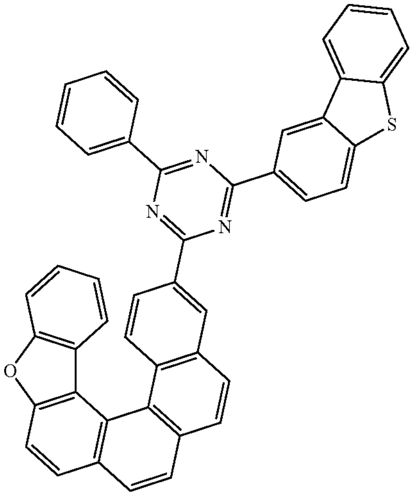
-continued
C-183
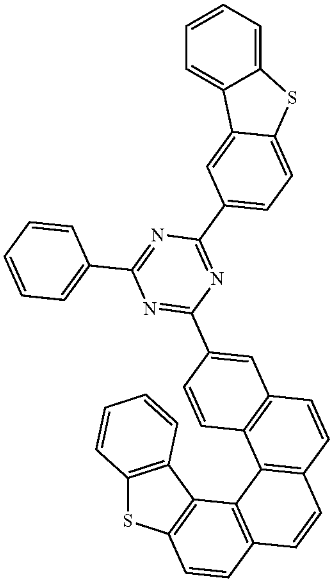
C-184
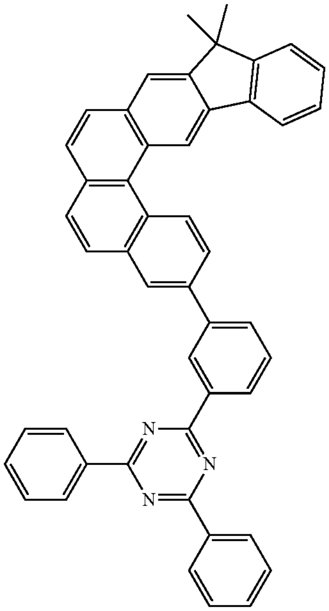

-continued
C-185
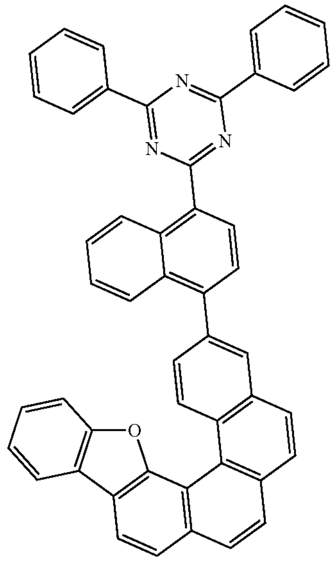
C-186
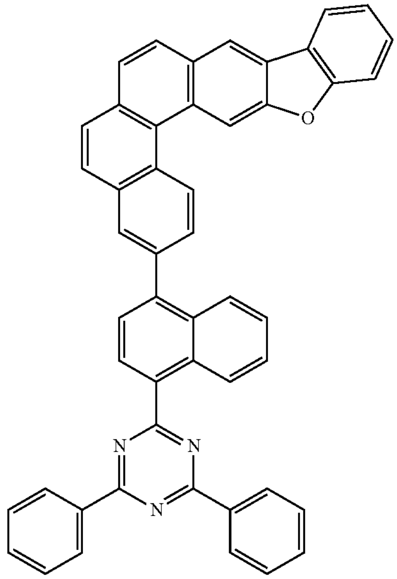
-continued
C-187
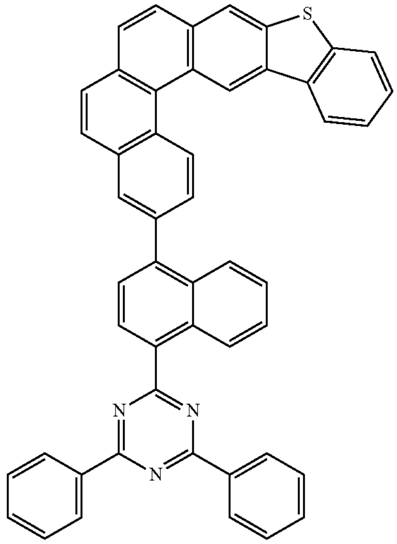
C-188
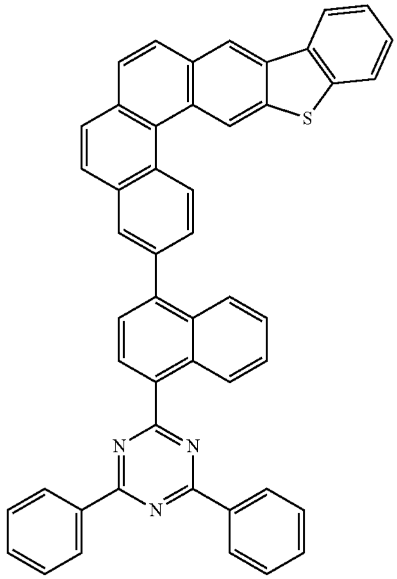

C-189
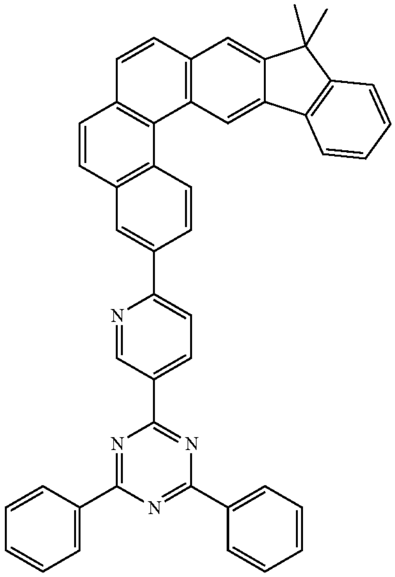
C-190
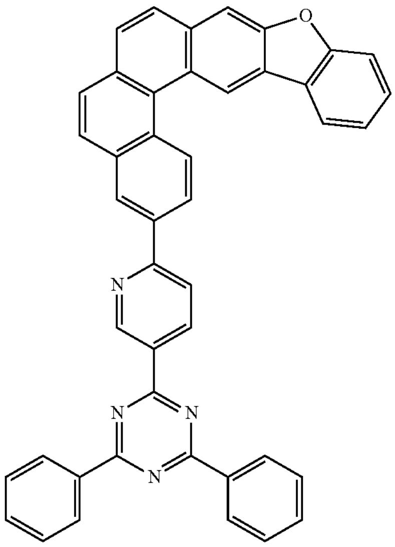
C-191
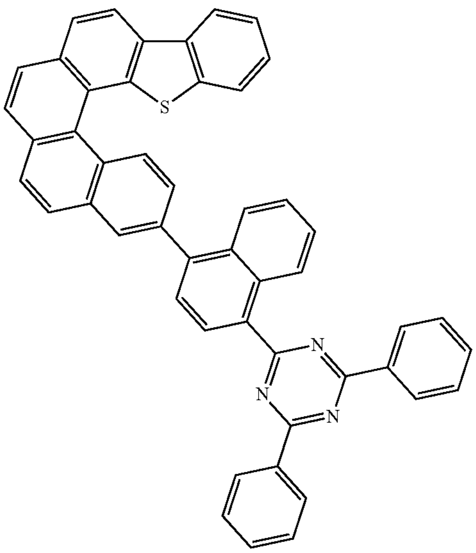
C-192
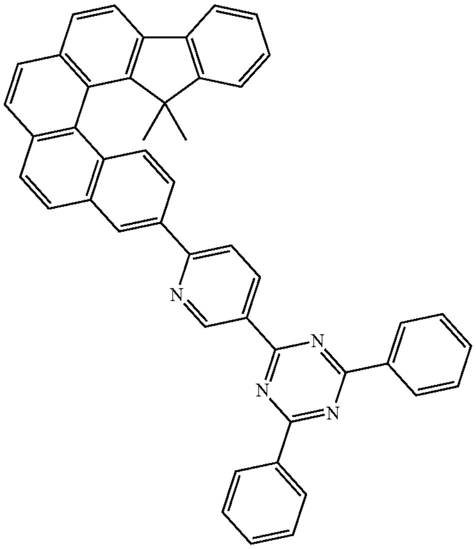

-continued
C-193
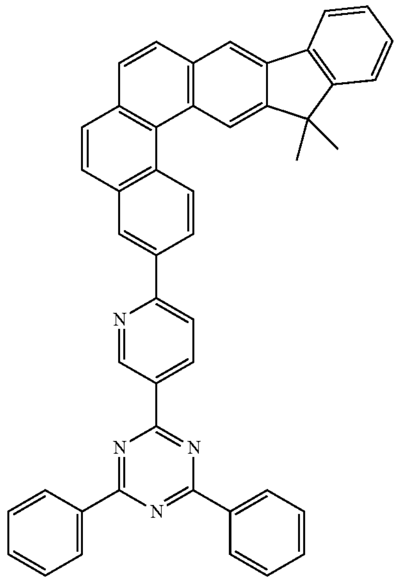
C-194
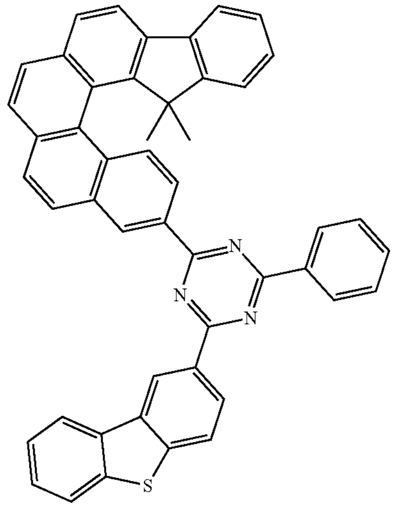
C-195
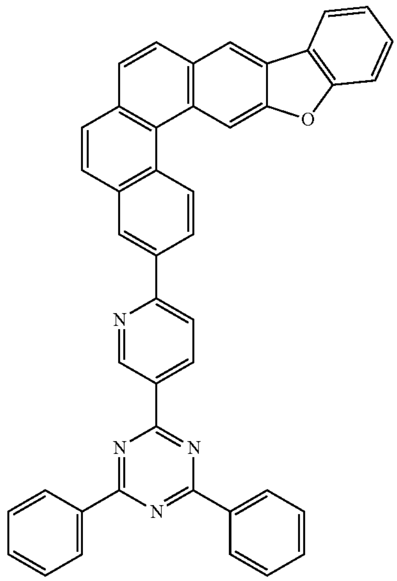
-continued
C-196
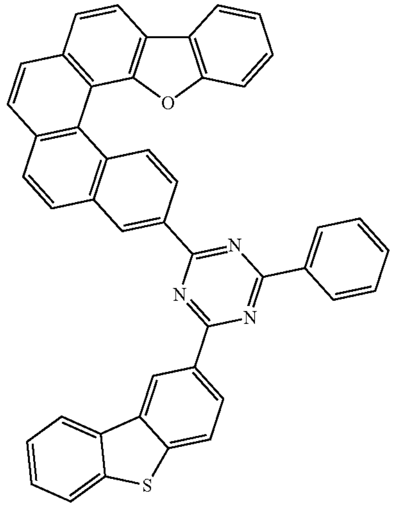
C-197
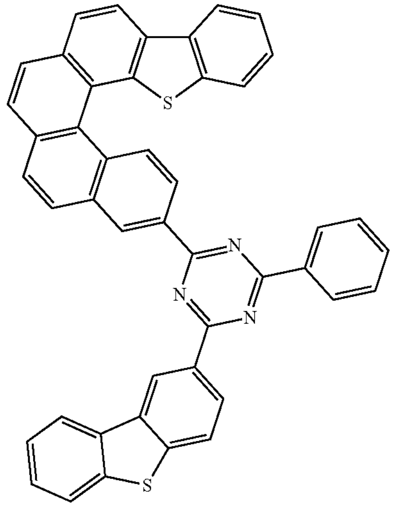
C-198
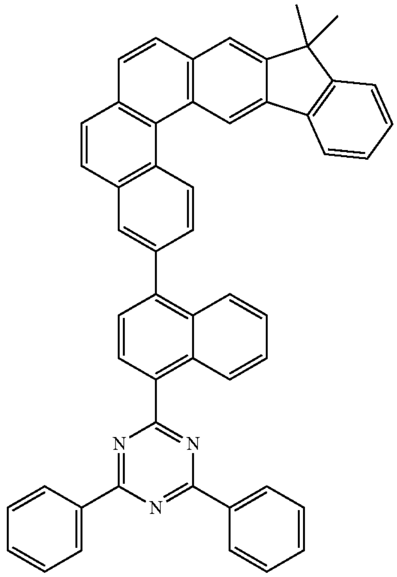

-continued
C-199
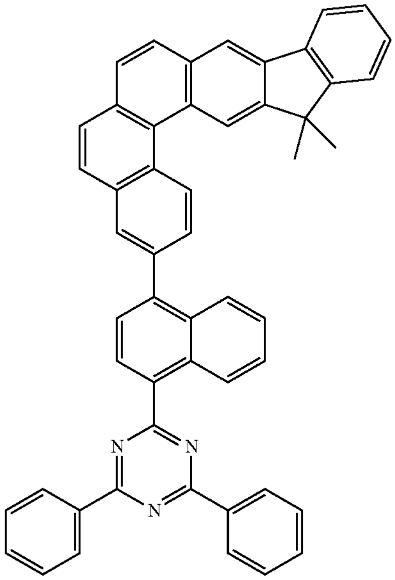
C-200
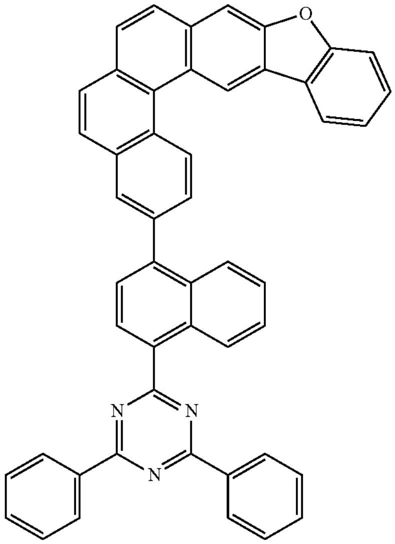
-continued
C-201
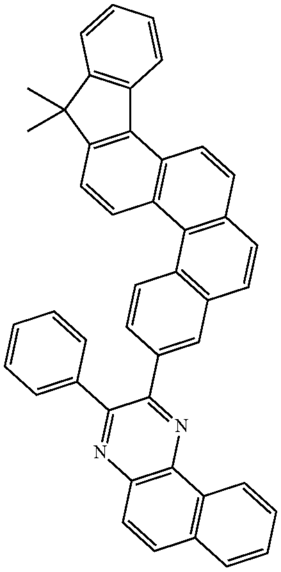
C-202
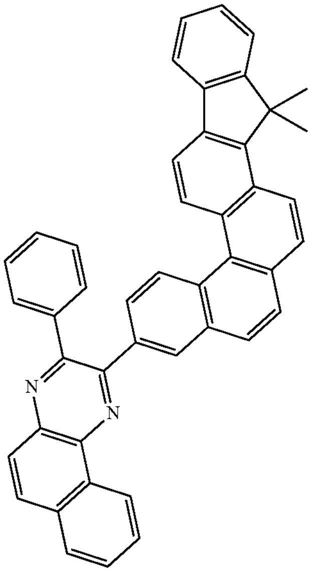

-continued
C-203
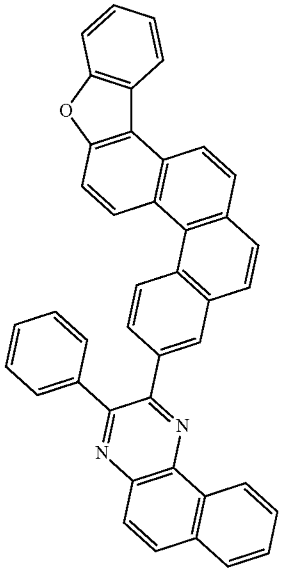
C-204
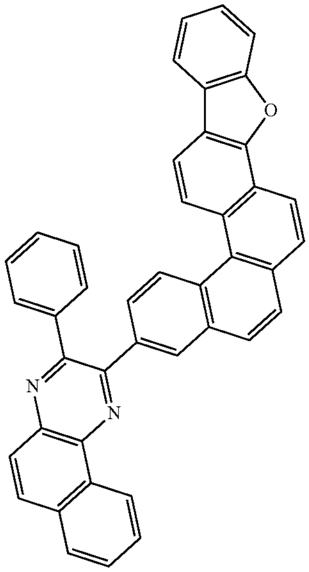
-continued
C-205
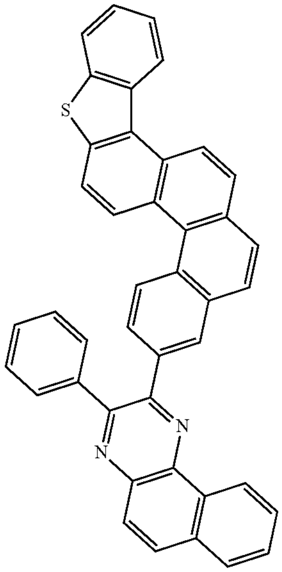
C-206
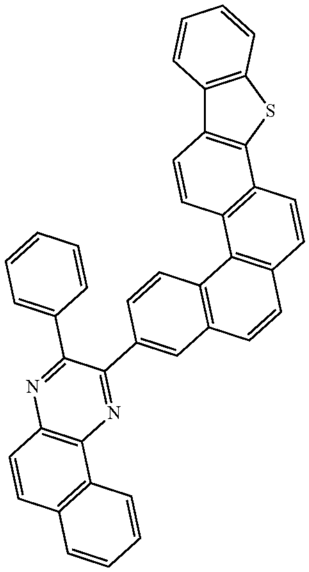

-continued
C-207
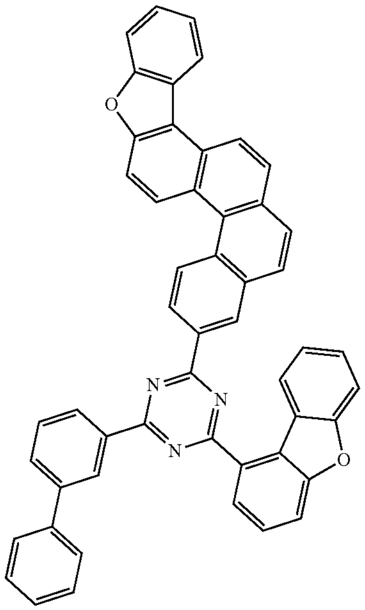
C-208
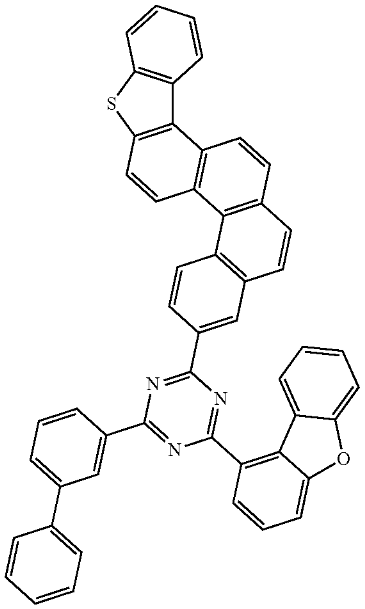
-continued
C-209
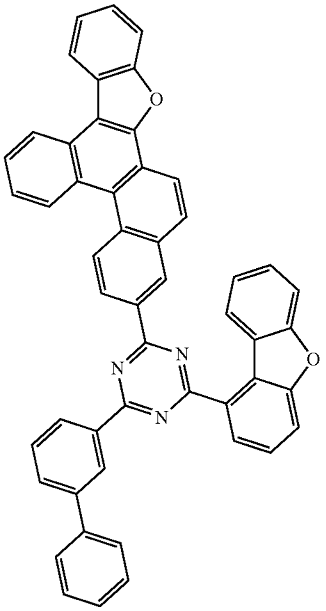
C-210
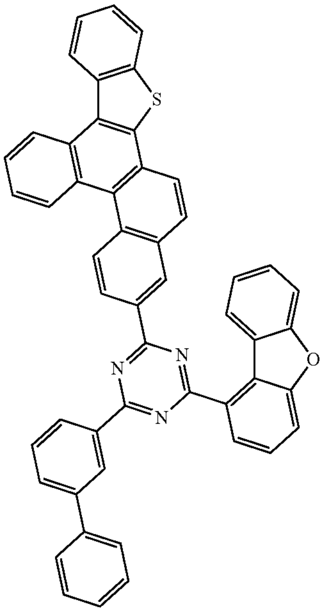

-continued
C-211
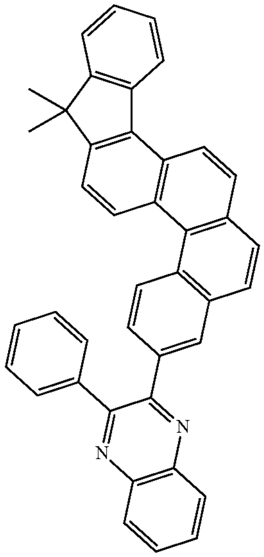
C-212
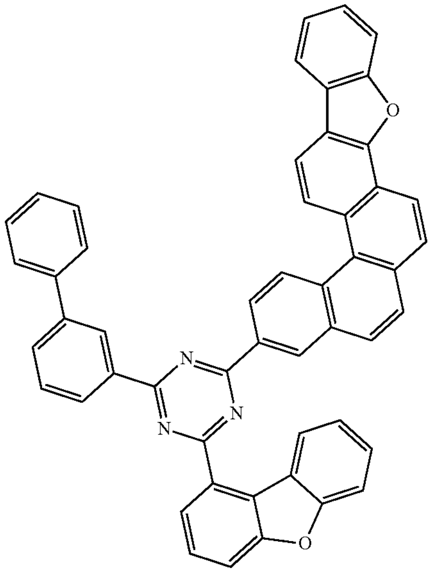
-continued
C-213
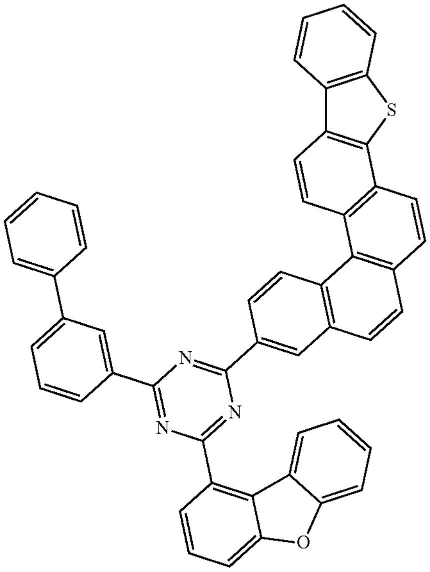
C-214
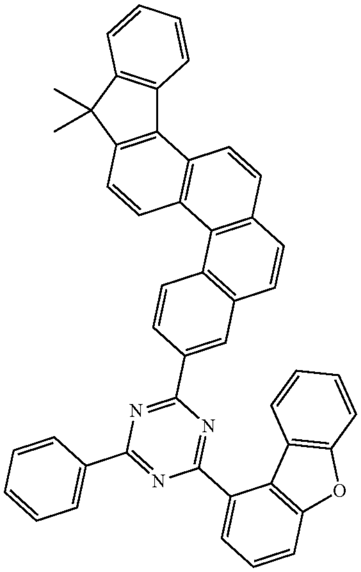

-continued
C-215
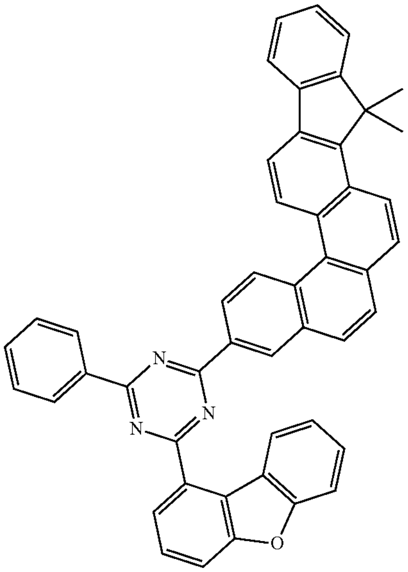
C-216
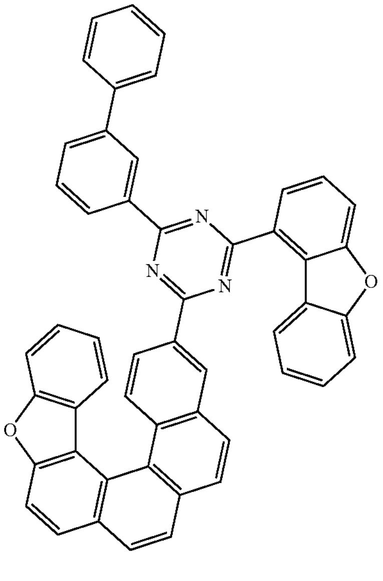
-continued
C-217
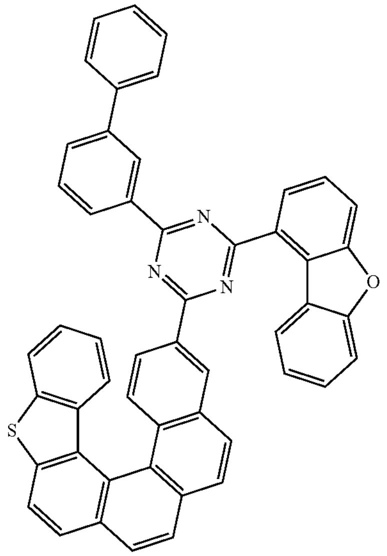
C-218
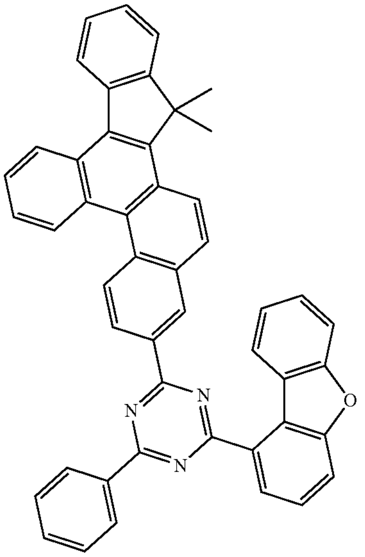
C-219
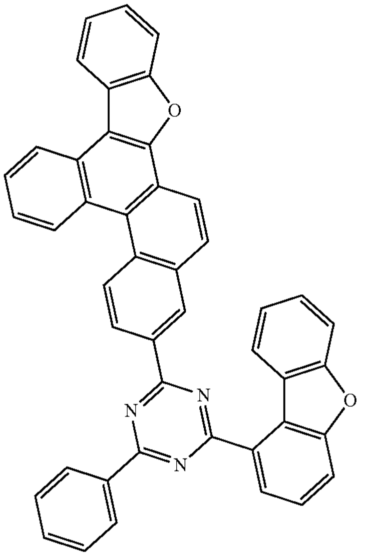

C-220
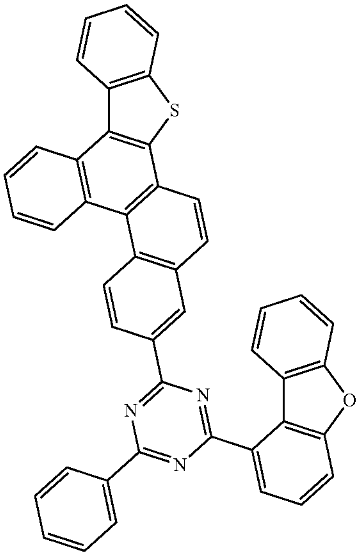
C-221
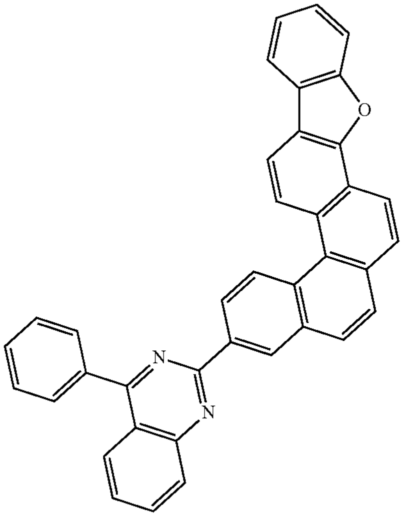
C-222
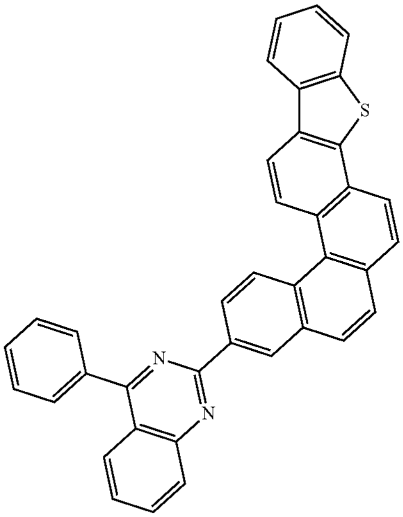
C-223
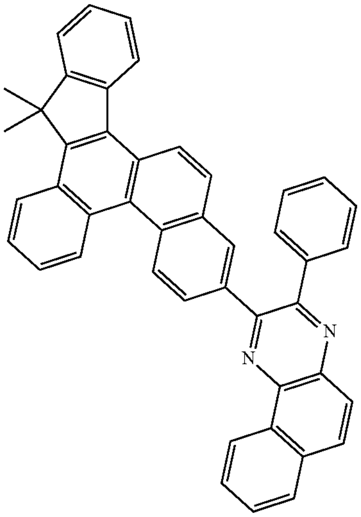
C-224
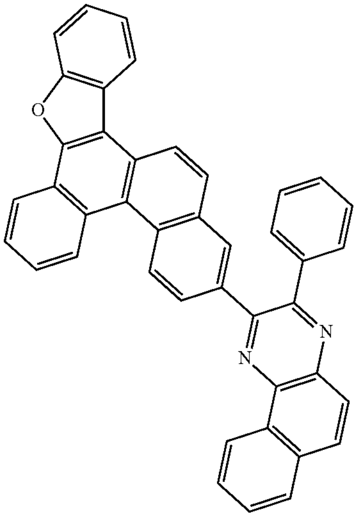
C-225
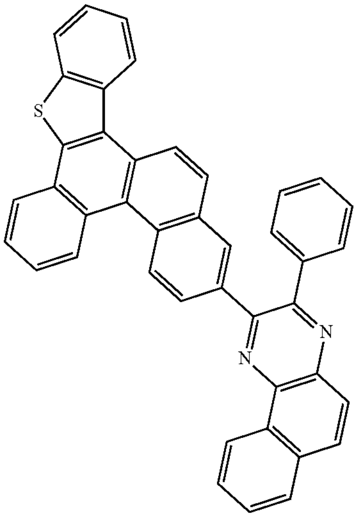

-continued
C-226
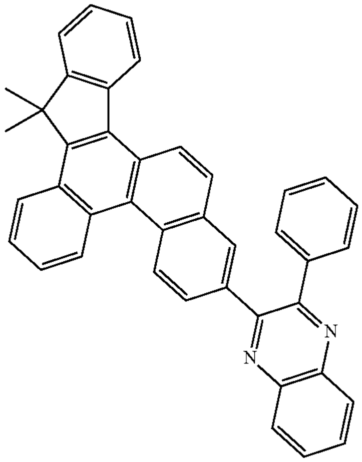
C-227
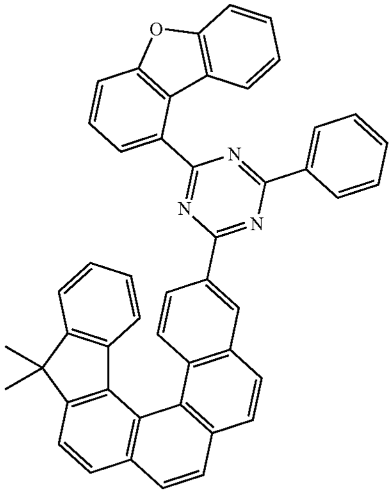
C-228
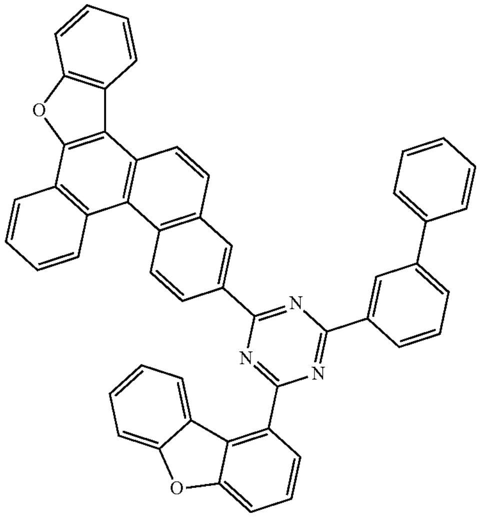
-continued
C-229
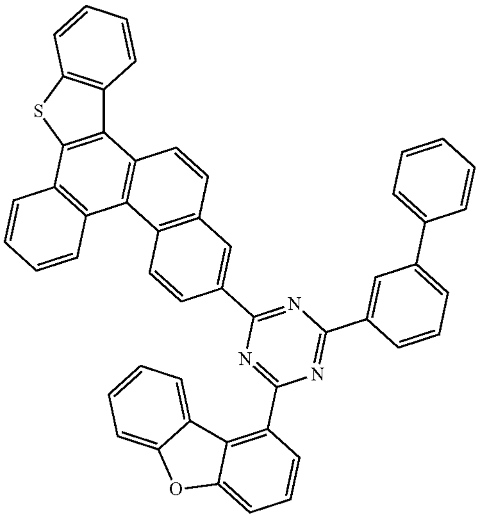
C-230
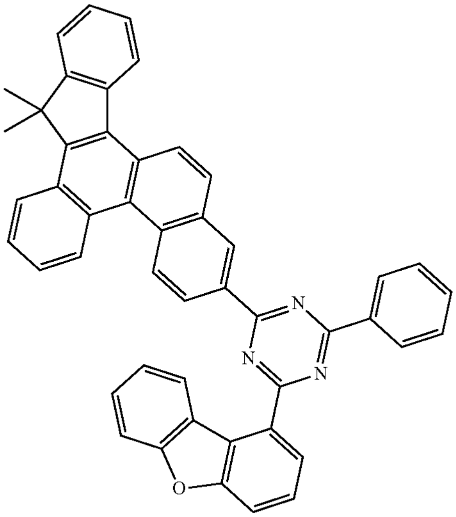
C-231
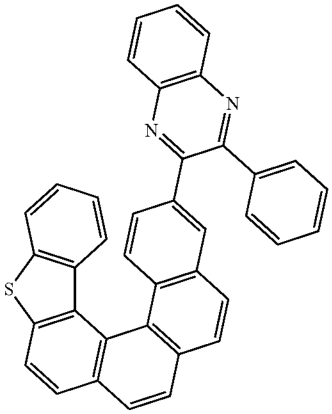

-continued
C-232
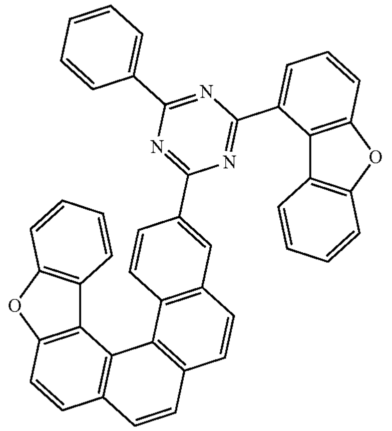
C-233
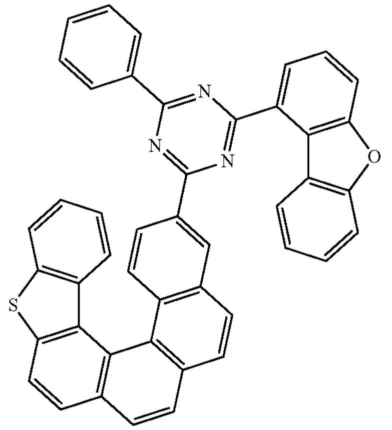
C-234
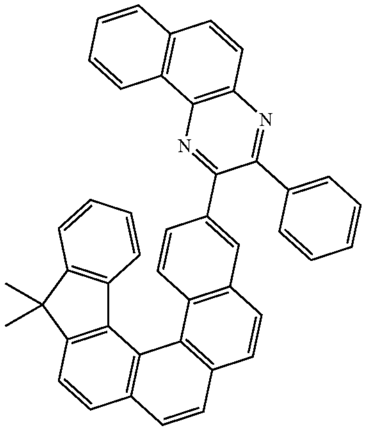
-continued
C-235
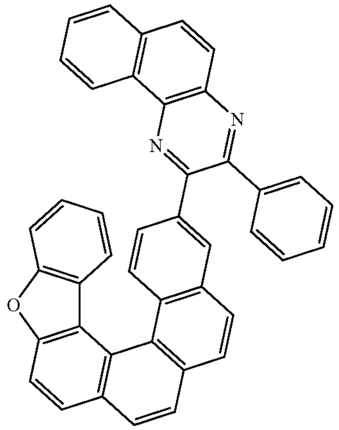
C-236
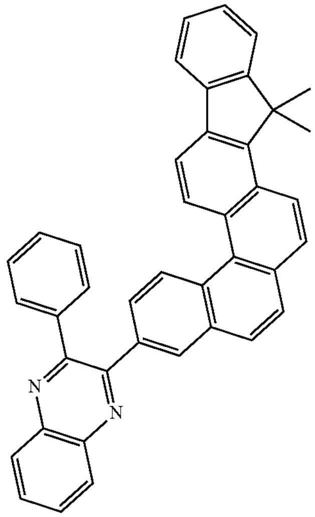
C-237
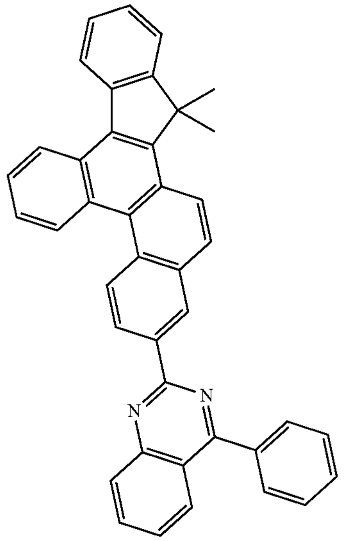

-continued
C-238
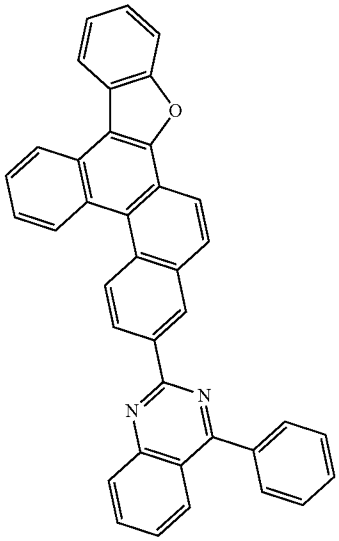
C-239
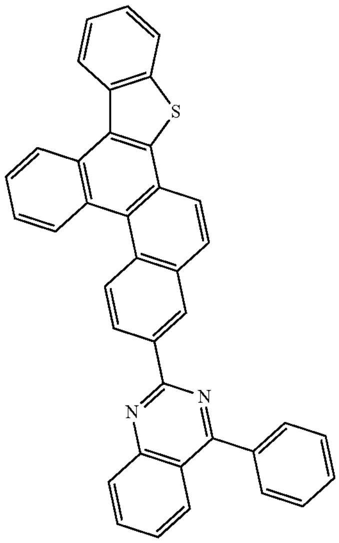
C-240
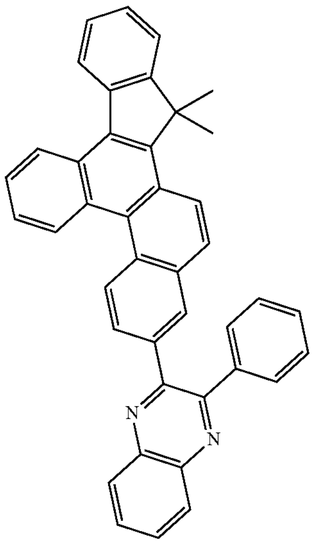
-continued
C-241
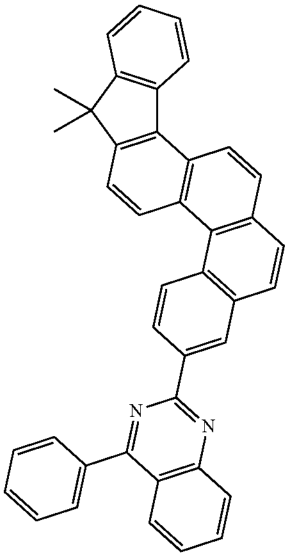
C-242
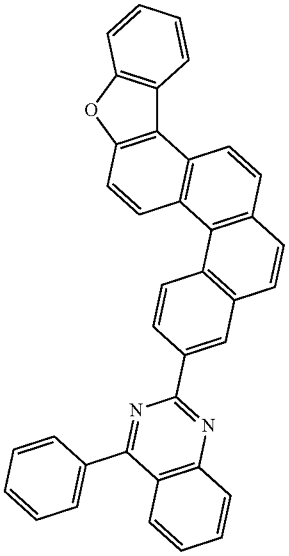
C-243
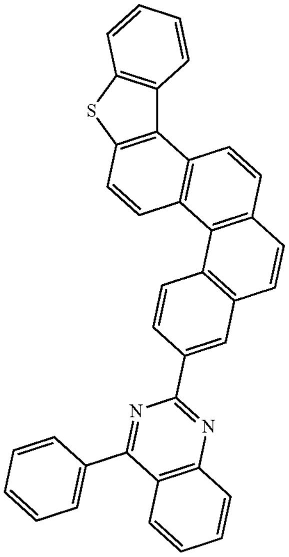

-continued
C-244
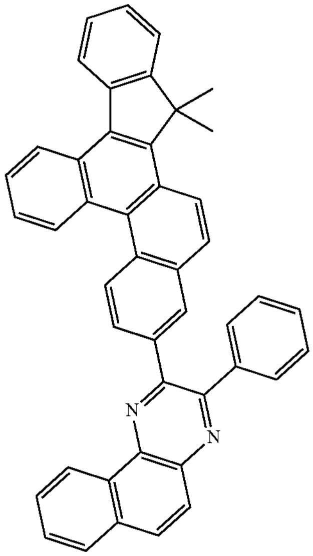
C-245
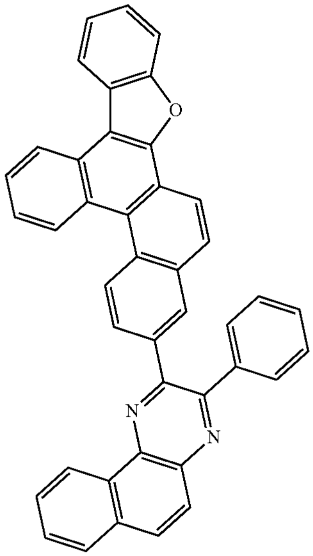
-continued
C-246
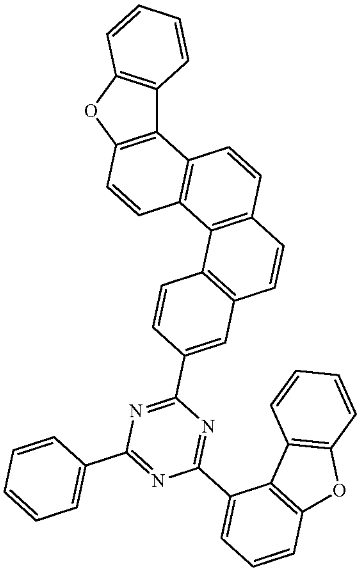
C-247
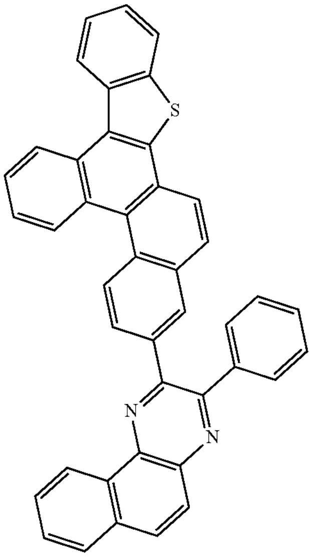

-continued
C-248
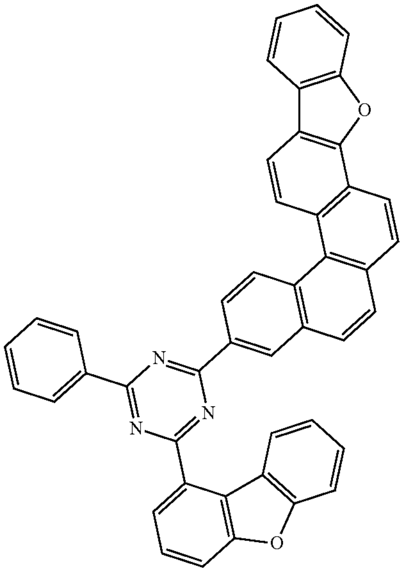
C-249
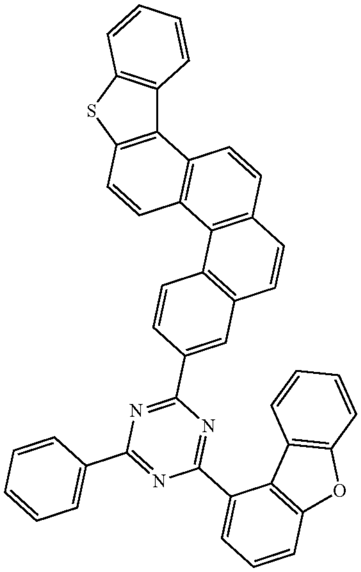
-continued
C-250
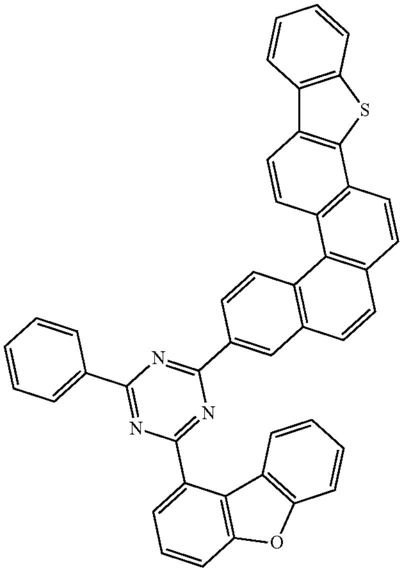
C-251
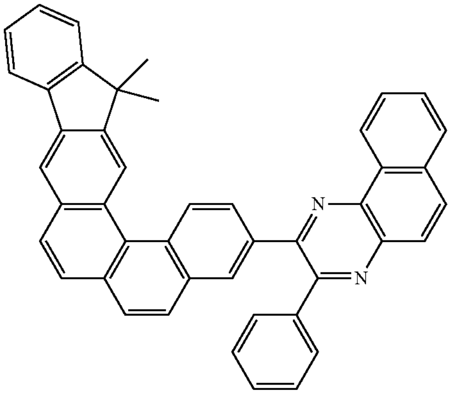
C-252
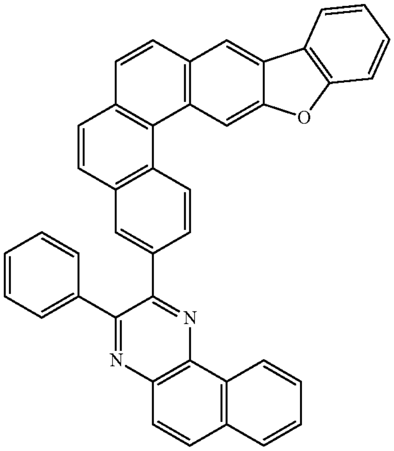

-continued
C-253
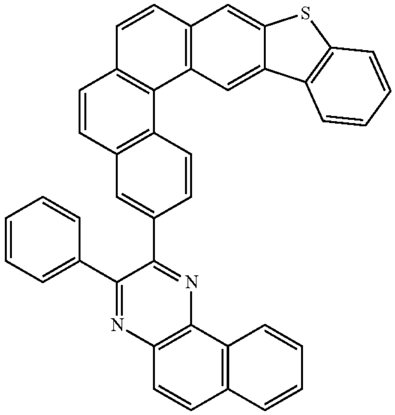
C-254
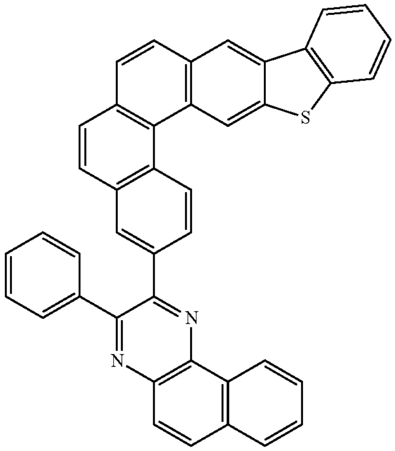
C-255
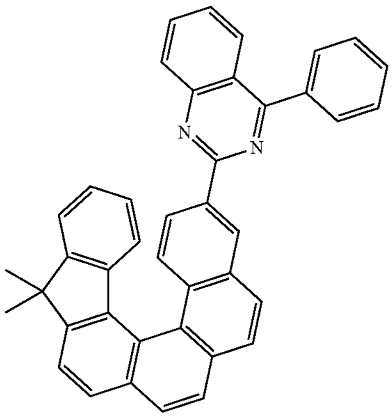
-continued
C-256
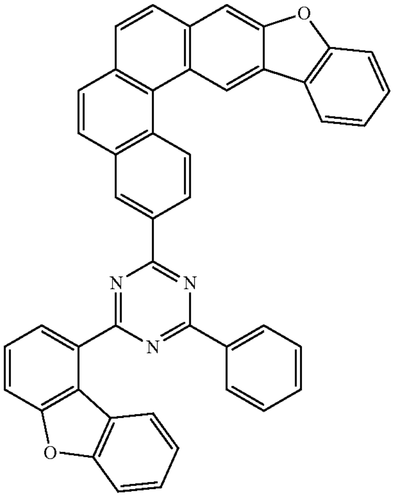
C-257
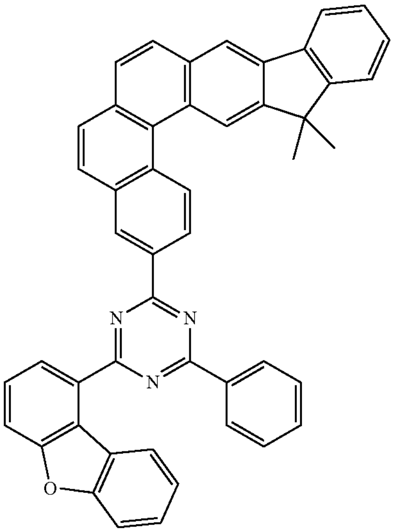
C-258
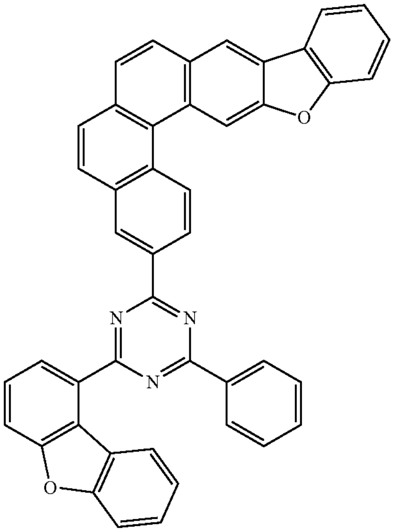

C-259
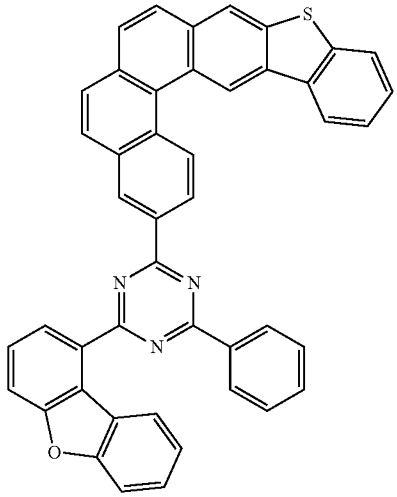
C-260
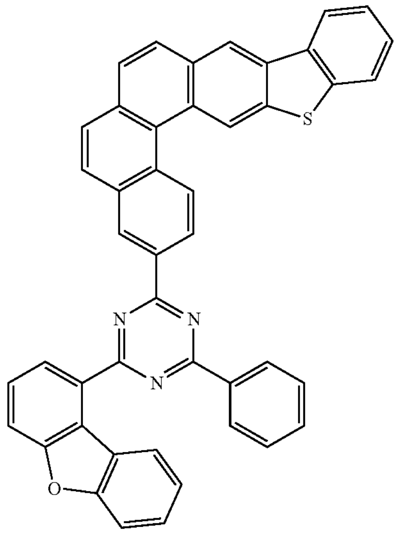
C-261
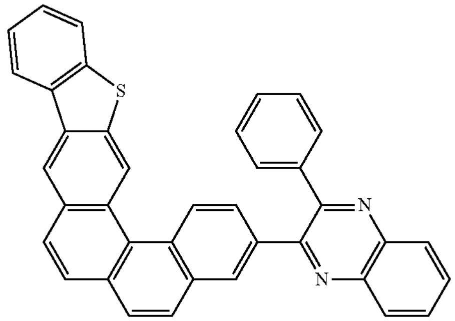
C-262
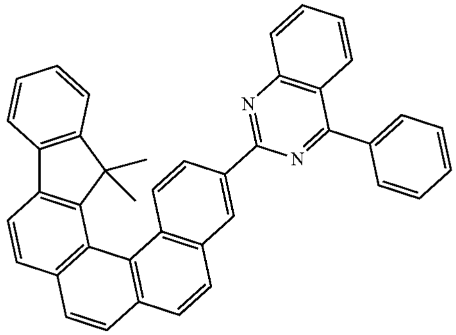
C-263
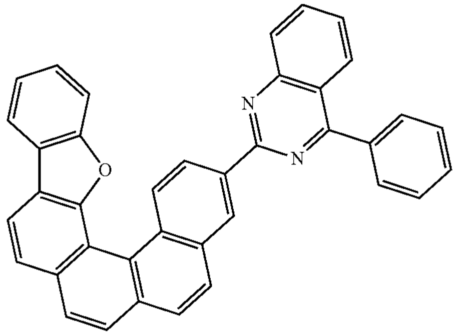
C-264
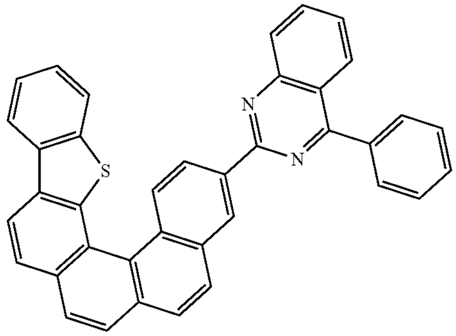
C-265
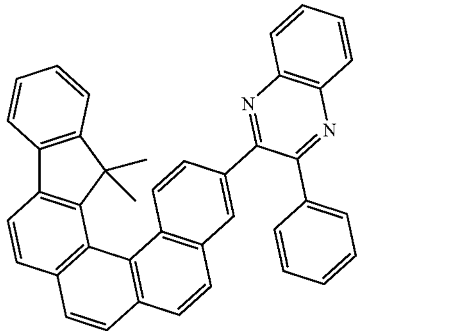

-continued
C-266
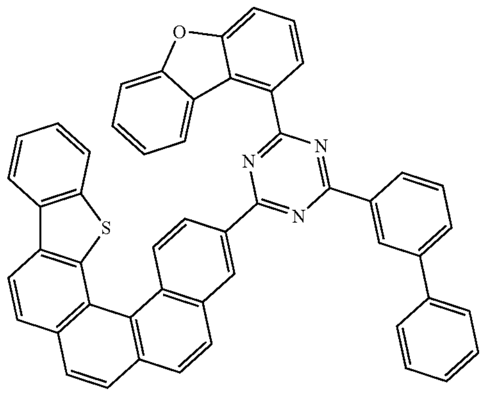
C-267
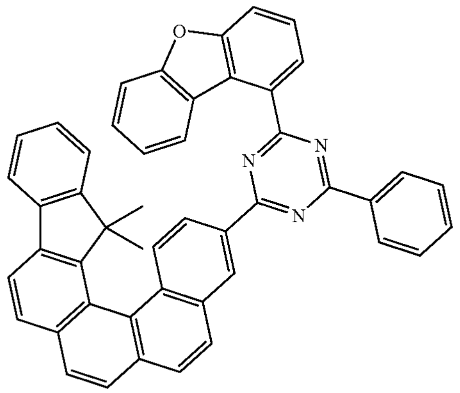
C-268
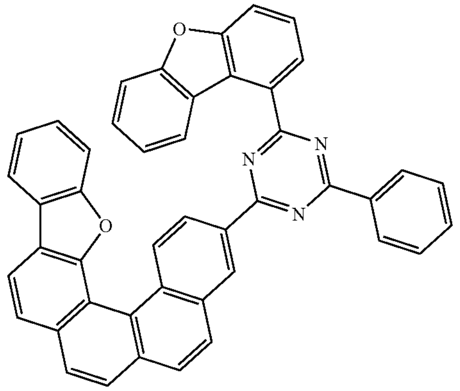
C-269
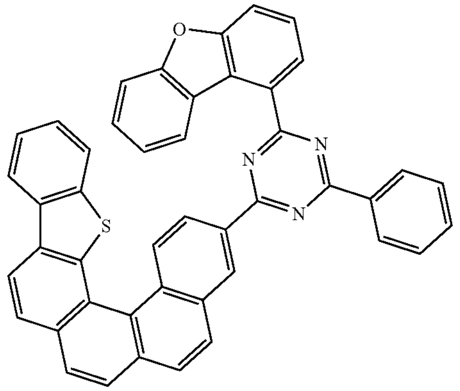
-continued
C-270
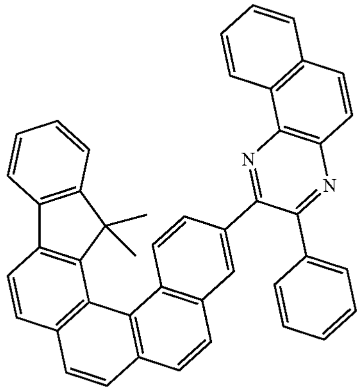
C-271
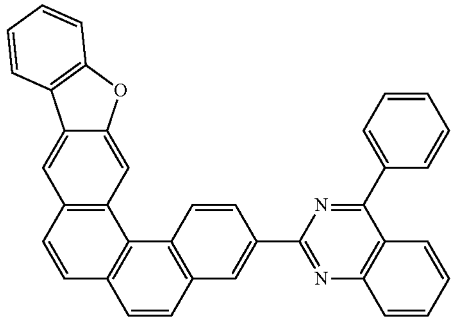
C-272
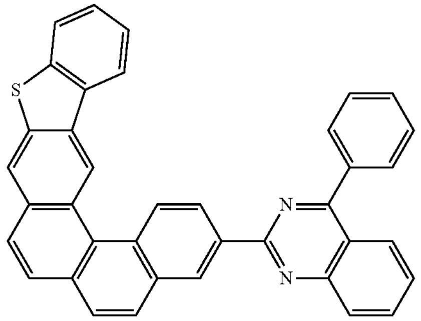
C-273
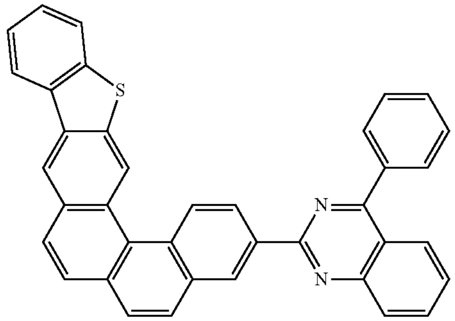

C-274
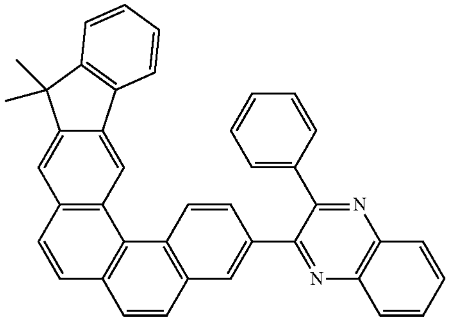
C-275
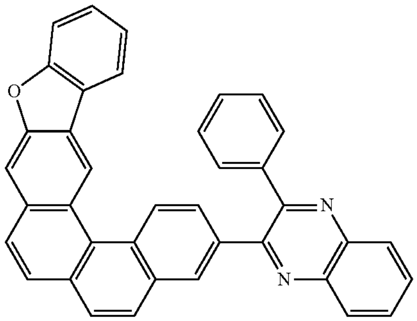
C-276
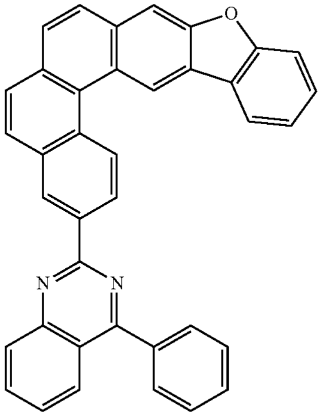
C-277
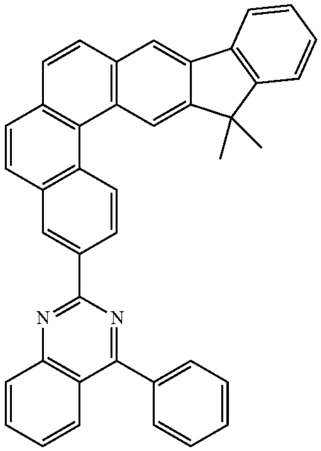
C-278
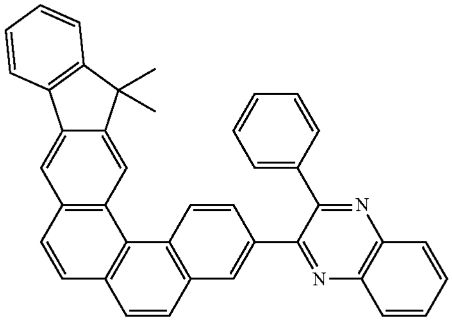
C-279
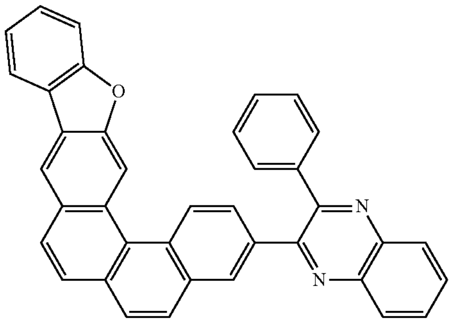
C-280
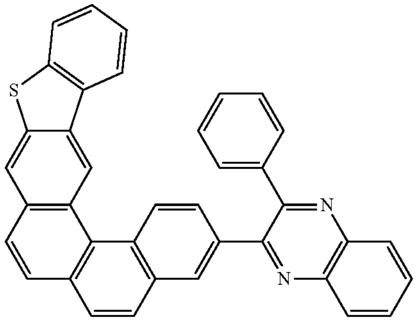
C-281
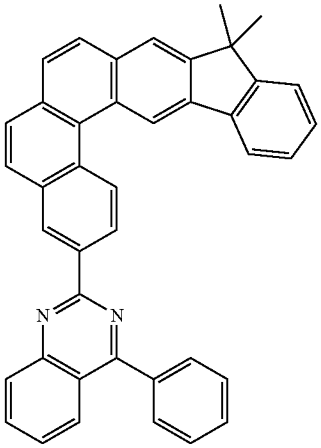

-continued
C-282
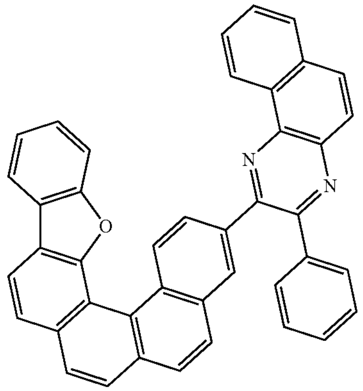
C-283
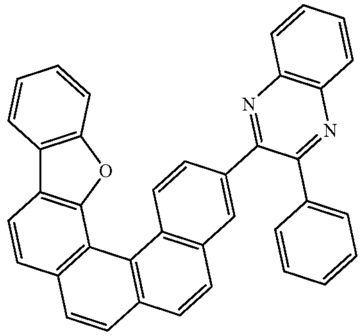
C-284
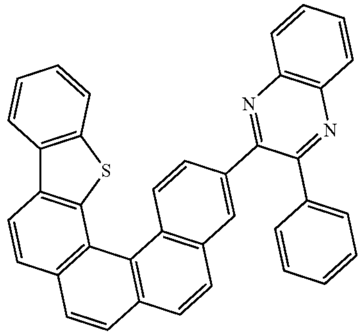
C-285
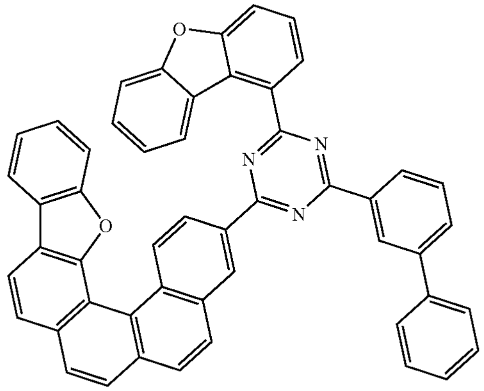
-continued
C-286
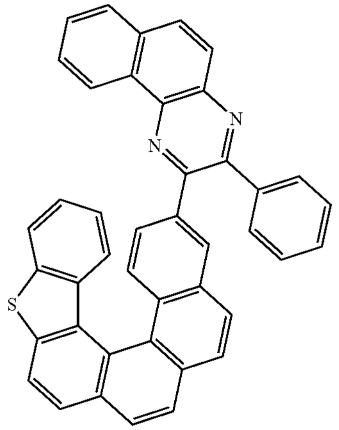
C-287
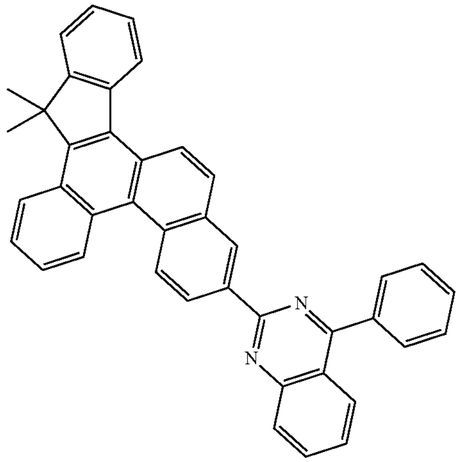
C-288
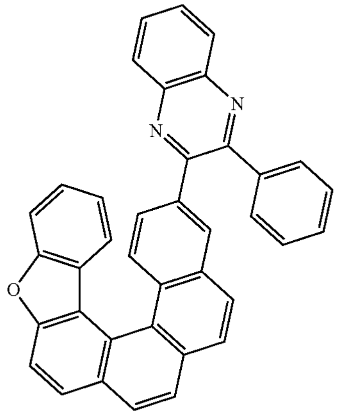

-continued
C-289
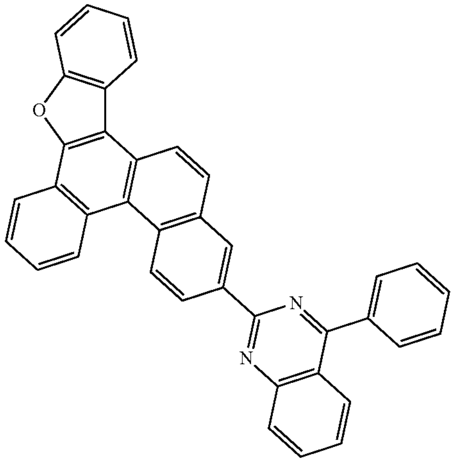
C-290
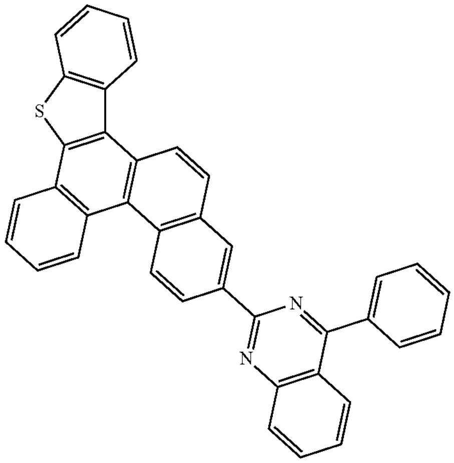
C-291
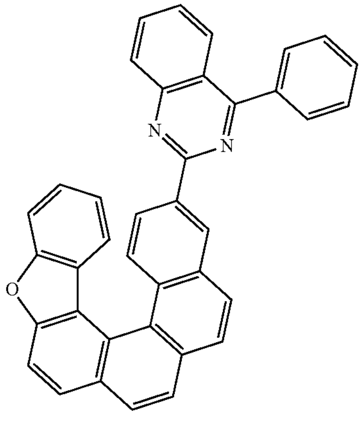
-continued
C-292
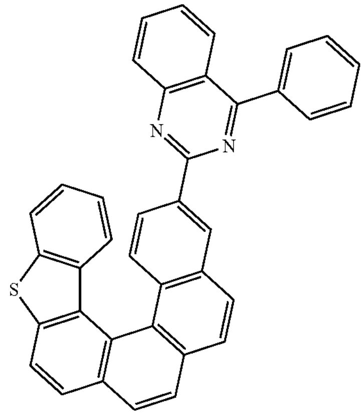
C-293
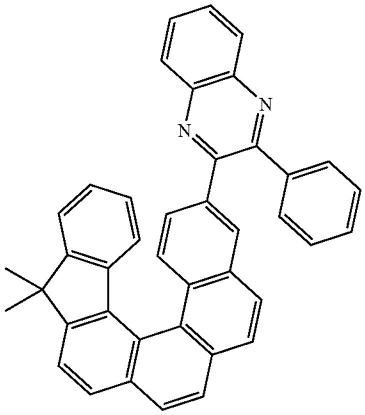
C-294
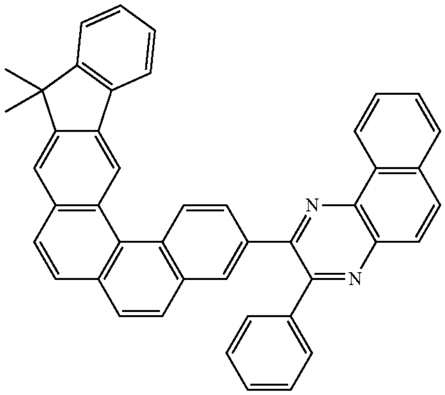
C-295
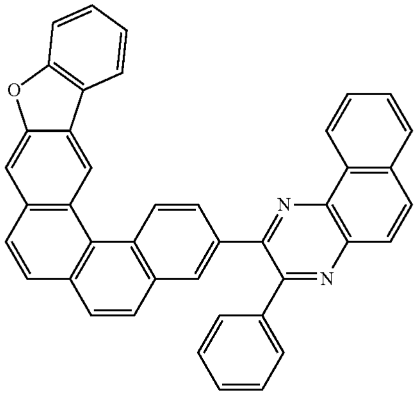

C-296
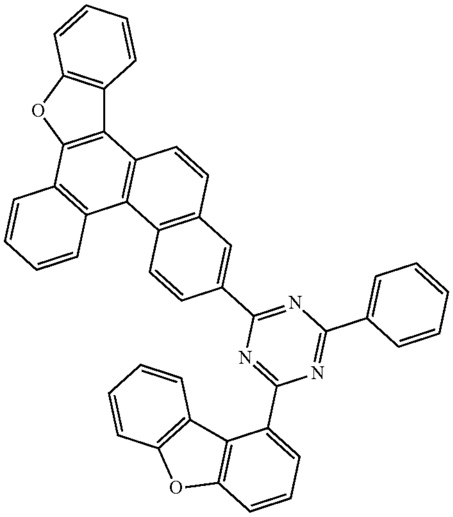
C-297
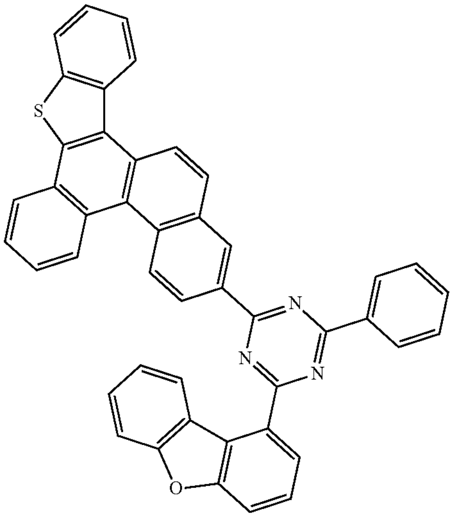
C-298
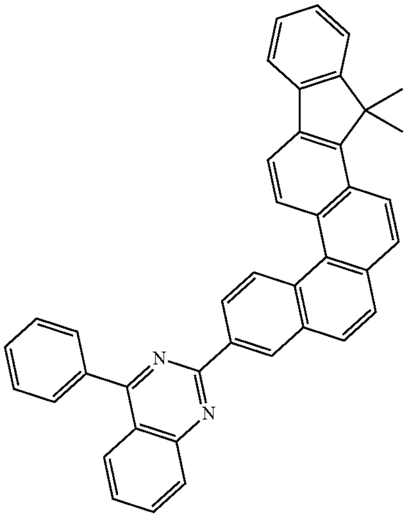
C-299
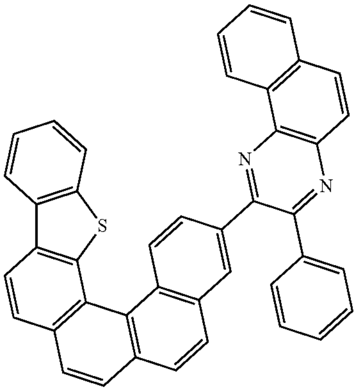
C-300
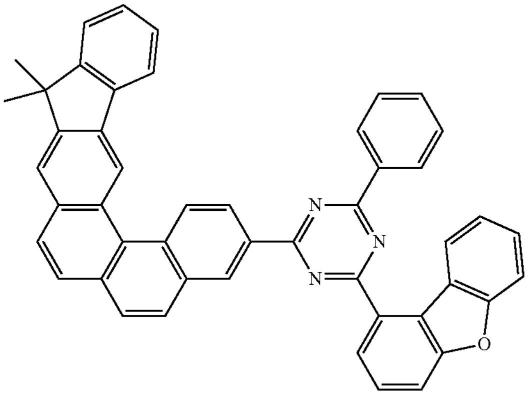
C-301
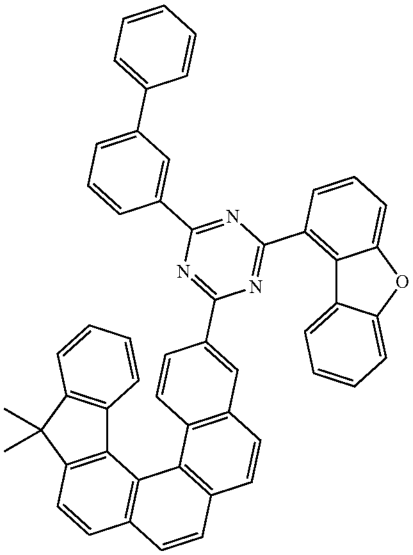

-continued
C-302
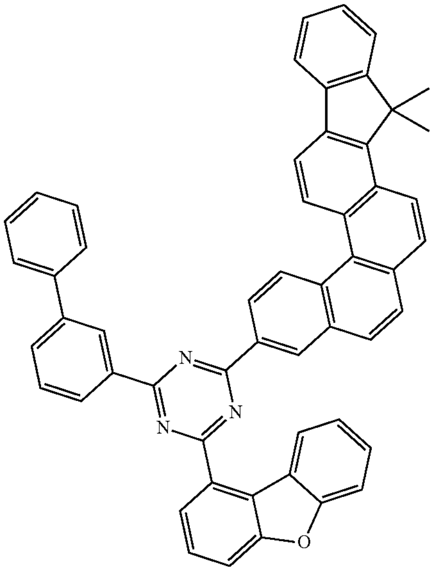
C-303
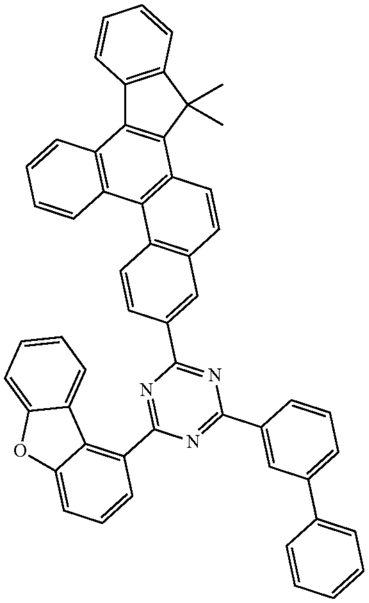
-continued
C-304
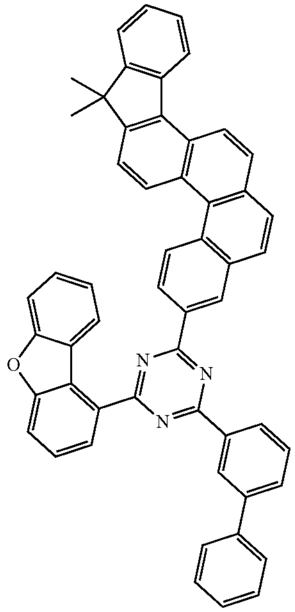
C-305
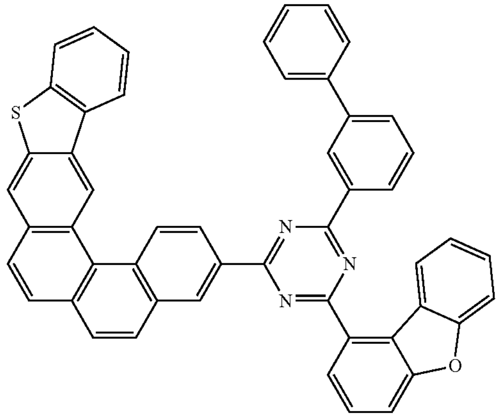
C-306
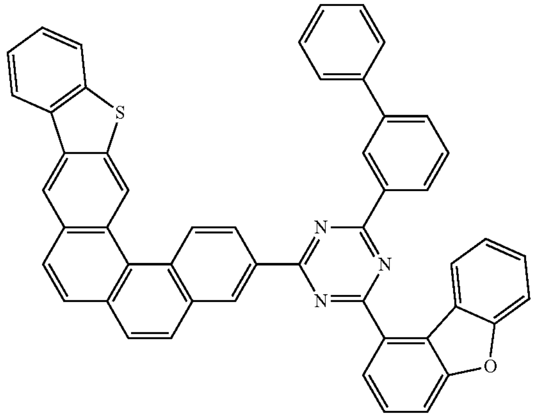

-continued
C-307
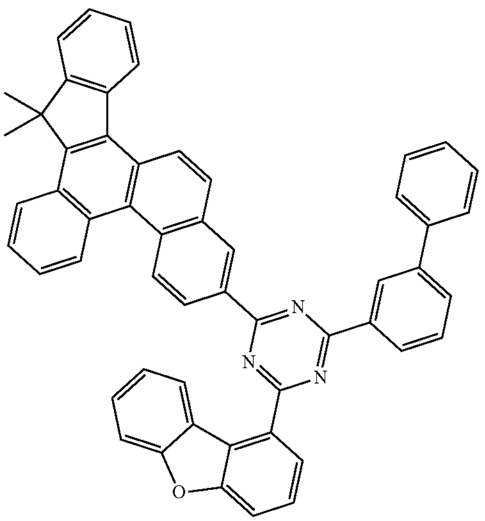
C-308
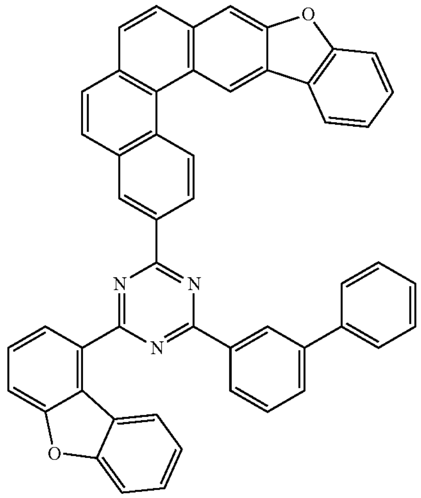
C-309
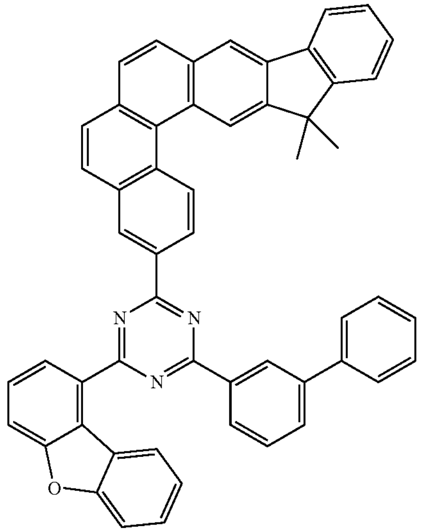
-continued
C-310
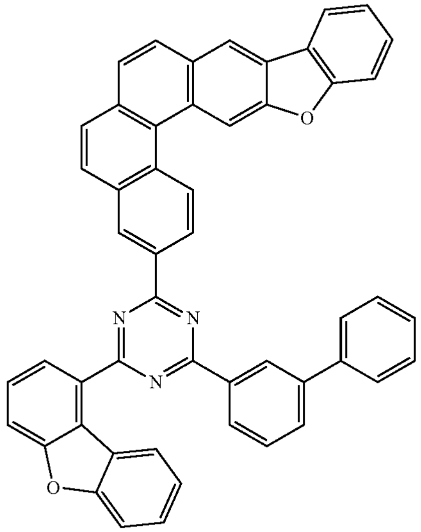
C-311
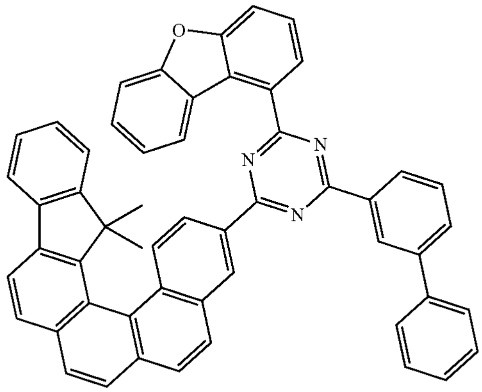
C-312
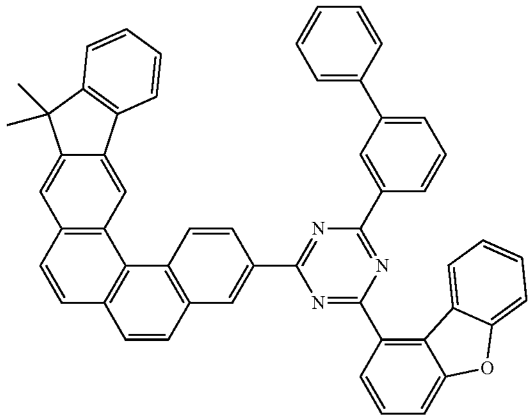

-continued
C-313
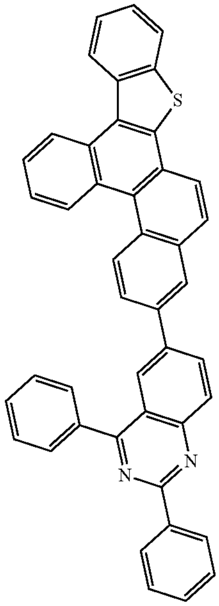
C-314
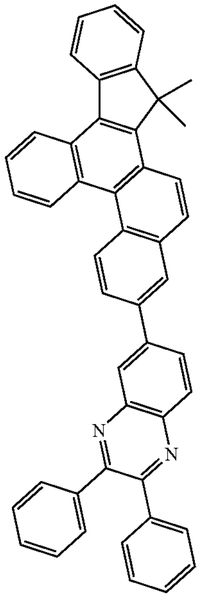
-continued
C-315
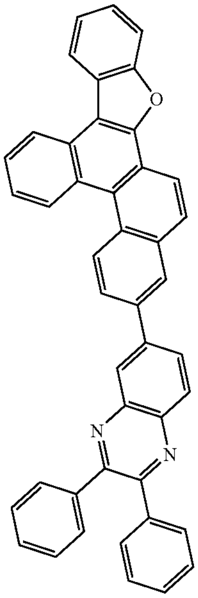
C-316
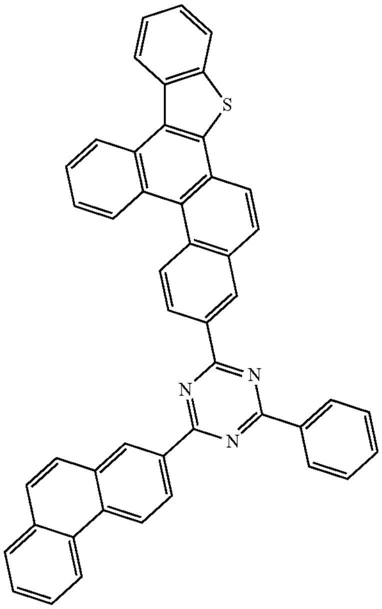

-continued
C-317
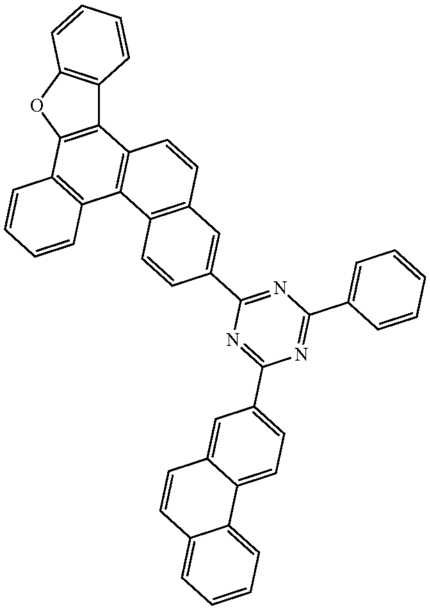
C-318
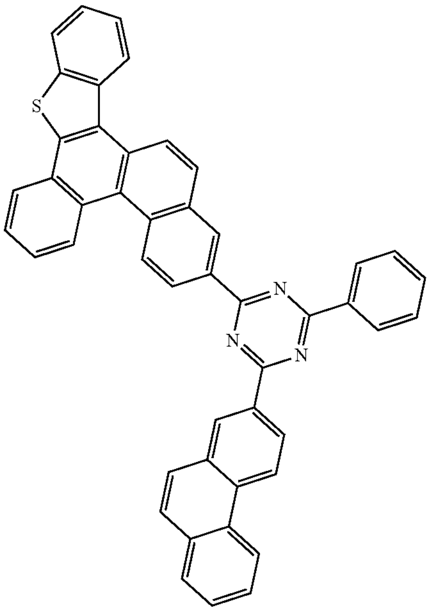
-continued
C-319
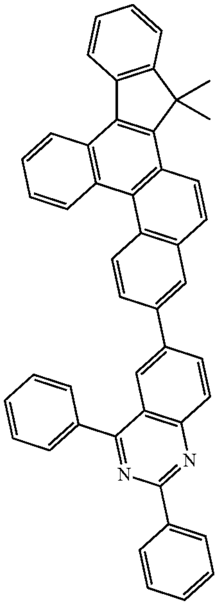
C-320
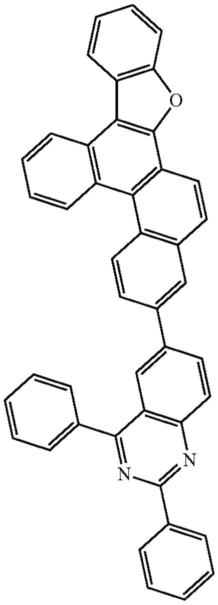

-continued
C-321
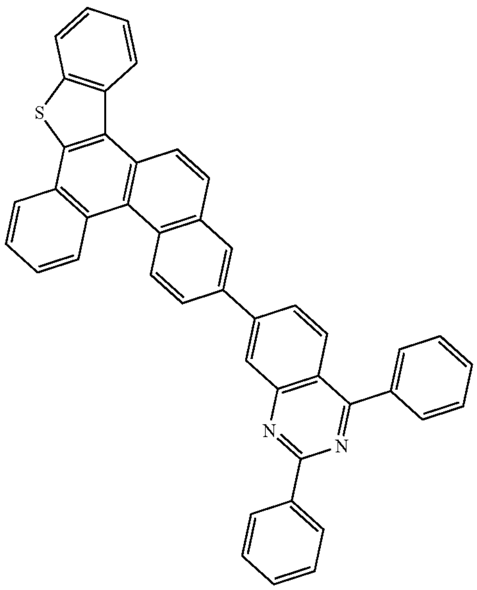
C-322
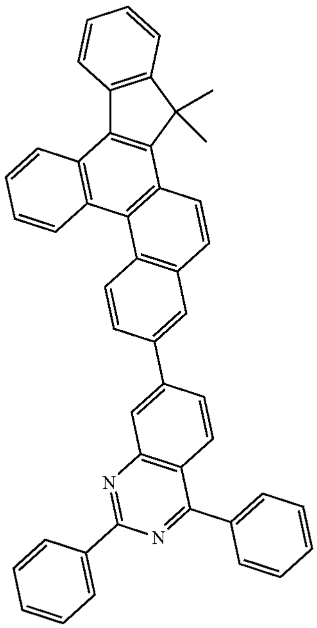
-continued
C-323
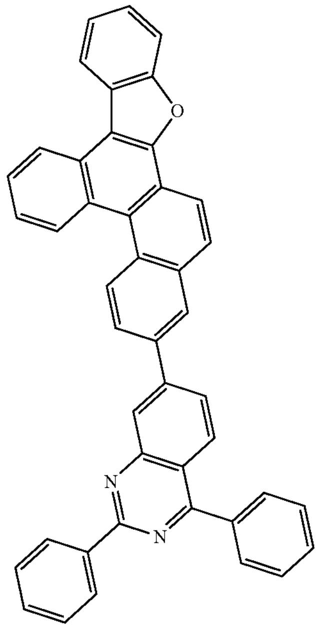
C-324
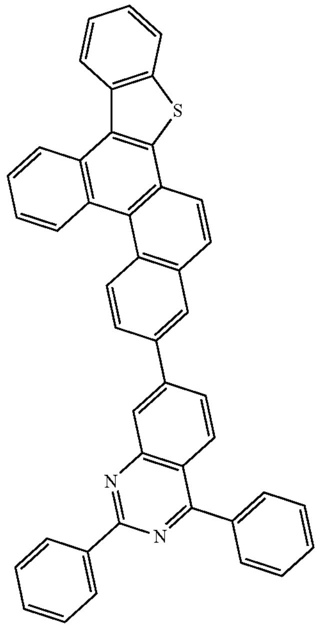

-continued
C-325
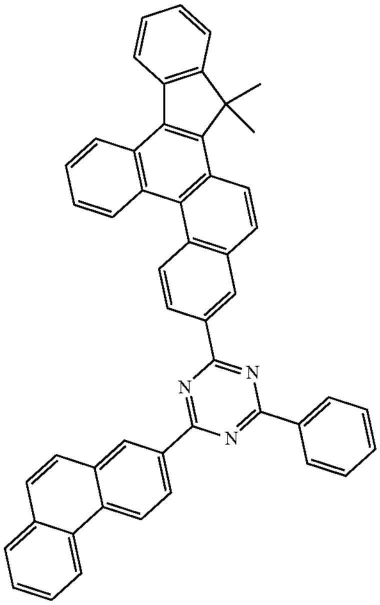
C-326
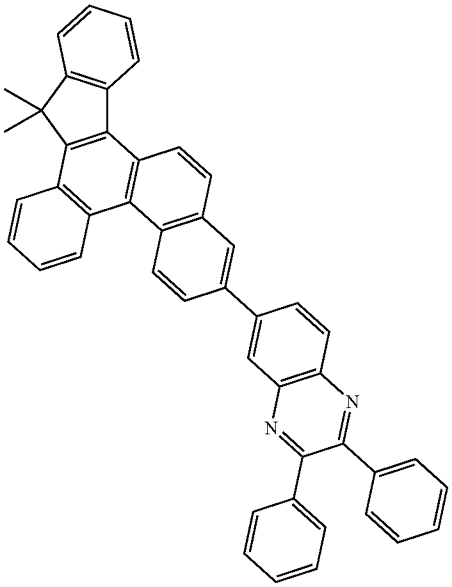
-continued
C-327
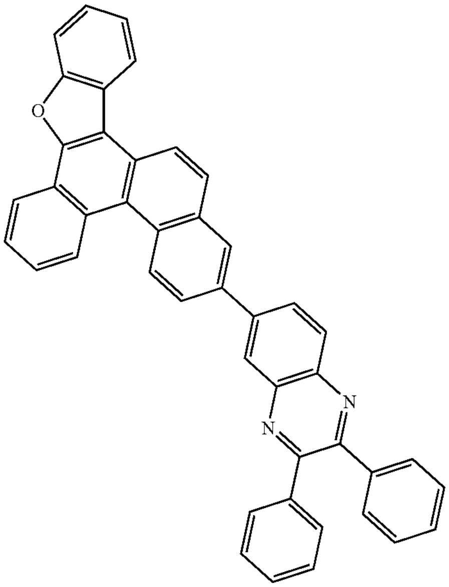
C-328
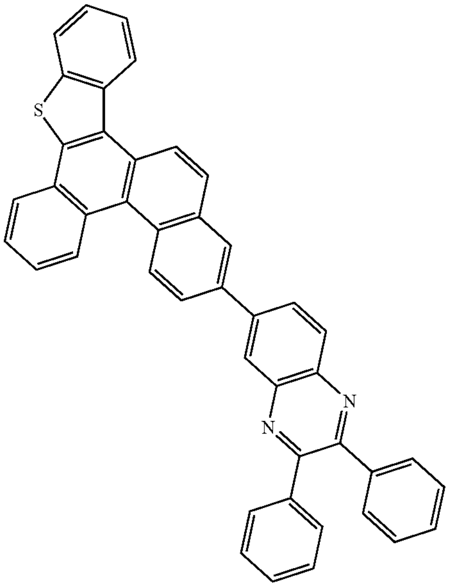

-continued
C-329
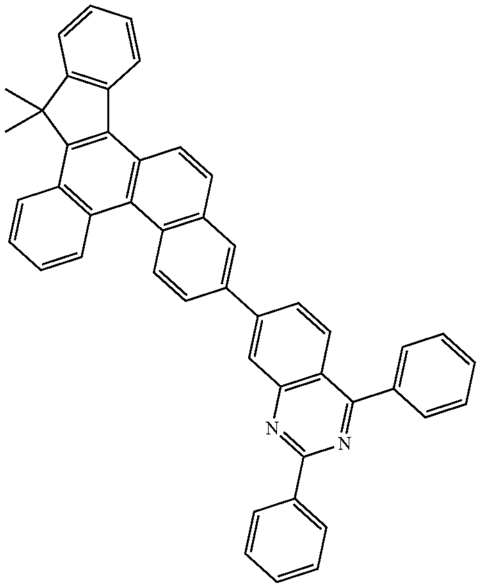
C-330
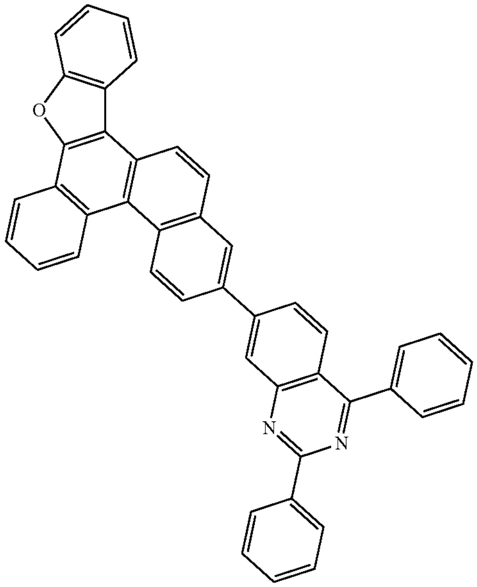
C-331
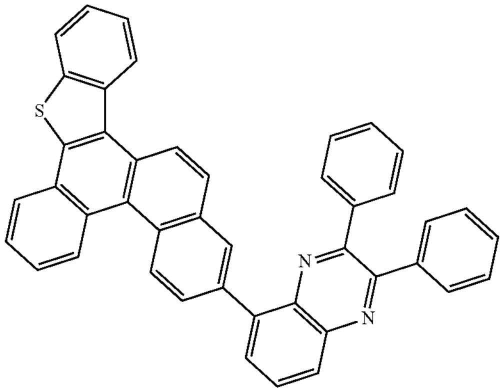
-continued
C-332
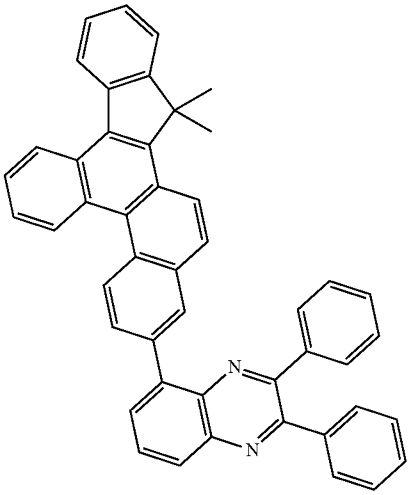
C-333
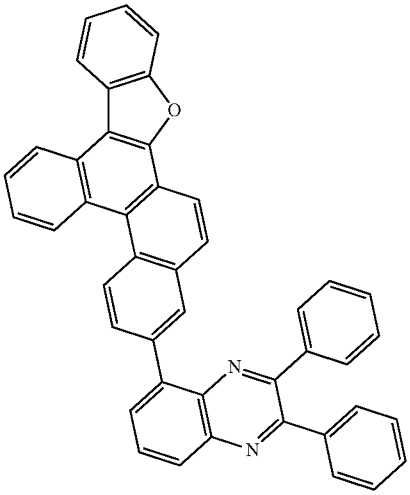
C-334
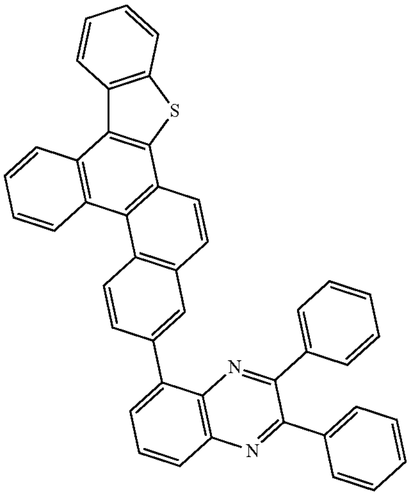

-continued
C-335
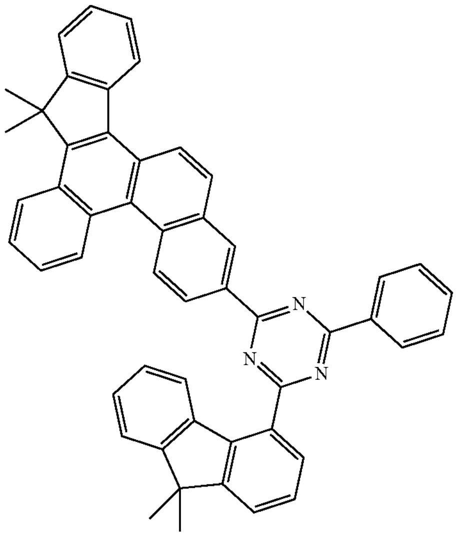
C-336
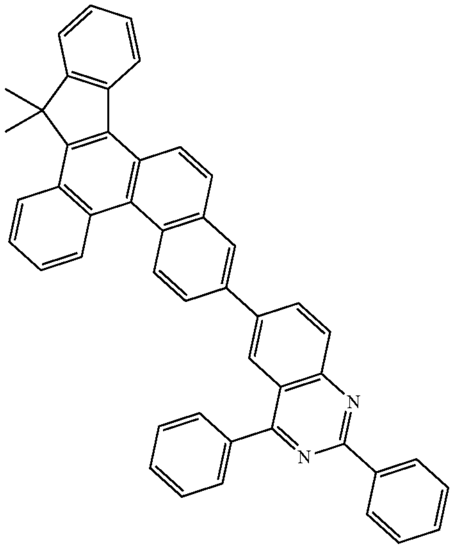
C-337
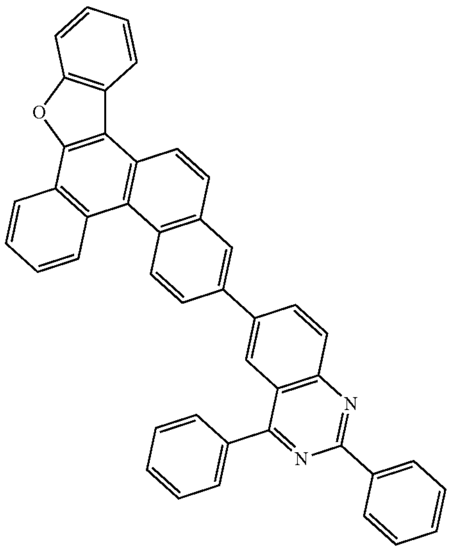
-continued
C-338
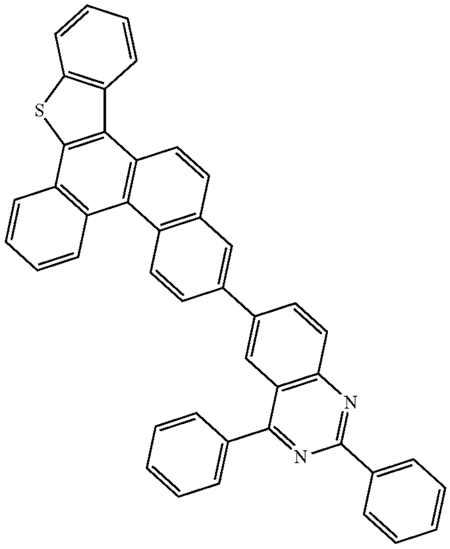
C-339
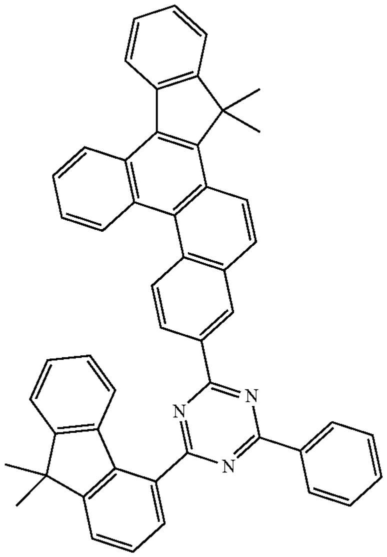
C-340
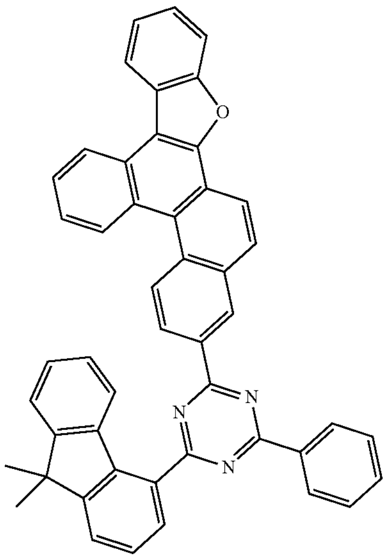

-continued
C-341
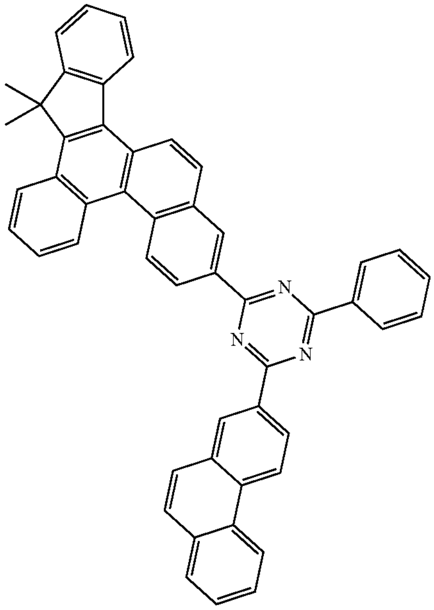
C-342
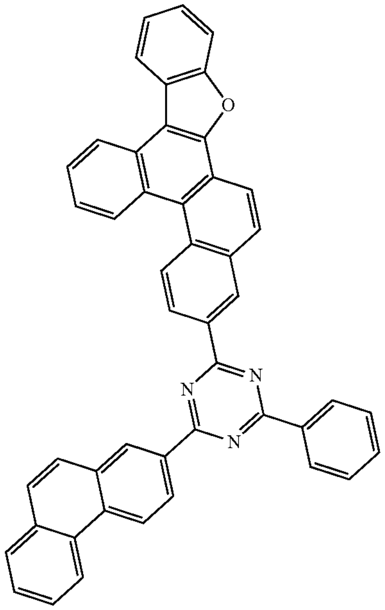
C-343
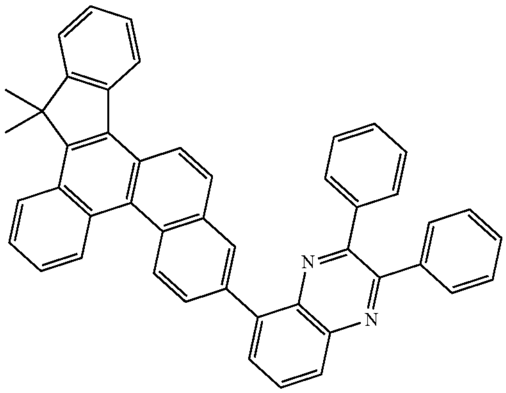
-continued
C-344
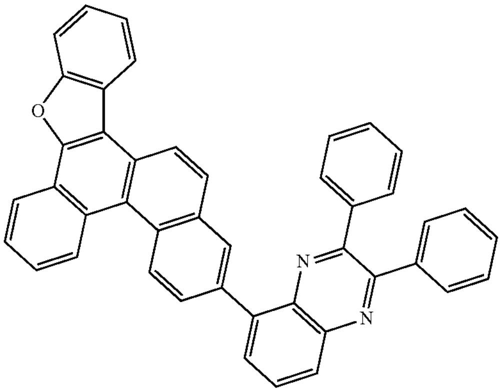
C-345
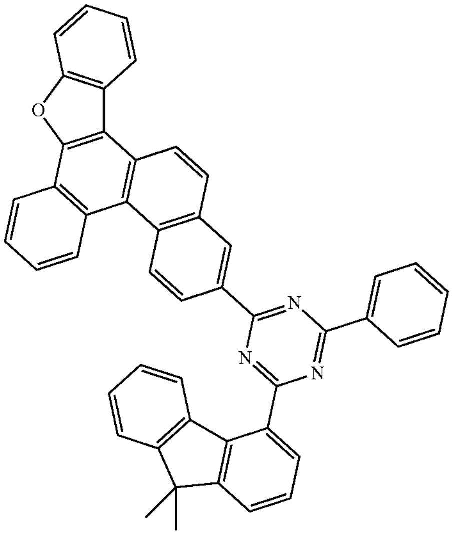
C-346
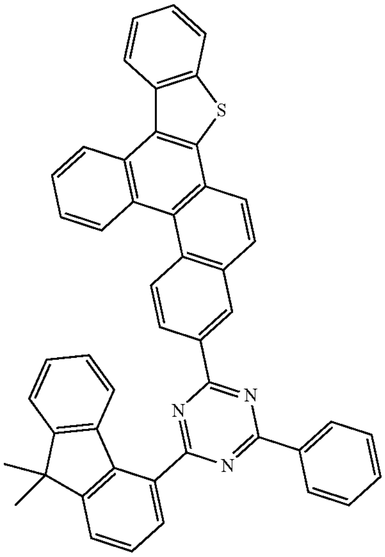

-continued
C-347
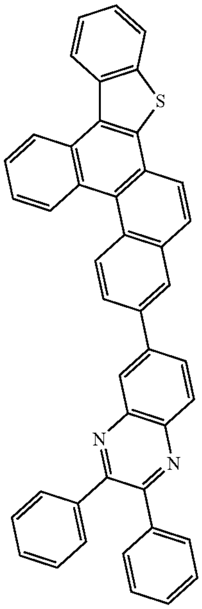
C-348
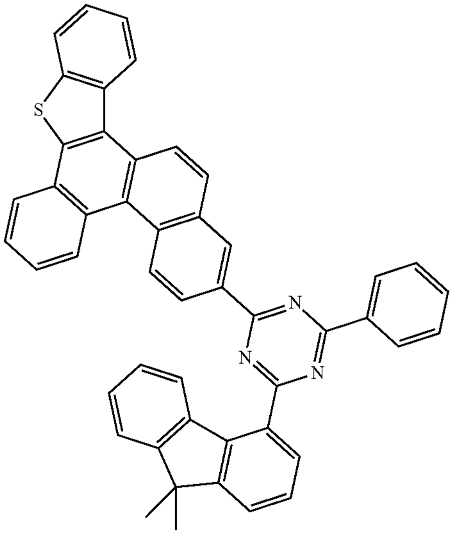
-continued
C-349
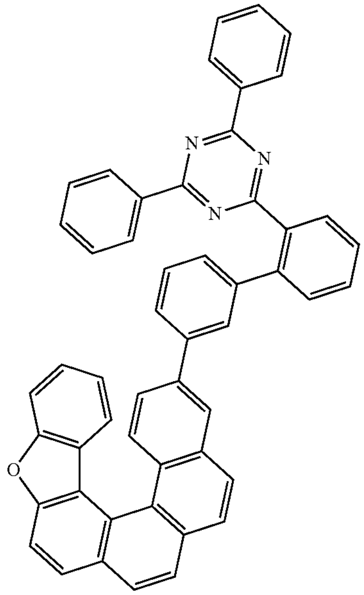
C-350
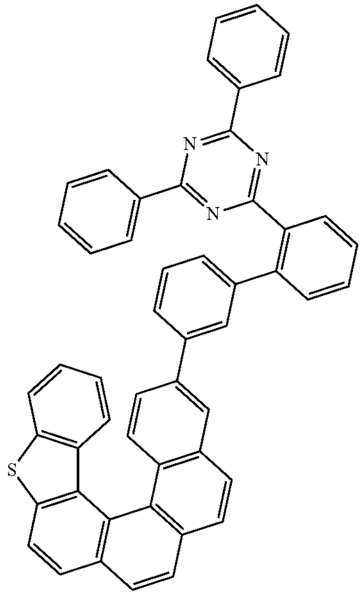
C-351
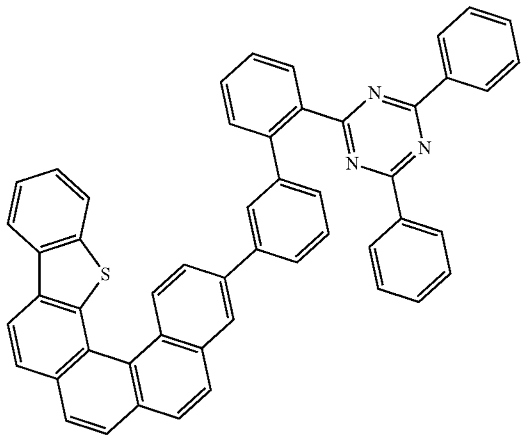

-continued
C-352
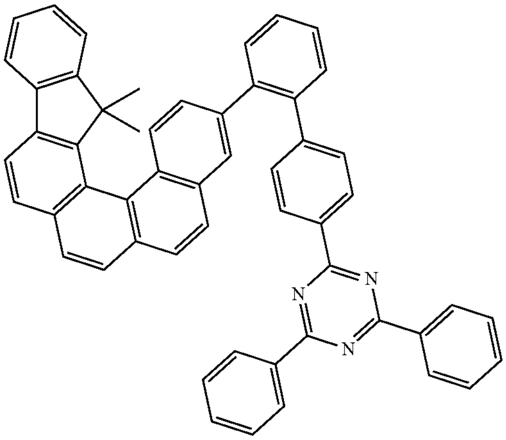
C-353
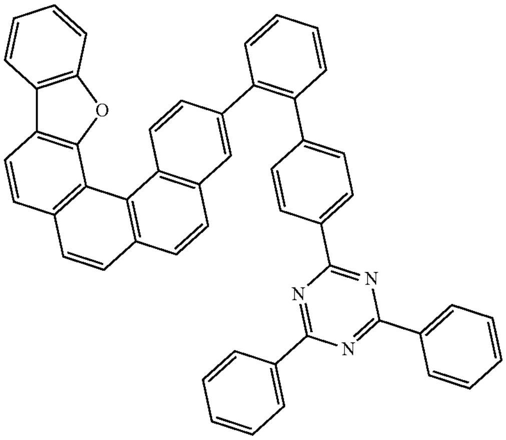
C-354
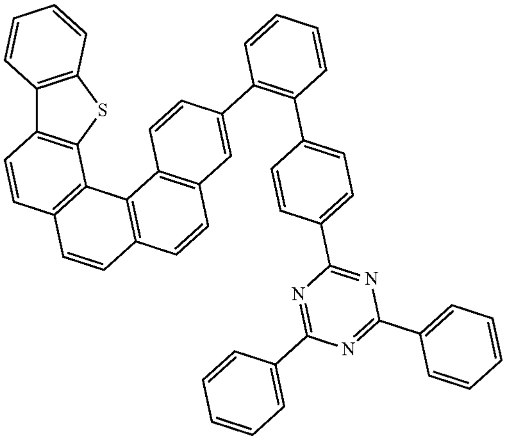
-continued
C-355
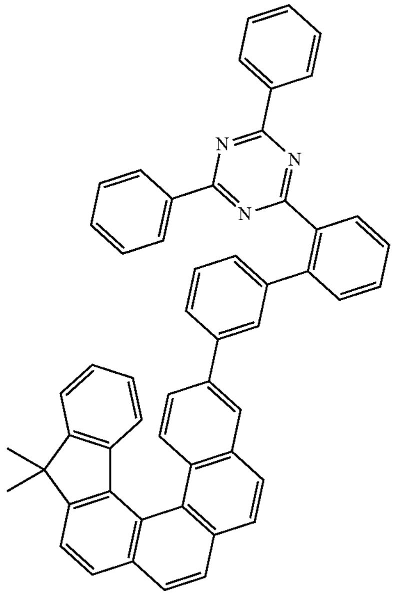
C-356
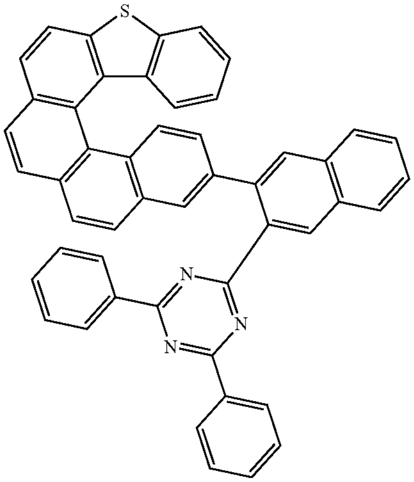
C-357
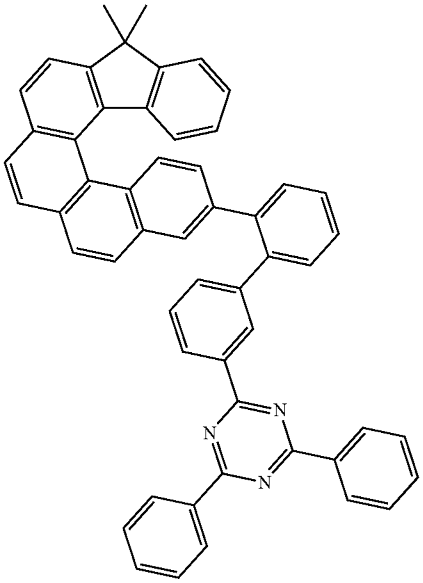

-continued
C-358
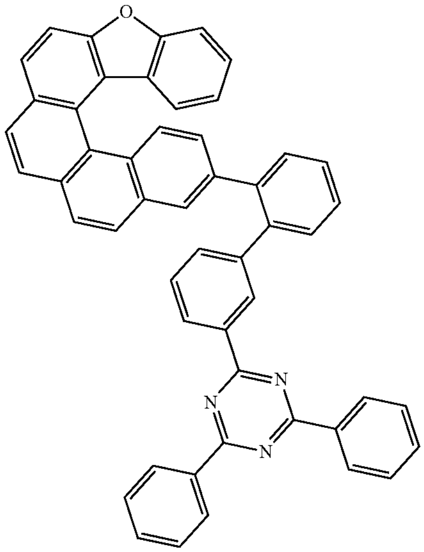
C-359
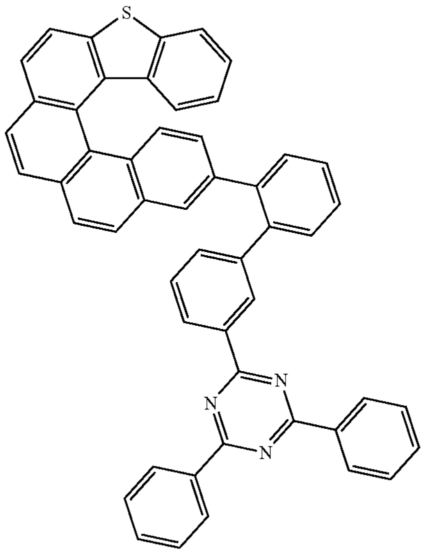
C-360
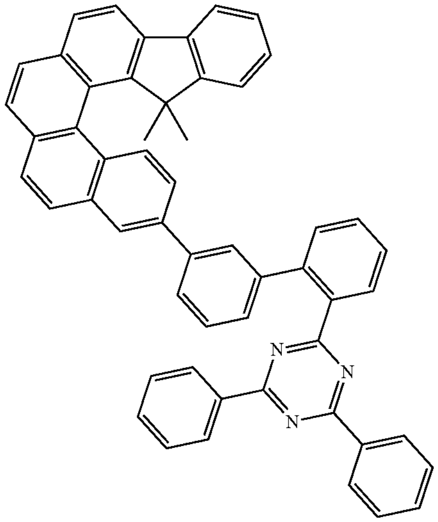
-continued
C-361
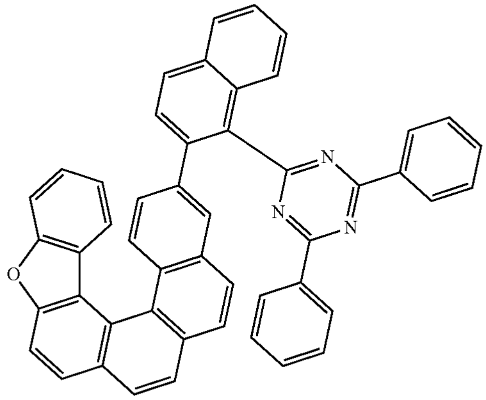
C-362
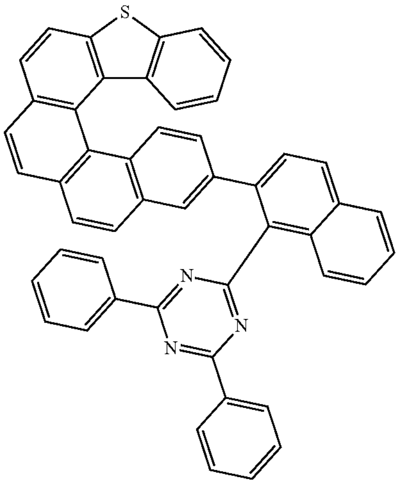
C-363
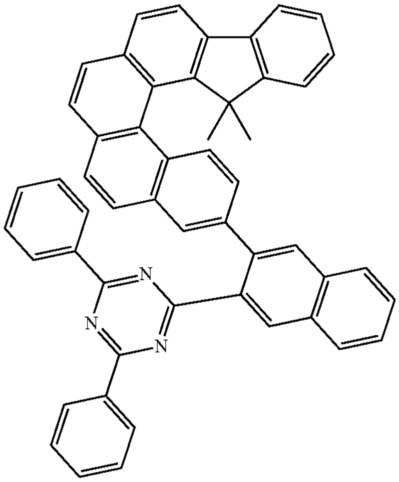

-continued
C-364
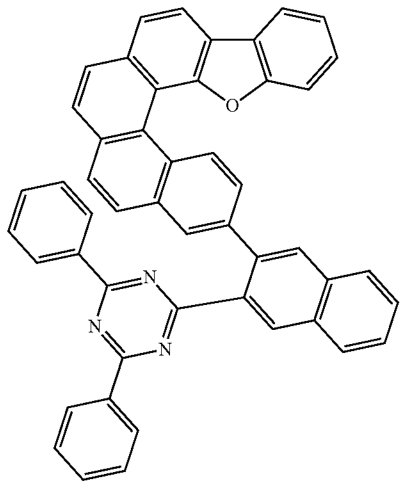
C-365
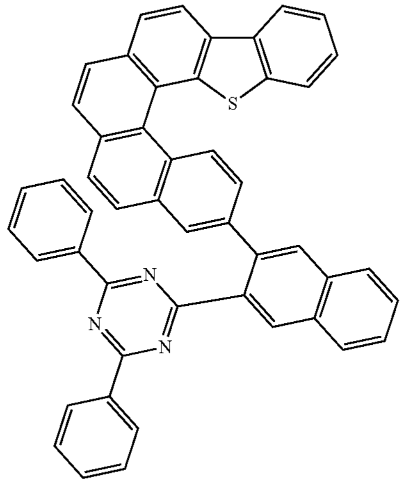
C-366
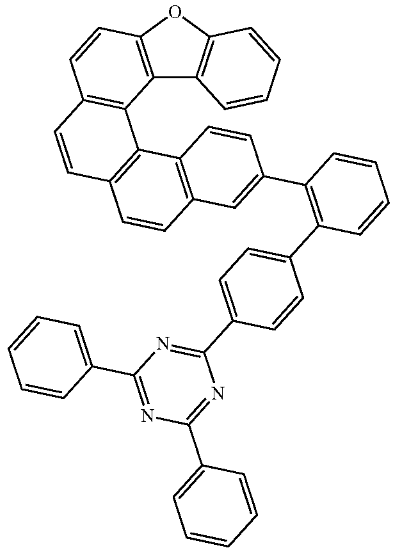
-continued
C-367
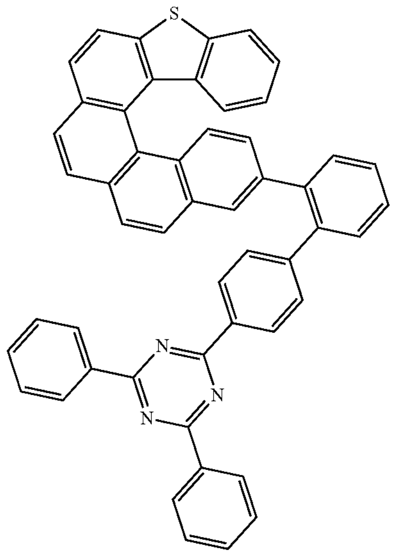
C-368
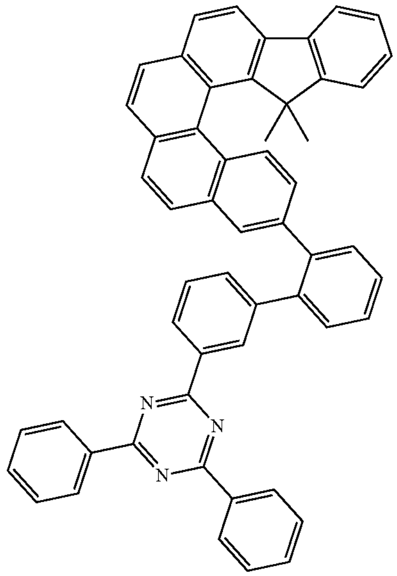

-continued
C-369
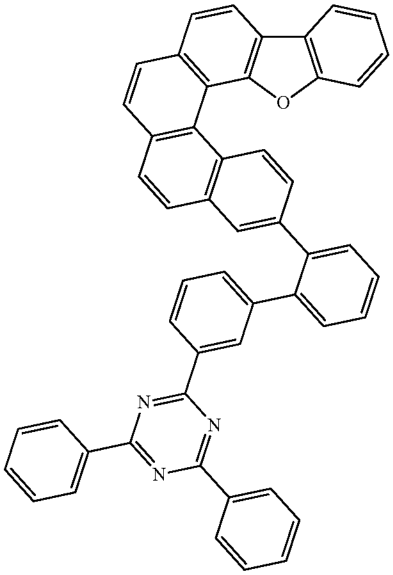
C-370
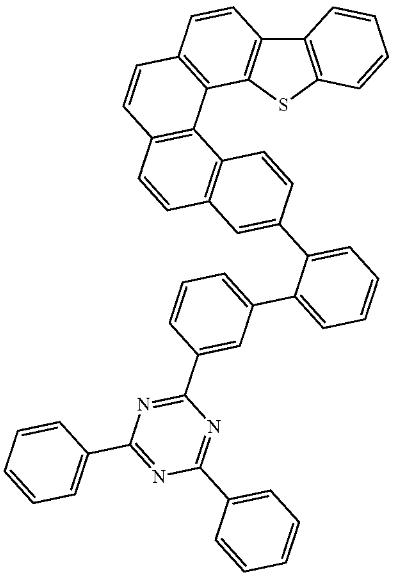
C-371
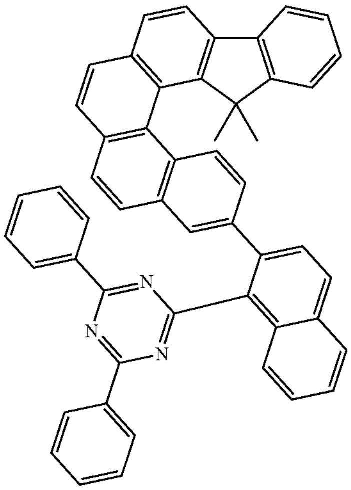
-continued
C-372
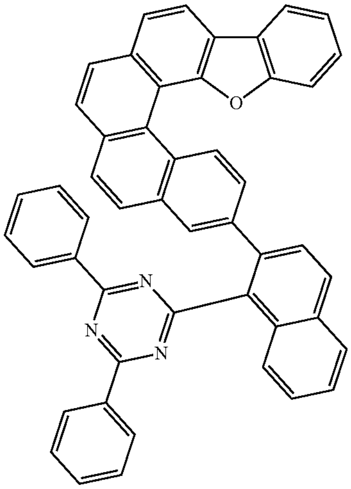
C-373
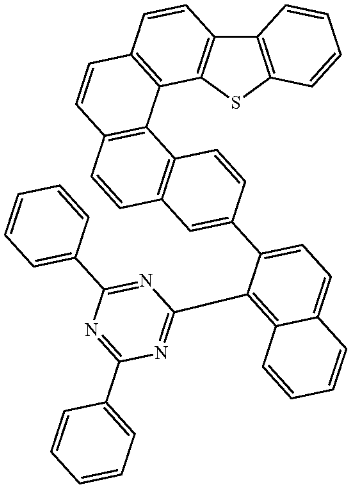
C-374
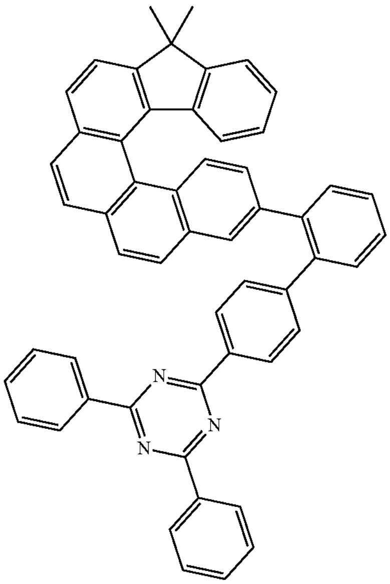

-continued
C-375
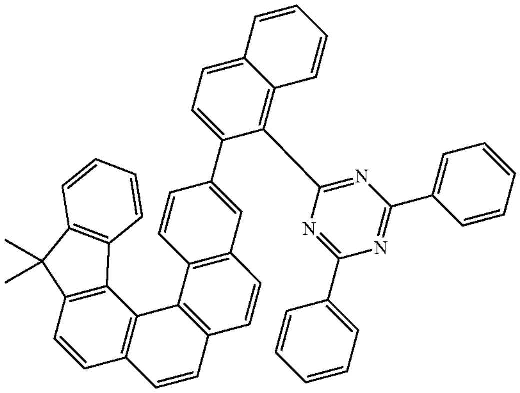
C-376
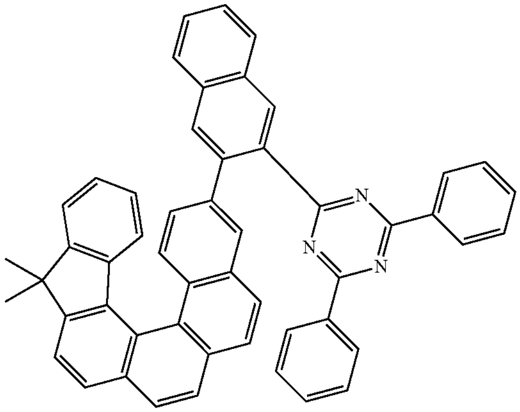
C-377
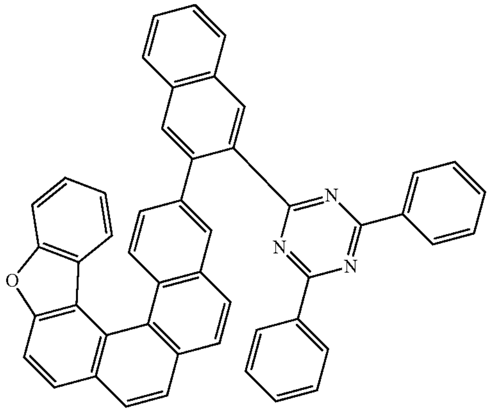
-continued
C-378
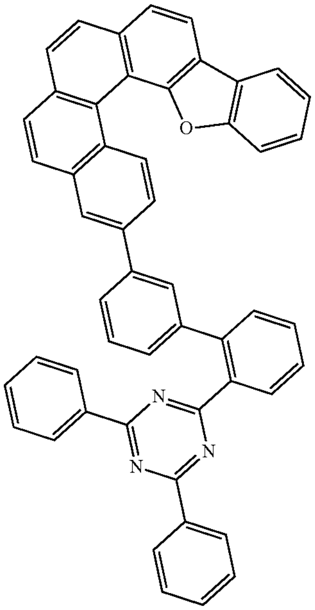
C-379
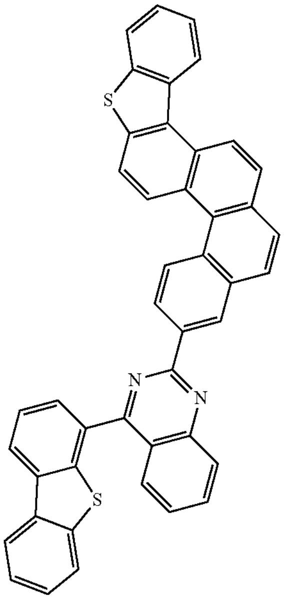

-continued
C-380
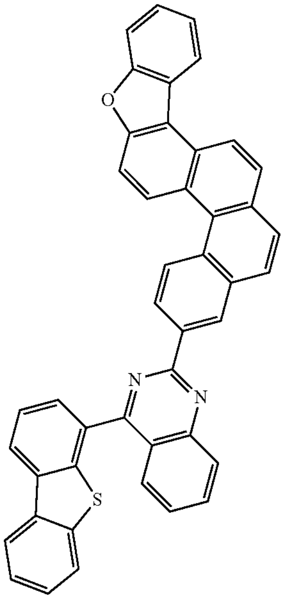
C-381
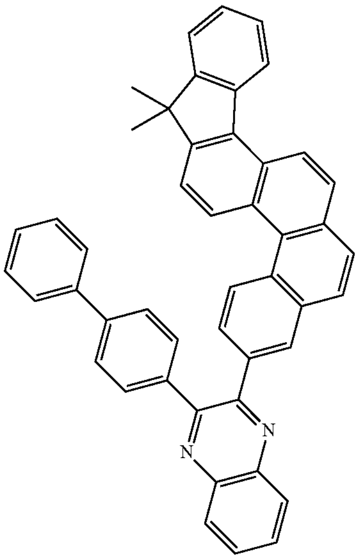
-continued
C-382
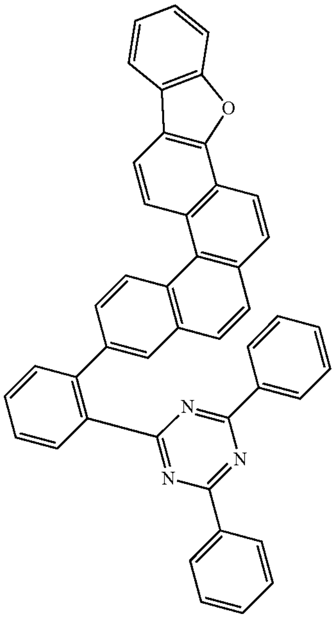
C-383
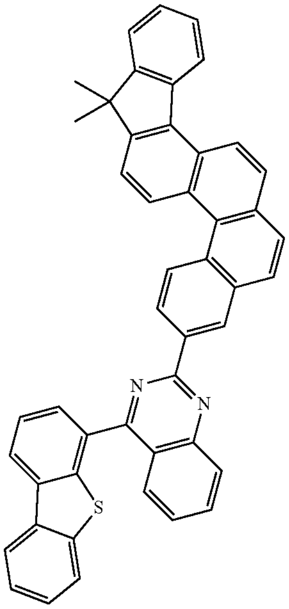

-continued
C-384
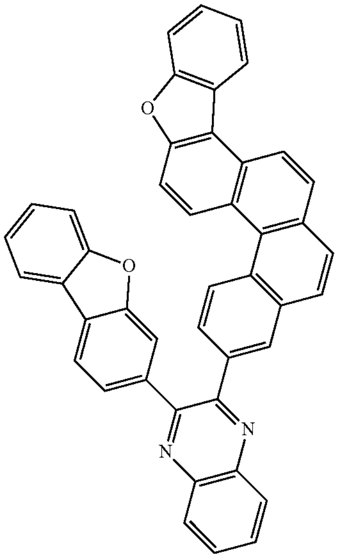
C-385
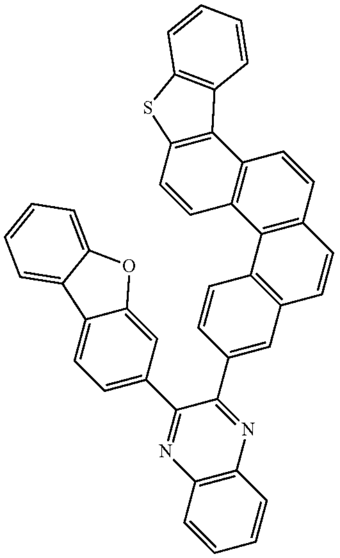
C-386
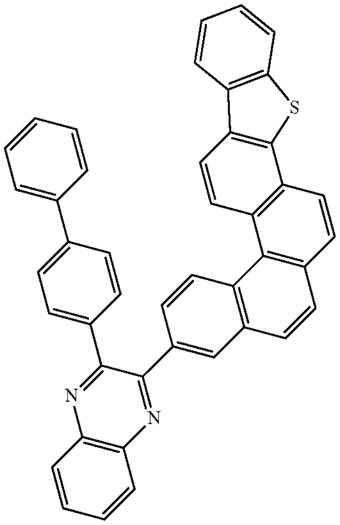
-continued
C-387
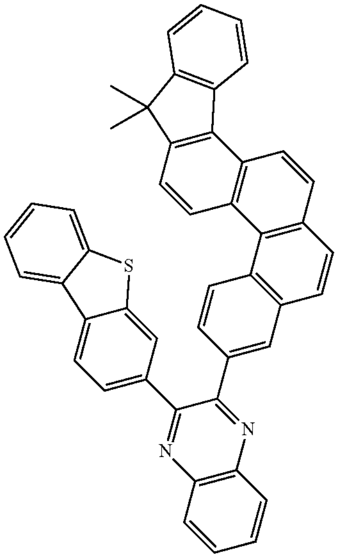
C-388
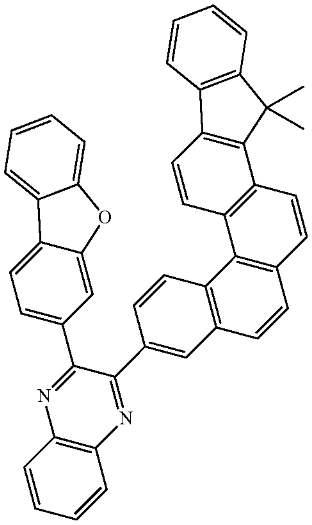
C-389
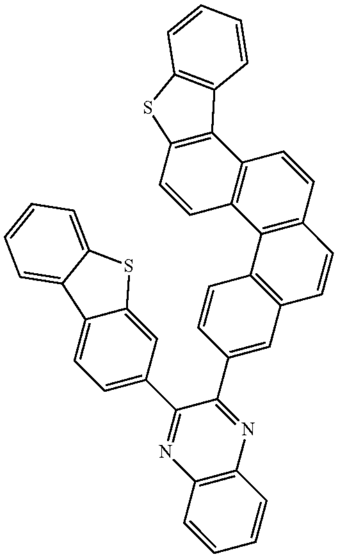

-continued
C-390
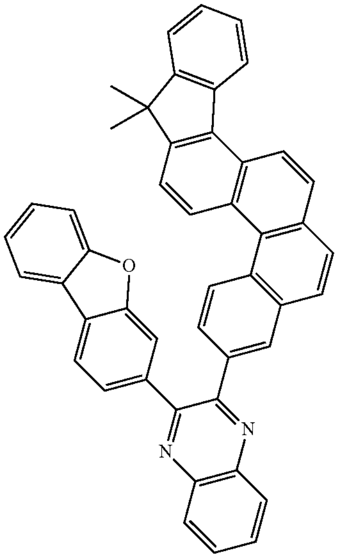
C-391
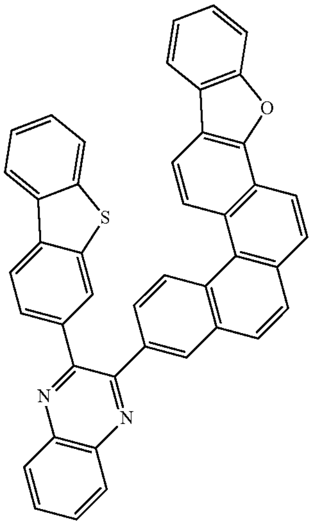
C-392
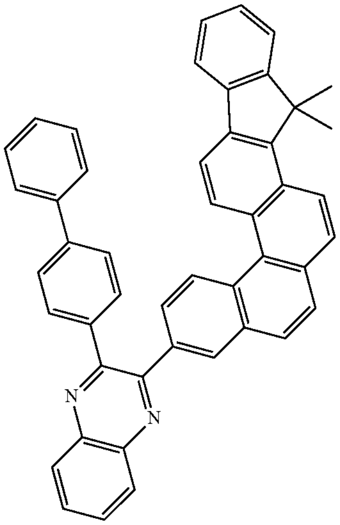
-continued
C-393
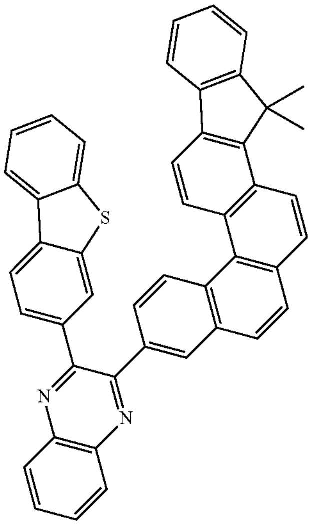
C-394
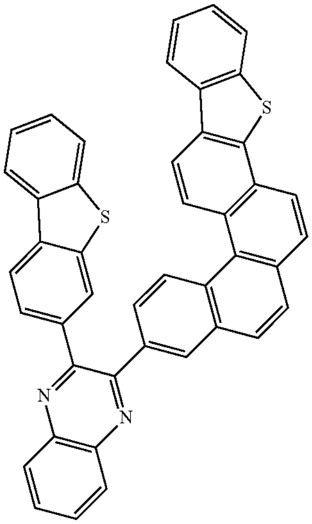
C-395
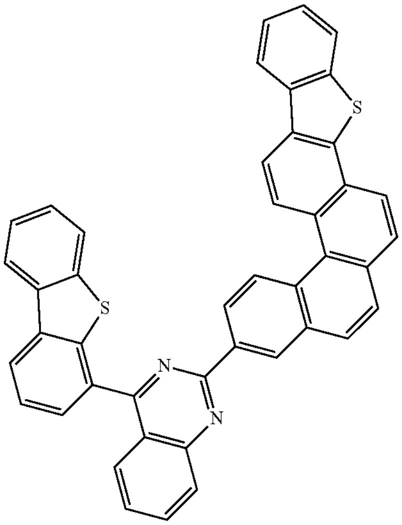

-continued
C-396
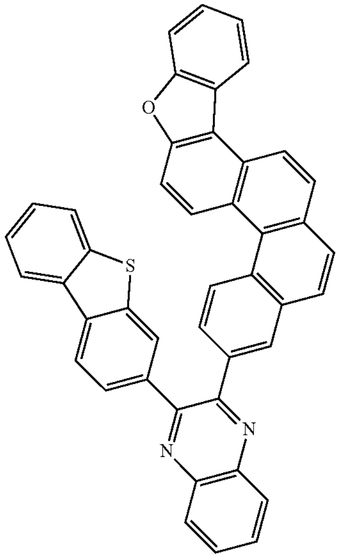
C-397
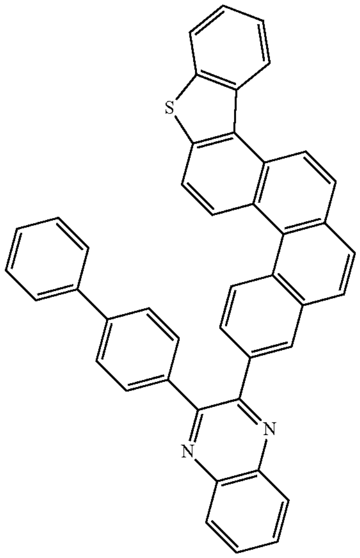
C-398
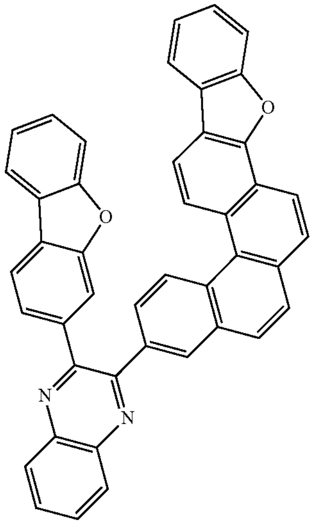
-continued
C-399
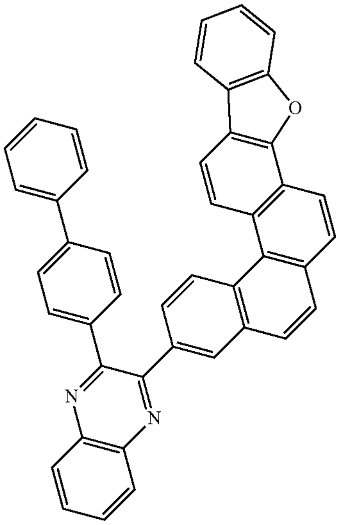
C-400
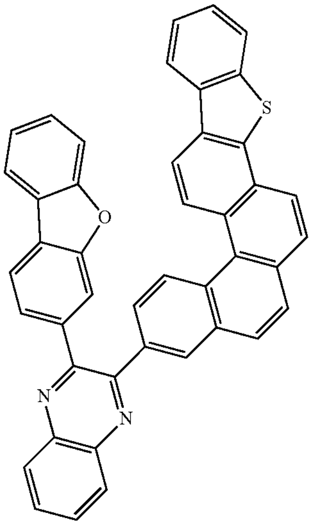
C-401
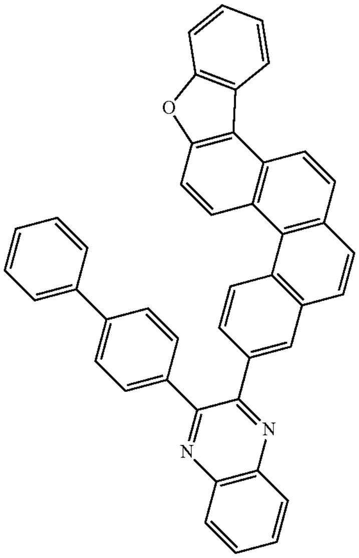

-continued
C-402
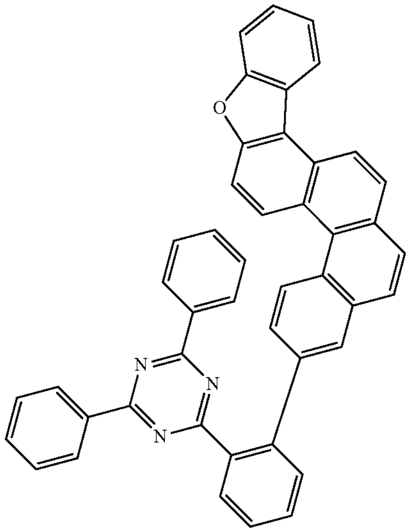
C-403
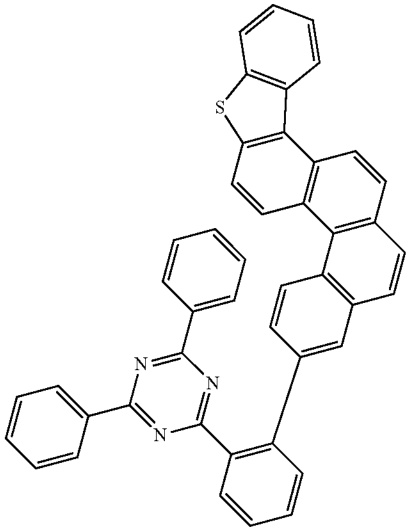
C-404
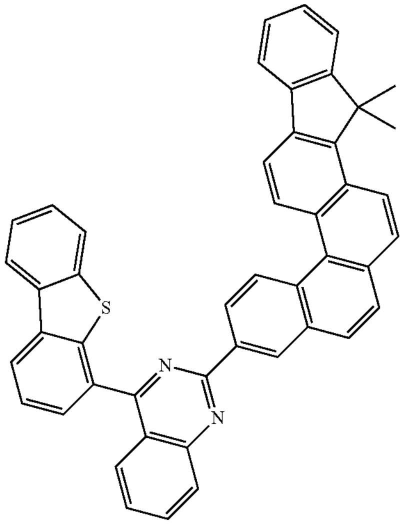
-continued
C-405
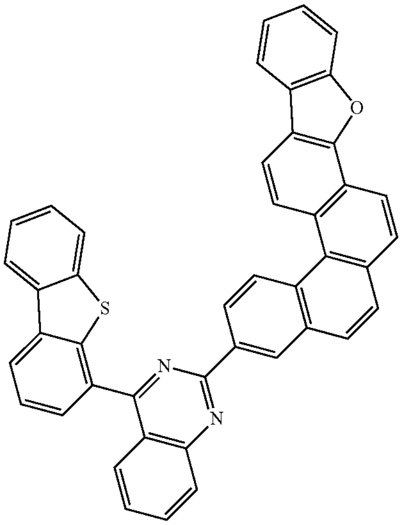
C-406
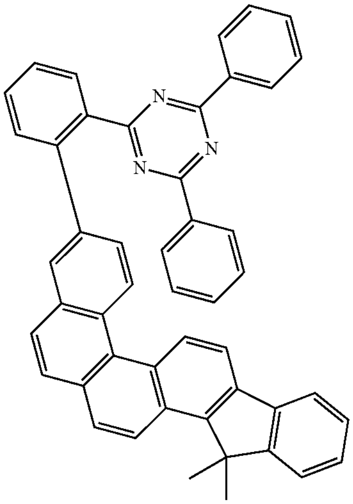
C-407
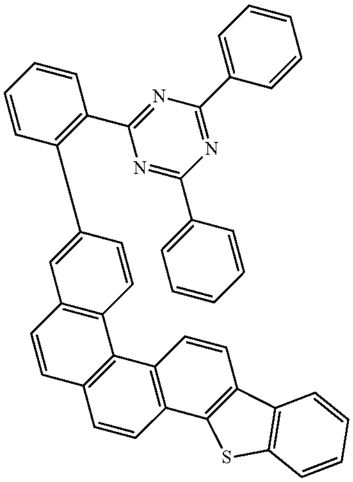

-continued
C-408
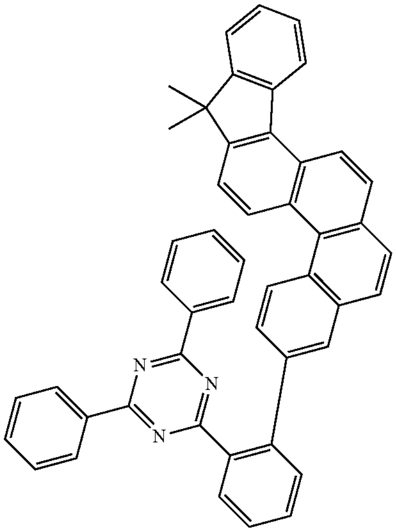
C-409
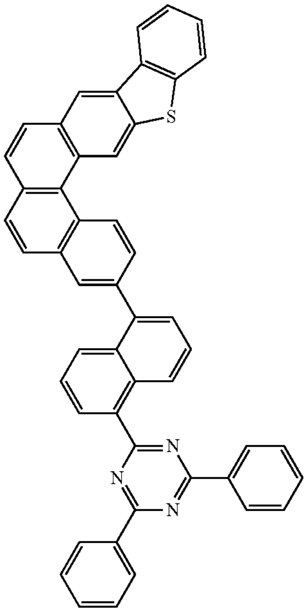
-continued
C-410
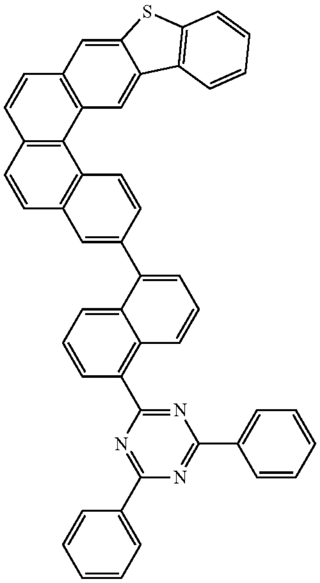
C-411
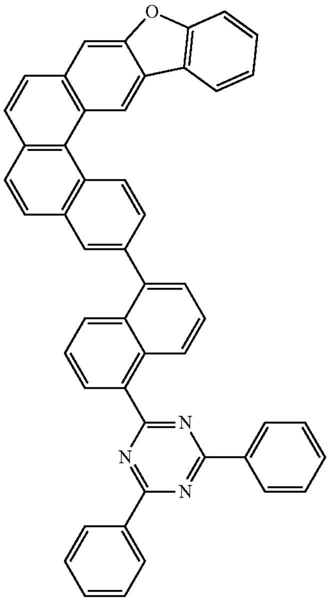

-continued
C-412
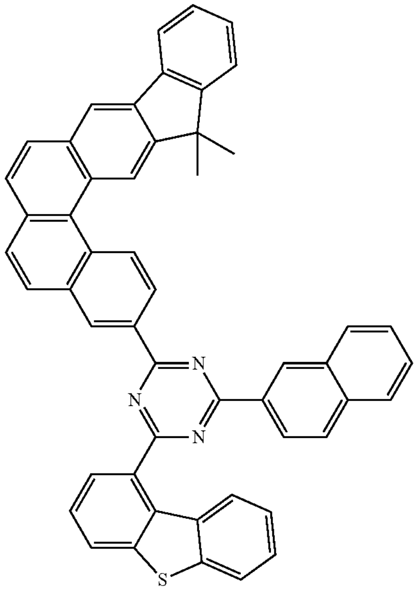
C-413
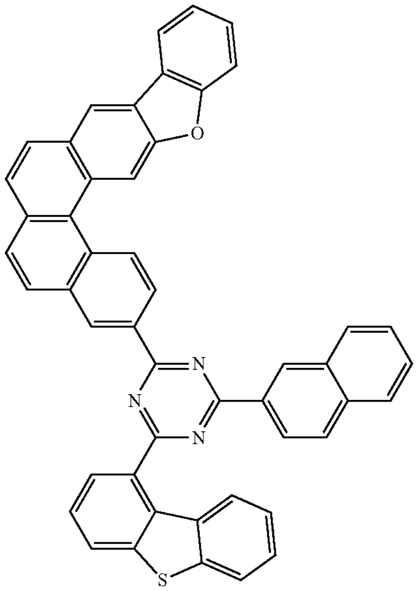
-continued
C-414
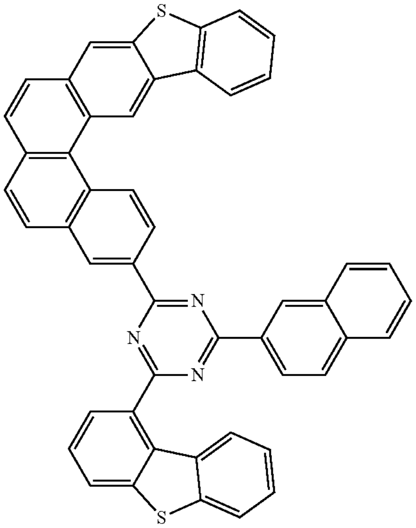
C-415
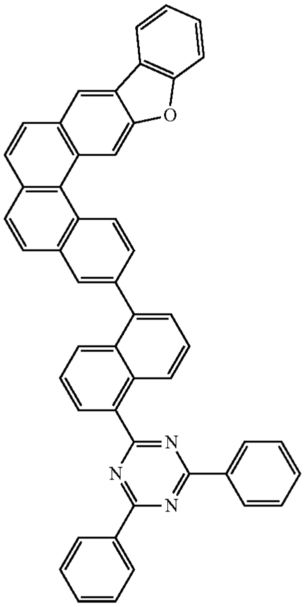

-continued
C-416
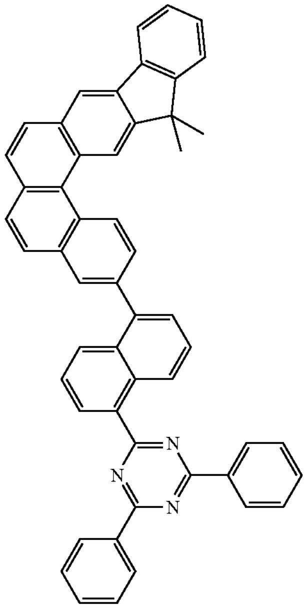
C-417
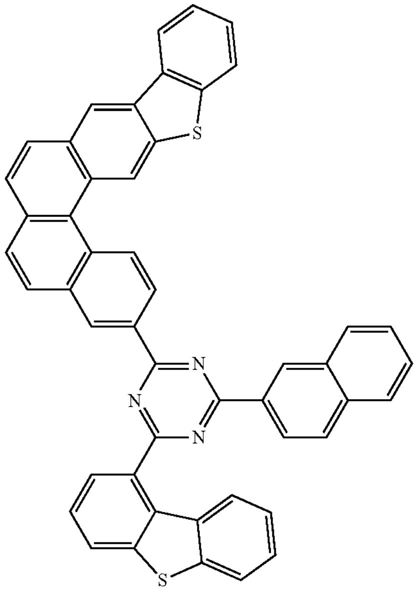
-continued
C-418
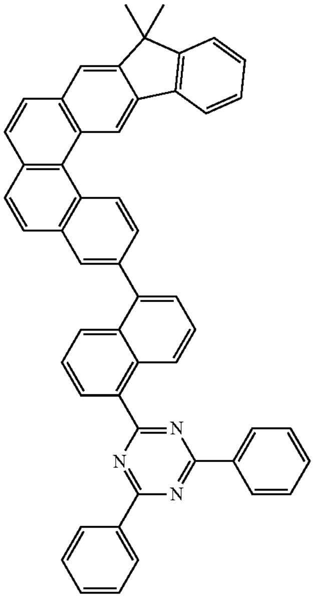
C-419
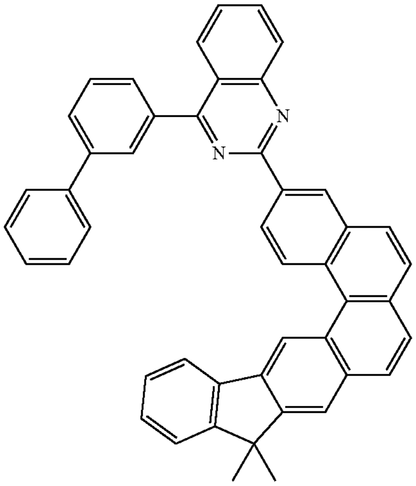
C-420
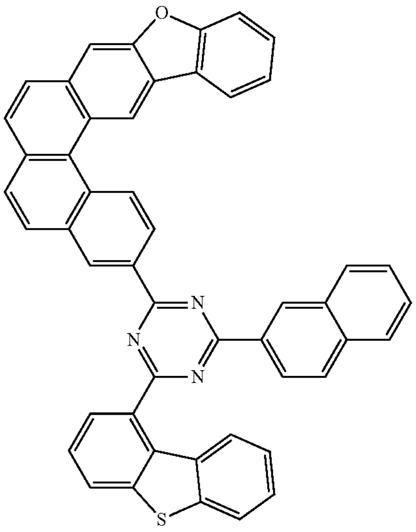

-continued
C-421
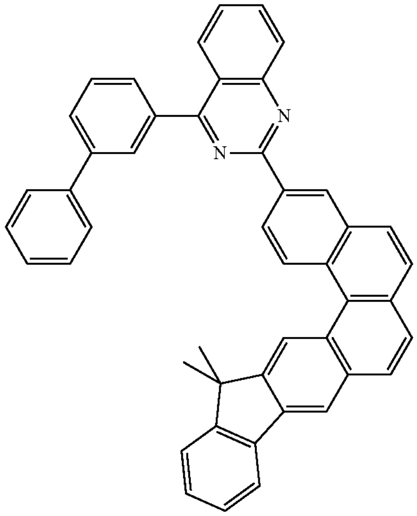
C-422
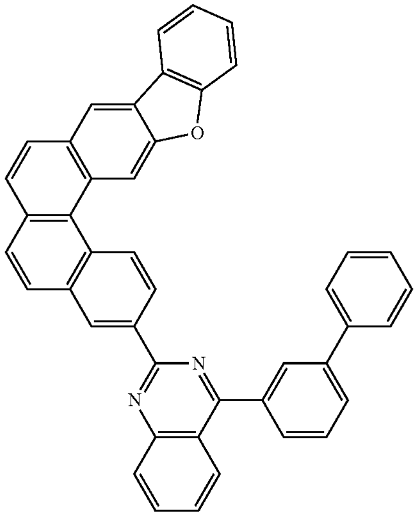
C-423
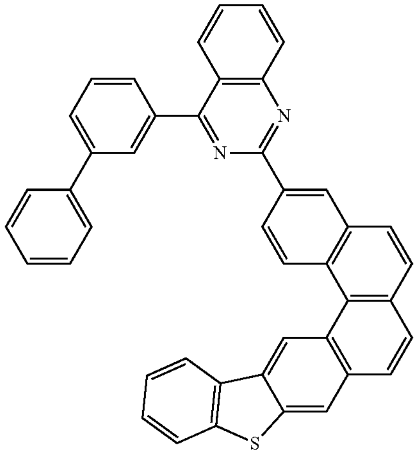
-continued
C-424
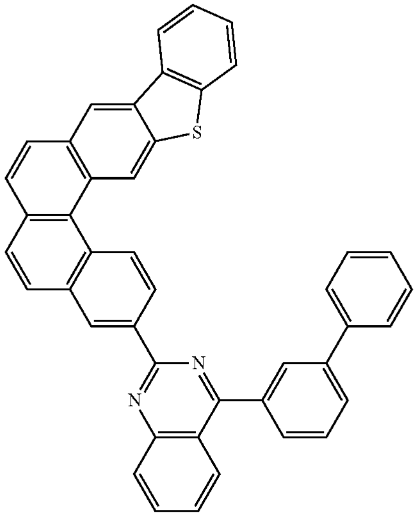
C-425
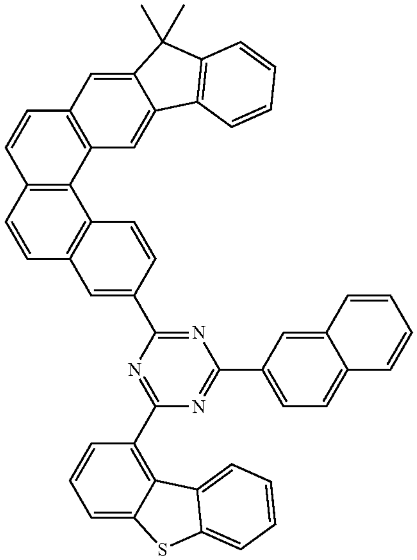
C-426
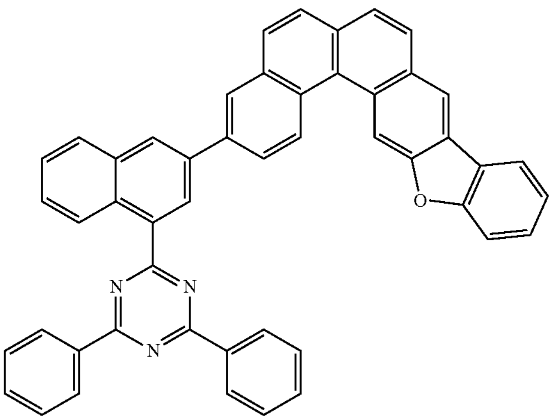

-continued
C-427
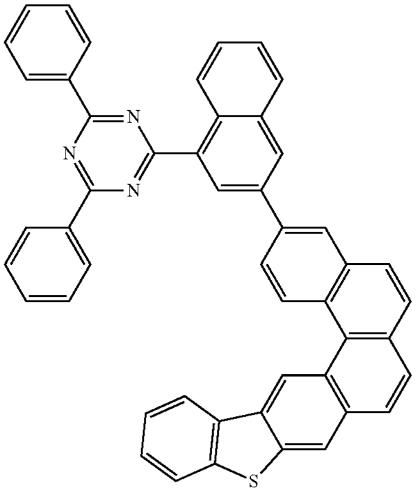
C-428
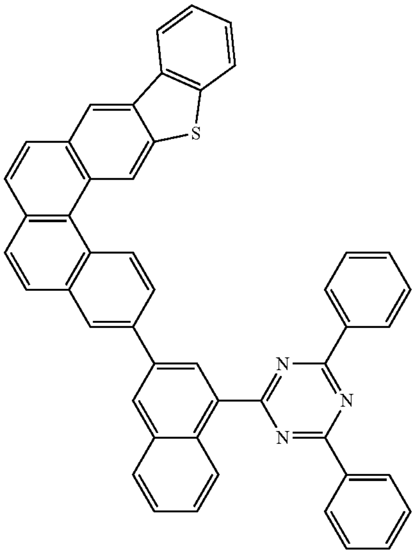
C-429
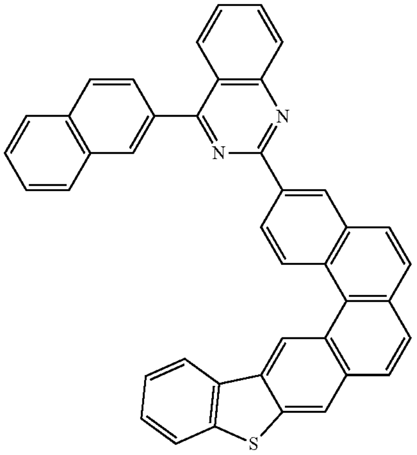
-continued
C-430
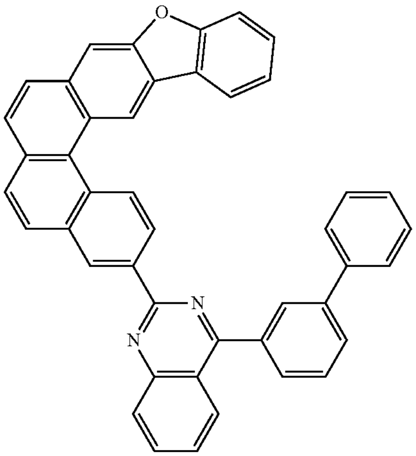
C-431
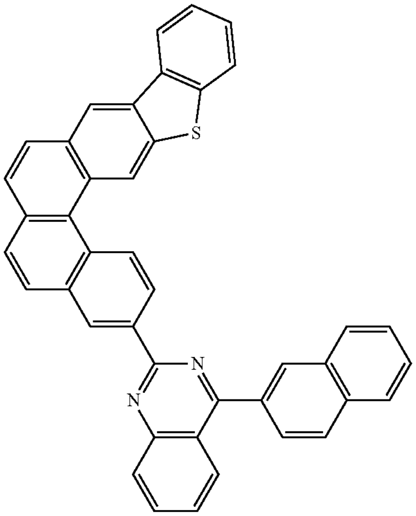
C-432
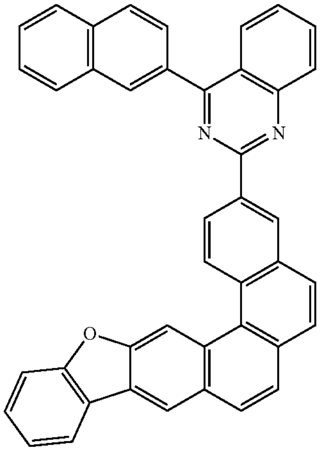

-continued
C-433
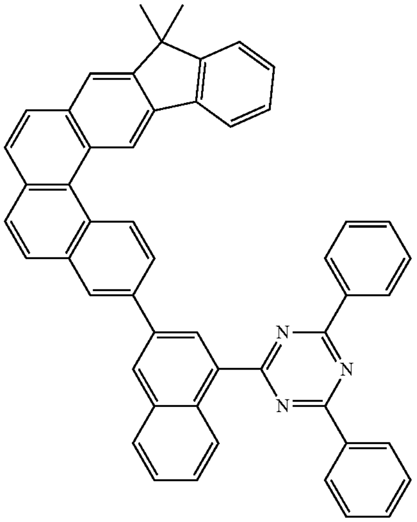
C-434
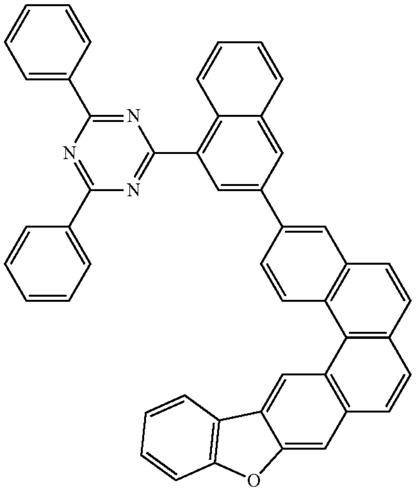
C-435
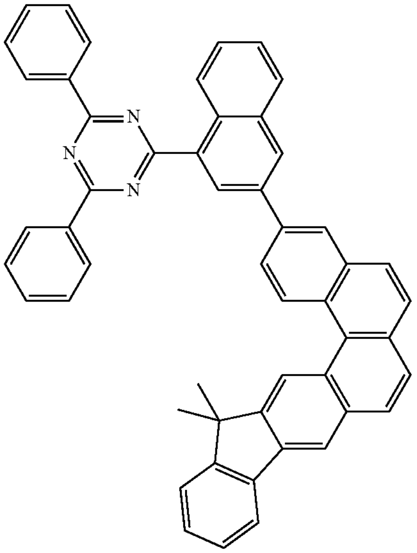
-continued
C-436
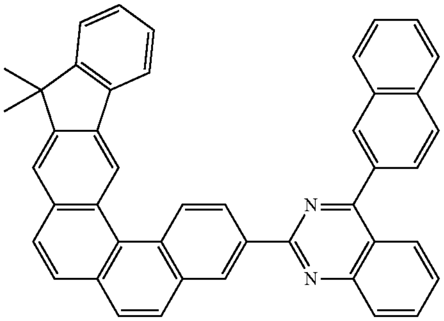
C-437
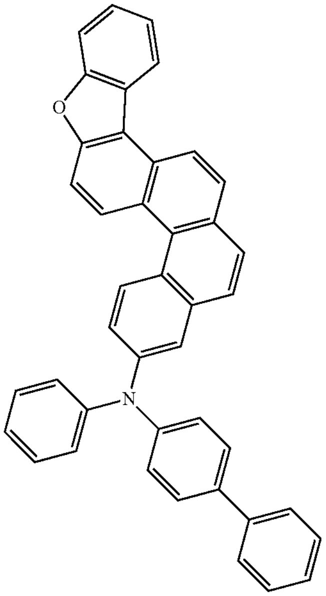
C-438
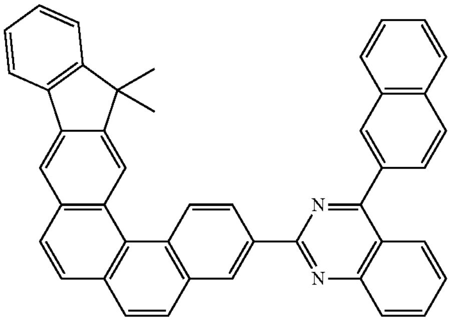

-continued
C-439
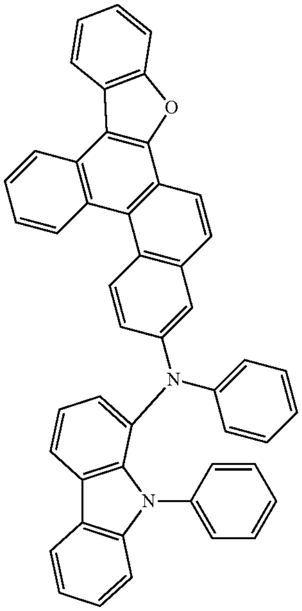
C-440
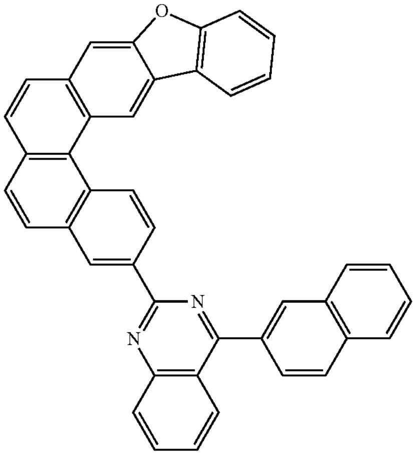
C-441
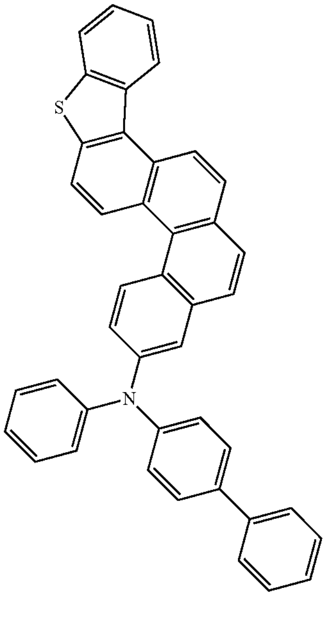
-continued
C-442
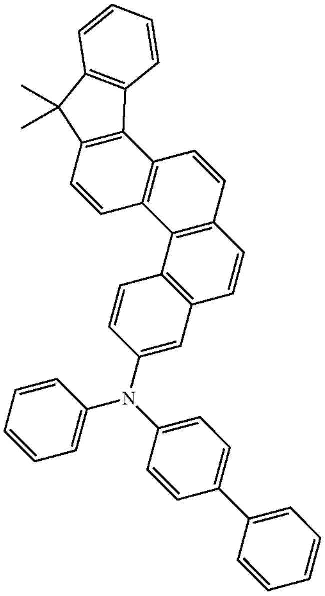
C-443
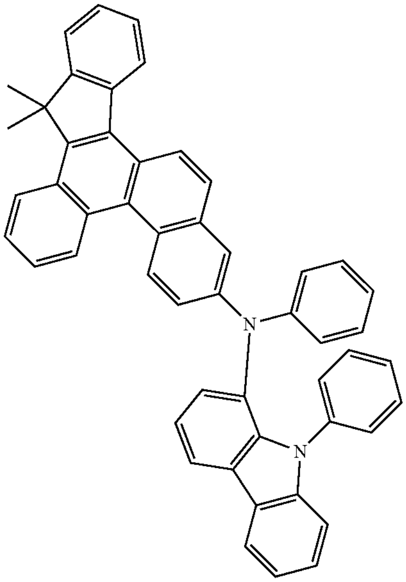

-continued
C-444
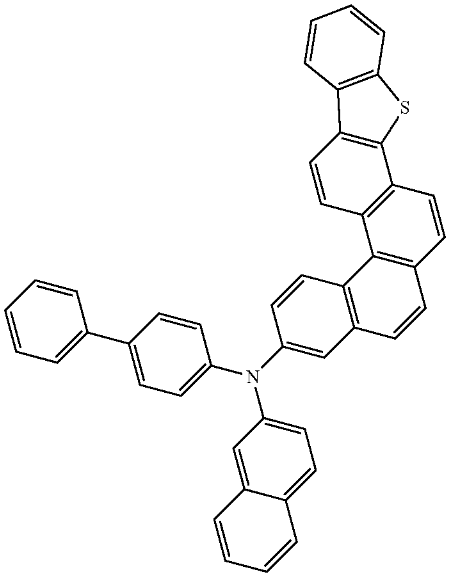
C-445
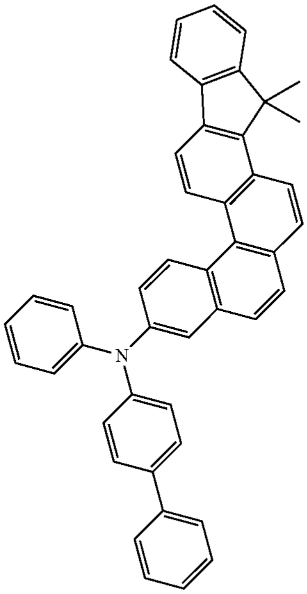
-continued
C-446
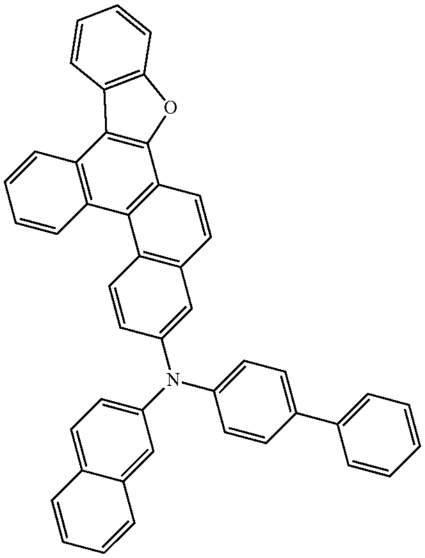
C-447
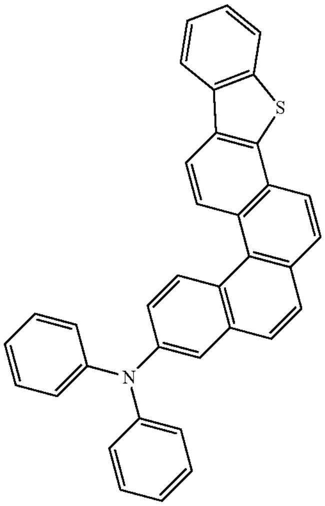
C-448
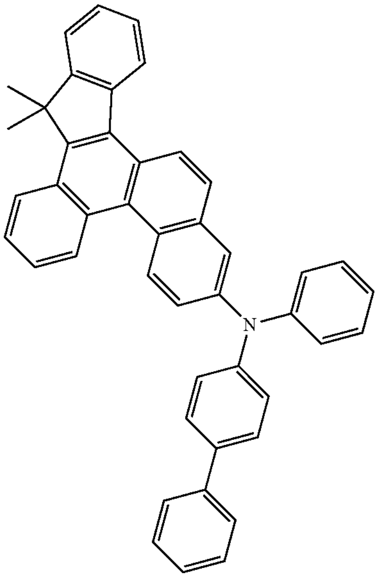

-continued
C-449
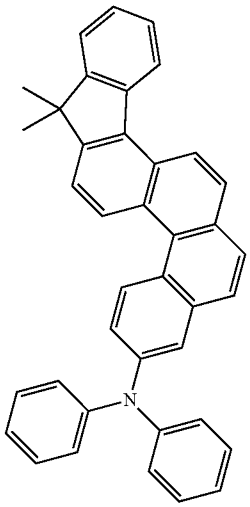
C-450
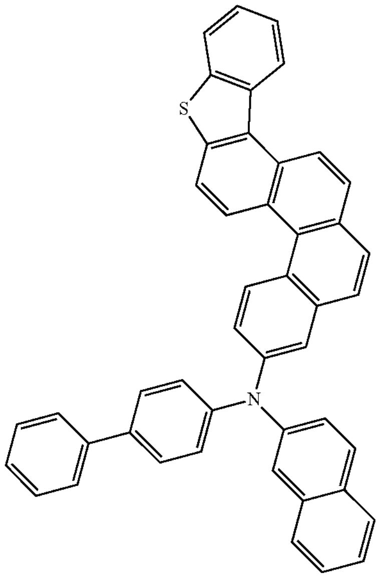
C-451
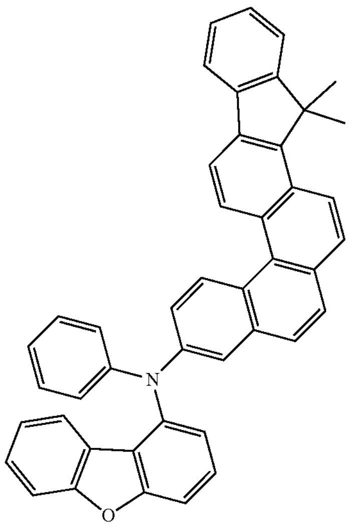
-continued
C-452
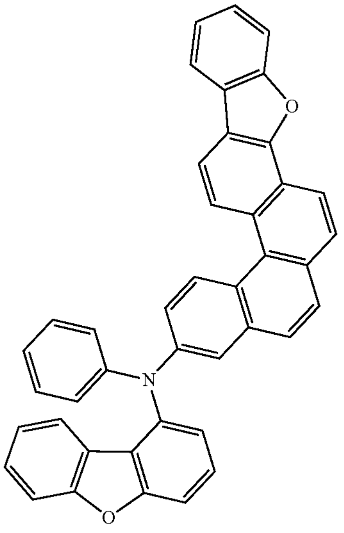
C-453
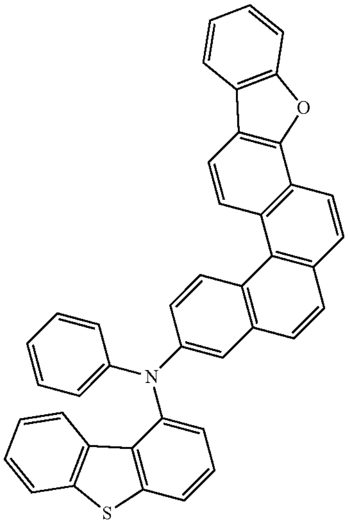
C-454
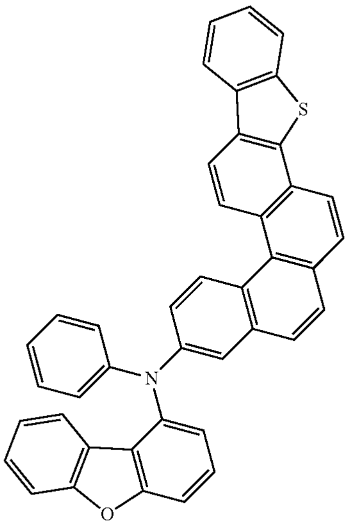

-continued
C-455
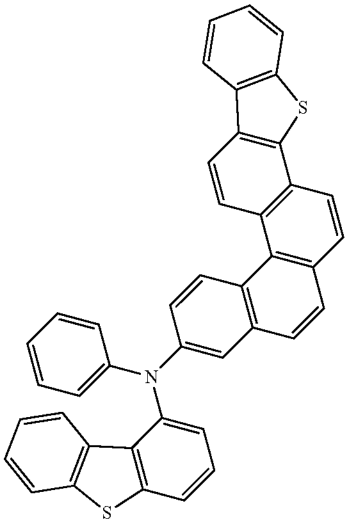
C-456
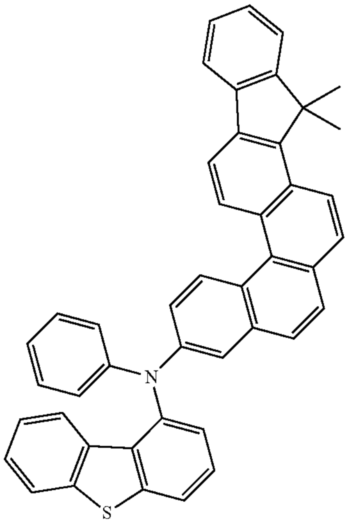
C-457
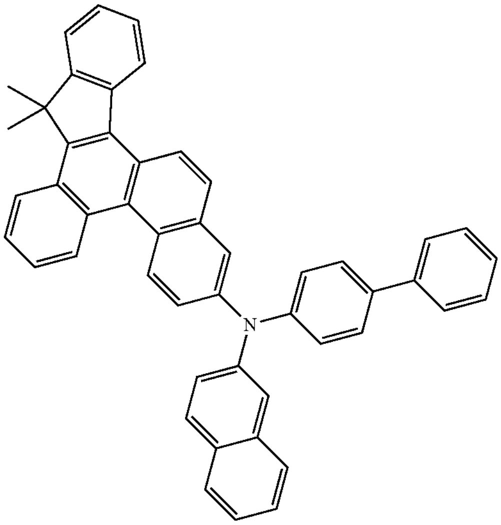
-continued
C-458
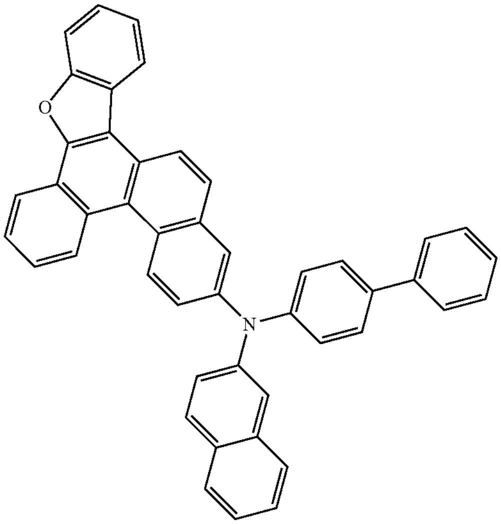
C-459
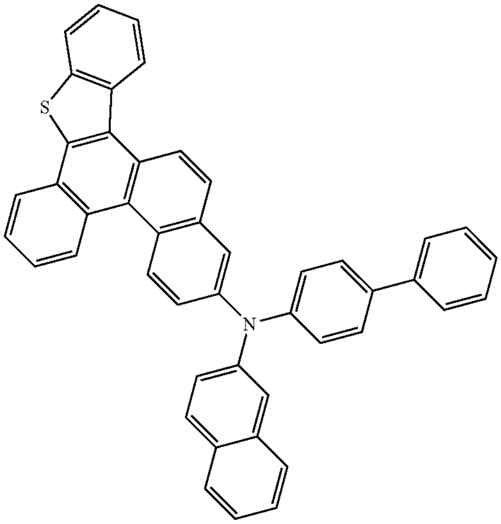
C-460
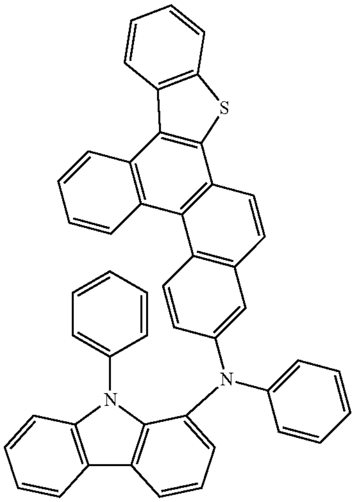

-continued
C-461
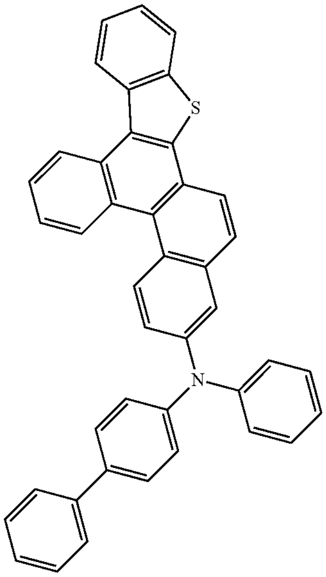
C-462
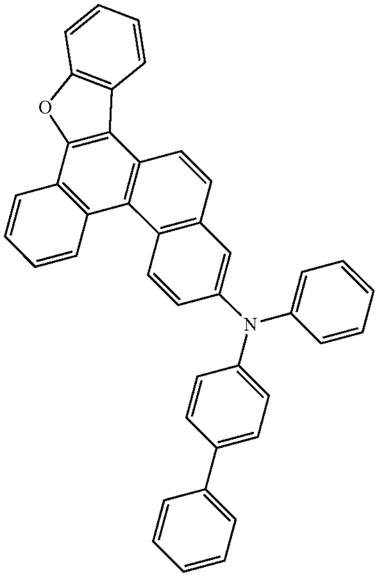
-continued
C-463
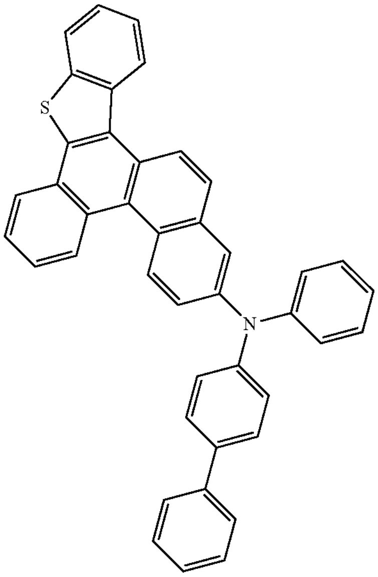
C-464
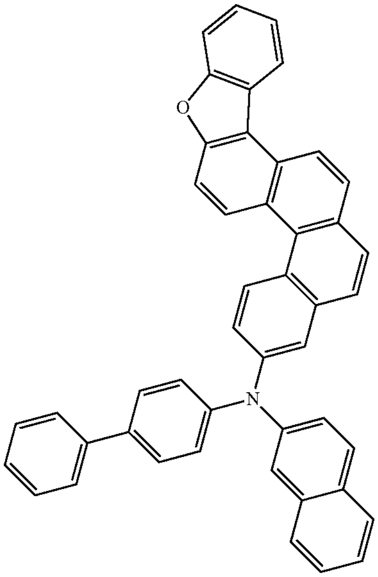

-continued
C-465
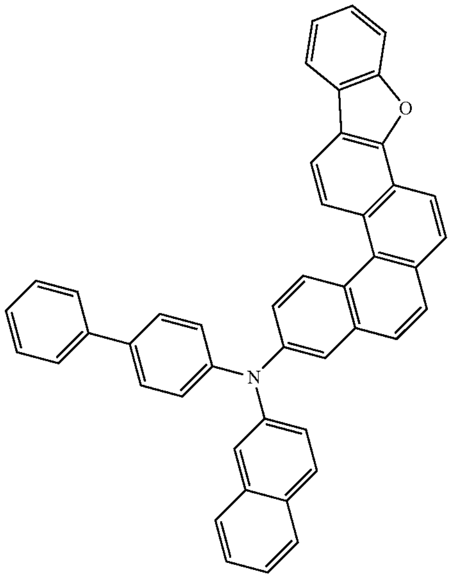
C-466
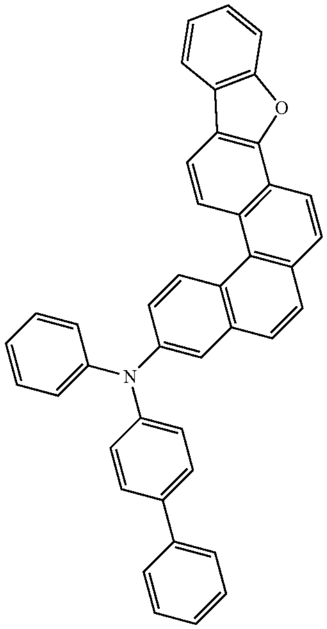
-continued
C-467
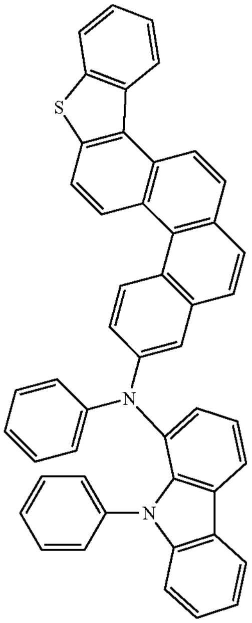
C-468
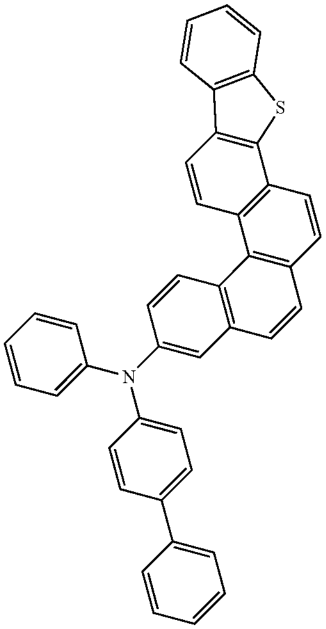

-continued
C-469
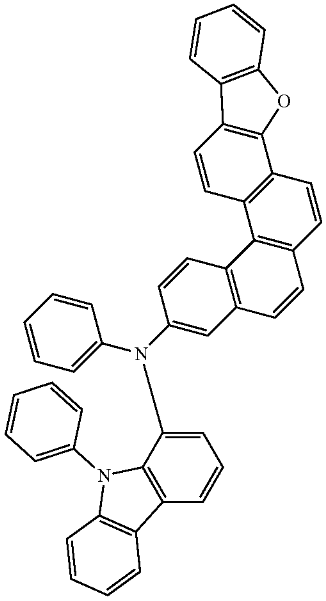
C-470
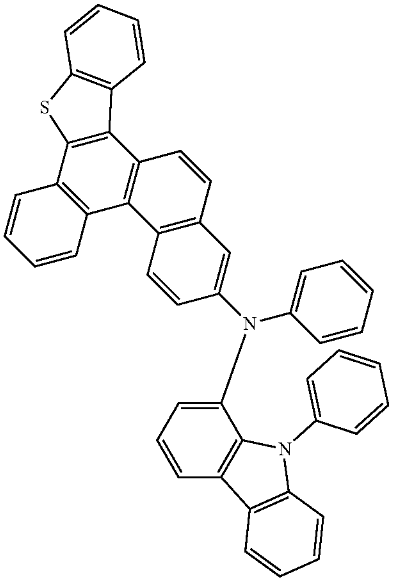
-continued
C-471
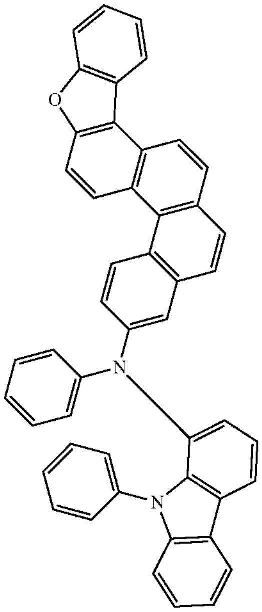
C-472
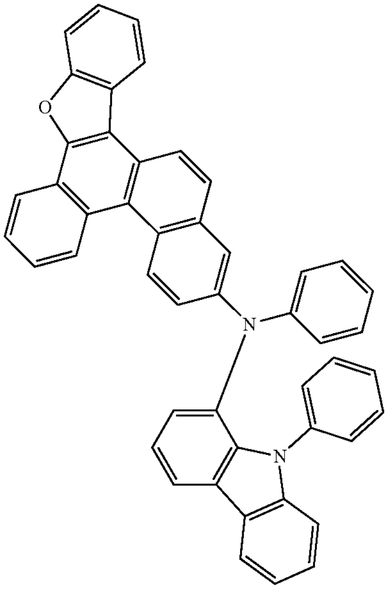

-continued
C-473
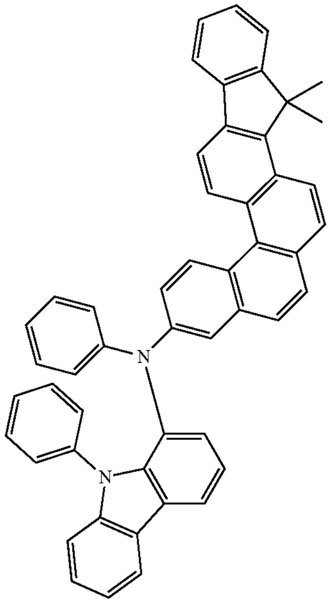
C-474
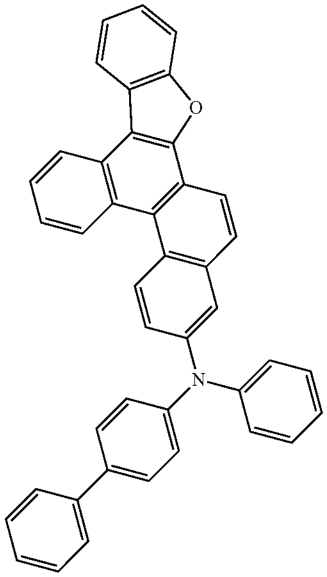
-continued
C-475
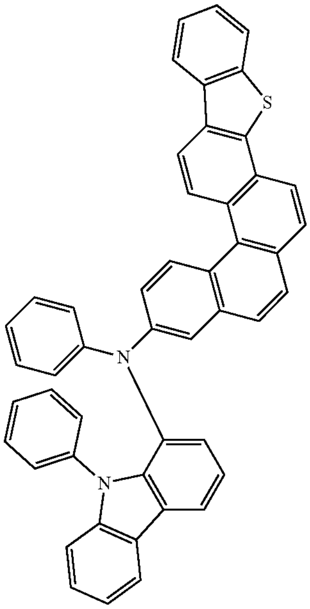
C-476
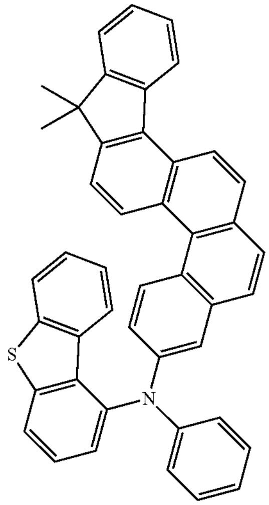
C-477
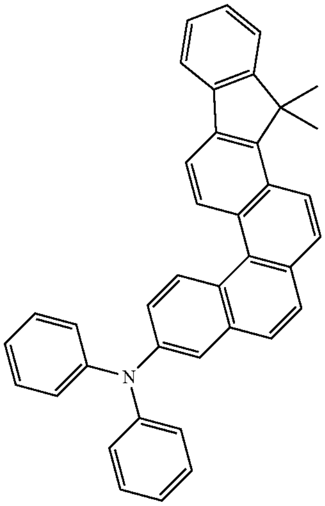

-continued
C-478
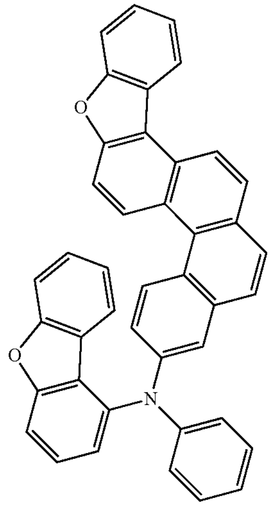
C-479
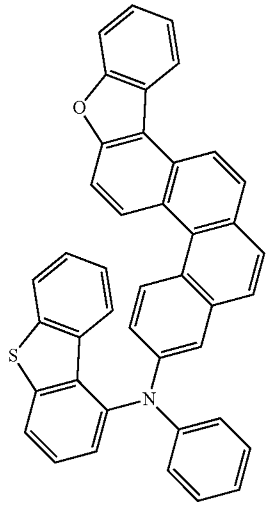
C-480
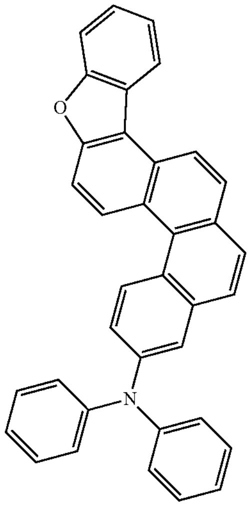
-continued
C-481
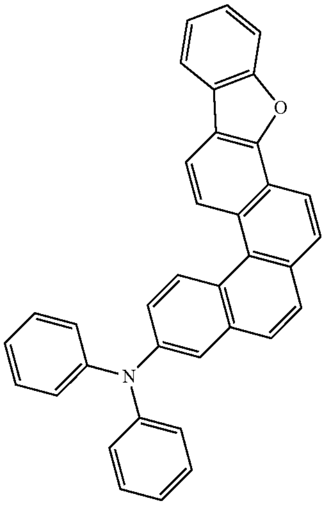
C-482
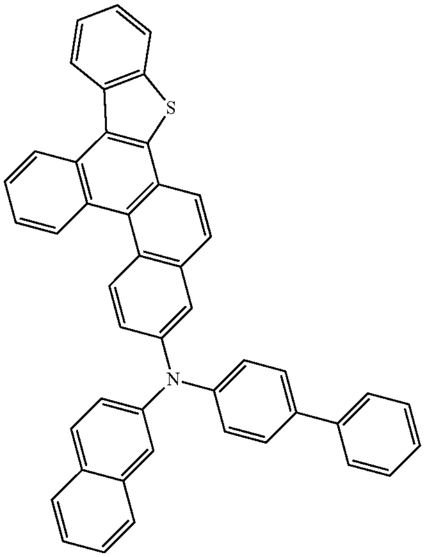
C-483
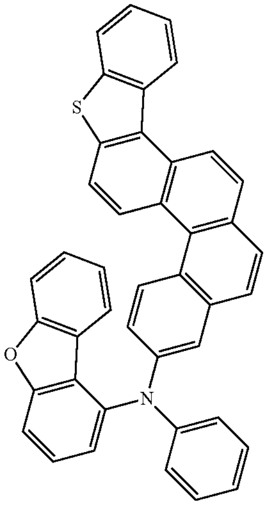

-continued
C-484
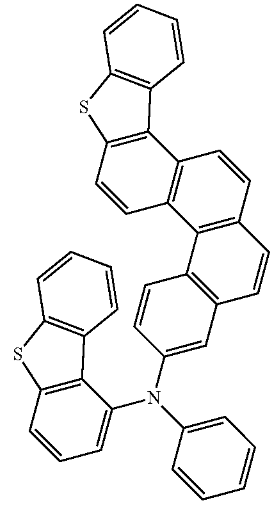
C-485
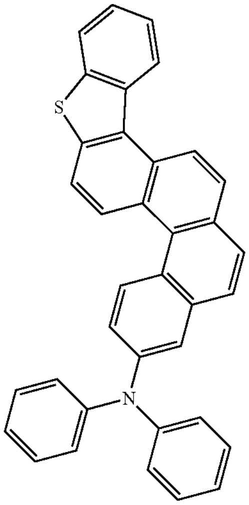
C-486
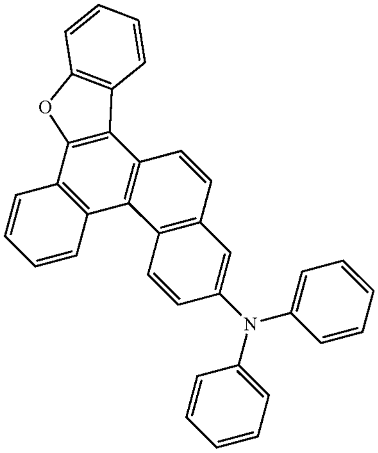
-continued
C-487
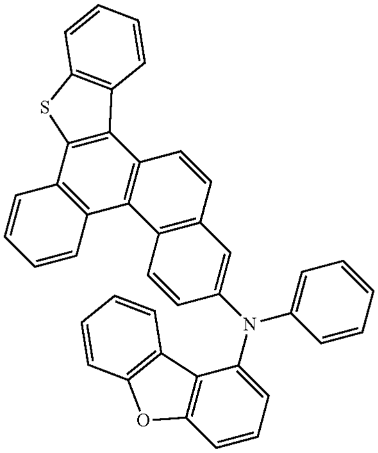
C-488
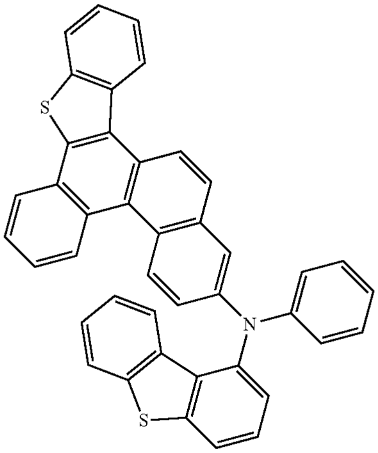
C-489
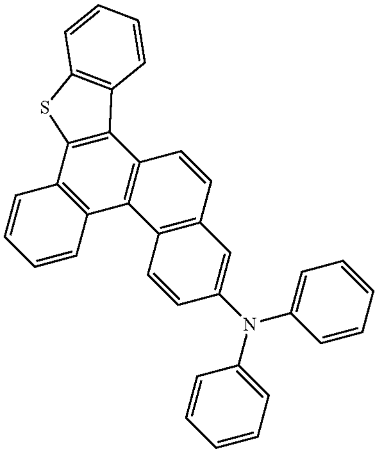

-continued
C-490
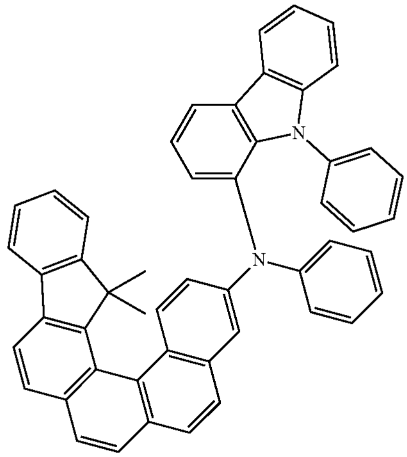
C-491
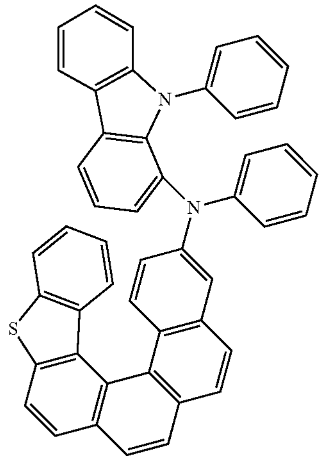
C-492
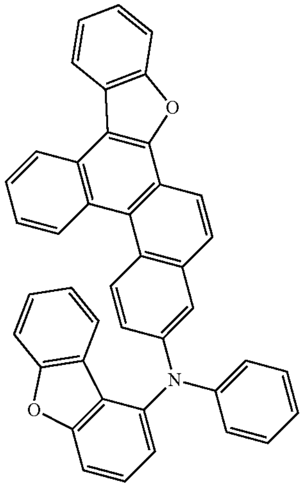
-continued
C-493
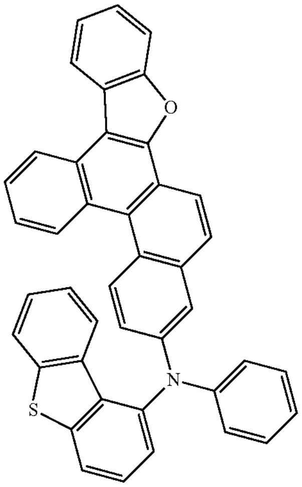
C-494
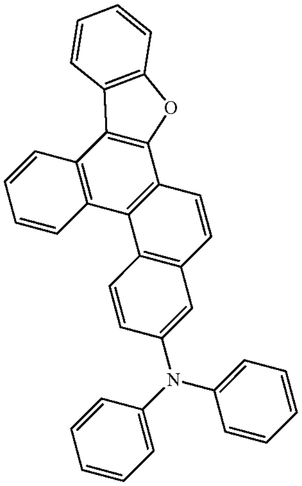
C-495
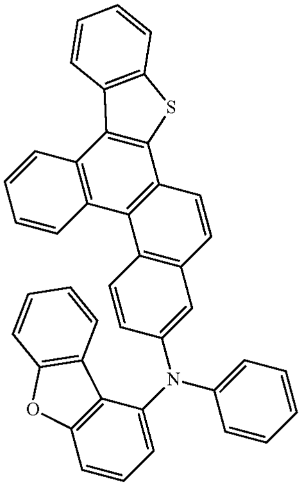

C-496
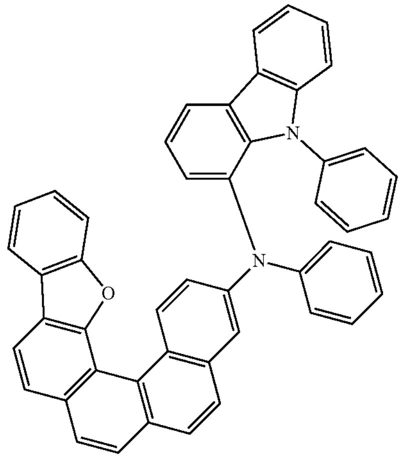
C-497
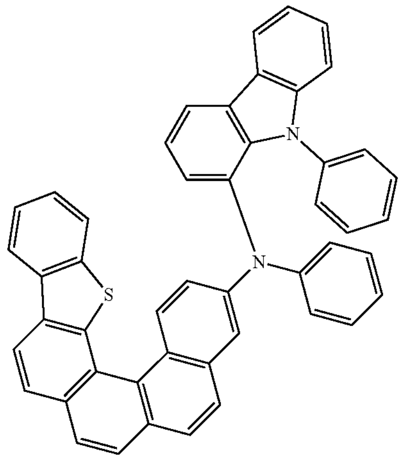
C-498
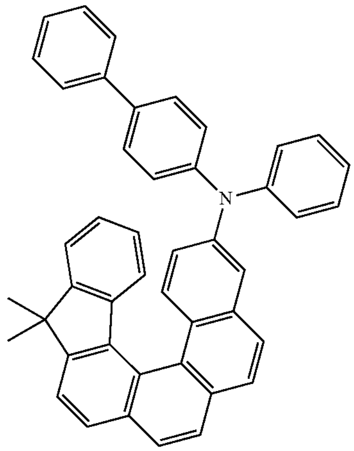
C-499
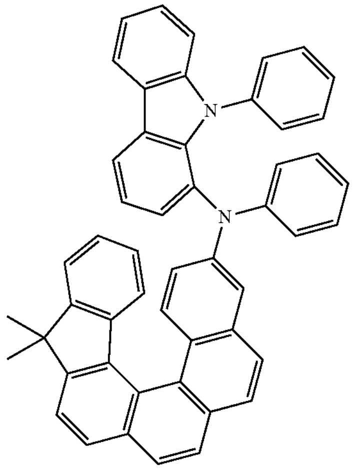
C-500
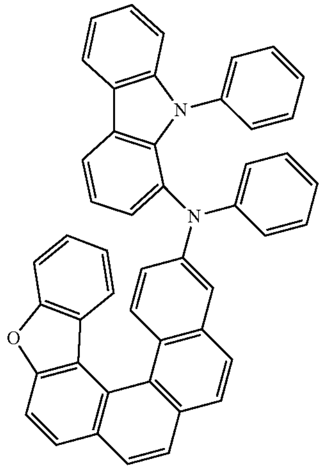
C-501
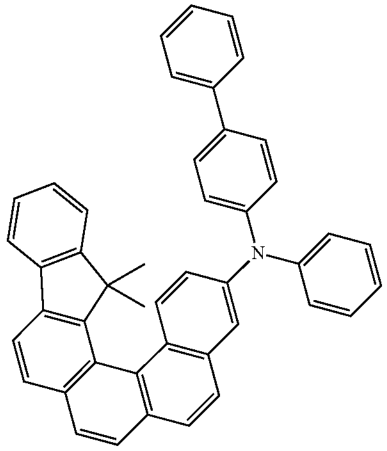

-continued
C-502
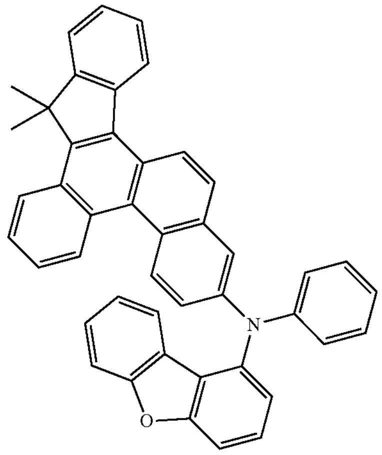
C-503
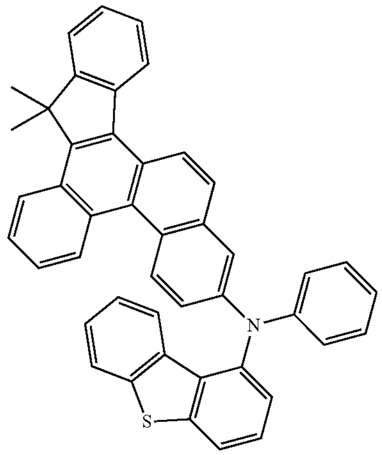
C-504
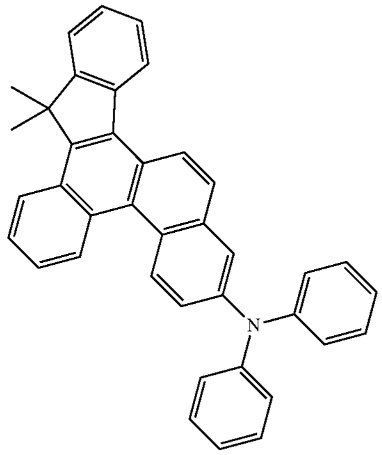
-continued
C-505
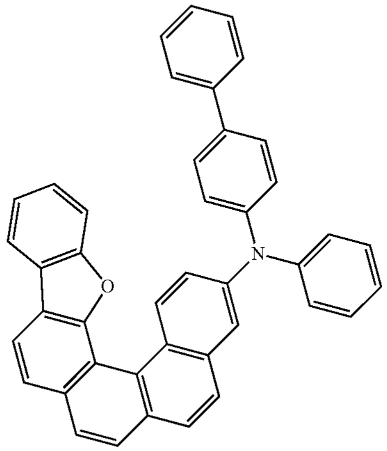
C-506
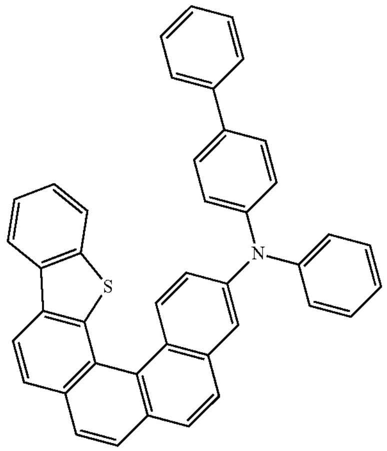
C-507
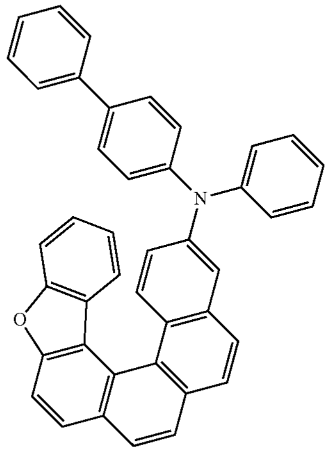

-continued
C-508
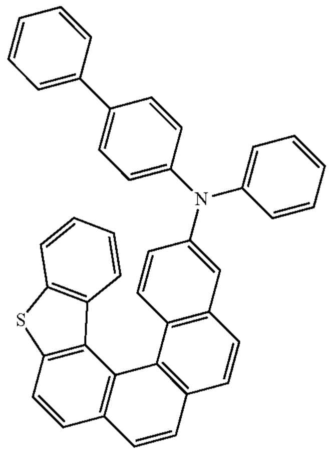
C-509
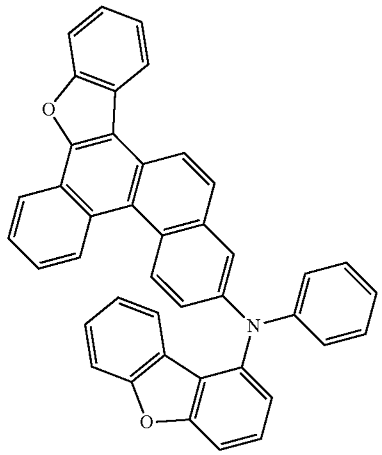
C-510
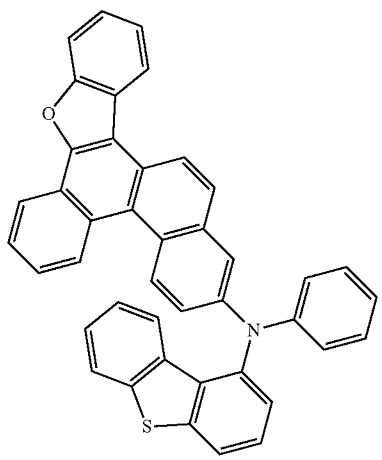
-continued
C-511
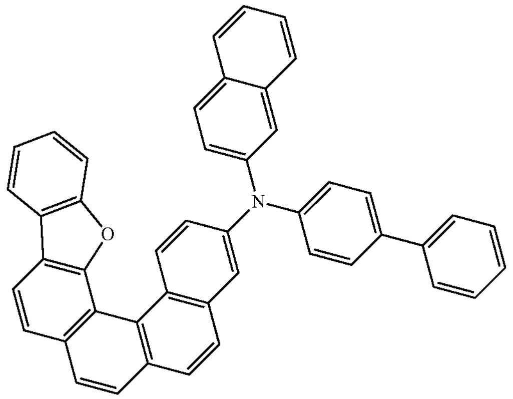
C-512
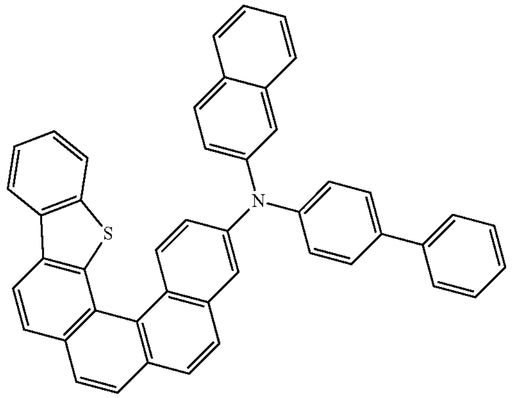
C-513
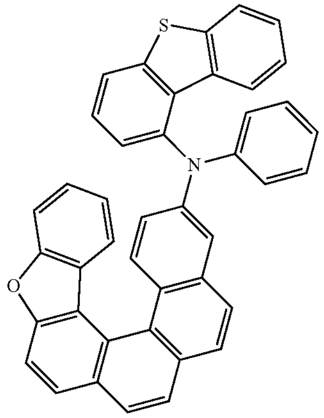

-continued
C-514
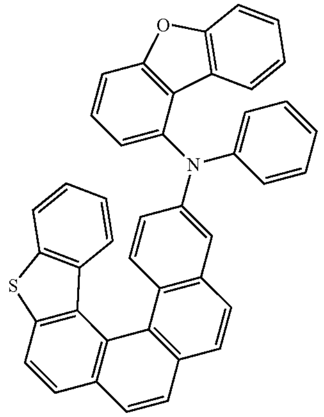
C-515
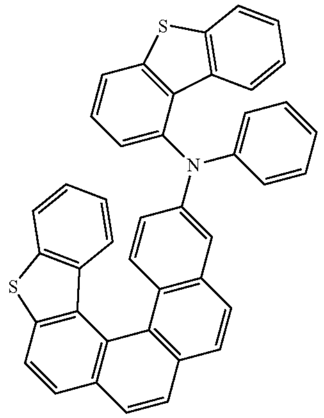
C-516
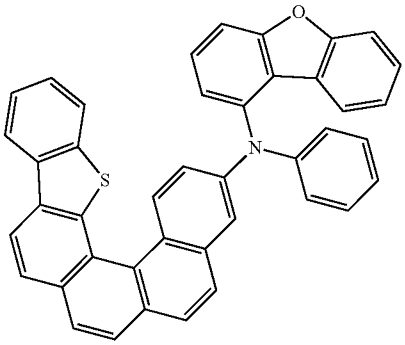
C-517
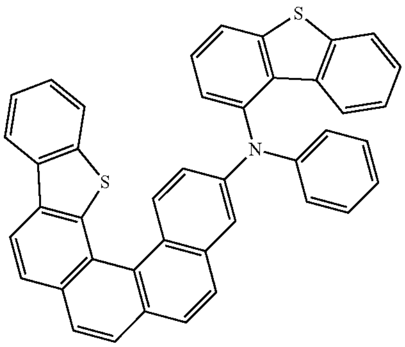
-continued
C-518
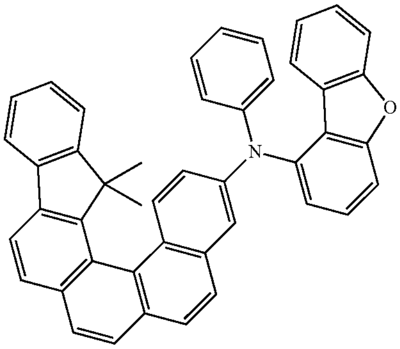
C-519
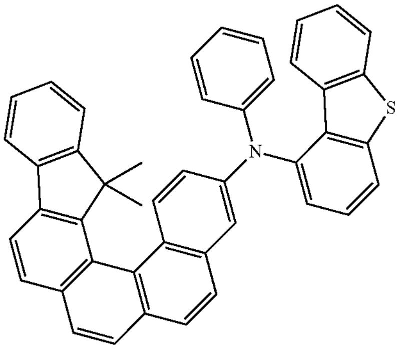
C-520
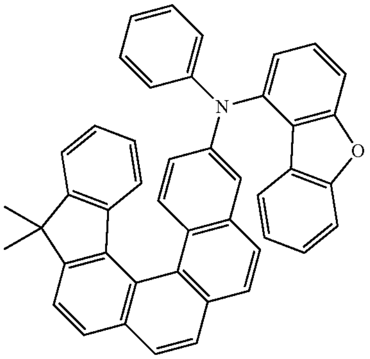
C-521
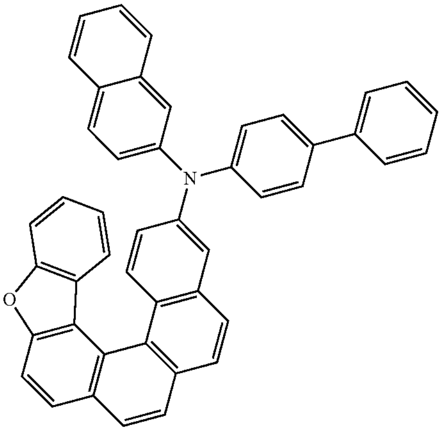

C-522
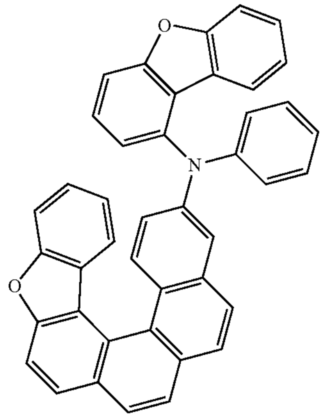
C-523
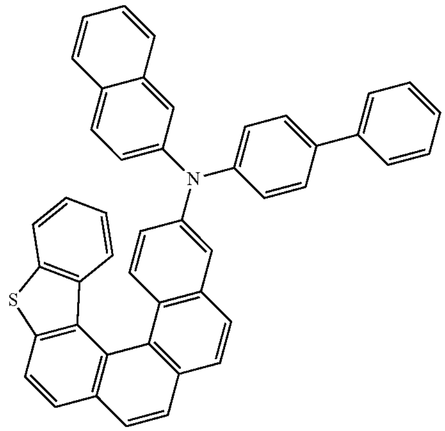
C-524
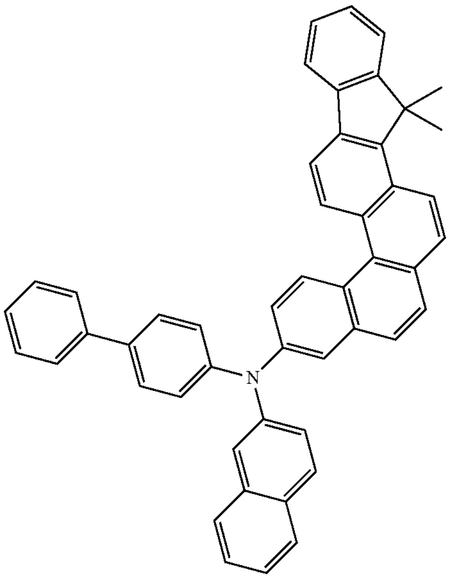
C-525
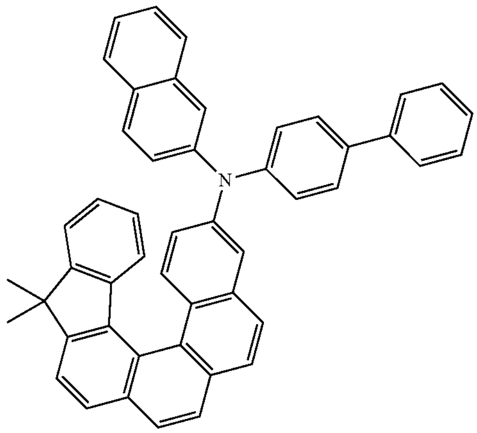
C-526
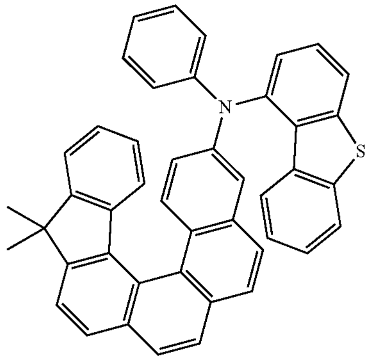
C-527
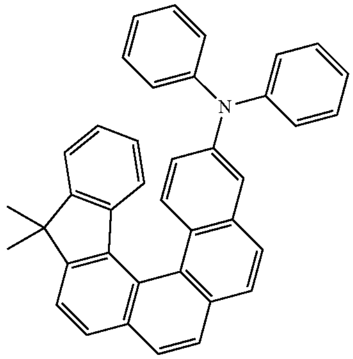
C-528
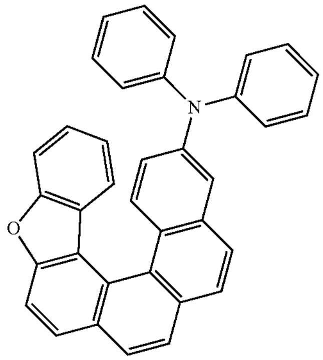

-continued
C-529
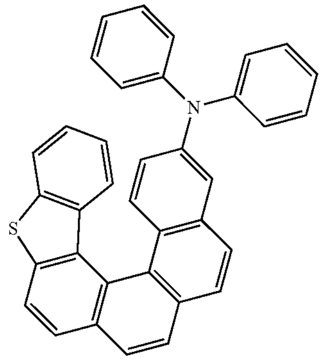
C-530
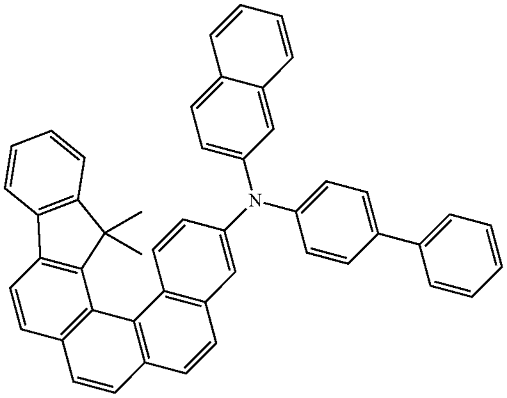
C-531
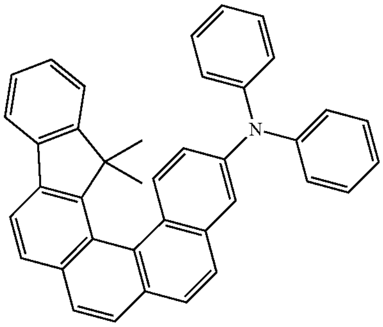
C-532
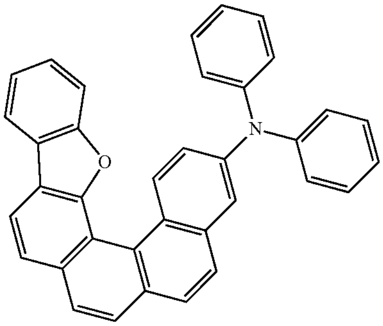
-continued
C-533
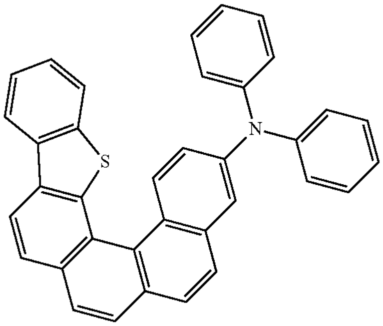
C-534
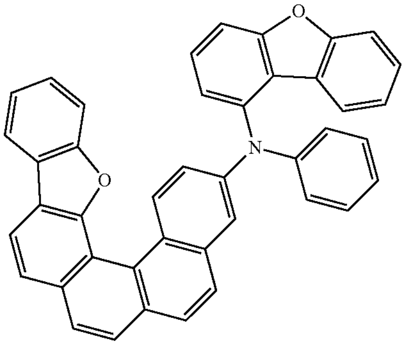
C-535
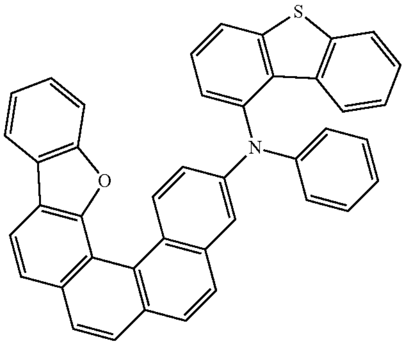
C-536
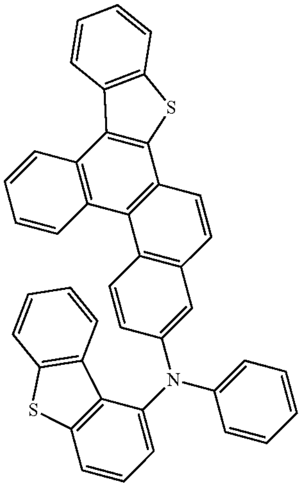

-continued
C-537
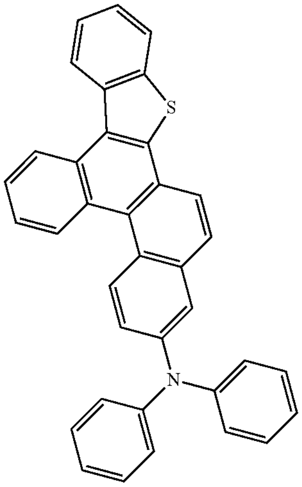
C-538
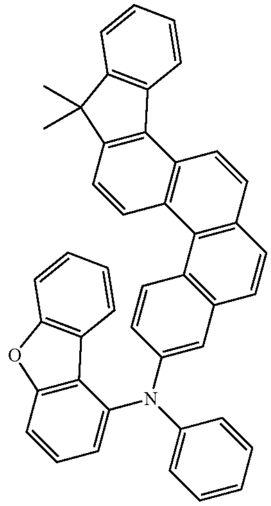
C-539
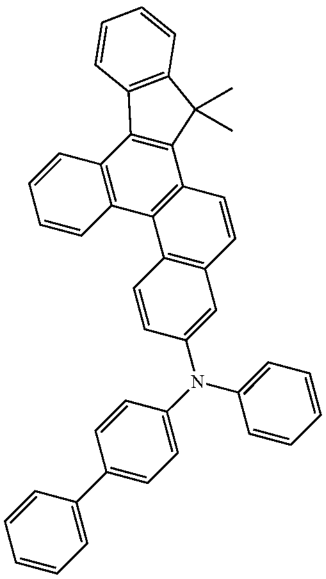
-continued
C-540
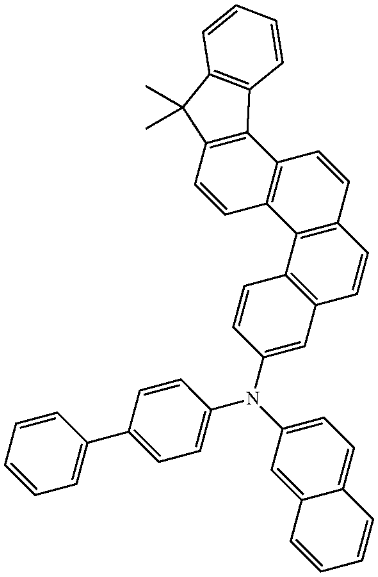
C-541
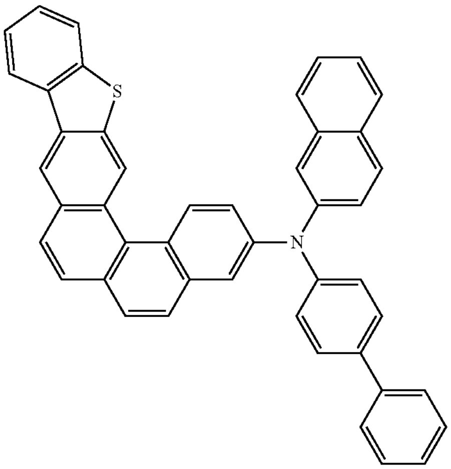
C-542
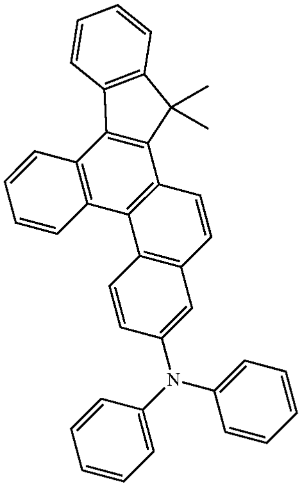

-continued
C-543
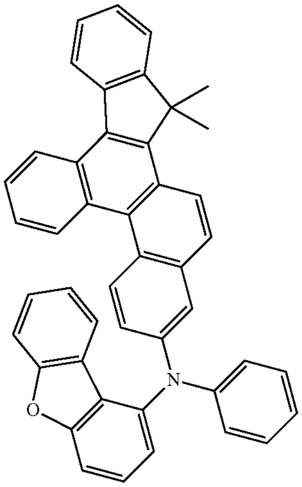
C-544
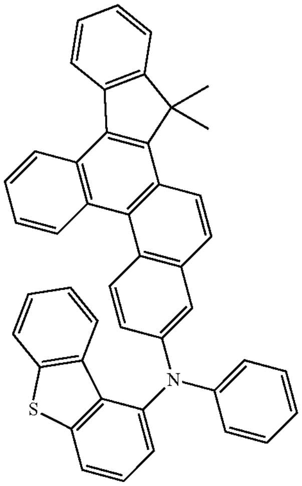
C-545
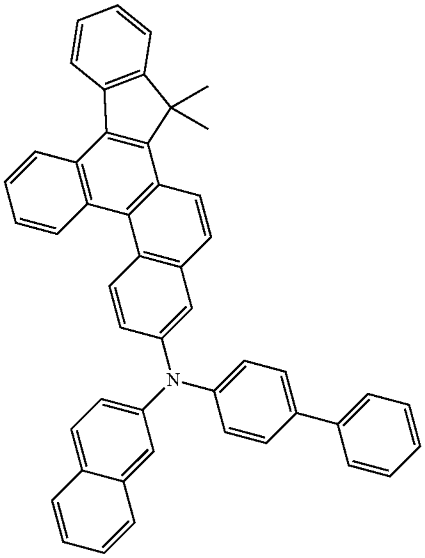
-continued
C-546
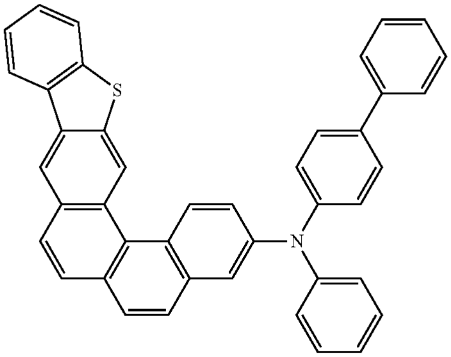
C-547
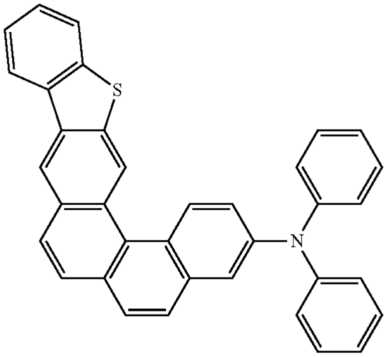
C-548
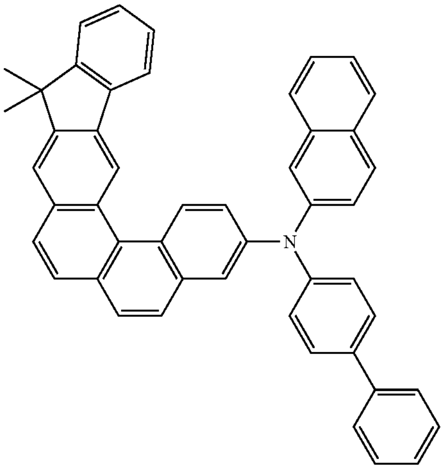

-continued
C-549
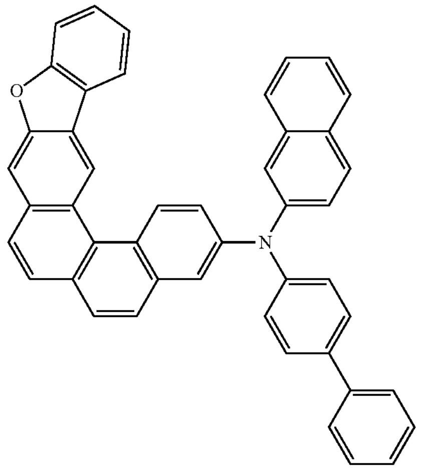
C-550
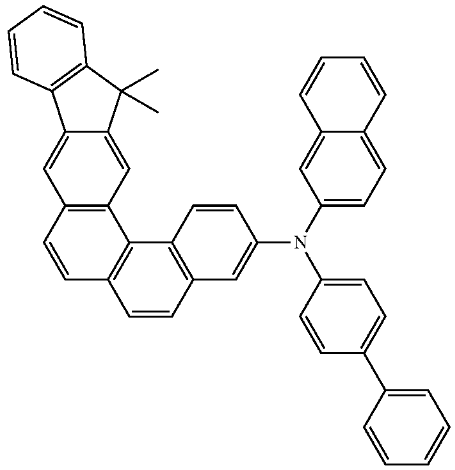
C-551
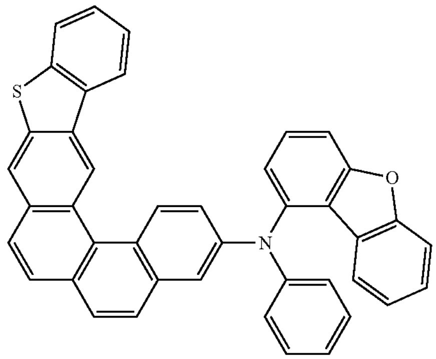
-continued
C-552
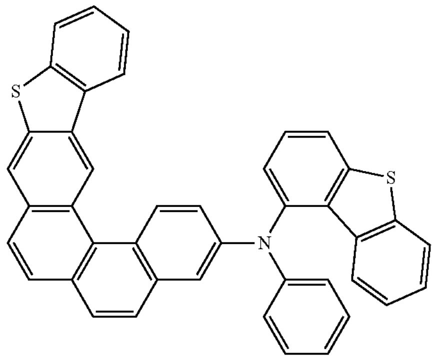
C-553
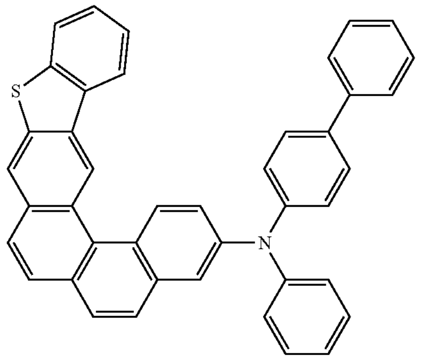
C-554
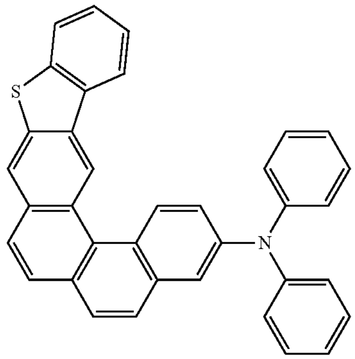
C-555
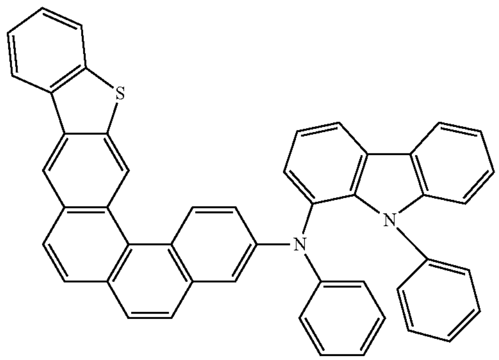

-continued
C-556
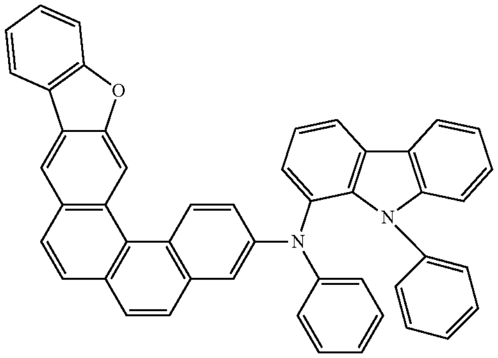
C-557
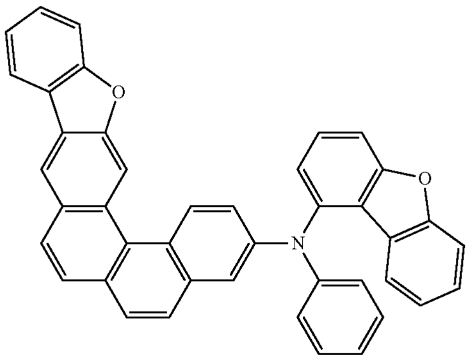
C-558
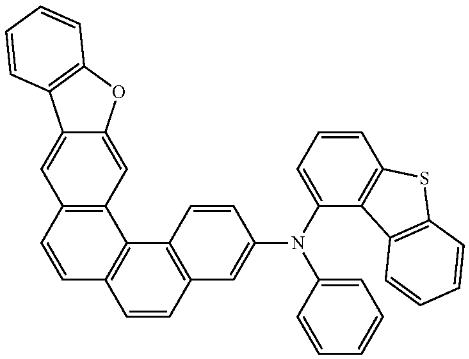
C-559
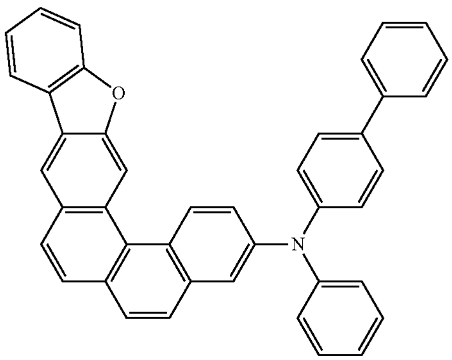
-continued
C-560
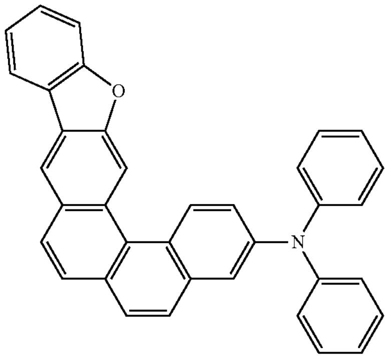
C-561
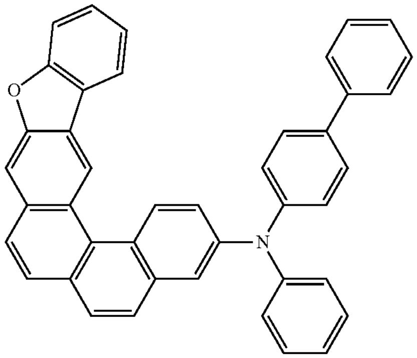
C-562
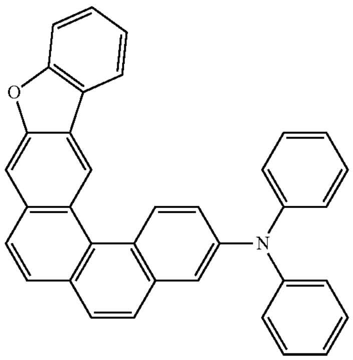
C-563
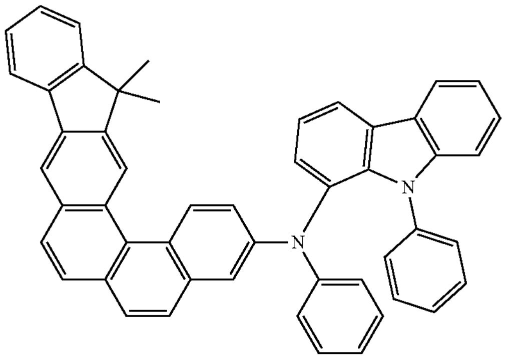

-continued
C-564
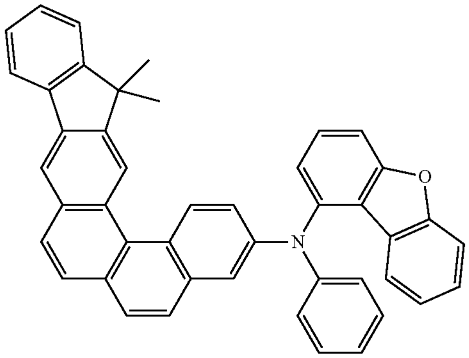
C-565
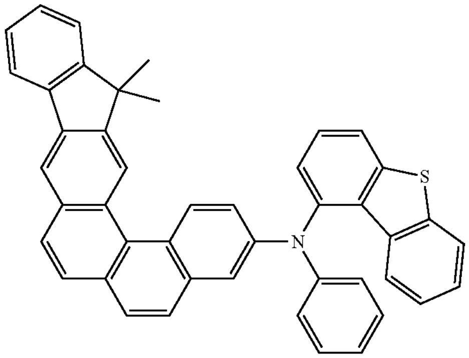
C-566
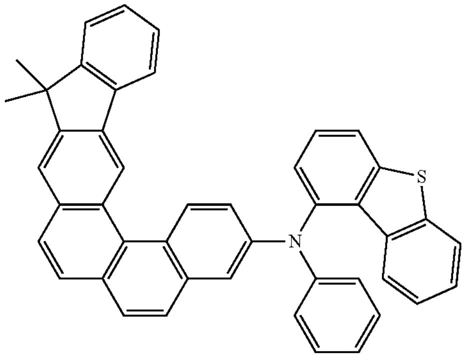
C-567
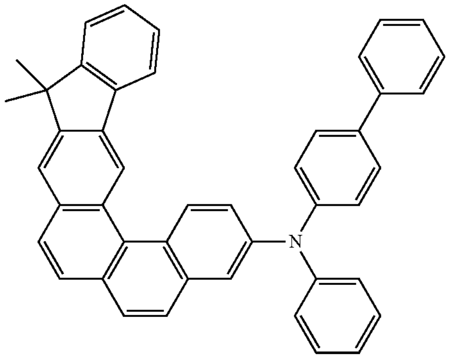
-continued
C-568
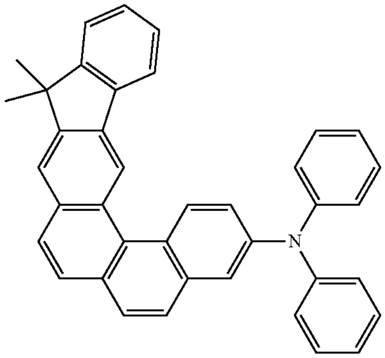
C-569
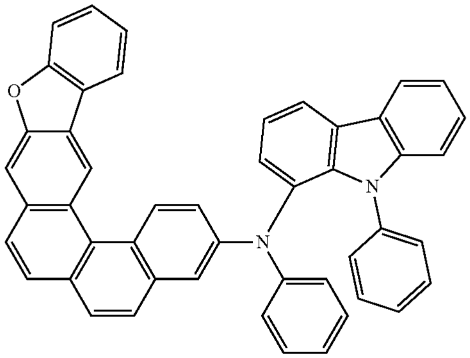
C-570
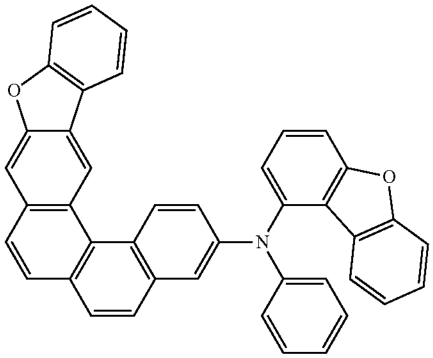
C-571
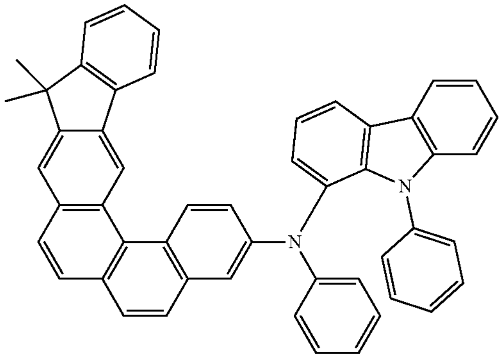

-continued
C-572
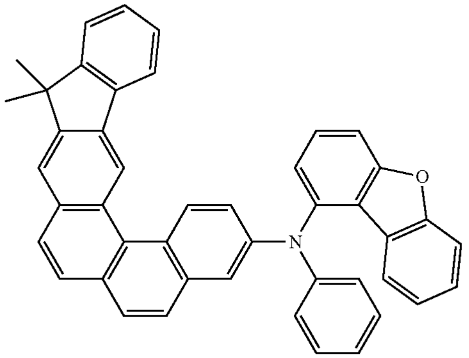
C-573
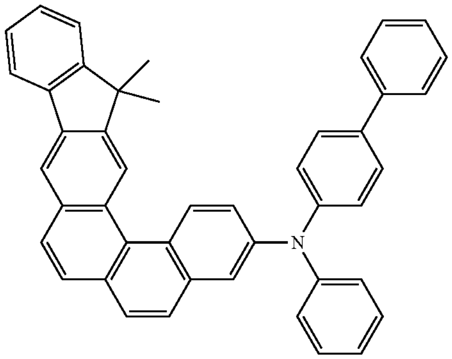
C-574
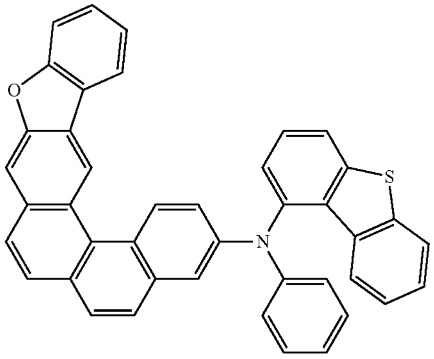
C-575
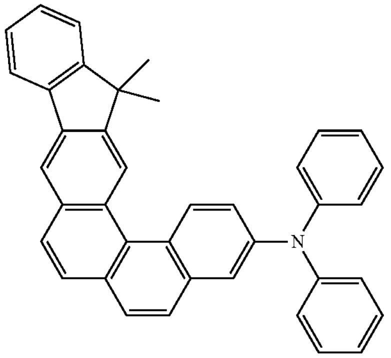
-continued
C-576
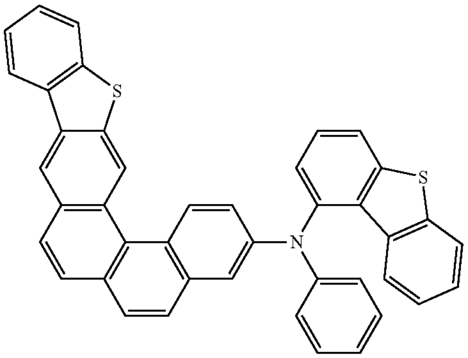
C-577
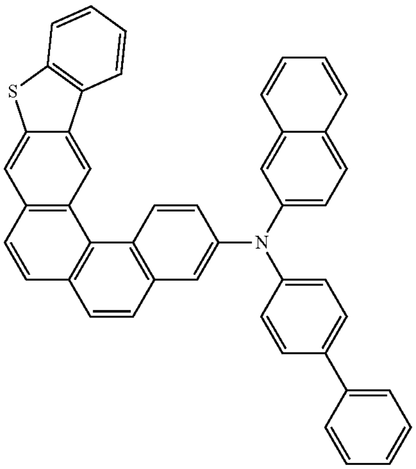
C-578
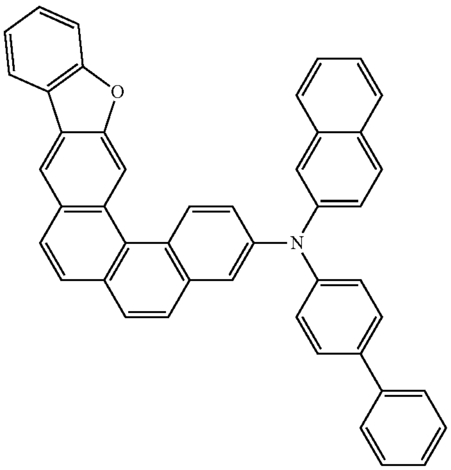

-continued
C-579
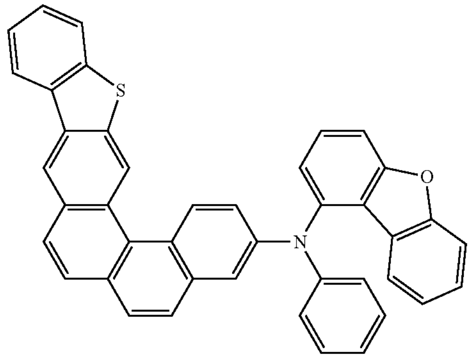
C-580
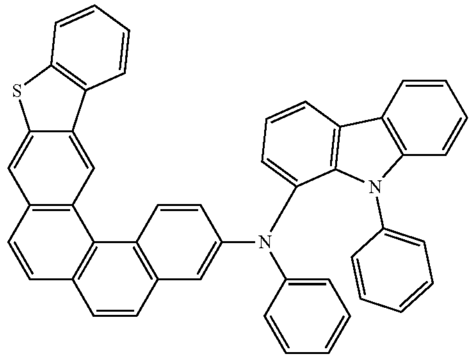
C-581
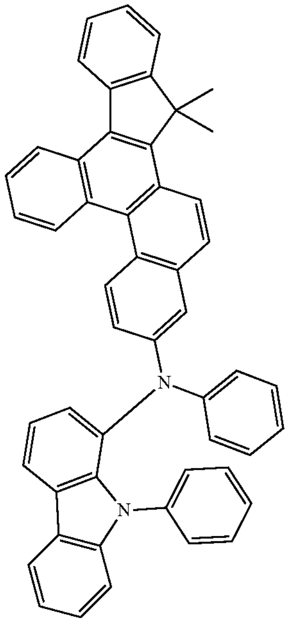
-continued
C-582
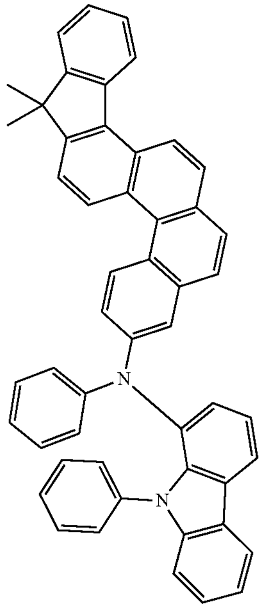
C-583
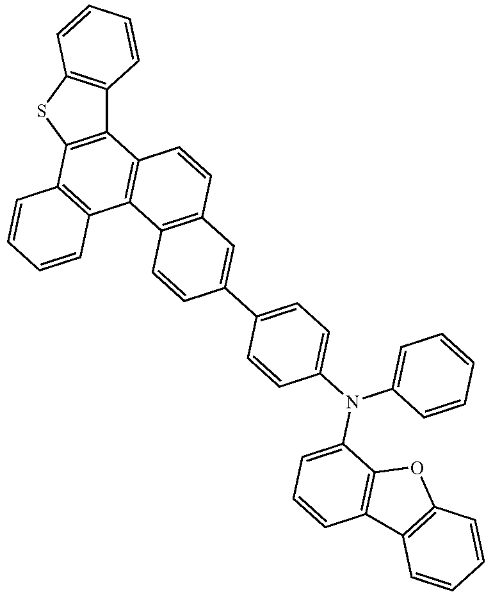

-continued
C-584
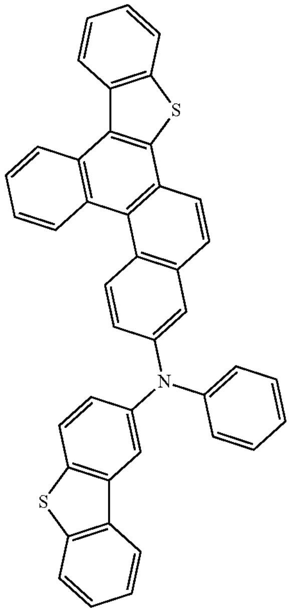
C-585
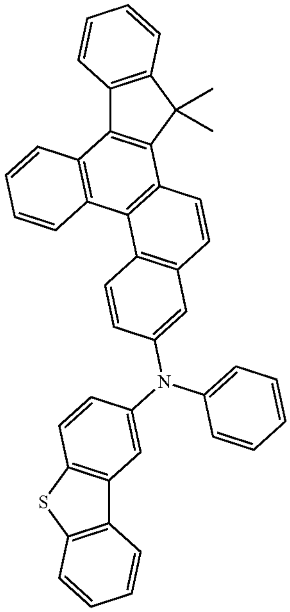
-continued
C-586
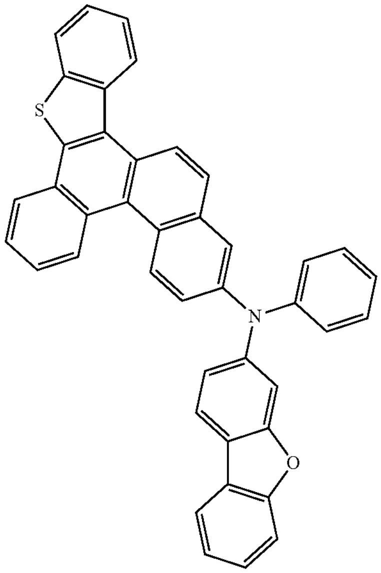
C-587
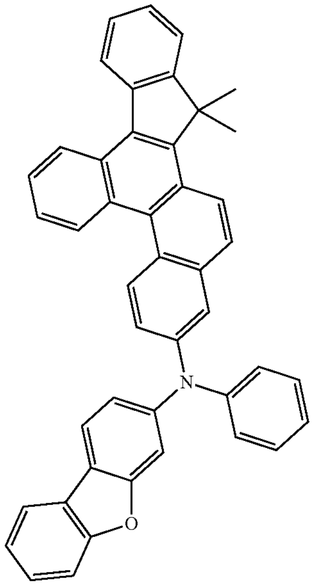

-continued
C-588
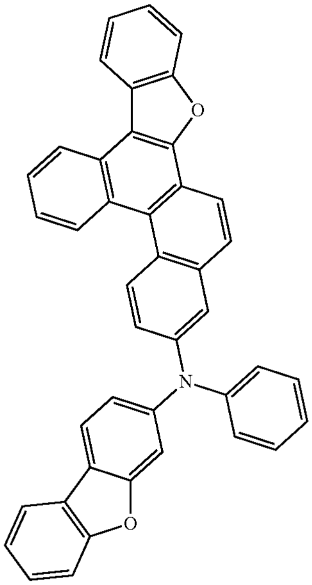
C-589
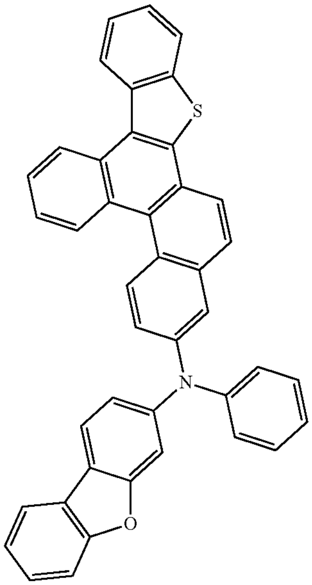
-continued
C-590
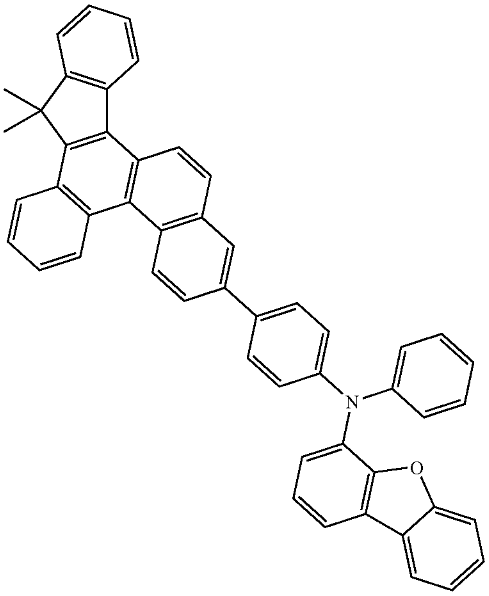
C-591
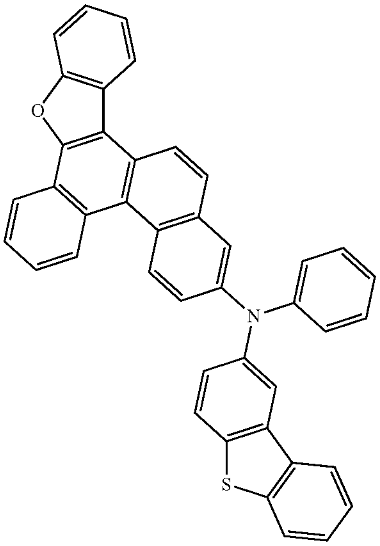

-continued
C-592
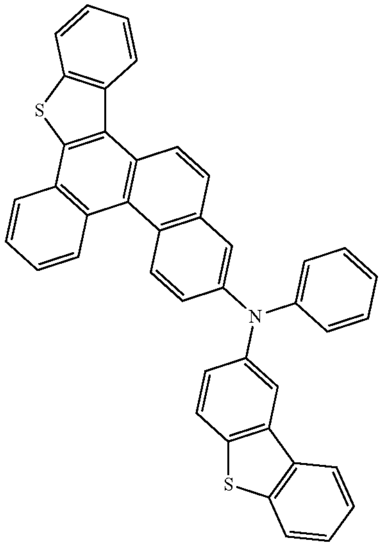
C-593
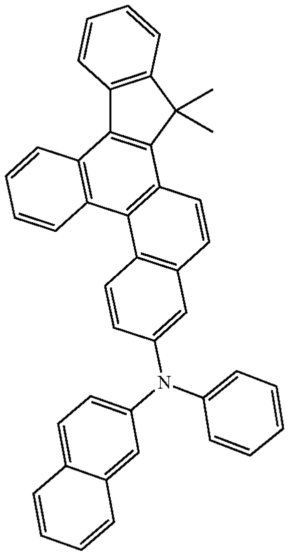
C-594
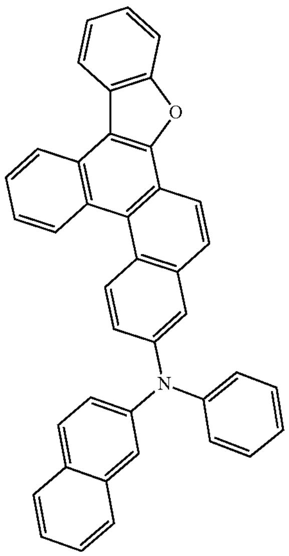
-continued
C-595
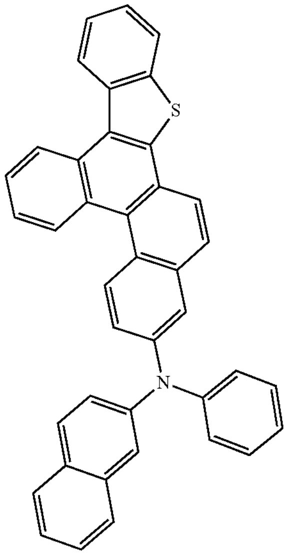
C-596
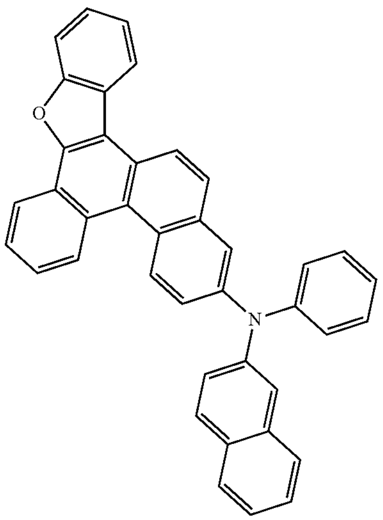
C-597
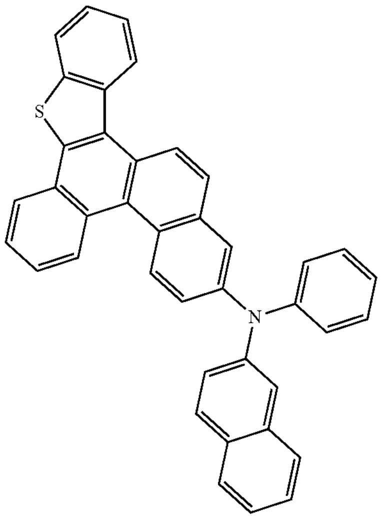

-continued
C-598
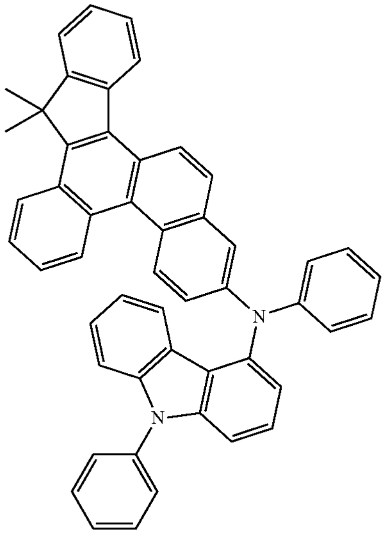
C-599
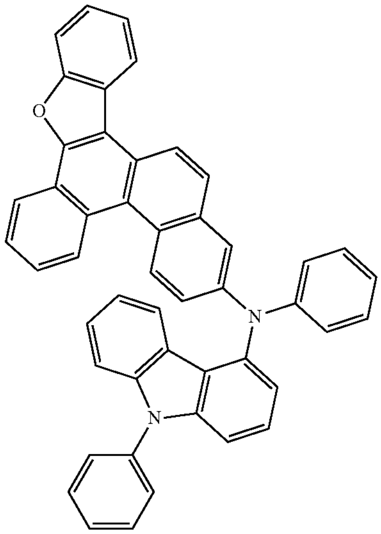
C-600
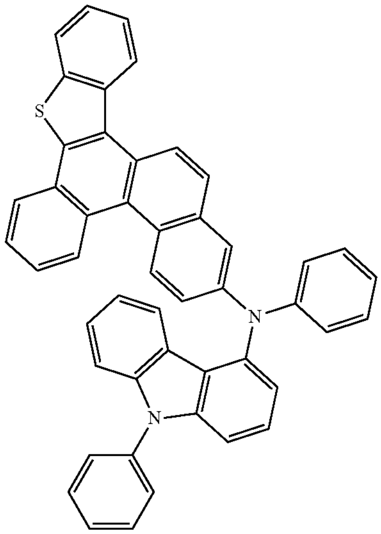
-continued
C-601
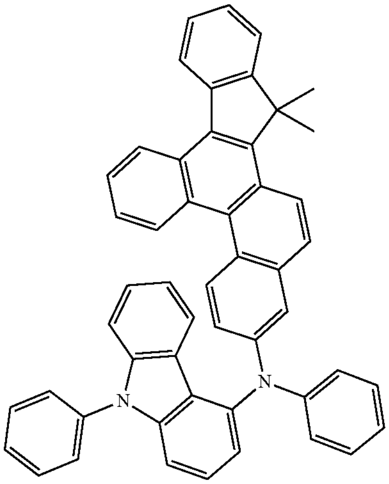
C-602
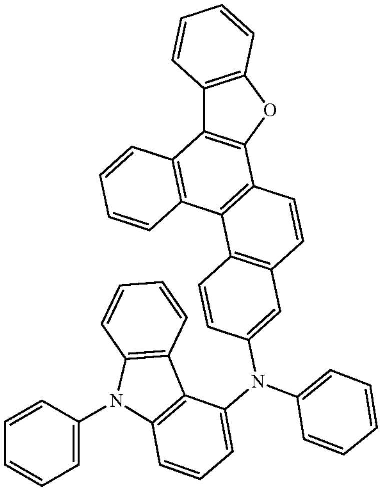
C-603
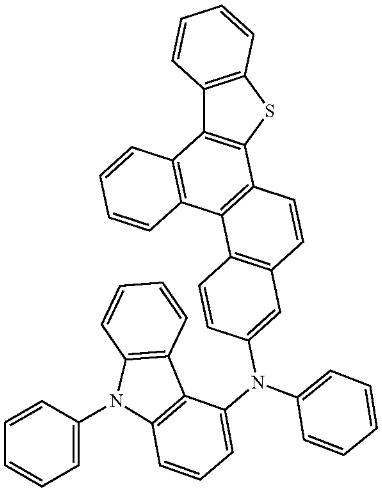

-continued
C-604
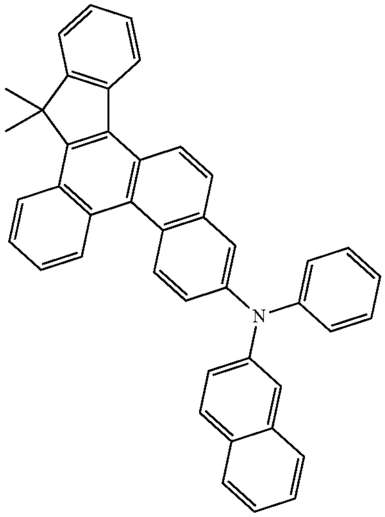
C-605
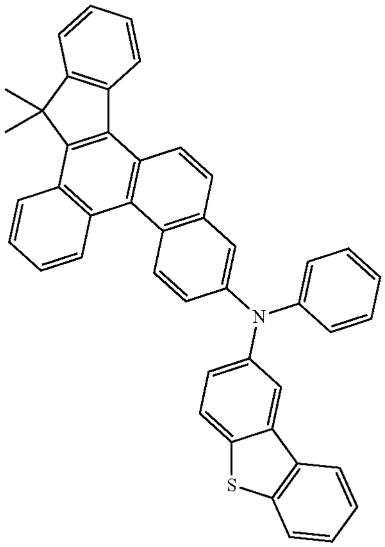
-continued
C-606
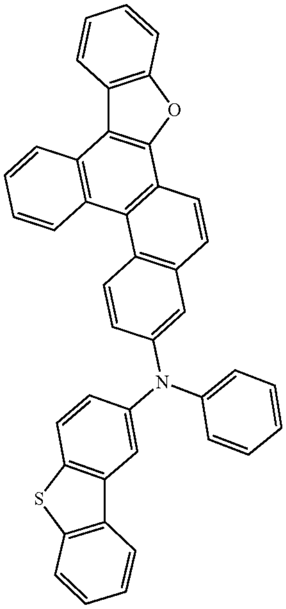
C-607
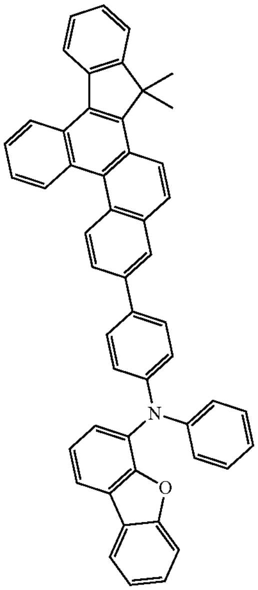

-continued
C-608
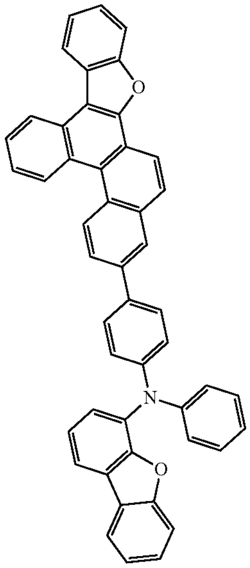
C-609
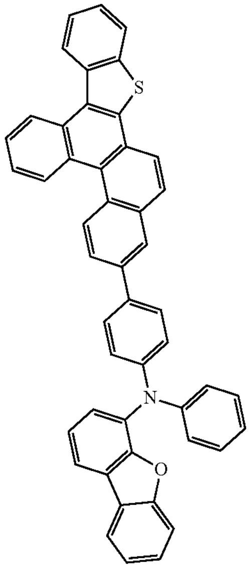
-continued
C-610
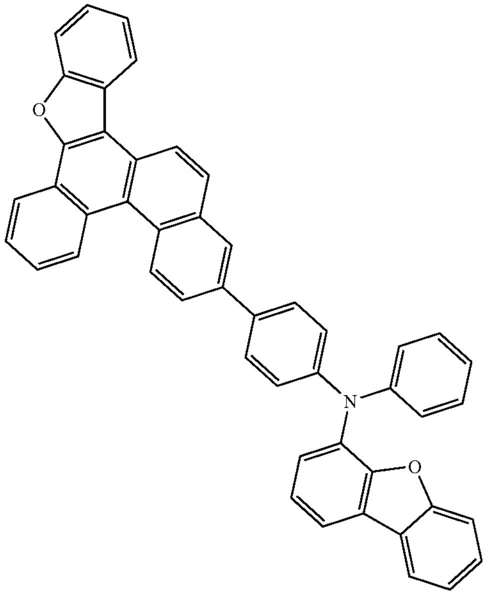
C-611
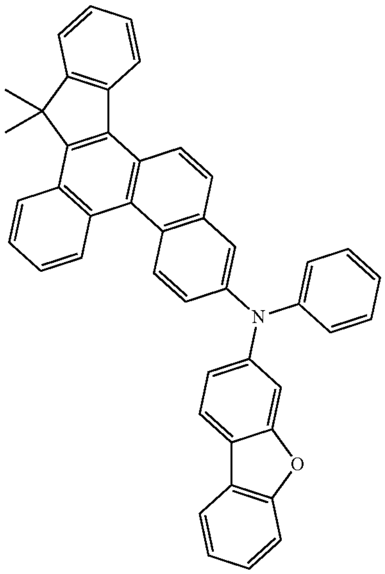

-continued
C-612
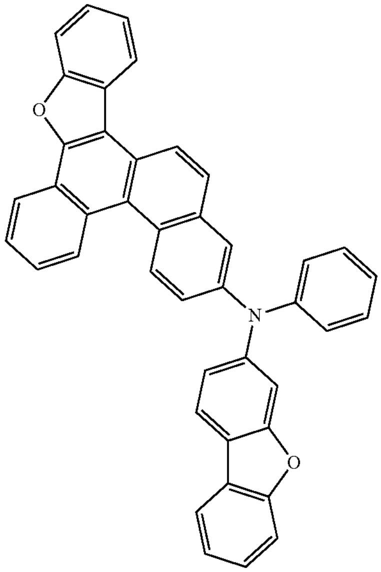
-continued
C-614
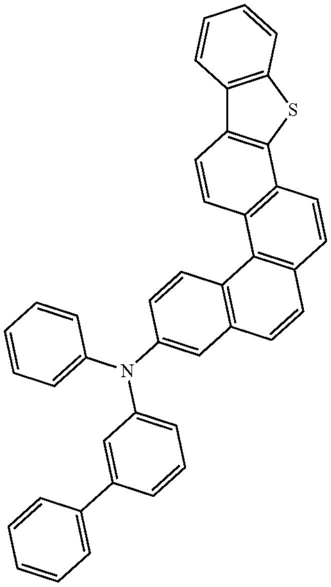
C-613
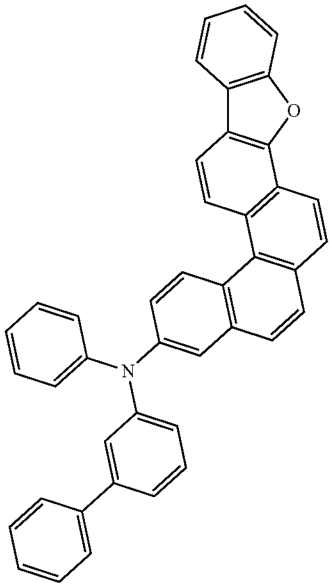
C-615
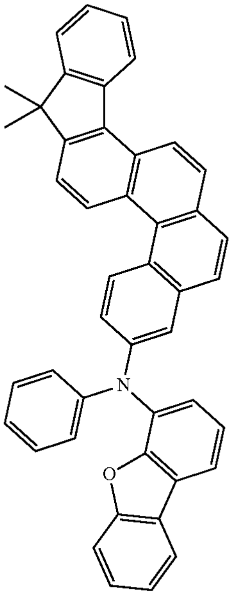

-continued
C-616
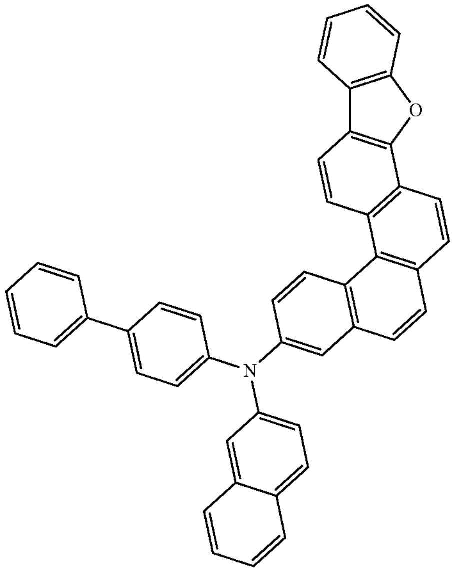
C-617
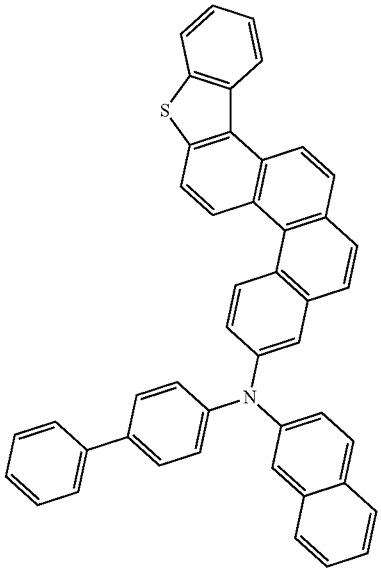
-continued
C-618
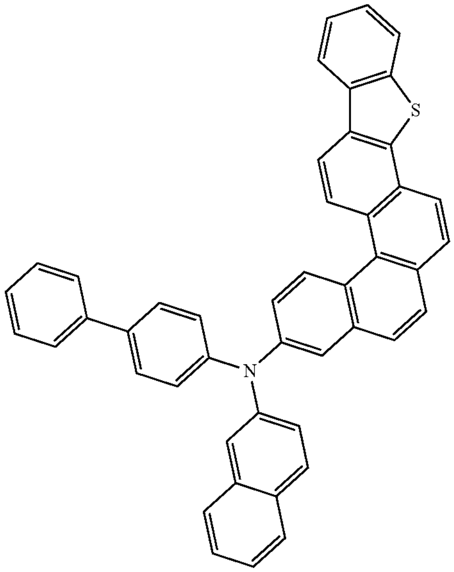
C-619
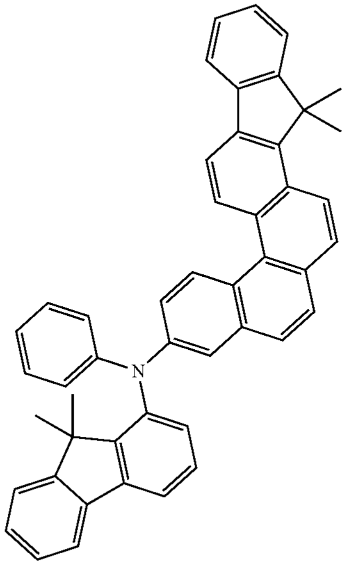

-continued
C-620
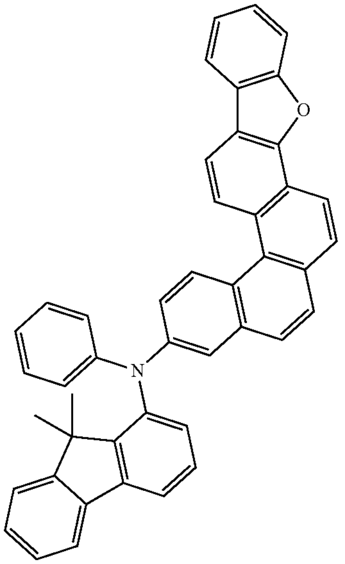
C-621
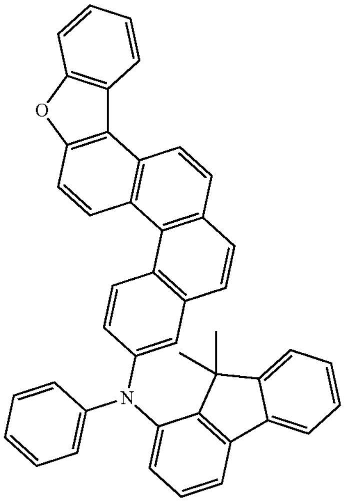
C-622
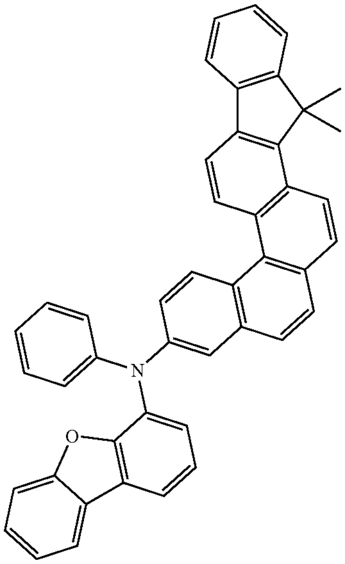
-continued
C-623
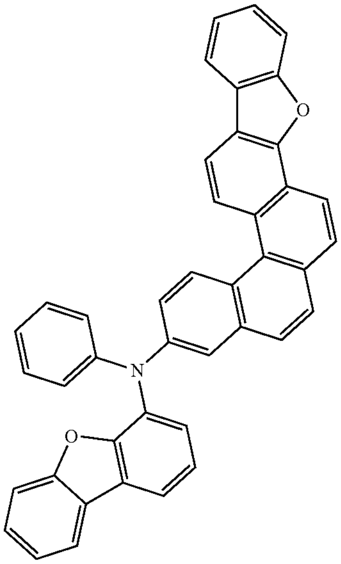
C-624
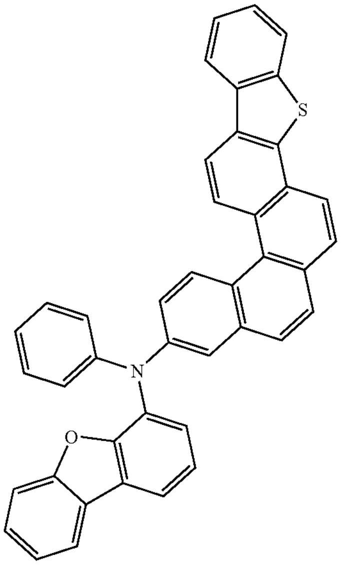

-continued
C-625
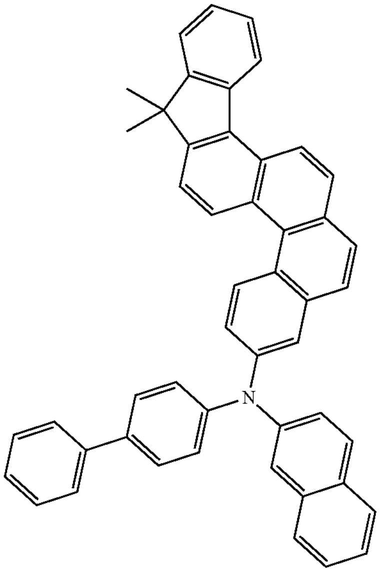
C-626
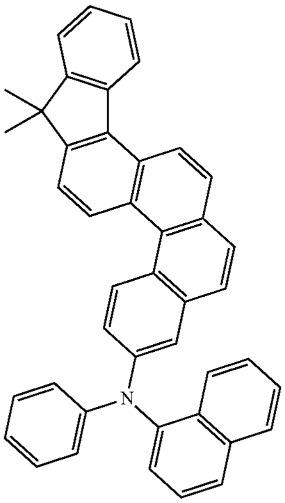
C-627
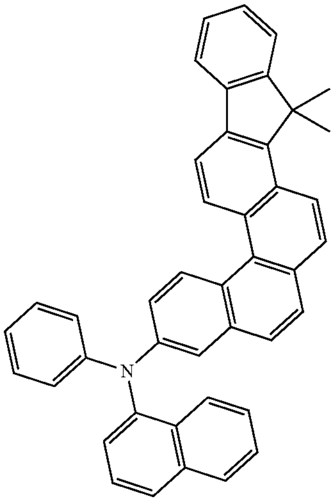
-continued
C-628
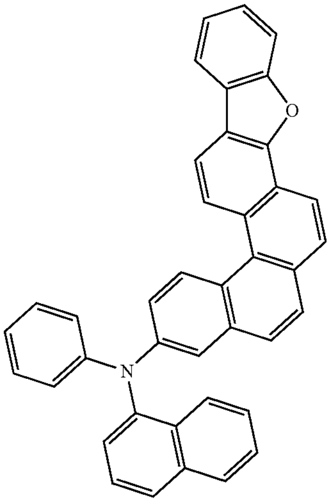
C-629
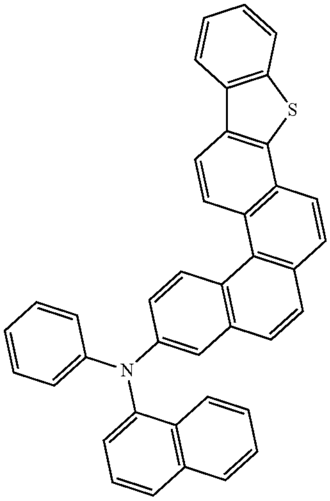
C-630
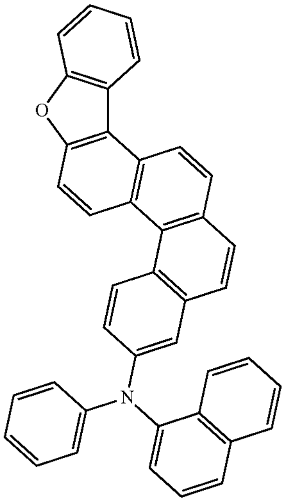

C-631
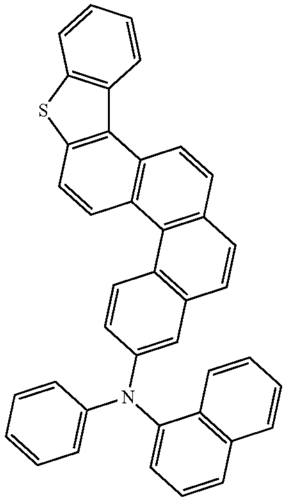
C-632
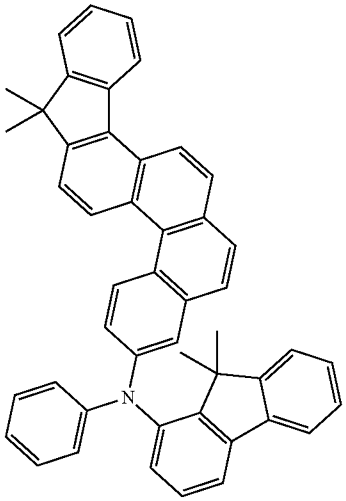
C-633
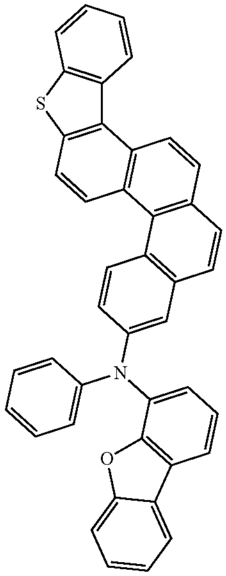
C-634
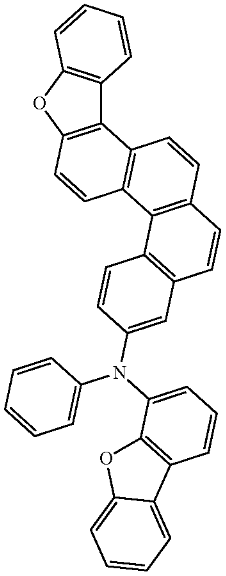
C-635
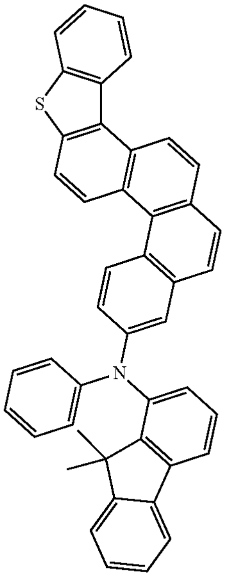

-continued
C-636
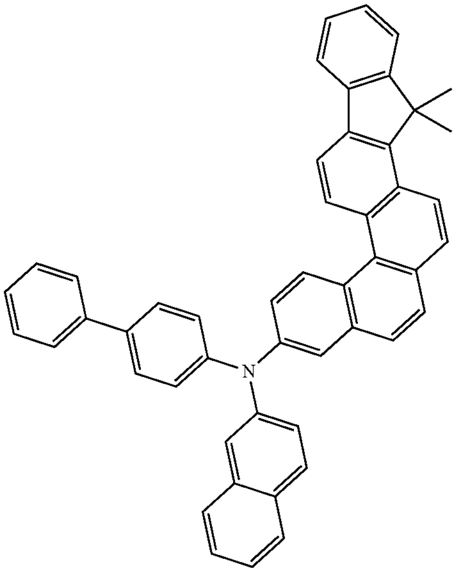
C-637
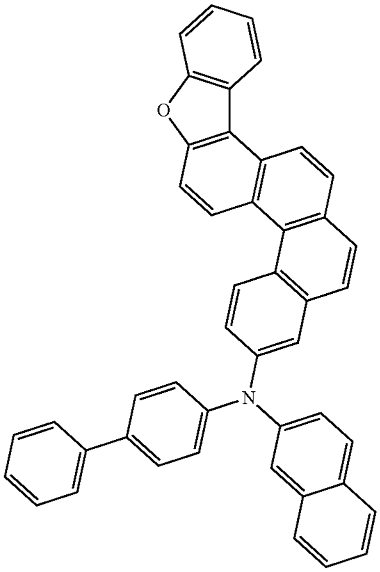
-continued
C-638
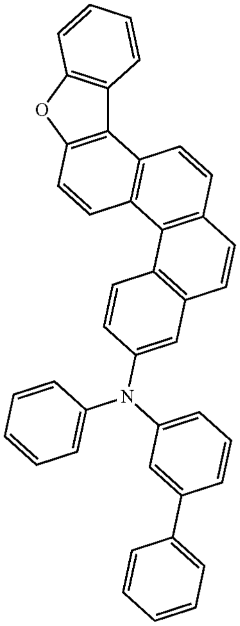
C-639
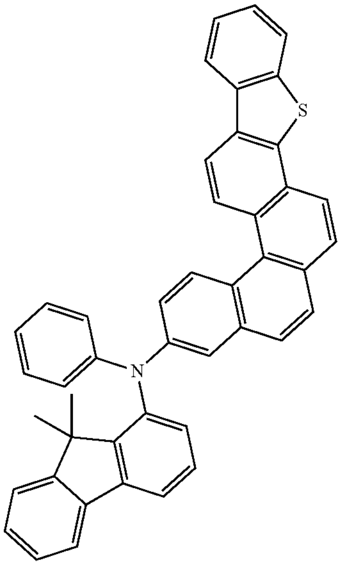

-continued
C-640
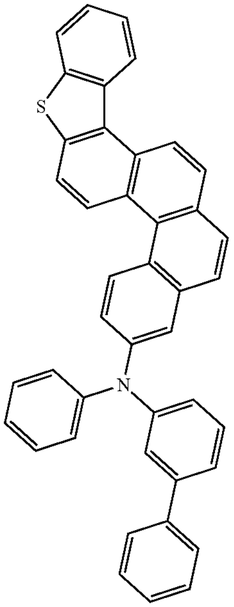
C-641
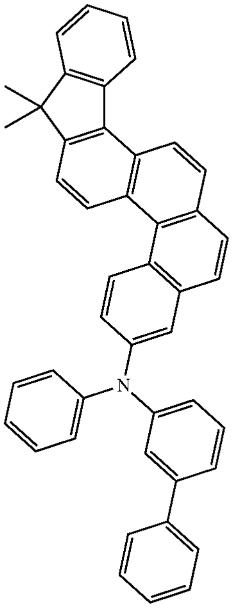
-continued
C-642
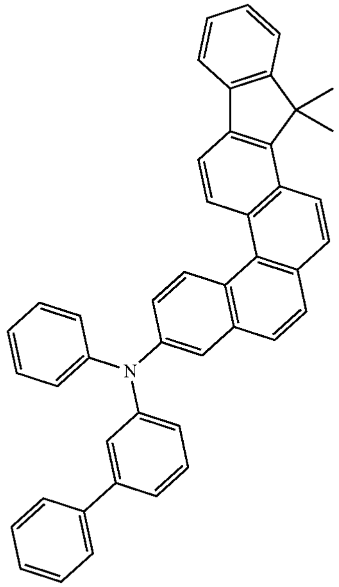
C-643
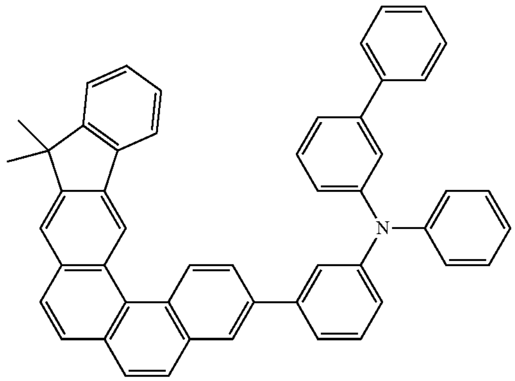
C-644
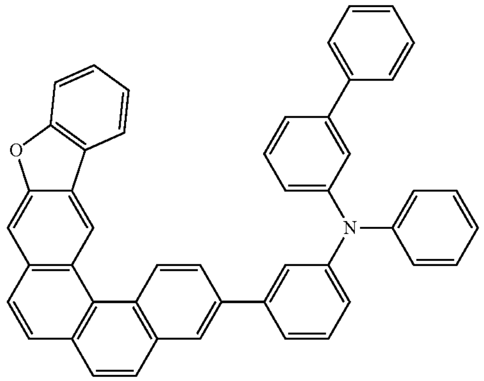

-continued
C-645
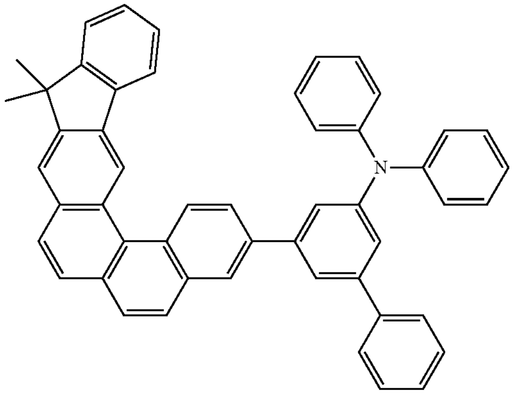
C-646
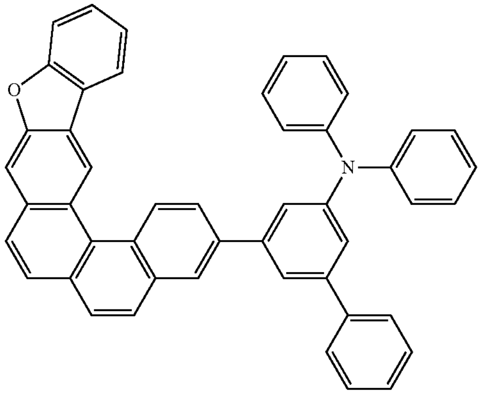
C-647
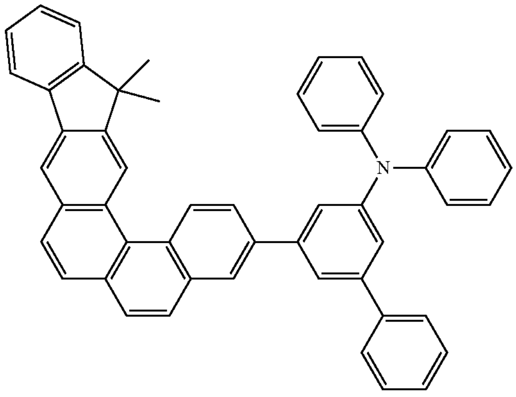
-continued
C-648
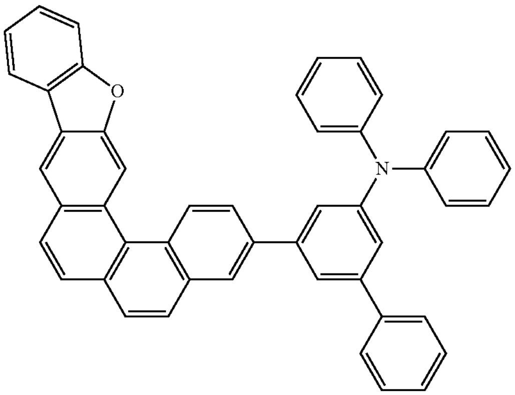
C-649
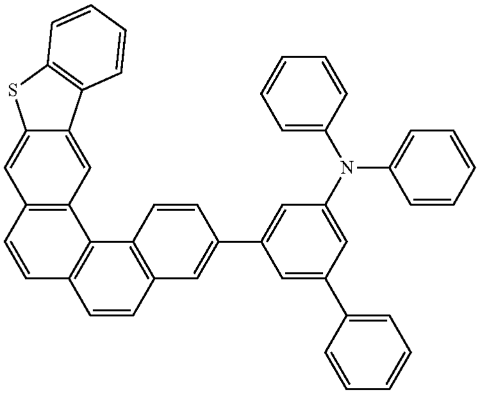
C-650
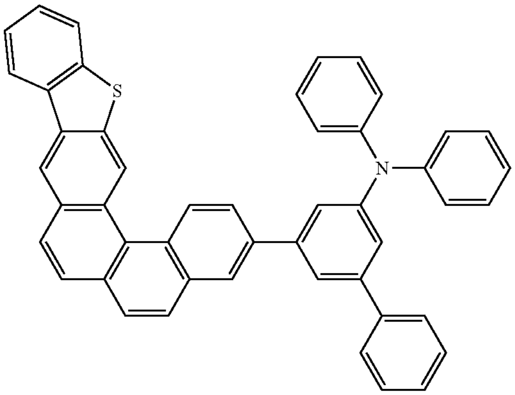
C-651
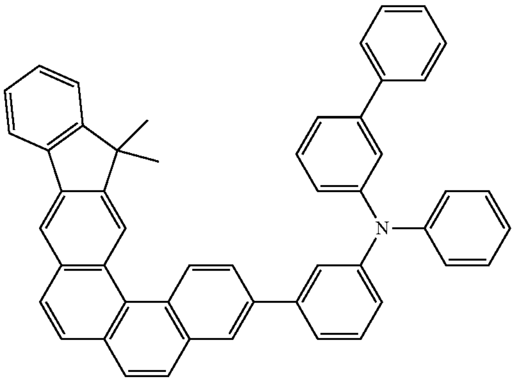

-continued
C-652
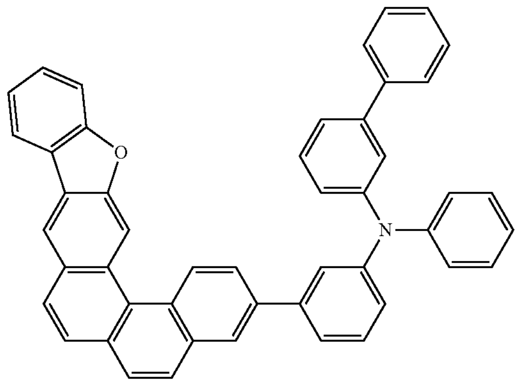
C-653
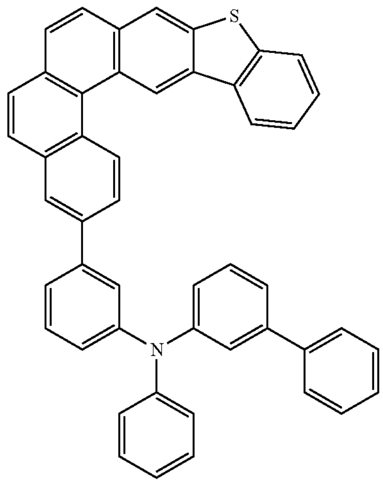
C-654
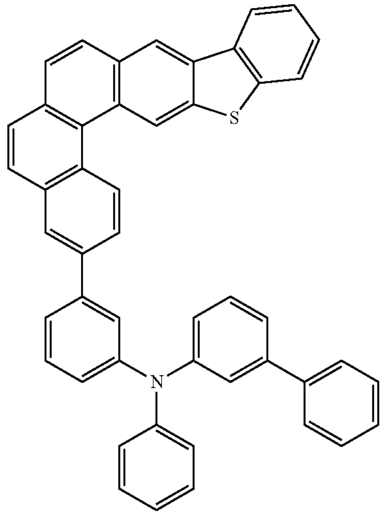
-continued
C-655
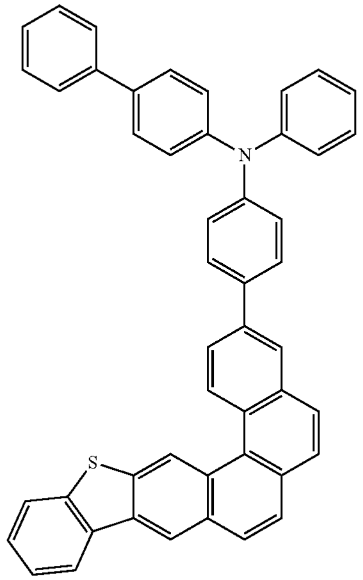
C-656
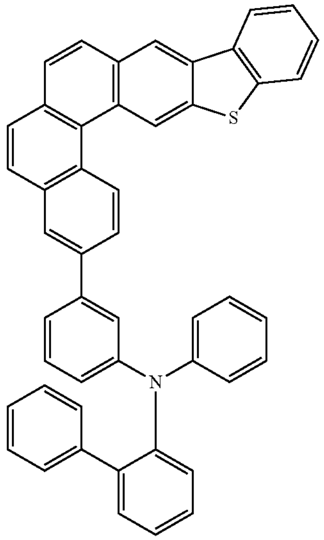
C-657
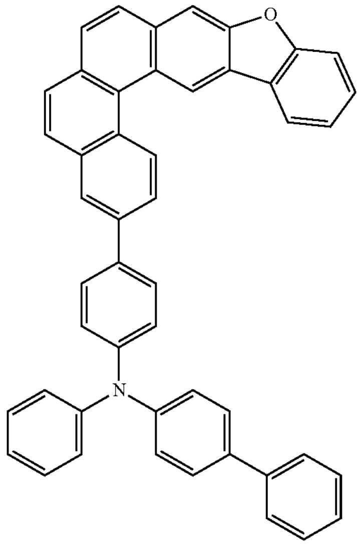

-continued
C-658
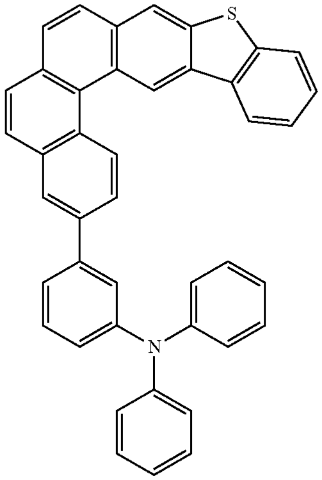
C-659
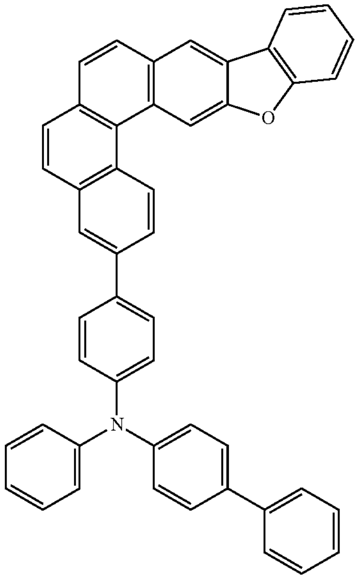
C-660
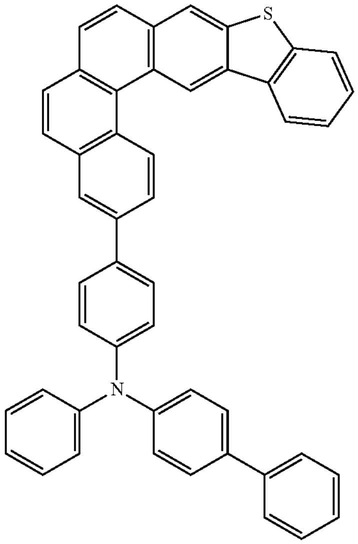
-continued
C-661
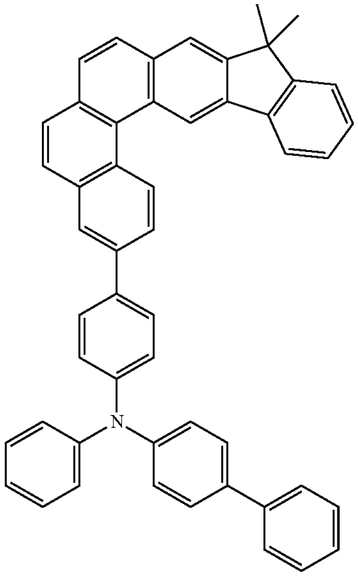
C-662
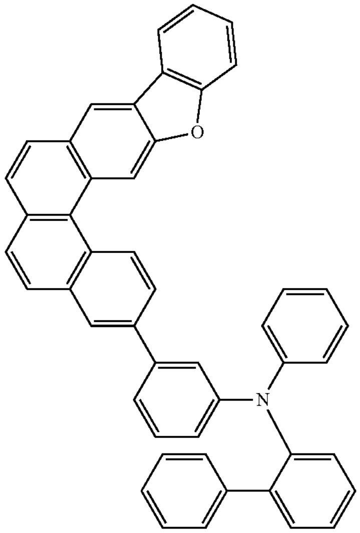

-continued
C-663
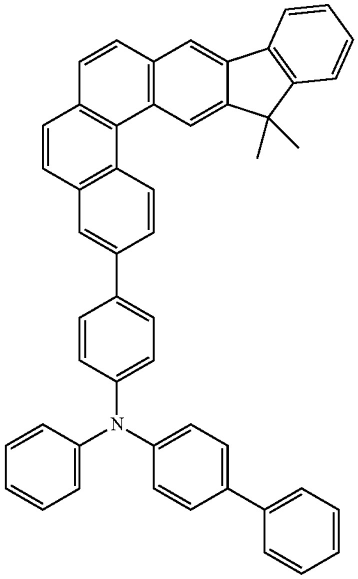
C-664
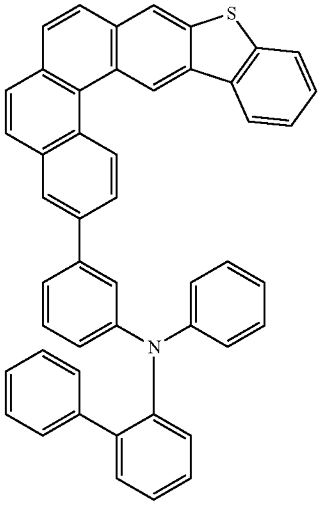
C-665
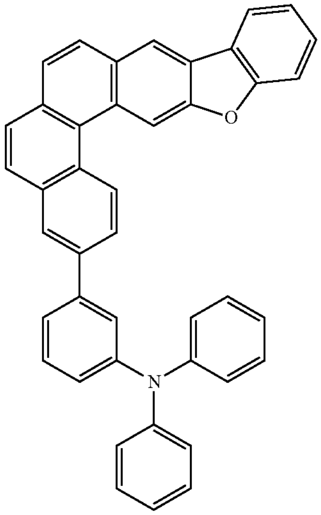
-continued
C-666
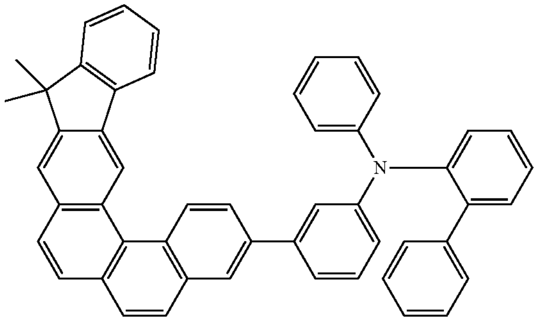
C-667
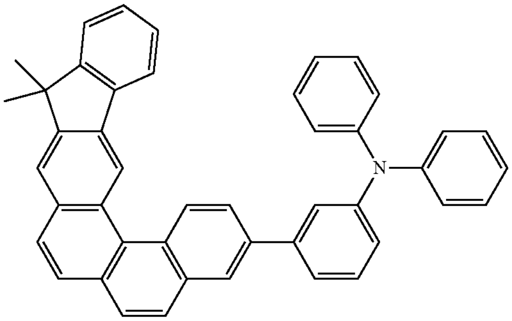
C-668
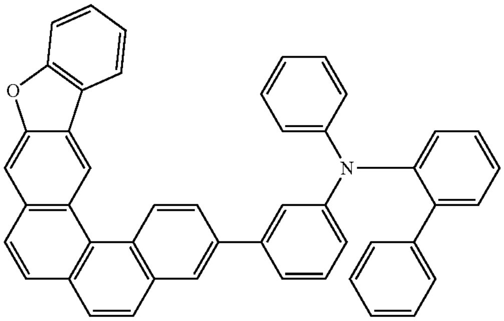
C-669
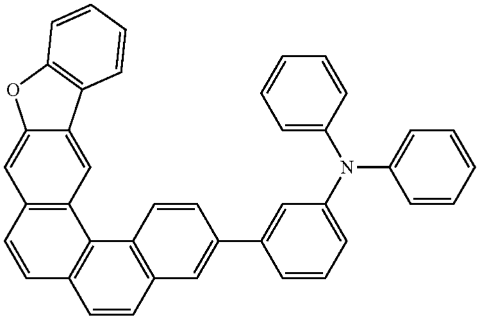

-continued
C-670
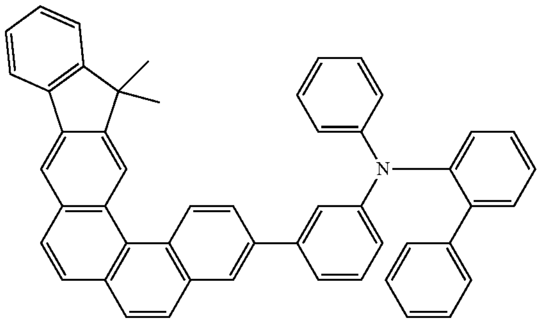
C-671
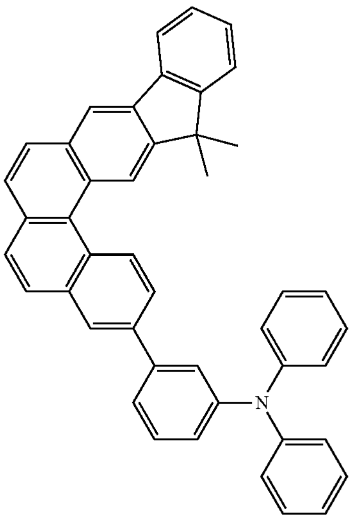
C-672
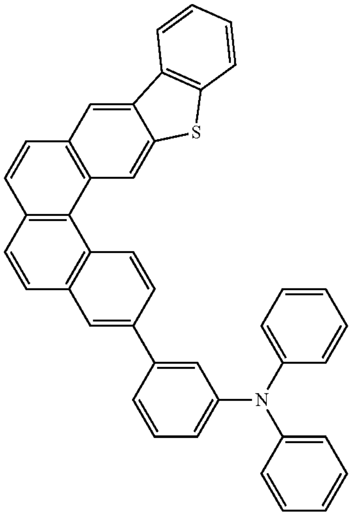
-continued
C-673
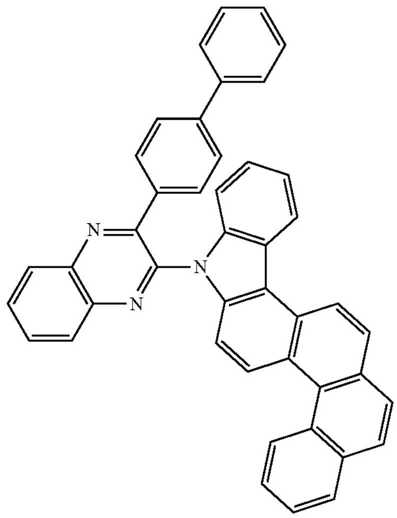
C-674
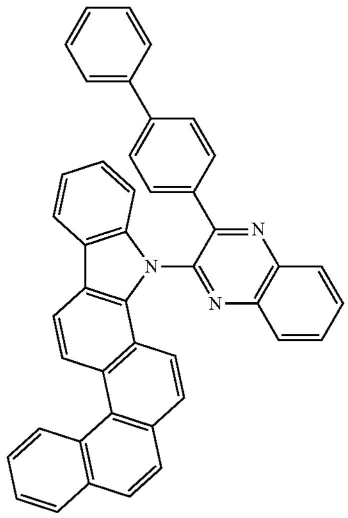
C-675
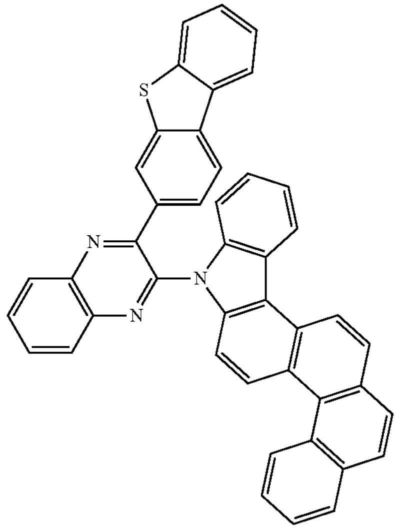

-continued
C-676
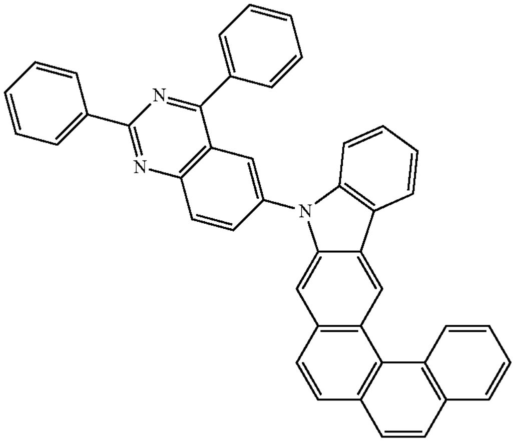
C-677
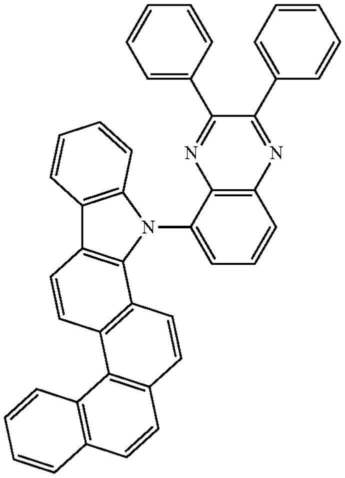
C-678
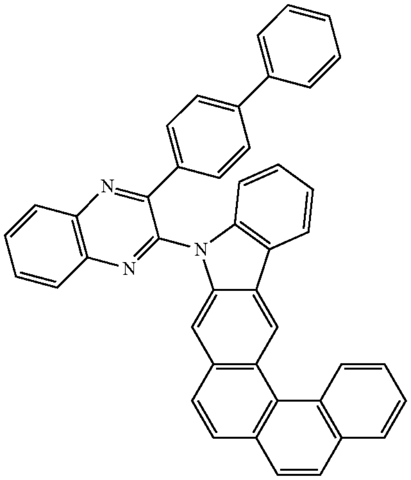
-continued
C-679
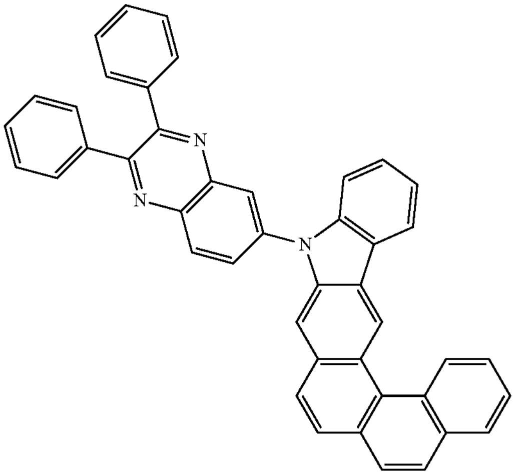
C-680
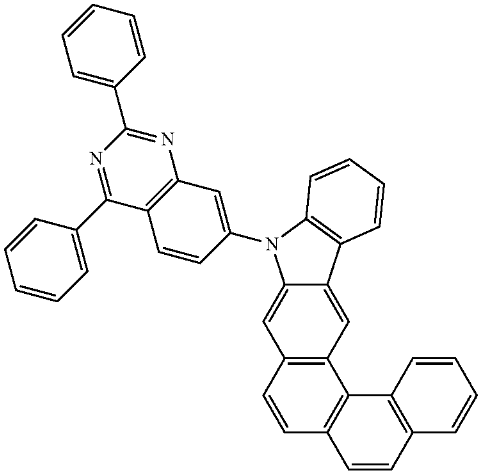
C-681
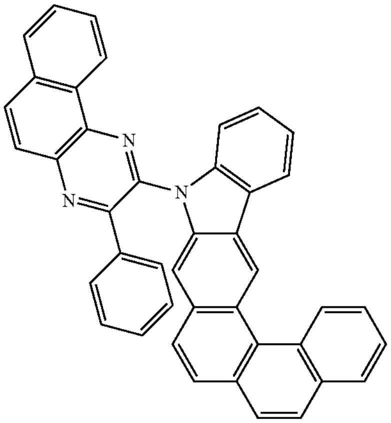

-continued
C-682
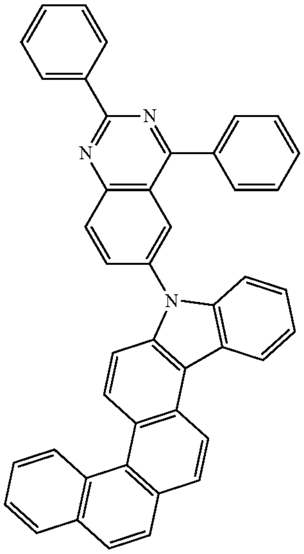
C-683
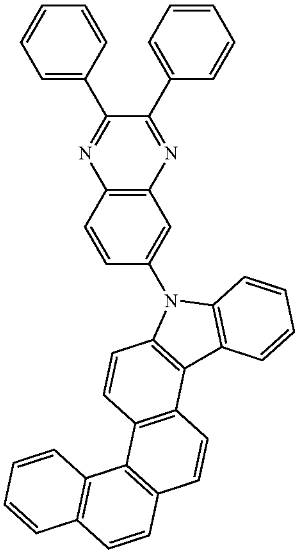
C-684
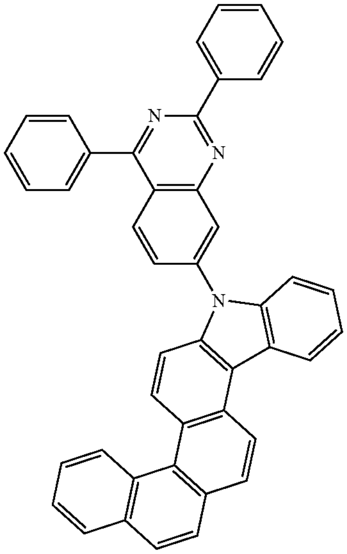
-continued
C-685
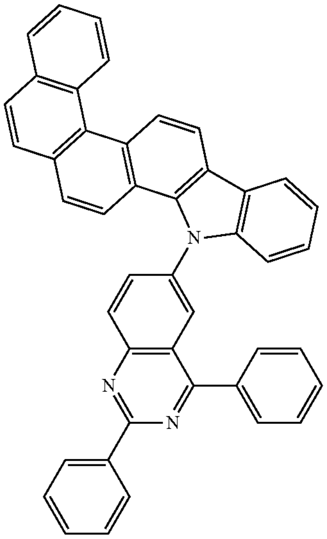
C-686
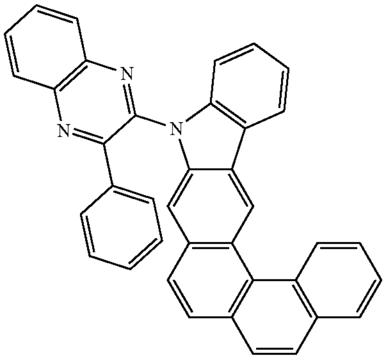
C-687
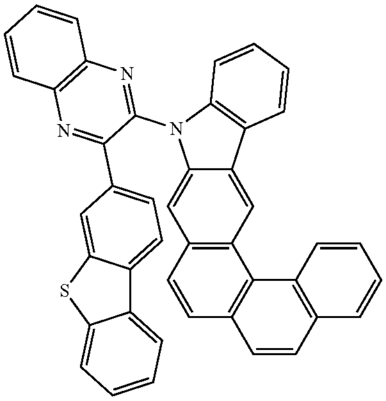

-continued
C-688
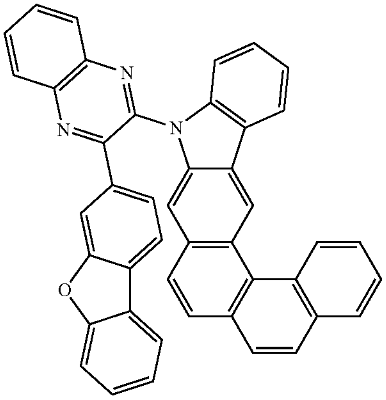
C-689
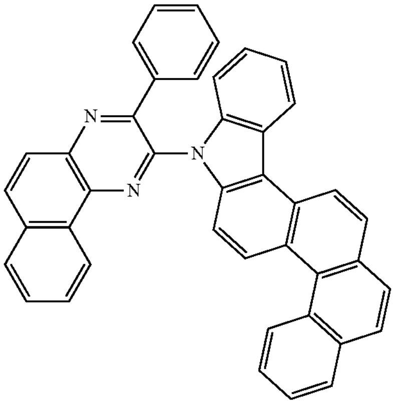
C-690
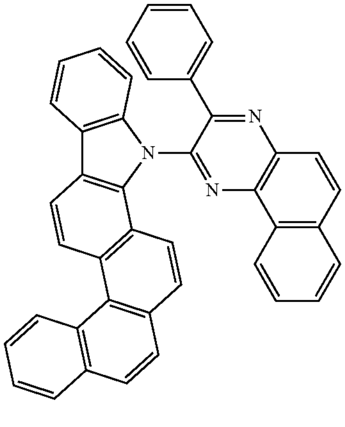
C-691
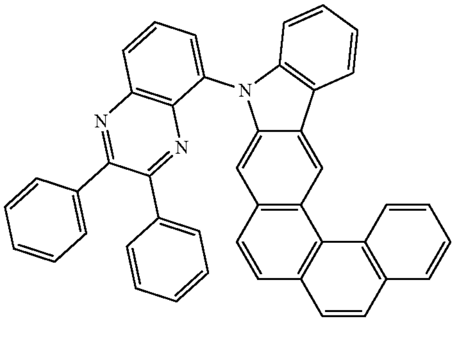
-continued
C-692
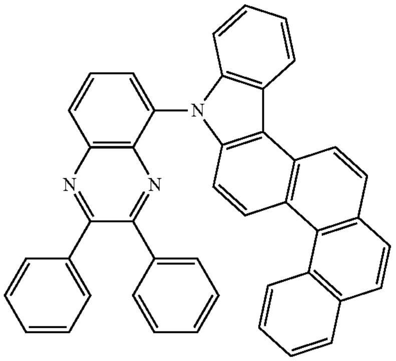
C-693
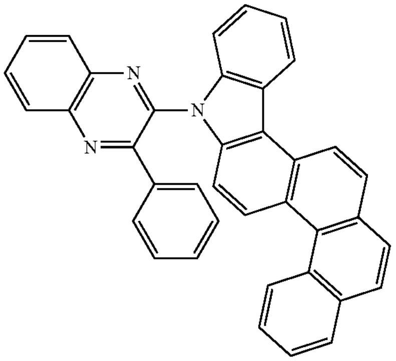
C-694
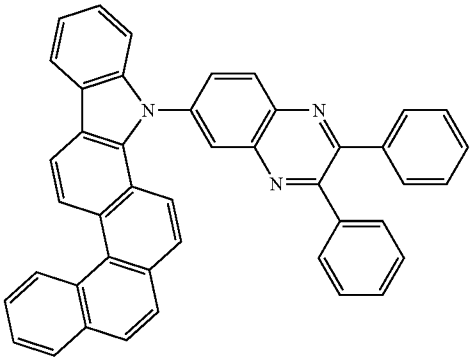
C-695
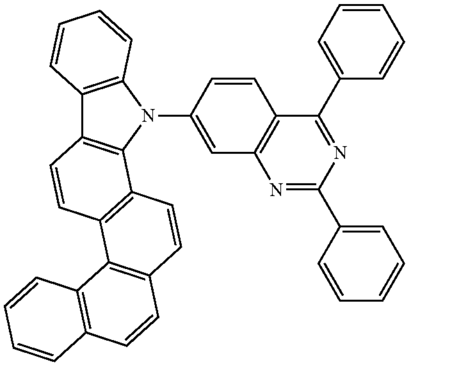

-continued
C-696
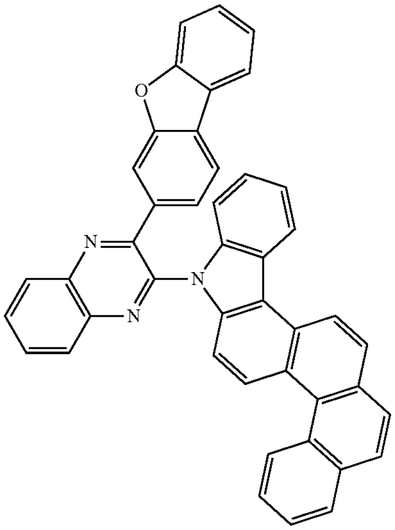
C-697
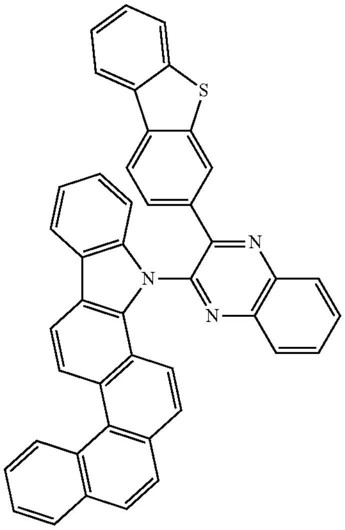
C-698
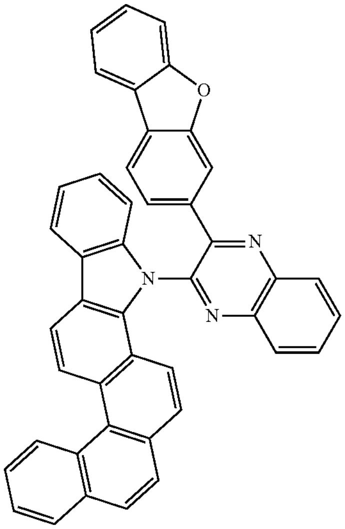
-continued
C-699
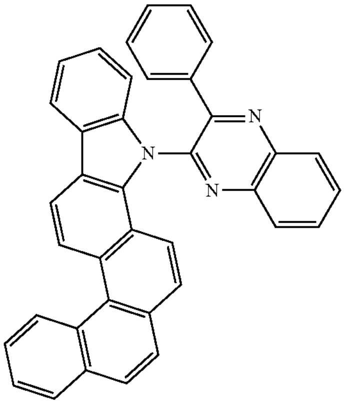
C-700
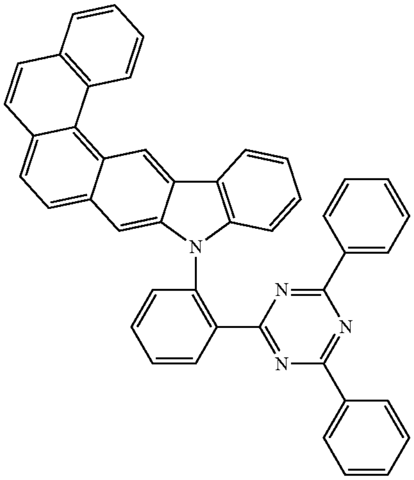
C-701
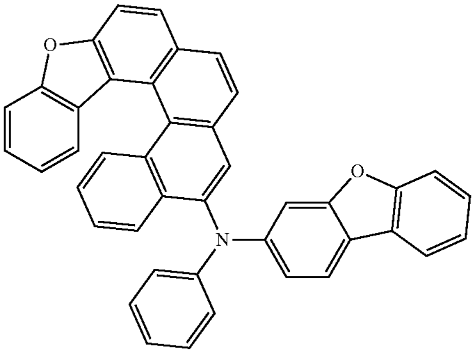

-continued
C-702
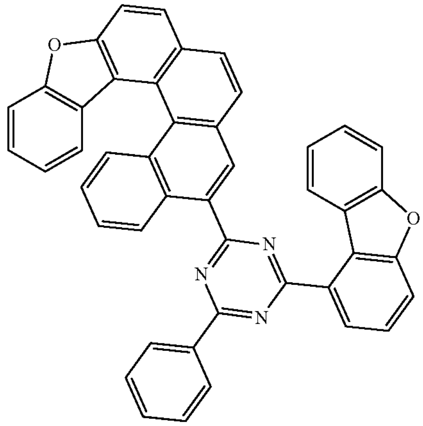
C-703
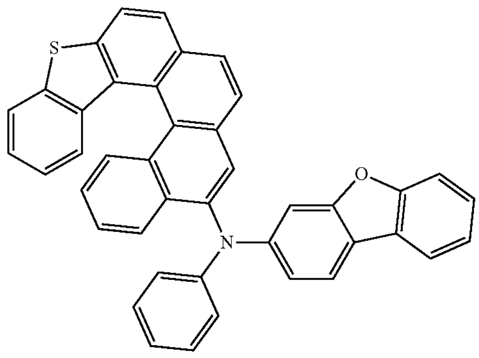
C-704
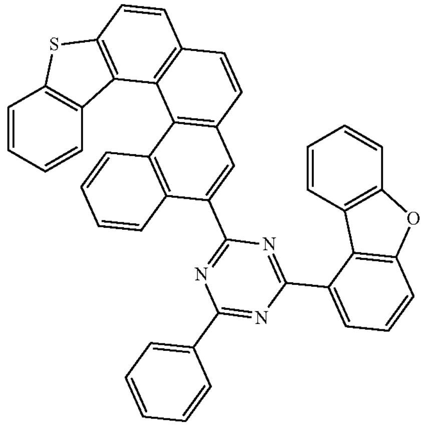
-continued
C-705
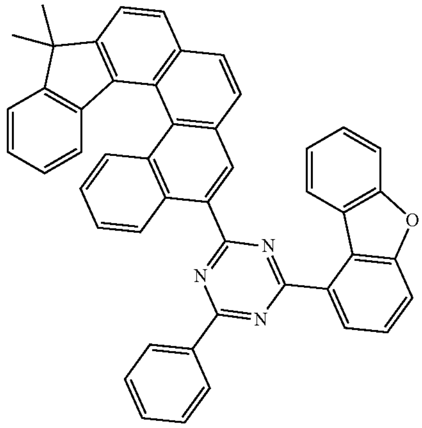
C-706
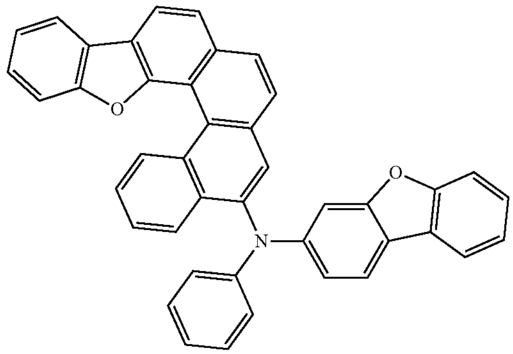
C-707
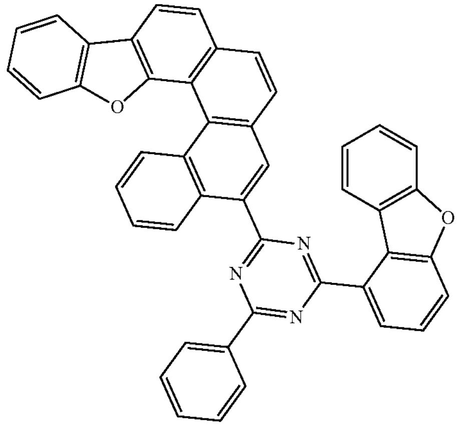
C-708
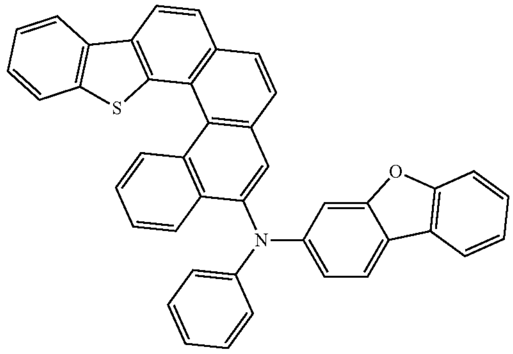

-continued
C-709
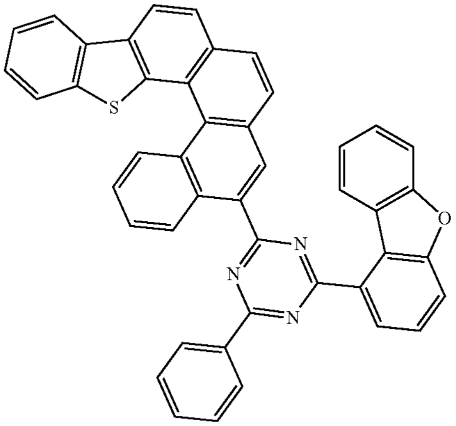
C-710
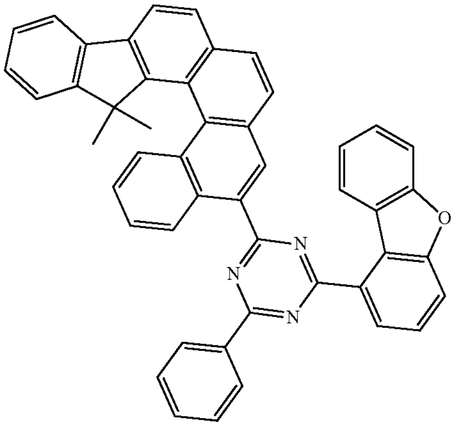
C-711
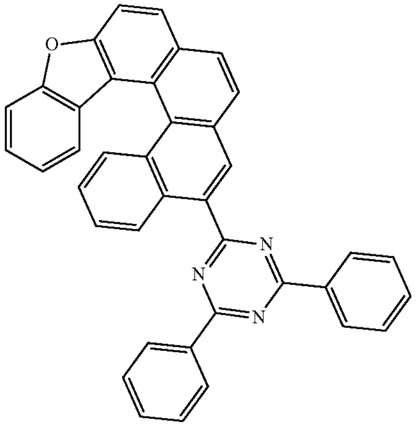
-continued
C-712
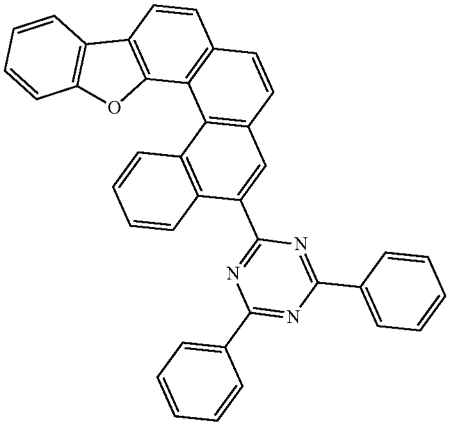
C-713
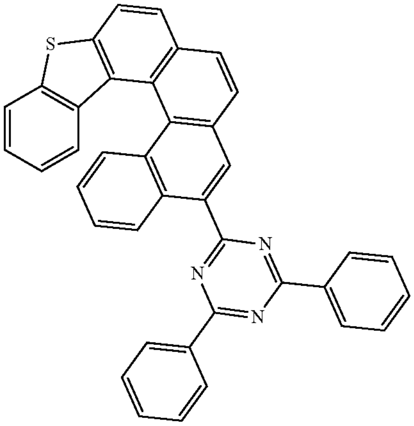
C-714
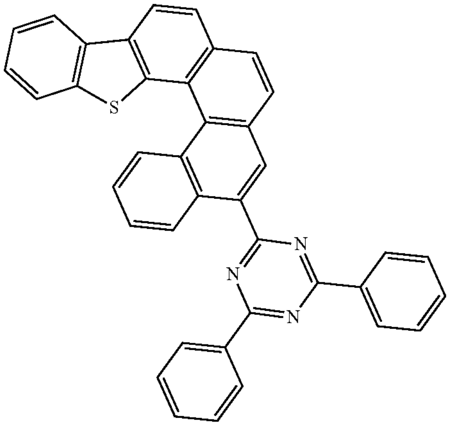
C-715
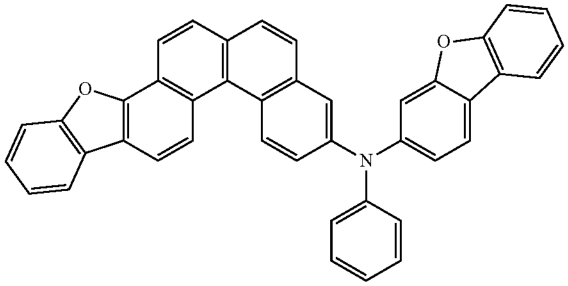

-continued
C-716
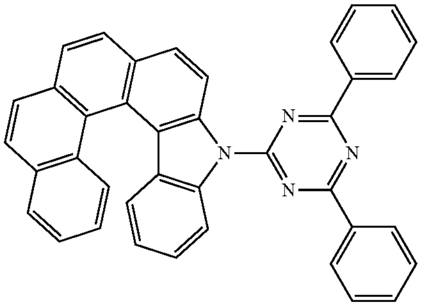
C-717
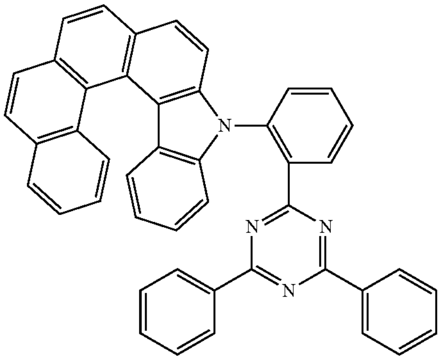
C-718
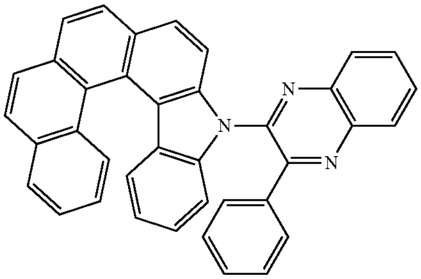
C-719
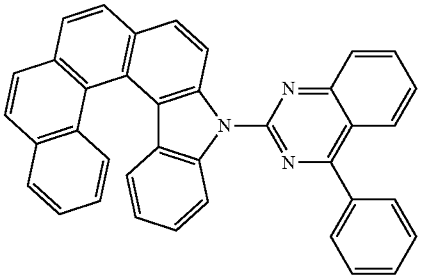
C-720
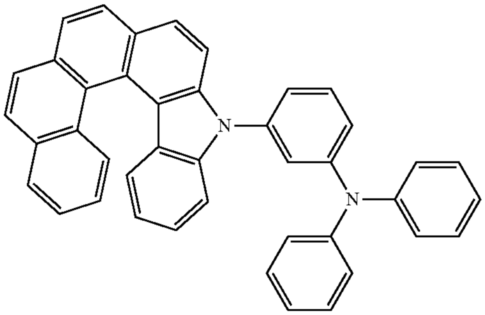
-continued
C-721
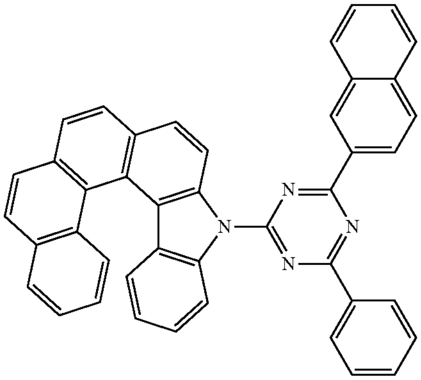
C-722
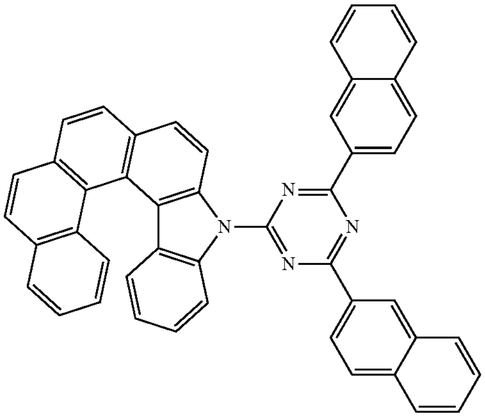
C-723
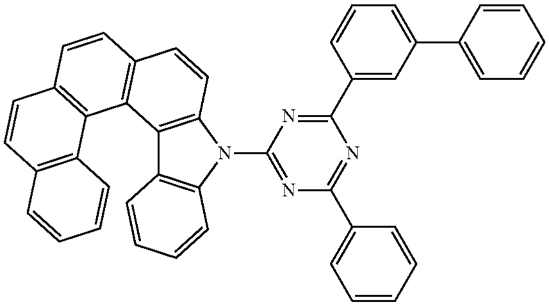
C-724
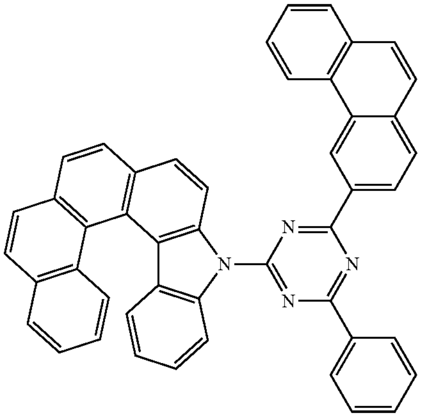

-continued

C-725

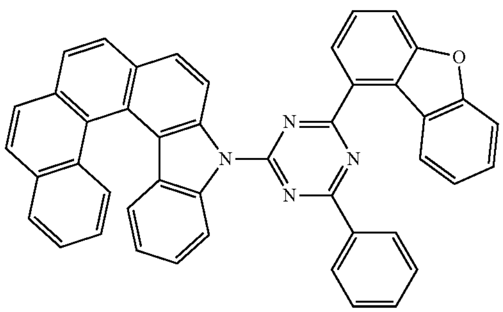

C-726

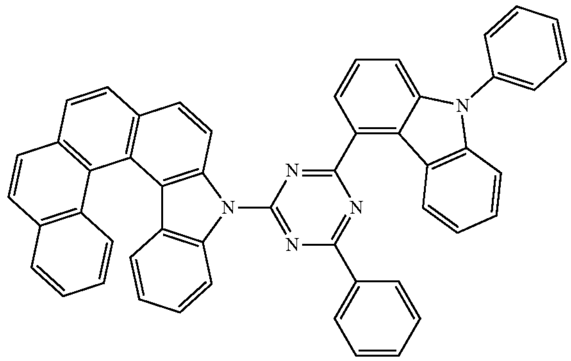

C-727

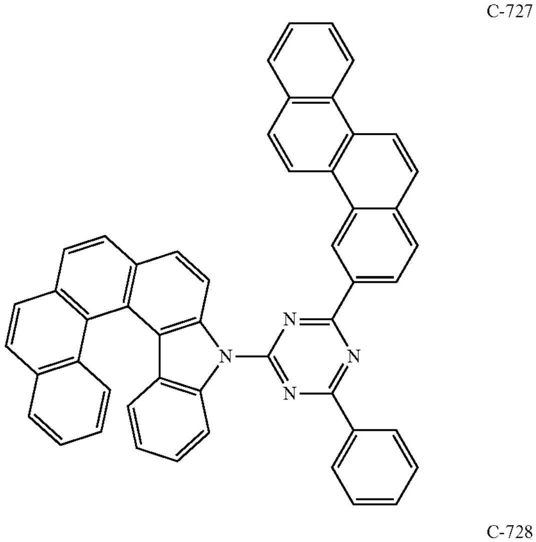

C-728

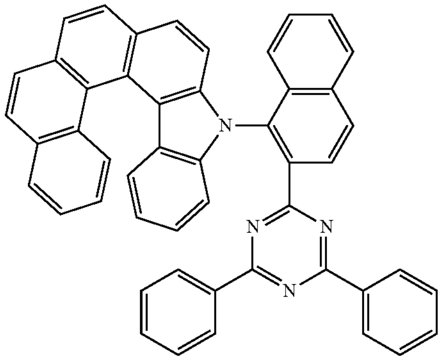

and

-continued

C-729

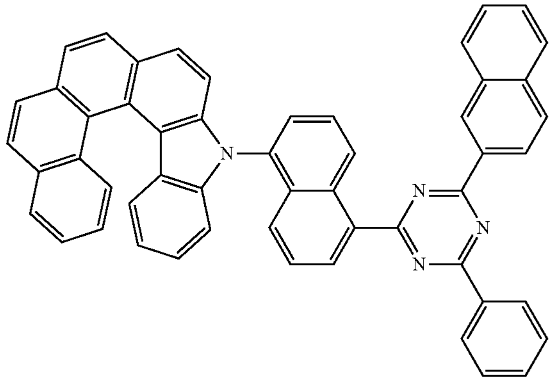

.

9. An organic electroluminescent material comprising the organic electroluminescent compound of claim 1.

10. An organic electroluminescent device comprising the organic electroluminescent compound of claim 1.

11. The organic electroluminescent device according to claim 10, wherein the organic electroluminescent compound is comprised in a light-emitting layer or a hole transport zone.

12. The organic electroluminescent device according to claim 11, wherein when the organic electroluminescent compound is comprised in a light-emitting layer, the light-emitting layer further comprises a compound represented by the following formula 2:

2

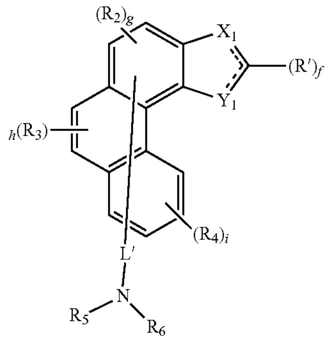

wherein $X_1$ and $Y_1$ each independently represent —N═, —$NR_7$—, —O—, or —S—, with the proviso that any one of $X_1$ and $Y_1$ represents —N═, and the other of $X_1$ and $Y_1$ represents-$NR_7$—, —O—, or —S—;

R' represents a substituted or unsubstituted C6-C30 aryl, or a substituted or unsubstituted 3- to 30-membered heteroaryl;

$R_2$ to $R_7$ each independently represent hydrogen, deuterium, a halogen, a cyano, a substituted or unsubstituted C1-C30 alkyl, a substituted or unsubstituted C6-C30 aryl, a substituted or unsubstituted 3- to 30-membered heteroaryl, a substituted or unsubstituted C3-C30 cycloalkyl, a substituted or unsubstituted C1-C30 alkoxy, a substituted or unsubstituted triC1-C30 alkylsilyl, a substituted or unsubstituted diC1-C30 alkylC6-C30 arylsilyl, a substituted or unsubstituted C1-C30 alkyldiC6-C30 arylsilyl, a substituted or unsubstituted triC6-C30 arylsilyl, a substituted or unsubstituted fused ring group of a C3-C30 aliphatic rings and a C6-C30 aromatic rings, a substituted or unsubstituted mono- or di-C1-C30 alkylamino, a substituted or unsubstituted mono- or di-C2-C30 alkenylamino, a substituted or unsubstituted C1-C30 alkylC2-C30 alkenylamino, a substituted or unsubstituted mono- or di-C6-C30 arylamino, a substituted or unsubstituted C1-C30 alkylC6-C30 arylamino, a substituted or unsubstituted mono- or di-3- to 30-membered heteroarylamino, a substituted or unsubstituted C1-C30 alkyl3- to 30-membered heteroarylamino, a substituted or unsubstituted C2-C30 alkenylC6-C30 arylamino, a substituted or unsubstituted C2-C30 alkenyl3- to 30-membered heteroarylamino, or a substituted or unsubstituted C6-C30 aryl3- to 30-membered heteroarylamino; or may be linked to an adjacent substituent to form a rings;

L' represents a single bond, a substituted or unsubstituted C6-C30 arylene, or a substituted or unsubstituted 3- to 30-membered heteroarylene; and f represents 1, g and h each independently represent 1 or 2, i represents an integer of 1 to 4, where if each of g to i is an integer of 2 or more, each of $R_2$ to each of $R_4$ may be the same or different.

13. The organic electroluminescent device according to claim 12, wherein the compound represented by formula 2 is selected from the following compounds:

H1-1

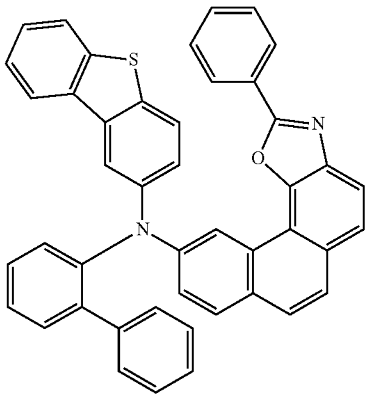

H1-2

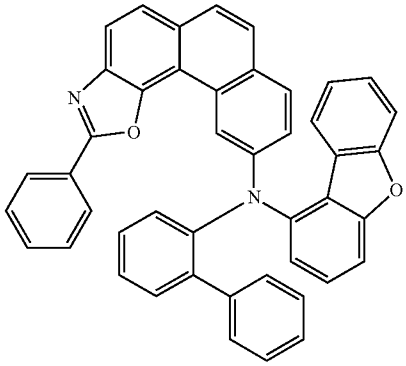

-continued

H1-3

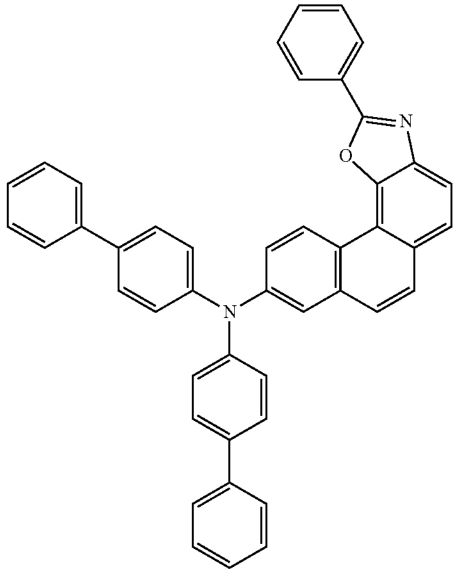

H1-4

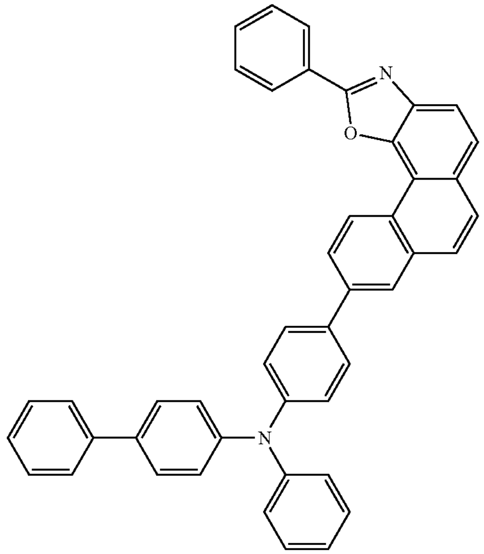

H1-5

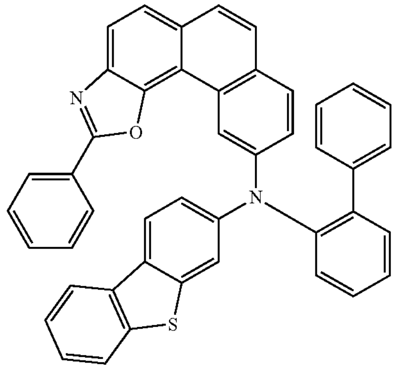

H1-6
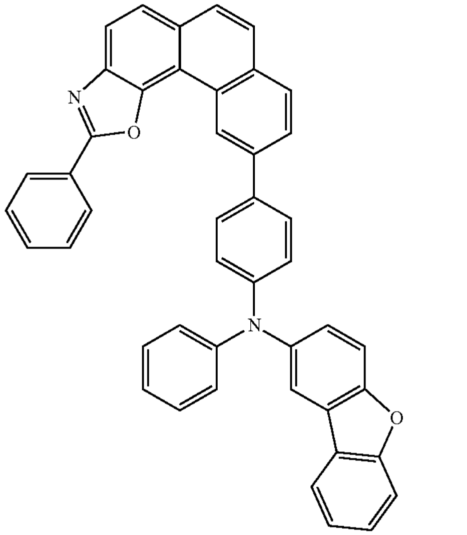
H1-7
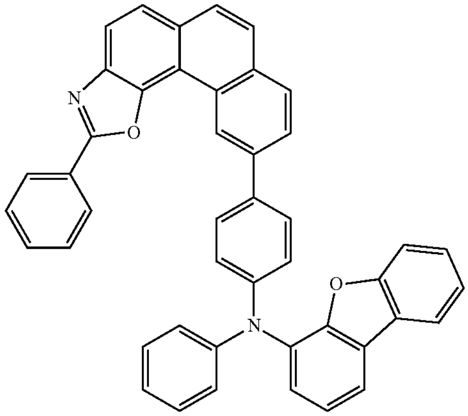
H1-8
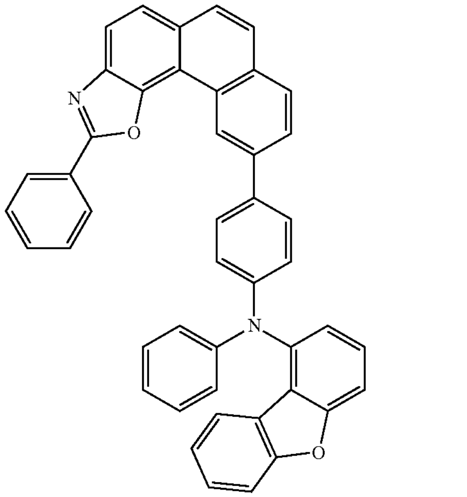
H1-9
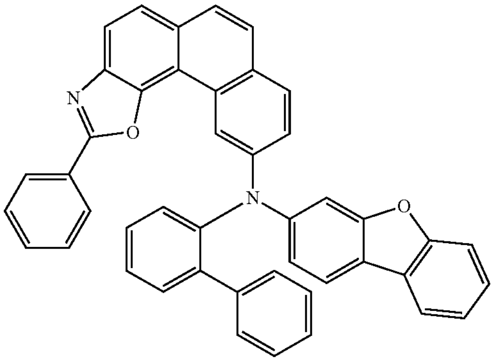
H1-10
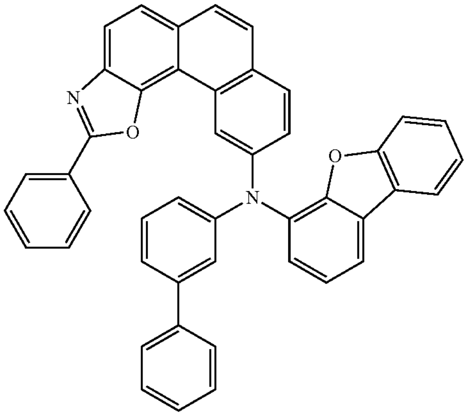
H1-11
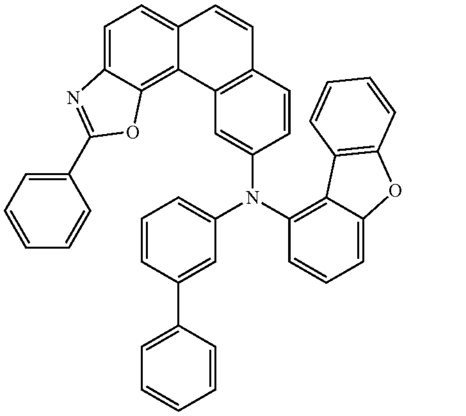
H1-12
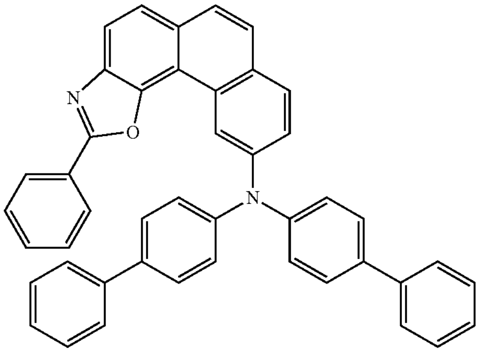

-continued
H1-13
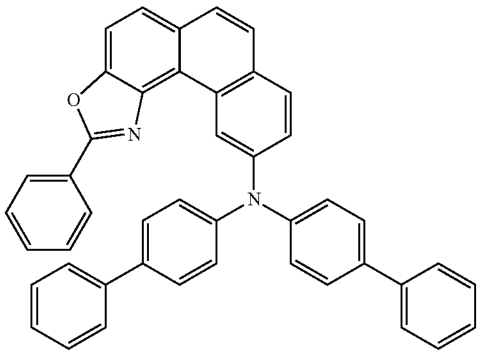
H1-14
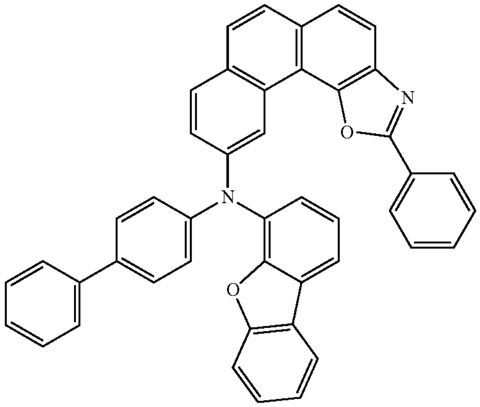
H1-15
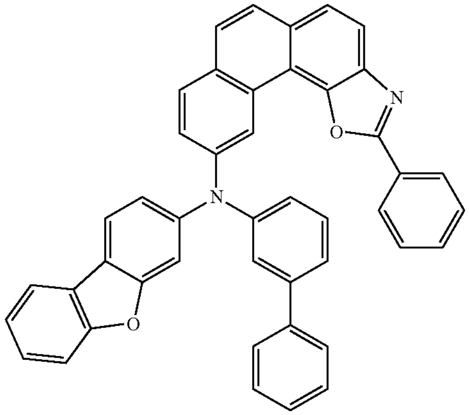
H1-16
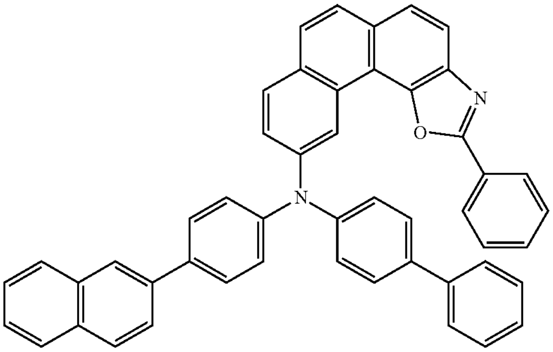
-continued
H1-17
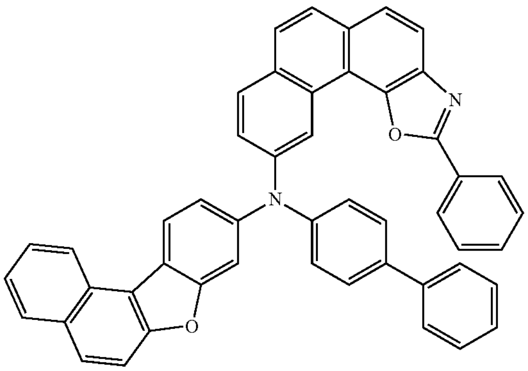
H1-18
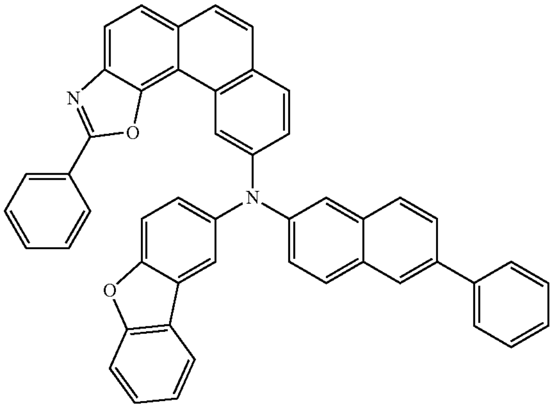
H1-19
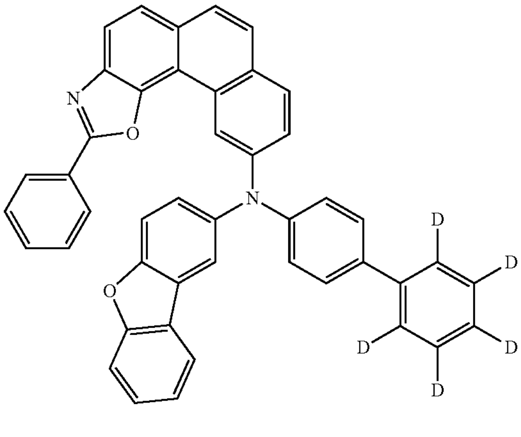

-continued
H1-20
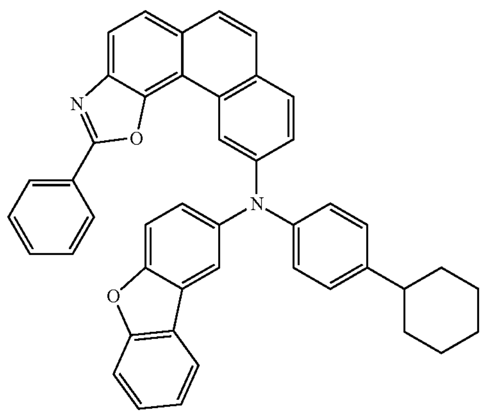
H1-21
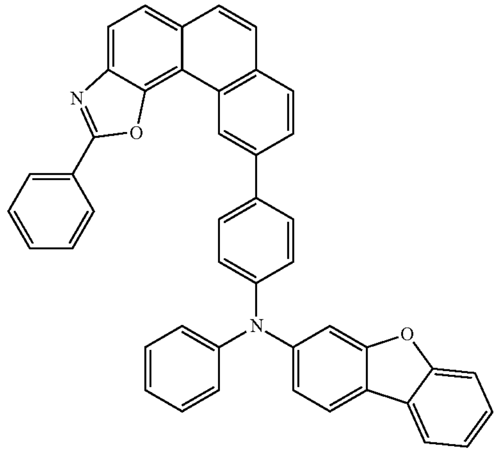
H1-22
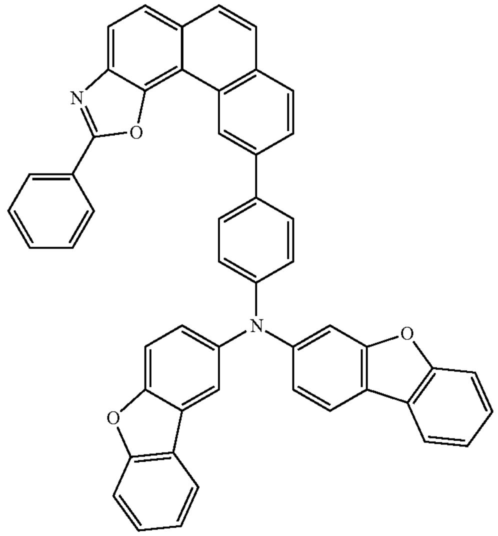
-continued
H1-23
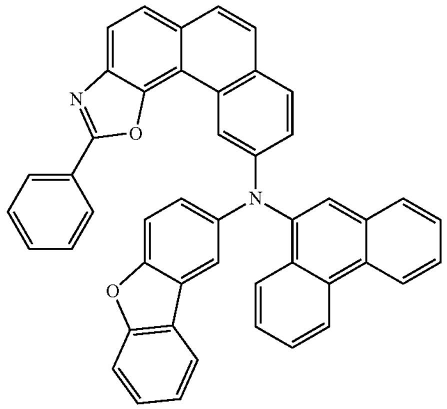
H1-24
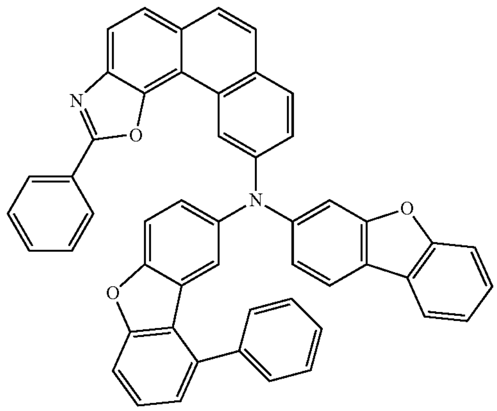
H1-25
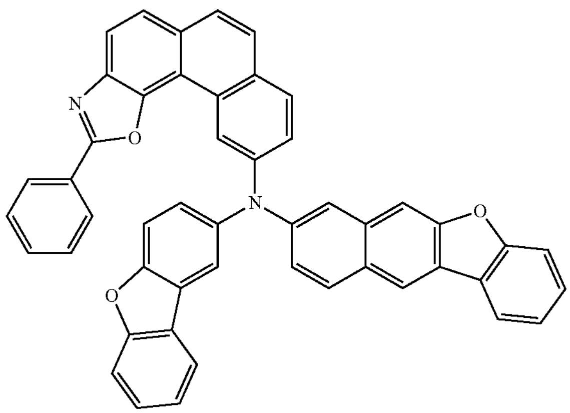

-continued
H1-26
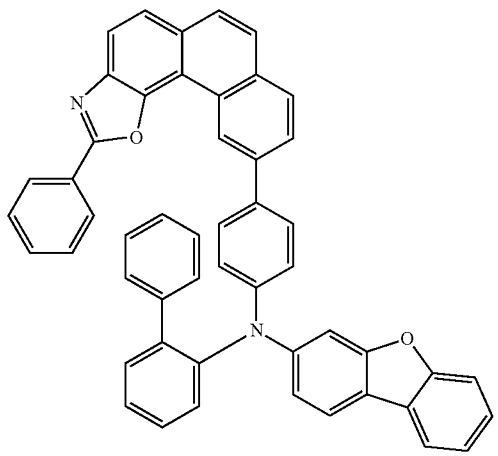
H1-27
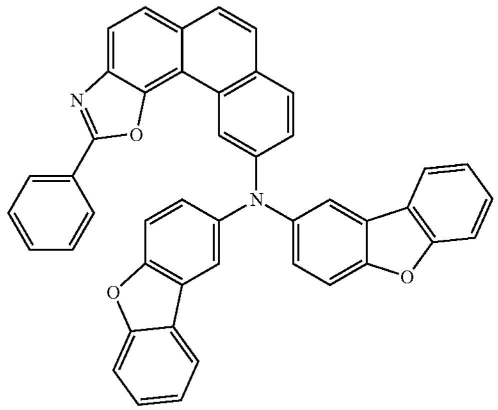
H1-28
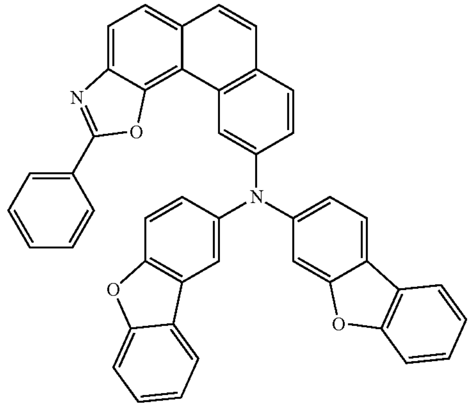
-continued
H1-29
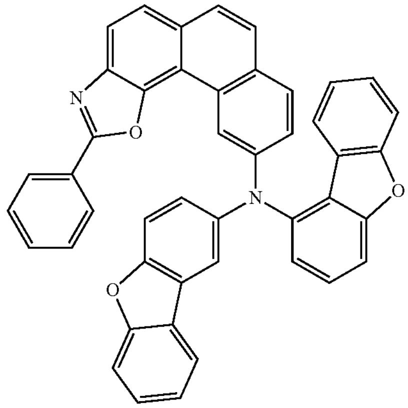
H1-30
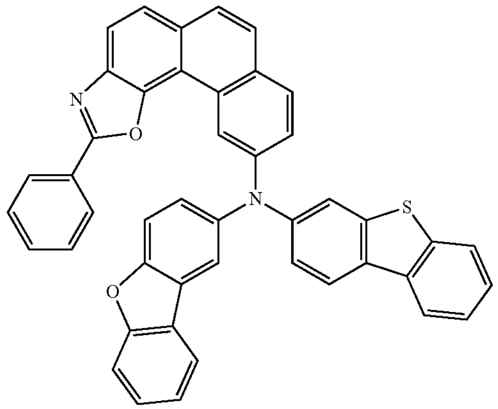
H1-31
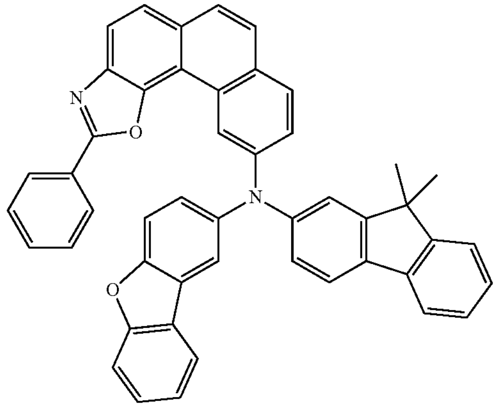

H1-32
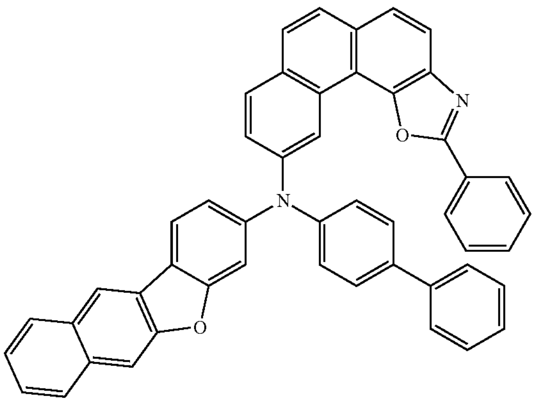
H1-33
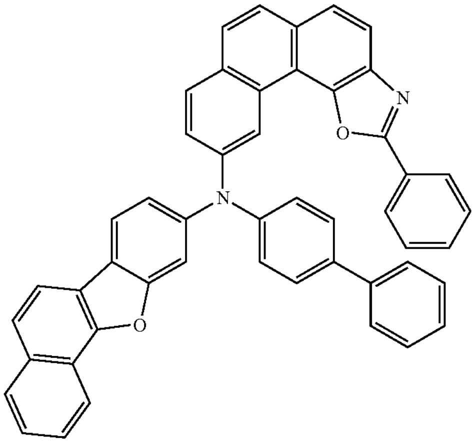
H1-34
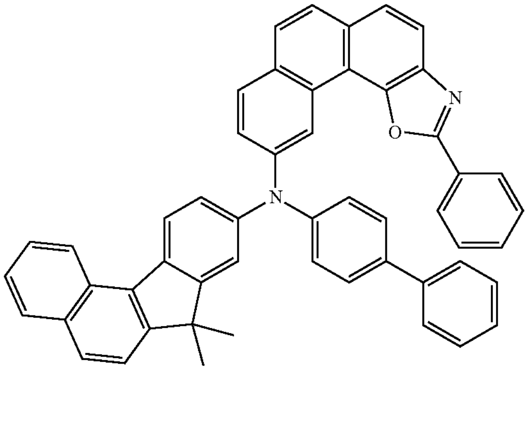
H1-35
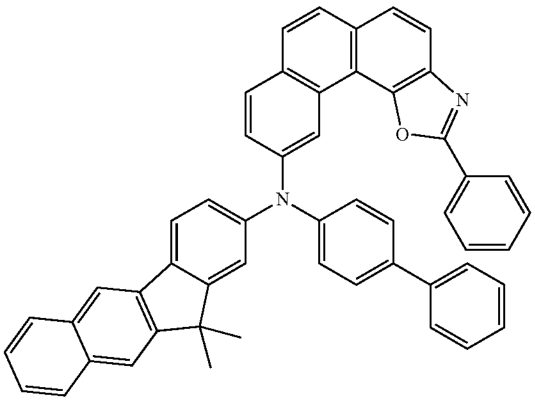
H1-36
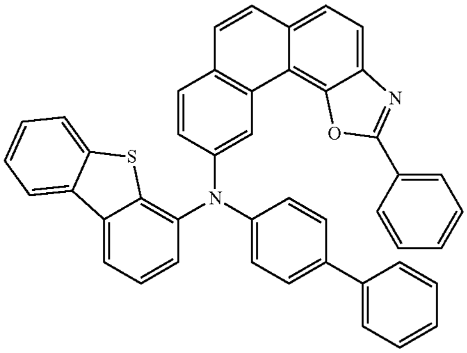
H1-37
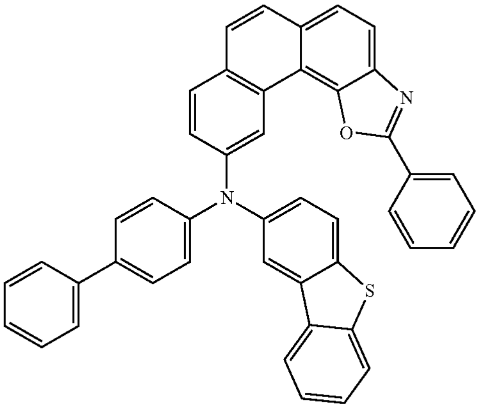
H1-38
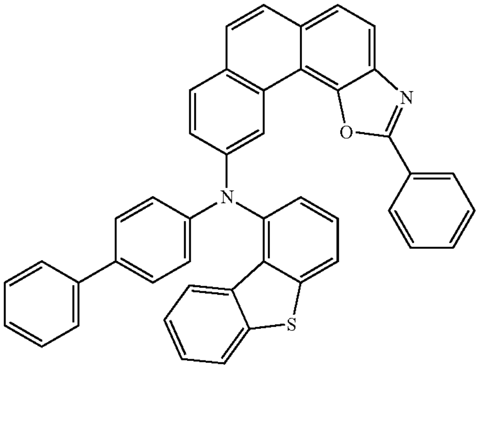

-continued
H1-39
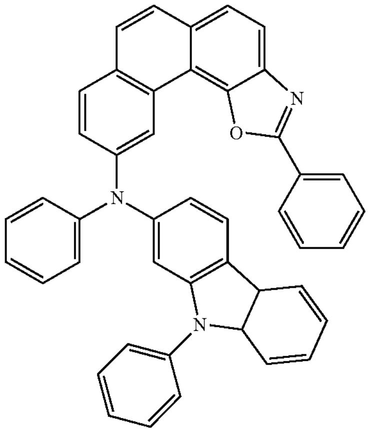
H1-40
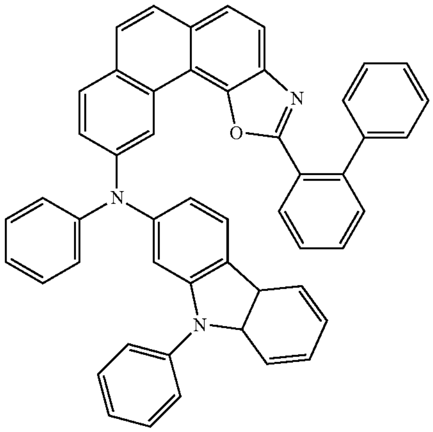
H1-41
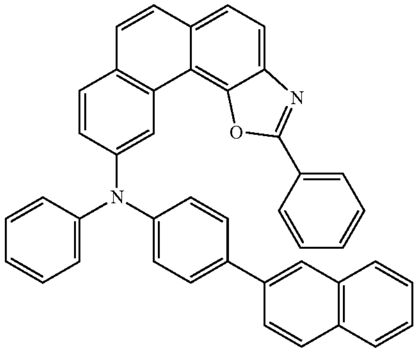
H1-42
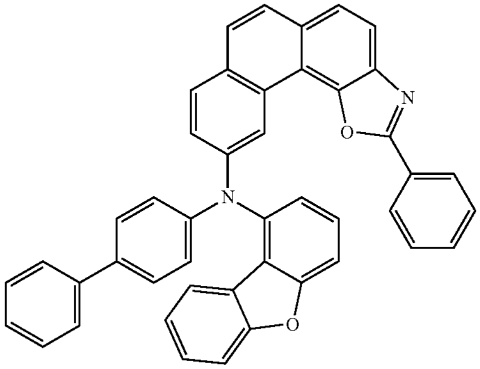
-continued
H1-43
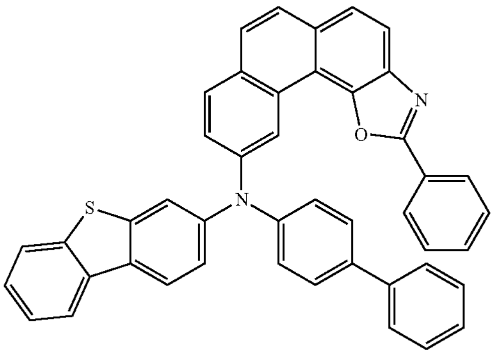
H1-44
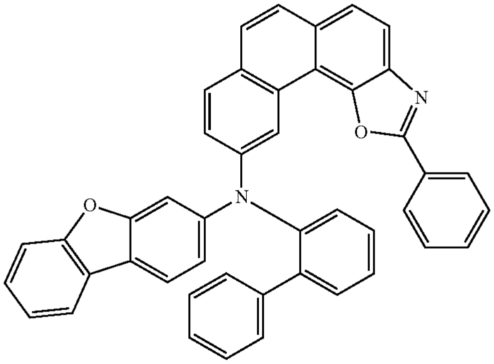
H1-45
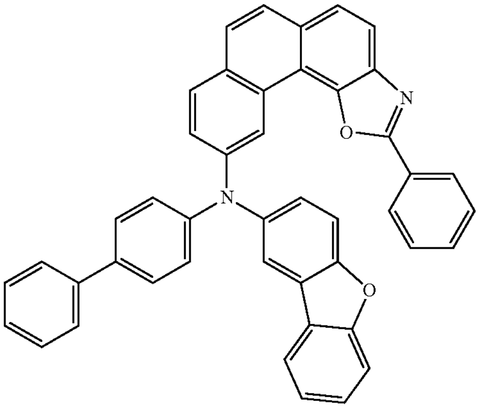
H1-46
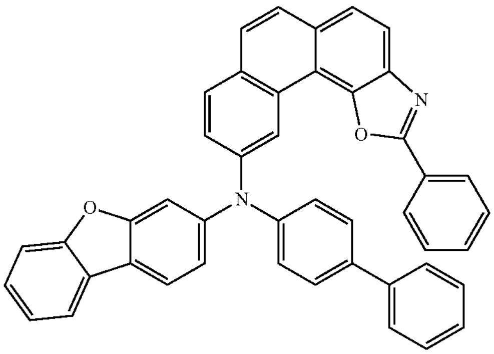

-continued
H1-47
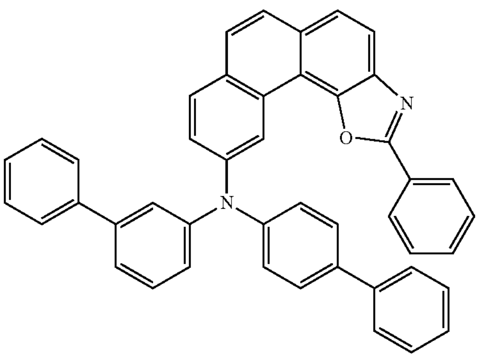
H1-48
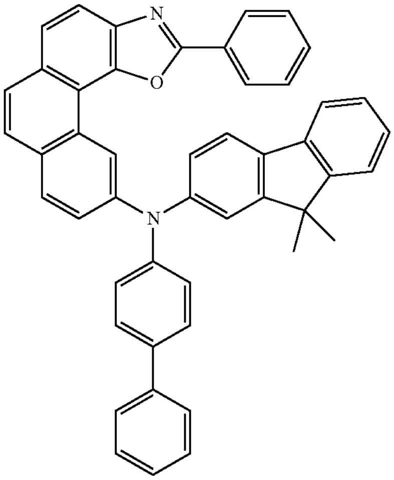
H1-49
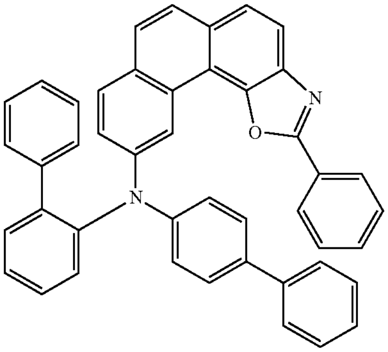
-continued
H1-50
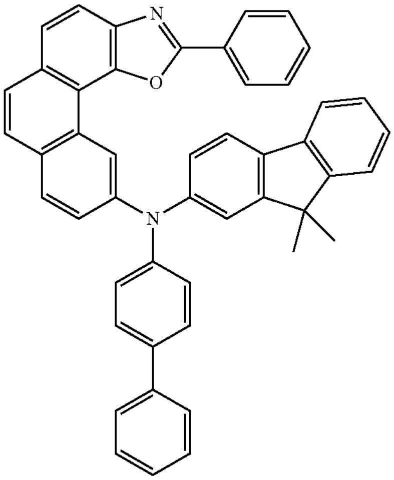
H1-51
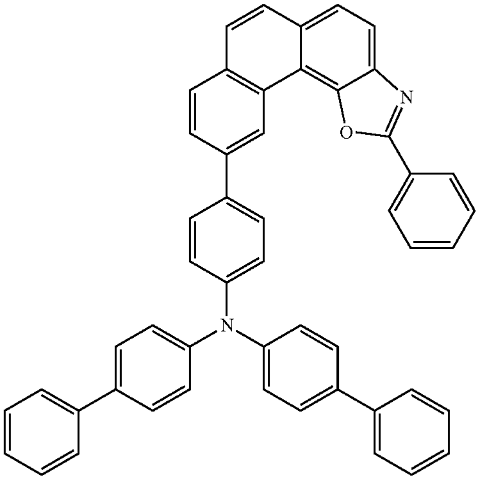
H1-52
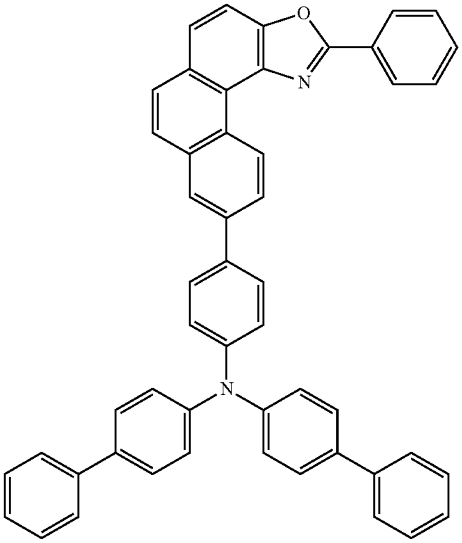

-continued
H1-53
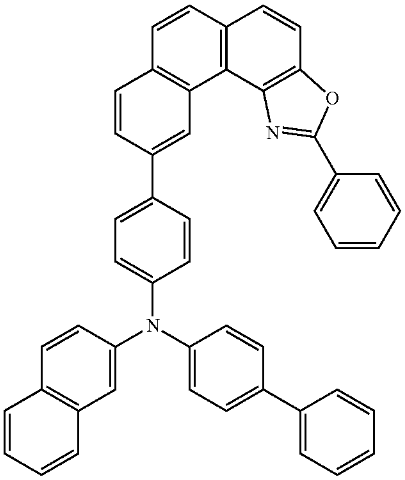
H1-54
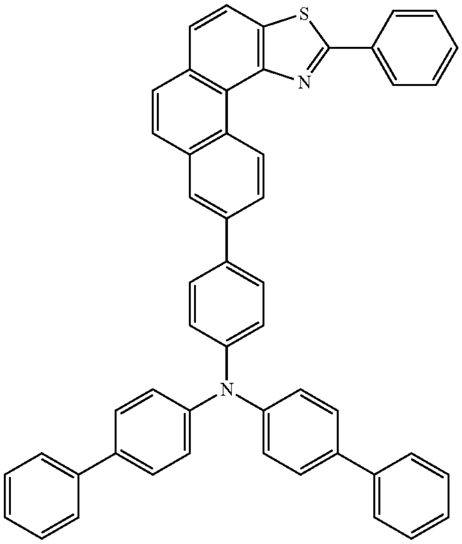
H1-55
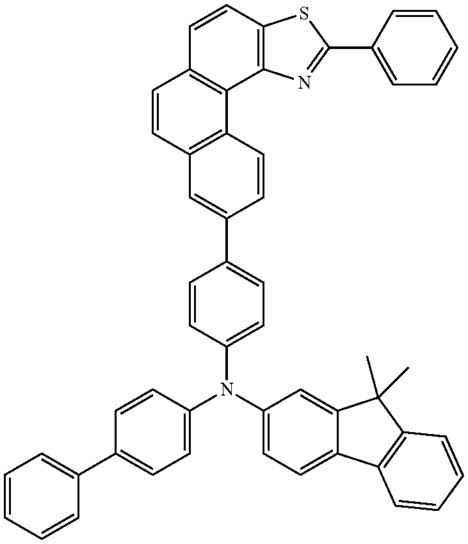
-continued
H1-56
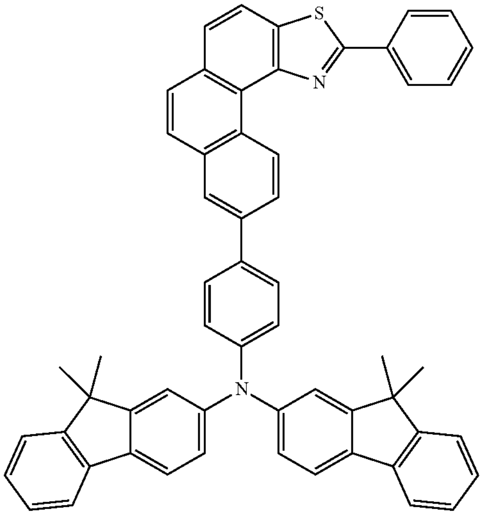
H1-57
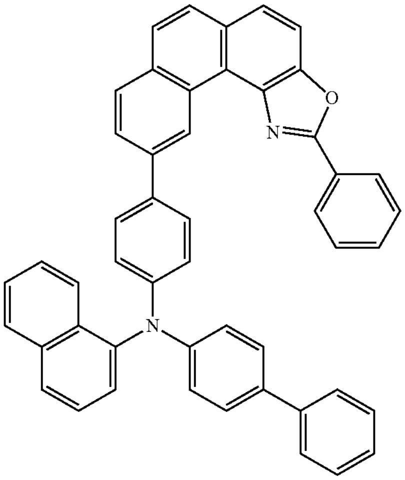
H1-58
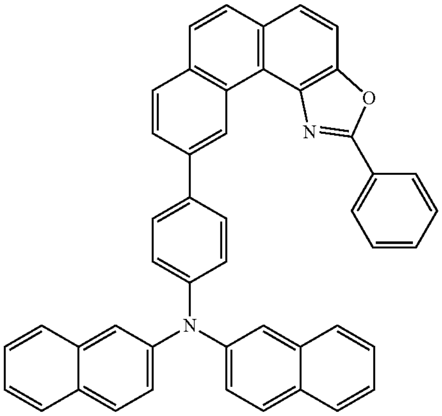

-continued
H1-59
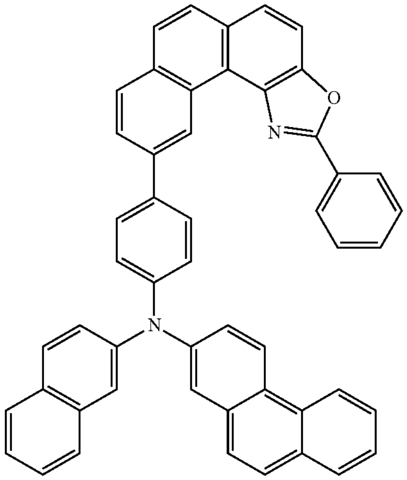
H1-60
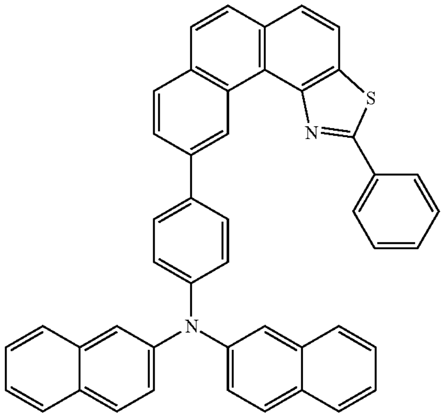
H1-61
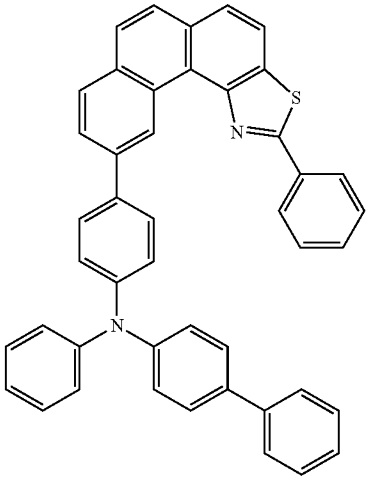
-continued
H1-62
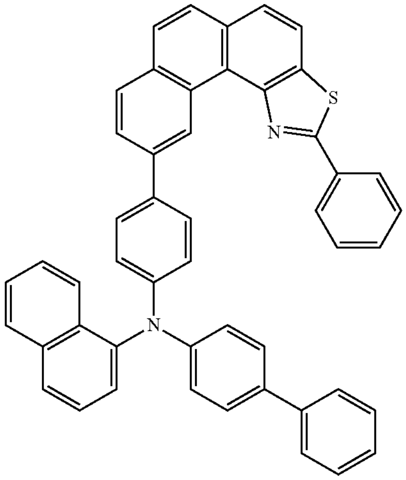
H1-63
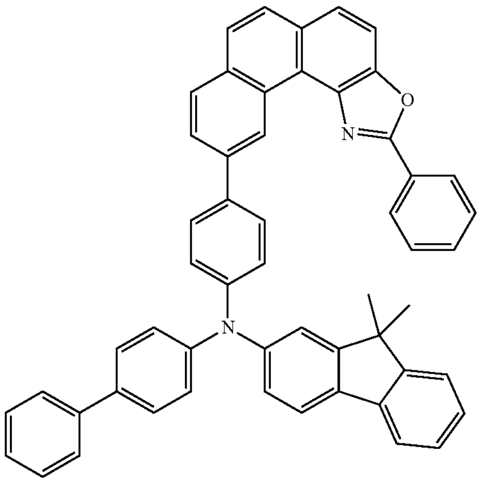
H1-64
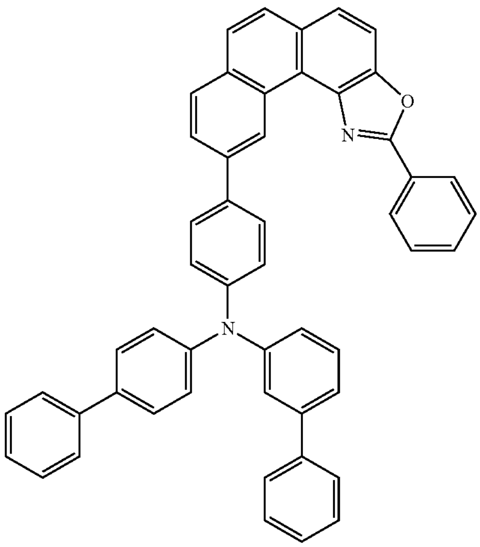

-continued
H1-65
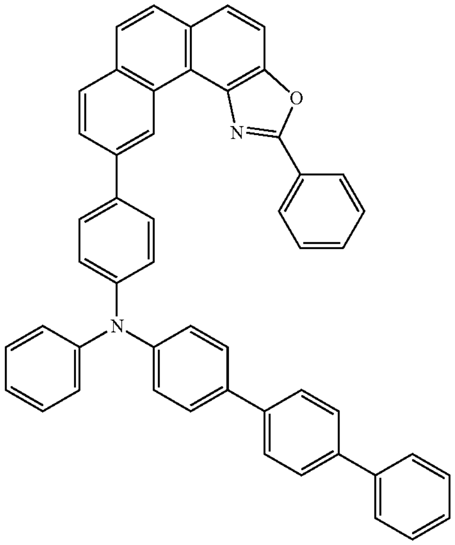
H1-66
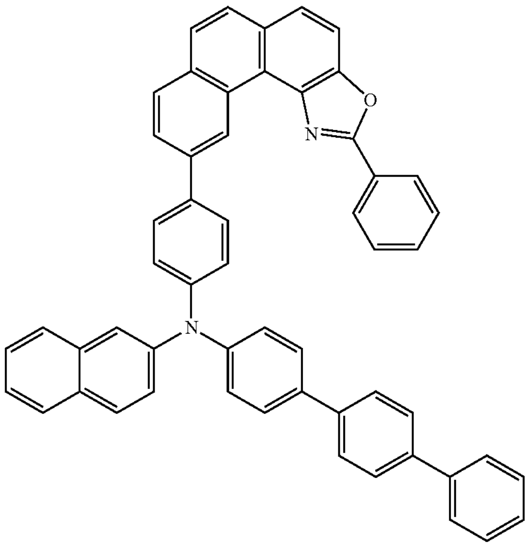
H1-67
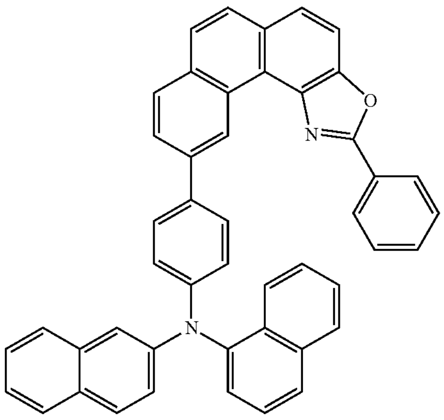
-continued
H1-68
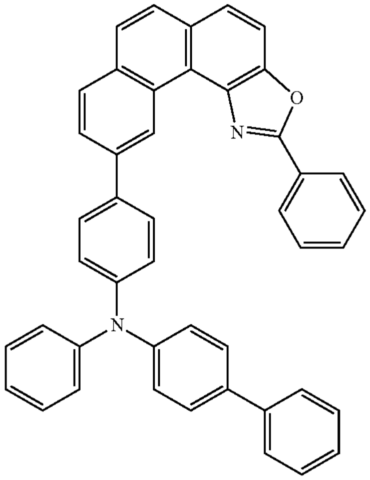
H1-69
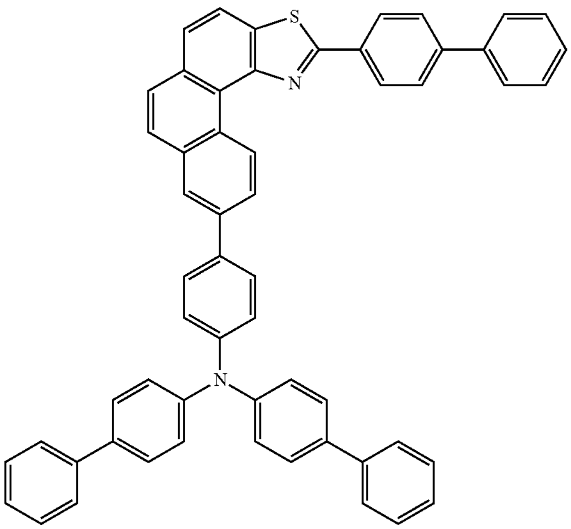
H1-70
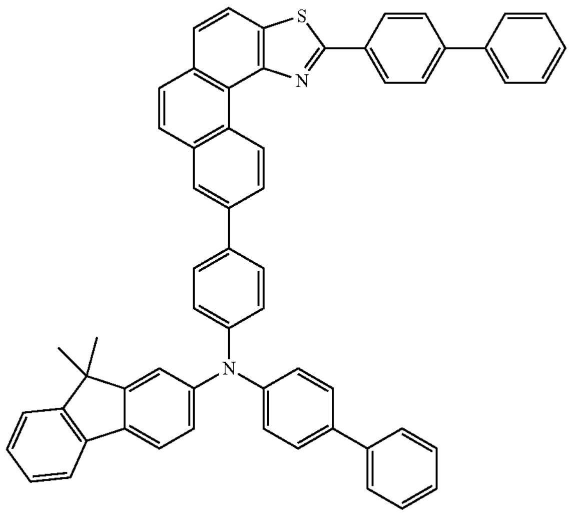

H1-71
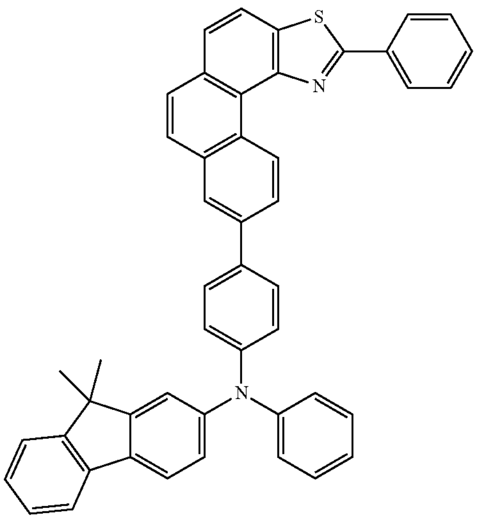
H1-72
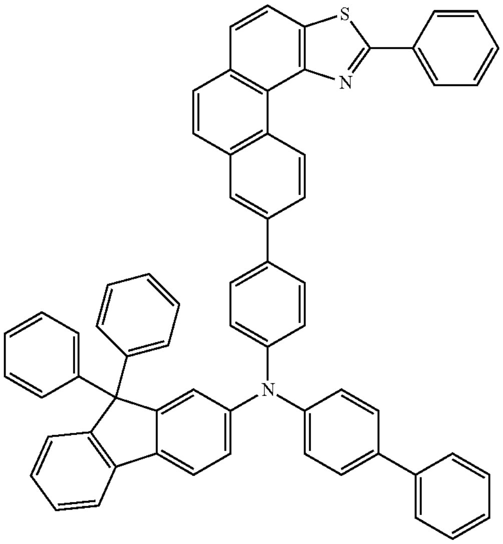
H1-73
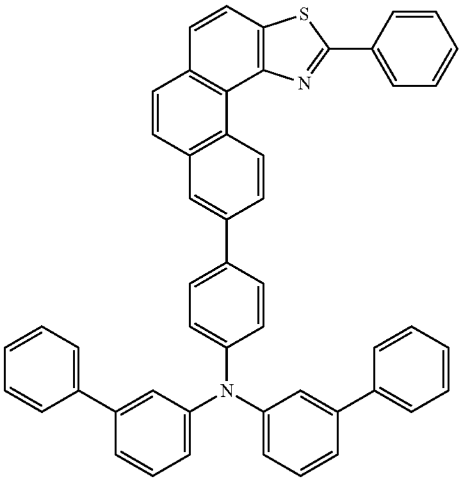
H1-74
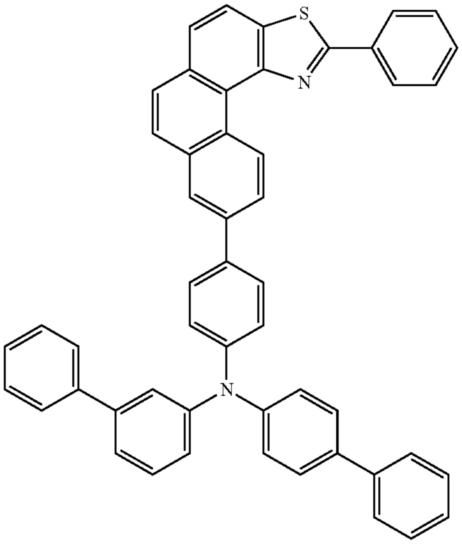
H1-75
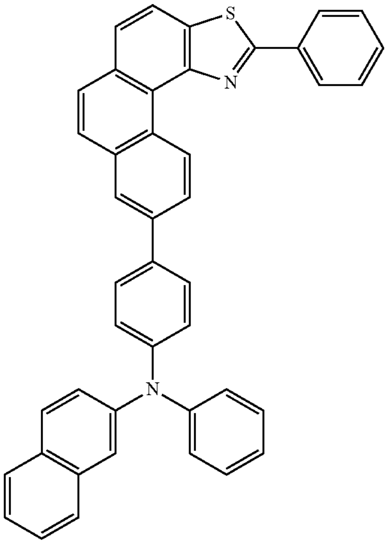
H1-76
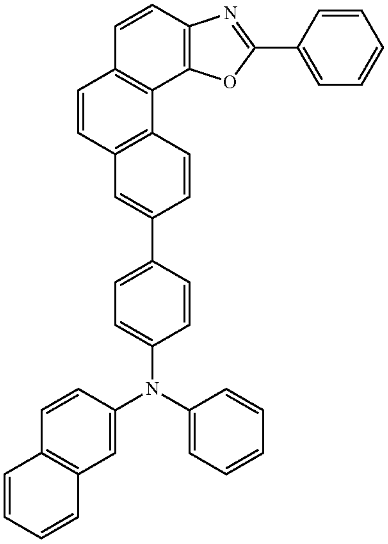

-continued
H1-77
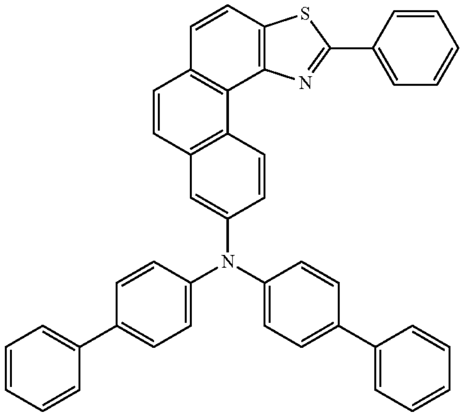
H1-78
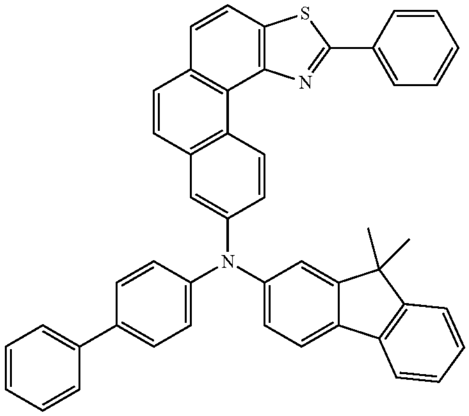
H1-79
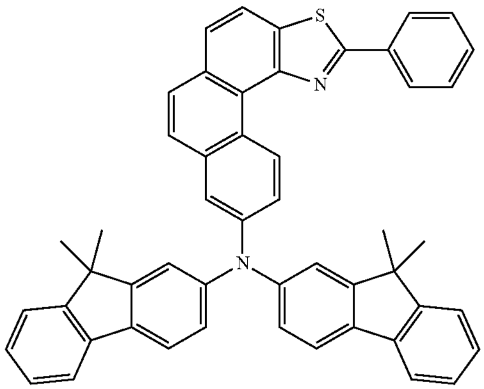
-continued
H1-80
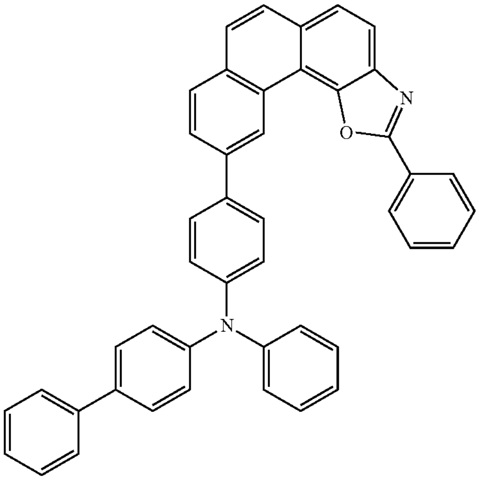
H1-81
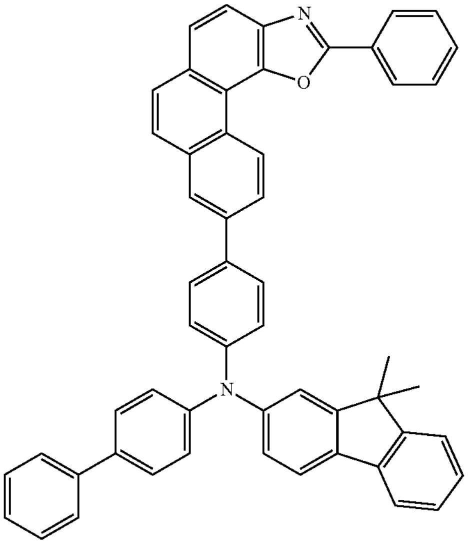
H1-82
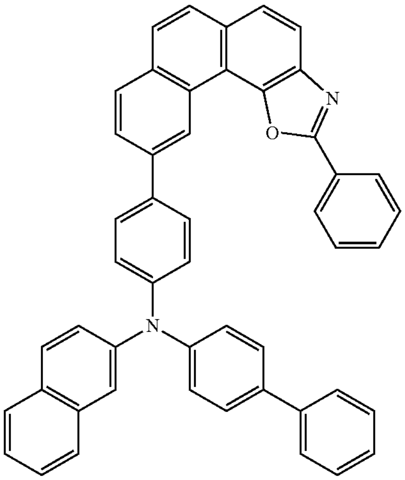

-continued
H1-83
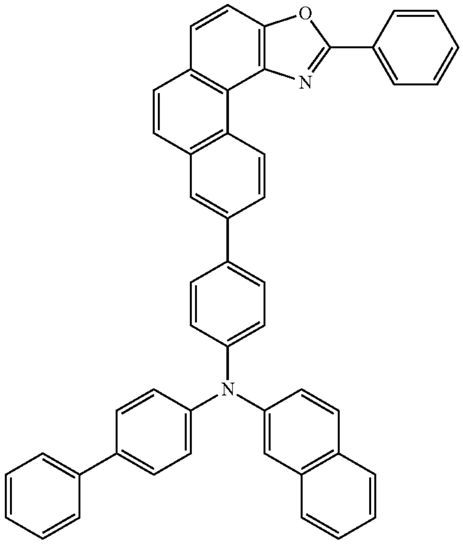
H1-84
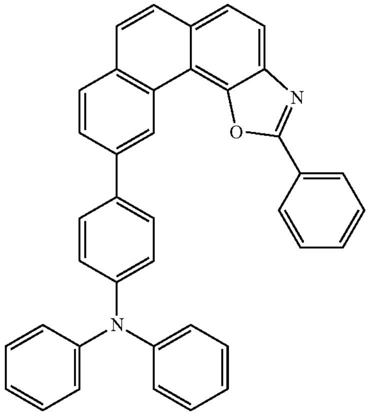
H1-85
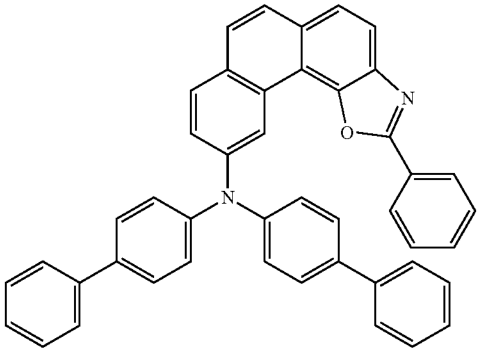
H1-86
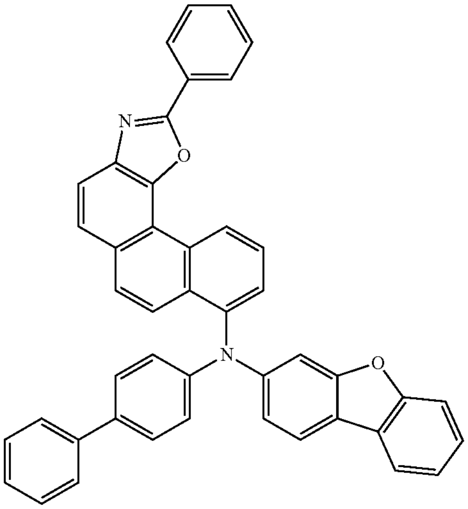
H1-87
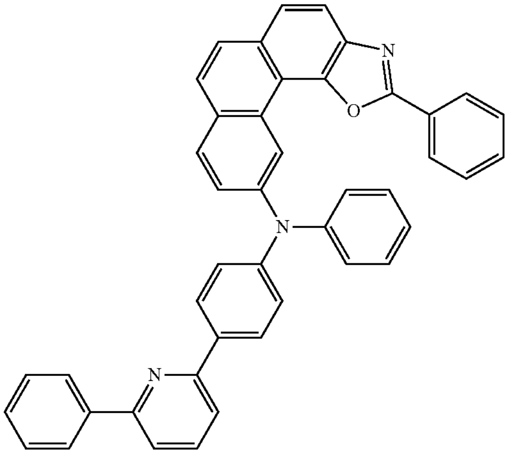
H1-88
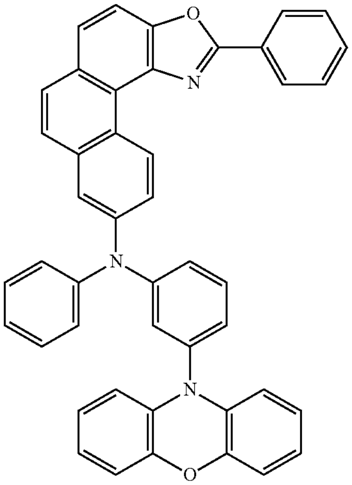

-continued
H1-89
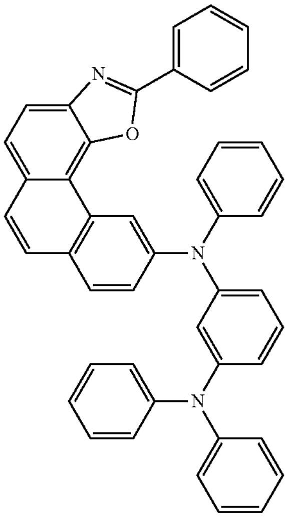
H1-90
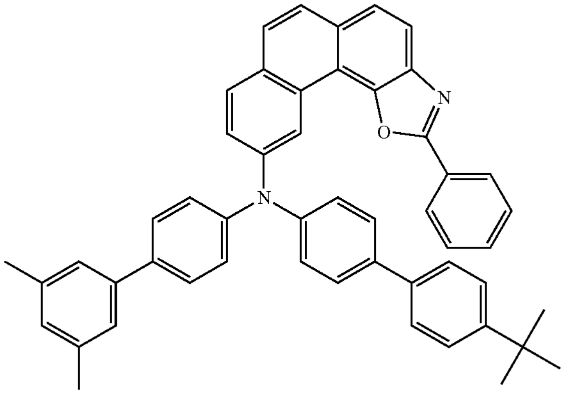
H1-91
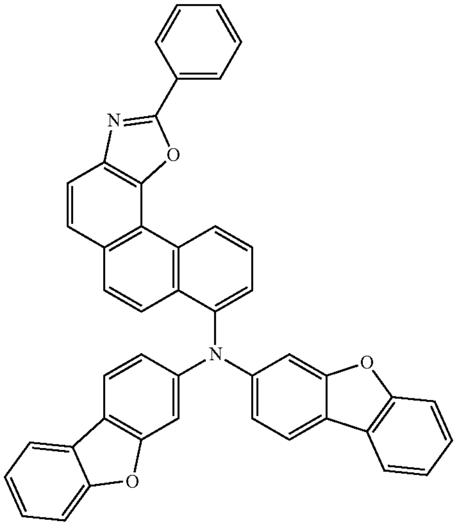
-continued
H1-92
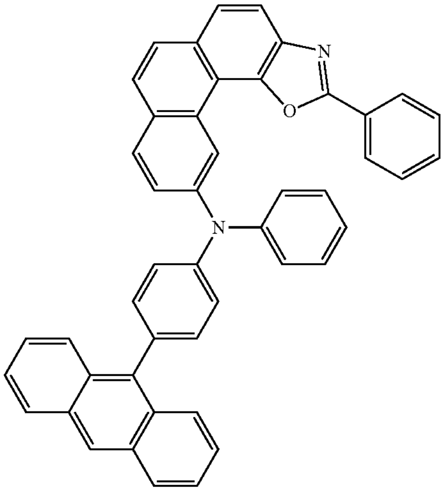
H1-93
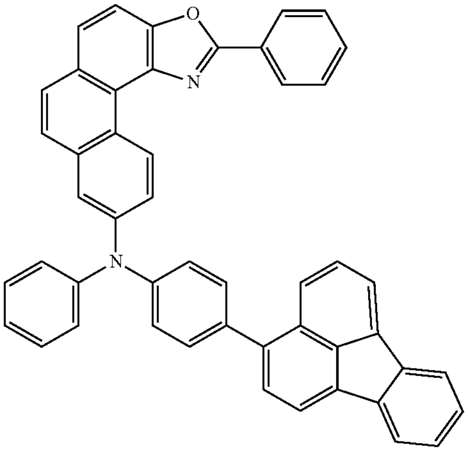
H1-94
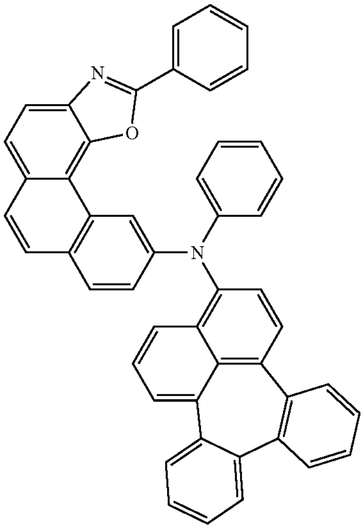

-continued
H1-95
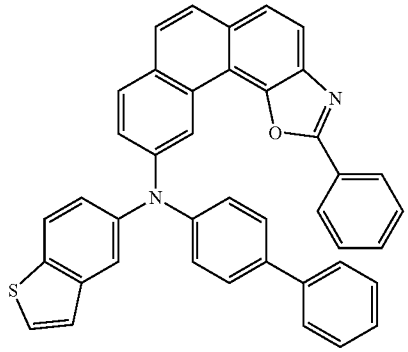
H1-96
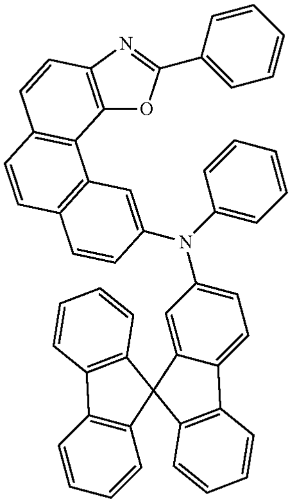
H1-97
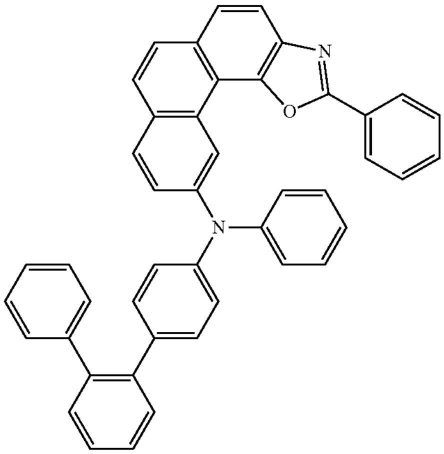
-continued
H1-98
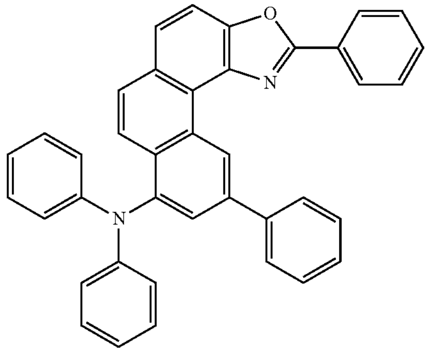
H1-99
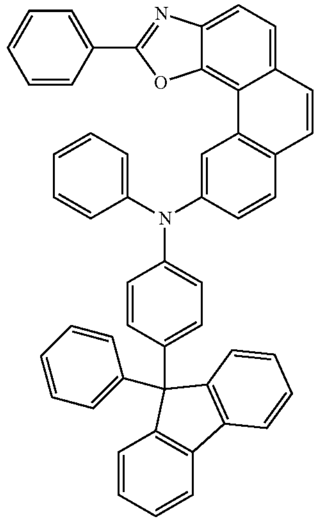
H1-100
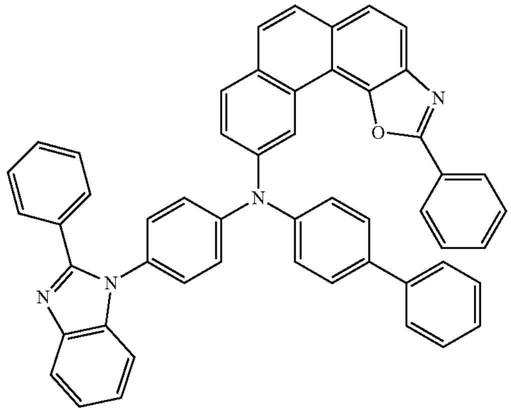

-continued
H1-101
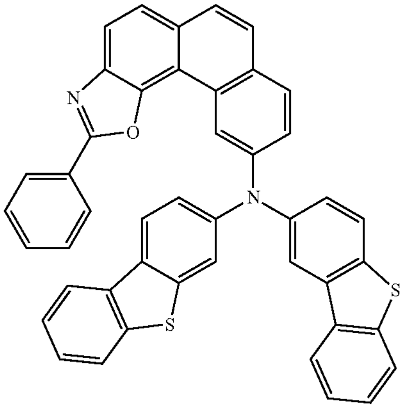
H1-102
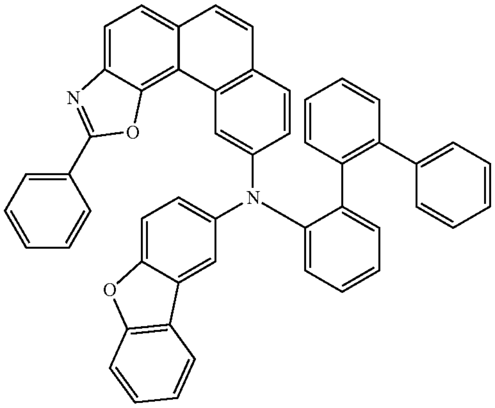
H1-103
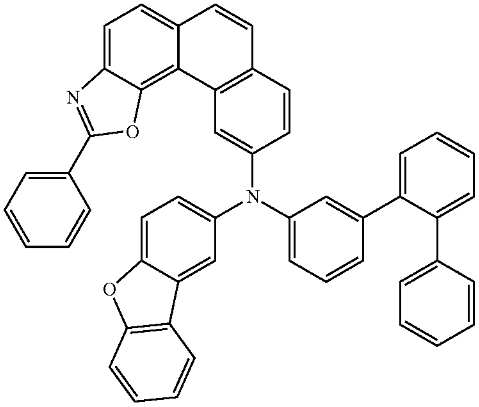
-continued
H1-104
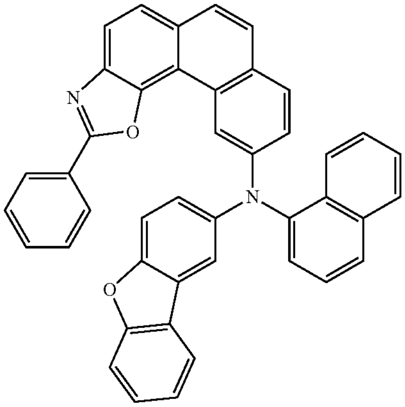
H1-105
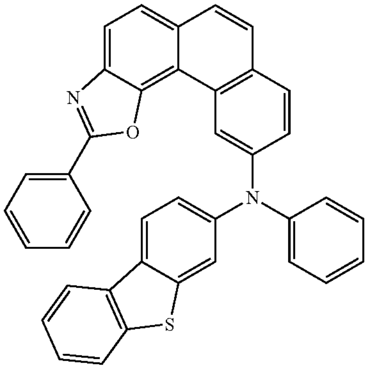
H1-106
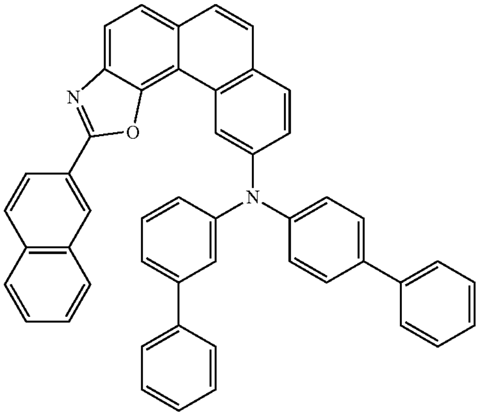

-continued
H1-107
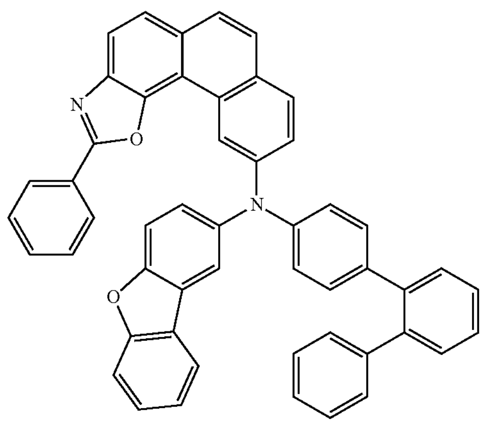
H1-108
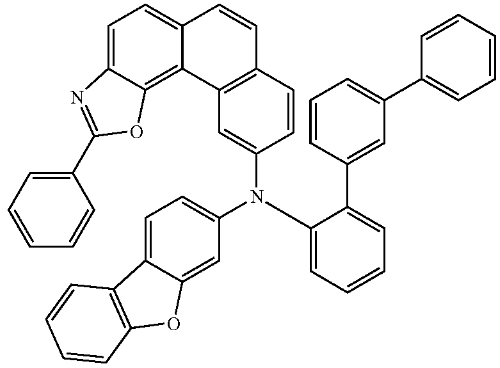
H1-109
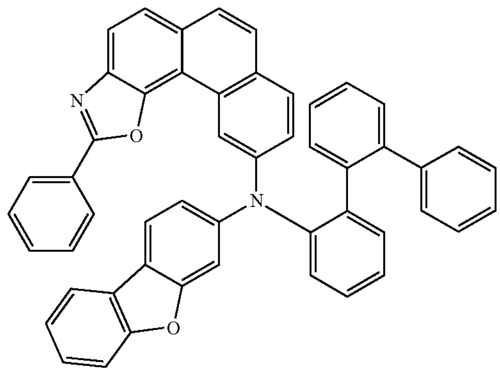
H1-110
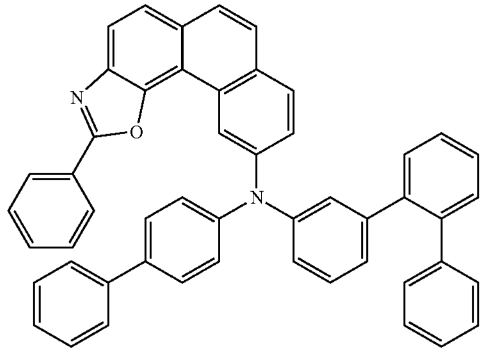
-continued
H1-111
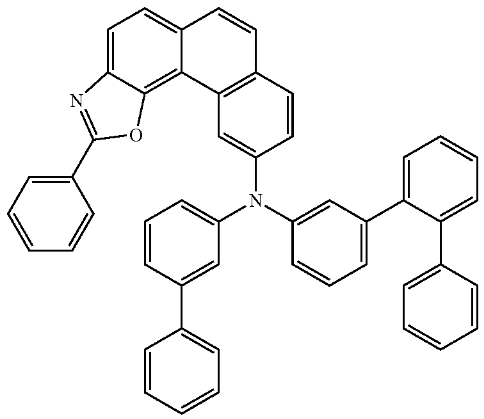
H1-112
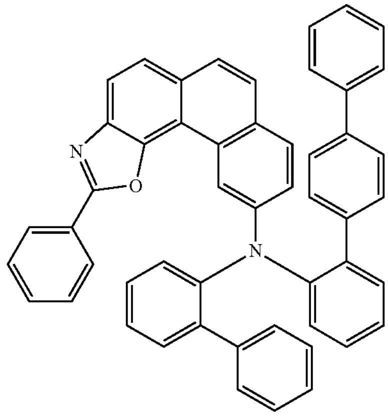
H1-113
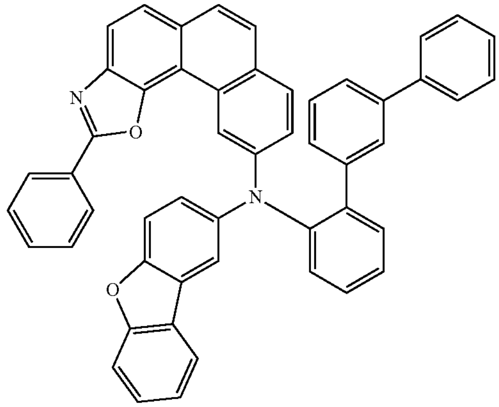

-continued
H1-114
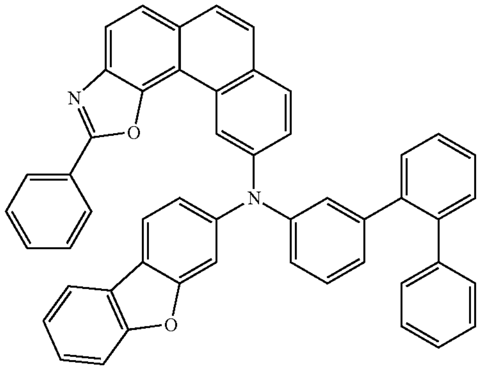
H1-115
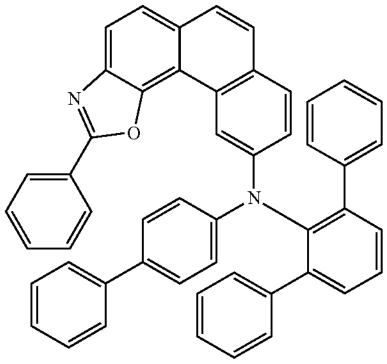
H1-116
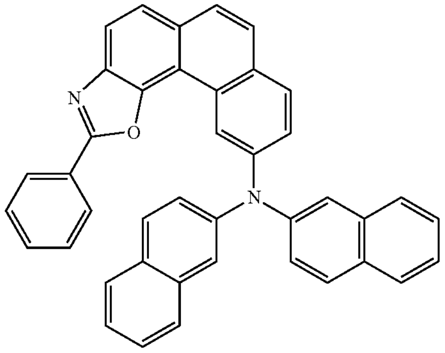
H1-117
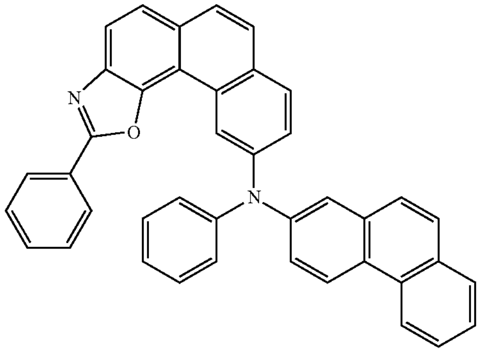
-continued
H1-118
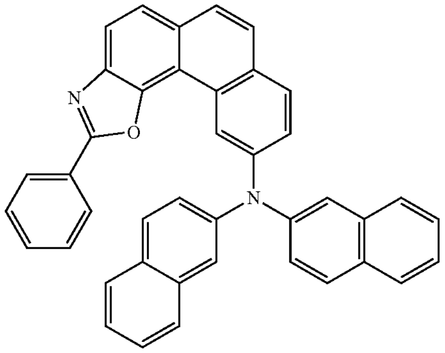
H1-119
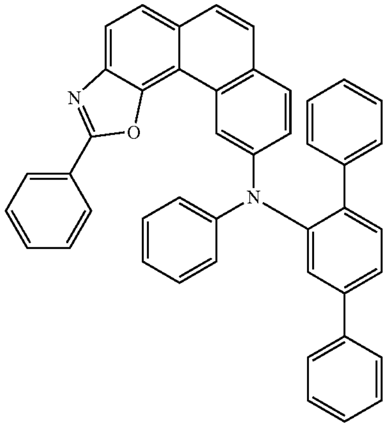
H1-120
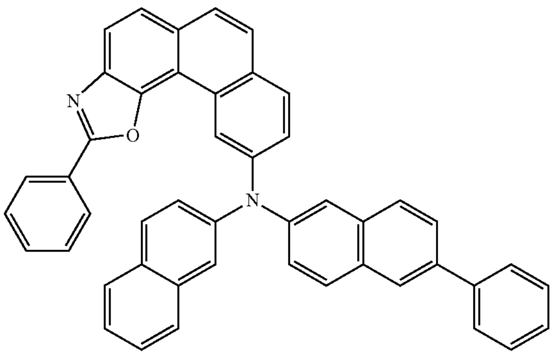
H1-121
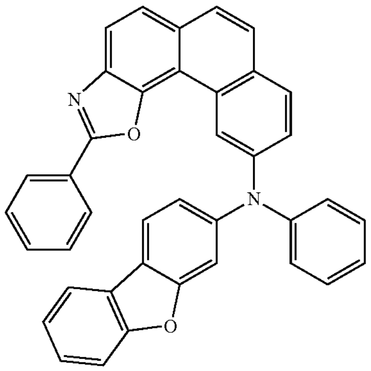

-continued

H1-122

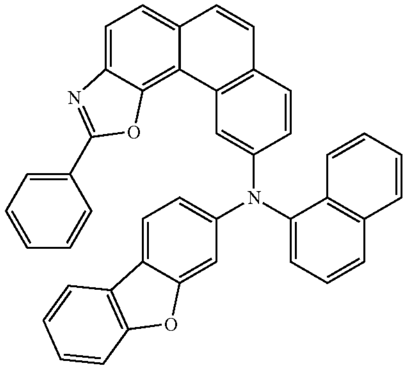

H1-123

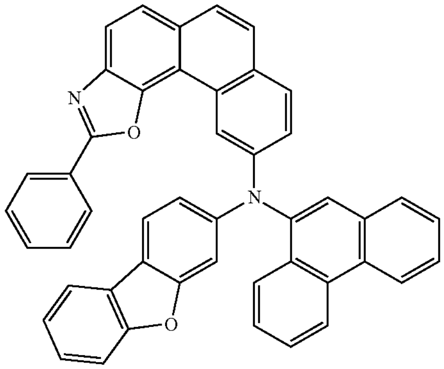

H1-124

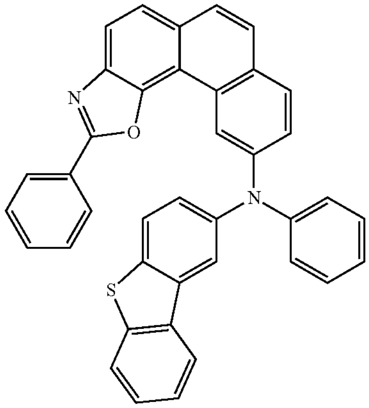

H1-125

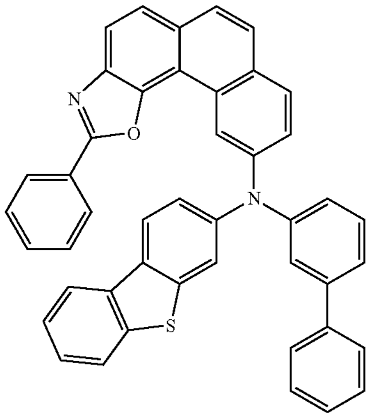

-continued

H1-126

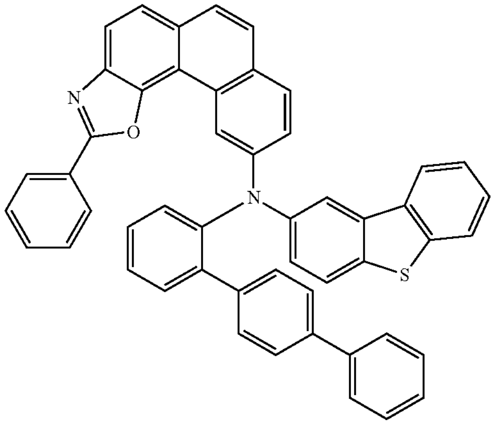

and

H1-127

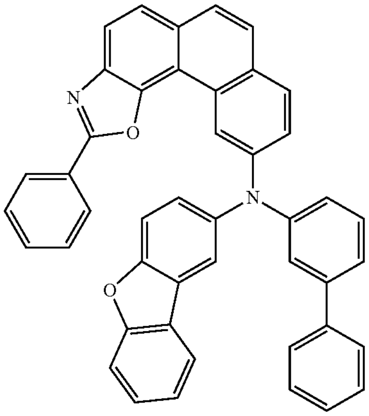

.

14. The organic electroluminescent device according to claim 11, wherein when the organic electroluminescent compound is comprised in a light-emitting layer, the light-emitting layer further comprises a compound represented by the following formula 3:

$$HAr—((L_2)_e—Ar_2)_d \quad (3)$$

wherein

HAr represents a substituted or unsubstituted 3- to 20-membered heteroaryl containing a nitrogen atoms;

$L_2$ each independently represents a substituted or unsubstituted C6-C30 arylene;

$Ar_2$ each independently represents a substituted or unsubstituted C6-C30 aryl, or the following formula 4, with the proviso that at least one of $Ar_2$ represents formula 4;

4

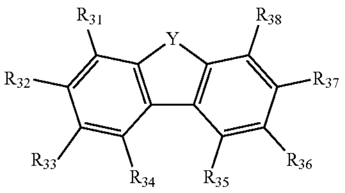

Y represents O, S, $CR_{41}R_{42}$, N—*, or $NR_{43}$;

$R_{41}$ to $R_{43}$ each independently represent a substituted or unsubstituted C1-C30 alkyl, or a substituted or unsubstituted C6-C30 aryl, or $R_{41}$ and $R_{42}$ may be linked to each other to form a ring;

$R_{31}$ to $R_{38}$ each independently represent a site linked to $L_2$; or represent hydrogen, deuterium, a halogen, a cyano, a substituted or unsubstituted C1-C30 alkyl, a substituted or unsubstituted C6-C30 aryl, a substituted or unsubstituted 3- to 30-membered heteroaryl, a substituted or unsubstituted C3-C30 cycloalkyl, a substituted or unsubstituted C1-C30 alkoxy, a substituted or unsubstituted triC1-C30 alkylsilyl, a substituted or unsubstituted diC1-C30 alkylC6-C30 arylsilyl, a substituted or unsubstituted C1-C30 alkyldiC6-C30 arylsilyl, a substituted or unsubstituted triC6-C30 arylsilyl, a substituted or unsubstituted fused ring group of a C3-C30 aliphatic rings and a C6-C30 aromatic rings, or $-L_4-NAr_3Ar_4$; or may be linked to an adjacent substituent to form a rings;

$L_4$ each independently represents a single bond, a substituted or unsubstituted C6-C30 arylene, or a substituted or unsubstituted 3- to 30-membered heteroarylene;

$Ar_3$ and $Ar_4$ each independently represent hydrogen, a substituted or unsubstituted C1-C30 alkyl, a substituted or unsubstituted C2-C30 alkenyl, a substituted or unsubstituted fused ring group of a C3-C30 aliphatic rings and a C6-C30 aromatic rings, a substituted or unsubstituted C6-C30 aryl, or a substituted or unsubstituted 3- to 30-membered heteroaryl;

d represents an integer of 1 to 3, where if d is an integer of 2 or more, each of $L_2$ e-$Ar_2$ may be the same or different;

e represents an integer of 0 to 2, where if e is 2, each of $L_2$ may be the same or different; and

* represents a site linked to $L_2$.

15. The organic electroluminescent device according to claim 14, wherein the compound represented by formula 3 is selected from the following compounds:

H2-1

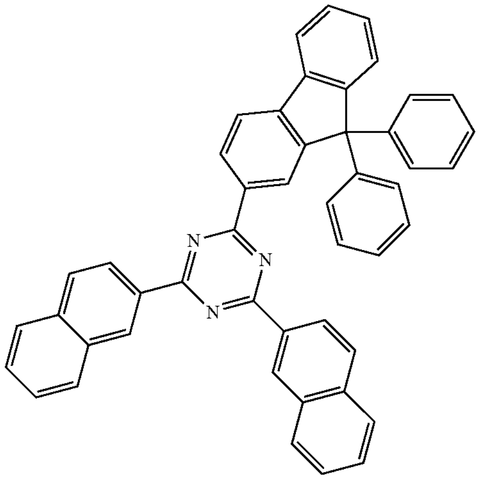

-continued

H2-2

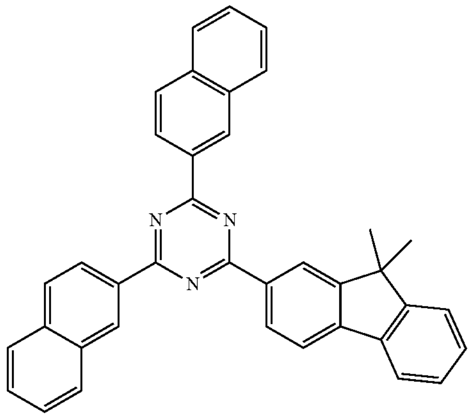

H2-3

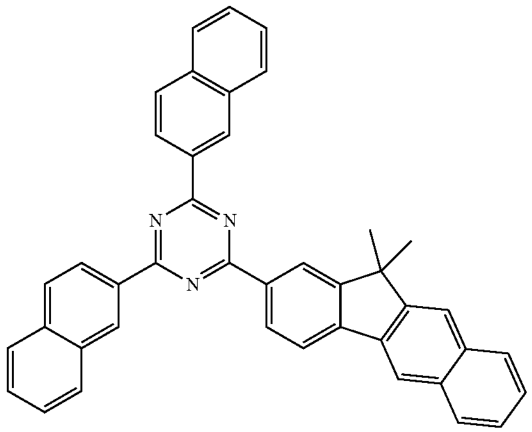

H2-4

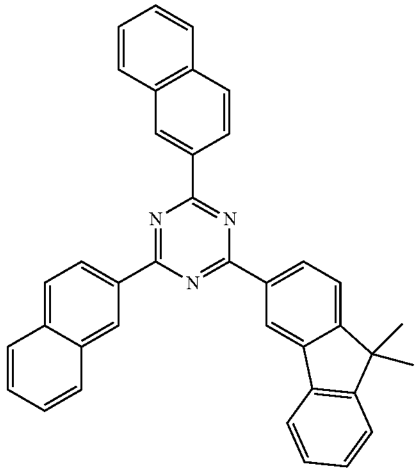

-continued
H2-5
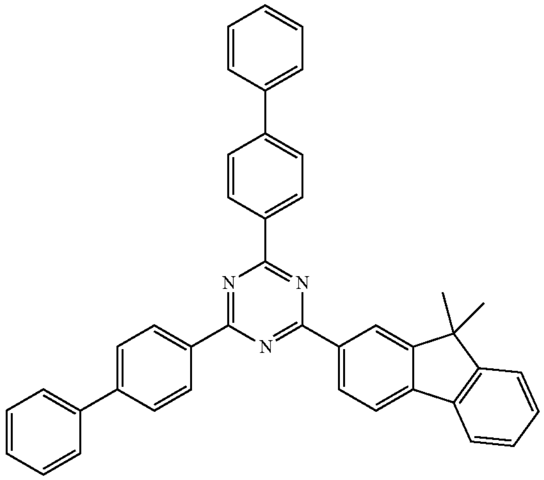
H2-6
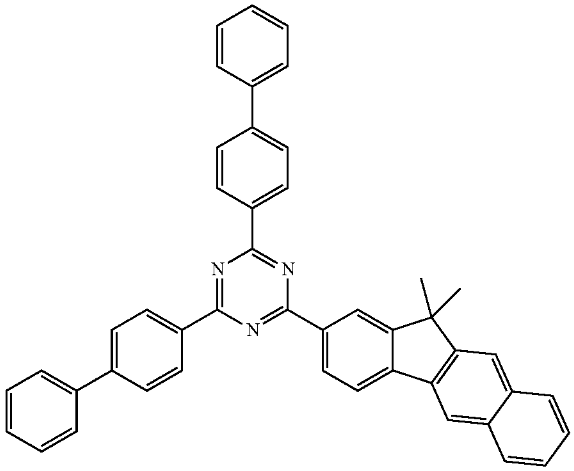
H2-7
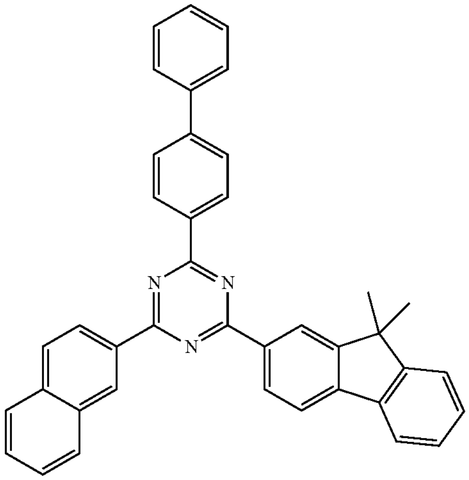
-continued
H2-8
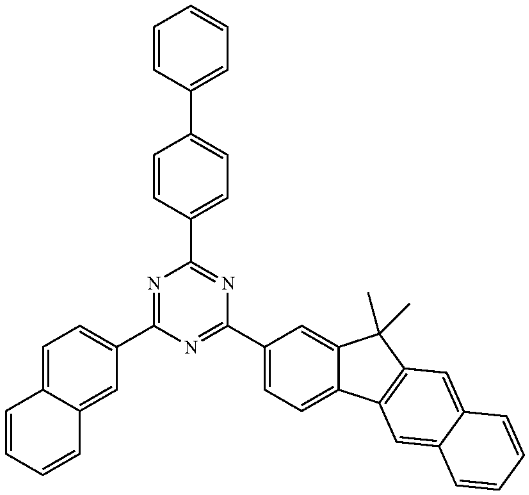
H2-9
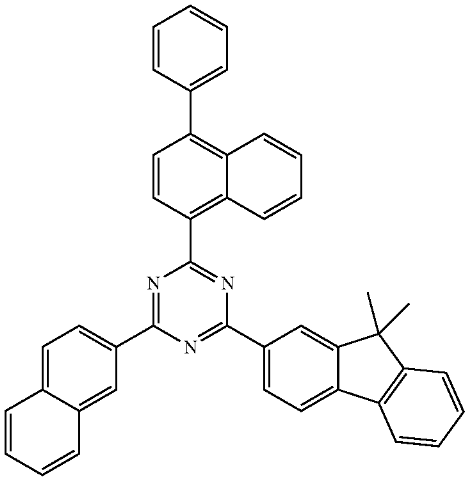
H2-10
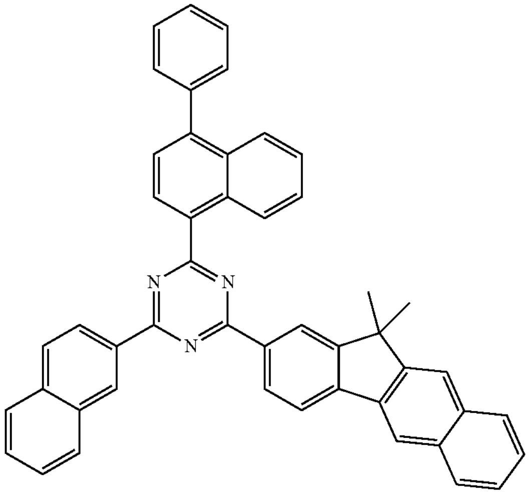

-continued
H2-11
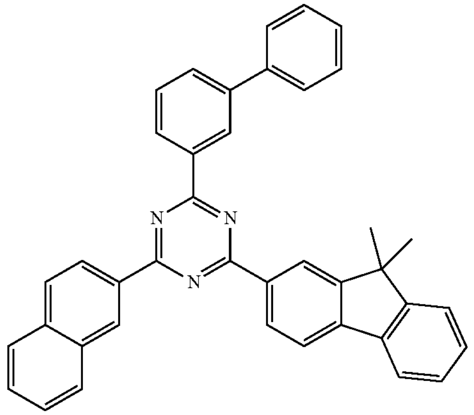
H2-12
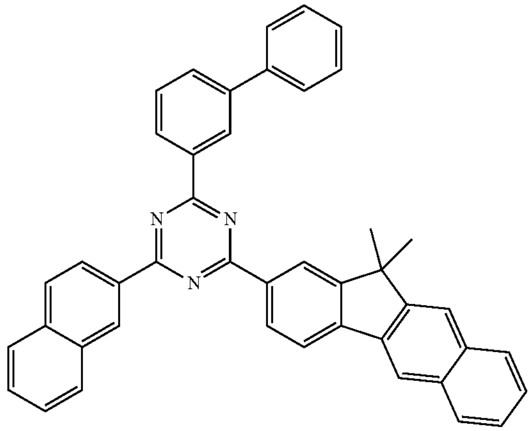
H2-13
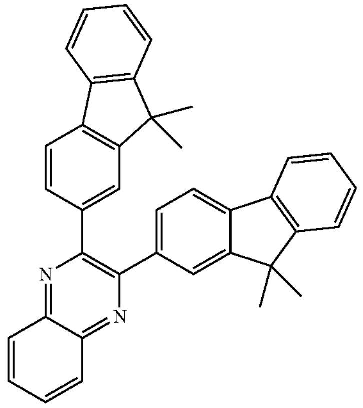
-continued
H2-14
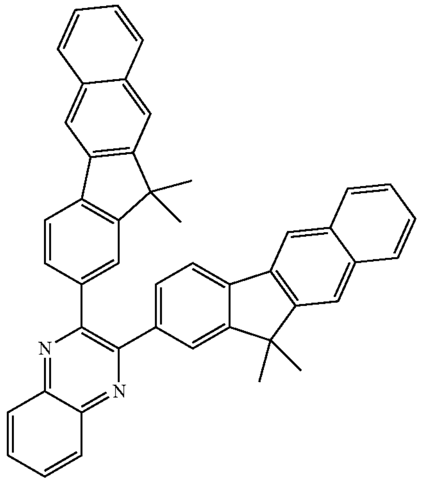
H2-15
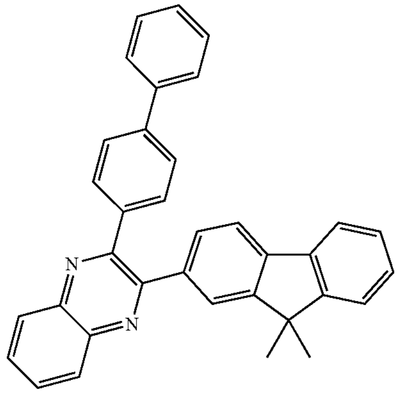
H2-16
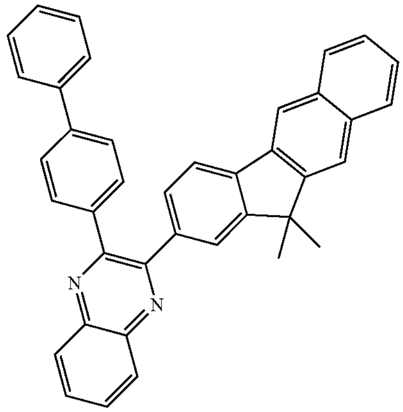

H2-17
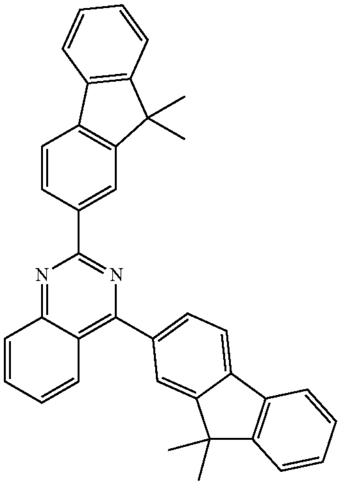
H2-18
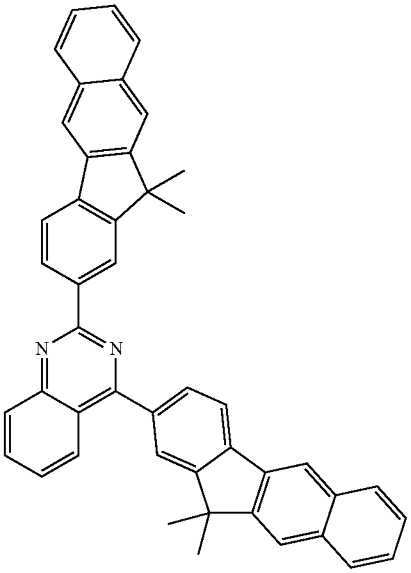
H2-19
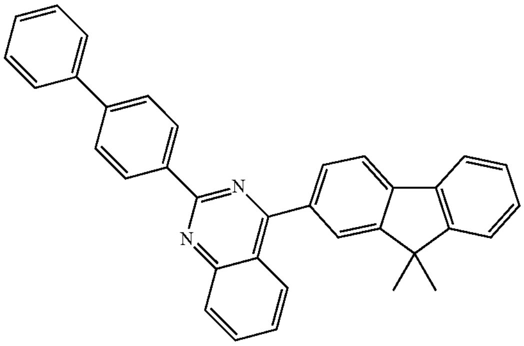
H2-20
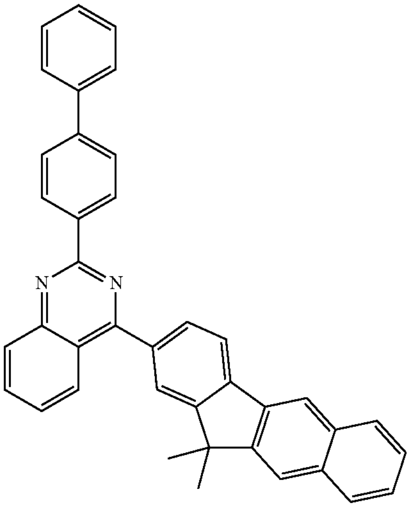
H2-21
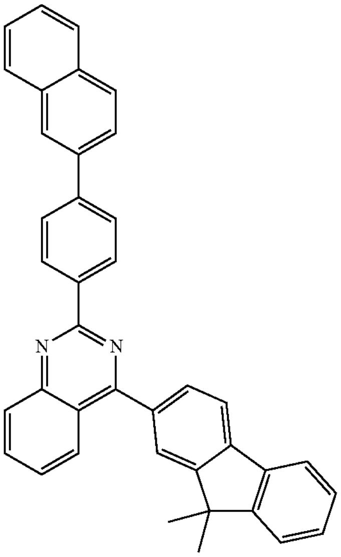
H2-22
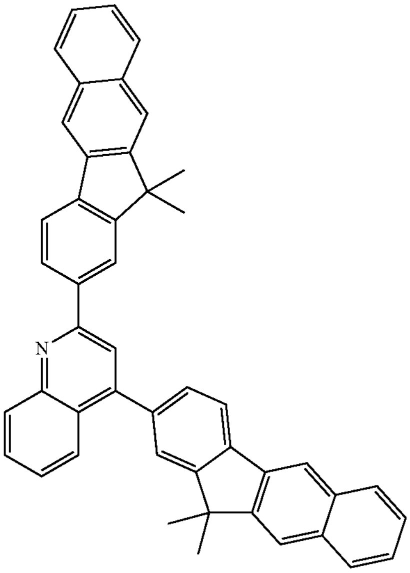

-continued
H2-23
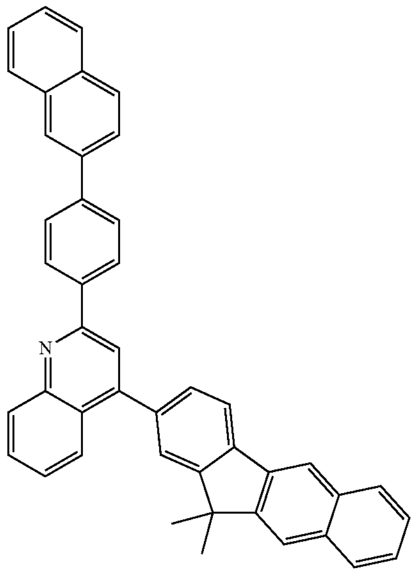
H2-24
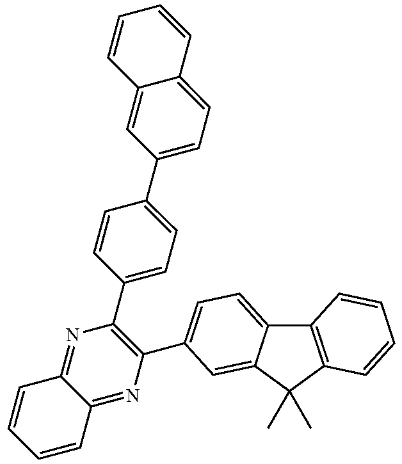
H2-25
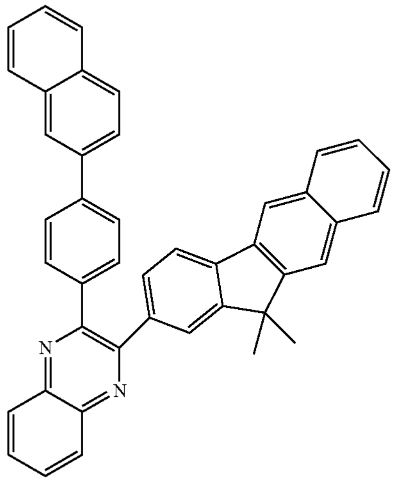
-continued
H2-26
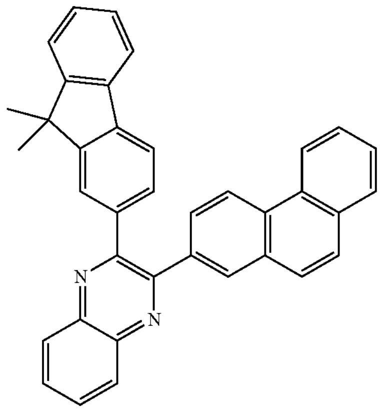
H2-27
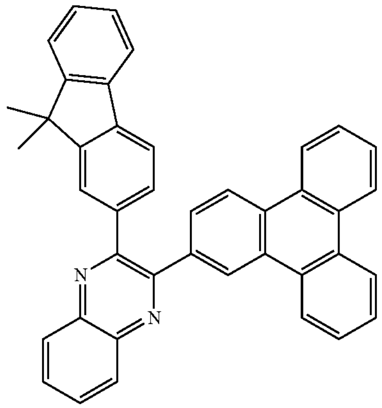
H2-28
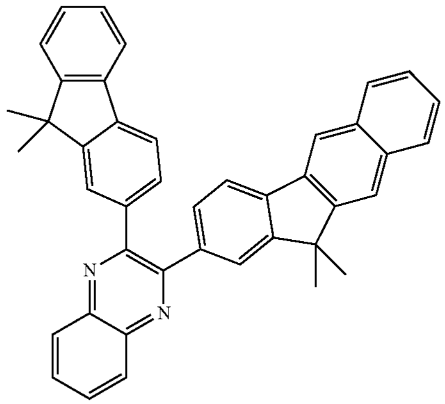

H2-29
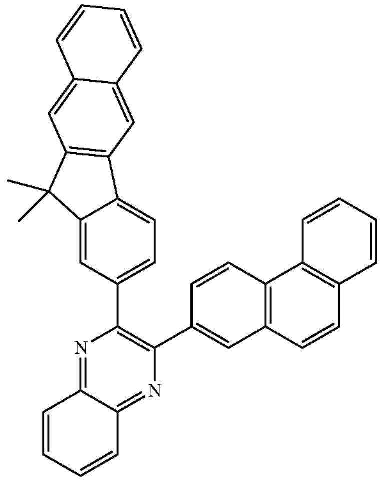
H2-30
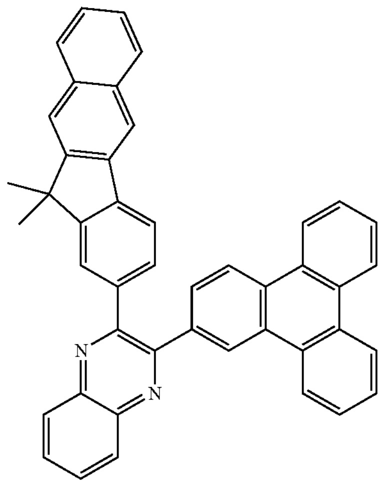
H2-31
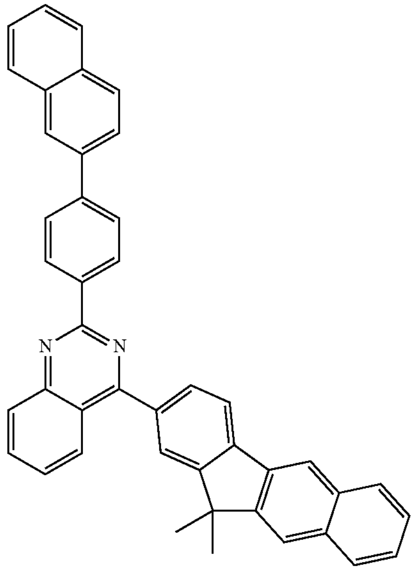
H2-32
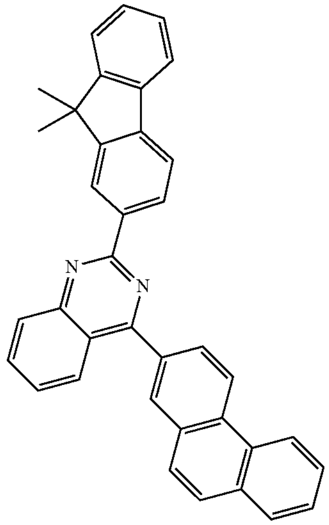
H2-33
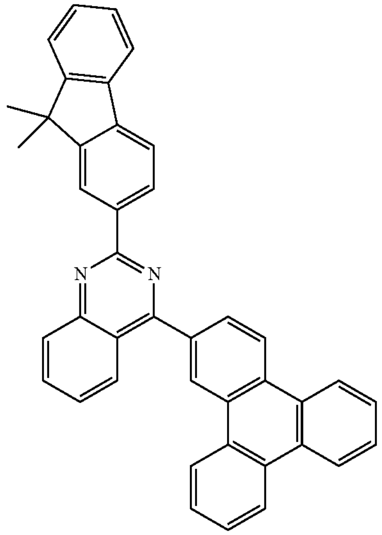
H2-34
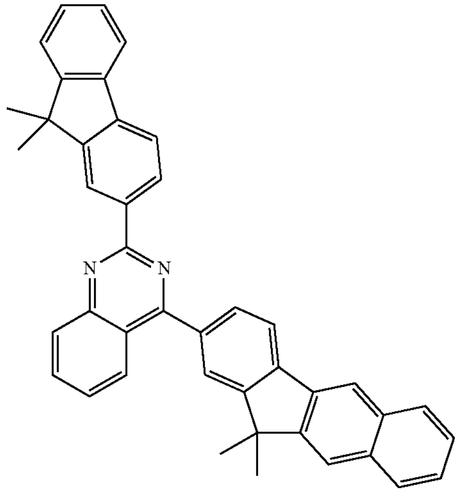

H2-35
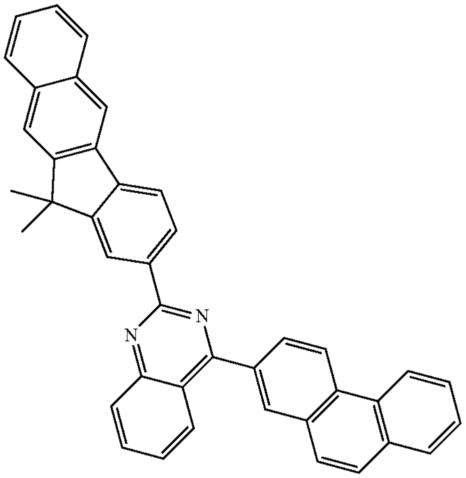
H2-36
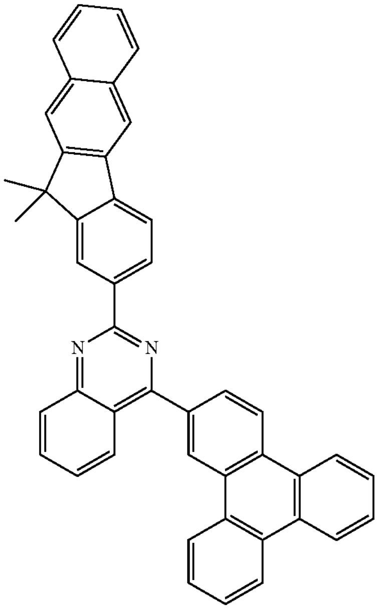
H2-37
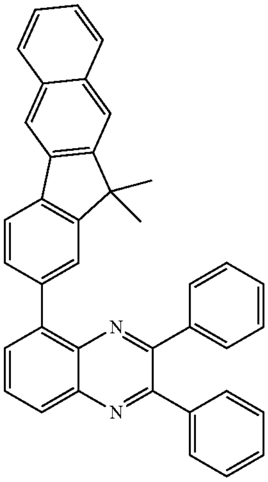
H2-38
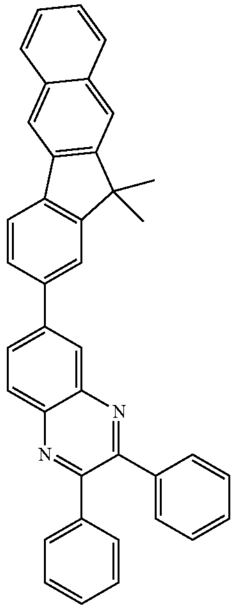
H2-39
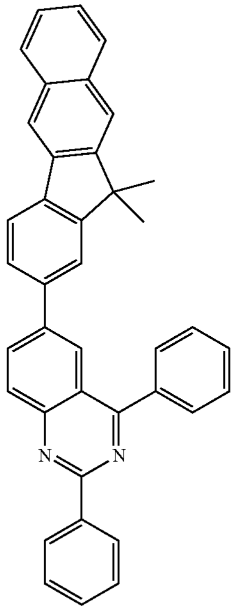
H2-40
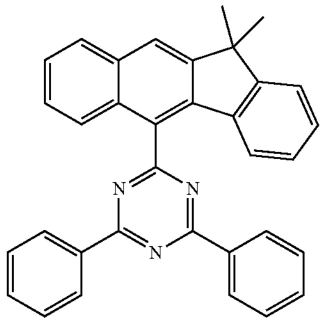

-continued
H2-41
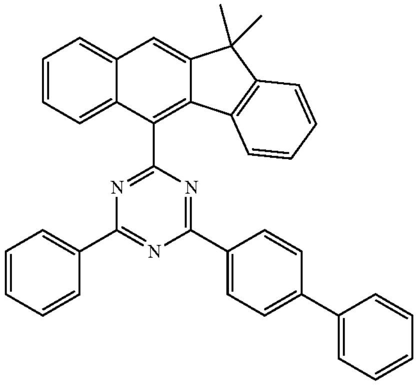
H2-42
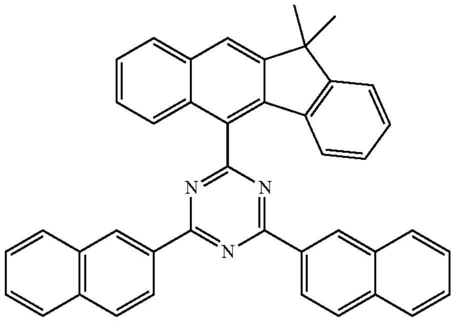
H2-43
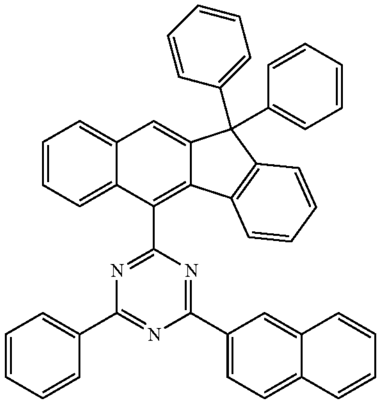
H2-44
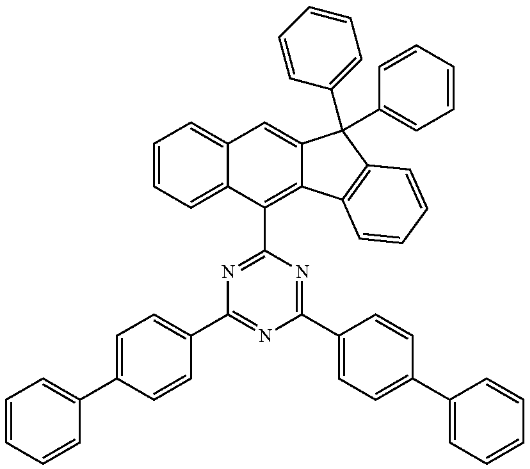
-continued
H2-45
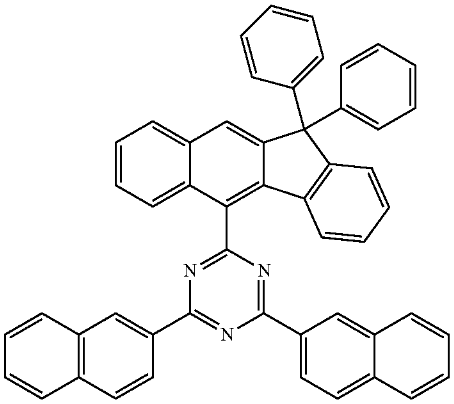
H2-46
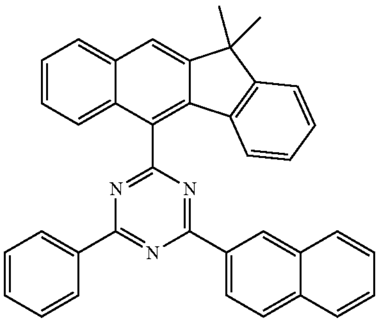
H2-47
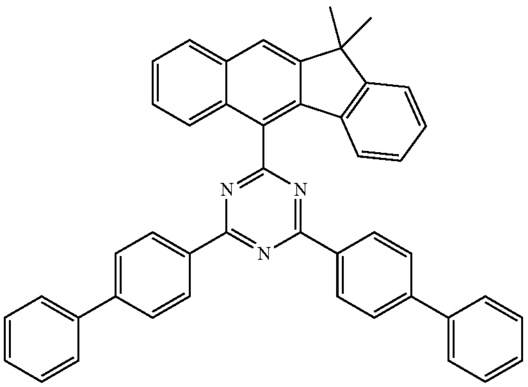
H2-48
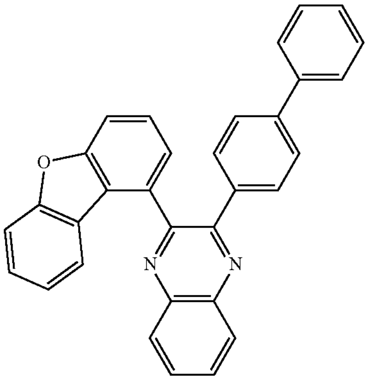

-continued
H2-49
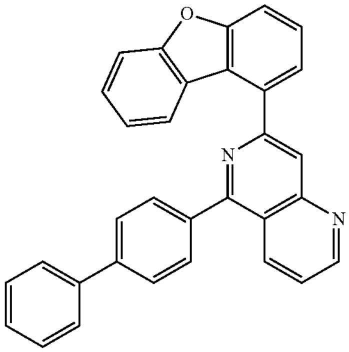
H2-50
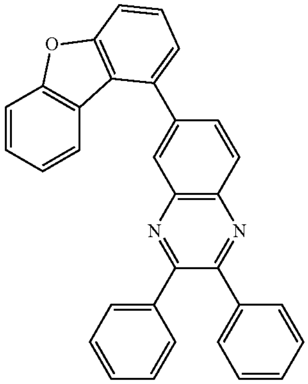
H2-51
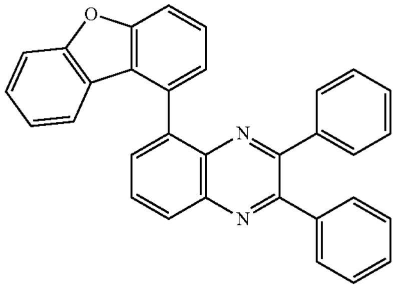
H2-52
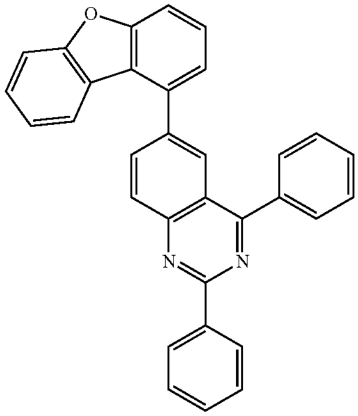
-continued
H2-53
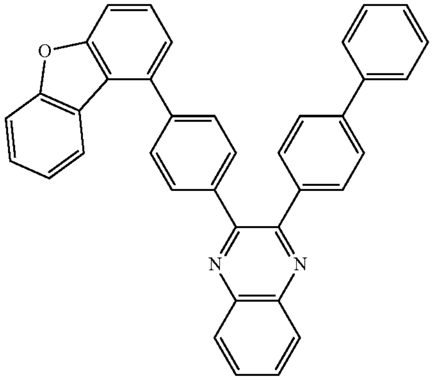
H2-54
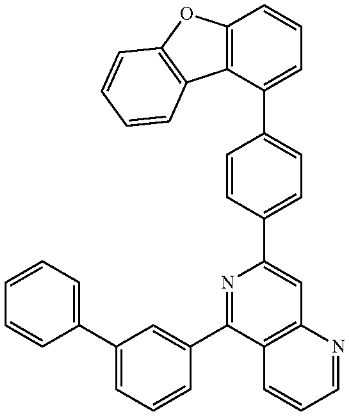
H2-55
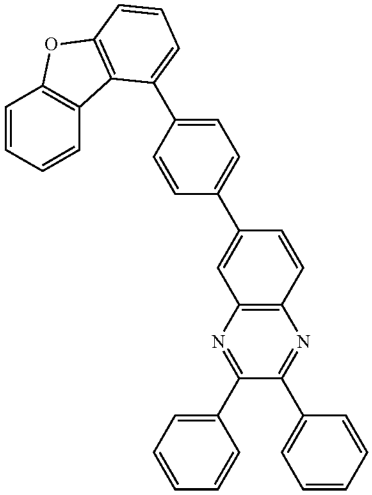

H2-56
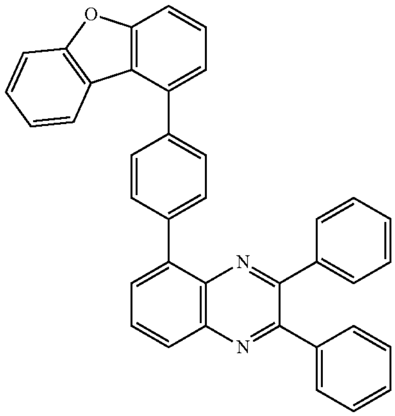
H2-57
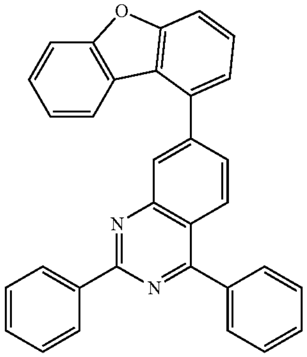
H2-58
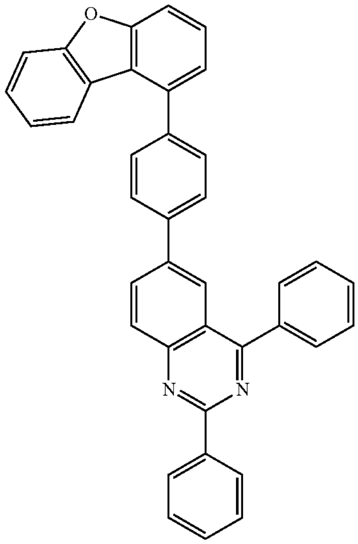
H2-59
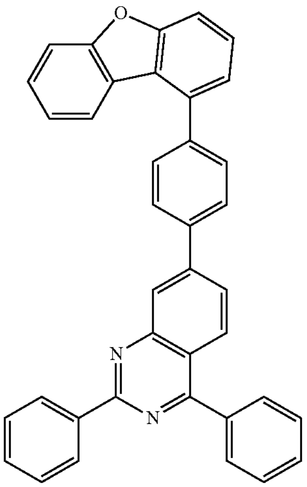
H2-60
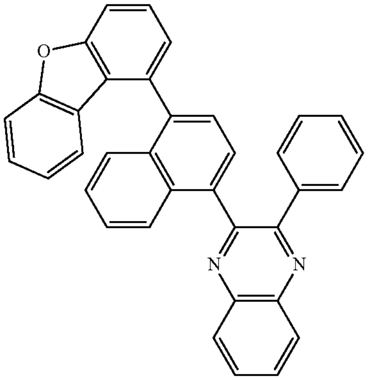
H2-61
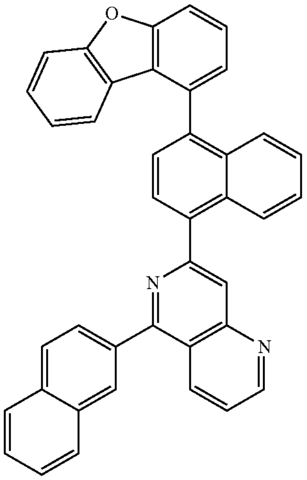

-continued
H2-62
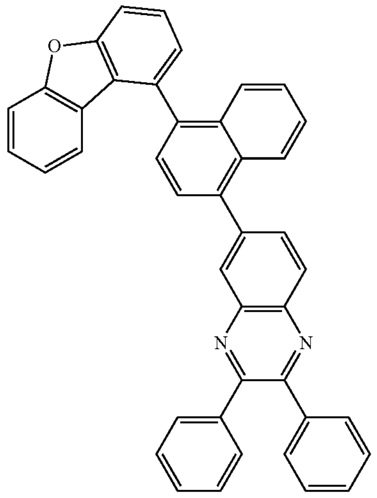
H2-63
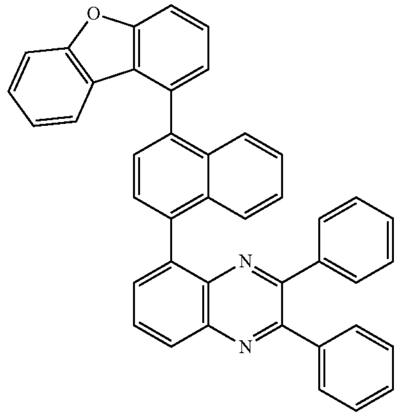
H2-64
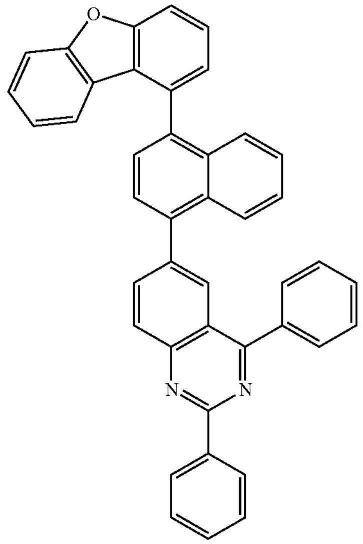
-continued
H2-65
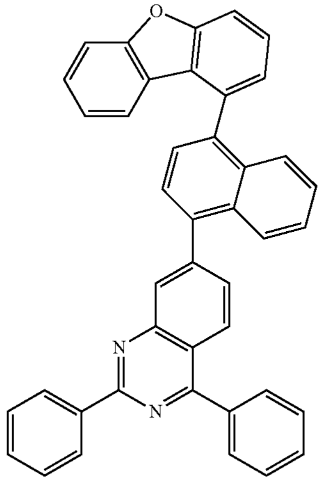
H2-66
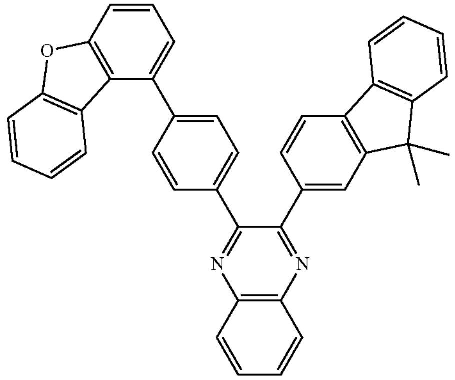
H2-67
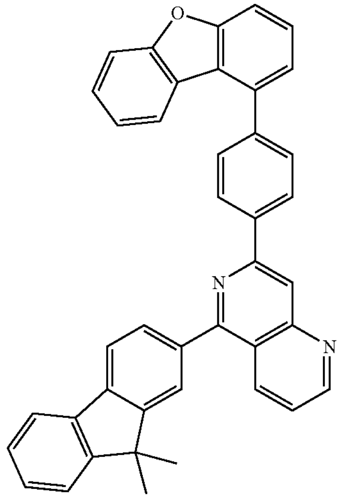

-continued
H2-68
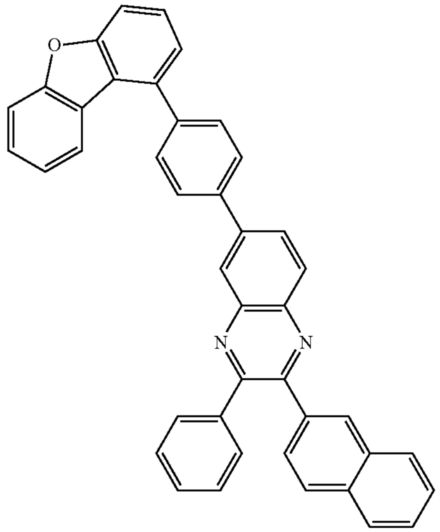
H2-69
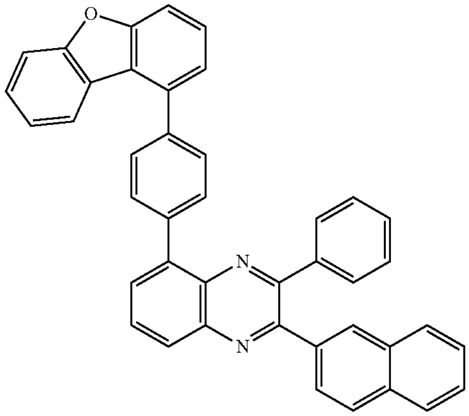
H2-70
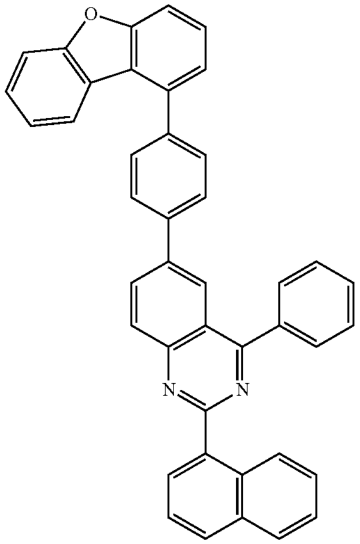
-continued
H2-71
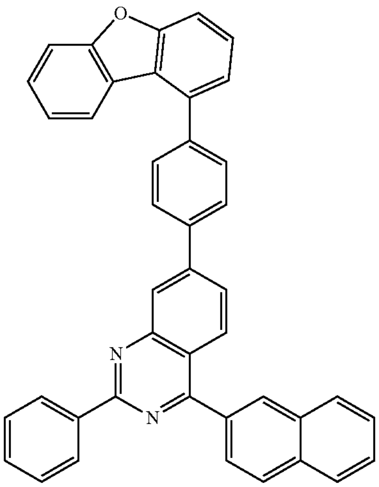
H2-72
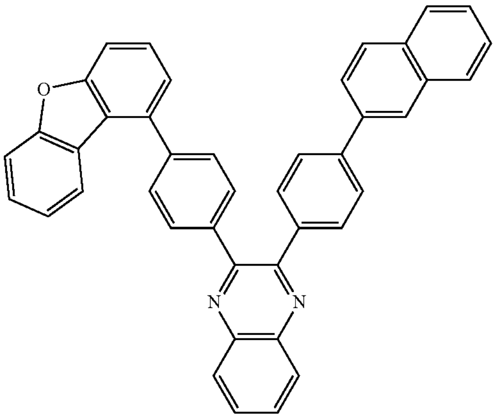
H2-73
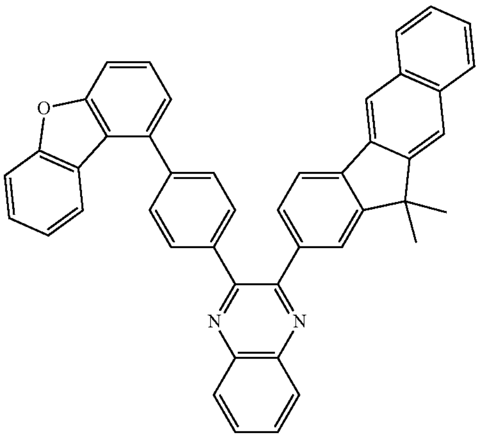

-continued
H2-74
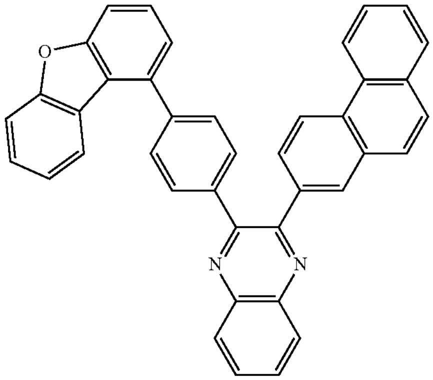
H2-75
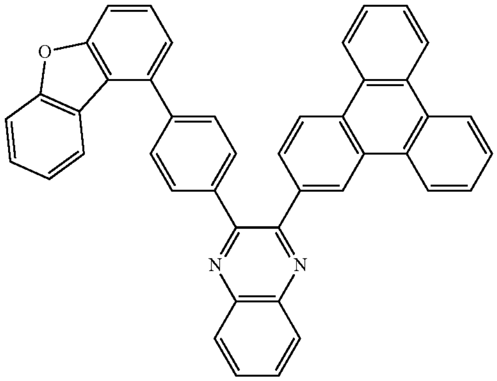
H2-76
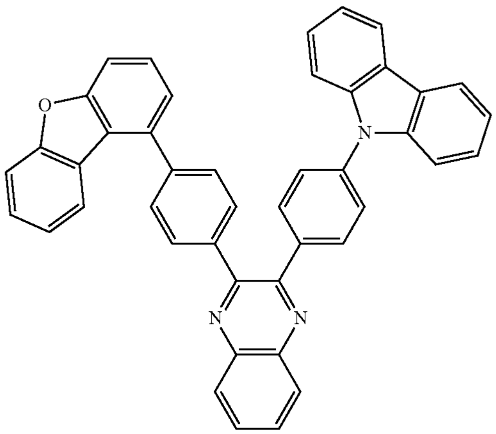
H2-77
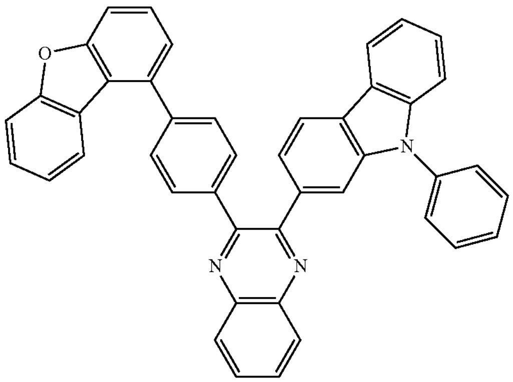
-continued
H2-78
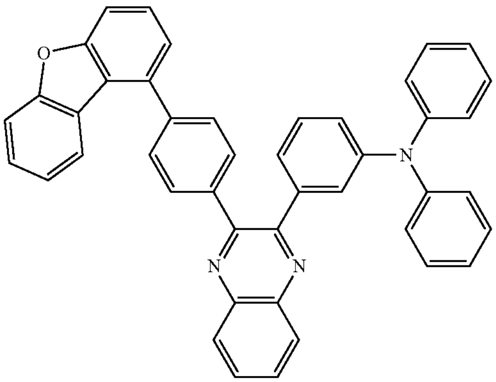
H2-79
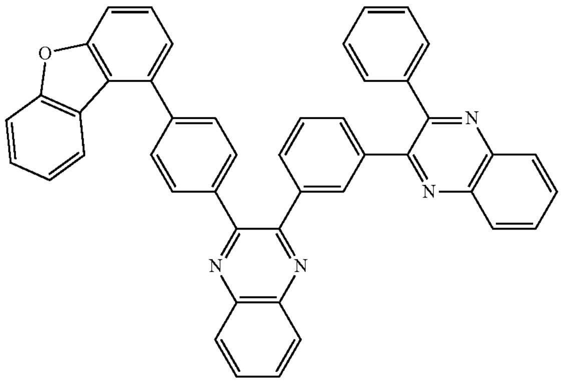
H2-80
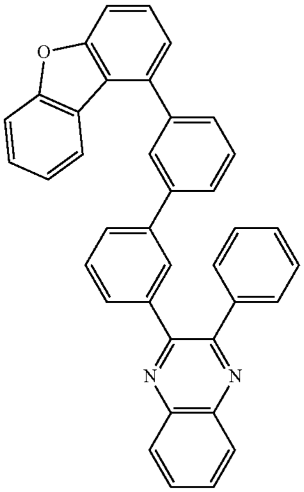

-continued
H2-81
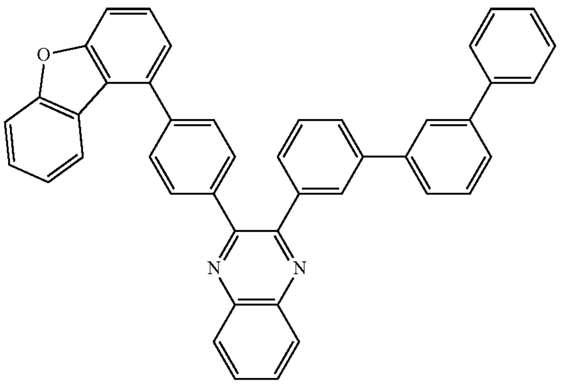
H2-82
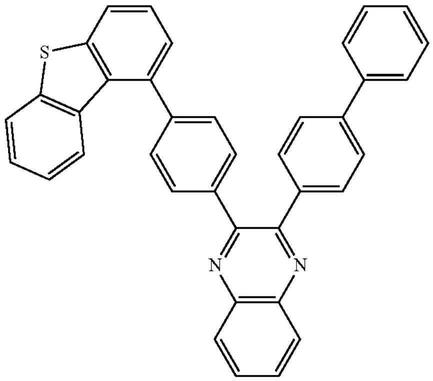
H2-83
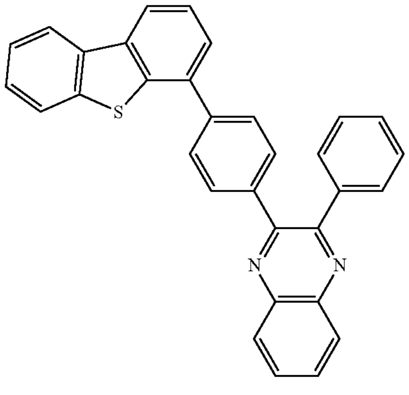
H2-84
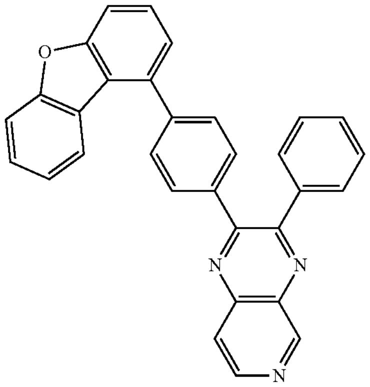
-continued
H2-85
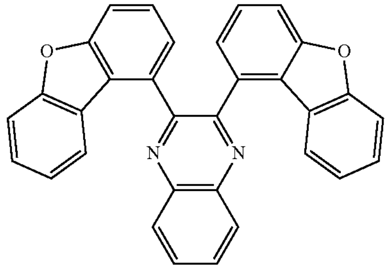
H2-86
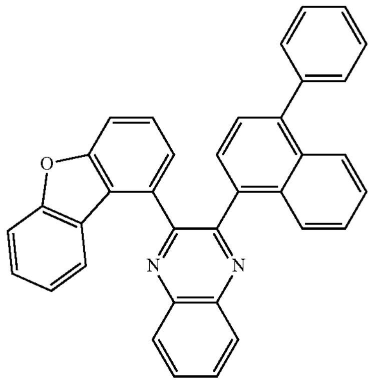
H2-87
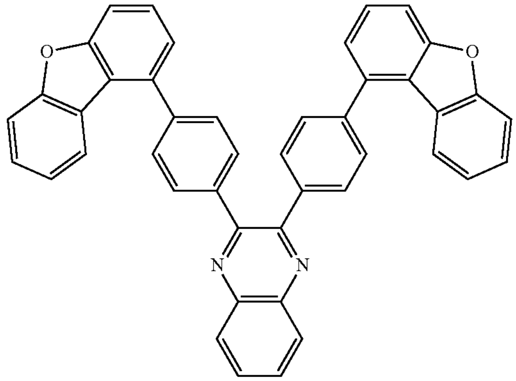
H2-88
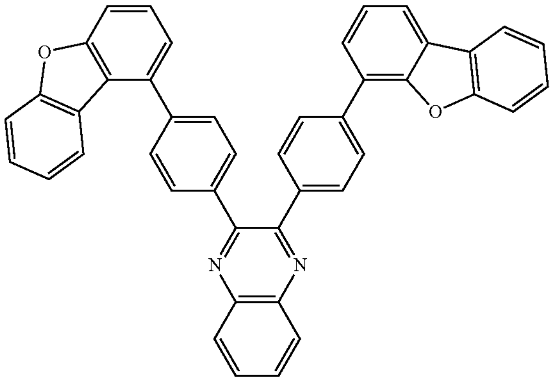

-continued
H2-89
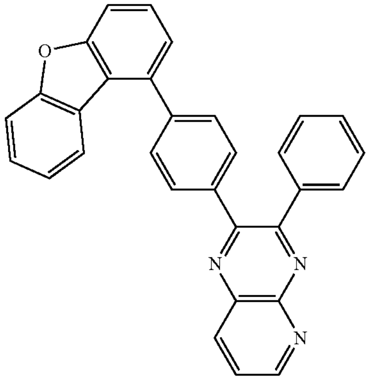
H2-90
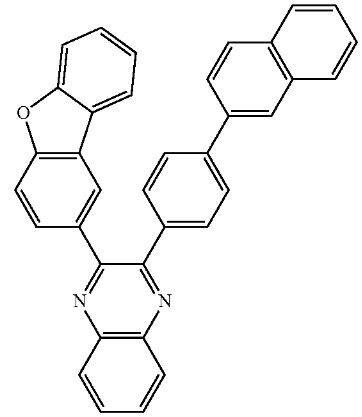
H2-91
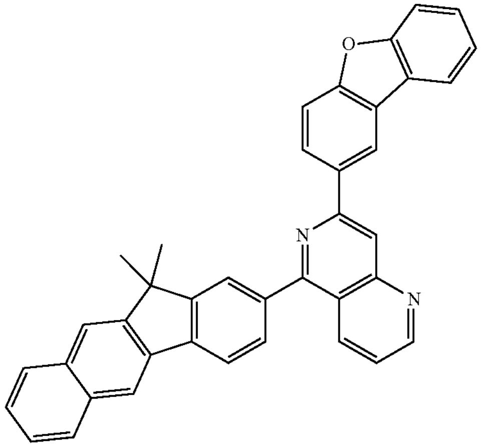
-continued
H2-92
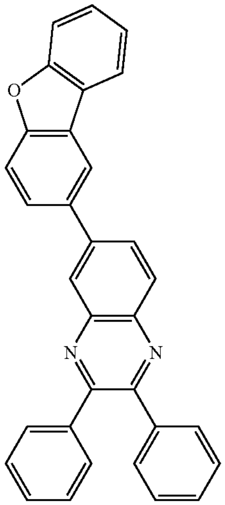
H2-93
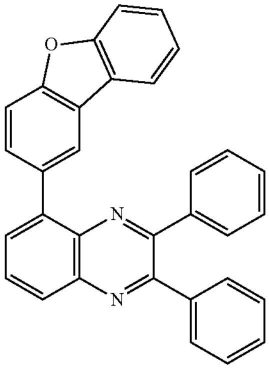
H2-94
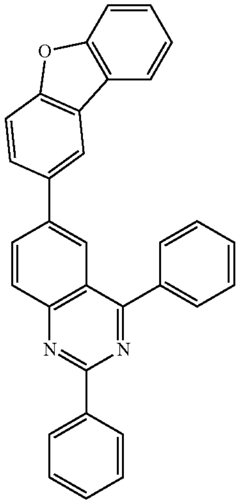

-continued
H2-95
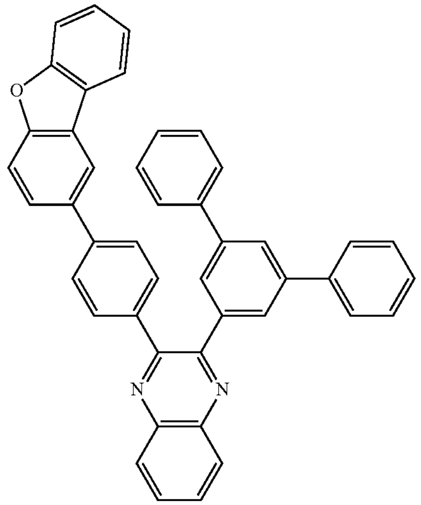
H2-96
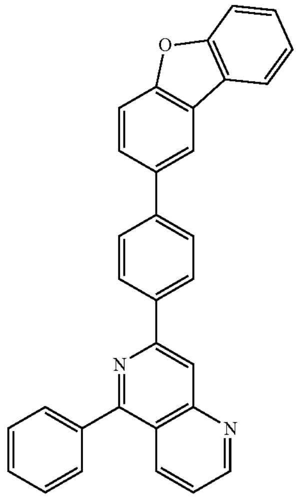
H2-97
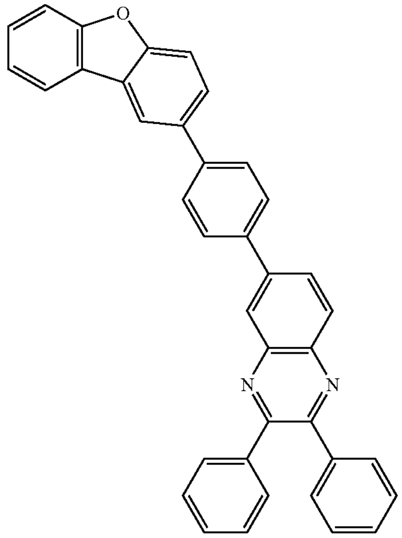
-continued
H2-98
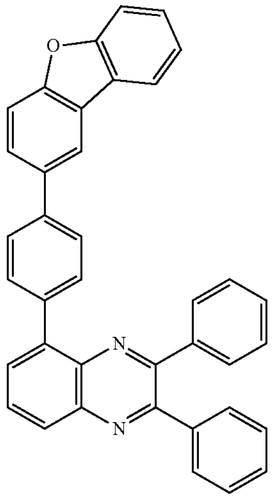
H2-99
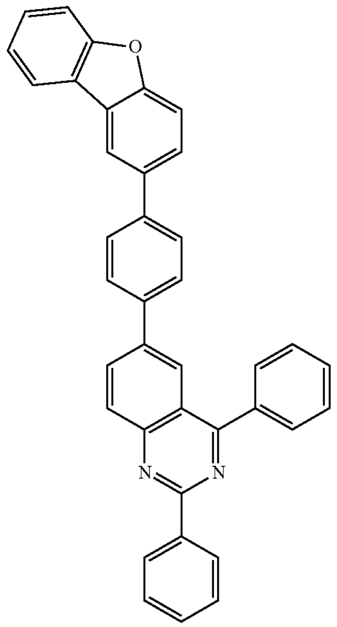
H2-100
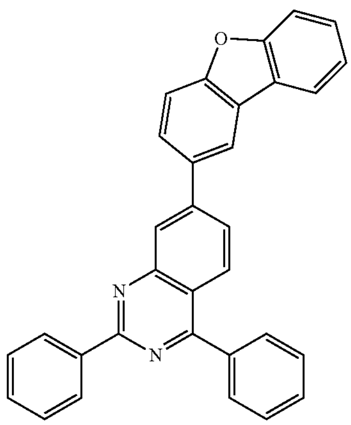

H2-101
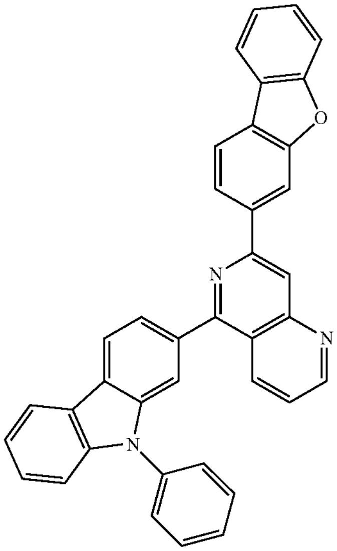
H2-102
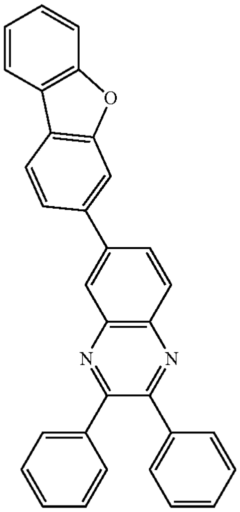
H2-103
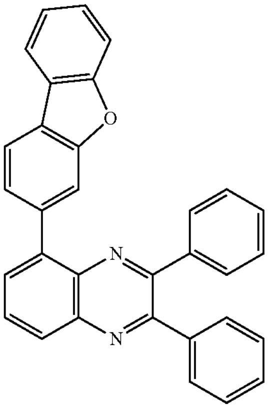
H2-104
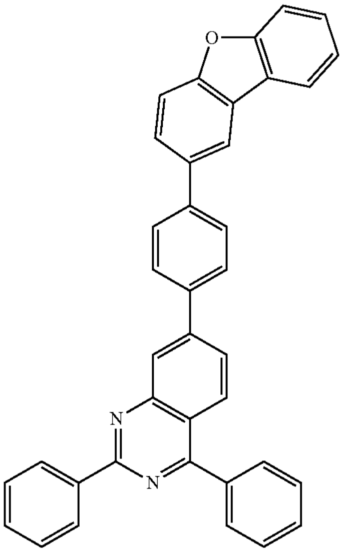
H2-105
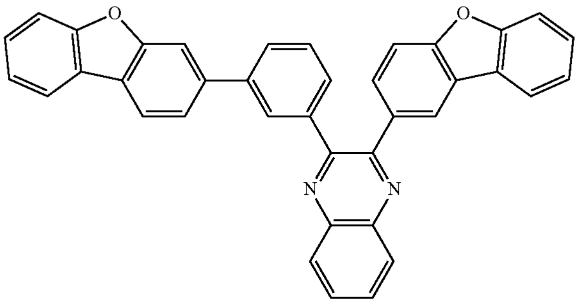
H2-106
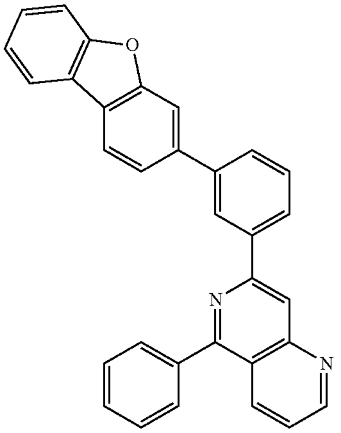

-continued
H2-107
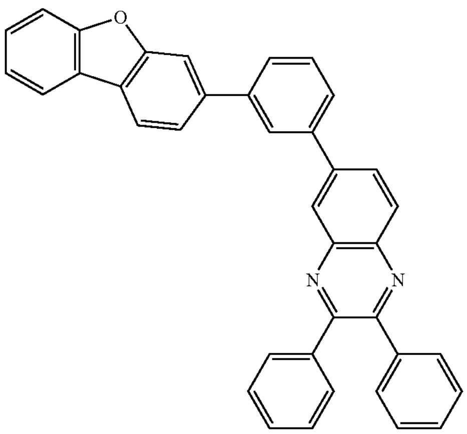
H2-108
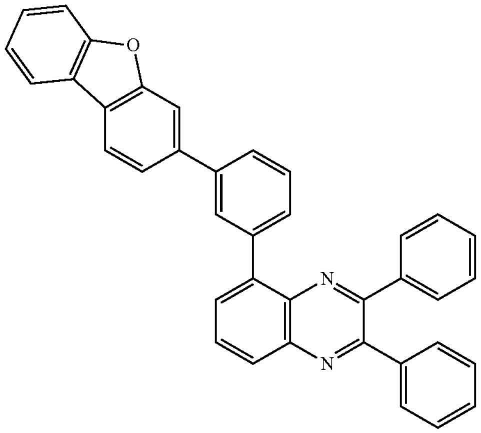
H2-109
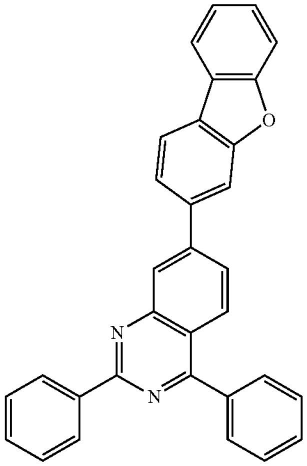
-continued
H2-110
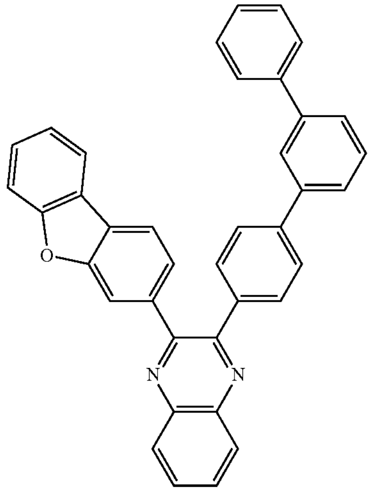
H2-111
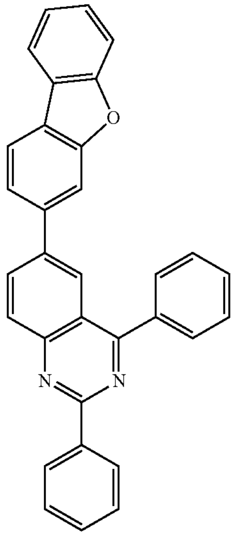
H2-112
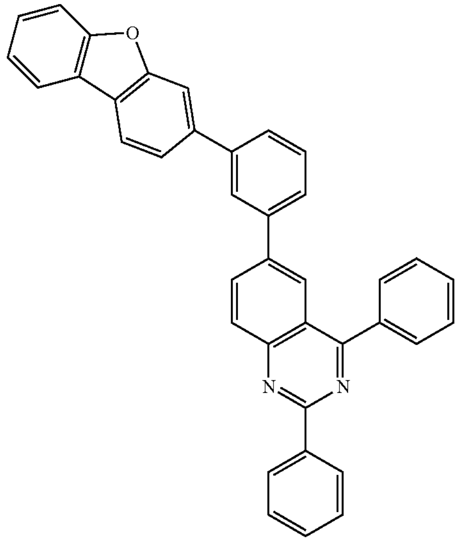

-continued
H2-113
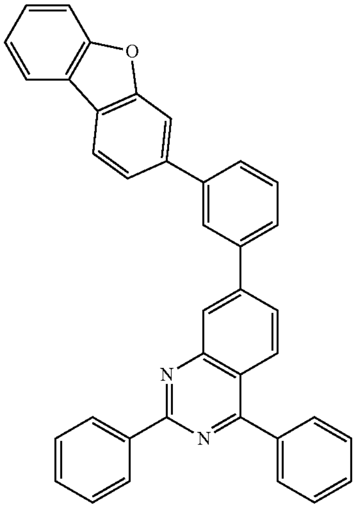
H2-114
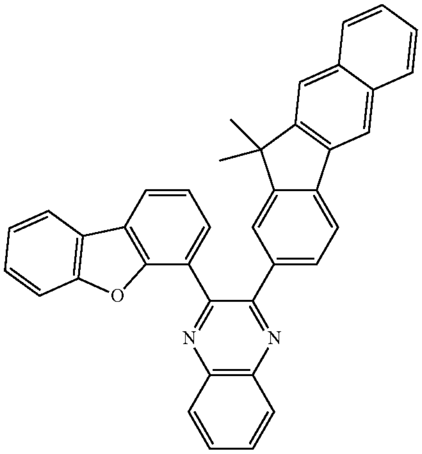
H2-115
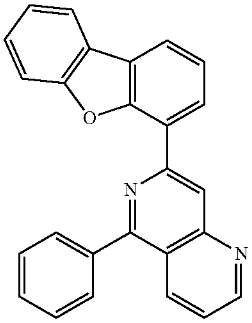
-continued
H2-116
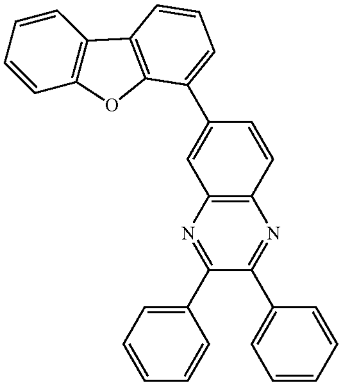
H2-117
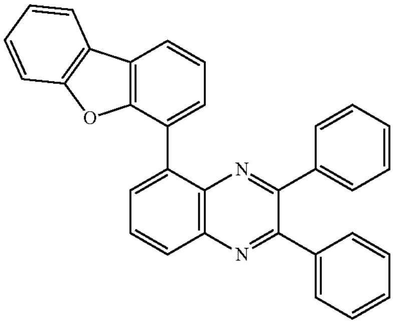
H2-118
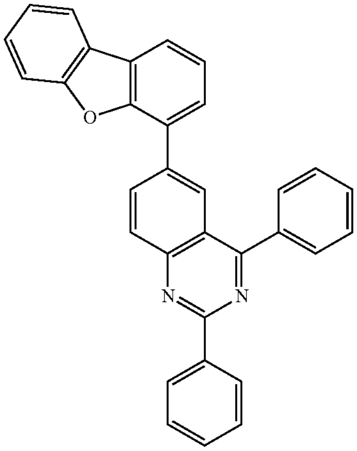
H2-119
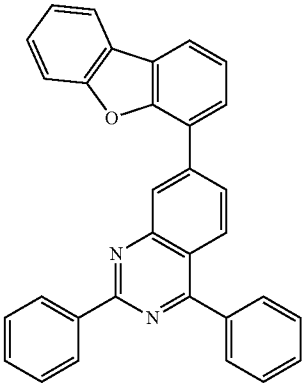

-continued
H2-120
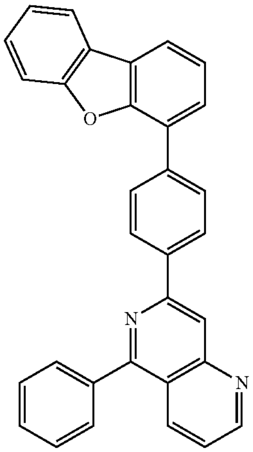
H2-121
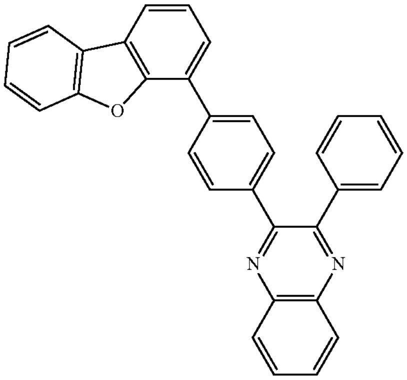
H2-122
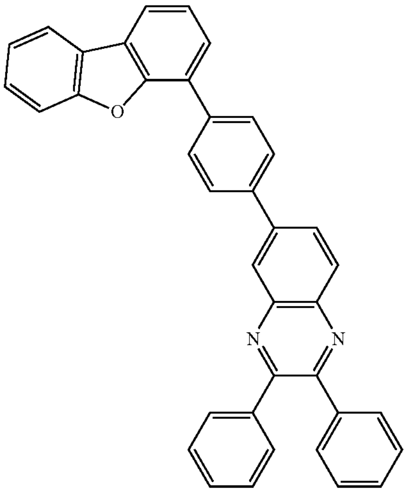
-continued
H2-123
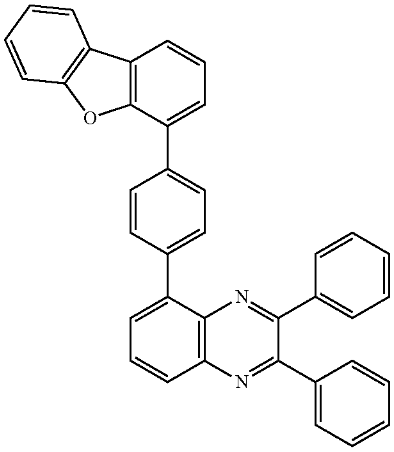
H2-124
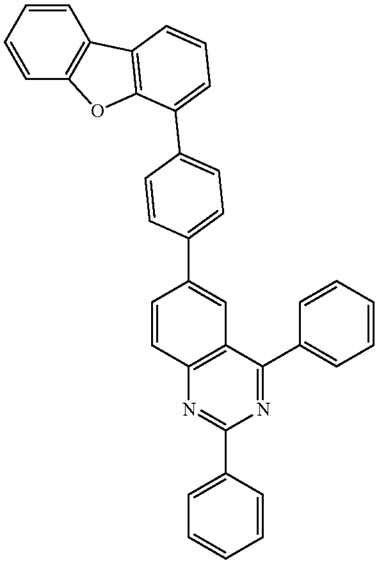
H2-125
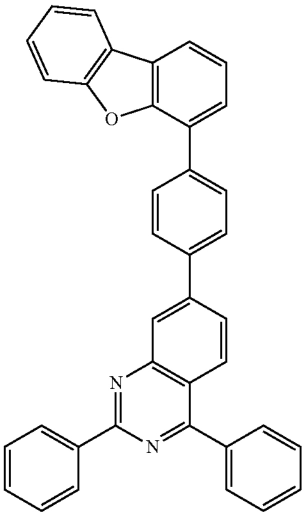

-continued
H2-126
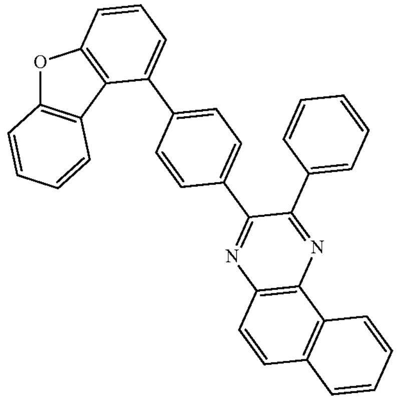
H2-127
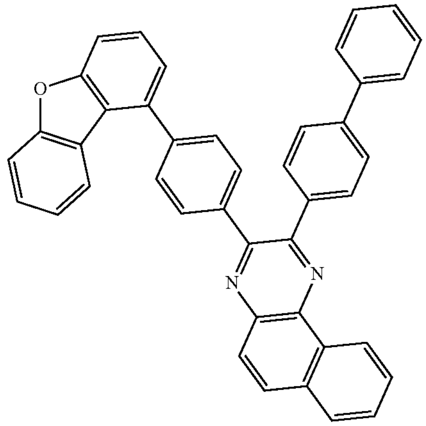
H2-128
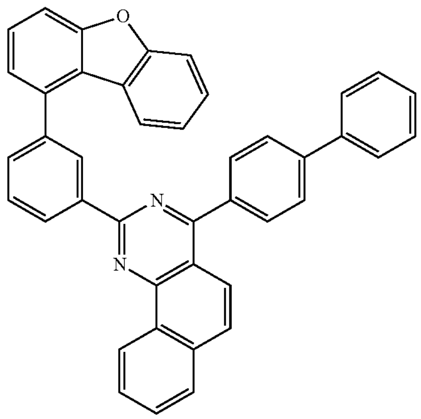
-continued
H2-129
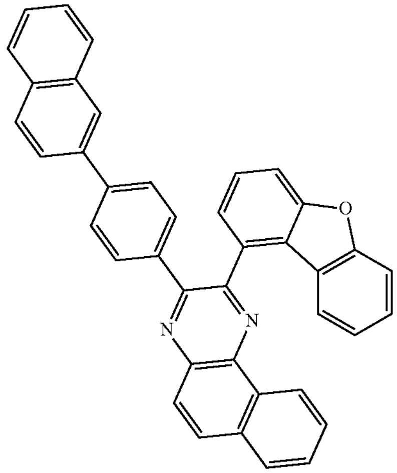
H2-130
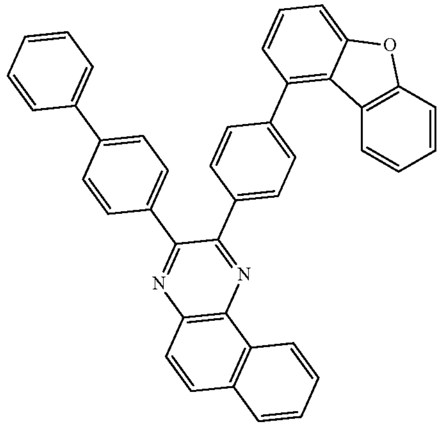
H2-131
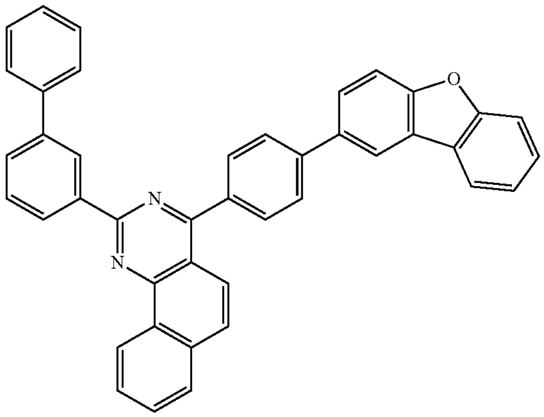

-continued
H2-132
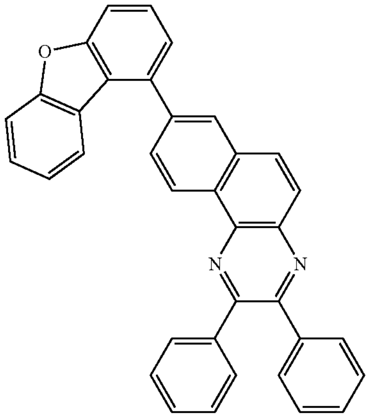
H2-133
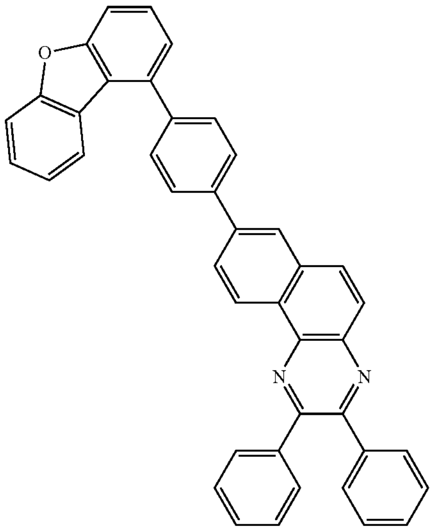
H2-134
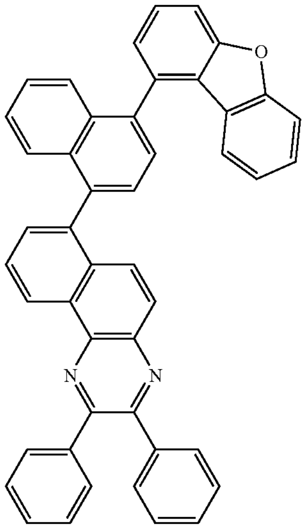
-continued
H2-135
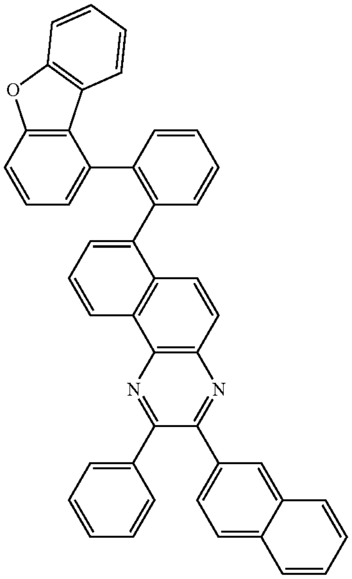
H2-136
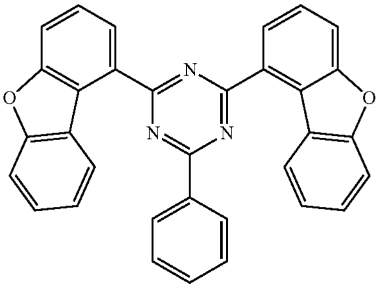
H2-137
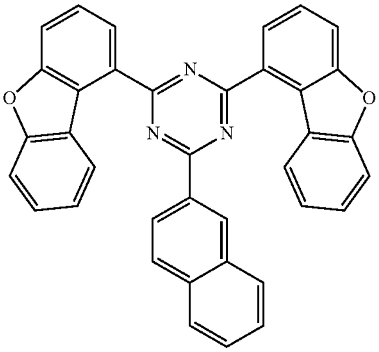

-continued
H2-138
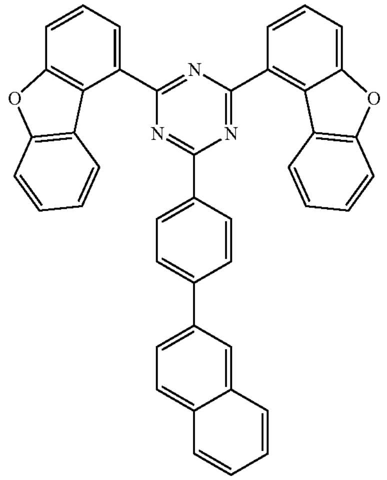
H2-139
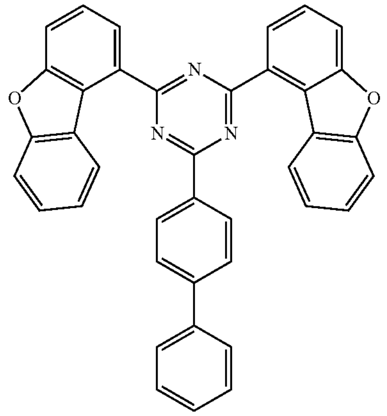
H2-140
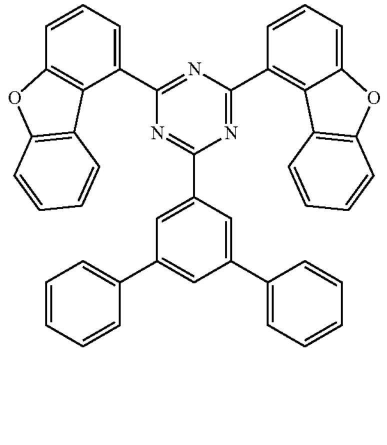
-continued
H2-141
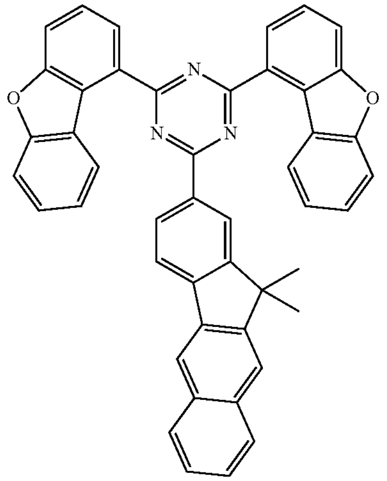
H2-142
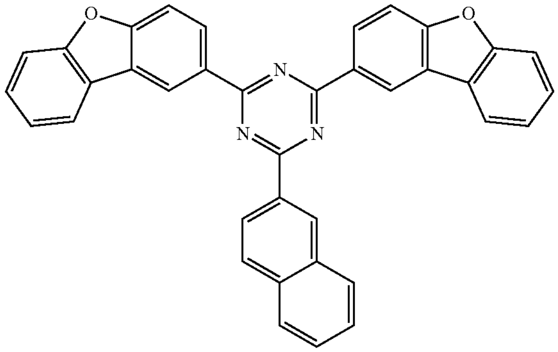
H2-143
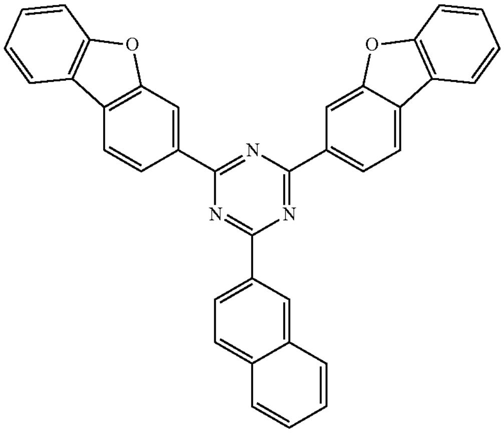

-continued
H2-144
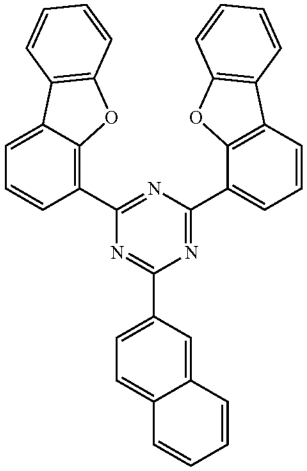
H2-145
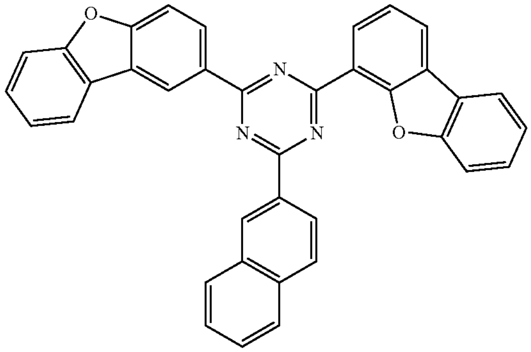
H2-146
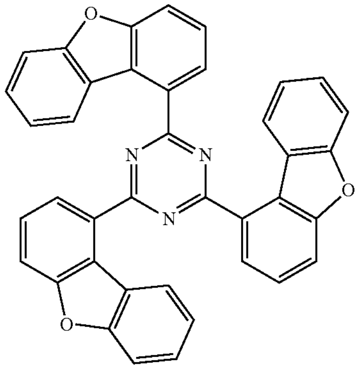
H2-147
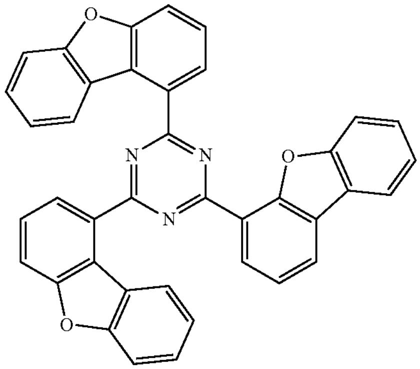
-continued
H2-148
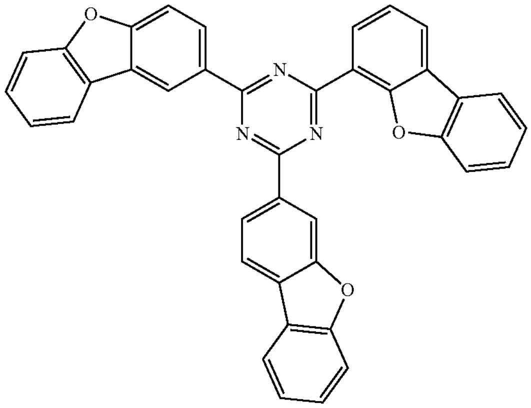
H2-149
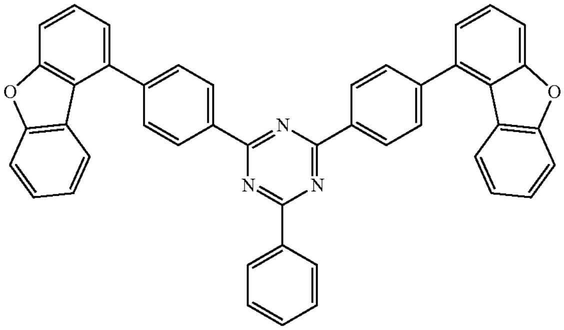
H2-150
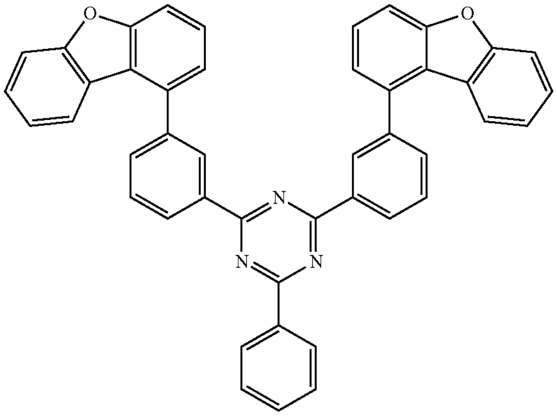
H2-151
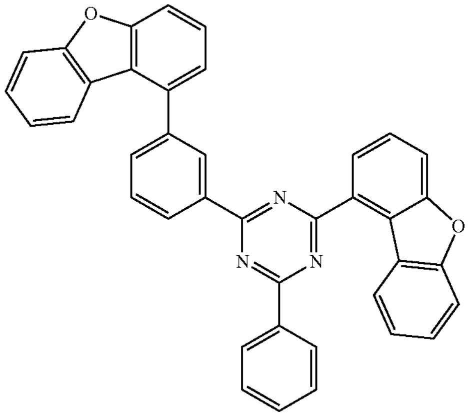

-continued
H2-152
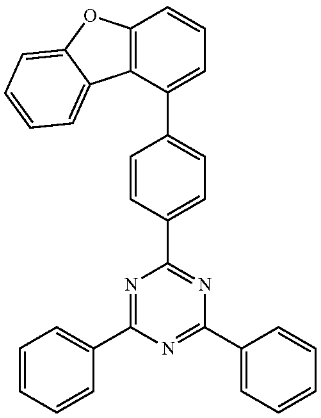
H2-153
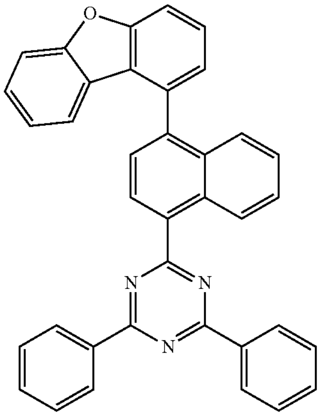
H2-154
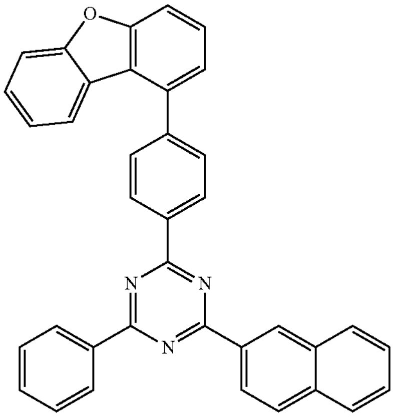
-continued
H2-155
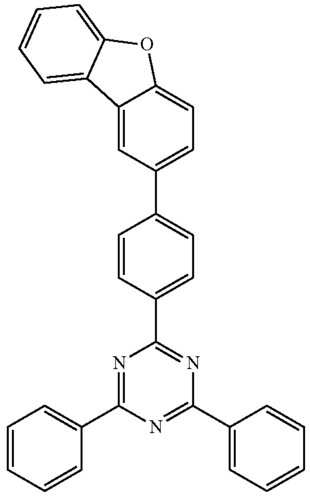
H2-156
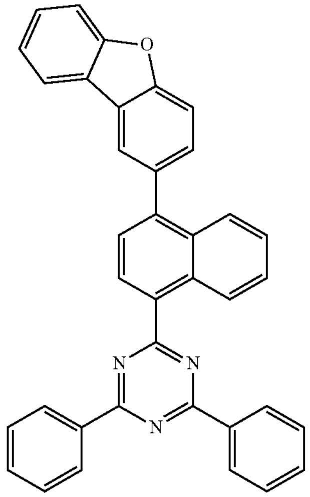
H2-157
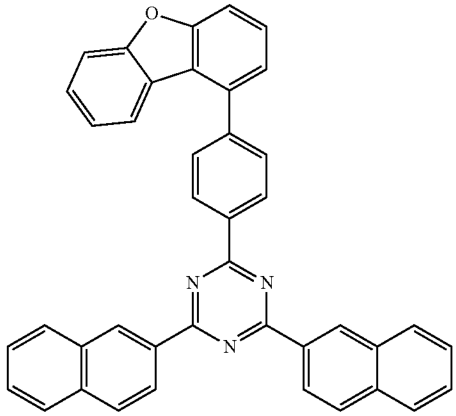

-continued
H2-158
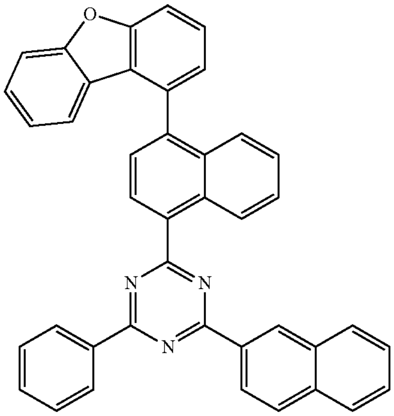
H2-159
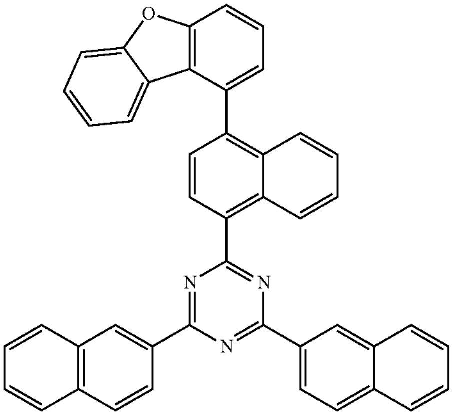
H2-160
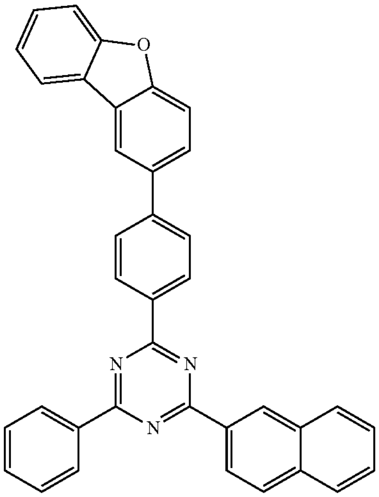
-continued
H2-161
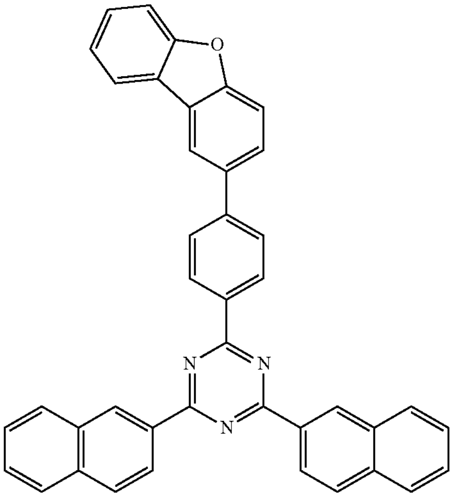
H2-162
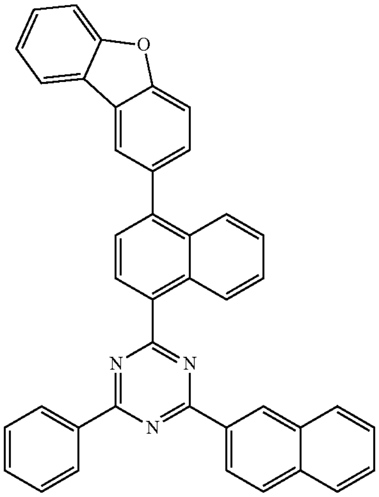
H2-163
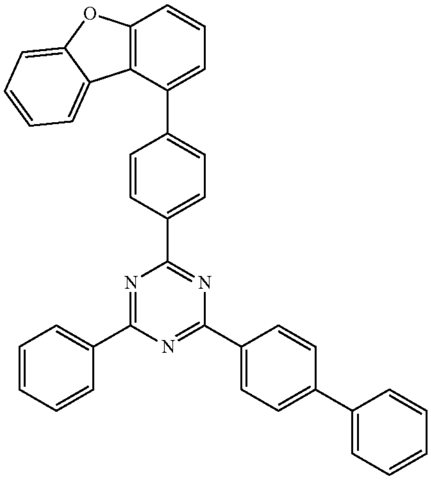

-continued
H2-164
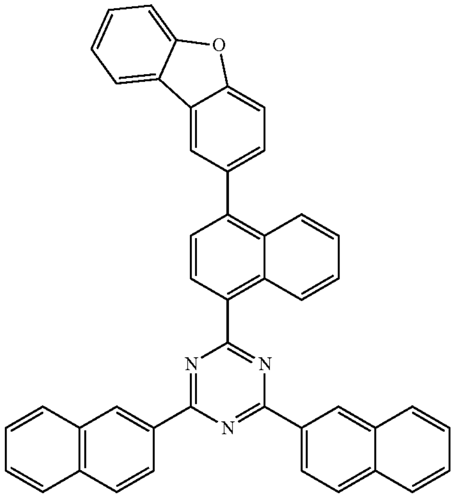
H2-165
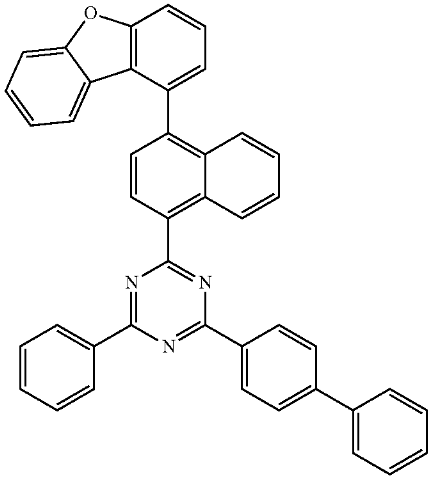
H2-166
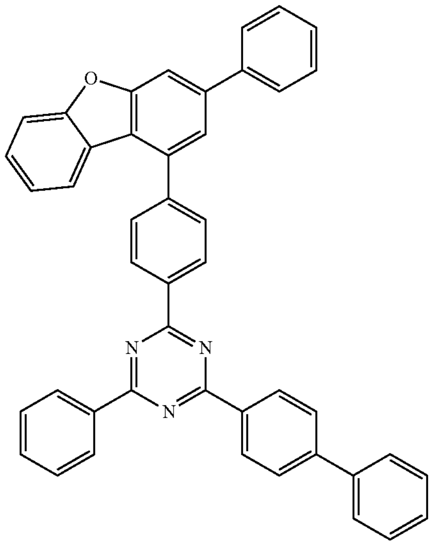
-continued
H2-167
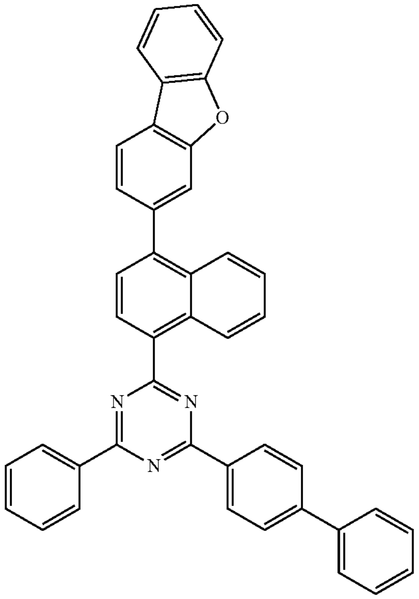
H2-168
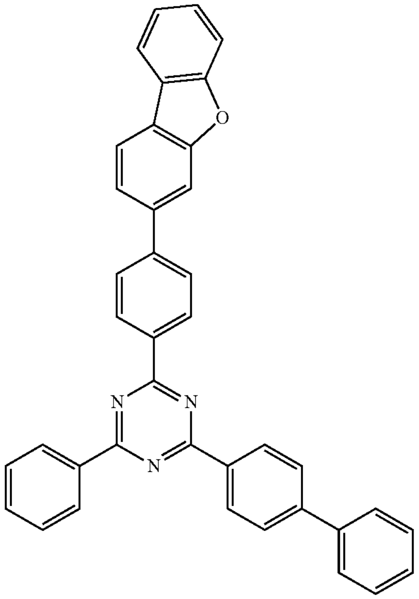

-continued
H2-169
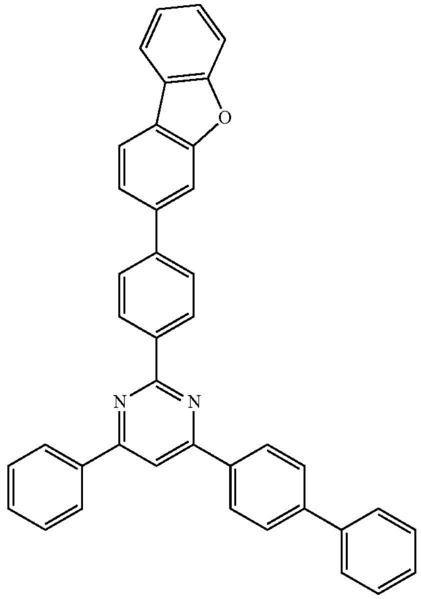
H2-170
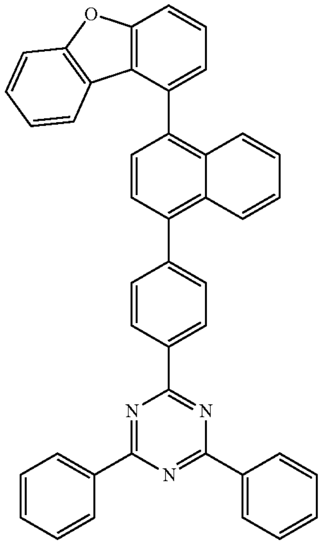
H2-171
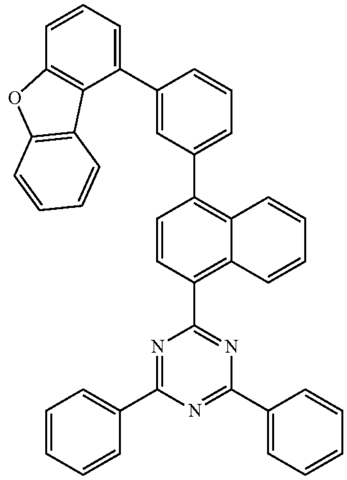
-continued
H2-172
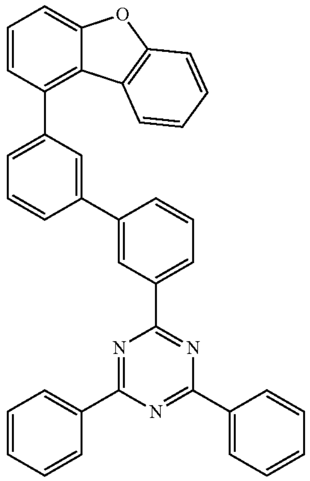
H2-173
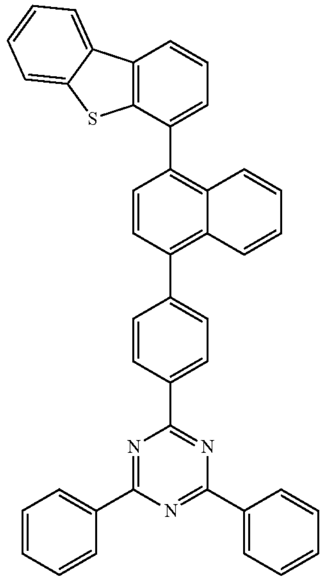
H2-174
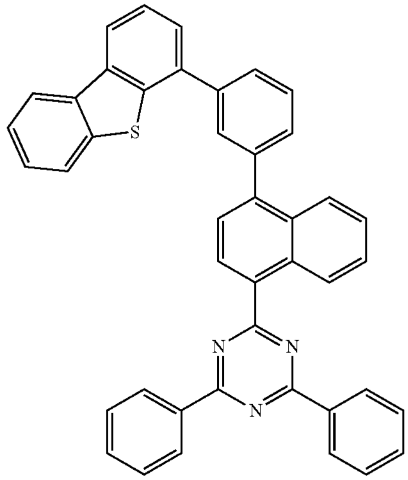

-continued
H2-175
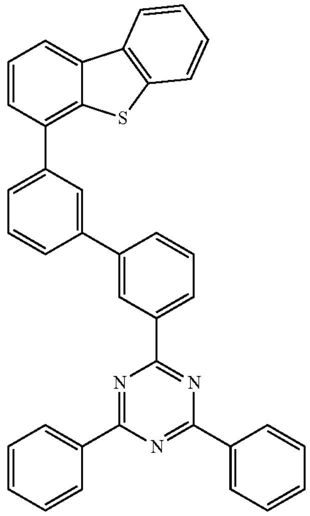
H2-176
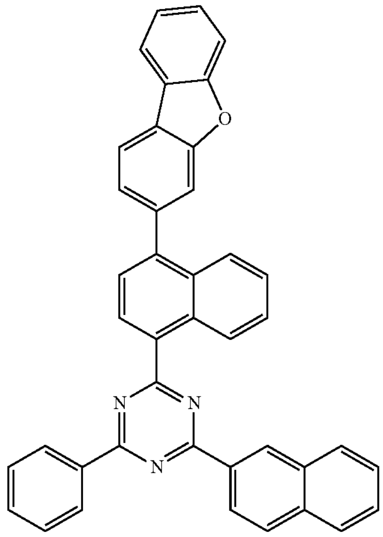
H2-177
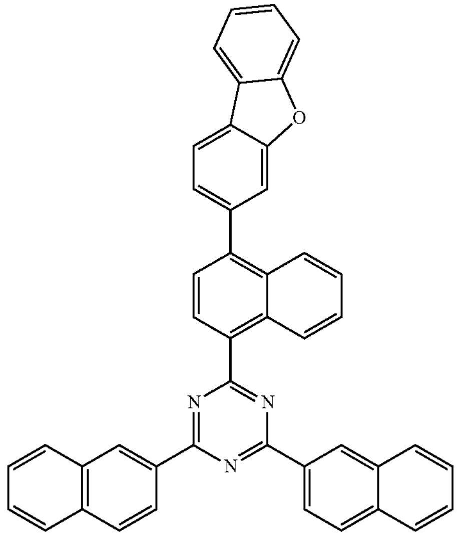
-continued
H2-178
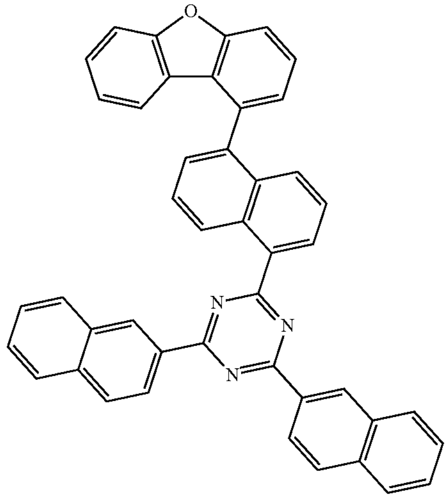
H2-179
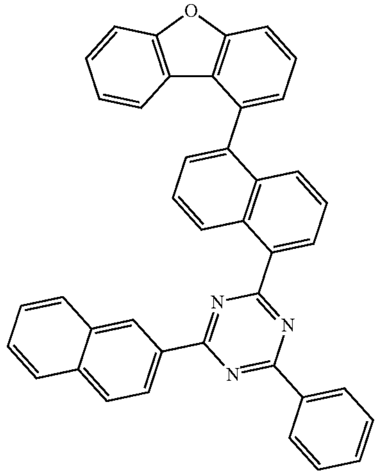
H2-180
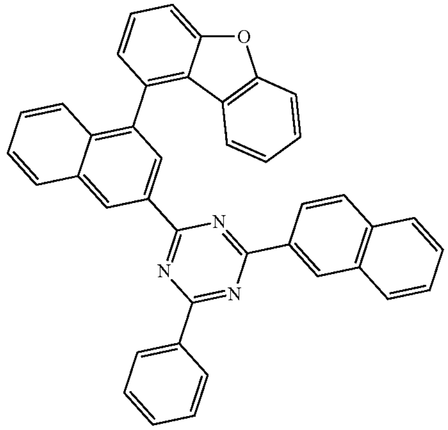

-continued
H2-181
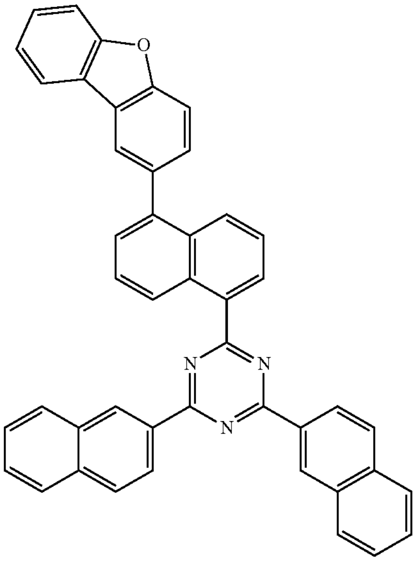
H2-182
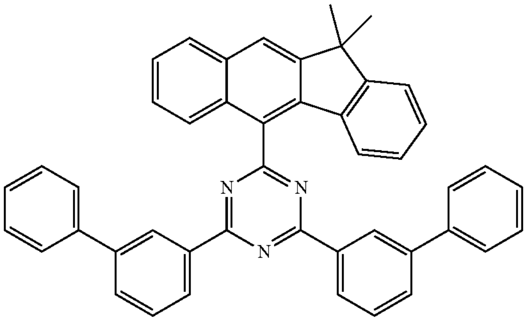
H2-183
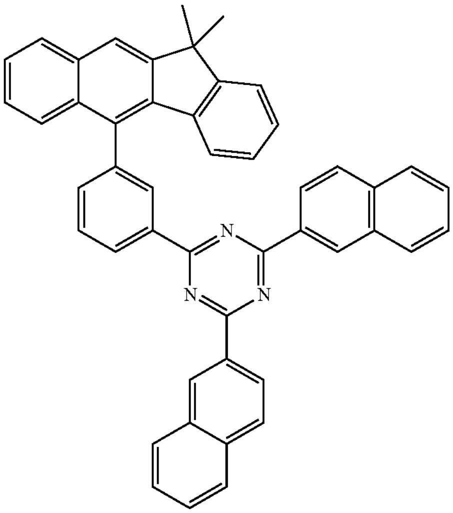
-continued
H2-184
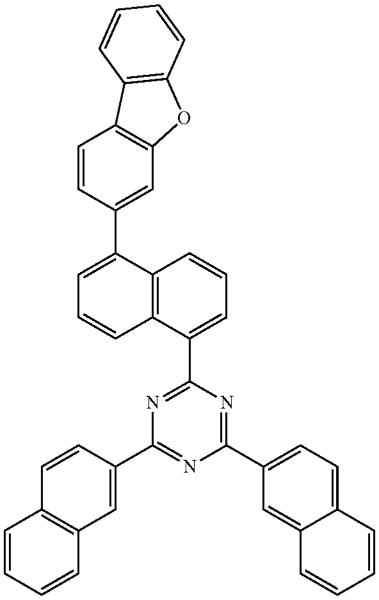
H2-185
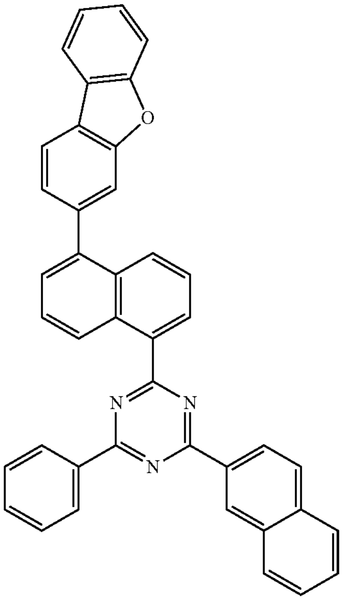

-continued
H2-186
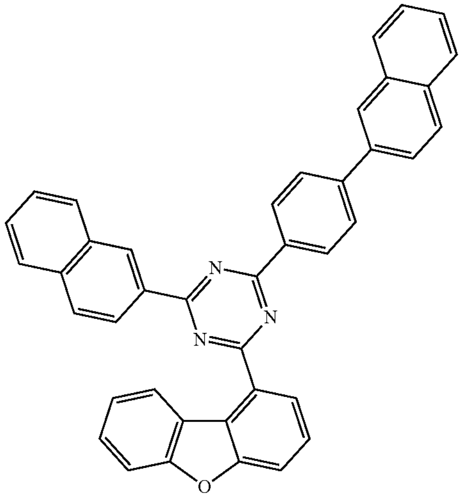
H2-187
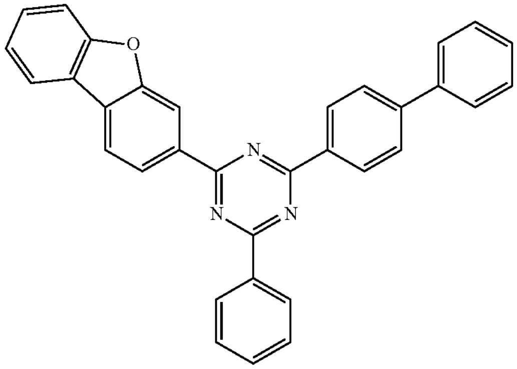
H2-188
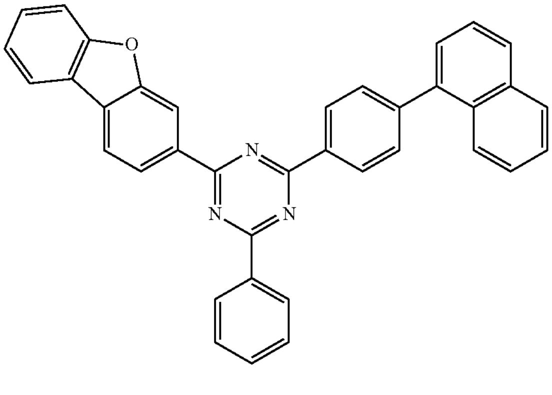
-continued
H2-189
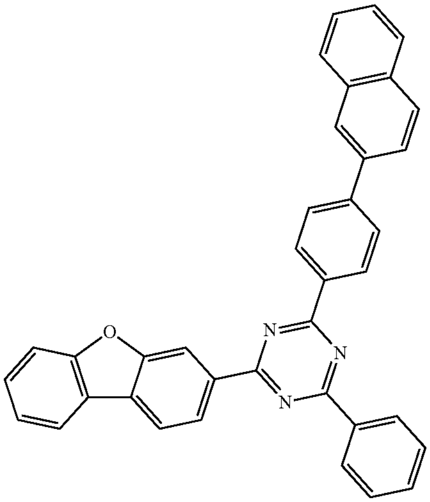
H2-190
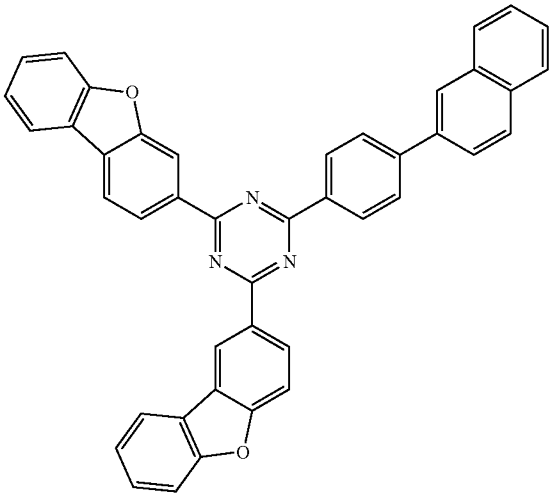
H2-191
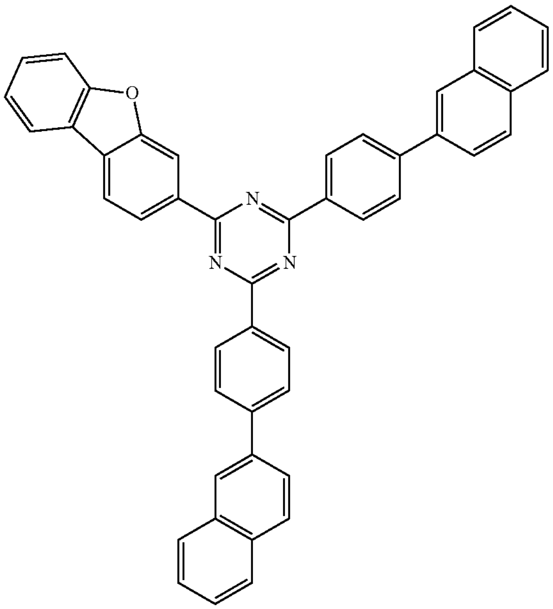

-continued
H2-192
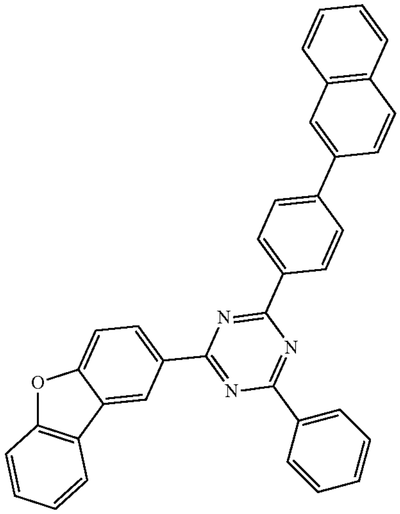
H2-193
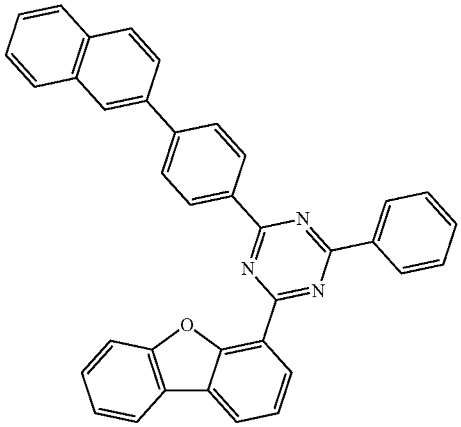
H2-194
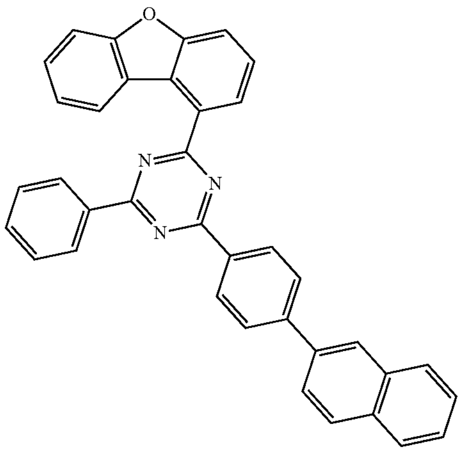
-continued
H2-195
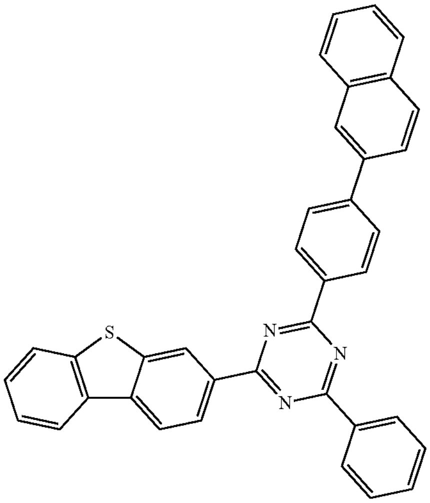
H2-196
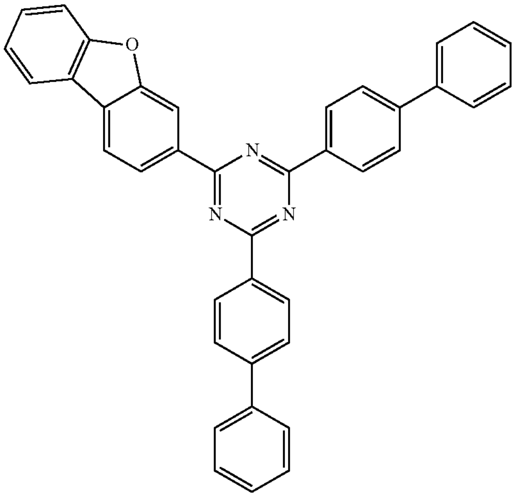
H2-197
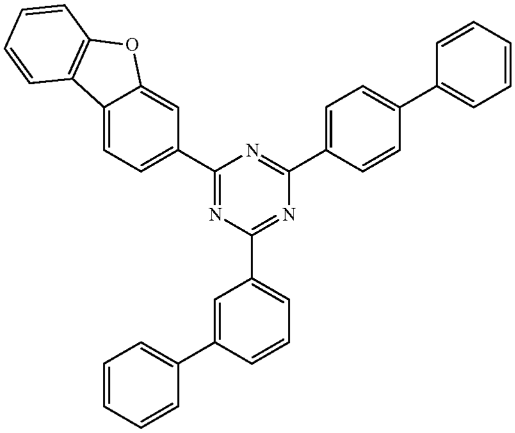

-continued
H2-198
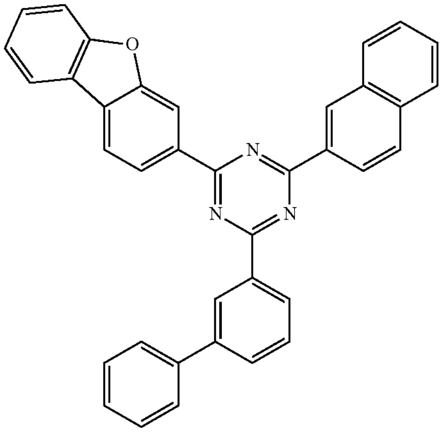
H2-199
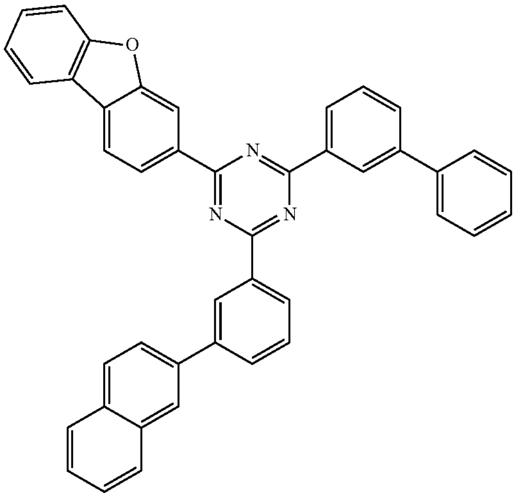
H2-200
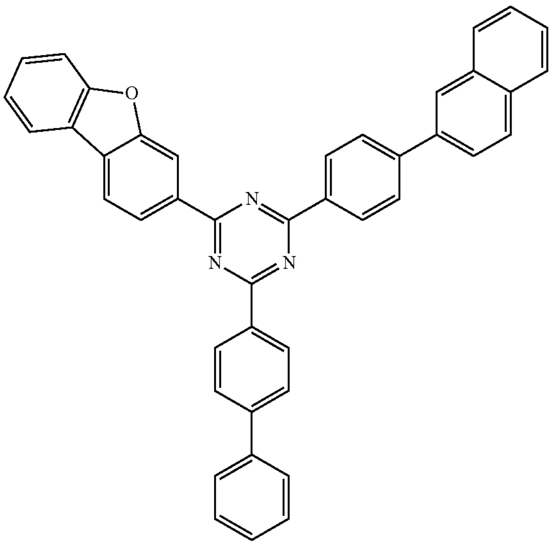
-continued
H2-201
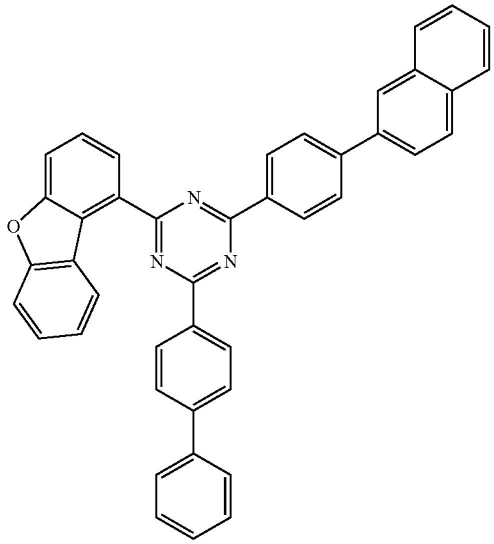
H2-202
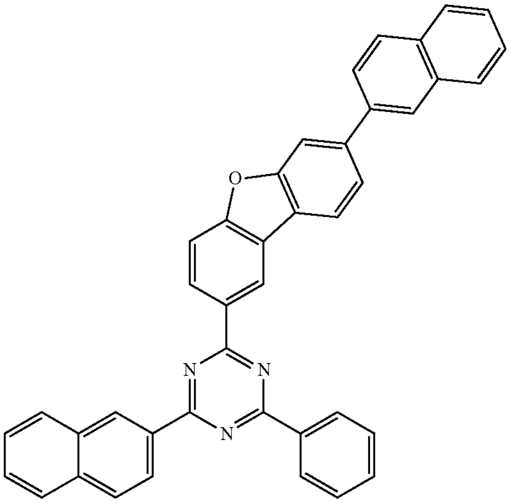
H2-203
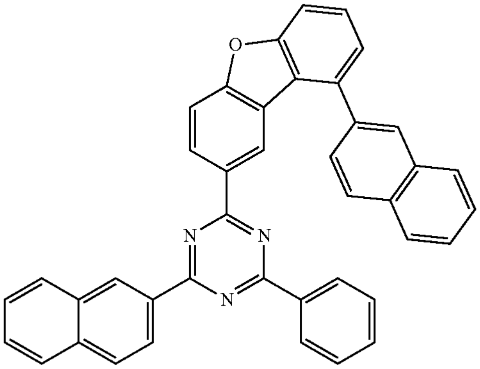

-continued
H2-204
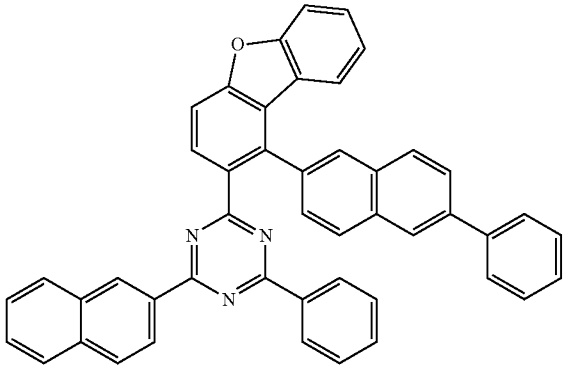
H2-205
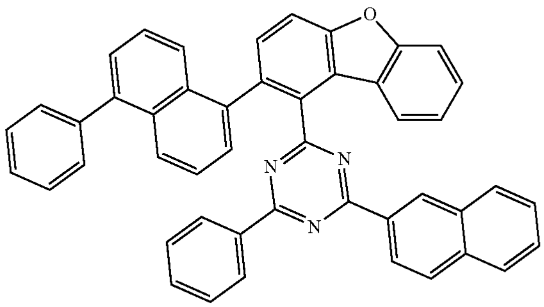
H2-206
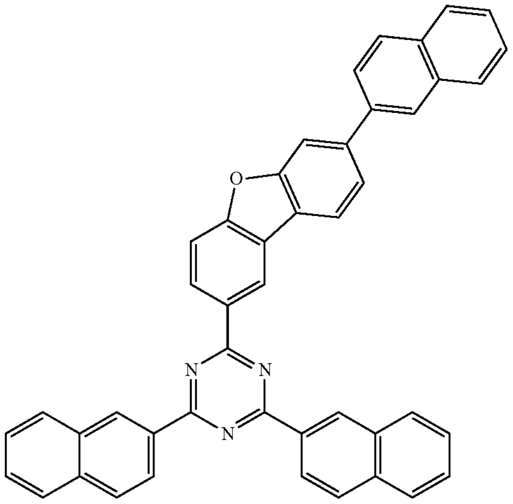
H2-207
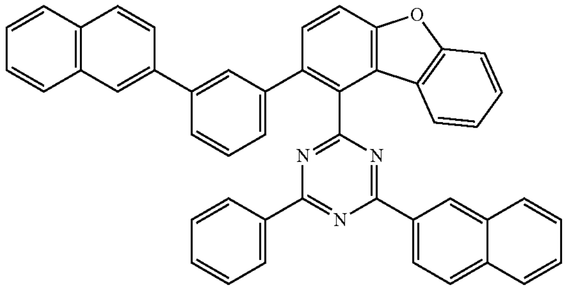
-continued
H2-208
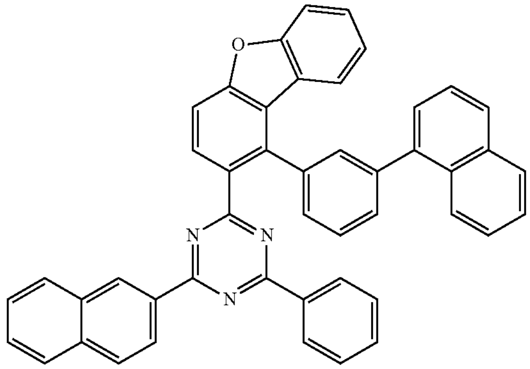
H2-209
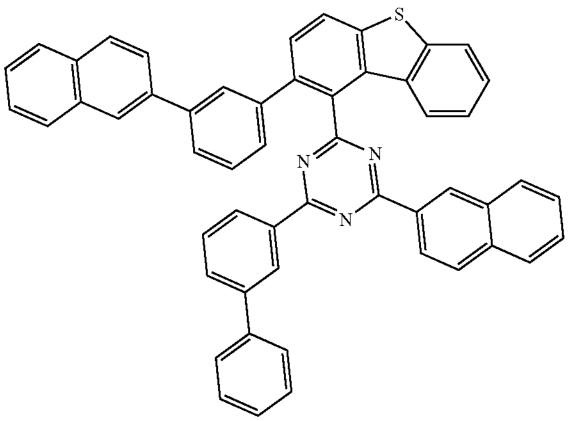
H2-210
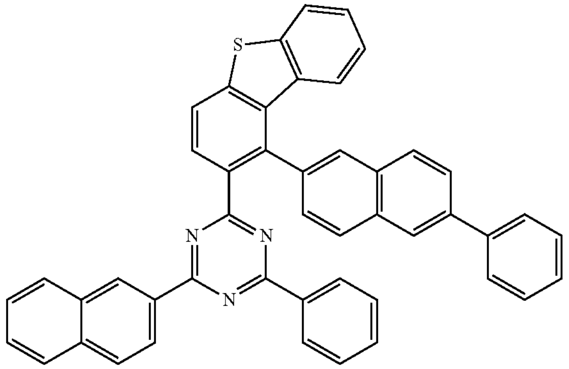
H2-211
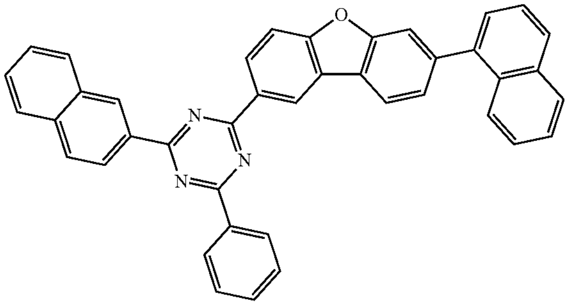

-continued
H2-212
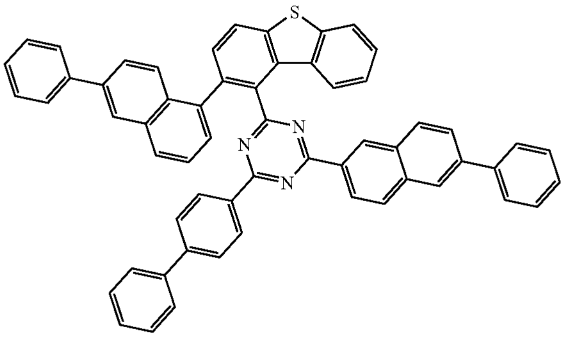
H2-213
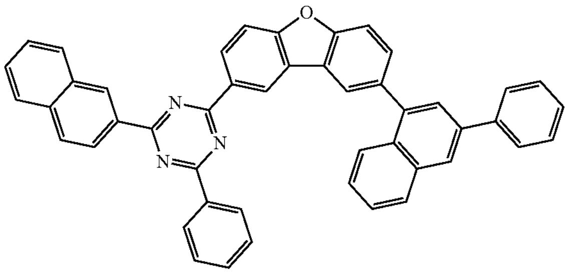
H2-214
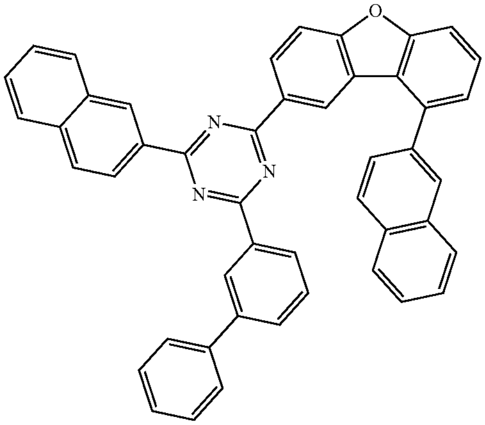
H2-215
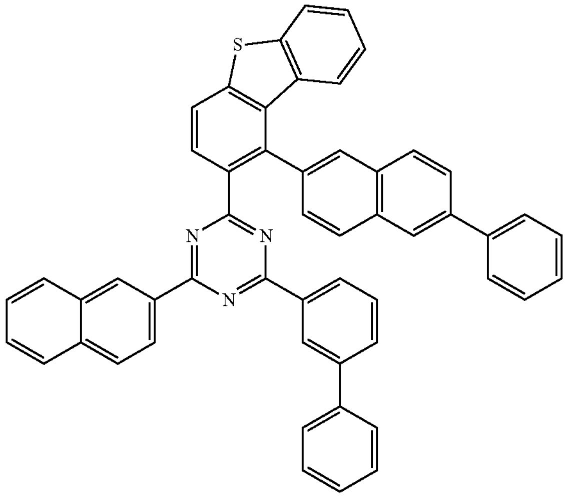
-continued
H2-216
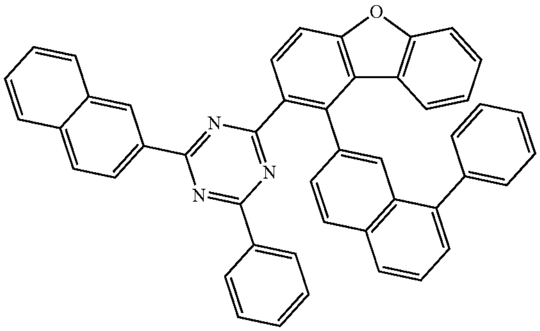
H2-217
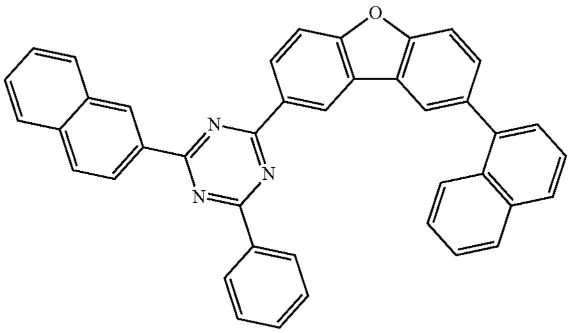
H2-218
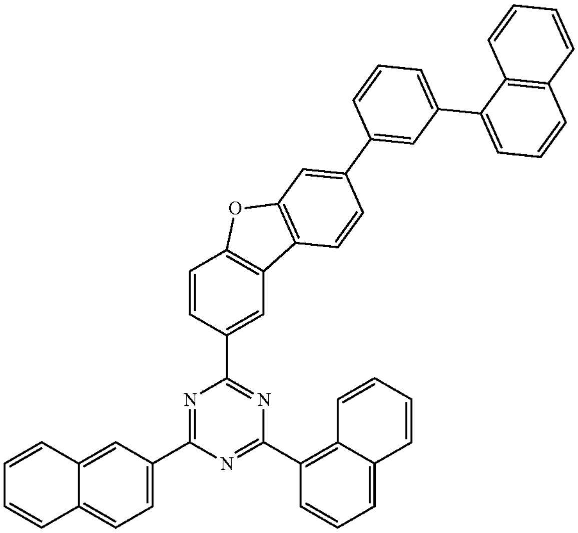

-continued
H2-219
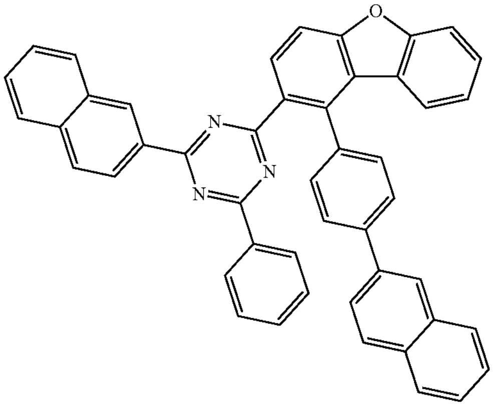
H2-220
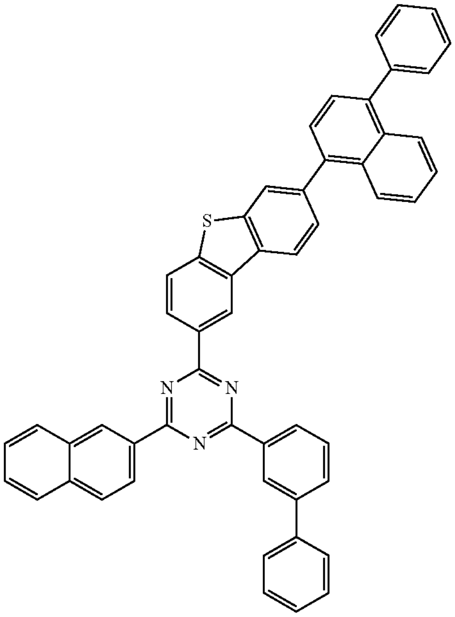
H2-221
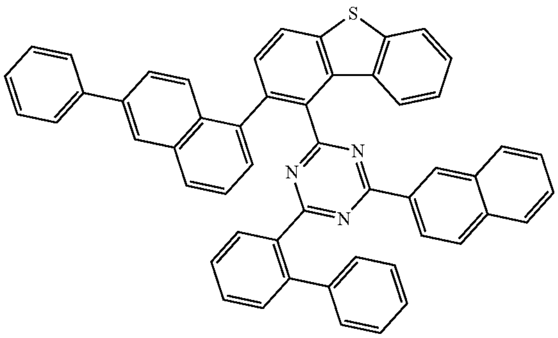
-continued
H2-222
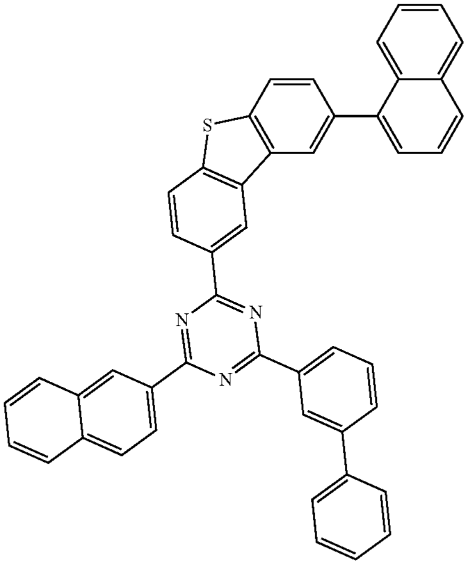
H2-223
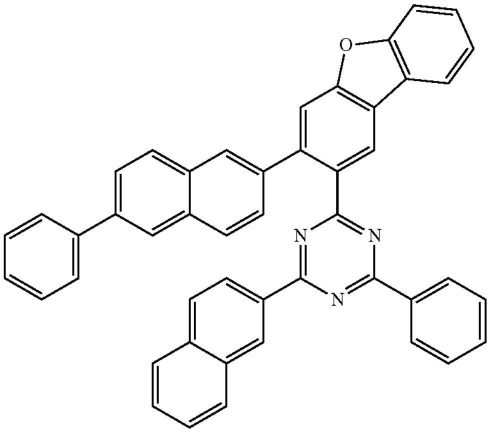
H2-224
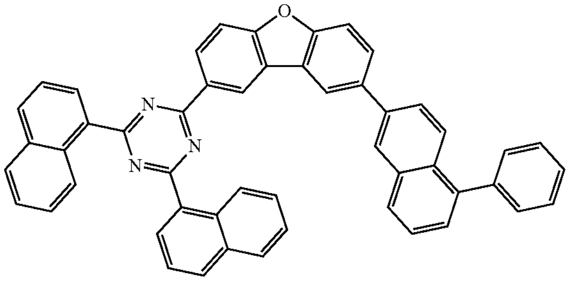

-continued
H2-225
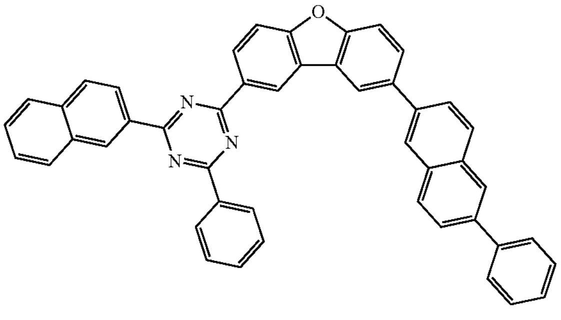
H2-226
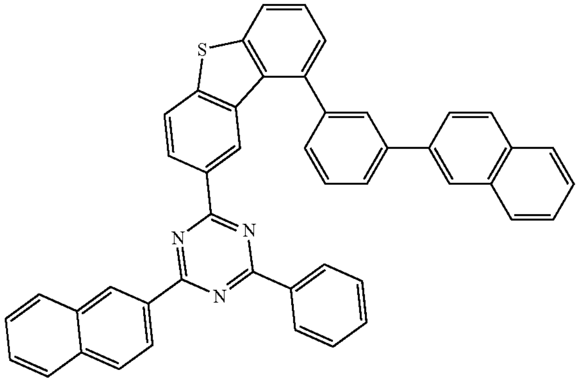
H2-227
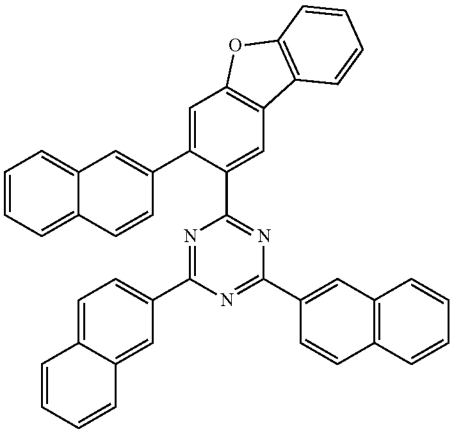
H2-228
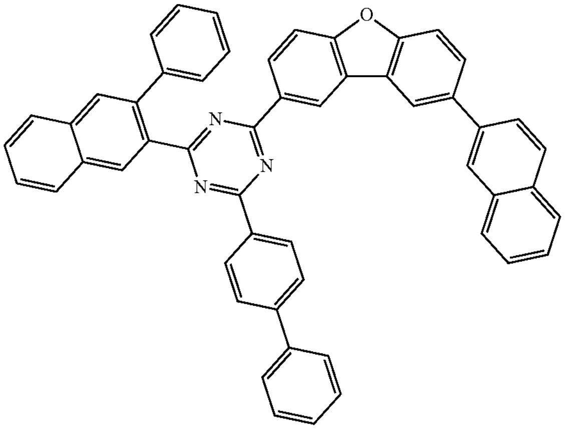
-continued
H2-229
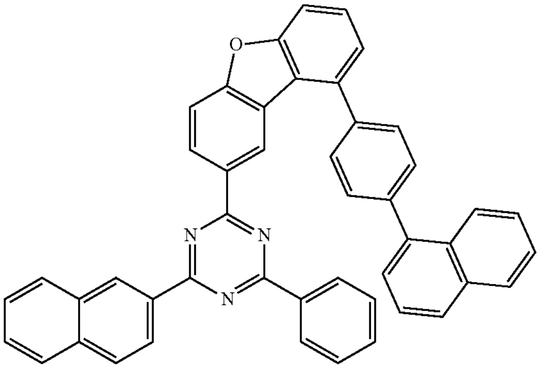
H2-230
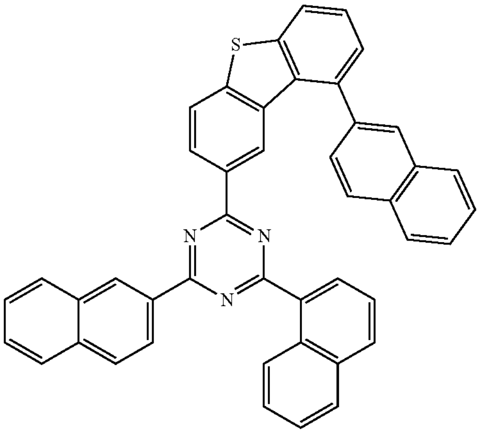
H2-231
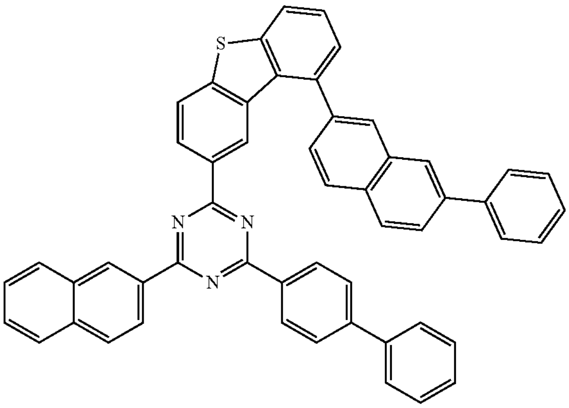

-continued
H2-232
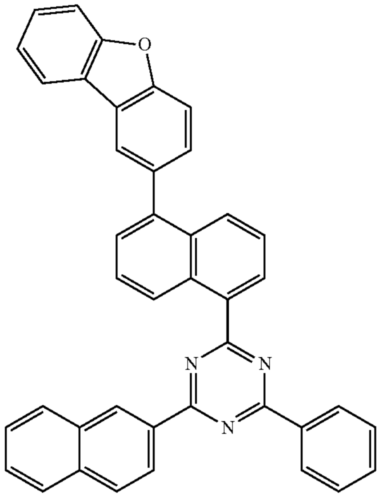
H2-233
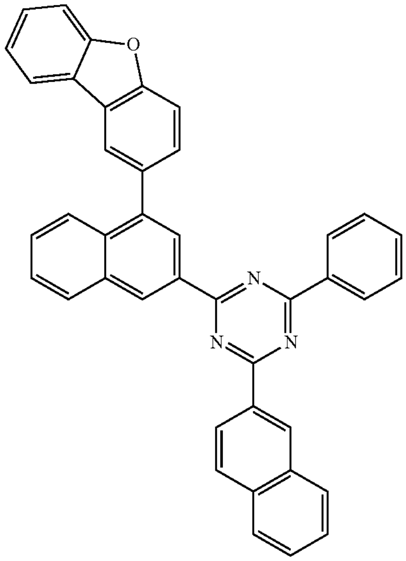
H2-234
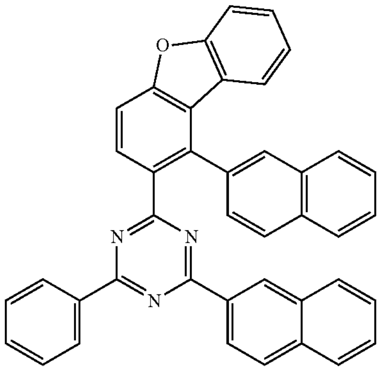
-continued
H2-235
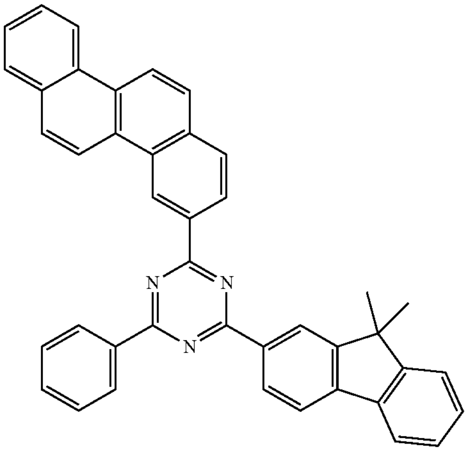
H2-236
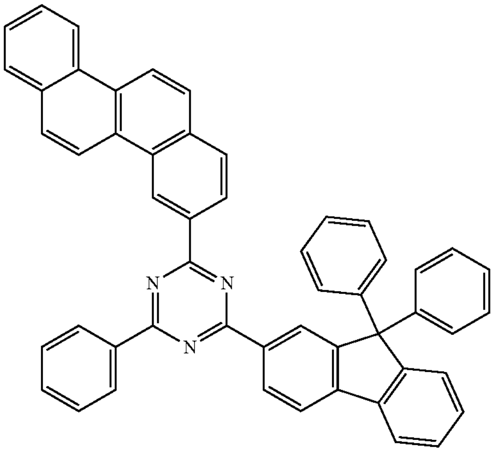
H2-237
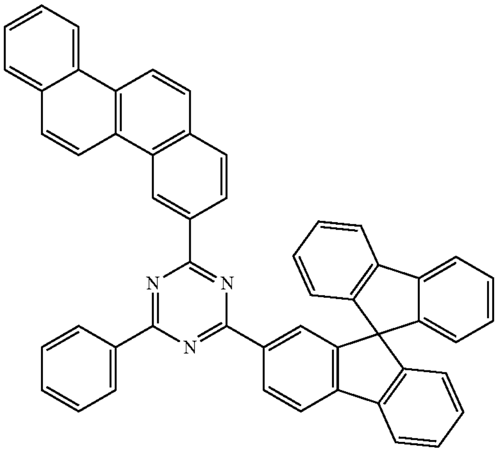

-continued
H2-238
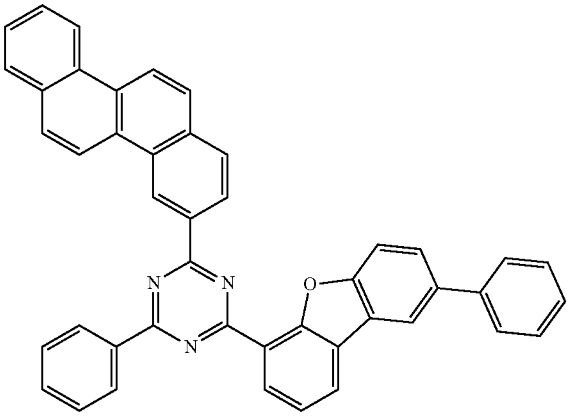
H2-239
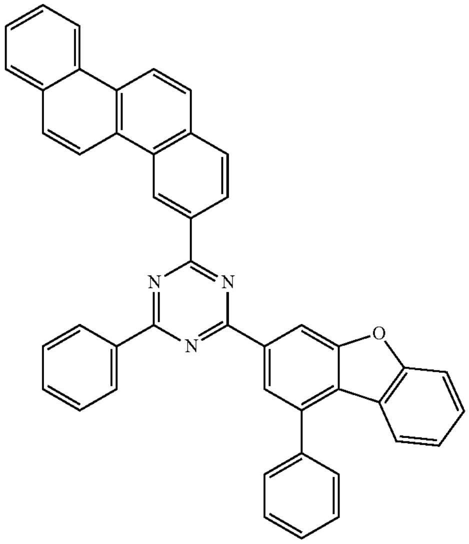
H2-240
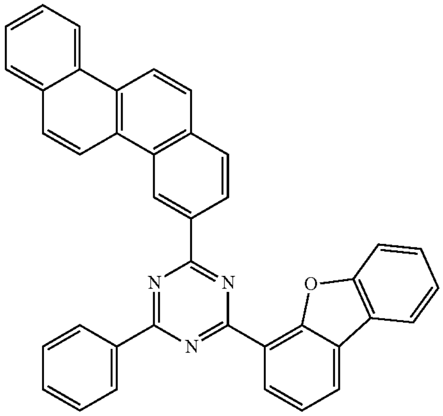
-continued
H2-241
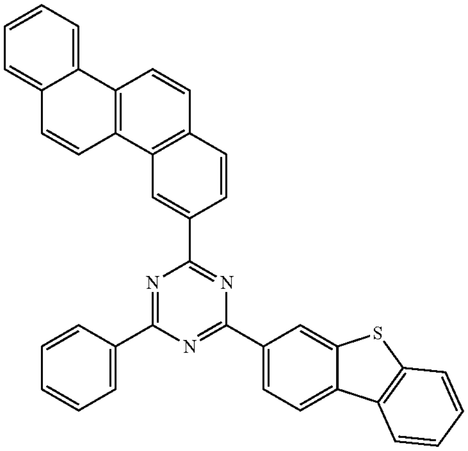
H2-242
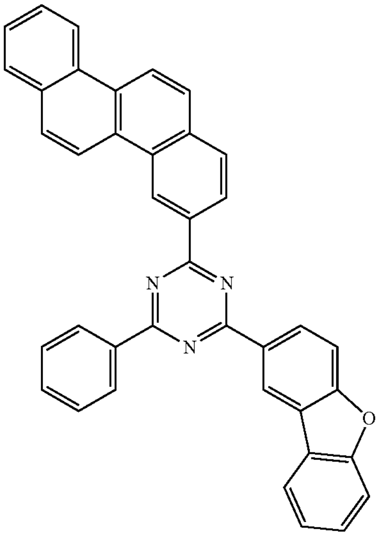
H2-243
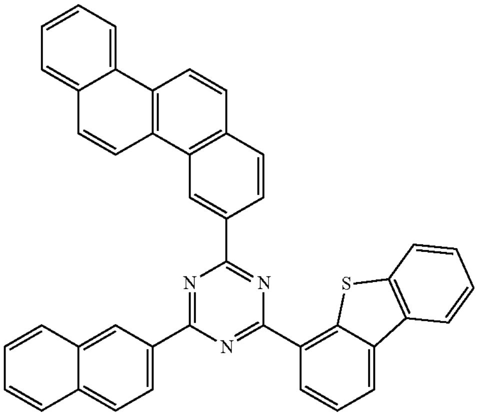

-continued
H2-244
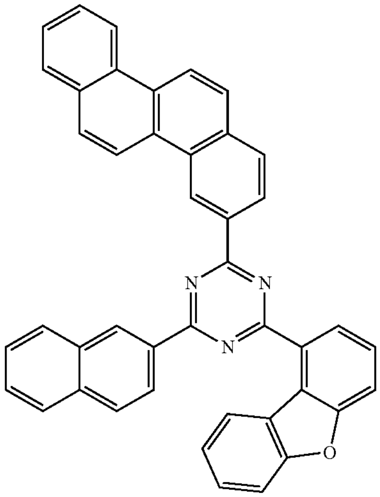
H2-245
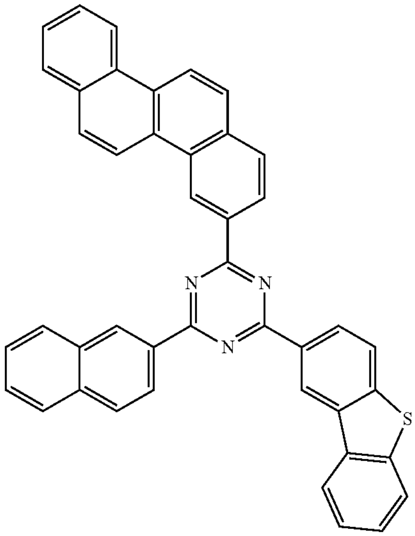
H2-246
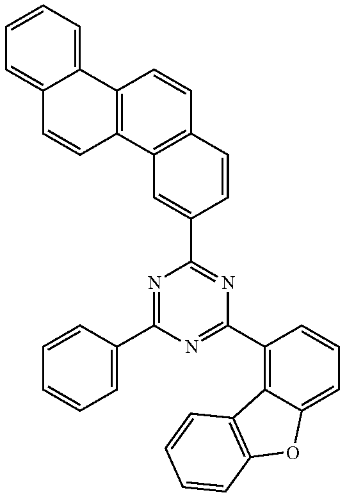
-continued
H2-247
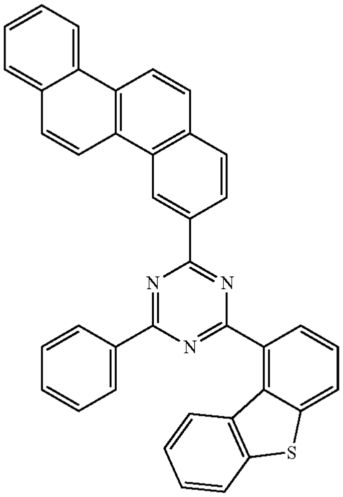
H2-248
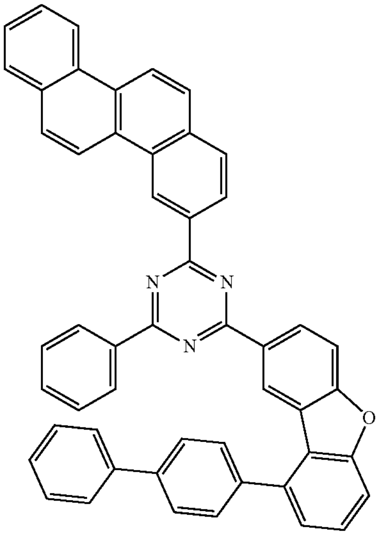
H2-249
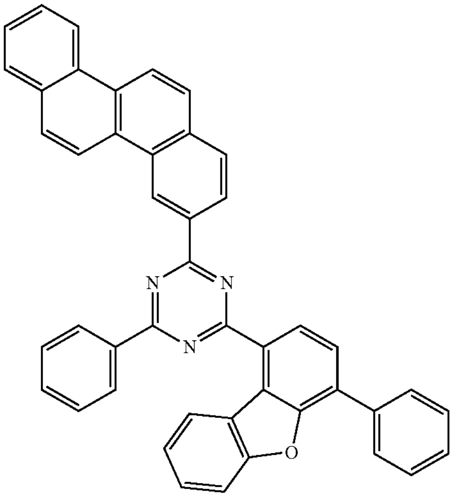

-continued
H2-250
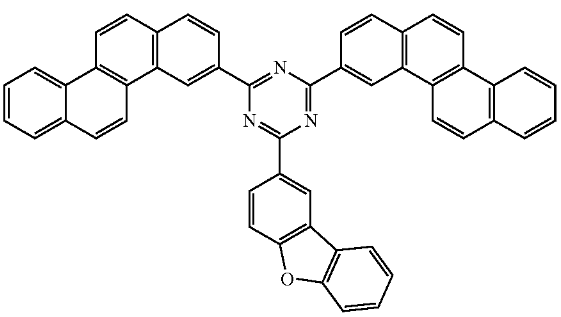
H2-251
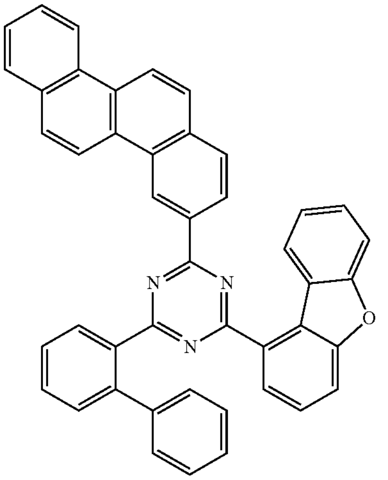
H2-252
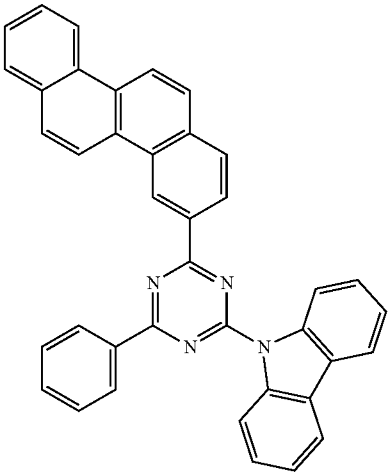
H2-253
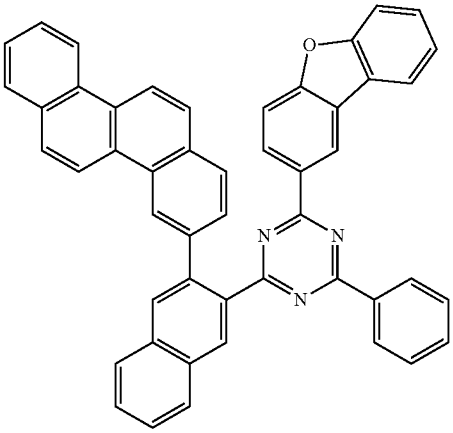
H2-254
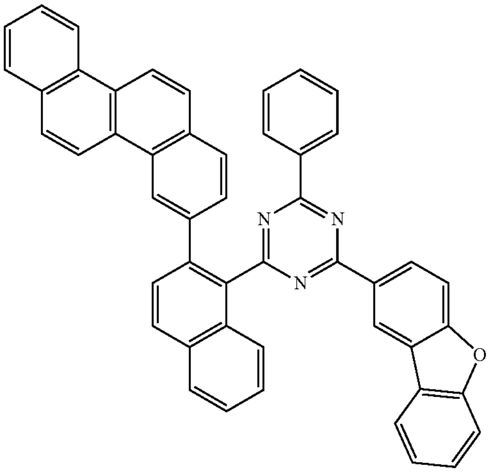
H2-255
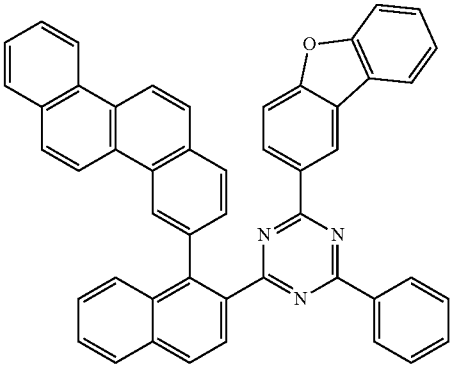

-continued
H2-256
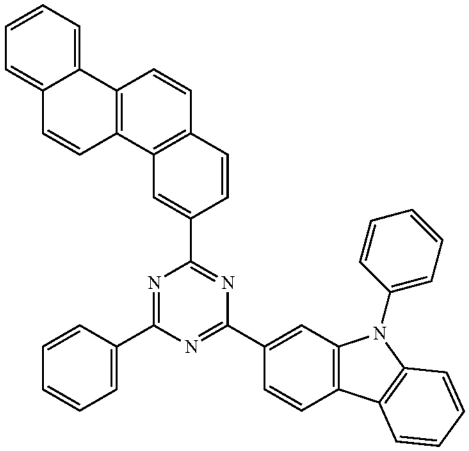
H2-257
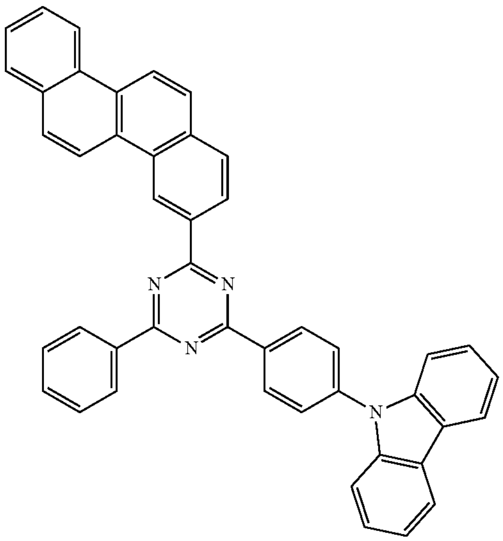
H2-258
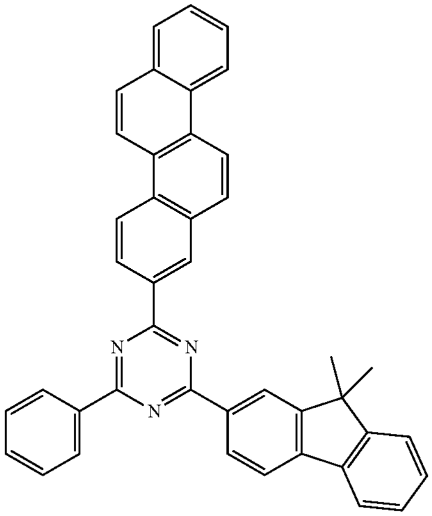
-continued
H2-259
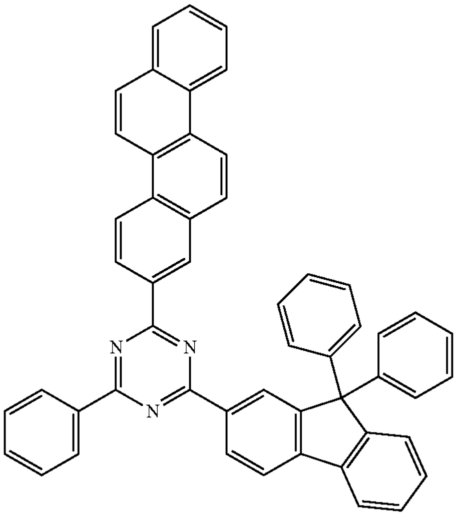
H2-260
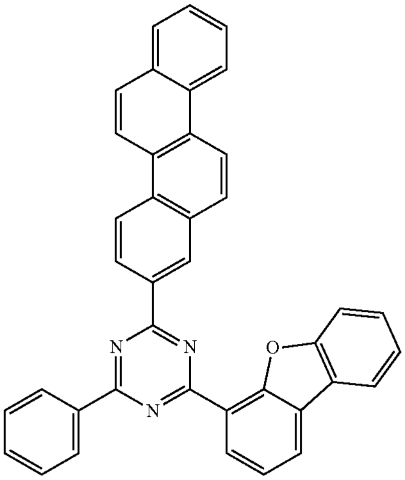
H2-261
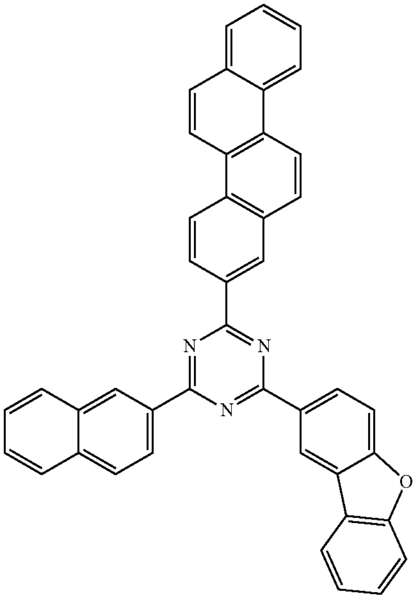

-continued
H2-262
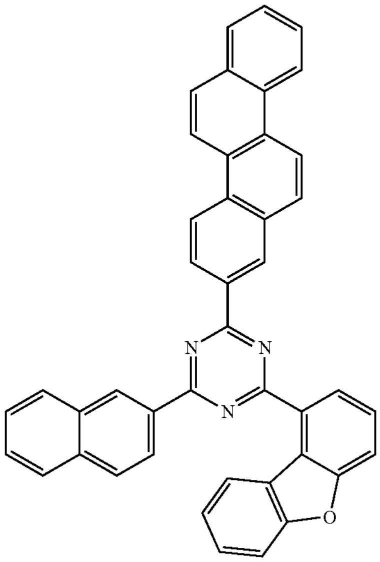
H2-263
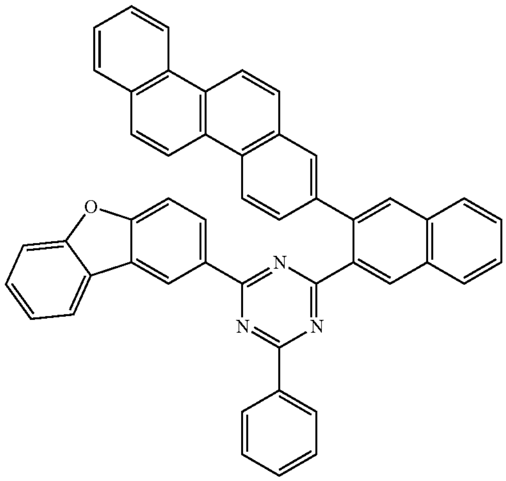
H2-264
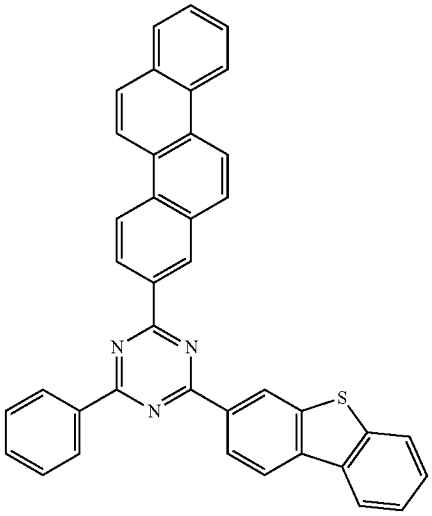
-continued
H2-265
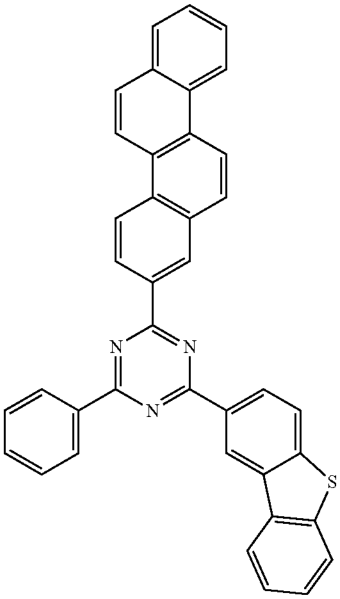
H2-266
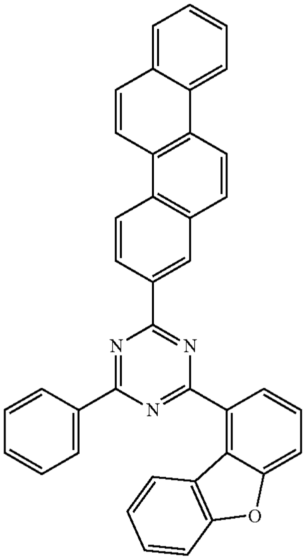
H2-267
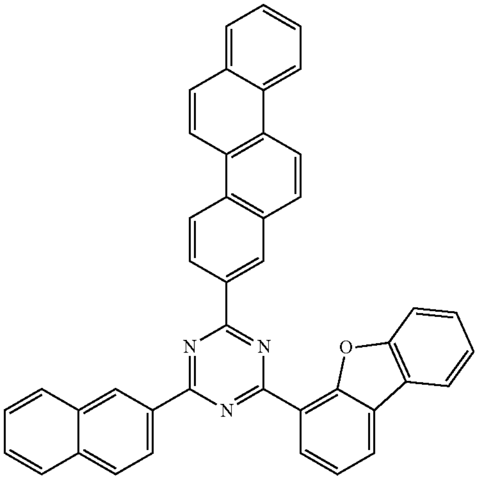

-continued
H2-268
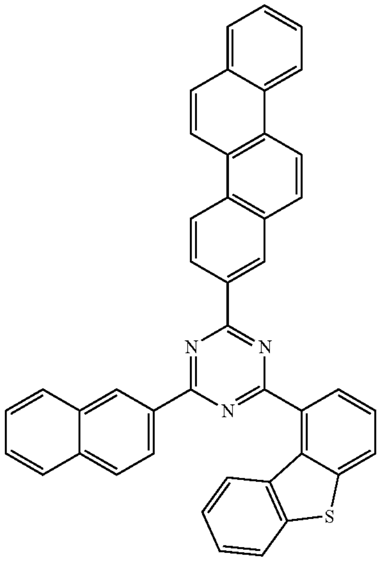
H2-269
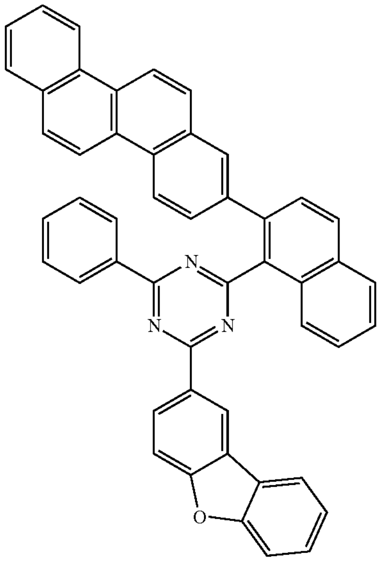
H2-270
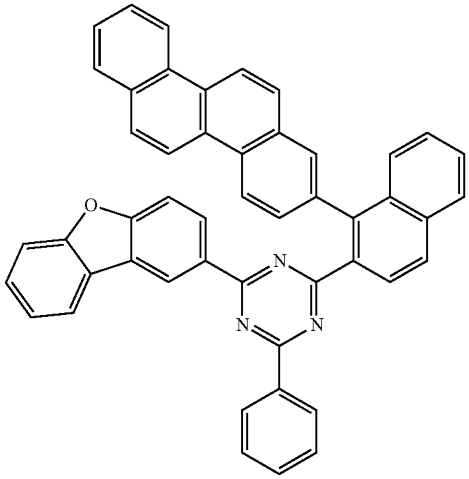
-continued
H2-271
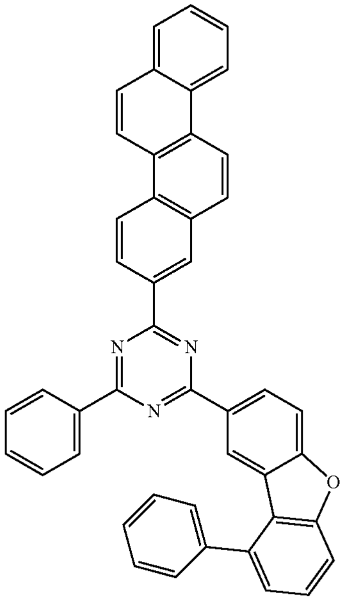
H2-272
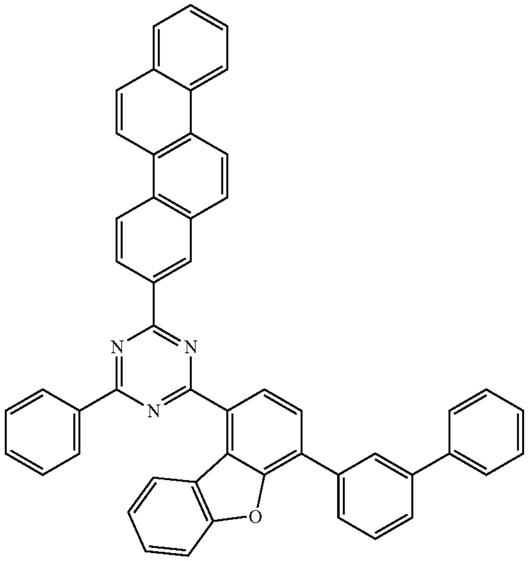

-continued
H2-273
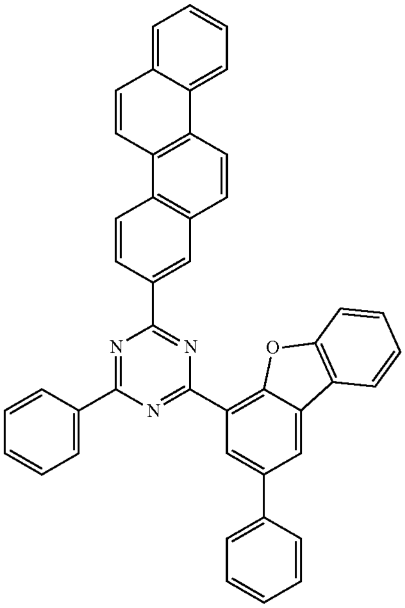
H2-274
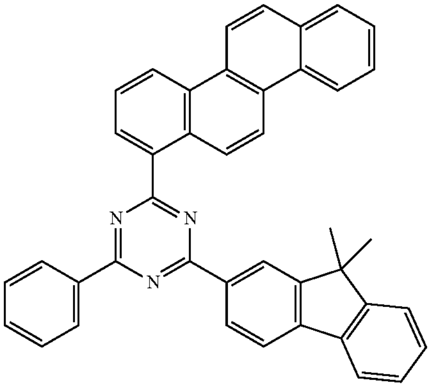
H2-275
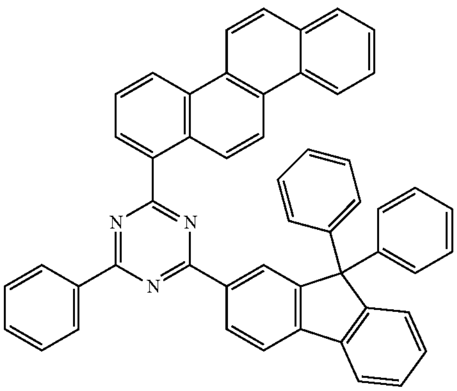
-continued
H2-276
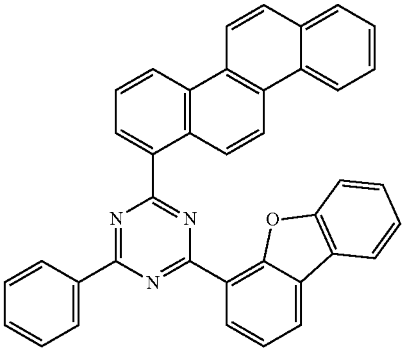
H2-277
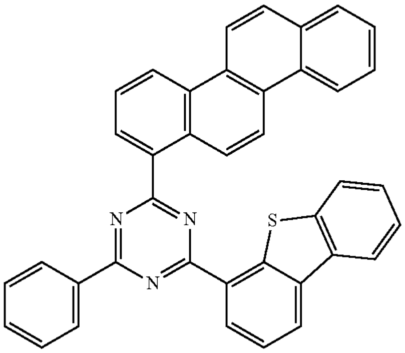
H2-278
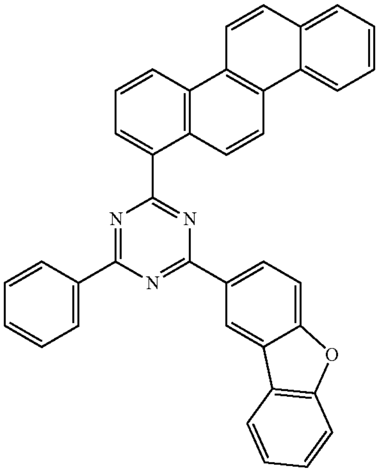
H2-279
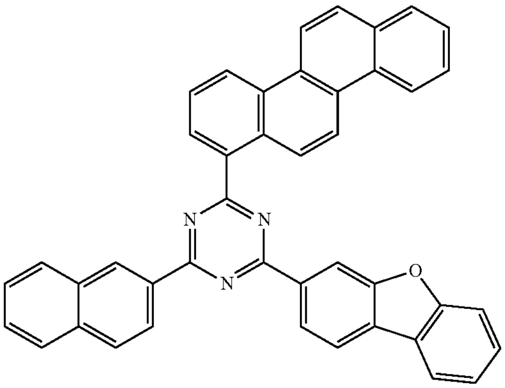

-continued
H2-280
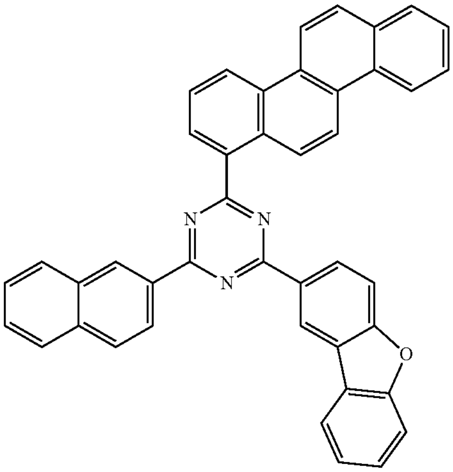
H2-281
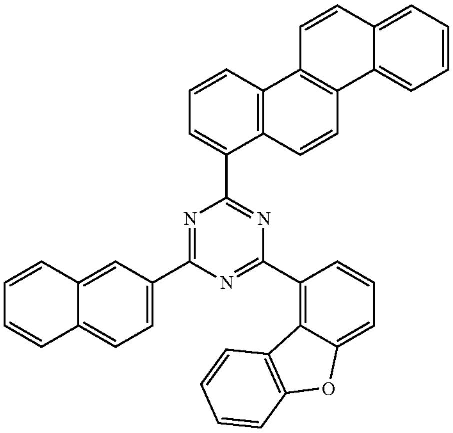
H2-282
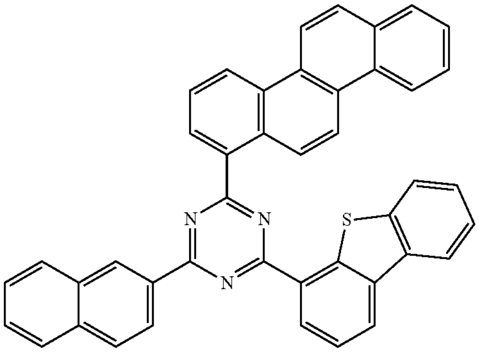
-continued
H2-283
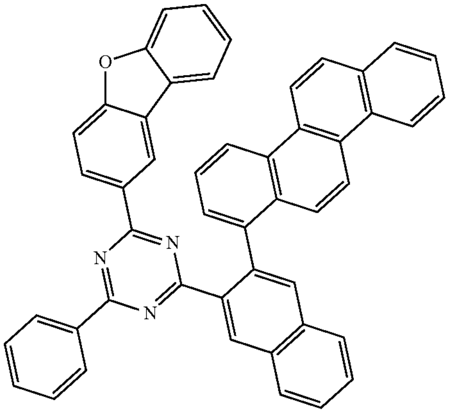
H2-284
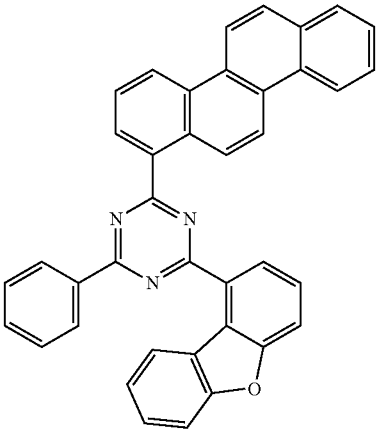
H2-285
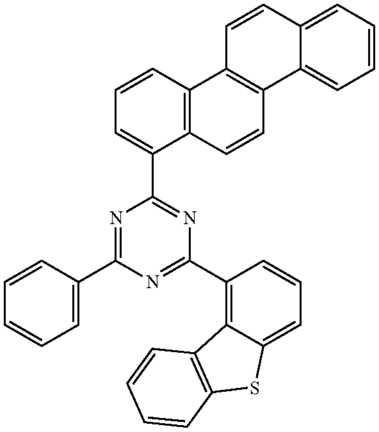
H2-286
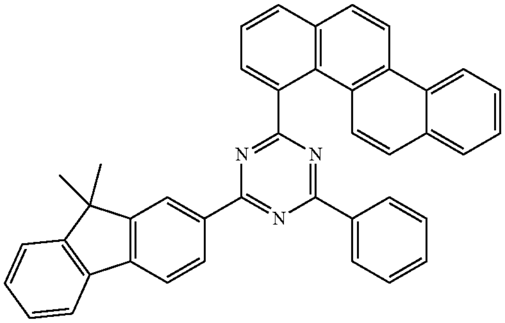

-continued
H2-287
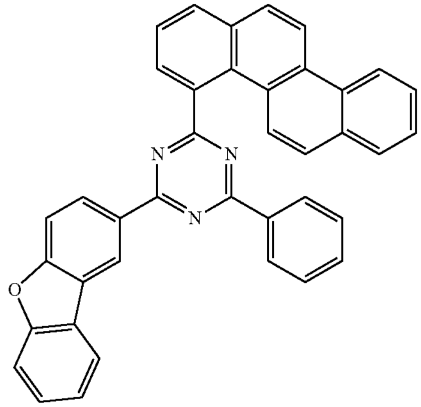
H2-288
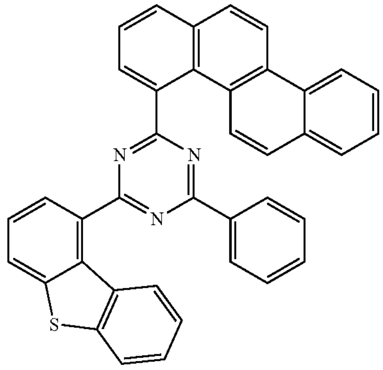
H2-289
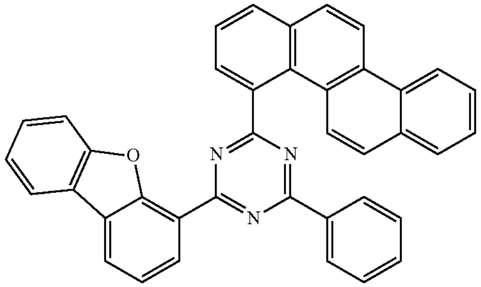
H2-290
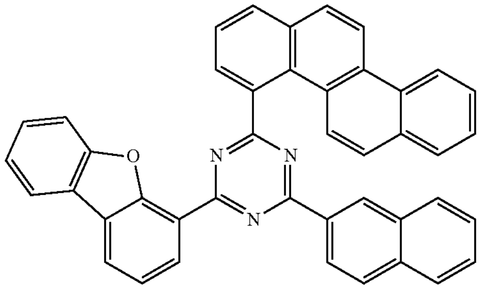
-continued
H2-291
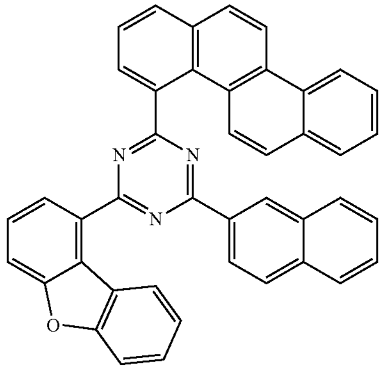
H2-292
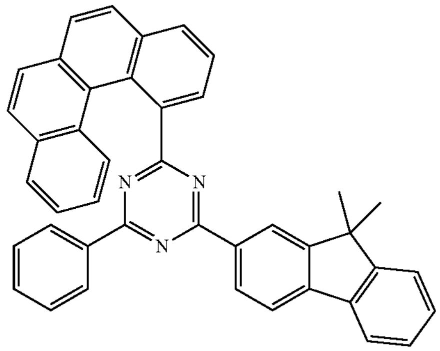
H2-293
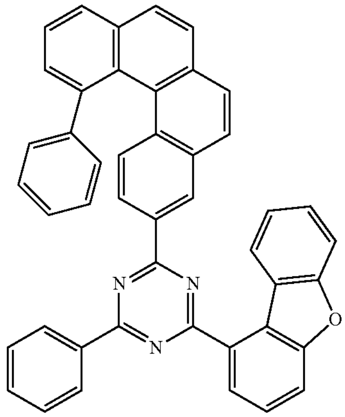
H2-294
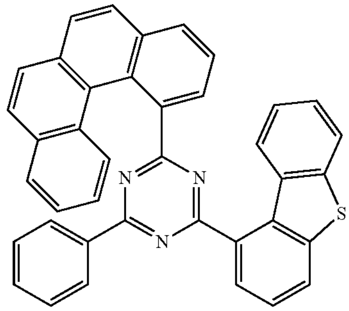

-continued
H2-295
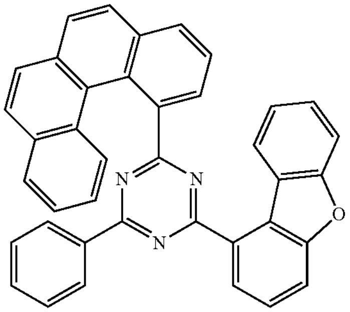
H2-296
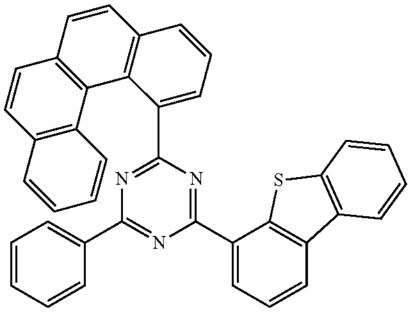
H2-297
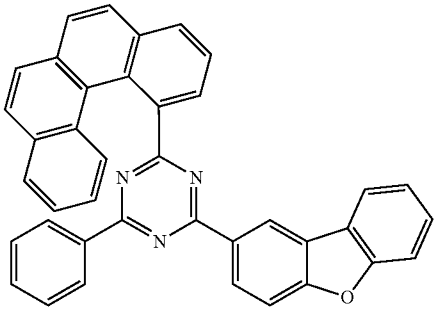
H2-298
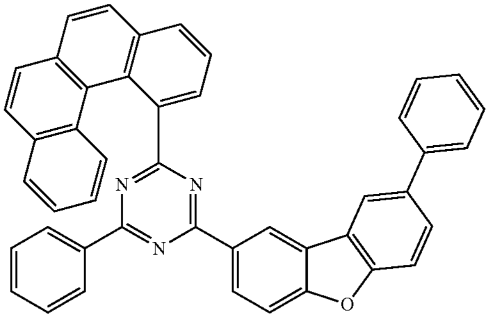
-continued
H2-299
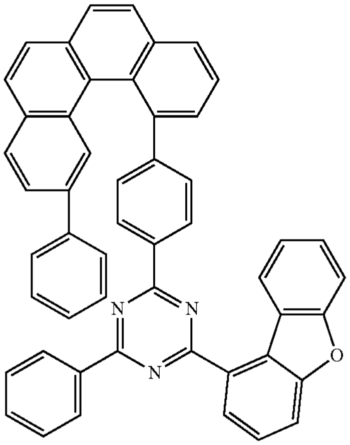
H2-300
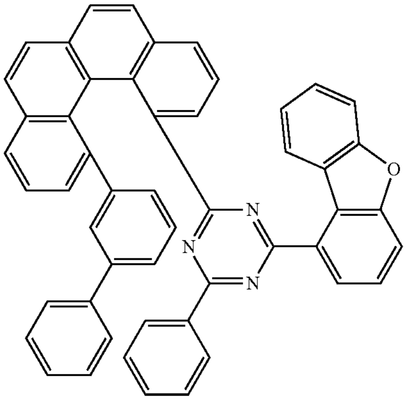
H2-301
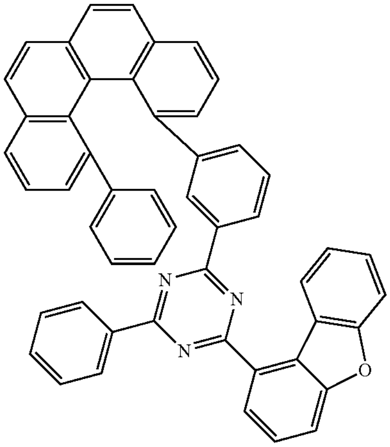

-continued
H2-302
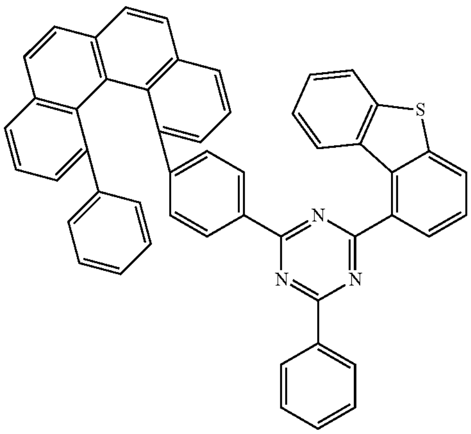
H2-303
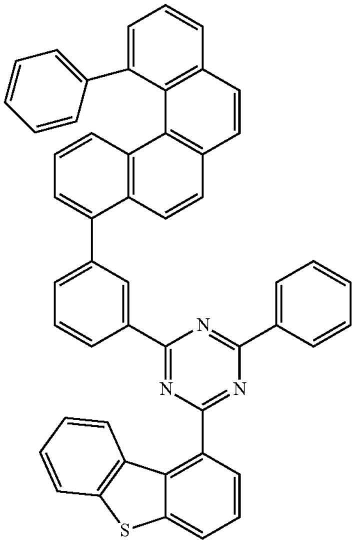
H2-304
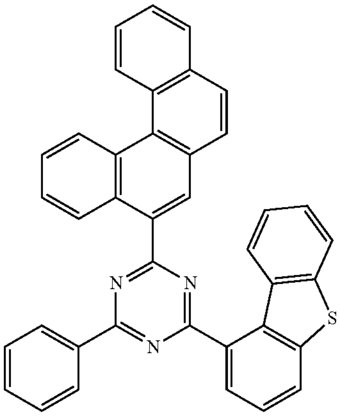
-continued
H2-305
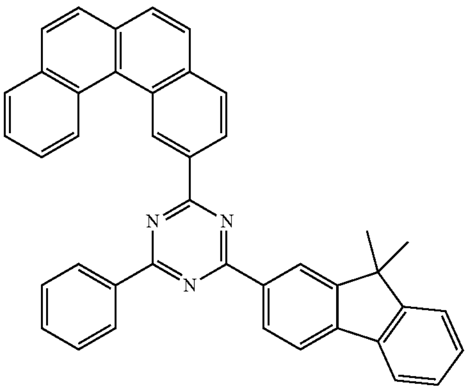
H2-306
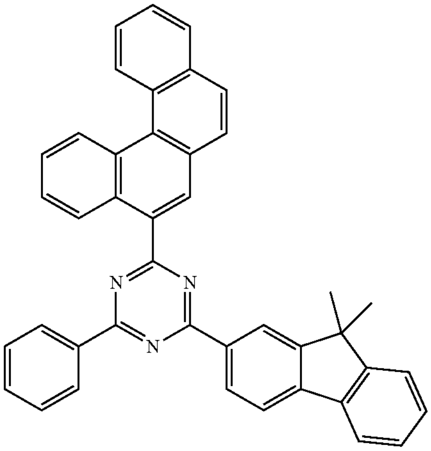
H2-307
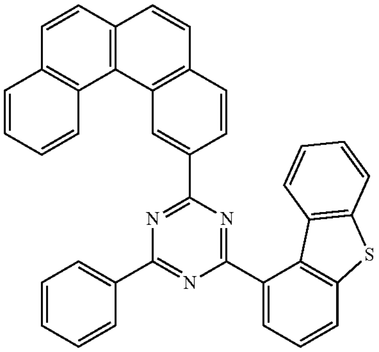
H2-308
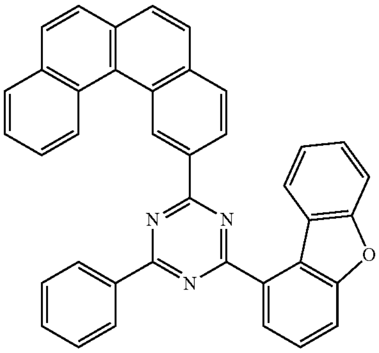

-continued
H2-309
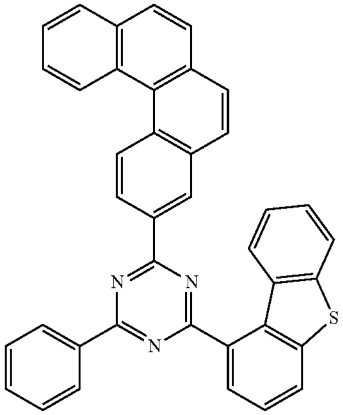
H2-310
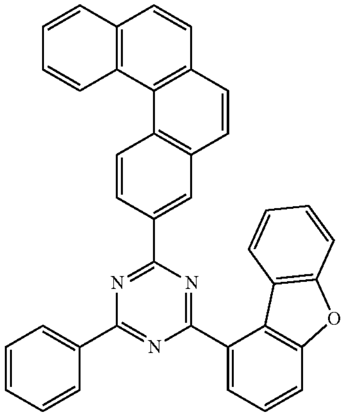
H2-311
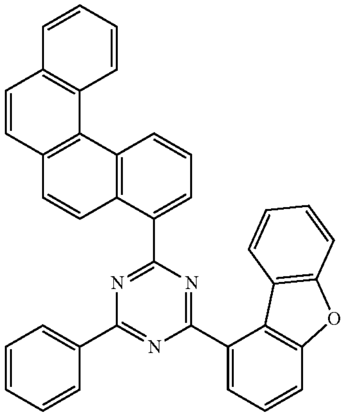
H2-312
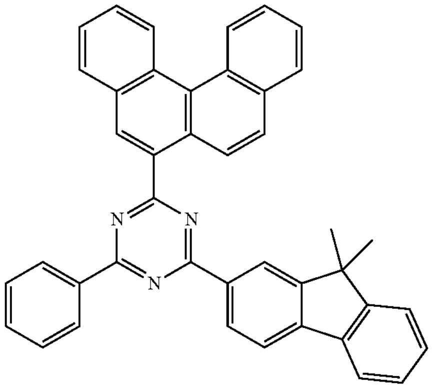
-continued
H2-313
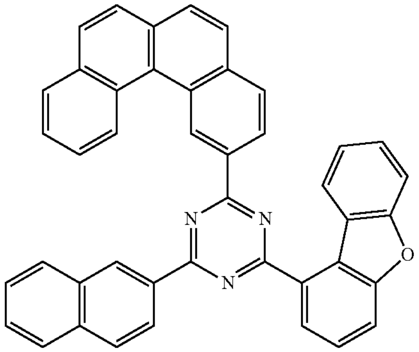
H2-314
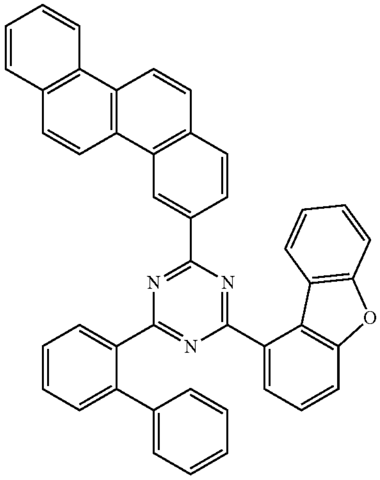
H2-315
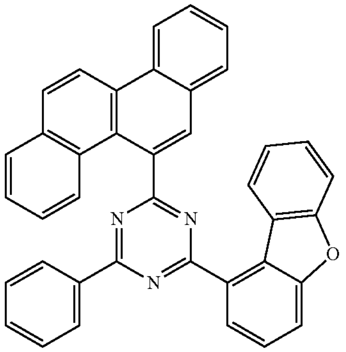
H2-316
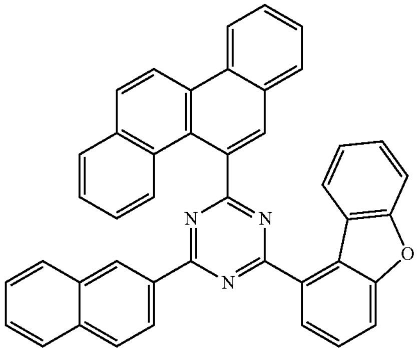

-continued
H2-317
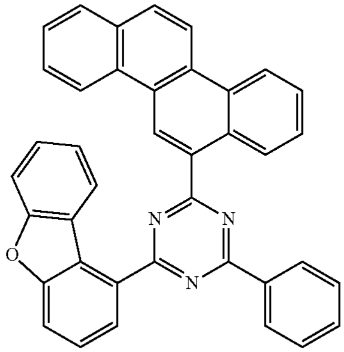
and
H2-318
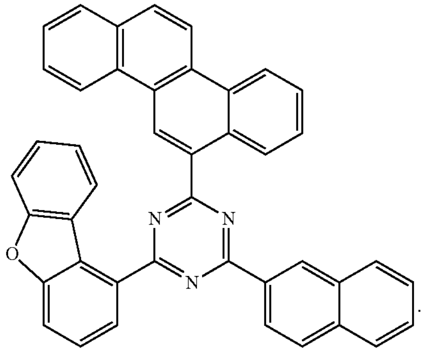
.
* * * * *